United States Patent
Park et al.

(10) Patent No.: US 12,018,022 B2
(45) Date of Patent: Jun. 25, 2024

(54) HETEROCYCLIC COMPOUND, ORGANIC LIGHT EMITTING DIODE COMPRISING SAME, COMPOSITION FOR ORGANIC LAYER OF ORGANIC LIGHT EMITTING DIODE, AND METHOD FOR MANUFACTURING ORGANIC LIGHT EMITTING DIODE

(71) Applicant: LT MATERIALS CO., LTD., Gyeonggi-do (KR)

(72) Inventors: Geon-Yu Park, Yongin (KR); Su-Yeon Kim, Yongin (KR); Dong-Jun Kim, Yongin (KR)

(73) Assignee: LT MATERIALS CO., LTD., Yongin (KR)

( * ) Notice: Subject to any disclaimer, the term of this patent is extended or adjusted under 35 U.S.C. 154(b) by 813 days.

(21) Appl. No.: 17/058,199

(22) PCT Filed: Jun. 18, 2019

(86) PCT No.: PCT/KR2019/007333
§ 371 (c)(1),
(2) Date: Nov. 24, 2020

(87) PCT Pub. No.: WO2019/245262
PCT Pub. Date: Dec. 26, 2019

(65) Prior Publication Data
US 2021/0179596 A1 Jun. 17, 2021

(30) Foreign Application Priority Data
Jun. 22, 2018 (KR) .................. 10-2018-0072029

(51) Int. Cl.
*C07D 409/14* (2006.01)
*C07D 403/04* (2006.01)
(Continued)

(52) U.S. Cl.
CPC ......... *C07D 409/14* (2013.01); *C07D 403/04* (2013.01); *C07D 405/04* (2013.01);
(Continued)

(58) Field of Classification Search
CPC .. C07D 405/02; C07D 405/04; C07D 405/14; C07D 409/02; C07D 409/14; H10K 50/10; H10K 50/16
See application file for complete search history.

(56) References Cited

U.S. PATENT DOCUMENTS

| 4,356,429 A | 10/1982 | Tang |
| 9,780,312 B2 | 10/2017 | Lee et al. |

(Continued)

FOREIGN PATENT DOCUMENTS

| JP | 2008-135498 A | 6/2008 |
| JP | 2018-536802 A | 11/2016 |

(Continued)

OTHER PUBLICATIONS

International Search Report (PCT/ISA/210) issued in PCT/KR2019/007333 dated Sep. 18, 2019.
(Continued)

*Primary Examiner* — Amanda C. Walke
(74) *Attorney, Agent, or Firm* — Birch, Stewart, Kolasch & Birch, LLP

(57) ABSTRACT

The present specification relates to a heterocyclic compound represented by Chemical Formula 1, an organic light emitting device comprising the same, a composition for an organic material layer of an organic light emitting device, and a method for manufacturing an organic light emitting device.

14 Claims, 2 Drawing Sheets

(51) Int. Cl.
*C07D 405/04* (2006.01)
*C07D 405/14* (2006.01)
*C07D 409/04* (2006.01)
*H10K 85/60* (2023.01)
*H10K 50/15* (2023.01)
*H10K 50/16* (2023.01)
*H10K 50/17* (2023.01)
*H10K 50/18* (2023.01)

(52) U.S. Cl.
CPC ......... *C07D 405/14* (2013.01); *C07D 409/04* (2013.01); *H10K 85/622* (2023.02); *H10K 85/654* (2023.02); *H10K 85/656* (2023.02); *H10K 85/6572* (2023.02); *H10K 85/6574* (2023.02); *H10K 85/6576* (2023.02); *H10K 50/15* (2023.02); *H10K 50/16* (2023.02); *H10K 50/171* (2023.02); *H10K 50/18* (2023.02)

(56) References Cited

U.S. PATENT DOCUMENTS

| | | | |
|---|---|---|---|
| 2014/0312331 A1 | 10/2014 | Inoue et al. | |
| 2015/0318487 A1 | 11/2015 | Ito et al. | |
| 2015/0336937 A1* | 11/2015 | Lee | C07D 471/04 544/216 |
| 2016/0111657 A1* | 4/2016 | Lee | C07D 491/048 544/216 |
| 2016/0226001 A1 | 8/2016 | Parham et al. | |
| 2017/0207399 A1 | 7/2017 | Parham et al. | |
| 2017/0213988 A1 | 7/2017 | Park et al. | |
| 2018/0037546 A1* | 2/2018 | Sugino | C07D 209/82 |
| 2018/0123055 A1 | 5/2018 | Park et al. | |
| 2019/0006602 A1 | 1/2019 | Chun et al. | |
| 2019/0165282 A1 | 5/2019 | Parham et al. | |
| 2019/0372024 A1 | 12/2019 | Heo et al. | |
| 2019/0393422 A1* | 12/2019 | Sakamoto | H10K 85/654 |

FOREIGN PATENT DOCUMENTS

| | | | |
|---|---|---|---|
| JP | 2017/524707 A | | 8/2017 |
| KR | 10-2013-0083817 A | | 7/2013 |
| KR | 10-2016-0045507 A | | 4/2016 |
| KR | 10-2016-0080090 A | | 7/2016 |
| KR | 20160080090 A | † | 7/2016 |
| KR | 10-2016-0129190 A | | 11/2016 |
| KR | 10-2017-0057660 A | | 5/2017 |
| KR | 20170057660 A | † | 5/2017 |
| KR | 10-2017-0102000 A | | 9/2017 |
| KR | 10-2017-0111387 A | | 10/2017 |
| KR | 20170111387 A | † | 10/2017 |
| KR | 10-2017-0136440 A | | 12/2017 |
| KR | 10-2018-0012199 A | | 2/2018 |
| KR | 10-2018-0031224 A | | 3/2018 |
| KR | 20180031224 A | † | 3/2018 |
| WO | WO 2012/108388 A1 | | 8/2012 |
| WO | WO 2017/018795 A2 | | 2/2017 |
| WO | WO 2017/178311 A1 | | 10/2017 |
| WO | WO 2018/190516 A1 | | 10/2018 |

OTHER PUBLICATIONS

Kuwabara et al., "Thermally Stable Multilayered Organic Electroluminescent Devices Using Novel Starburst Molecules, 4,4',4"-Tri(N-carbazoly)triphenylamine (TCTA) and 4,4',4"-Tris(3-methylphenylphenylamino)triphenylamine (m-MTDATA), as Hole-Transport Materials", Advanced Materials, 1994, vol. 6, No. 9, pp. 677-679.

\* cited by examiner
† cited by third party

【FIG. 1】
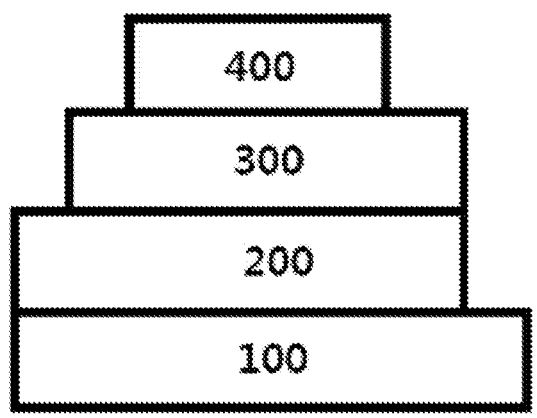
【FIG. 2】
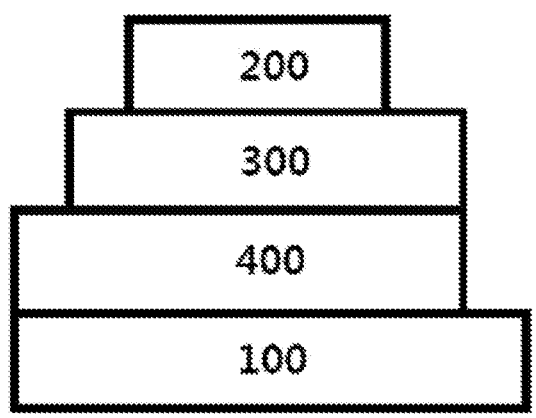

[FIG. 3]
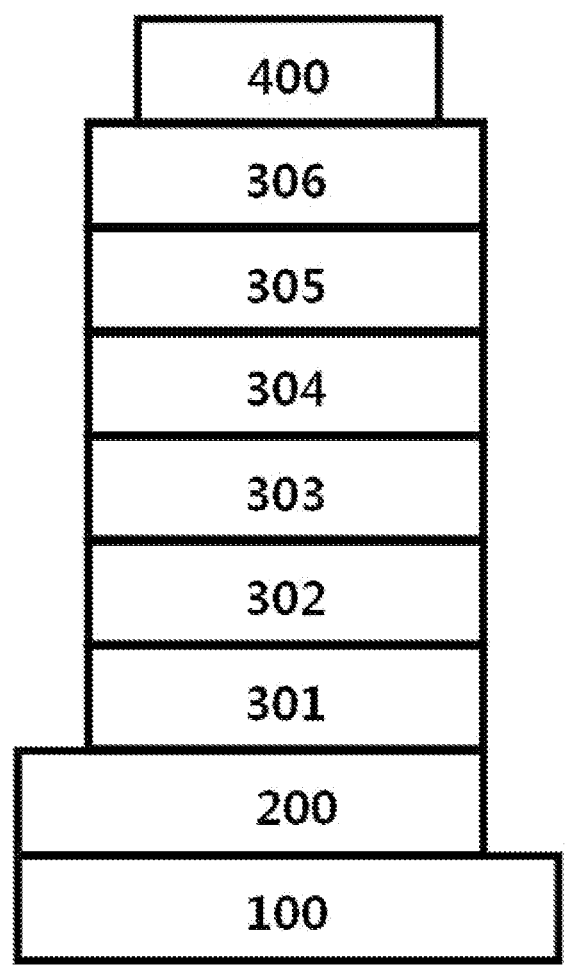

HETEROCYCLIC COMPOUND, ORGANIC LIGHT EMITTING DIODE COMPRISING SAME, COMPOSITION FOR ORGANIC LAYER OF ORGANIC LIGHT EMITTING DIODE, AND METHOD FOR MANUFACTURING ORGANIC LIGHT EMITTING DIODE

TECHNICAL FIELD

This application claims priority to and the benefits of Korean Patent Application No. 10-2018-0072029, filed with the Korean Intellectual Property Office on Jun. 22, 2018, the entire contents of which are incorporated herein by reference.

The present specification relates to a heterocyclic compound, an organic light emitting device comprising the same, a composition for an organic material layer of an organic light emitting device, and a method for manufacturing an organic light emitting device.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents

U.S. Pat. No. 4,356,429

DISCLOSURE

Technical Problem

The present application is directed to providing a heterocyclic compound, an organic light emitting device comprising the same, a composition for an organic material layer of an organic light emitting device, and a method for manufacturing an organic light emitting device.

Technical Solution

One embodiment of the present application provides a heterocyclic compound represented by the following Chemical Formula 1.

[Chemical Formula 1]

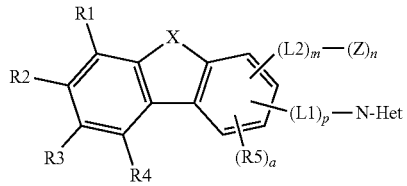

In Chemical Formula 1,
N-Het is a monocyclic or polycyclic heterocyclic group substituted or unsubstituted and comprising one or more Ns,
X is O; or S,
L1 and L2 are the same as or different from each other, and each independently a direct bond; a substituted or unsubstituted arylene group formed with one to three 6-membered rings; or a substituted or unsubstituted heteroarylene group, p and m are an integer of 1 to 3, and when p is 2 or greater, L1s are the same as or different from each other, and when m is 2 or greater, L2s are the same as or different from each other, and
Z is a substituted or unsubstituted alkyl group; a substituted or unsubstituted aryl group formed with one to three 6-membered rings; a triphenylene group; P(=O)RR'; SiRR'R''; a substituted or unsubstituted amine group; a substituted or unsubstituted heteroaryl group comprising two or more Ns; or represented by the following Chemical Formula 2, n is an integer of 1 to 5, and when n is 2 or greater, Zs are the same as or different from each other,

[Chemical Formula 2]

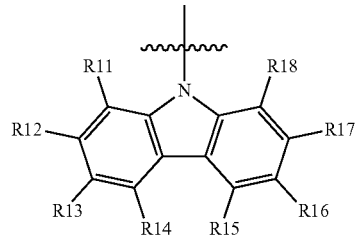

in Chemical Formula 2,
R11 to R18 are the same as or different from each other, and each independently hydrogen; or a substituted or unsubstituted heteroaryl group; or two or more groups adjacent to each other bond to each other to form a substituted or unsubstituted aromatic hydrocarbon ring or a substituted or unsubstituted heteroring,
R1 to R4 are hydrogen, and
R5, R, R' and R" are the same as or different from each other, and each independently selected from the group consisting of hydrogen; deuterium; halogen; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; and a substituted or unsubstituted amine group, or two or more groups adjacent to each other bond to each other to form a substituted or unsubstituted aromatic hydrocarbon ring or a substituted or unsubstituted heteroring, a is an integer of 0 to 2, and when a is 2 or greater, R5s are the same as or different from each other.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

Another embodiment of the present application provides an organic light emitting device, wherein the organic material layer comprising the heterocyclic compound represented by Chemical Formula 1 further comprises a heterocyclic compound represented by the following Chemical Formula 3.

[Chemical Formula 3]

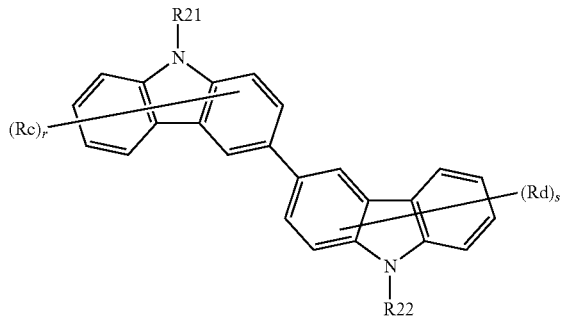

In Chemical Formula 3,

Rc and Rd are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —$SiR_{31}R_{32}R_{33}$; —$P(=O)R_{31}R_{32}$; and an amine group unsubstituted or substituted with a substituted or unsubstituted alkyl group, a substituted or unsubstituted aryl group or a substituted or unsubstituted heteroaryl group, or two or more groups adjacent to each other bond to each other to form a substituted or unsubstituted aliphatic or aromatic hydrocarbon ring, $R_{31}$, $R_{32}$, and $R_{33}$ are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group, R21 and R22 are the same as or different from each other, and each independently a substituted or unsubstituted aryl group; or a substituted or unsubstituted heteroaryl group, and r and s are an integer of 0 to 7, and when r and s are an integer of 2 or greater, substituents in the parentheses are the same as or different from each other.

In addition, another embodiment of the present application provides a composition for an organic material layer of an organic light emitting device comprising the heterocyclic compound represented by Chemical Formula 1 and the heterocyclic compound represented by Chemical Formula 3.

Lastly, one embodiment of the present application provides a method for manufacturing an organic light emitting device, the method comprising preparing a substrate; forming a first electrode on the substrate; forming one or more organic material layers on the first electrode; and forming a second electrode on the organic material layer, wherein the forming of organic material layers comprises forming one or more organic material layers using the composition for an organic material layer described above.

Advantageous Effects

A compound described in the present specification can be used as a material of an organic material layer of an organic light emitting device. The compound is capable of performing a role of a hole injection material, a hole transfer material, a light emitting material, an electron transfer material, an electron injection material and the like in the organic light emitting device. Particularly, the compound can be used as a light emitting layer material of the organic light emitting device. For example, the compound alone can be used as a light emitting material, or the compound can be used as a host material of a light emitting layer.

Particularly, by Chemical Formula 1 being substituted with another substituent while being substituted with an N-containing ring on the position of one side benzene ring of a dibenzofuran or dibenzothiophene structure, p-type and n-type substituents are both included in one side benzene ring, and therefore, a structure of electron stability is obtained, which resultantly enhances a device lifetime.

DESCRIPTION OF DRAWINGS

FIG. 1 to FIG. 3 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group includes linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group includes linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group includes linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenzyloxy and the like, but are not limited thereto.

In the present specification, the cycloalkyl group includes monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group includes O, S, Se, N or Si as a heteroatom, includes monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group includes monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group includes a spiro group. The number of carbon atoms of the aryl group may be from 6 to 60, specifically from 6 to 40 and more specifically from 6 to 25. Specific examples of the aryl group may include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the fluorenyl group may be substituted, and adjacent substituents may bond to each other to form a ring.

When the fluorenyl group is substituted,

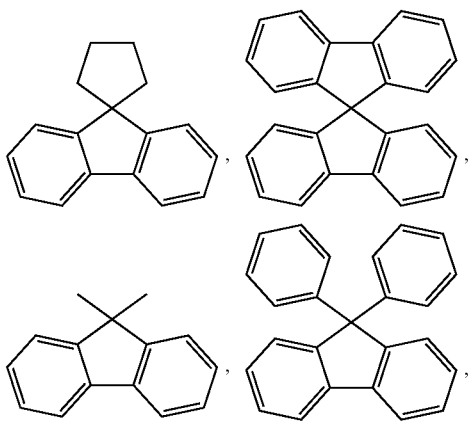

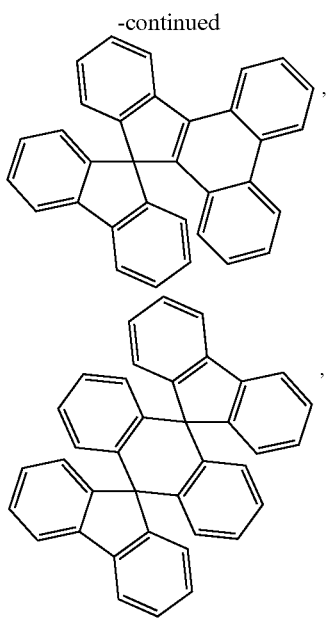

and the like may be included, however, the structure is not limited thereto.

In the present specification, the heteroaryl group includes O, S, Se, N or Si as a heteroatom, includes monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group.

Descriptions on the aryl group provided above may be applied thereto except for those that are each a divalent. In addition, the heteroarylene group means the heteroaryl group having two bonding sites, that is, a divalent group. Descriptions on the heteroaryl group provided above may be applied thereto except for those that are each a divalent.

In the present specification, the phosphine oxide group may specifically be substituted with an aryl group, and the examples described above may be applied to the aryl group. Examples of the phosphine oxide group may include a diphenylphosphine oxide group, a dinaphthylphosphine oxide group and the like, but are not limited thereto.

In the present specification, the silyl group is a substituent including Si, having the Si atom directly linked as a radical, and is represented by —SiR$_{104}$R$_{105}$R$_{106}$. R$_{104}$ to R$_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

The structures illustrated as the cycloalkyl group, the cycloheteroalkyl group, the aryl group and the heteroaryl group described above may be applied to the aliphatic or aromatic hydrocarbon ring or heteroring that adjacent groups may form except for those that are not a monovalent group.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

One embodiment of the present application provides a compound represented by Chemical Formula 1.

In one embodiment of the present application, Chemical Formula 1 may be represented by the following Chemical Formula 4 or 5.

[Chemical Formula 4]

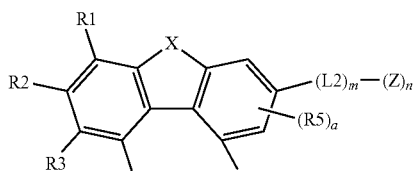

[Chemical Formula 5]

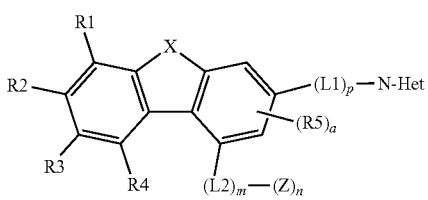

In Chemical Formulae 4 and 5,

R1 to R5, X, L1, L2, N-Het, Z, m, n, p, and a have the same definitions as in Chemical Formula 1.

Particularly, when Chemical Formula 1 of the present application is represented by Chemical Formulae 4 and 5 as above, N-Het pulls electrons injected into a light emitting layer for stabilization, and no interference effect of oxygen of dibenzofuran or sulfur of dibenzothiophene, which donates electrons, occurs, and as a result, an effect of stabilizing electrons injected to N-Het and a property of increasing a device lifetime are obtained.

In one embodiment of the present application, N-Het is a monocyclic or polycyclic heteroring substituted or unsubstituted and comprising one or more Ns.

In another embodiment, N-Het is a monocyclic or polycyclic heteroring unsubstituted or substituted with one or more substituents selected from the group consisting of an aryl group and a heteroaryl group and comprising one or more Ns.

In another embodiment, N-Het is a monocyclic or polycyclic heteroring unsubstituted or substituted with one or more substituents selected from the group consisting of a phenyl group, a biphenyl group, a naphthyl group, a dimethylfluorene group, a dibenzofuran group and a dibenzothiophene group and comprising one or more Ns.

In another embodiment, N-Het is a monocyclic or polycyclic heteroring unsubstituted or substituted with one or more substituents selected from the group consisting of a phenyl group, a biphenyl group, a naphthyl group, a dimethylfluorene group, a dibenzofuran group and a dibenzothiophene group and comprising one or more and three or less Ns.

In one embodiment of the present application, N-Het is a monocyclic heteroring substituted or unsubstituted and comprising one or more Ns.

In one embodiment of the present application, N-Het is a dicyclic or higher heteroring substituted or unsubstituted and comprising one or more Ns.

In one embodiment of the present application, N-Het is a monocyclic or polycyclic heteroring substituted or unsubstituted and comprising two or more Ns.

In one embodiment of the present application, N-Het is a dicyclic or higher polycyclic heteroring comprising two or more Ns.

In one embodiment of the present application, N-Het may be a pyridine group unsubstituted or substituted with a phenyl group; a pyrimidine group unsubstituted or substituted with a phenyl group; a triazine group unsubstituted or substituted with one or more substituents selected from the group consisting of a phenyl group, a biphenyl group, a naphthyl group, a dimethylfluorene group, a diphenylfluorene group, a spirobifluorene group, a triphenylene group, a pyridine group, a dibenzofuran group and a dibenzothiophene group; a benzo[4,5]thieno[3,2-d]pyrimidine group unsubstituted or substituted with a phenyl group; a benzimidazole group unsubstituted or substituted with a phenyl group; a benzothiazole group; a quinoline group unsubstituted or substituted with a phenyl group; a quinazoline group unsubstituted or substituted with one or more substituents selected from the group consisting of a phenyl group and a biphenyl group; or a phenanthroline group unsubstituted or substituted with a phenyl group.

In one embodiment of the present application, N-Het may be substituted again with a phenyl group; —CN; SiRR'R"; or P(=O)RR'.

In one embodiment of the present application, N-Het may be represented by the following Chemical Formula 6 or 7.

[Chemical Formula 6]

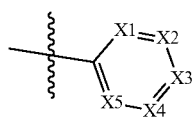

[Chemical Formula 7]

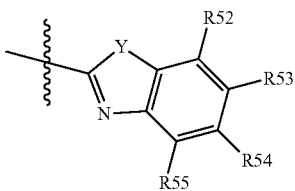

In Chemical Formulae 6 and 7,

X1 is CR41 or N, X2 is CR42 or N, X3 is CR43 or N, X4 is CR44 or N, and X5 is CR45 or N, at least one of X1 to X5 is N, Y is NR51 or S, R41 to R45 and R51 to R55 are the same as or different from each other, and each independently selected from the group consisting of hydrogen; deuterium; a halogen group; —CN; a substituted or unsubstituted alkyl group; a substituted or unsubstituted aryl group; a substituted or unsubstituted heteroaryl group; P(=O)RR'; SiRR'R"; and an amine group unsubstituted or substituted with a substituted or unsubstituted alkyl group, a substituted or unsubstituted aryl group or a substituted or unsubstituted heteroaryl group, or two or more groups adjacent to each other bond to each other to form a substituted or unsubstituted aromatic hydrocarbon ring or a substituted or unsubstituted heteroring, and R, R' and R" have the same definitions as in Chemical Formula 1.

In one embodiment of the present application, Chemical Formula 6 may be represented by any one of the following Chemical Formulae 8 to 12.

[Chemical Formula 8]

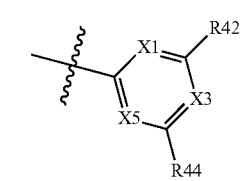

[Chemical Formula 9]

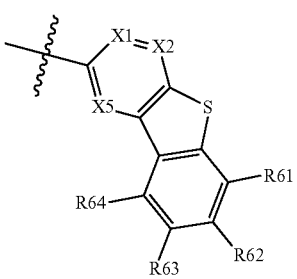

[Chemical Formula 10]

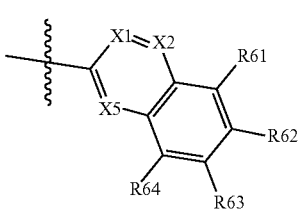

[Chemical Formula 11]

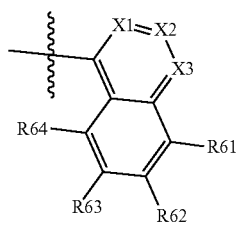

[Chemical Formula 12]

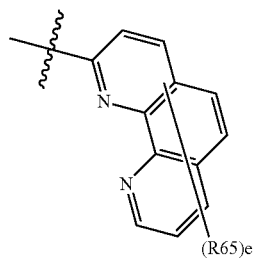

In Chemical Formulae 8 to 12,

X1, X2, X3, X5, R42 and R44 have the same definitions as in Chemical Formula 6, in Chemical Formula 8, one or more of X1, X3 and X5 are N, in Chemical Formulae 9 and 10, one or more of X1, X2 and X5 are N, in Chemical Formula 11, one or more of X1 to X3 are N, R61 to R65 are the same as or different from each other, and each independently selected from the group consisting of hydrogen; deuterium; a halogen group; —CN; a substituted or unsubstituted alkyl group; a substituted or unsubstituted aryl group; a substituted or unsubstituted heteroaryl group; P(=O)RR'; SiRR'R"; and an amine group unsubstituted or substituted with a substituted or unsubstituted alkyl group, a substituted or unsubstituted aryl group or a substituted or unsubstituted heteroaryl group, or two or more groups adjacent to each other bond to each other to form a substituted or unsubstituted aliphatic or aromatic hydrocarbon ring, and e is an integer of 0 to 7, and when e is 2 or greater, substituents in the parentheses are the same as or different from each other.

In one embodiment of the present application, R1 to R5 may be hydrogen.

In one embodiment of the present application, X may be O.

In one embodiment of the present application, X may be S.

In one embodiment of the present application, L1 and L2 are the same as or different from each other, and may be each independently a direct bond; a substituted or unsubstituted arylene group formed with one to three 6-membered rings; or a substituted or unsubstituted heteroarylene group.

The meaning of being formed with one to three 6-membered rings comprises both 6-membered rings being fused to be formed or 6-membered rings being linked to each other to be formed.

In another embodiment, L1 and L2 are the same as or different from each other, and may be each independently a direct bond; a substituted or unsubstituted arylene group having 6 to 60 carbon atoms formed with one to three 6-membered rings; or a substituted or unsubstituted heteroarylene group having 2 to 60 carbon atoms.

In another embodiment, L1 and L2 are the same as or different from each other, and may be each independently a direct bond; a substituted or unsubstituted arylene group having 6 to 40 carbon atoms formed with one to three 6-membered rings; or a substituted or unsubstituted heteroarylene group having 2 to 40 carbon atoms.

In another embodiment, L1 and L2 are the same as or different from each other, and may be each independently a direct bond; an arylene group having 6 to 40 carbon atoms formed with one to three 6-membered rings; or a heteroarylene group having 2 to 40 carbon atoms.

In another embodiment, L1 and L2 are the same as or different from each other, and may be each independently a direct bond; a phenylene group; a naphthalene group; a biphenylene group; or a divalent pyridine group.

In one embodiment of the present application, Z is a substituted or unsubstituted alkyl group; a substituted or unsubstituted aryl group formed with one to three 6-membered rings; a triphenylene group; P(=O)RR'; SiRR'R"; a substituted or unsubstituted amine group; a substituted or unsubstituted heteroaryl group comprising two or more Ns; or may be represented by the following Chemical Formula 2.

[Chemical Formula 2]

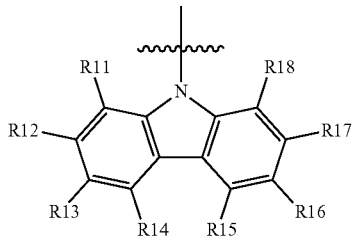

In Chemical Formula 2,

R11 to R18 are the same as or different from each other, and each independently hydrogen; or a substituted or unsubstituted heteroaryl group; or two or more groups adjacent to each other bond to each other to form a substituted or unsubstituted aromatic hydrocarbon ring or a substituted or unsubstituted heteroring.

In one embodiment of the present application, R11 to R18 are the same as or different from each other, and each independently hydrogen; or a substituted or unsubstituted heteroaryl group having 2 to 60 carbon atoms; or two or more groups adjacent to each other bond to each other to form a substituted or unsubstituted aromatic hydrocarbon ring having 6 to 60 carbon atoms or a substituted or unsubstituted heteroring having 2 to 60 carbon atoms.

In another embodiment, R11 to R18 are the same as or different from each other, and each independently hydrogen; or a substituted or unsubstituted heteroaryl group having 2 to 40 carbon atoms; or two or more groups adjacent to each other bond to each other to form a substituted or unsubstituted aromatic hydrocarbon ring having 6 to 40 carbon atoms or a substituted or unsubstituted heteroring having 2 to 40 carbon atoms.

In another embodiment, R11 to R18 are the same as or different from each other, and each independently hydrogen; or a heteroaryl group having 2 to 40 carbon atoms unsubstituted or substituted with an aryl group having 6 to 40 carbon atoms; or two or more groups adjacent to each other bond to each other to form an aromatic hydrocarbon ring having 6 to 40 carbon atoms unsubstituted or substituted with an alkyl group having 1 to 40 carbon atoms or an aryl group having 6 to 40 carbon atoms, or a heteroring having 2 to 40 carbon atoms unsubstituted or substituted with an alkyl group having 1 to 40 carbon atoms or an aryl group having 6 to 40 carbon atoms.

In another embodiment, R11 to R18 are the same as or different from each other, and each independently hydrogen; a dibenzofuran group; a dibenzothiophene group; a carbazole group unsubstituted or substituted with a phenyl group; or two or more groups adjacent to each other may bond to each other to form an indole ring unsubstituted or substituted with a methyl group or a phenyl group, a benzothiophene ring, a benzofuran ring, or an indene ring unsubstituted or substituted with a methyl group.

In one embodiment of the present application, at least one of R11 to R18 is a substituted or unsubstituted heteroaryl group; or two or more groups adjacent to each other bond to each other to form a substituted or unsubstituted aromatic hydrocarbon ring or a substituted or unsubstituted heteroring.

In another embodiment, Z may be a substituted or unsubstituted alkyl group having 1 to 60 carbon atoms; a substituted or unsubstituted aryl group having 6 to 60 carbon atoms formed with one to three 6-membered rings; a triphenylene group; P(=O)RR'; SiRR'R''; a substituted or unsubstituted heteroaryl group having 2 to 60 carbon atoms and comprising two or more Ns; or a substituted or unsubstituted amine group.

In another embodiment, Z may be a substituted or unsubstituted alkyl group having 1 to 40 carbon atoms; a substituted or unsubstituted aryl group having 6 to 40 carbon atoms formed with one to three 6-membered rings; a triphenylene group; P(=O)RR'; SiRR'R''; a substituted or unsubstituted heteroaryl group having 2 to 40 carbon atoms and comprising two or more Ns; or a substituted or unsubstituted amine group.

In another embodiment, Z may be an alkyl group having 1 to 40 carbon atoms unsubstituted or substituted with an aryl group having 6 to 40 carbon atoms; an aryl group having 6 to 40 carbon atoms formed with one to three 6-membered rings; a triphenylene group; a heteroaryl group having 2 to 40 carbon atoms unsubstituted or substituted with one or more substituents selected from the group consisting of an aryl group having 6 to 40 carbon atoms and a heteroaryl group having 2 to 40 carbon atoms and comprising two or more Ns; P(=O)RR'; or SiRR'R''.

In another embodiment, Z may be a phenyl group; a biphenyl group; a naphthyl group; a phenanthrene group; a triphenylene group; a methyl group unsubstituted or substituted with a phenyl group; a triazine group unsubstituted or substituted with one or more substituents selected form the group consisting of a phenyl group and a dibenzofuran group; a pyrimidine group unsubstituted or substituted with a phenyl group; an imidazole group unsubstituted or substituted with a phenyl group; a quinoline group unsubstituted or substituted with a phenyl group; P(=O)RR'; or SiRR'R''.

In one embodiment of the present application, R, R' and R'' are the same as or different from each other, and may be each independently a substituted or unsubstituted aryl group.

In another embodiment, R, R' and R'' are the same as or different from each other, and may be each independently a substituted or unsubstituted aryl group having 6 to 60 carbon atoms.

In another embodiment, R, R' and R'' are the same as or different from each other, and may be each independently a substituted or unsubstituted aryl group having 6 to 40 carbon atoms.

In another embodiment, R, R' and R'' are the same as or different from each other, and may be each independently an aryl group having 6 to 40 carbon atoms.

In another embodiment, R, R' and R'' are the same as or different from each other, and may be each independently a phenyl group.

In one embodiment of the present application, when R15 and R16; R16 and R17; or R17 and R18 of Chemical Formula 2 bond to each other to form a substituted or unsubstituted aromatic hydrocarbon ring or a substituted or unsubstituted heteroring, it may be represented by the following Chemical Formula 13.

[Chemical Formula 13]

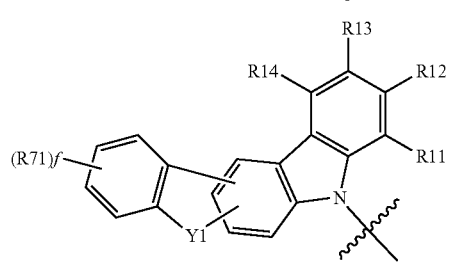

In Chemical Formula 13,

R11 to R14 are the same as or different from each other, and each independently hydrogen; a substituted or unsubstituted heteroaryl group; or two or more groups adjacent to each other bond to each other to form a substituted or unsubstituted aromatic hydrocarbon ring or a substituted or unsubstituted heteroring, Y1 is O; S; NR81; or CR82R83, R71 and R81 to R83 are the same as or different from each other, and each independently hydrogen; a substituted or unsubstituted alkyl group; a substituted or unsubstituted aryl group; or a substituted or unsubstituted heteroaryl group, f is an integer of 0 to 4, and when f is an integer of 2 or greater, substituents in the parentheses are the same as or different from each other.

In one embodiment of the present application, R41 to R45 are the same as or different from each other, and each independently hydrogen; a substituted or unsubstituted aryl group; or a substituted or unsubstituted heteroaryl group, or two or more groups adjacent to each other may bond to each other to form a substituted or unsubstituted aromatic hydrocarbon ring or a substituted or unsubstituted heteroring.

In another embodiment, R41 to R45 are the same as or different from each other, and each independently hydrogen; a substituted or unsubstituted aryl group having 6 to 60 carbon atoms; or a substituted or unsubstituted heteroaryl group having 2 to 60 carbon atoms, or two or more groups adjacent to each other may bond to each other to form a substituted or unsubstituted aromatic hydrocarbon ring having 6 to 60 carbon atoms or a substituted or unsubstituted heteroring having 2 to 60 carbon atoms.

In another embodiment, R41 to R45 are the same as or different from each other, and each independently hydrogen; a substituted or unsubstituted aryl group having 6 to 40 carbon atoms; or a substituted or unsubstituted heteroaryl group having 2 to 40 carbon atoms, or two or more groups adjacent to each other may bond to each other to form a substituted or unsubstituted aromatic hydrocarbon ring having 6 to 40 carbon atoms or a substituted or unsubstituted heteroring having 2 to 40 carbon atoms.

In another embodiment, R41 to R45 are the same as or different from each other, and each independently hydrogen; an aryl group having 6 to 40 carbon atoms unsubstituted or substituted with one or more substituents selected form the group consisting of CN, an alkyl group having 1 to 40 carbon atoms, an aryl group having 6 to 40 carbon atoms, SiRR'R" and P(=O)RR'; or a heteroaryl group having 2 to 40 carbon atoms, or two or more groups adjacent to each other may bond to each other to form an aromatic hydrocarbon ring having 6 to 40 carbon atoms or a heteroring having 2 to 40 carbon atoms.

In another embodiment, R41 to R45 are the same as or different from each other, and each independently hydrogen; a phenyl group unsubstituted or substituted with one or more substituents selected form the group consisting of CN, a biphenyl group, a triphenylene group, SiRR'R" and P(=O)RR'; a biphenyl group; a naphthyl group; a triphenylene group; a dimethylfluorene group; a diphenylfluorene group; a spirobifluorene group; a pyridine group; a dibenzothiophene group; or a dibenzofuran group, or two or more groups adjacent to each other may bond to each other to form a benzene ring, a quinoline ring or a benzothiophene ring.

In one embodiment of the present application, R51 to R55 are the same as or different from each other, and each independently hydrogen; a substituted or unsubstituted aryl group; or a substituted or unsubstituted heteroaryl group, or two or more groups adjacent to each other may bond to each other to form a substituted or unsubstituted aromatic hydrocarbon ring or a substituted or unsubstituted heteroring.

In another embodiment, R51 to R55 are the same as or different from each other, and may be each independently hydrogen; or a substituted or unsubstituted aryl group having 6 to 60 carbon atoms.

In another embodiment, R51 to R55 are the same as or different from each other, and may be each independently hydrogen; or an aryl group having 6 to 40 carbon atoms.

In another embodiment, R51 to R55 are the same as or different from each other, and may be each independently hydrogen; or a phenyl group.

In one embodiment of the present application, R61 to R65 may be hydrogen.

In one embodiment of the present application, R71 may be hydrogen.

In one embodiment of the present application, Y1 may be O; S; NR81; or CR82R83.

In one embodiment of the present application, R81 may be hydrogen; or a substituted or unsubstituted aryl group.

In another embodiment, R81 may be hydrogen; or an aryl group having 6 to 40 carbon atoms.

In another embodiment, R81 may be hydrogen; or a phenyl group.

In one embodiment of the present application, R82 and R83 are the same as or different from each other, and may be each independently hydrogen; or a substituted or unsubstituted alkyl group.

In another embodiment, R82 and R83 are the same as or different from each other, and may be each independently a substituted or unsubstituted alkyl group having 1 to 40 carbon atoms.

In another embodiment, R82 and R83 may be a methyl group.

In one embodiment of the present application,

means a site linked to a substituent. Specifically,

of Chemical Formula 2 means a site linked to L2, and

of Chemical Formulae 6 to 13 each mean a site linked to L1.

According to one embodiment of the present application, Chemical Formula 1 may be represented by any one of the following compounds, but is not limited thereto.

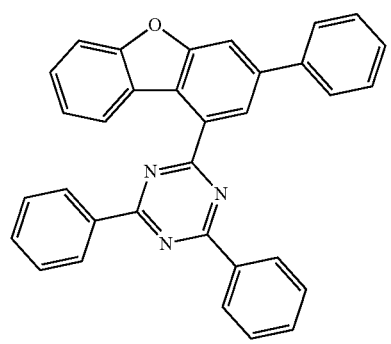 [SMILES: c1ccc(-c2cc(-c3nc(-c4ccccc4)nc(-c4ccccc4)n3)c3c(c2)oc2ccccc23)cc1]
1-1
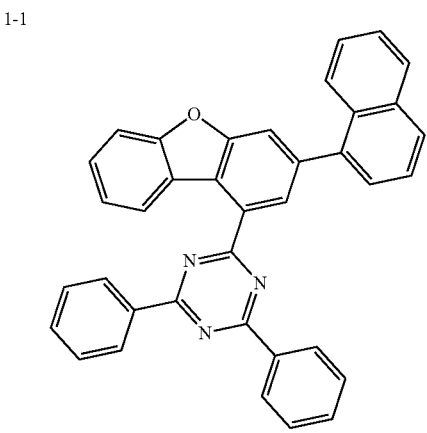
1-2
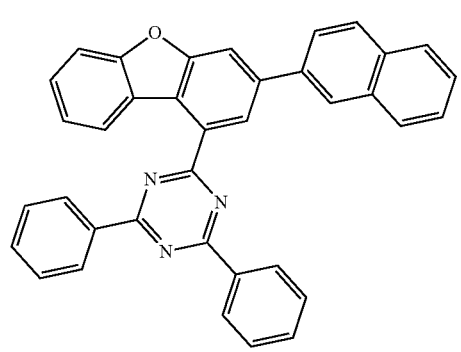
1-3
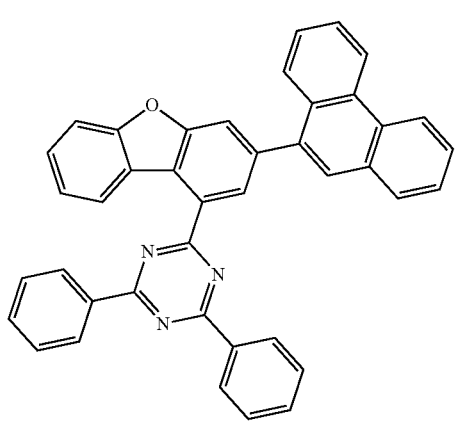
1-4
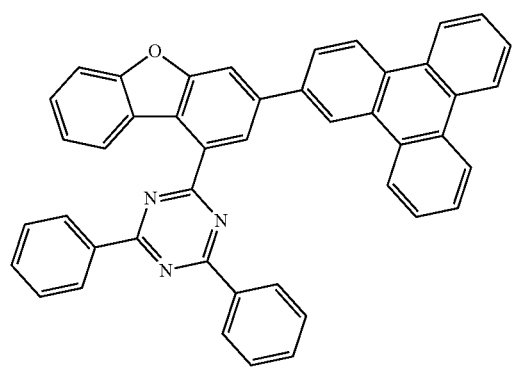
1-5
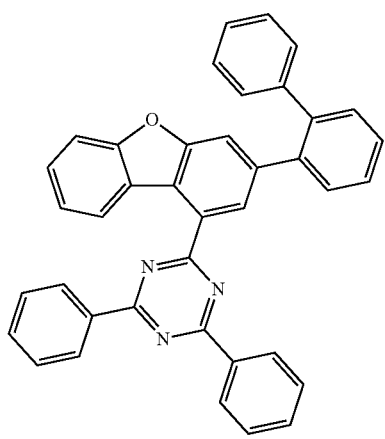
1-6

-continued
1-7
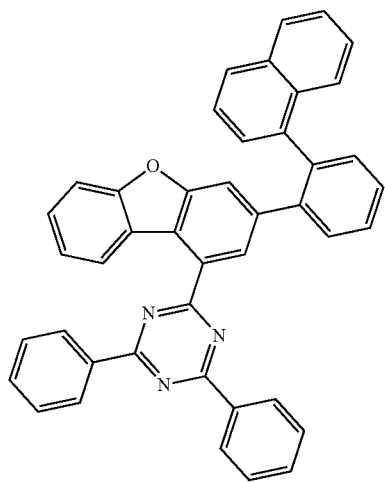
1-8
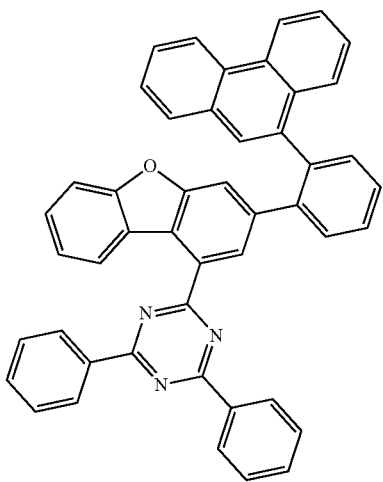
1-9
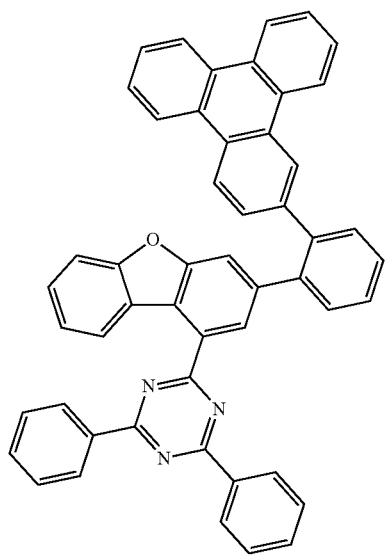
1-10
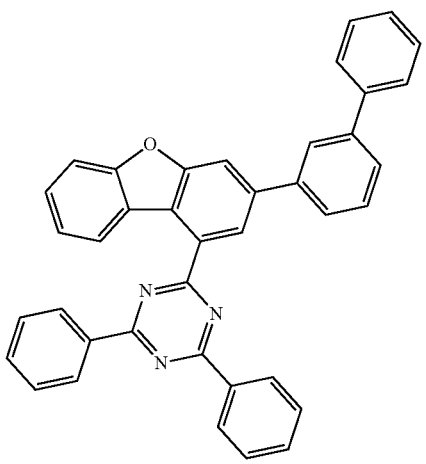 [SMILES: c1ccc(-c2cccc(-c3cc(-c4nc(-c5ccccc5)nc(-c5ccccc5)n4)c4c(c3)oc3ccccc34)c2)cc1]
1-11
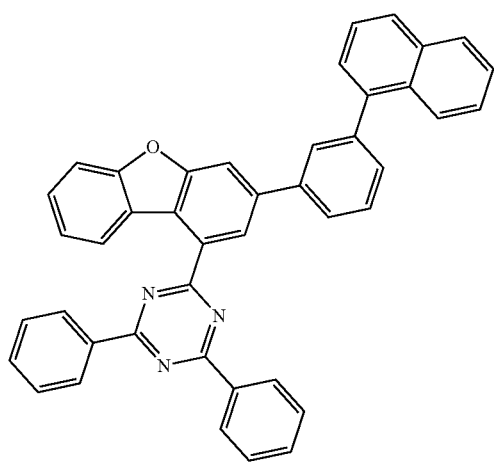
1-12
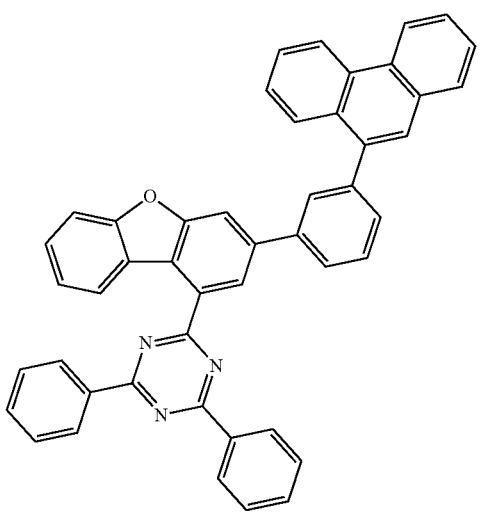

-continued
1-13
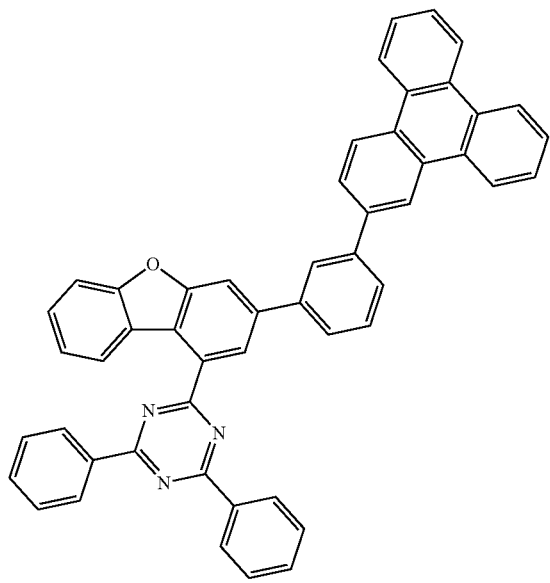 [SMILES: c1ccc(-c2nc(-c3ccccc3)nc(-c3cc(-c4cccc(-c5ccc6c7ccccc7c7ccccc7c6c5)c4)cc4oc5ccccc5c34)n2)cc1]
1-14
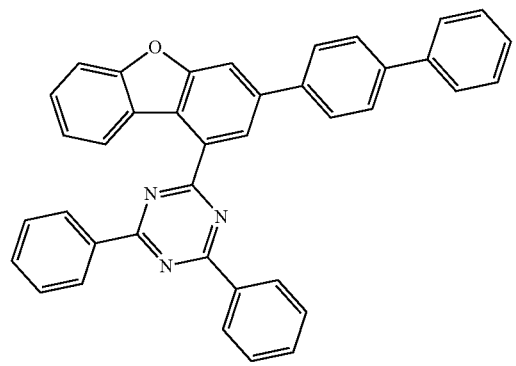 [SMILES: c1ccc(-c2ccc(-c3cc(-c4nc(-c5ccccc5)nc(-c5ccccc5)n4)c4c(c3)oc3ccccc34)cc2)cc1]
1-15
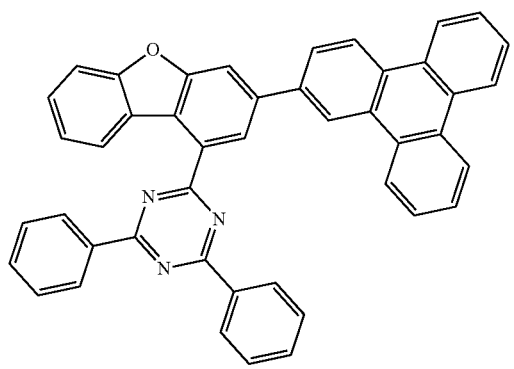
1-16
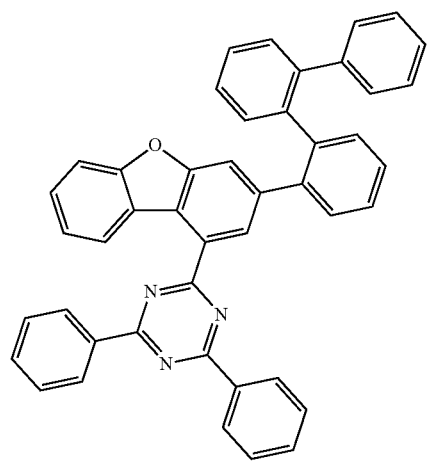
1-17
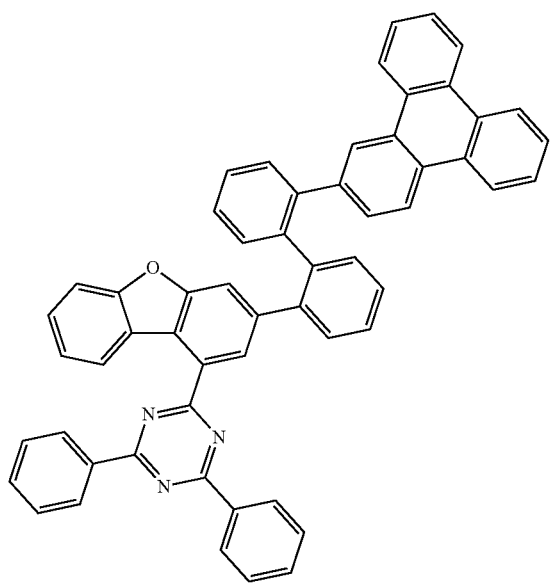
1-18
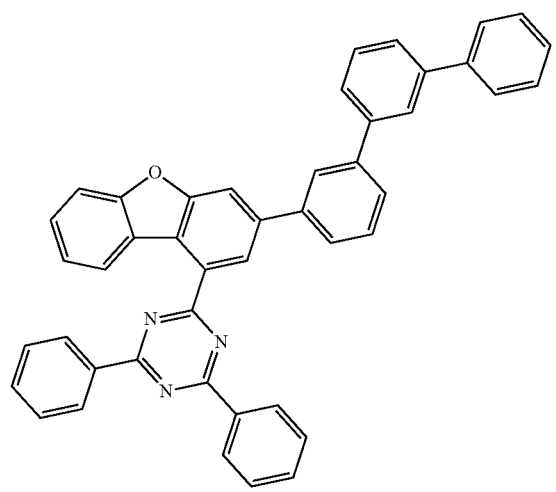

-continued
1-19
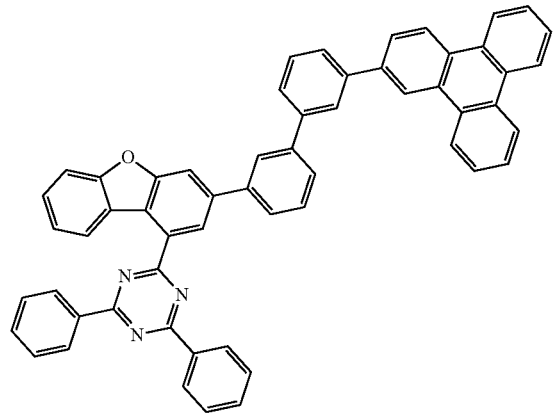 [SMILES: c1ccc(-c2nc(-c3ccccc3)nc(-c3cc(-c4cccc(-c5cccc(-c6ccc7c8ccccc8c8ccccc8c7c6)c5)c4)cc4oc5ccccc5c34)n2)cc1]
1-20
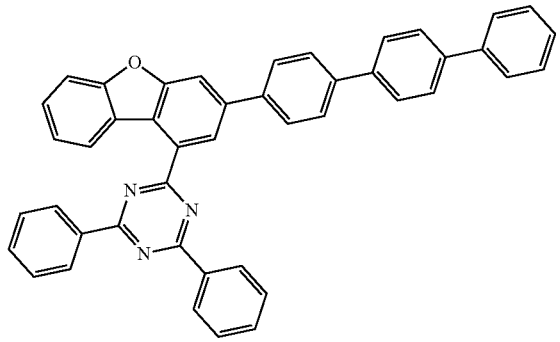 [SMILES: c1ccc(-c2ccc(-c3ccc(-c4cc(-c5nc(-c6ccccc6)nc(-c6ccccc6)n5)c5c(c4)oc4ccccc45)cc3)cc2)cc1]
1-21
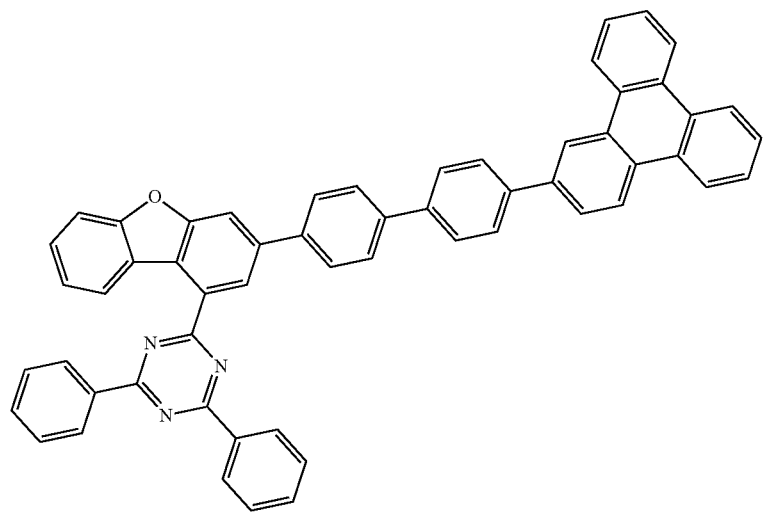 [SMILES: c1ccc(-c2nc(-c3ccccc3)nc(-c3cc(-c4ccc(-c5ccc(-c6ccc7c8ccccc8c8ccccc8c7c6)cc5)cc4)cc4oc5ccccc5c34)n2)cc1]
1-22
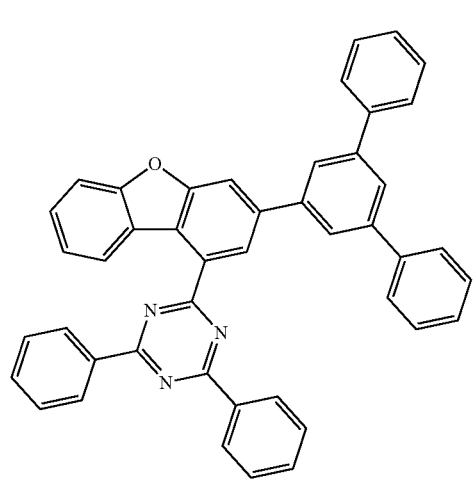 [SMILES: c1ccc(-c2cc(-c3ccccc3)cc(-c3cc(-c4nc(-c5ccccc5)nc(-c5ccccc5)n4)c4c(c3)oc3ccccc34)c2)cc1]
1-23
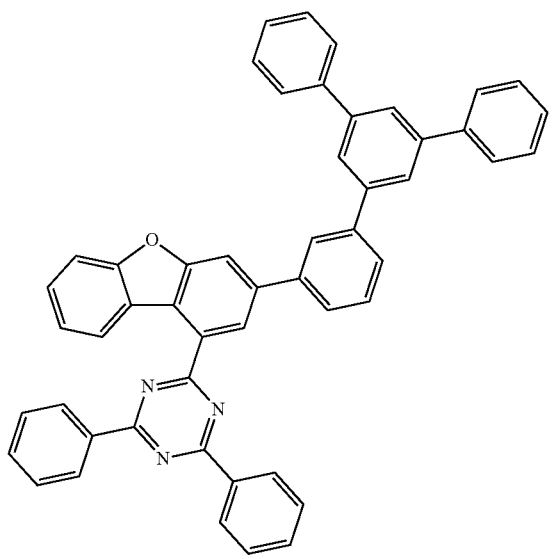 [SMILES: c1ccc(-c2cc(-c3ccccc3)cc(-c3cccc(-c4cc(-c5nc(-c6ccccc6)nc(-c6ccccc6)n5)c5c(c4)oc4ccccc45)c3)c2)cc1]

-continued
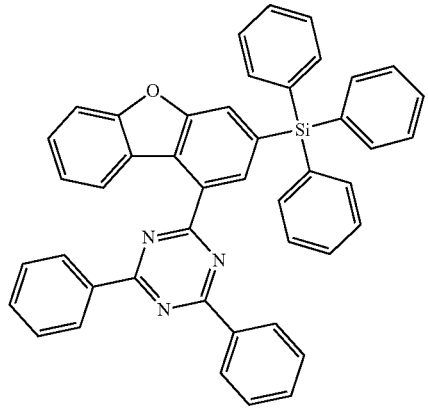
1-24
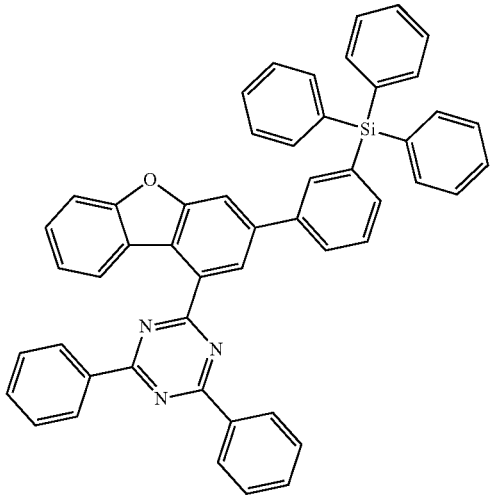 [SMILES: c1ccc(-c2nc(-c3ccccc3)nc(-c3cc(-c4cccc([Si](c5ccccc5)(c5ccccc5)c5ccccc5)c4)cc4oc5ccccc5c34)n2)cc1]
1-25
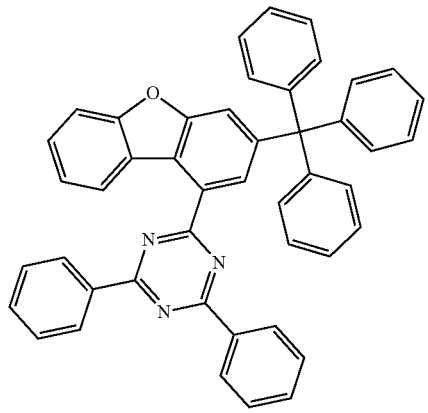
1-26
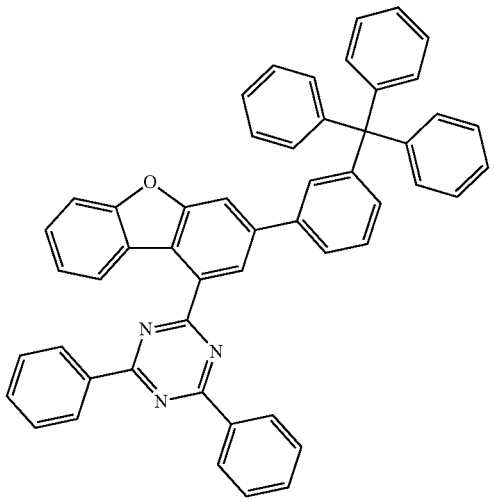
1-27
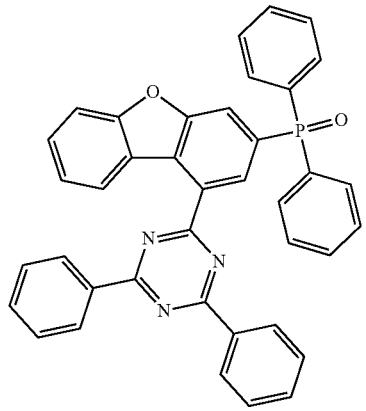
1-28
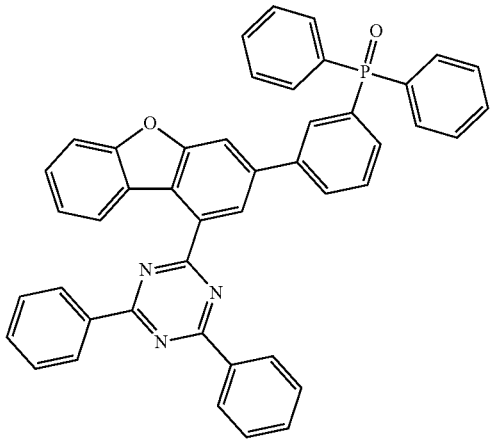
1-29

-continued
1-30
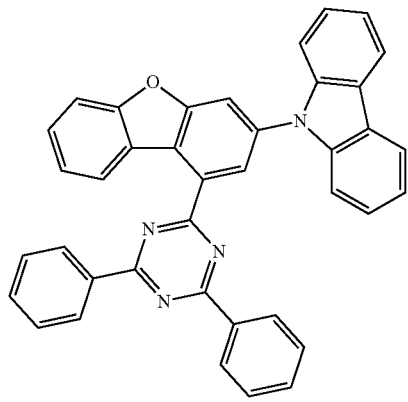
1-31
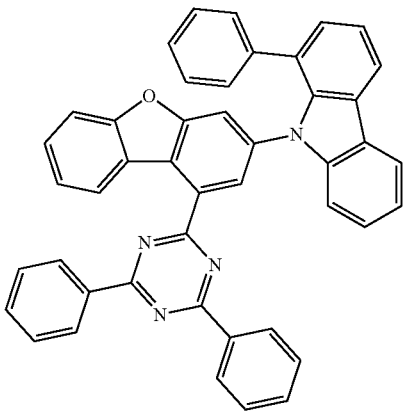
1-32
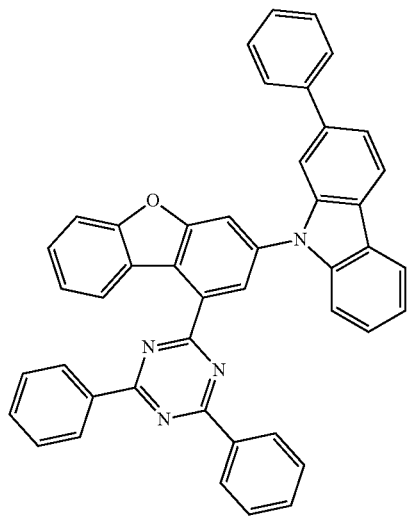
1-33
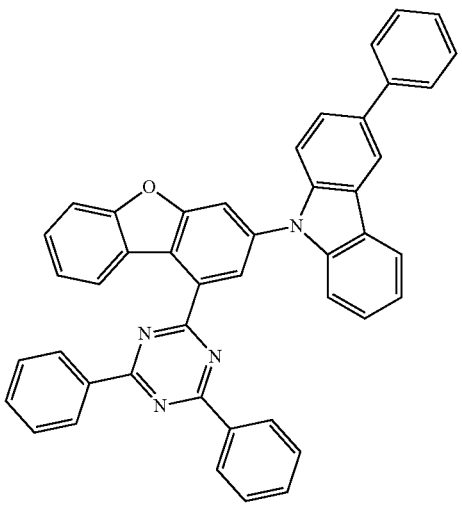
1-34
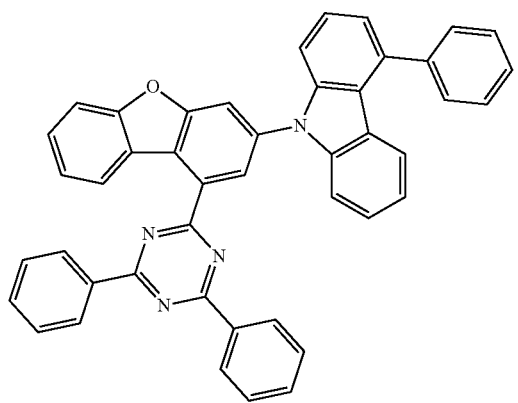
1-35
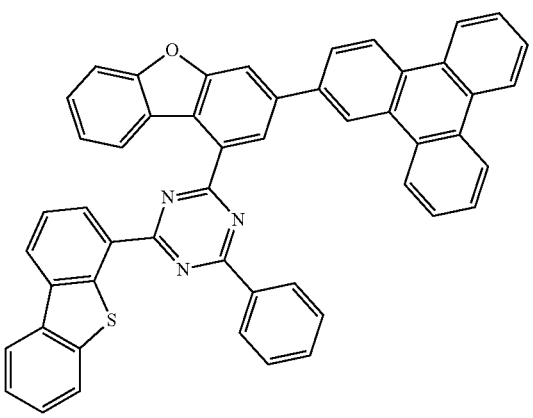

-continued
1-36
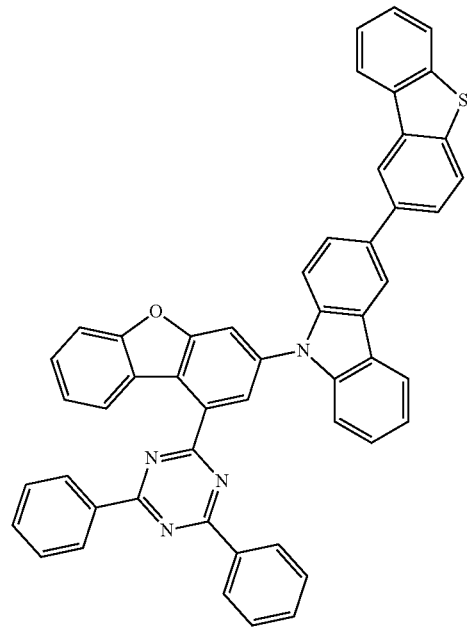
1-37
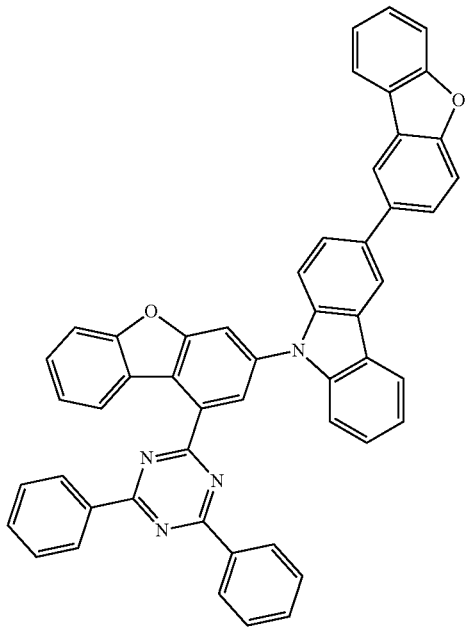
1-38
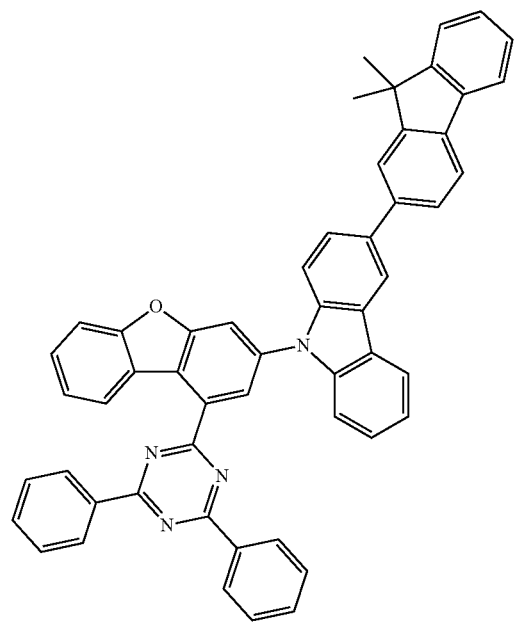
1-39
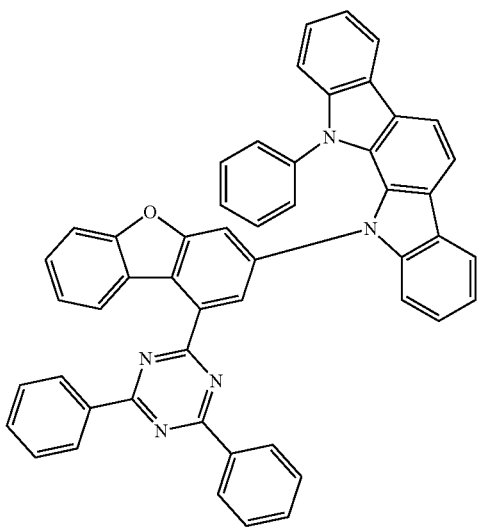

-continued
1-40
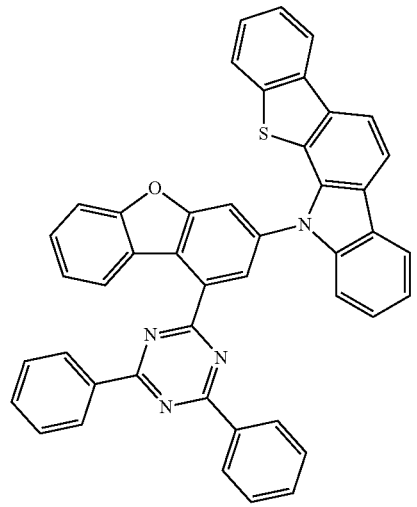
1-41
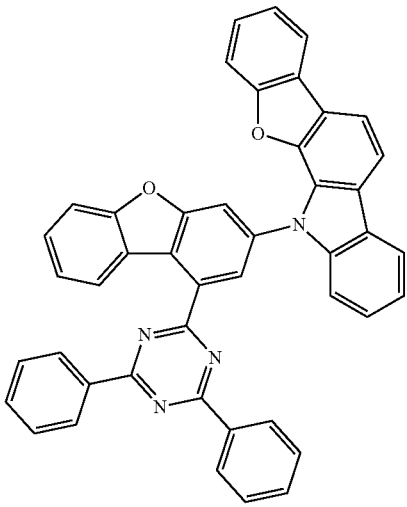
1-42
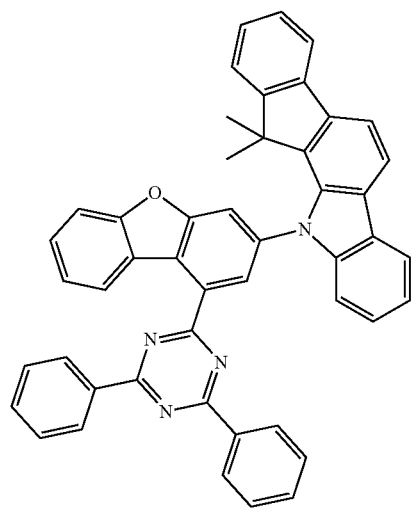
1-43
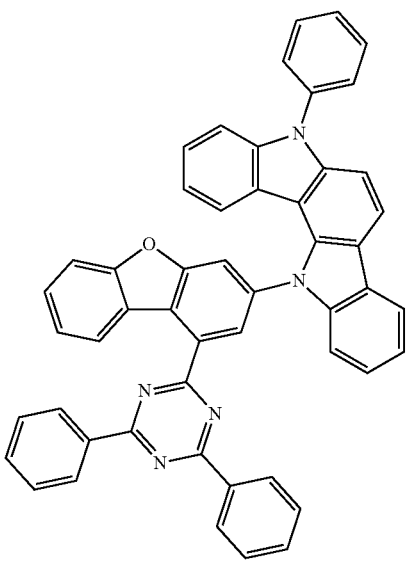
1-44
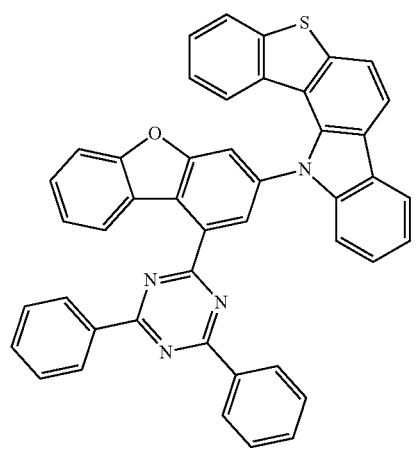
1-45
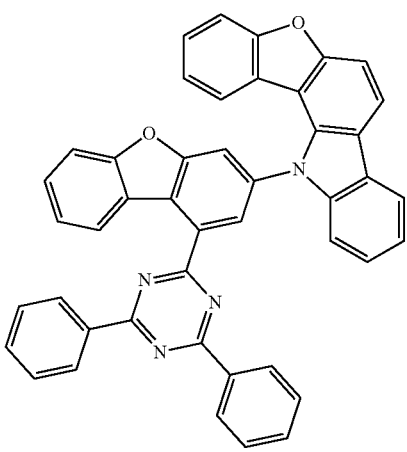

-continued
1-46
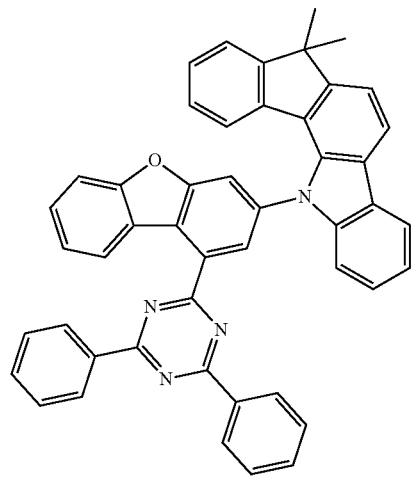
1-47
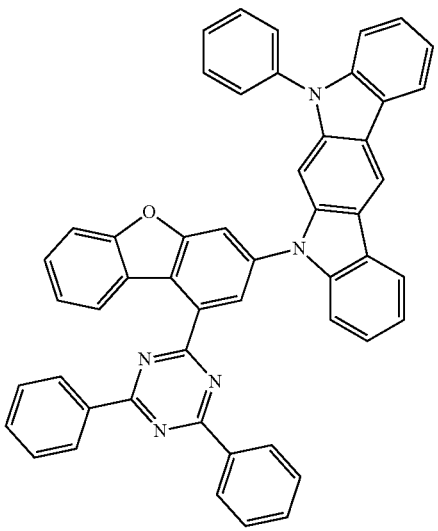
1-48
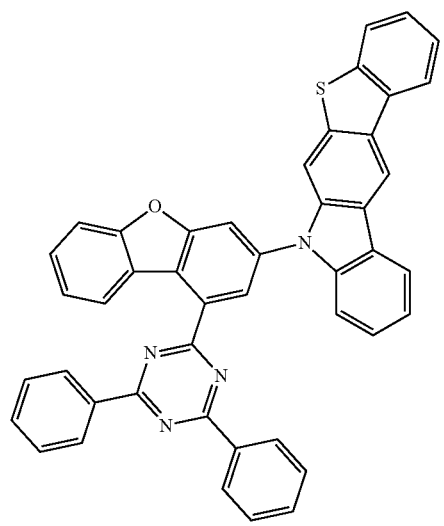
1-49
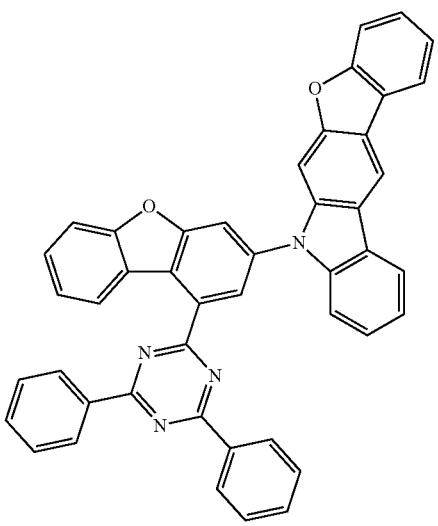
1-50
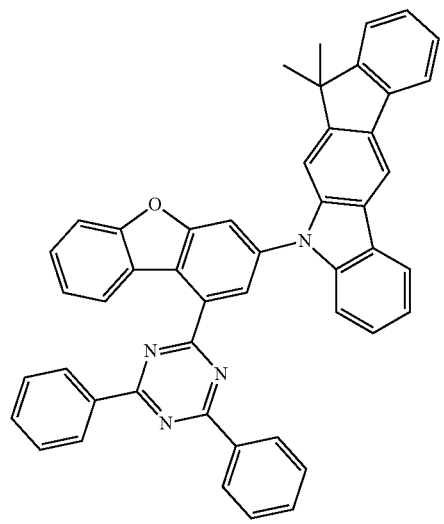
1-51
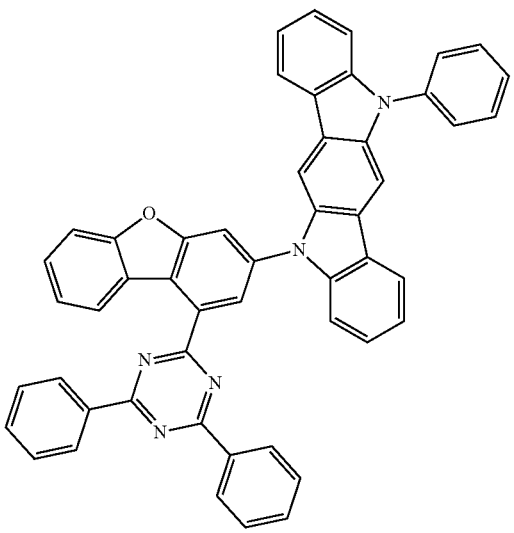

-continued
1-52
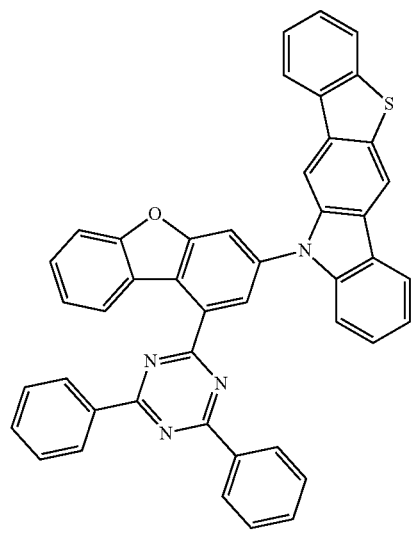
1-53
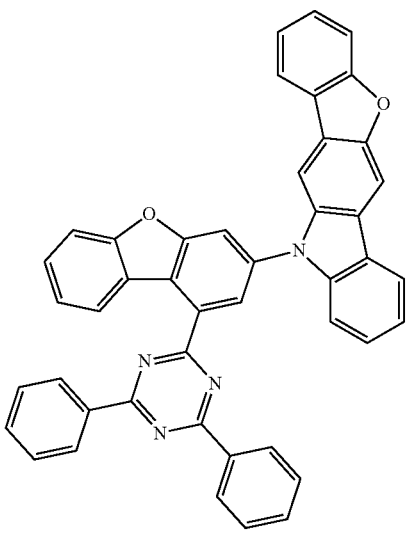
1-54
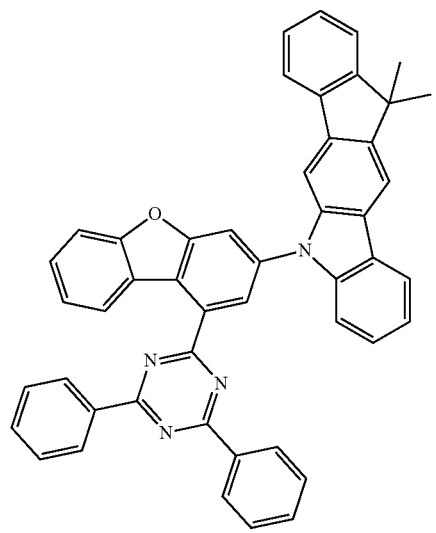
1-55
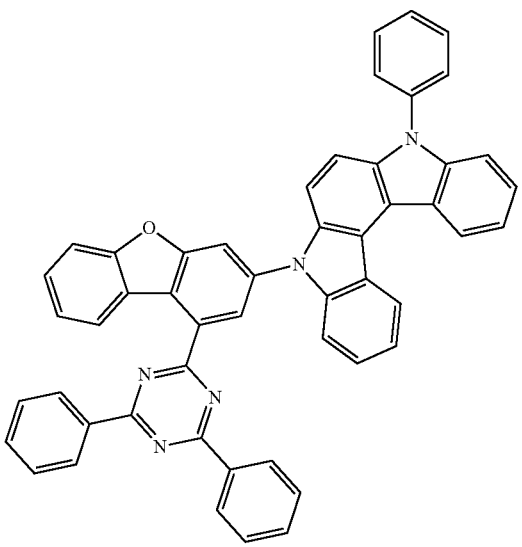
1-56
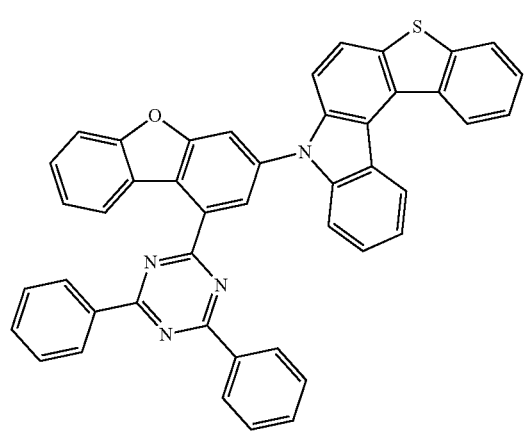
1-57
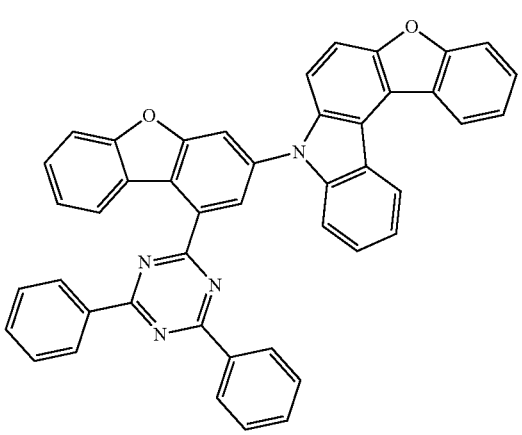

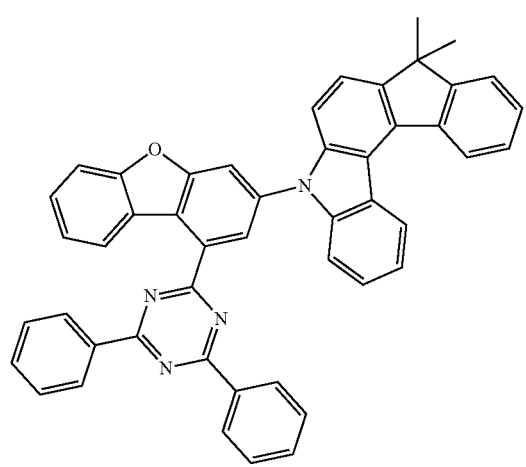
1-58
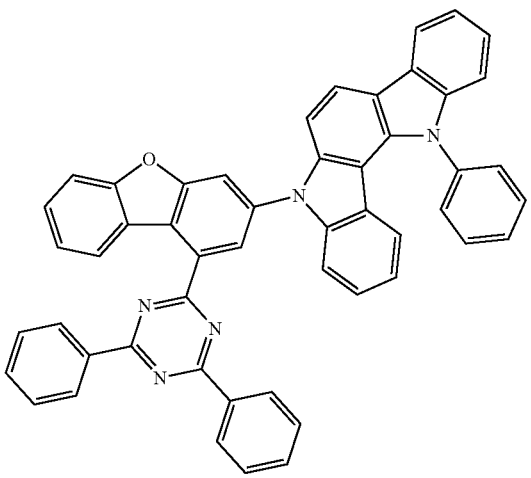
1-59
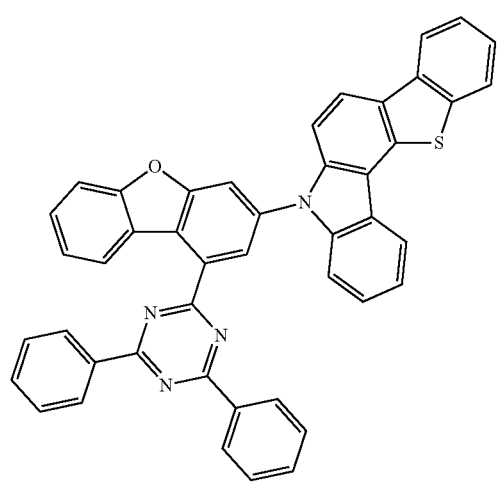
1-60
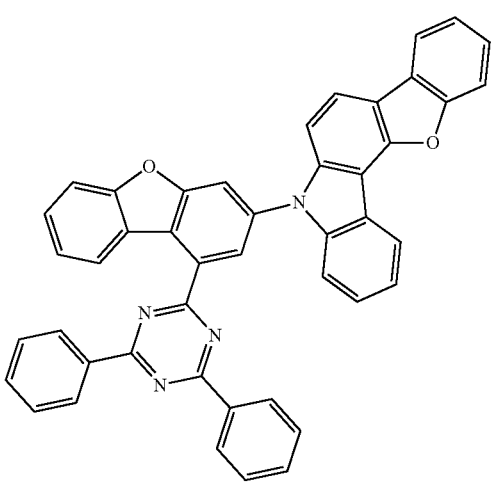
1-61
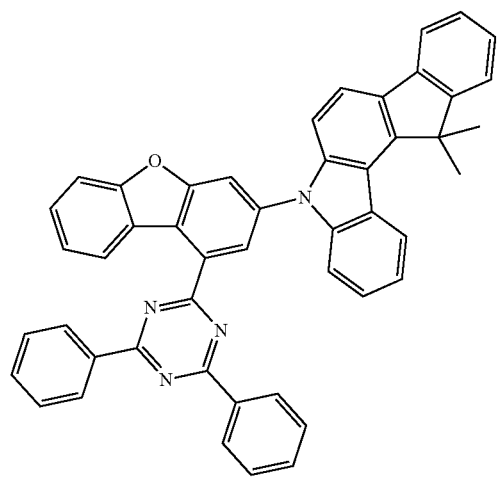
1-62
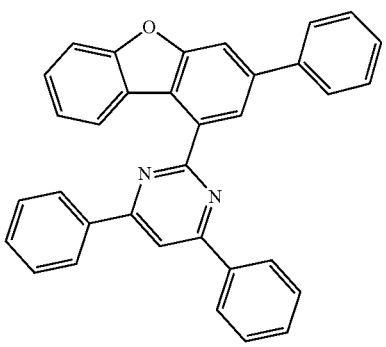
1-63

-continued
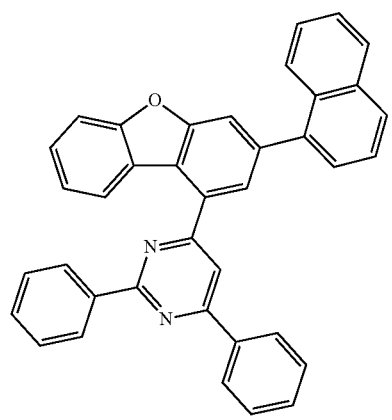
1-64
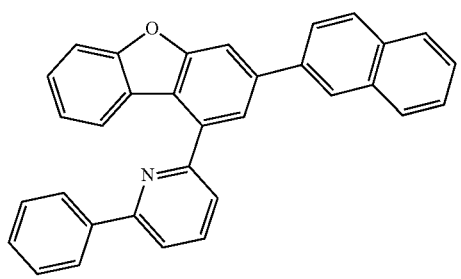
1-65
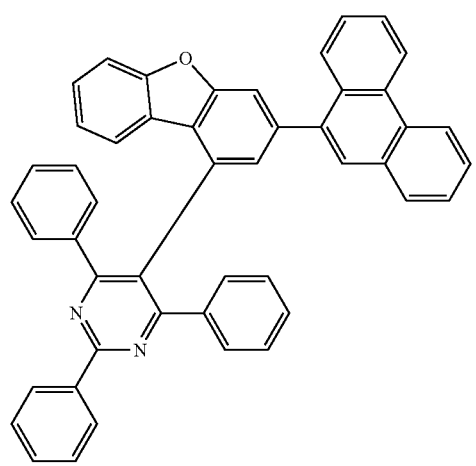
1-66
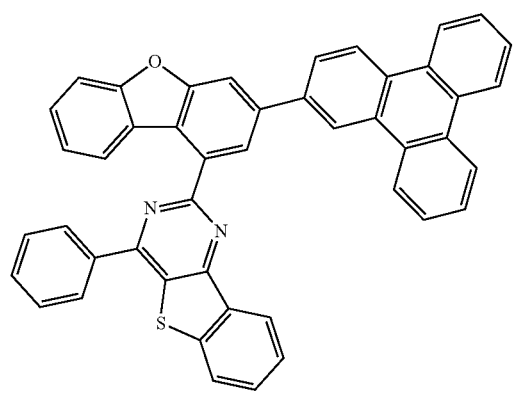
1-67
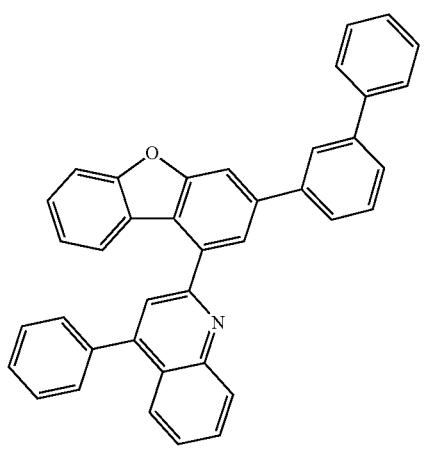
1-68

-continued
1-69
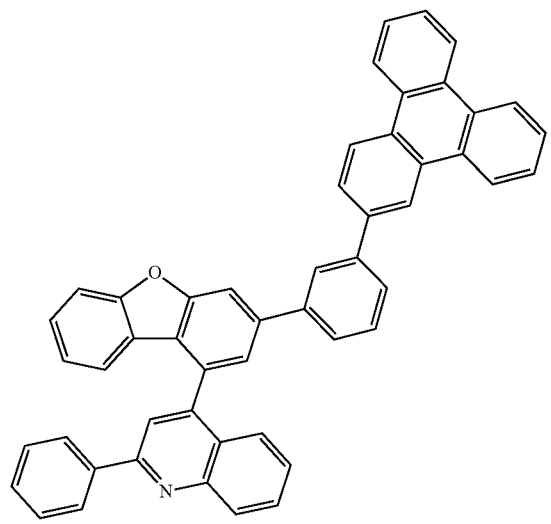
1-70
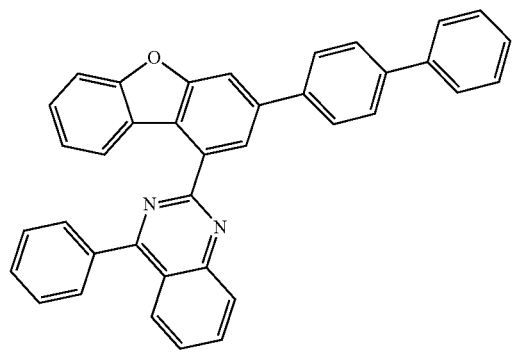
1-71
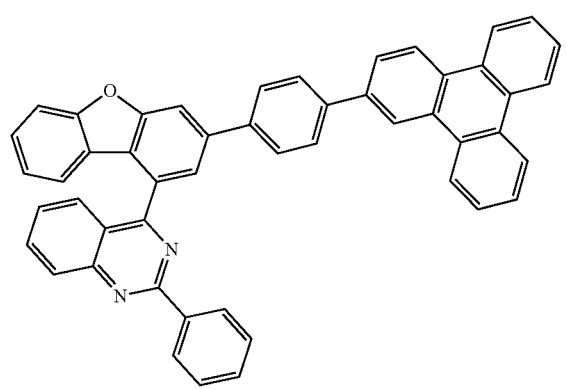
1-72
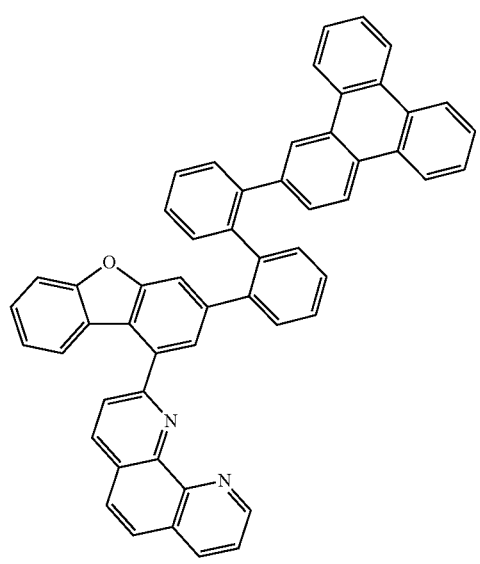
1-73
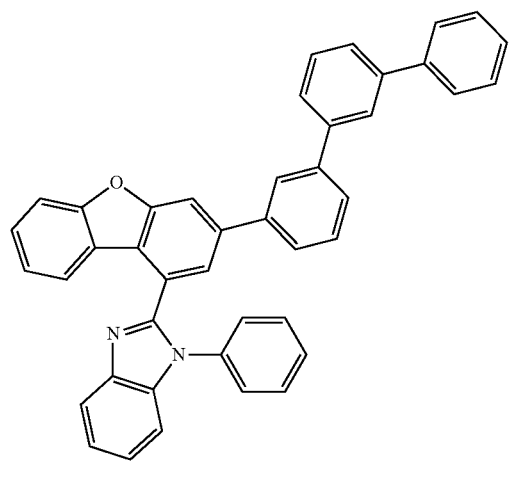
1-74
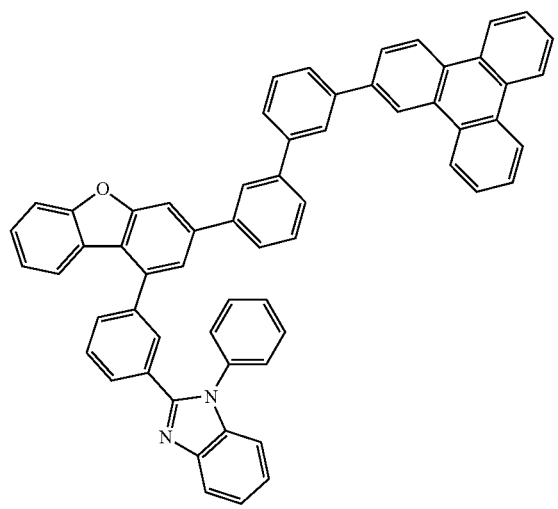

-continued
1-75
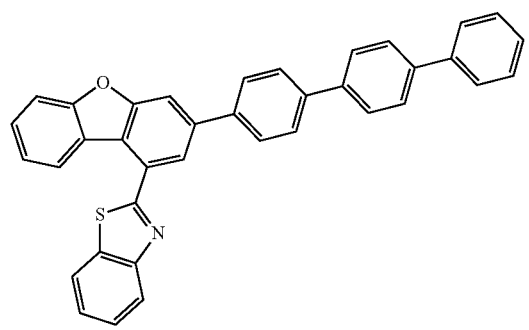
1-76
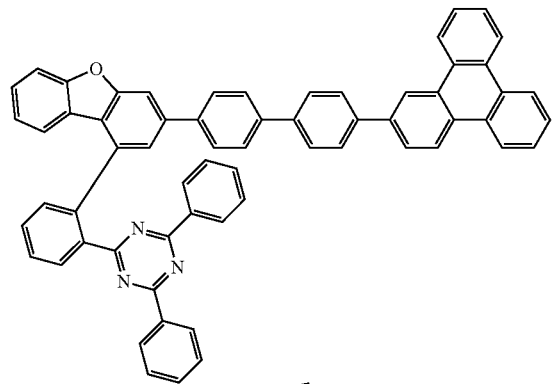
1-77
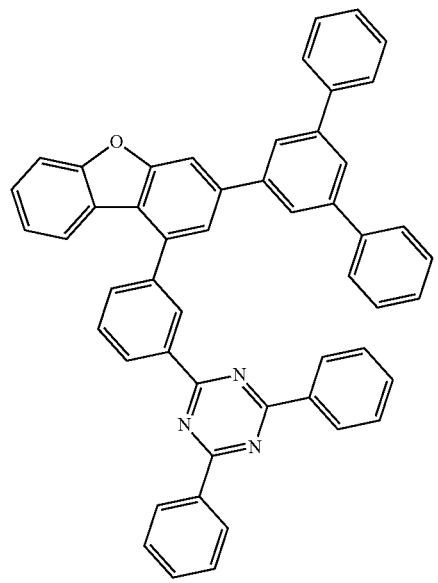 [SMILES: c1ccc(-c2cc(-c3ccccc3)cc(-c3cc(-c4cccc(-c5nc(-c6ccccc6)nc(-c6ccccc6)n5)c4)c4c(c3)oc3ccccc34)c2)cc1]
1-78
1-79
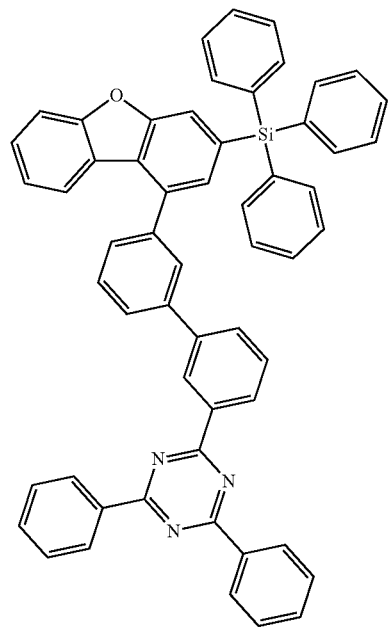
1-80
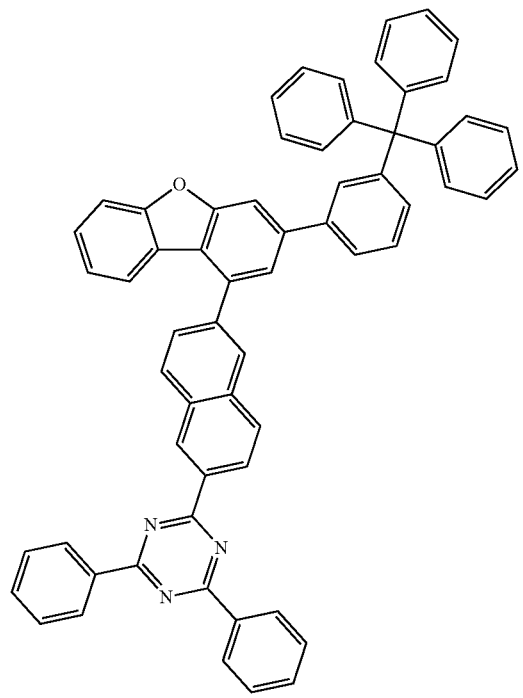

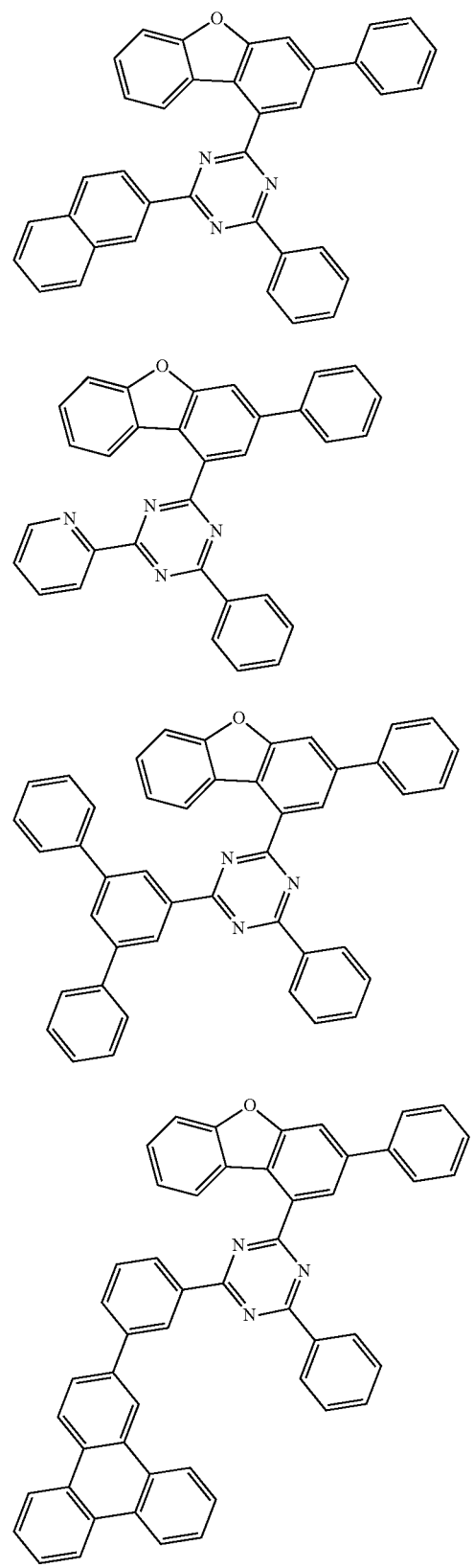

-continued
1-109
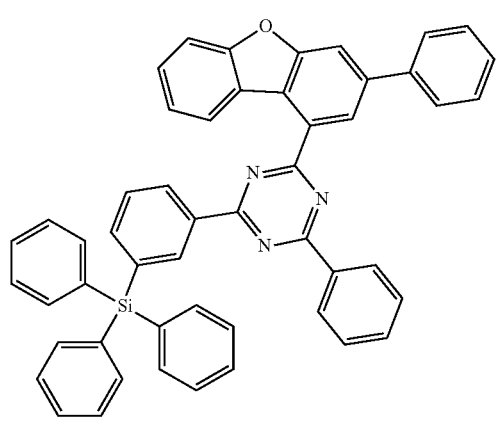
1-110
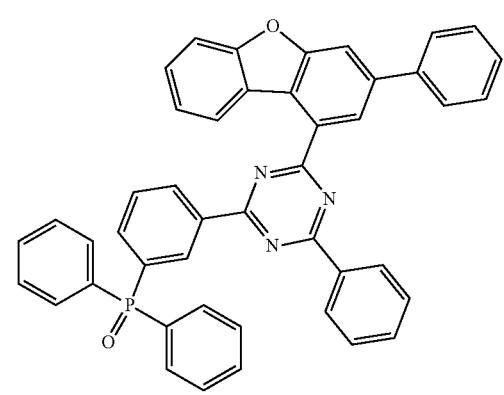
1-111
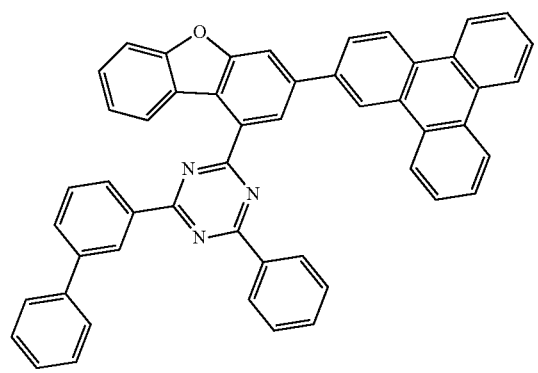
1-112
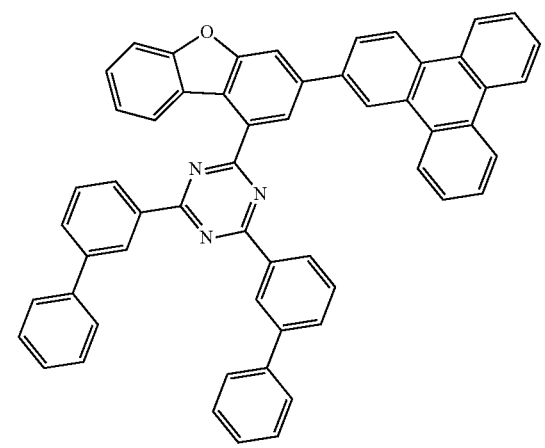 [SMILES: c1ccc(-c2cccc(-c3nc(-c4cccc(-c5ccccc5)c4)nc(-c4cc(-c5ccc6c7ccccc7c7ccccc7c6c5)cc5oc6ccccc6c45)n3)c2)cc1]
1-113
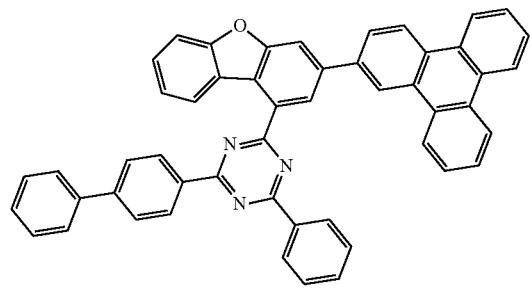
1-114
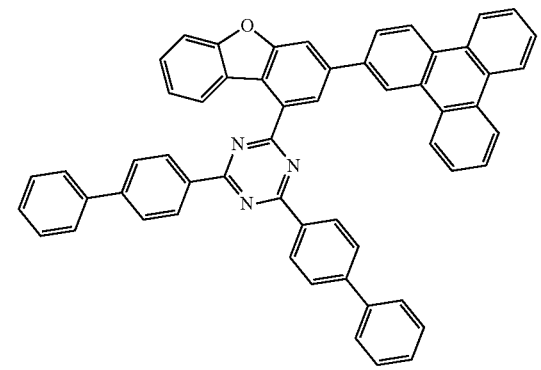 [SMILES: c1ccc(-c2ccc(-c3nc(-c4ccc(-c5ccccc5)cc4)nc(-c4cc(-c5ccc6c7ccccc7c7ccccc7c6c5)cc5oc6ccccc6c45)n3)cc2)cc1]
1-115
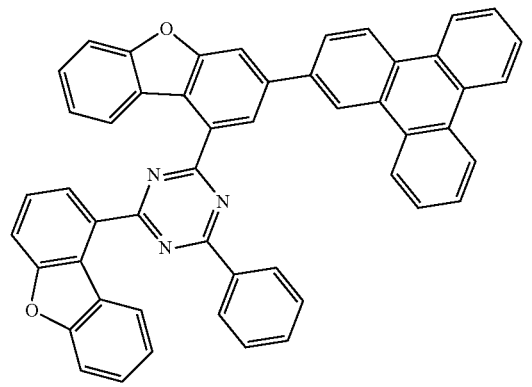
1-116
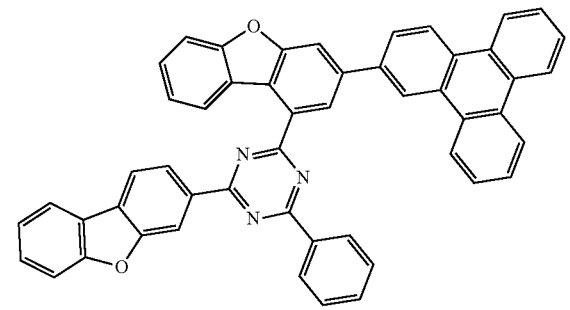

1-117
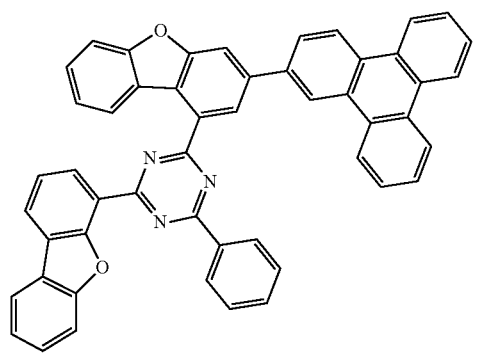
1-118
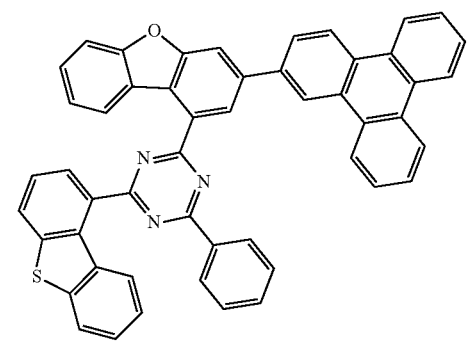 [SMILES: c1ccc(-c2nc(-c3cccc4oc5ccccc5c34)nc(-c3cc(-c4ccc5c6ccccc6c6ccccc6c5c4)cc4oc5ccccc5c34)n2)cc1]
1-119
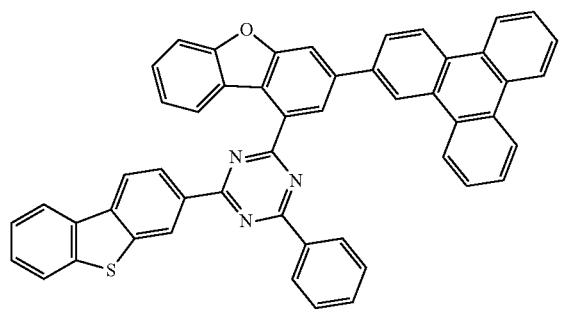
2-1
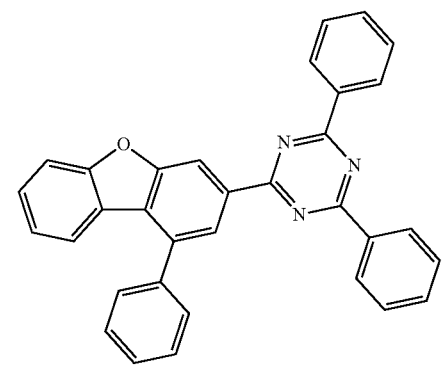
2-2
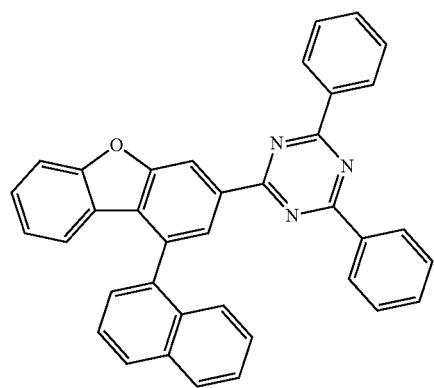
2-3
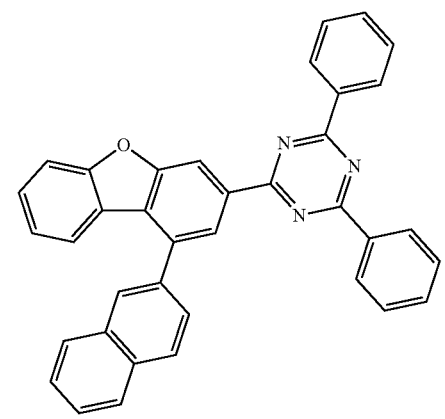
2-4
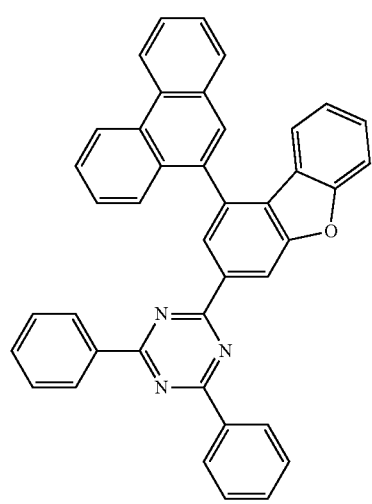
2-5
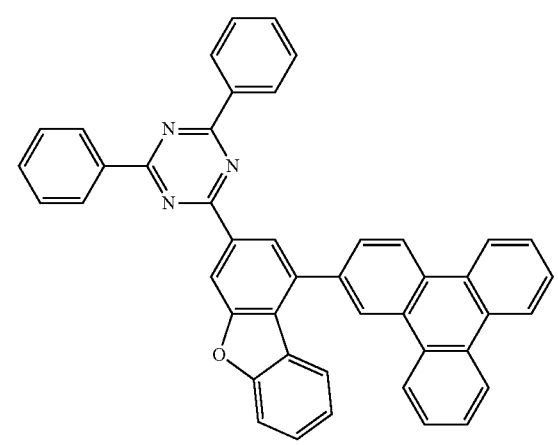

2-6
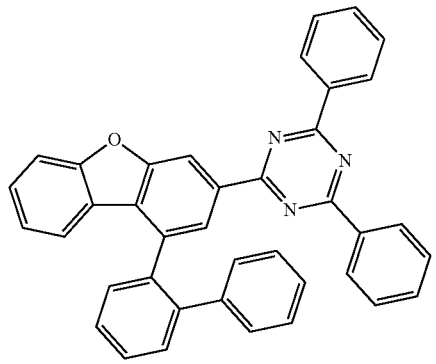
2-7
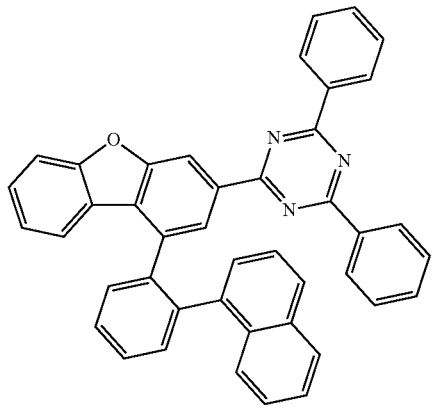
2-8
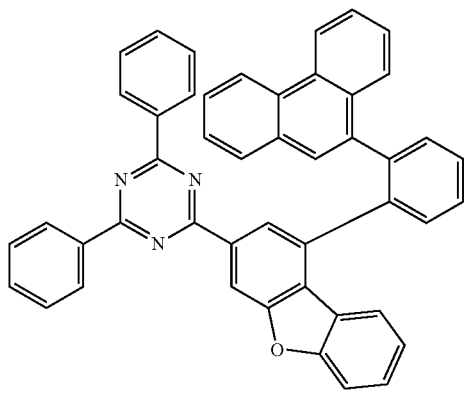
2-9
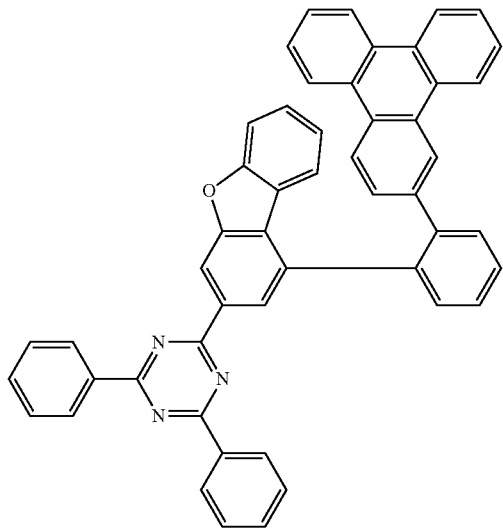
2-10
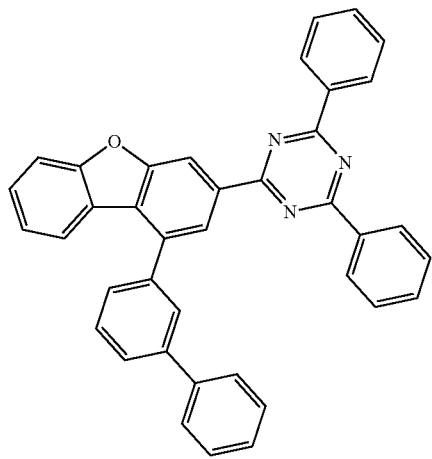
2-11
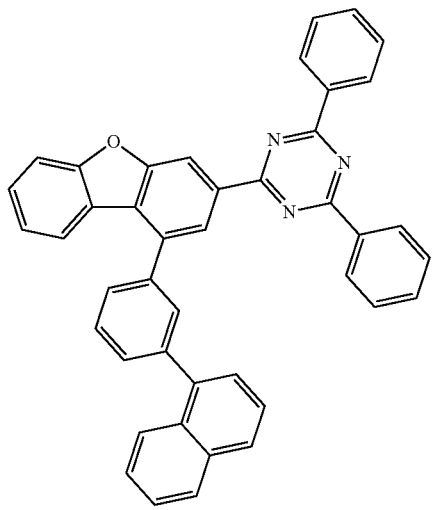

2-12
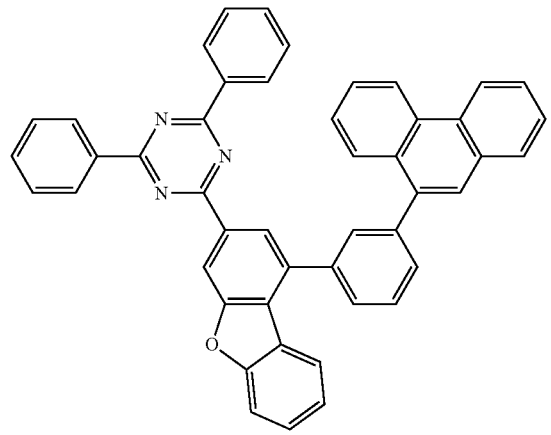
2-13
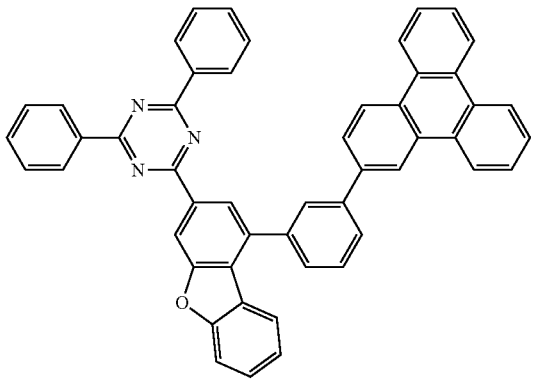
2-14
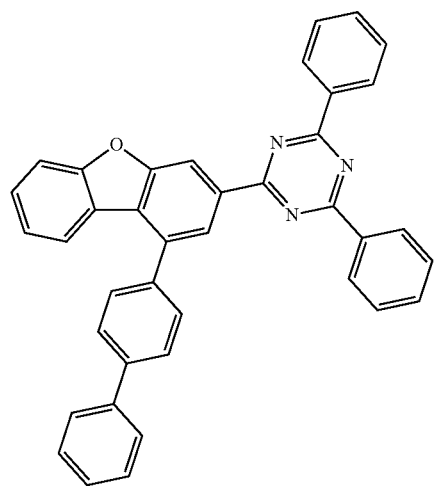
2-15
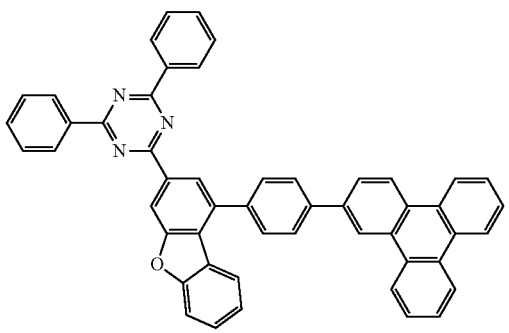
2-16
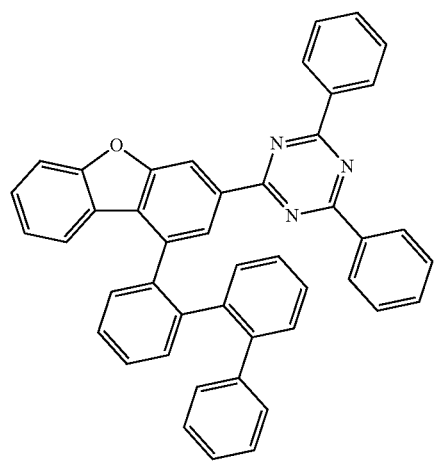
2-17
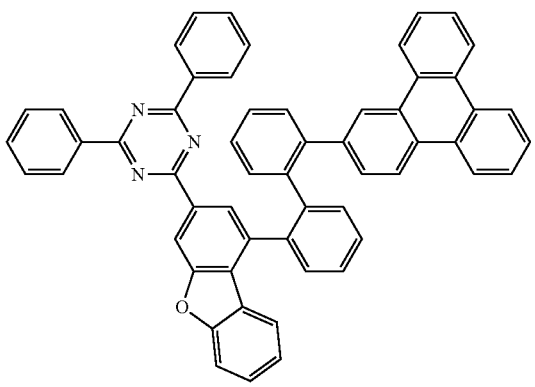

2-18
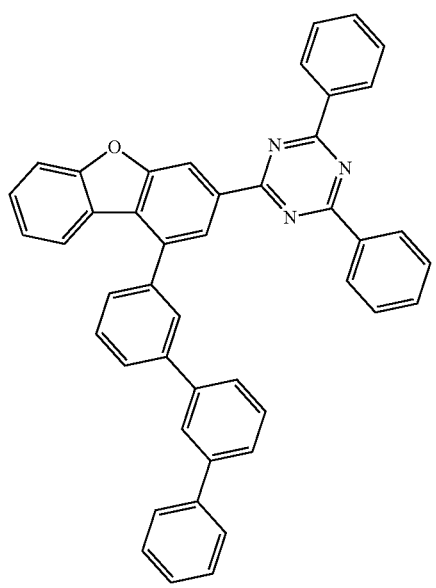
2-19
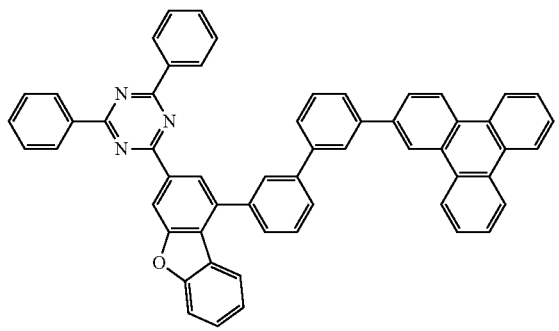
2-20
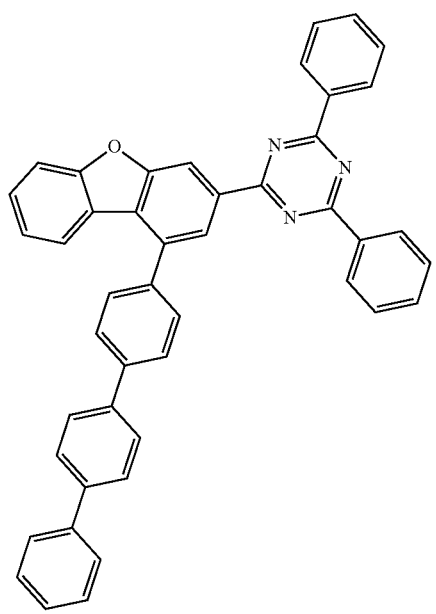 [SMILES: c1ccc(-c2ccc(-c3ccc(-c4cc(-c5nc(-c6ccccc6)nc(-c6ccccc6)n5)cc5oc6ccccc6c45)cc3)cc2)cc1]
2-21
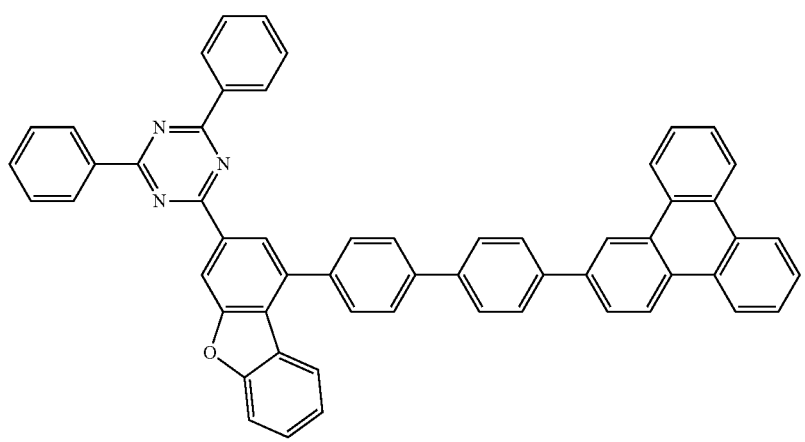

-continued
2-22
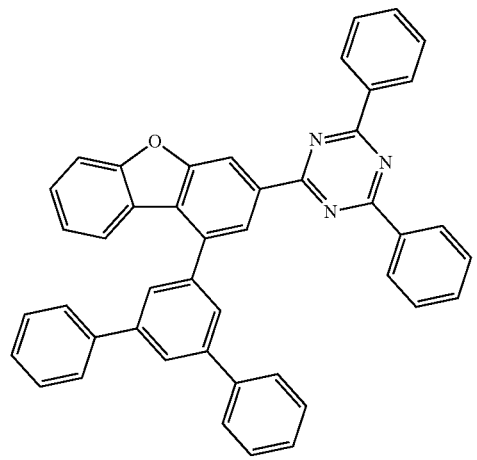
2-23
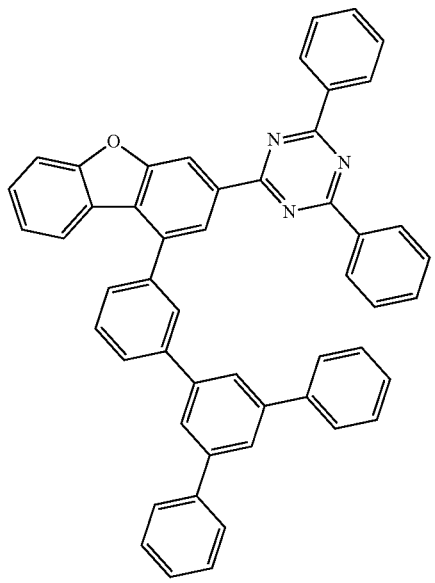 [SMILES: c1ccc(-c2cc(-c3ccccc3)cc(-c3cccc(-c4cc(-c5nc(-c6ccccc6)nc(-c6ccccc6)n5)cc5oc6ccccc6c45)c3)c2)cc1]
2-24
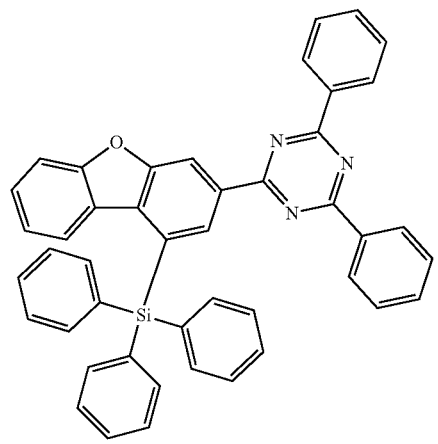
2-25
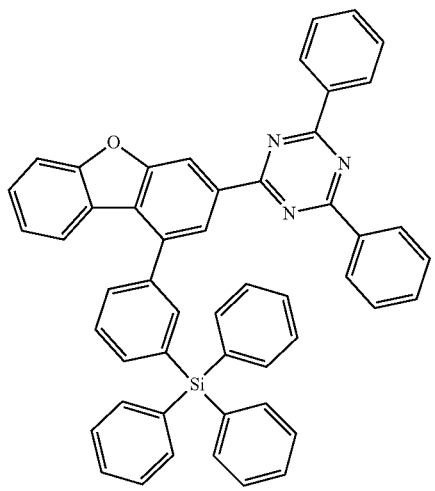
2-26
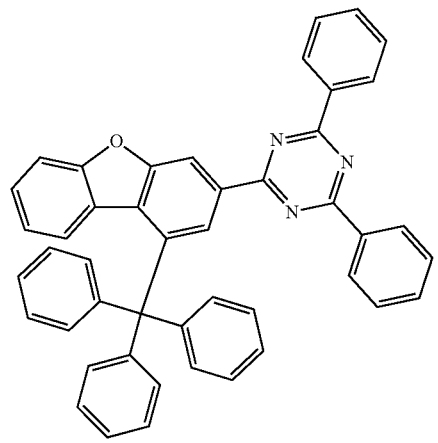
2-27
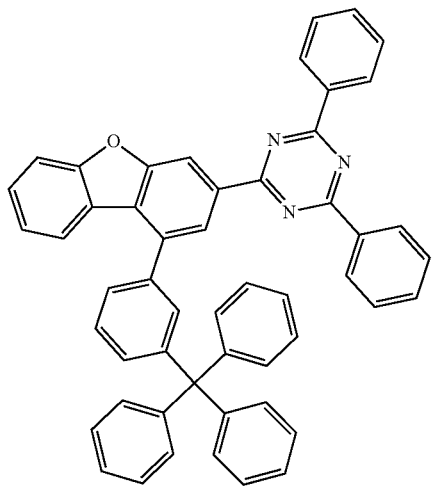 [SMILES: c1ccc(-c2nc(-c3ccccc3)nc(-c3cc(-c4cccc([Si](c5ccccc5)(c5ccccc5)c5ccccc5)c4)c4c(c3)oc3ccccc34)n2)cc1]

-continued
2-28
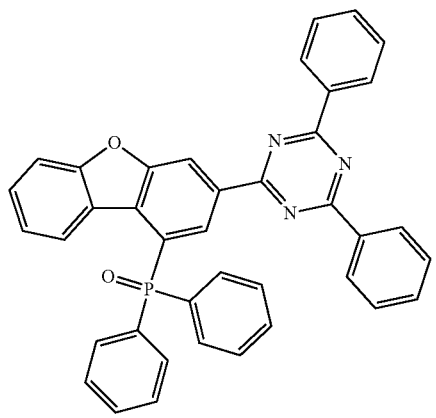
2-29
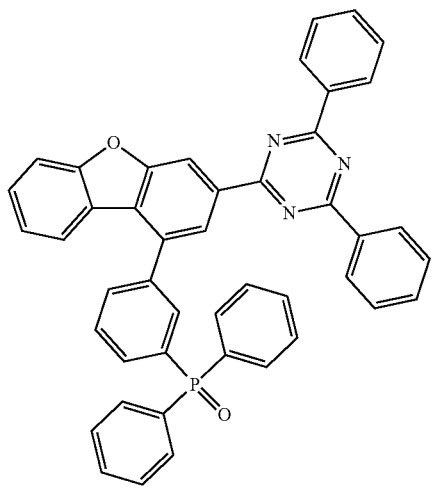
2-30
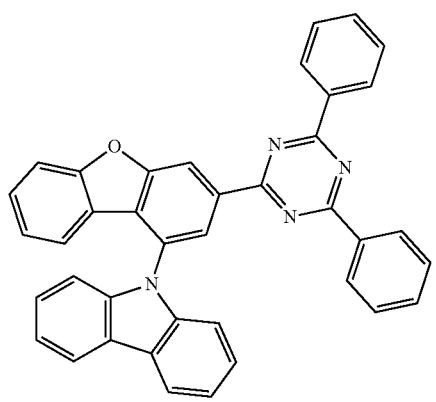
2-31
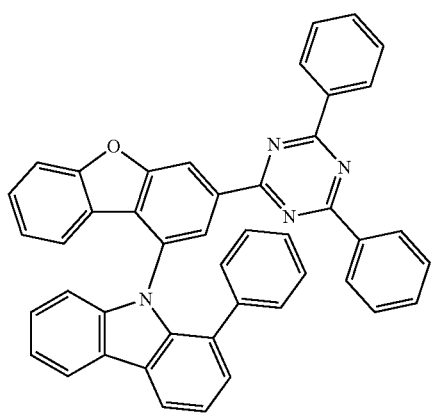
2-32
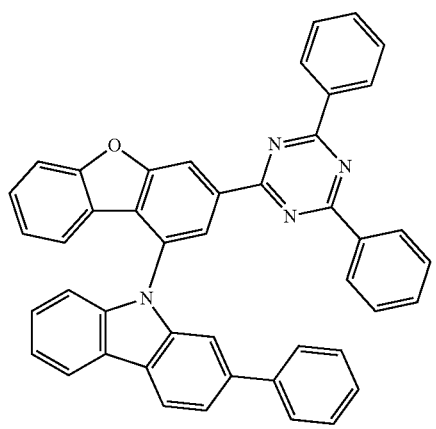
2-33
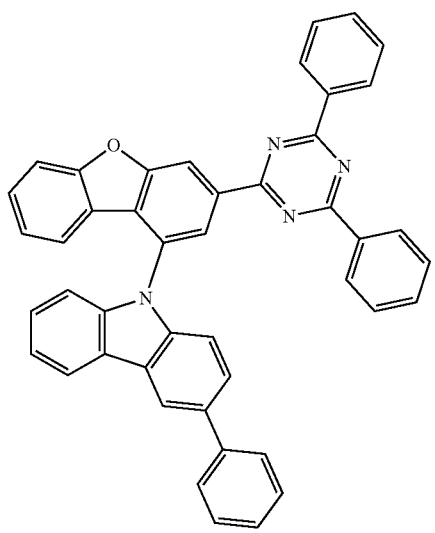

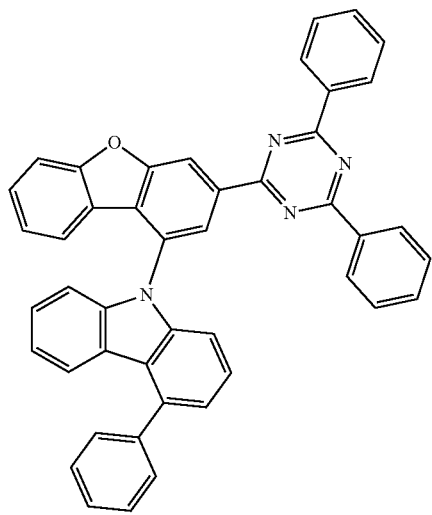
2-34
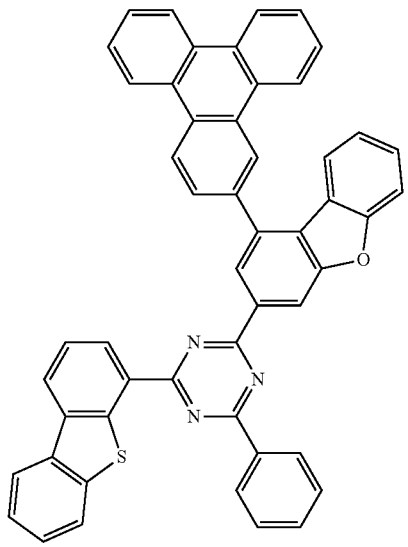
2-35
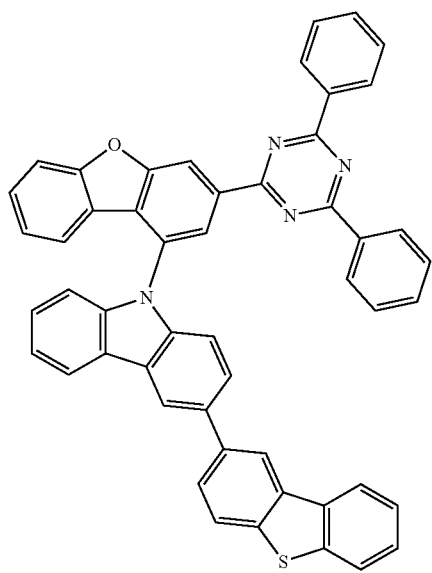
2-36
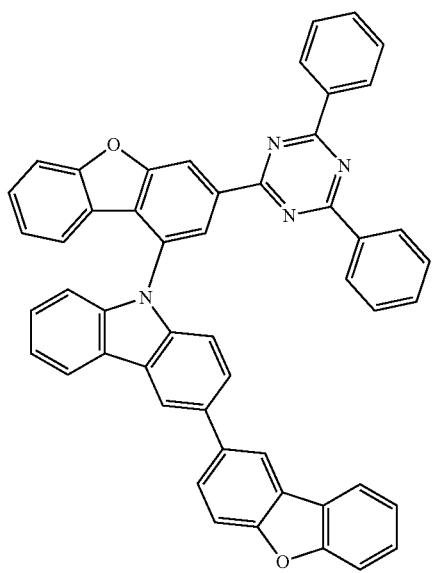
2-37

-continued
2-38
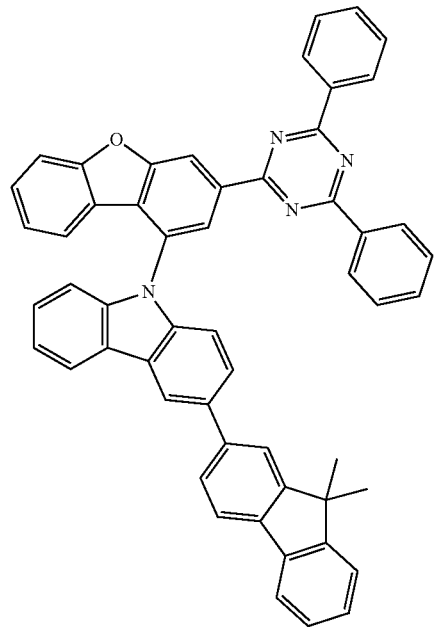
2-39
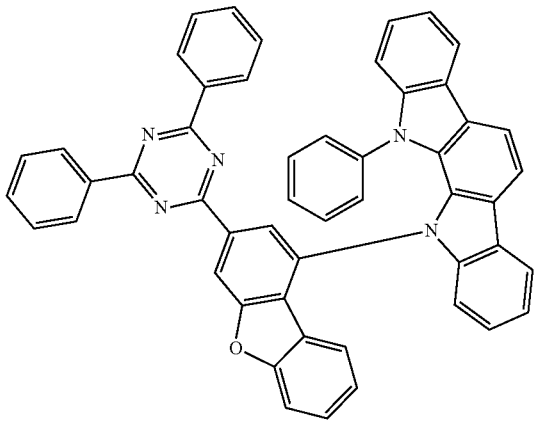
2-40
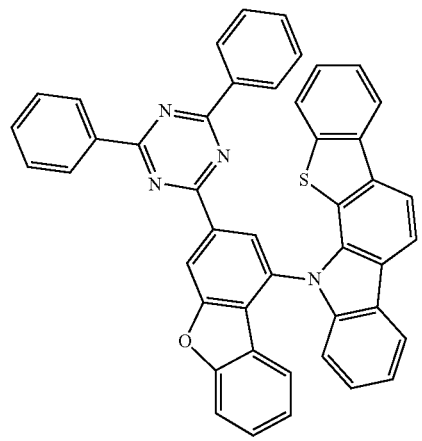
2-41
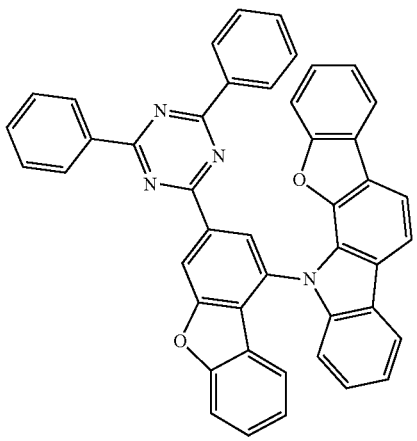
2-42
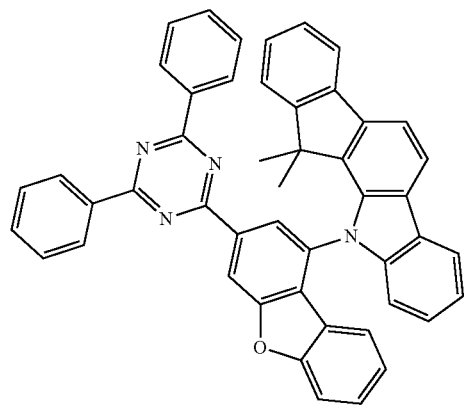
2-43
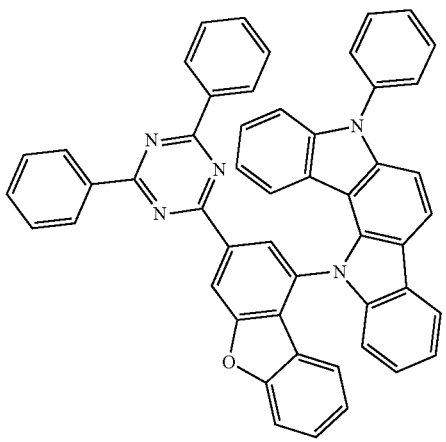

-continued
2-44
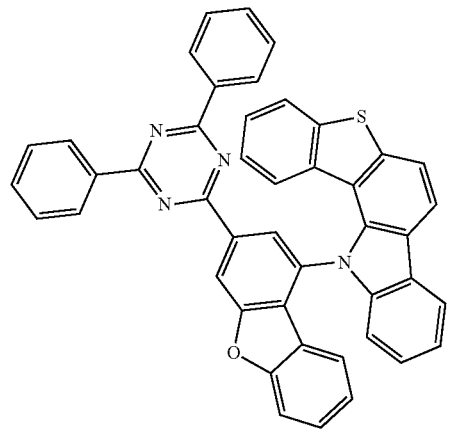
2-45
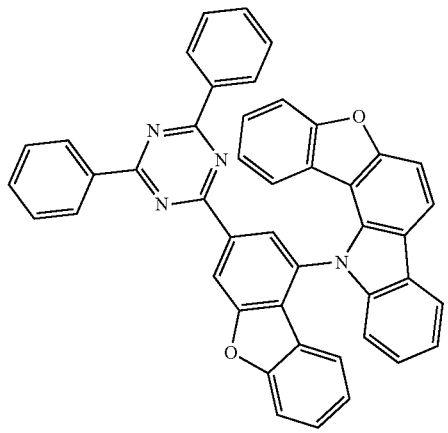
2-46
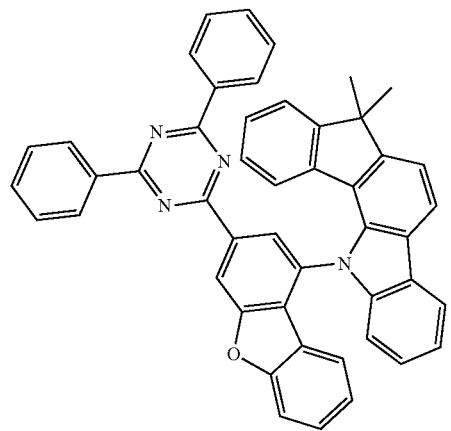
2-47
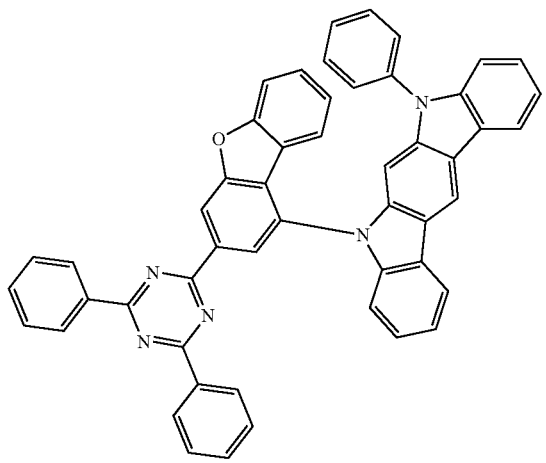
2-48
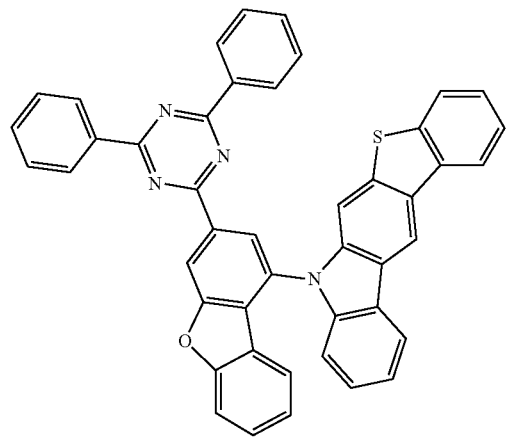
2-49
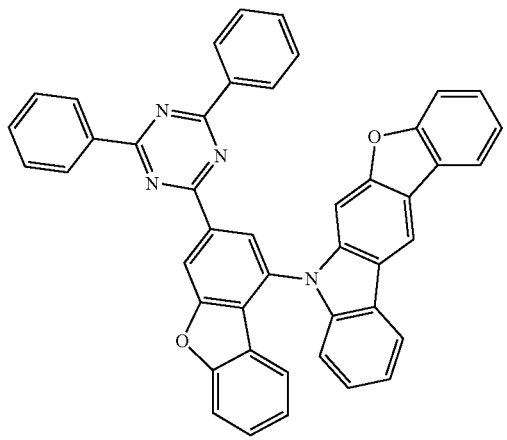

-continued
2-50
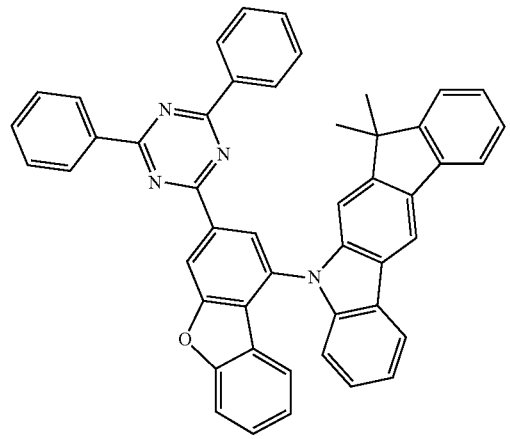
2-51
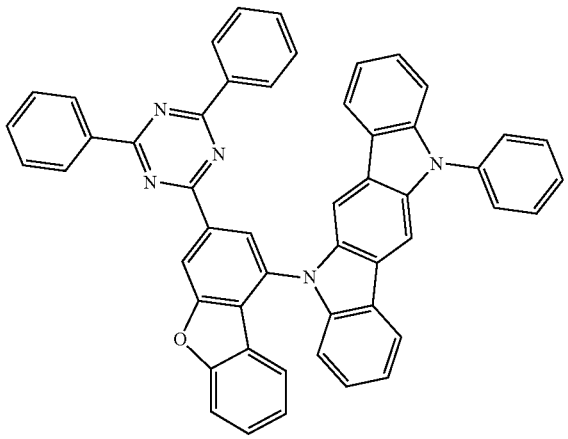
2-52
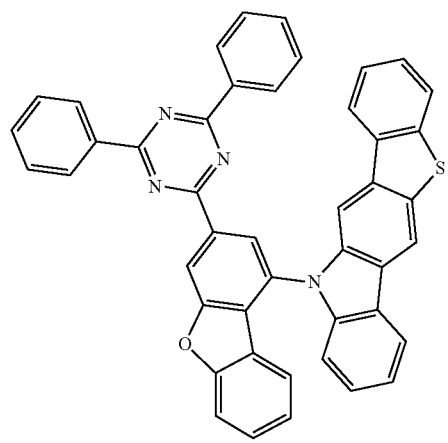
2-53
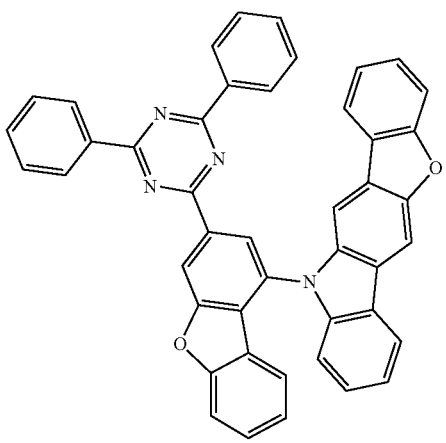
2-54
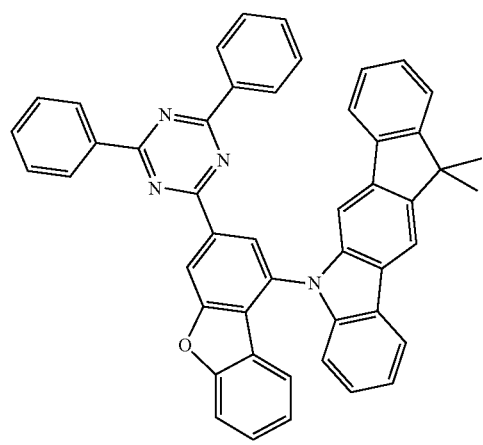
2-55
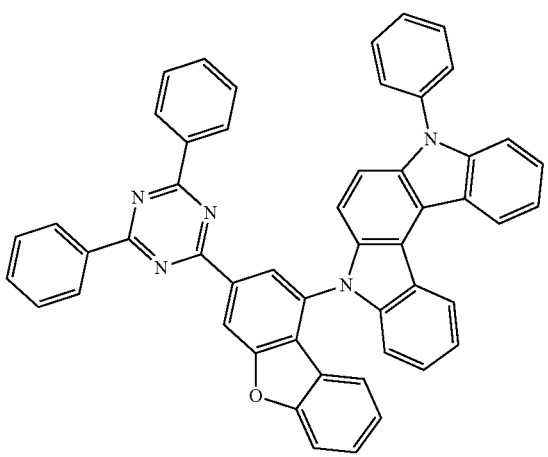

-continued
2-56
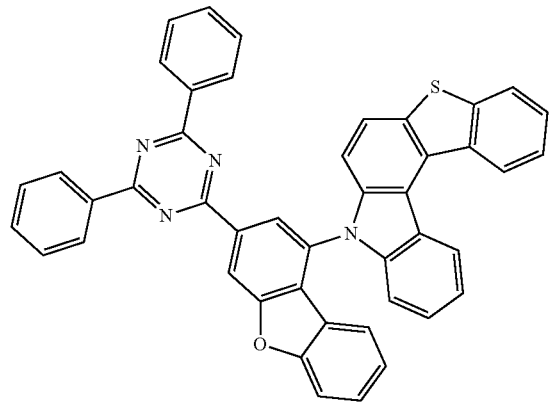
2-57
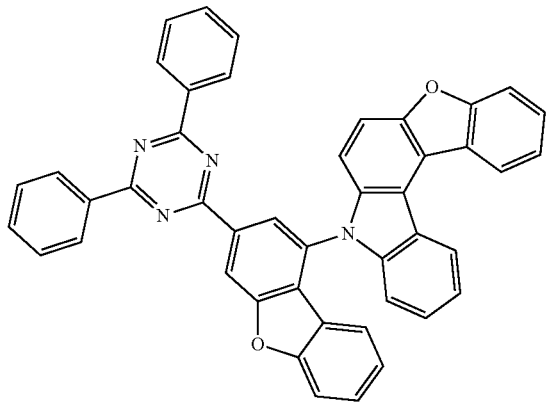
2-58
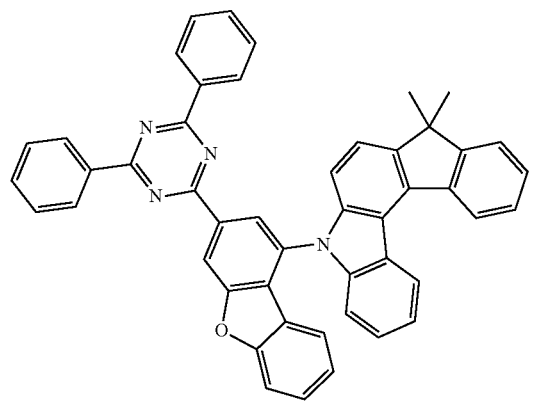
2-59
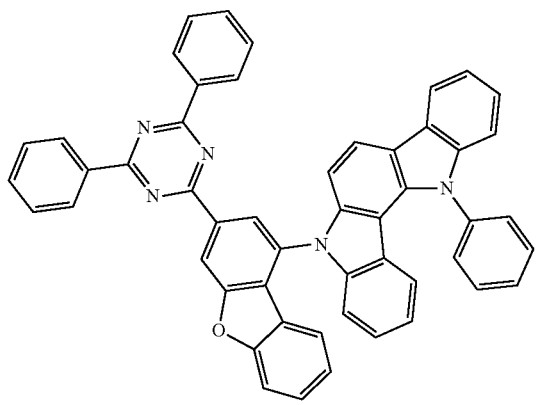
2-60
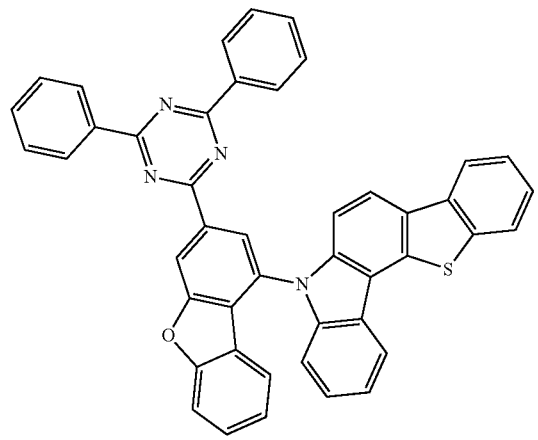
2-61
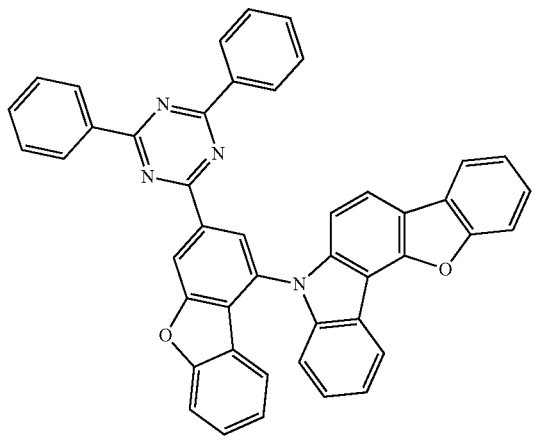

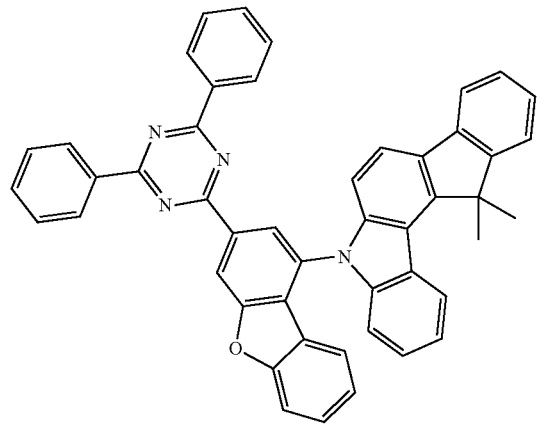
2-62
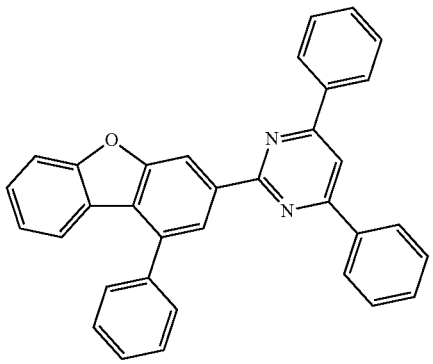
2-63
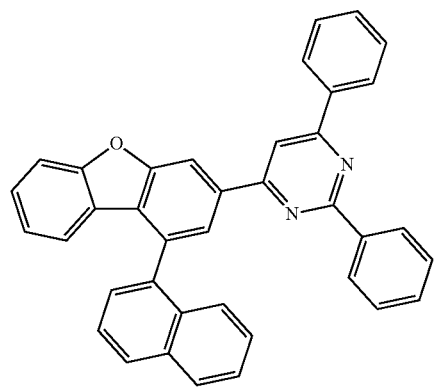
2-64
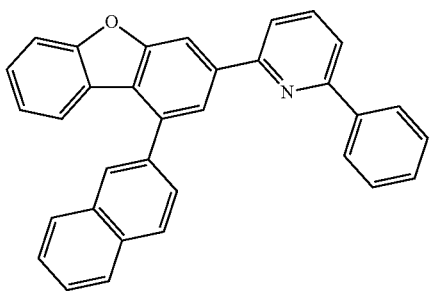
2-65
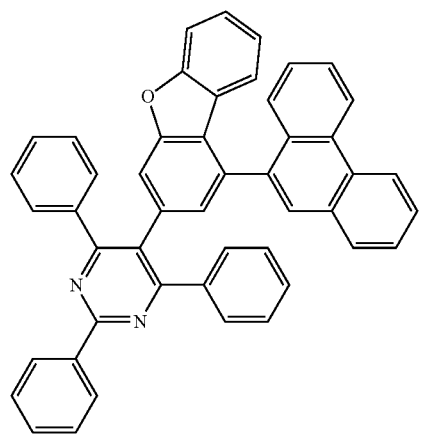
2-66
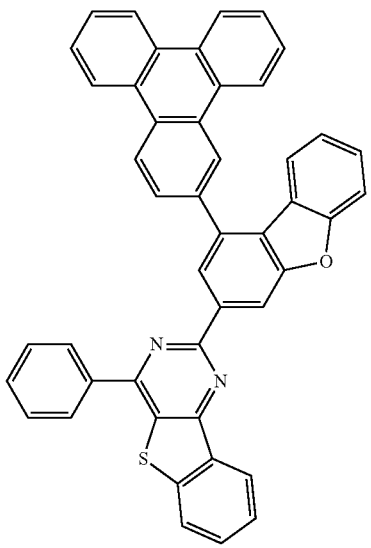
2-67

-continued
2-68
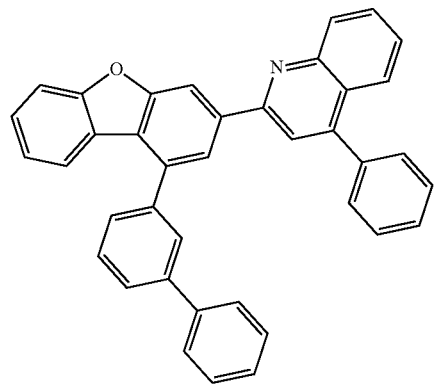
2-69
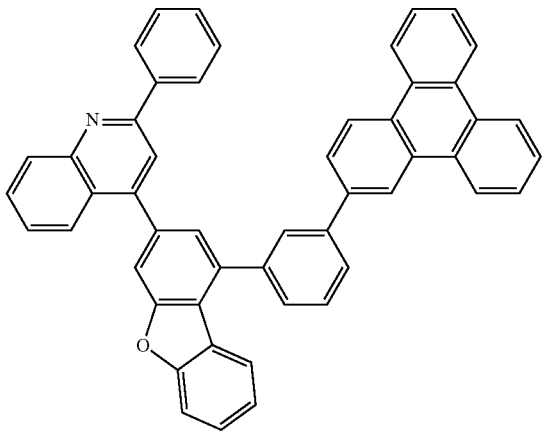
2-70
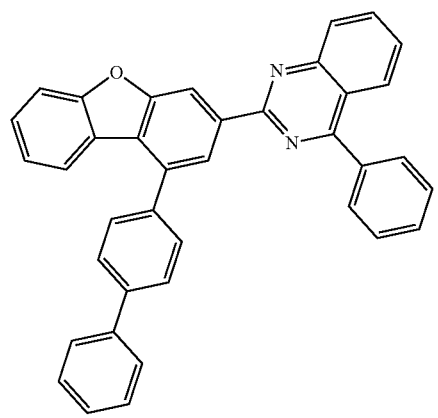
2-71
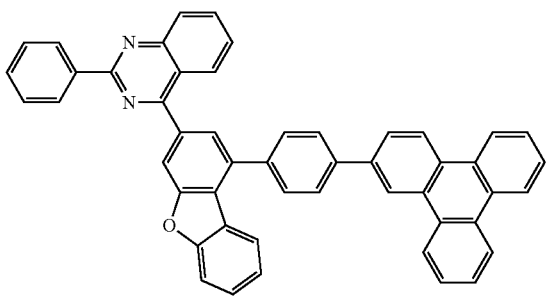
2-72
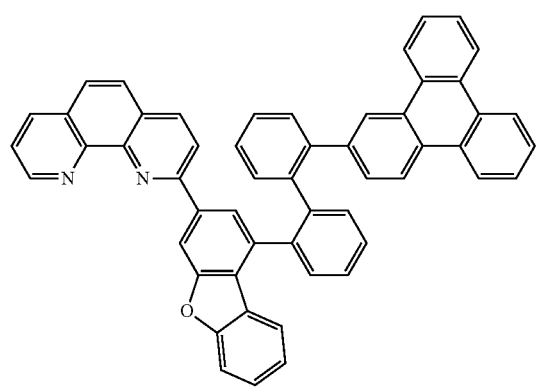
2-73
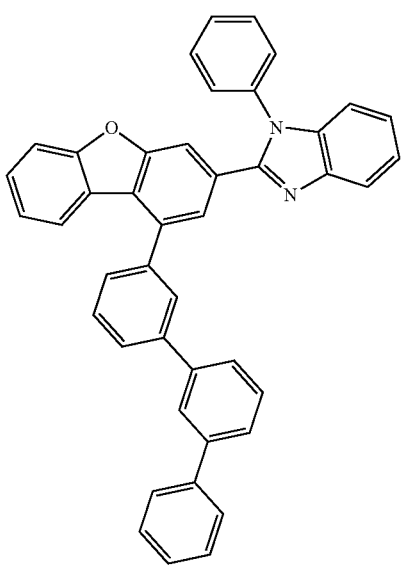

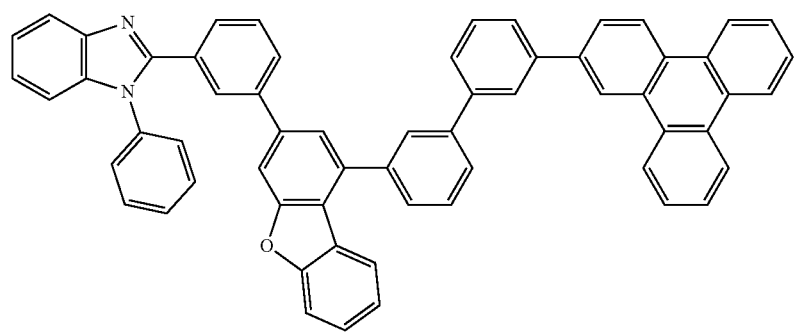
2-74
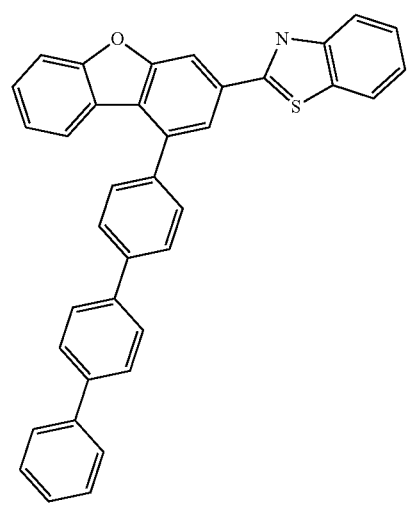
2-75
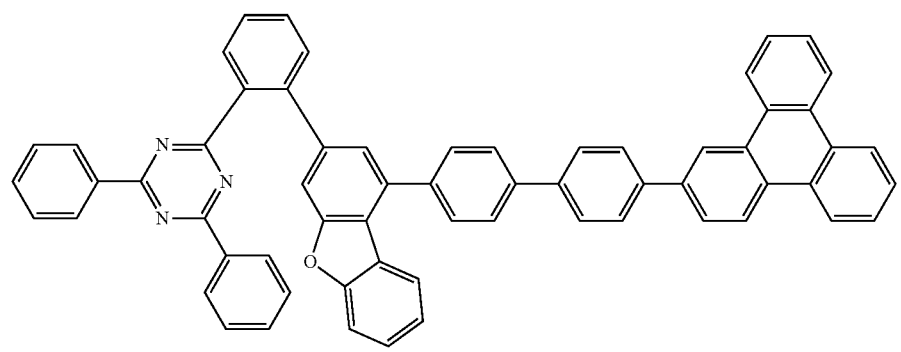
2-76

-continued
2-77
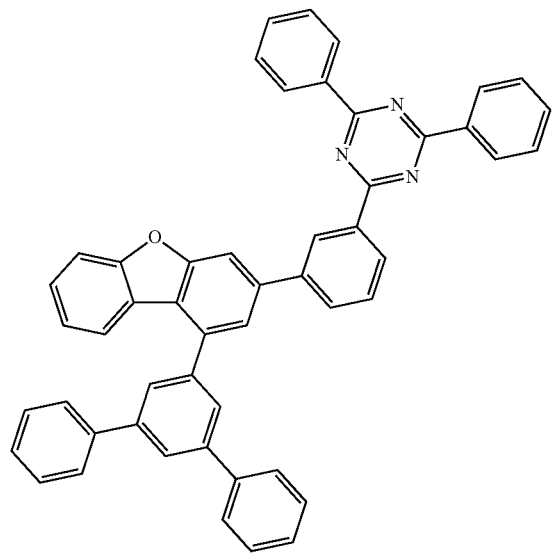
2-78
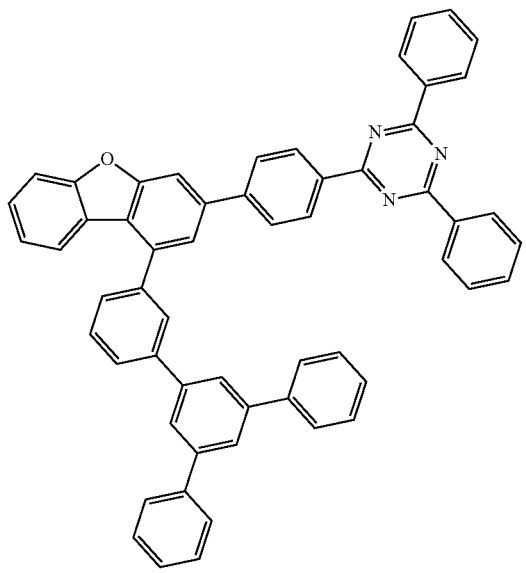
2-79
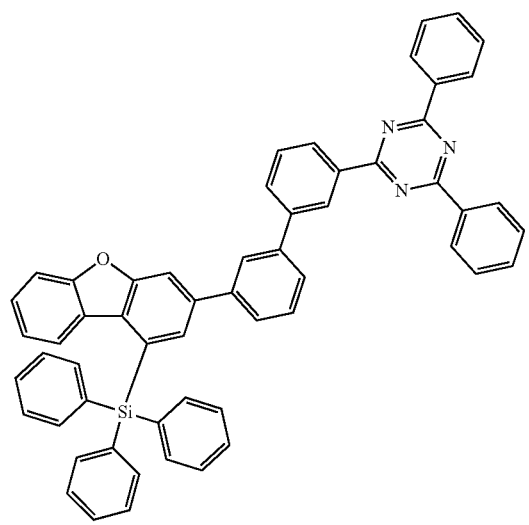
2-80
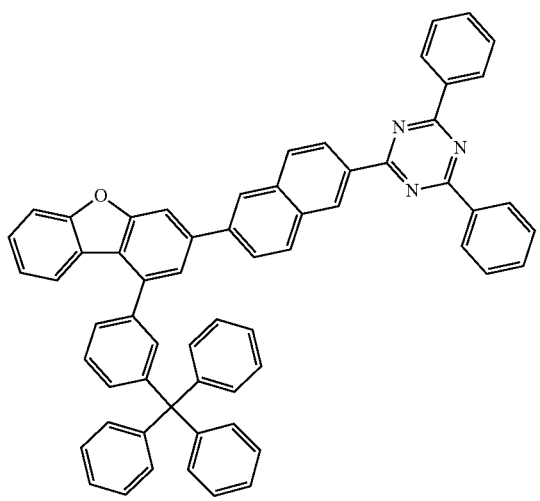
2-81
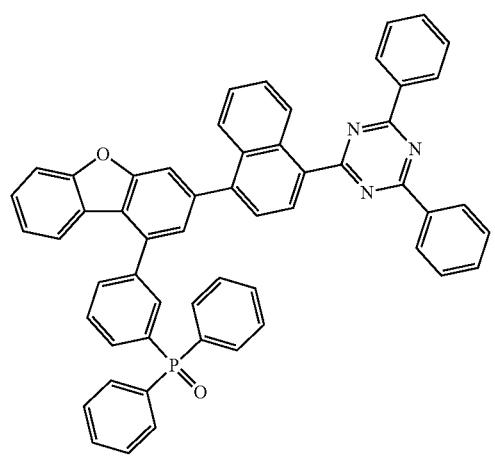
2-82
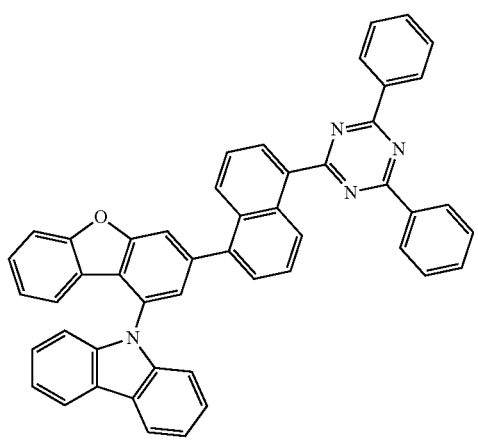

-continued
2-83
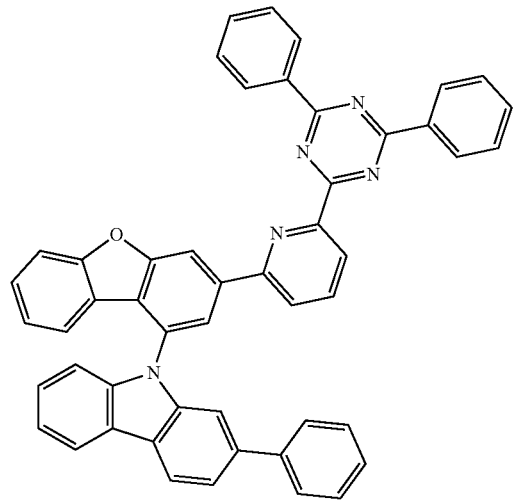
2-84
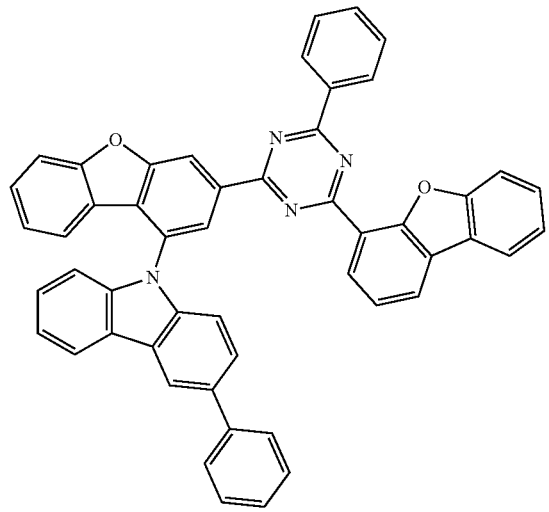
2-85
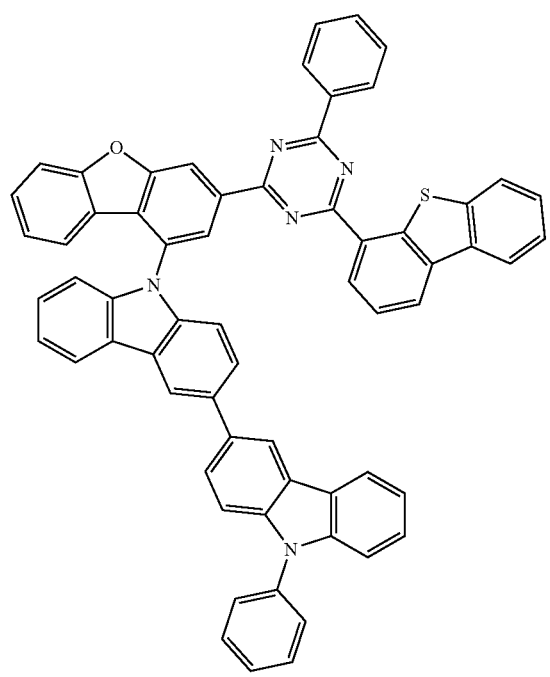
2-86
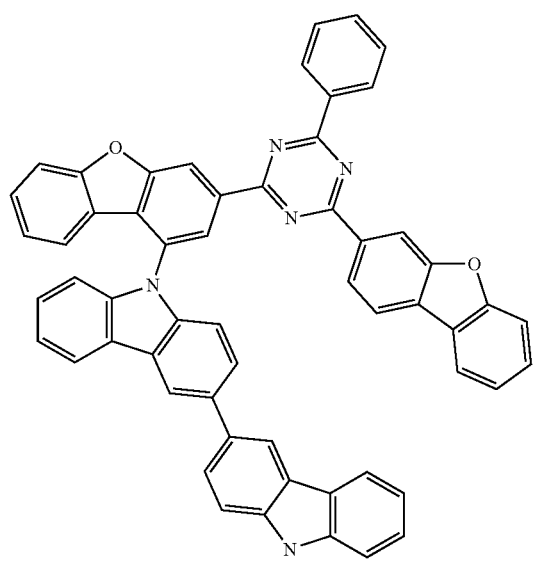

2-87
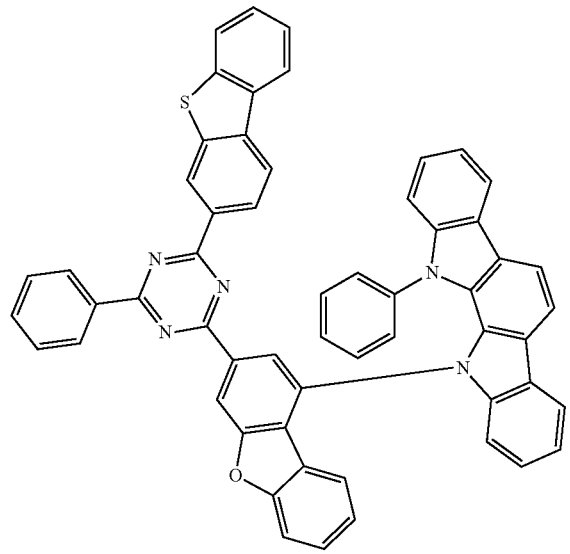
2-88
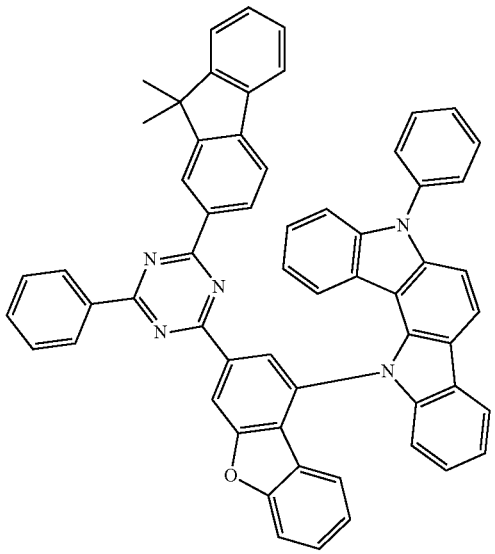
2-89
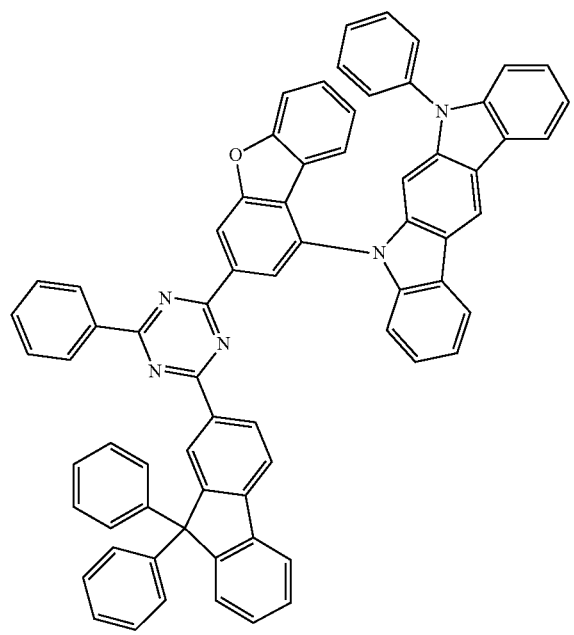
2-90
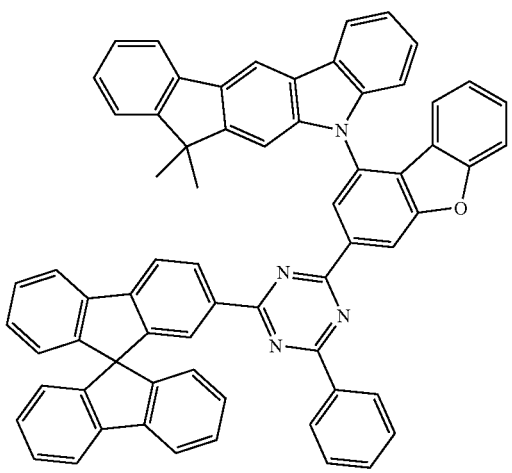

-continued
2-91
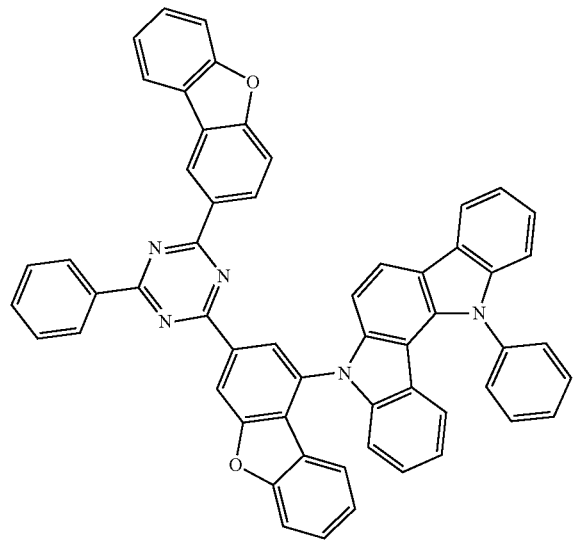
2-92
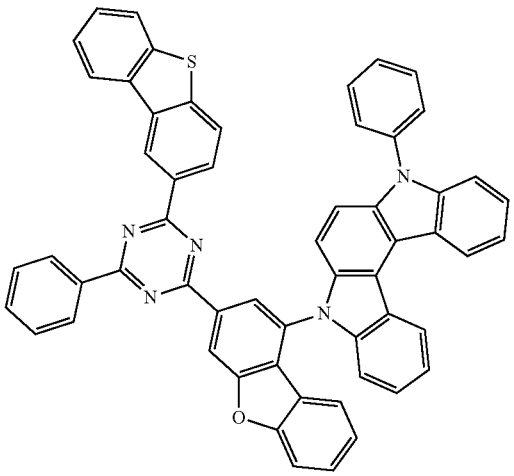
2-93
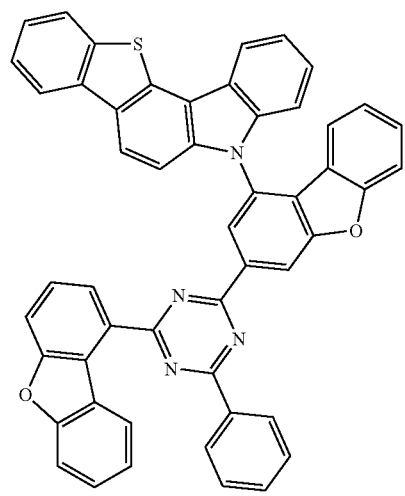
2-94
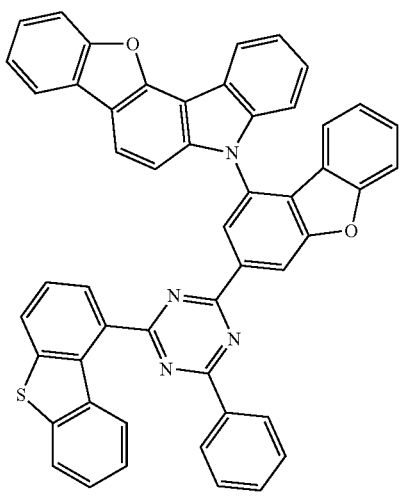
2-95
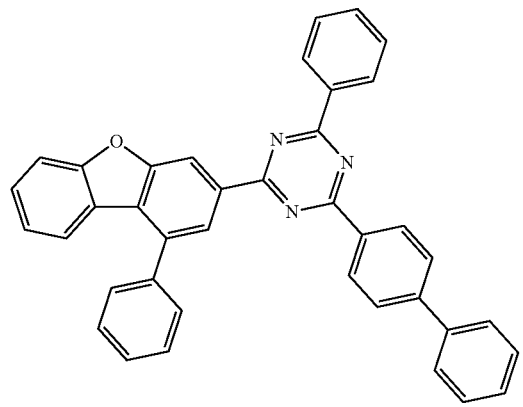
2-96
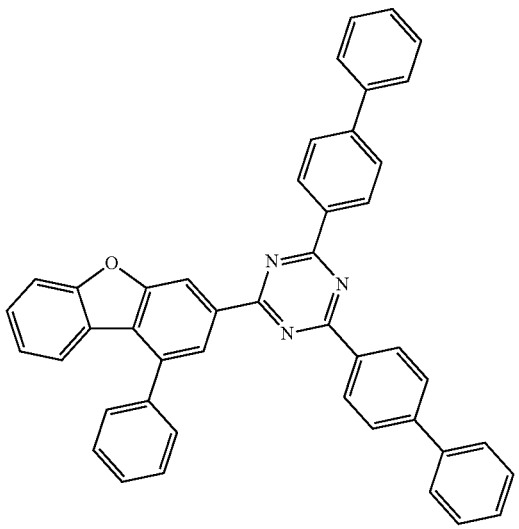

-continued
2-97
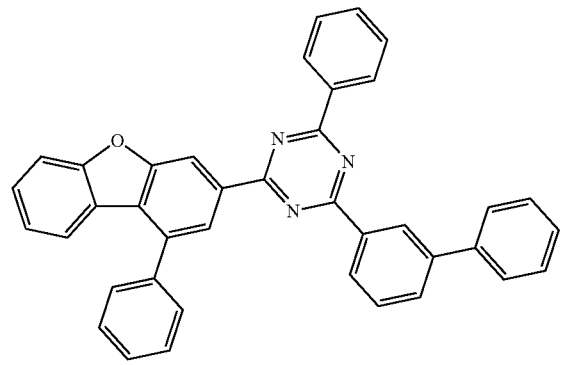
2-98
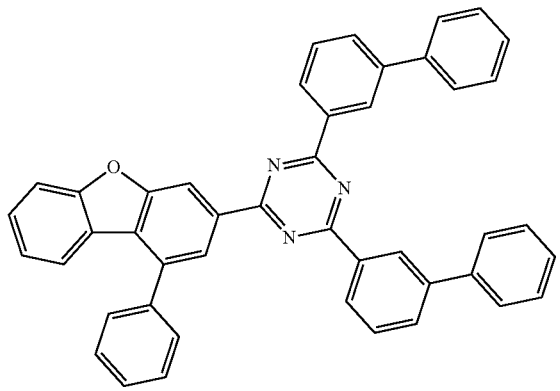
2-99
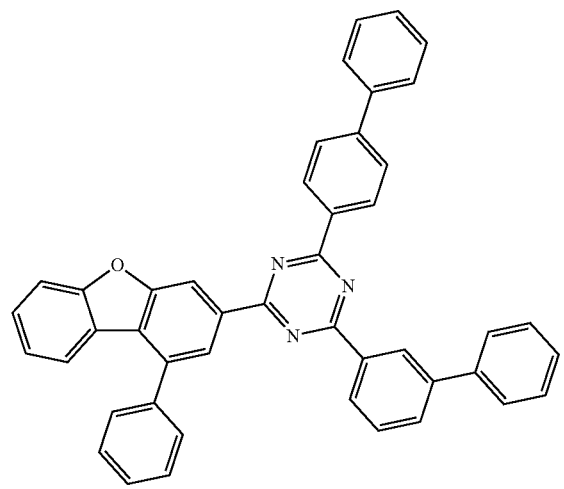
2-100
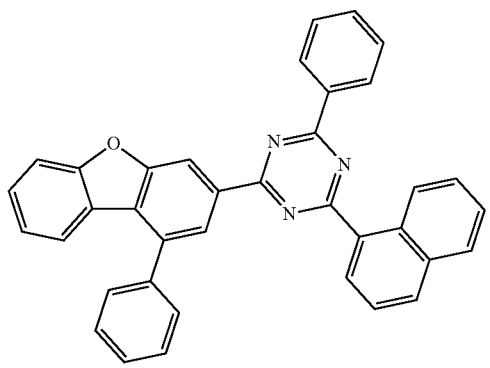
2-101
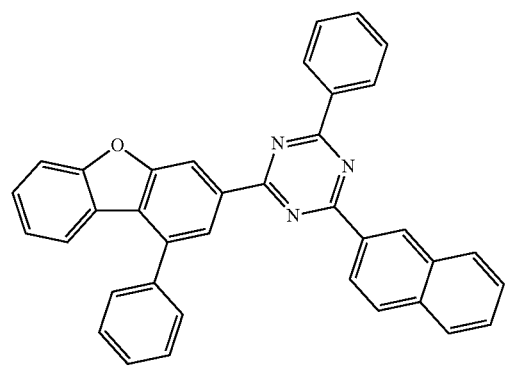
2-102
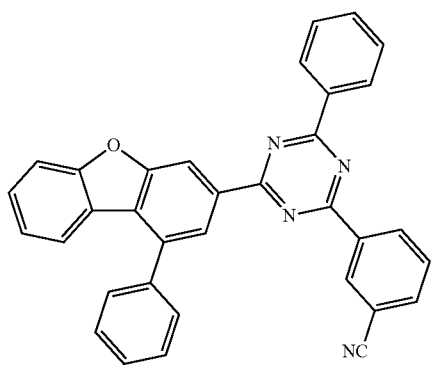

-continued
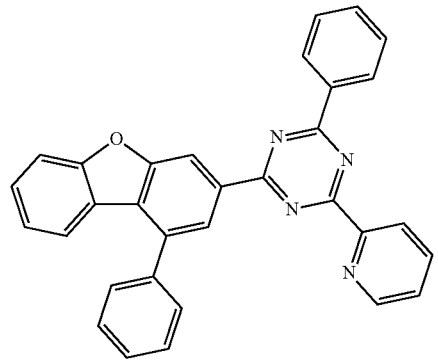
2-103
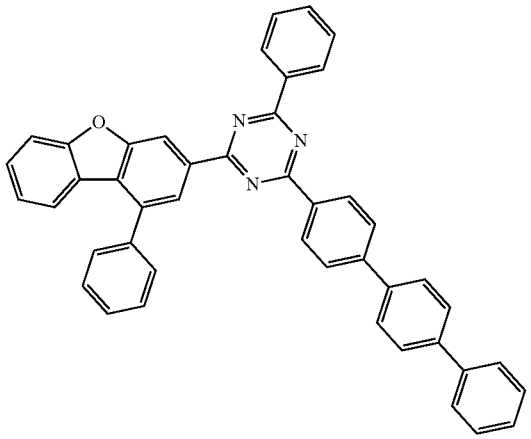
2-104
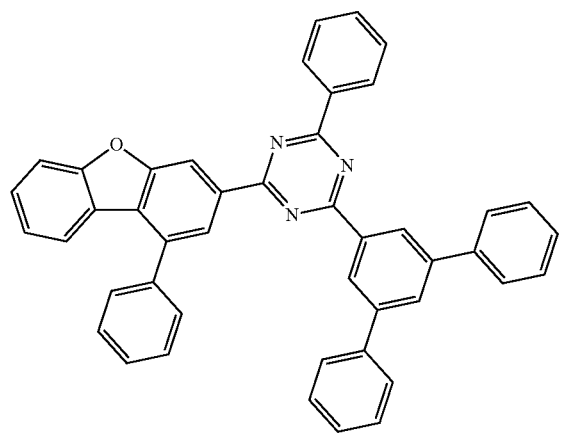
2-105
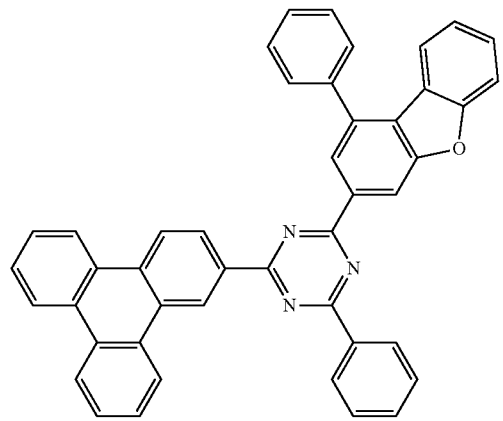
2-106
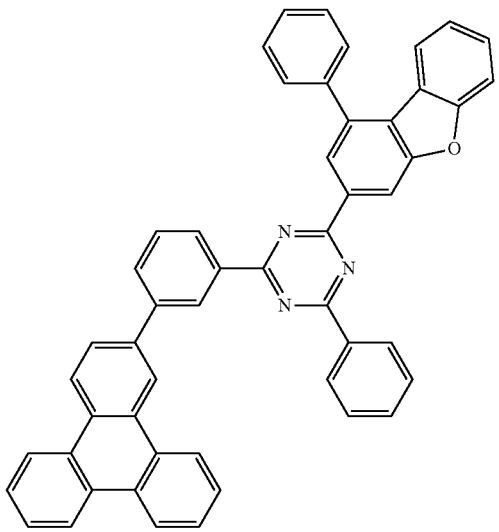 [SMILES: c1ccc(-c2nc(-c3cccc(-c4ccc5c6ccccc6c6ccccc6c5c4)c3)nc(-c3cc(-c4ccccc4)c4c(c3)oc3ccccc34)n2)cc1]
2-107

-continued
2-108
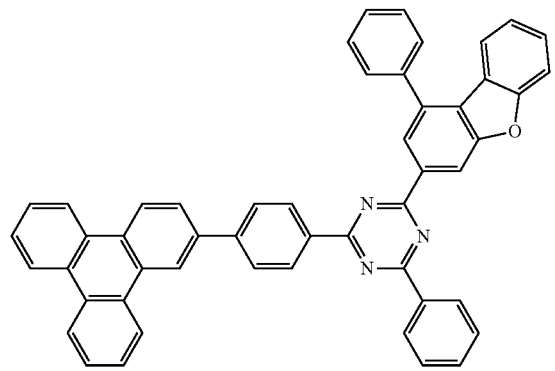
2-109
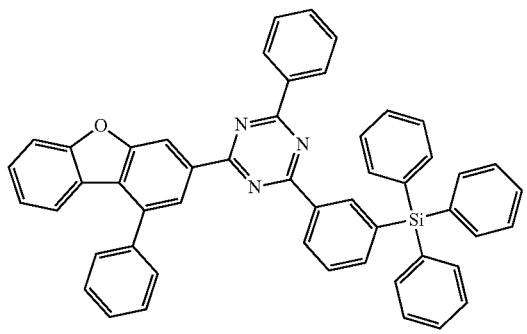
2-110
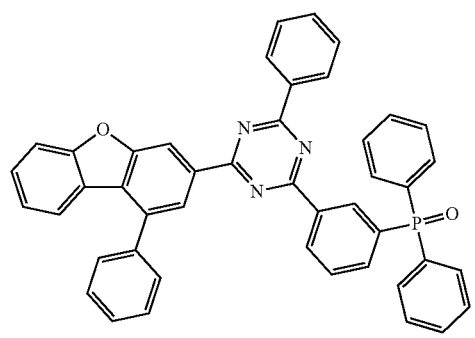
2-111
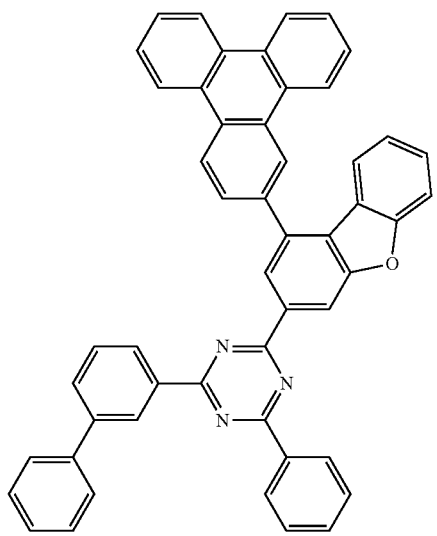
2-112
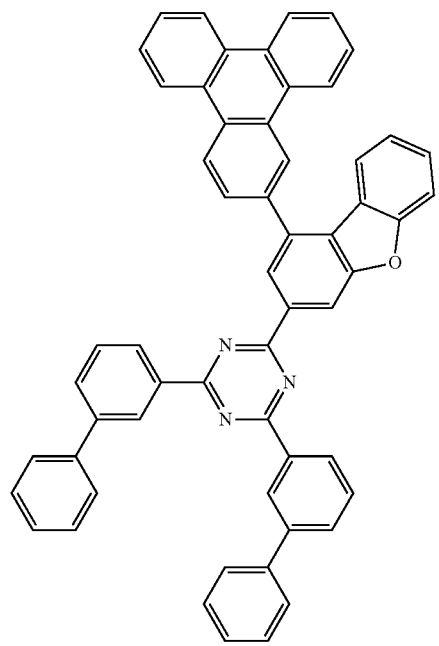
2-113
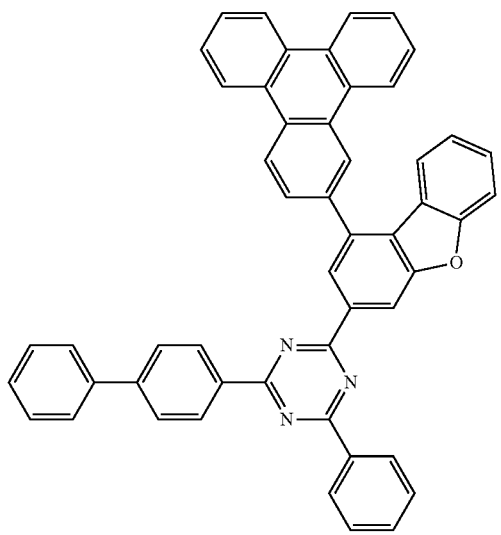

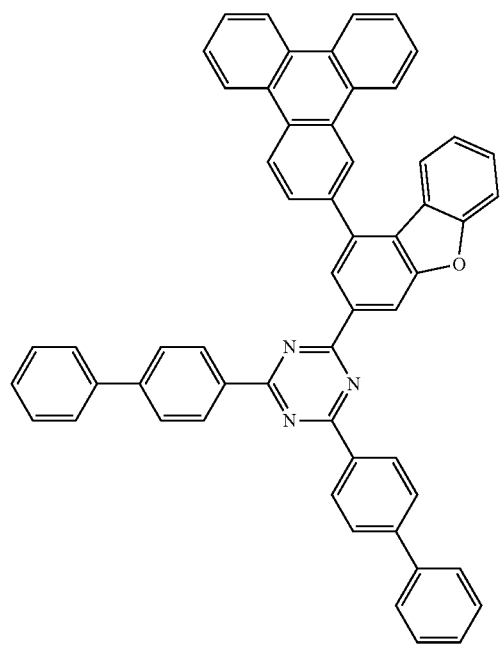
2-114
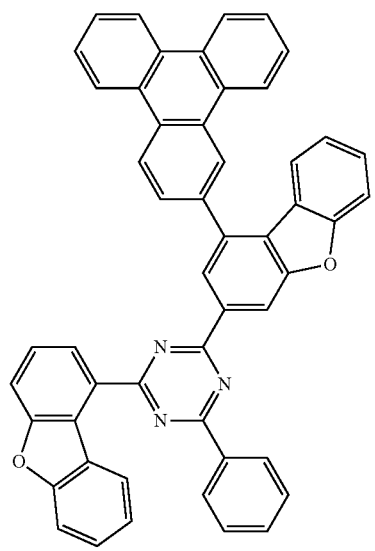
2-115
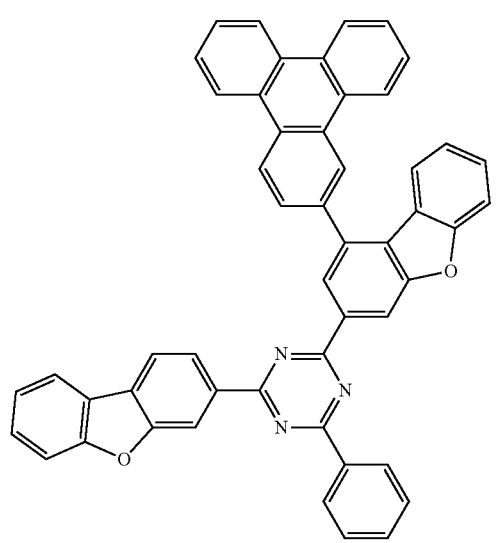
2-116
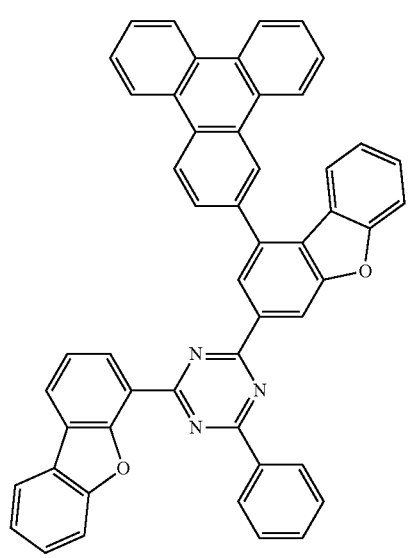
2-117

-continued
2-118
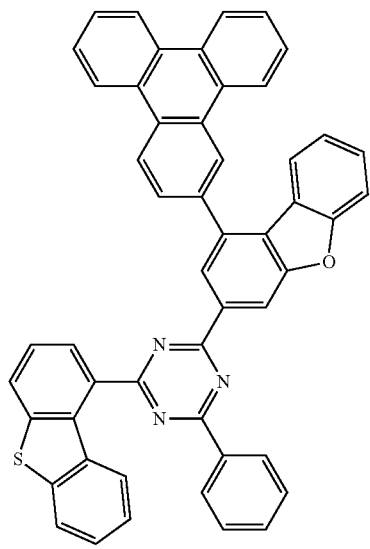
2-119
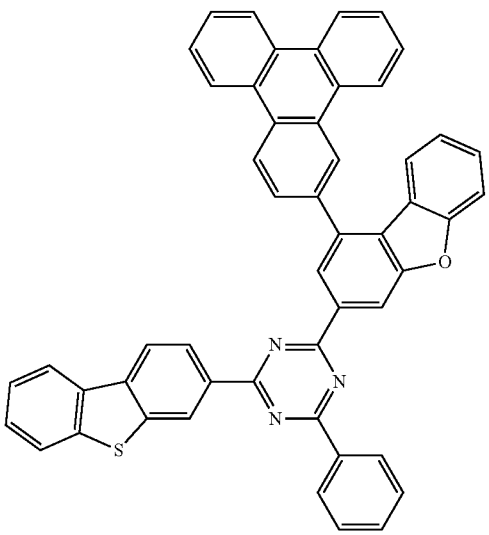
2-220
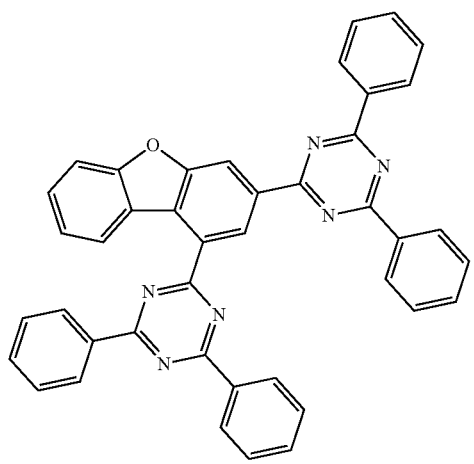
2-121
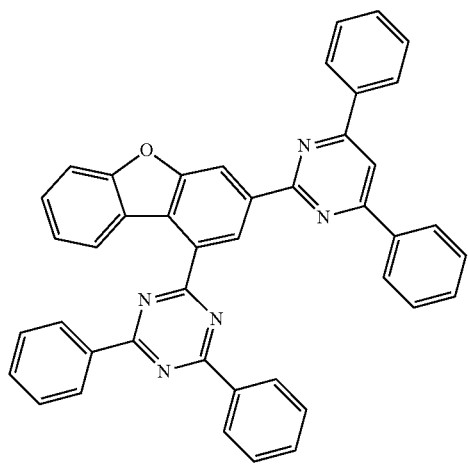
2-122
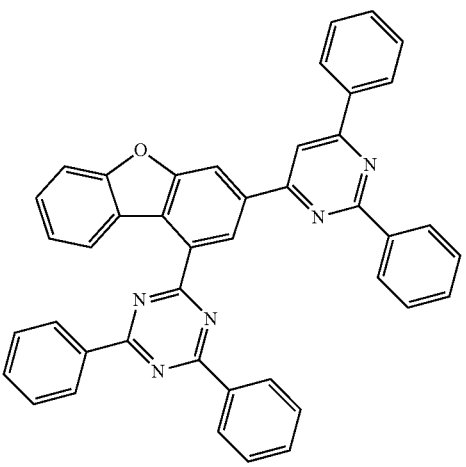

-continued
2-123
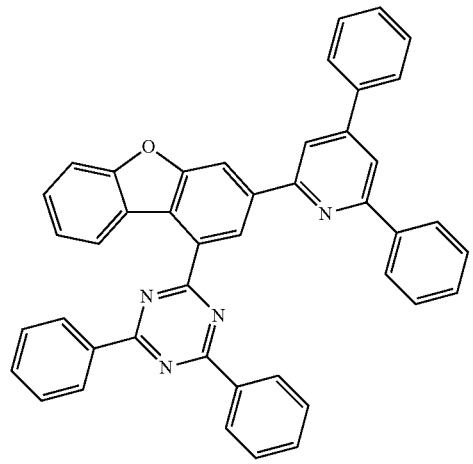
2-124
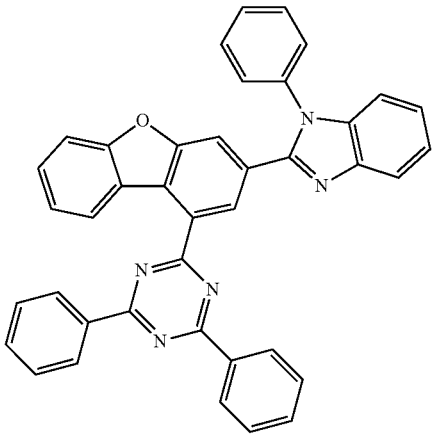
2-125
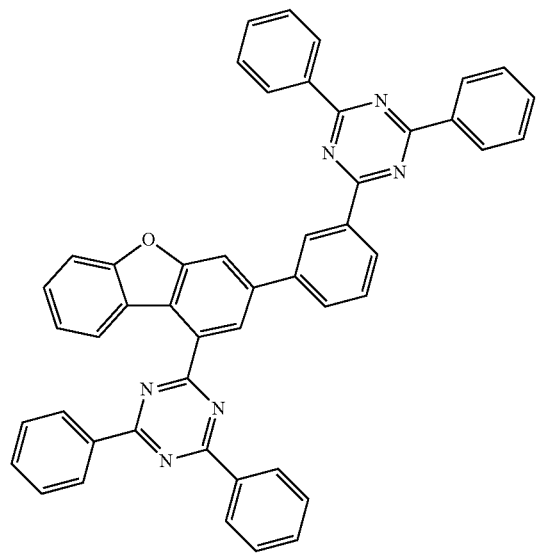
2-126
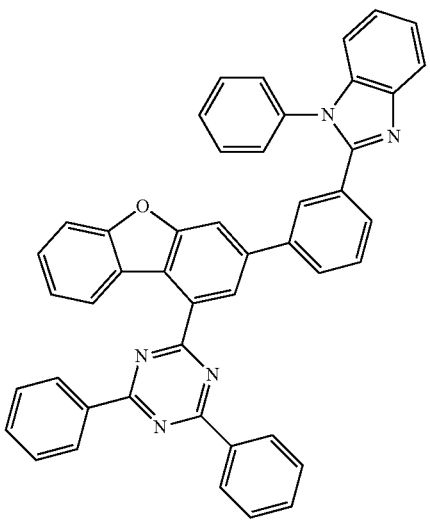
2-127
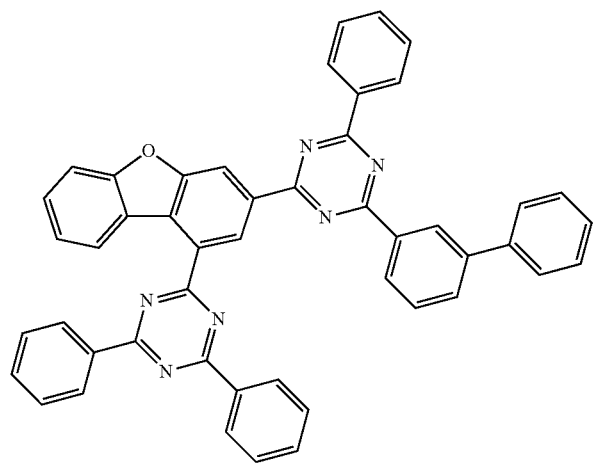
2-128
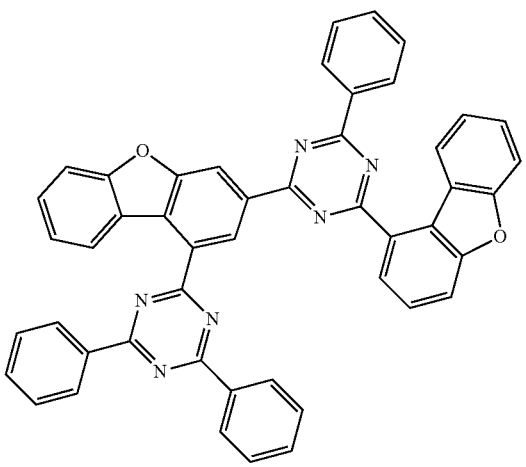

-continued
2-129
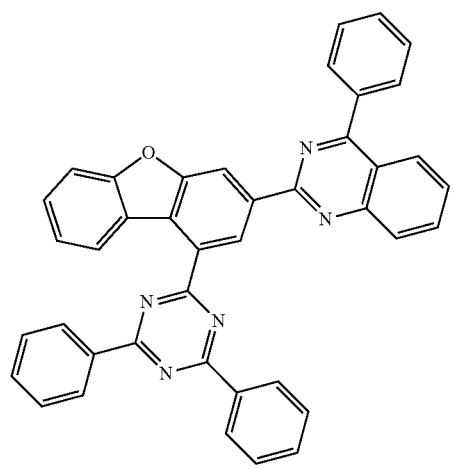
2-130
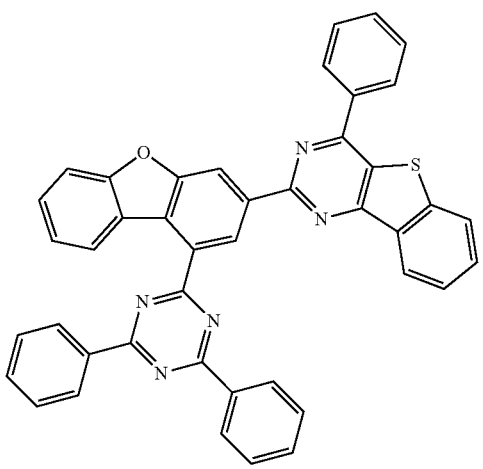
2-131
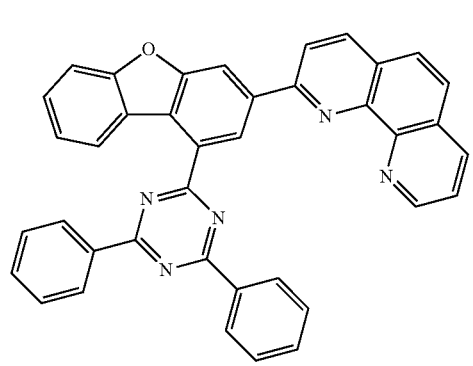
2-132
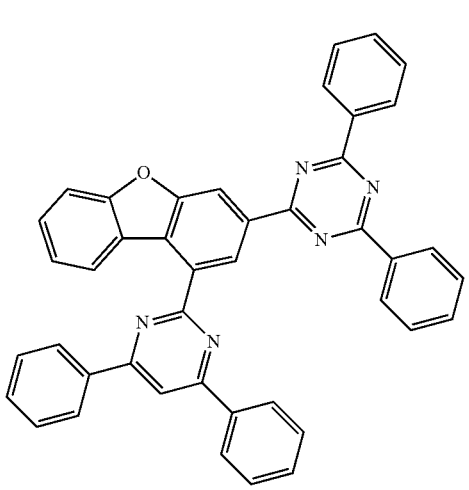
2-133
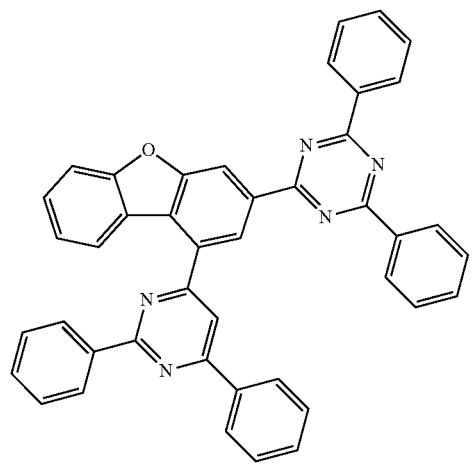
2-134
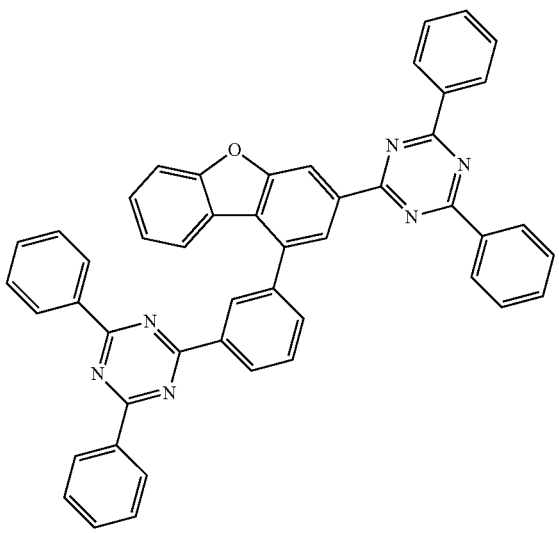

2-135
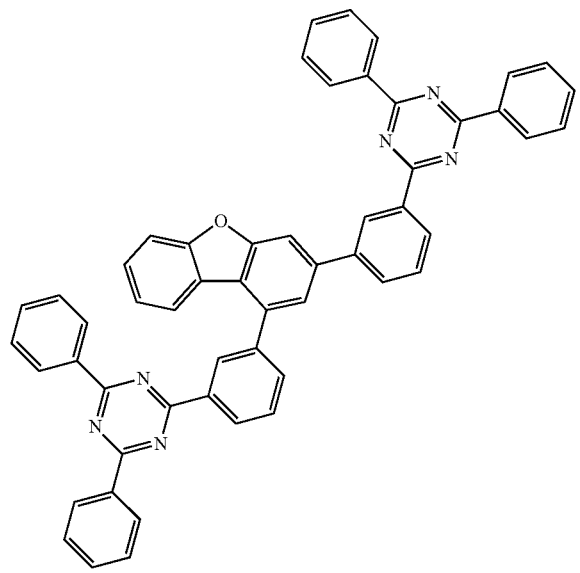
3-1
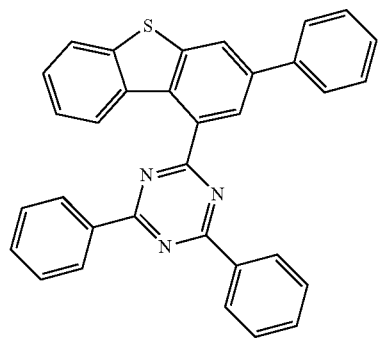
3-2
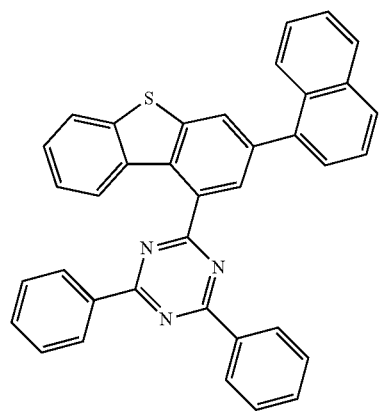
3-3
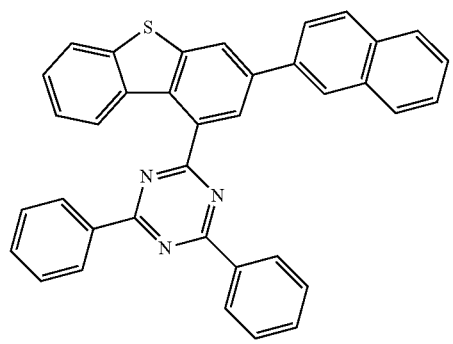
3-4
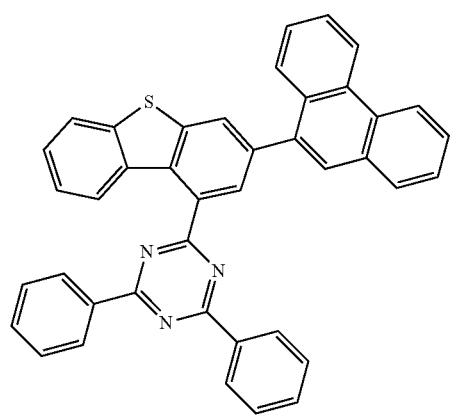
3-5
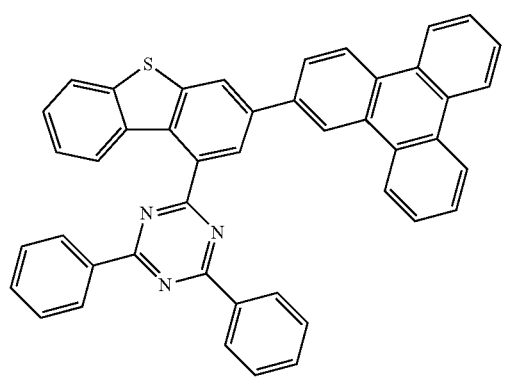

-continued
3-6
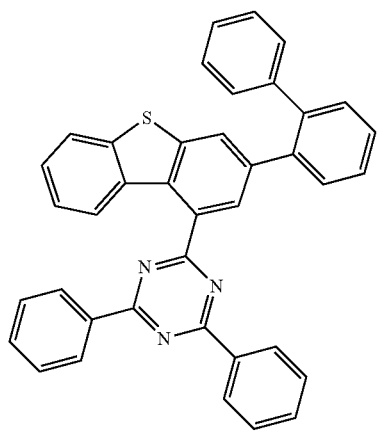
3-7
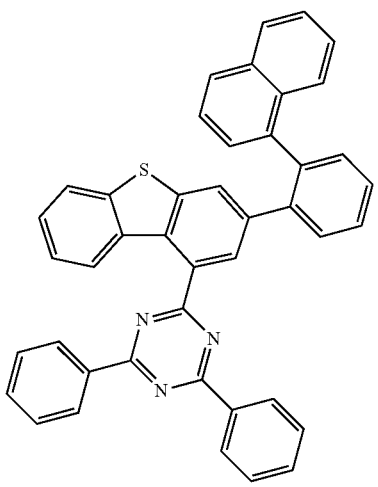
3-8
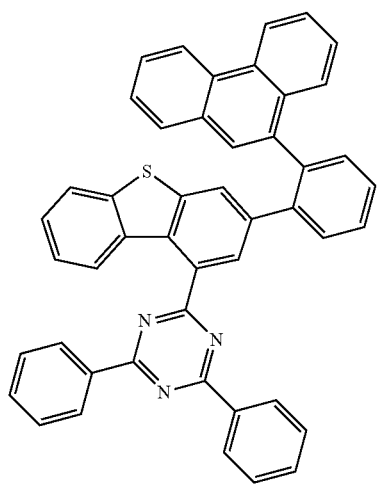
3-9
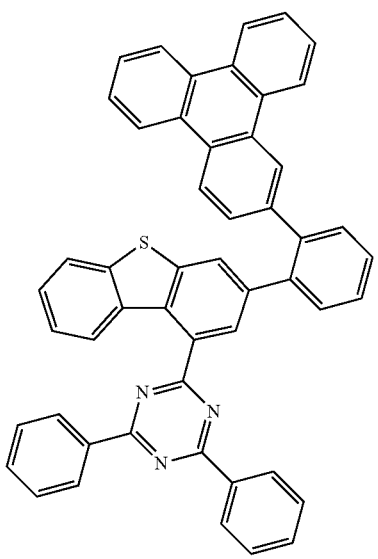
3-10
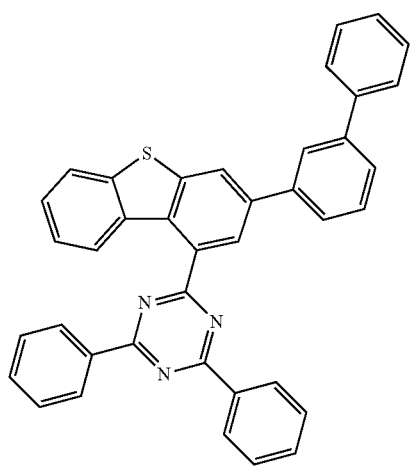
3-11
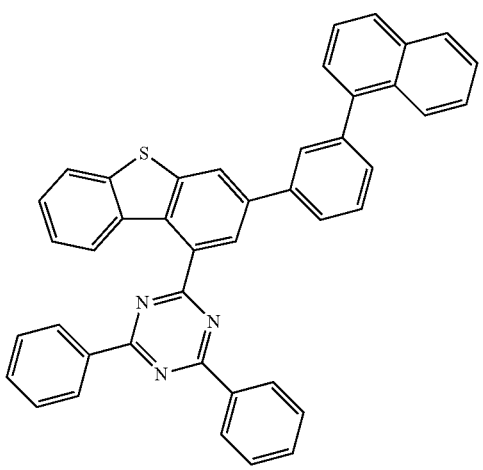

-continued
3-12
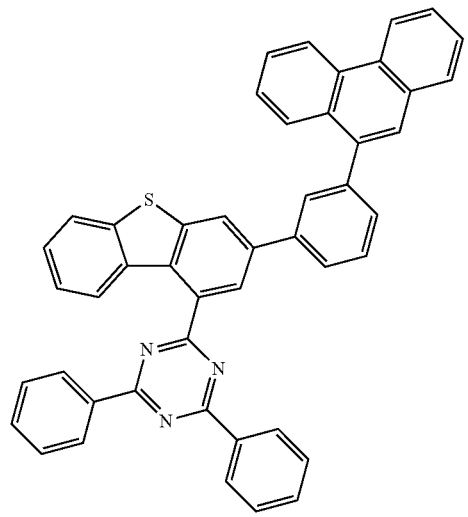
3-13
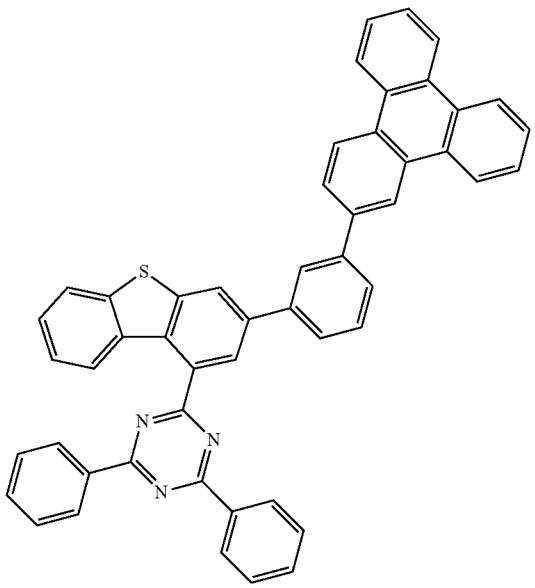
3-14
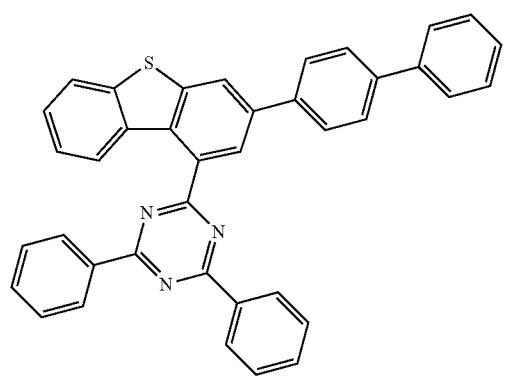
3-15
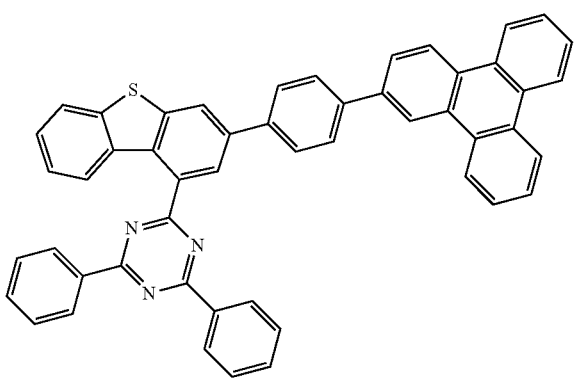
3-16
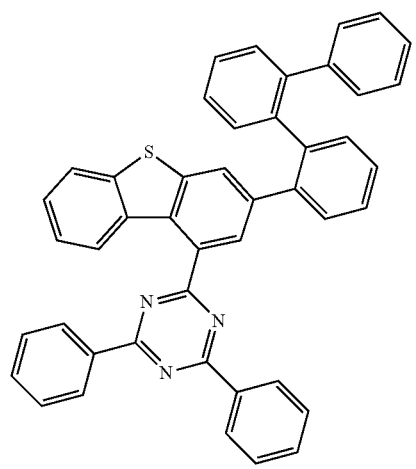
3-17
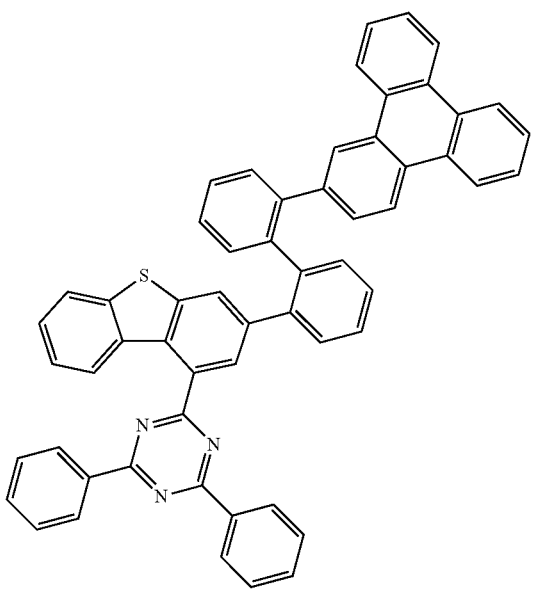

-continued
3-18
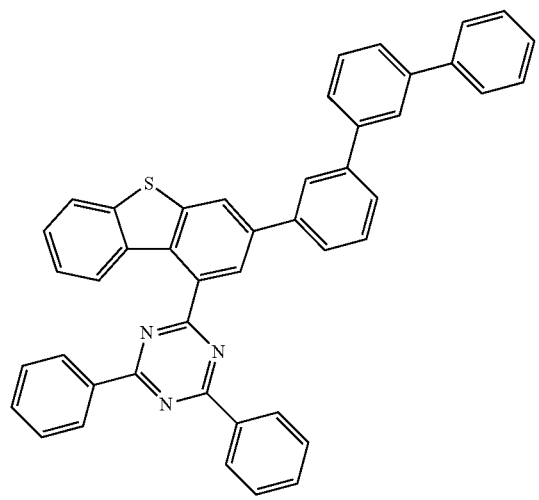
3-19
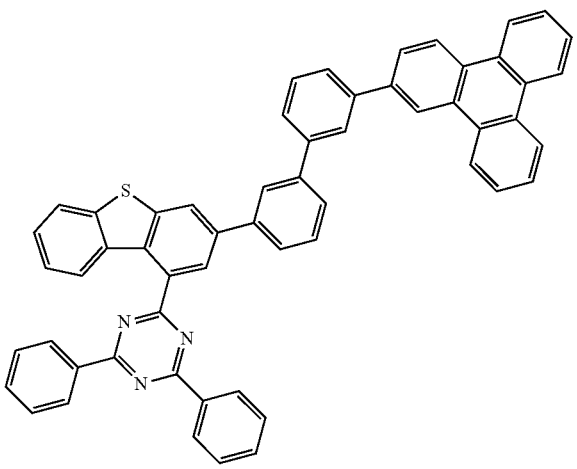
3-20
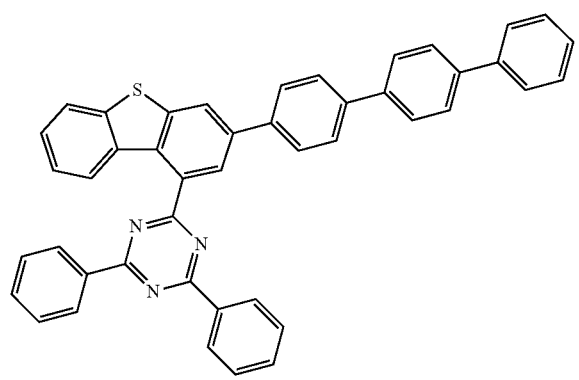
3-21
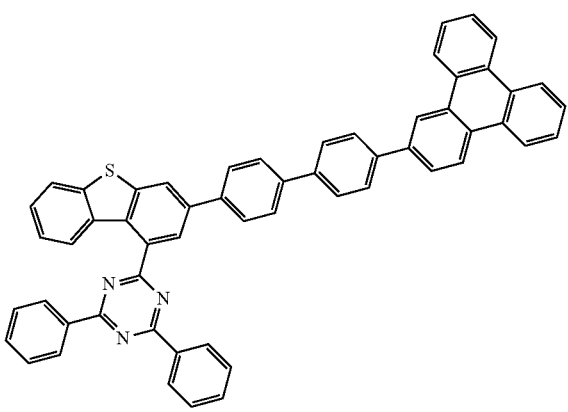
3-22
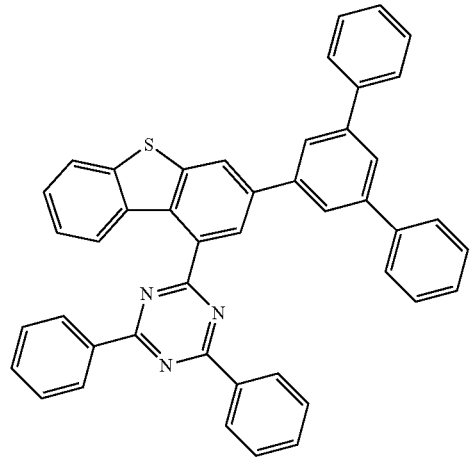
3-23
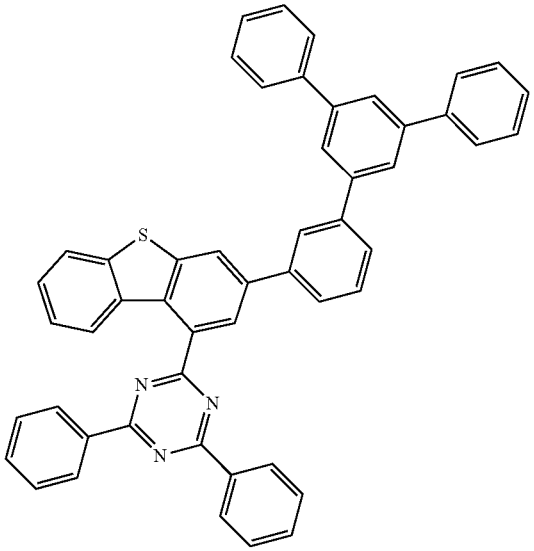

-continued
3-24
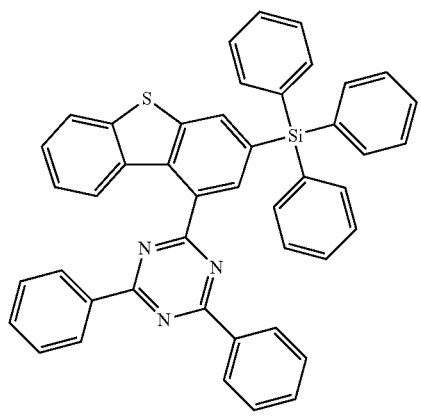
3-25
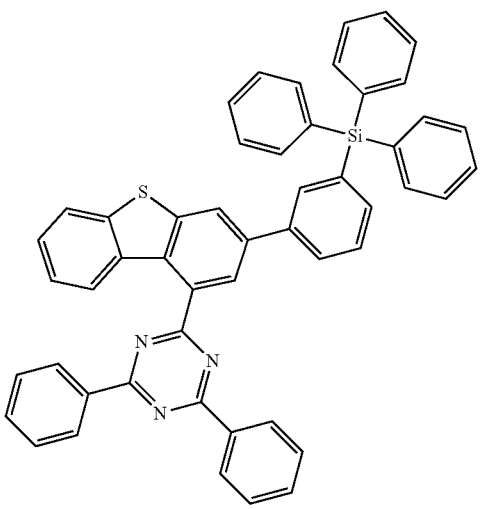
3-26
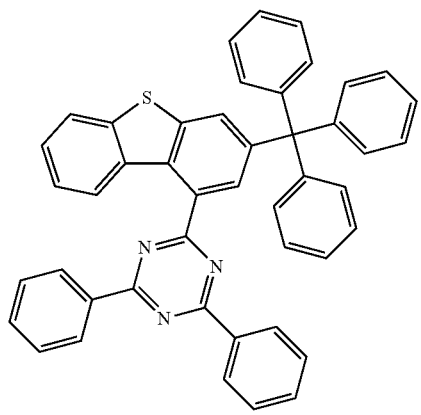
3-27
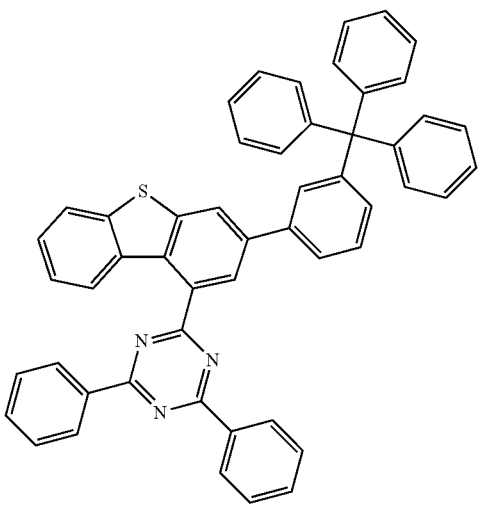
3-28
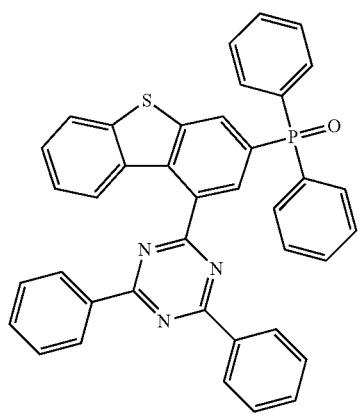
3-29
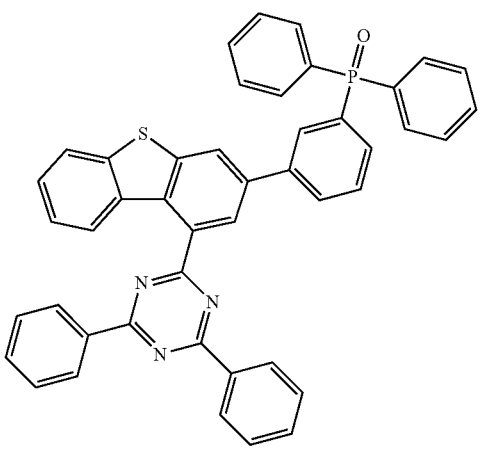

-continued
3-30
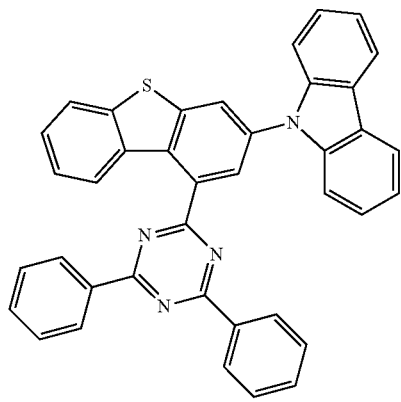
3-31
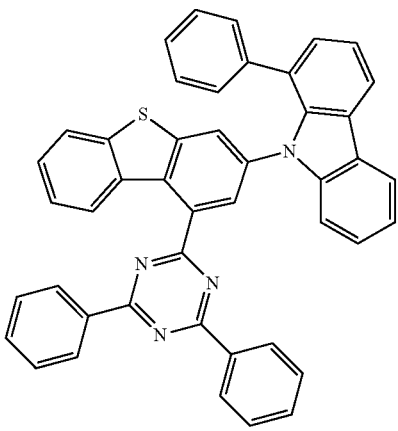
3-32
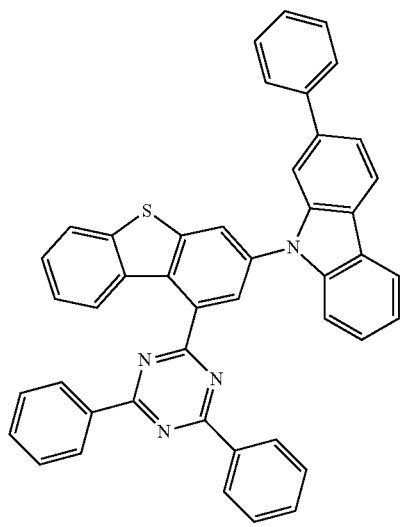
3-33
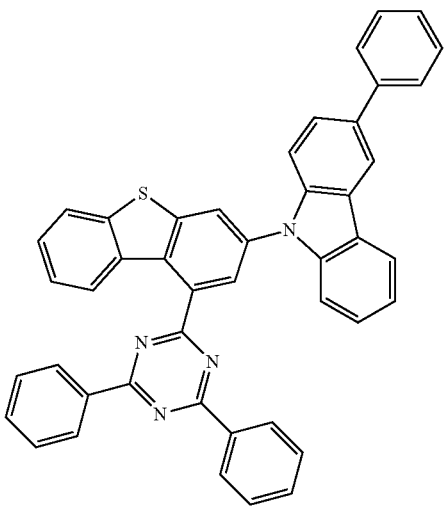
3-34
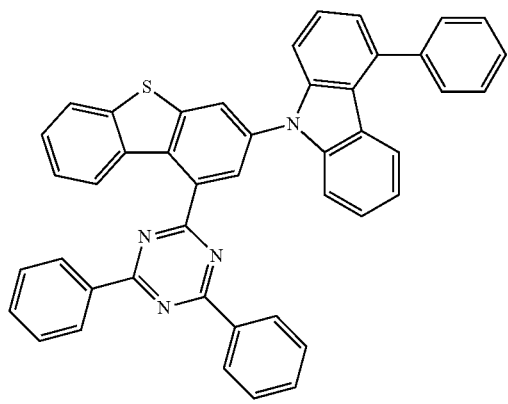
3-35
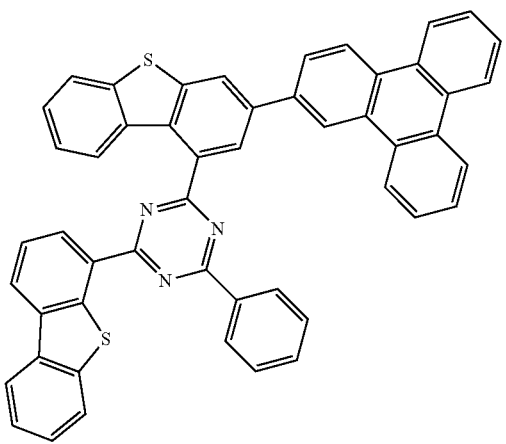

-continued
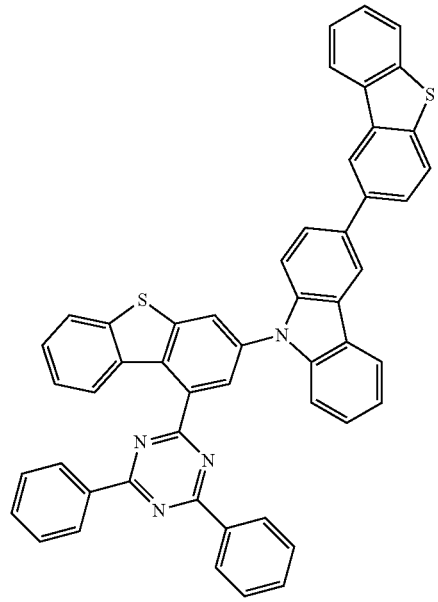
3-36
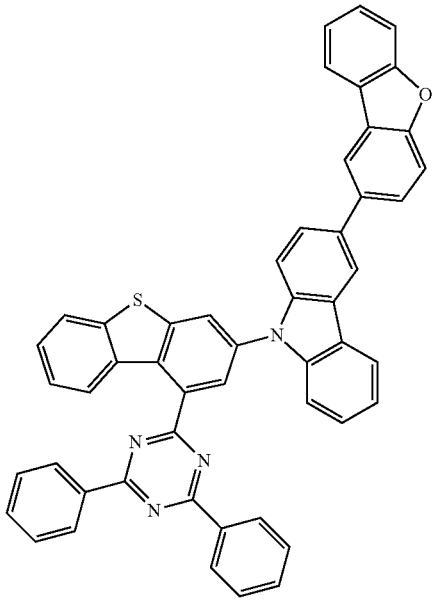
3-37
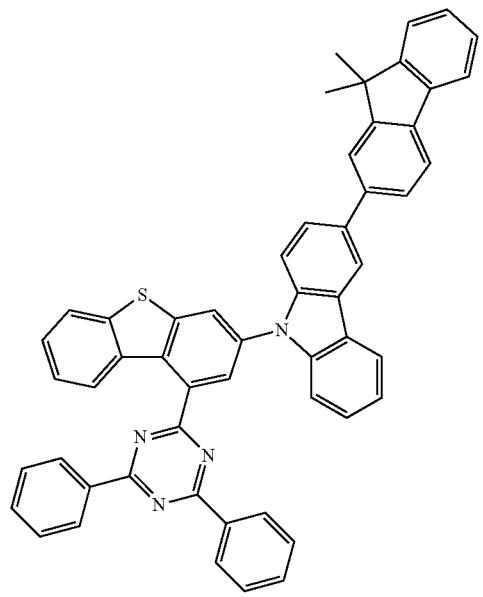
3-38
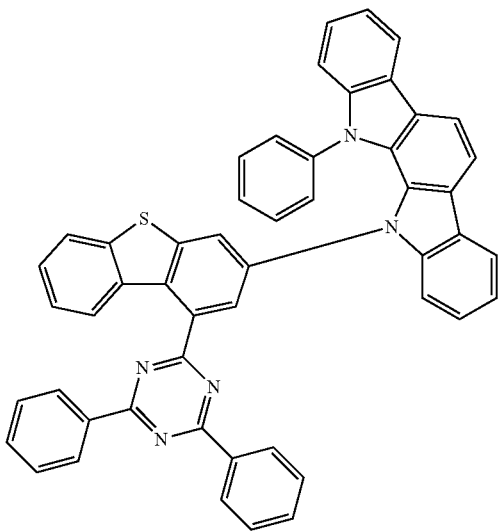
3-39

3-40
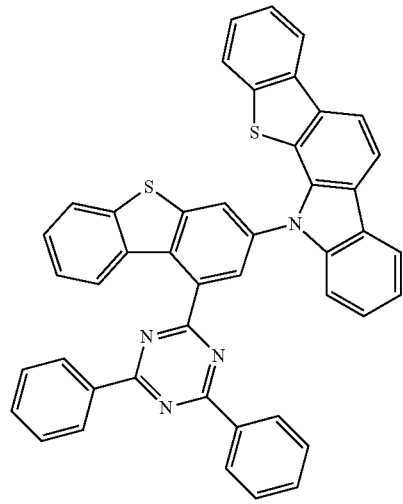
3-41
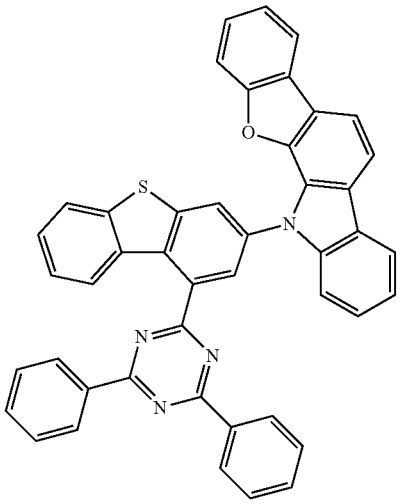
3-42
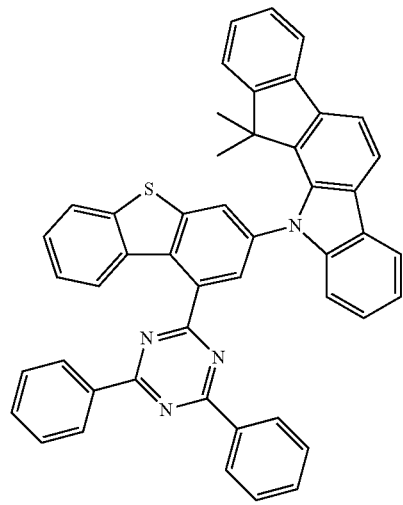
3-43
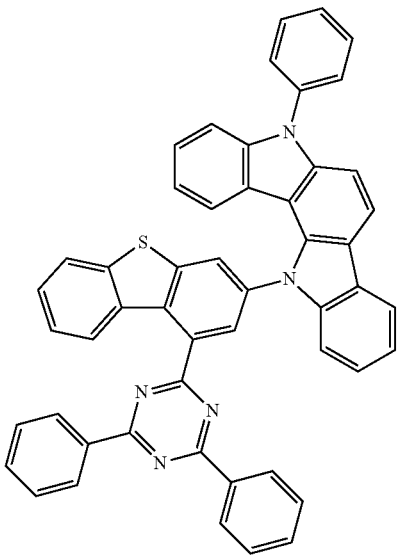
3-44
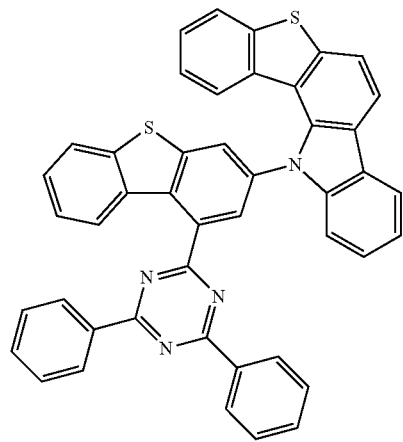
3-45
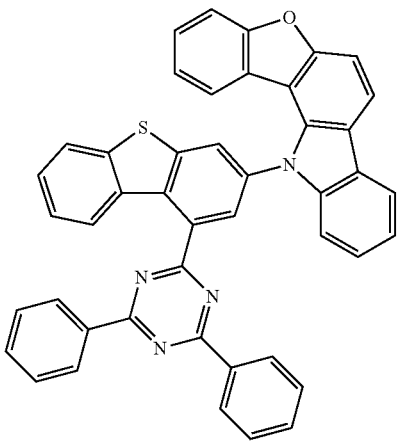

-continued
3-46
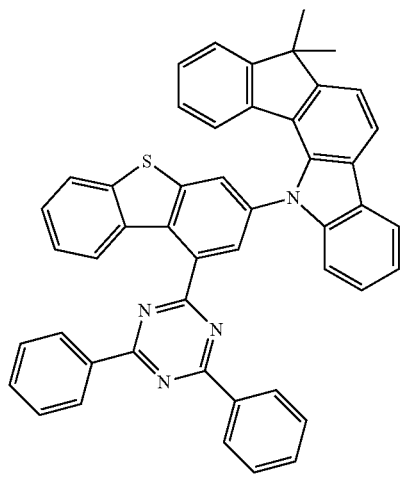
3-47
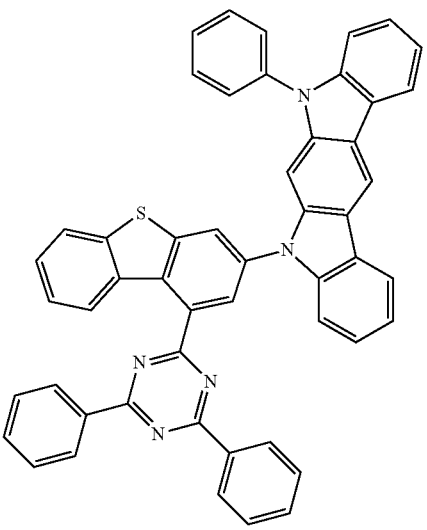
3-48
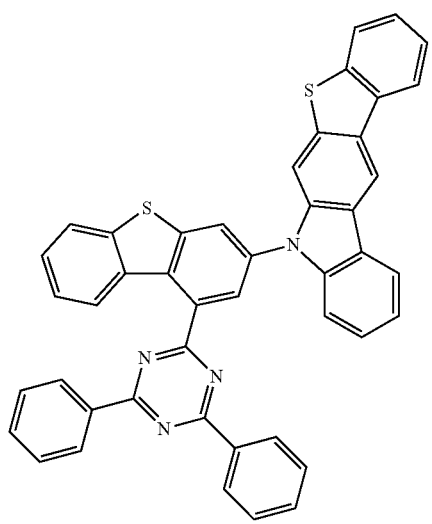
3-49
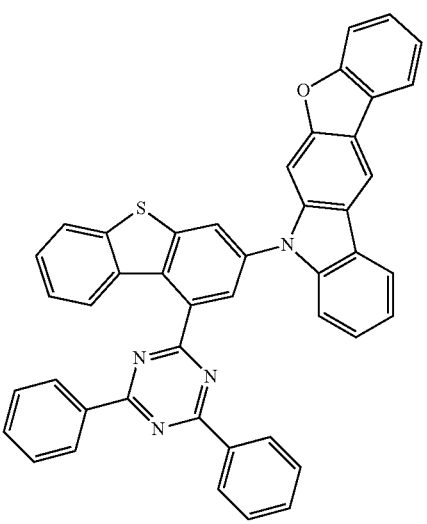
3-50
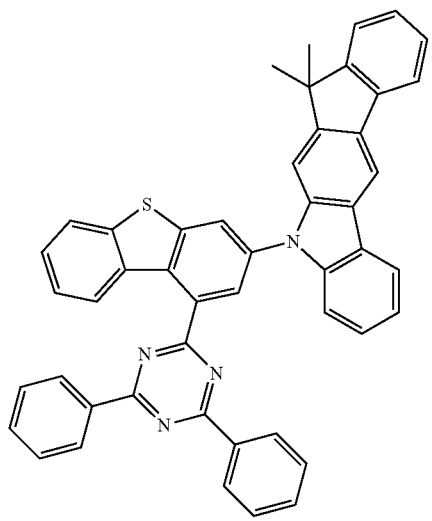
3-51
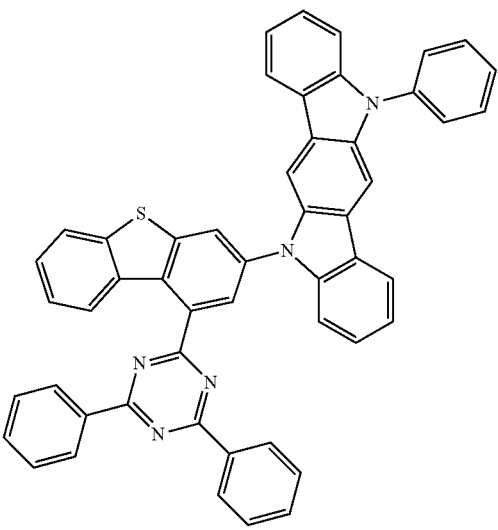

-continued
3-52
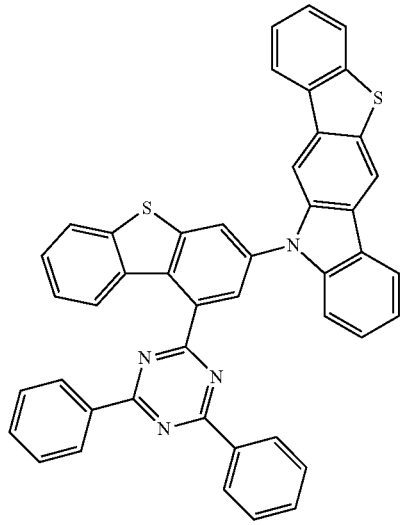
3-53
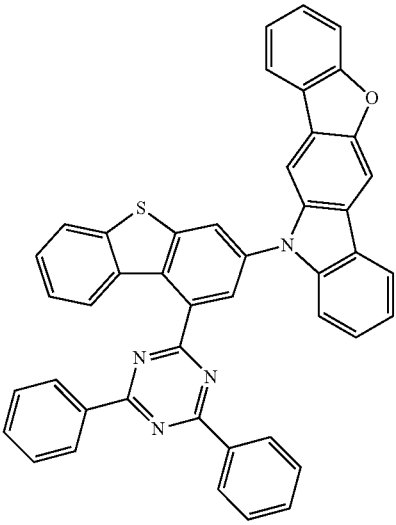
3-54
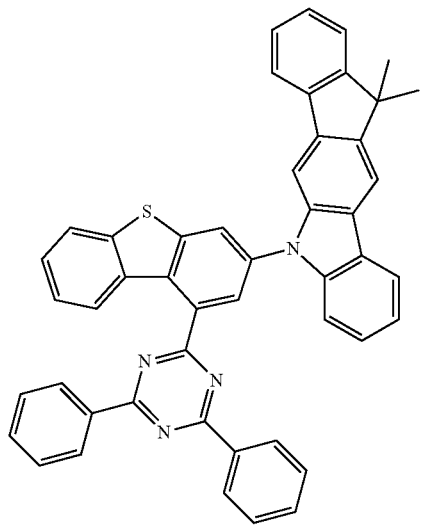
3-55
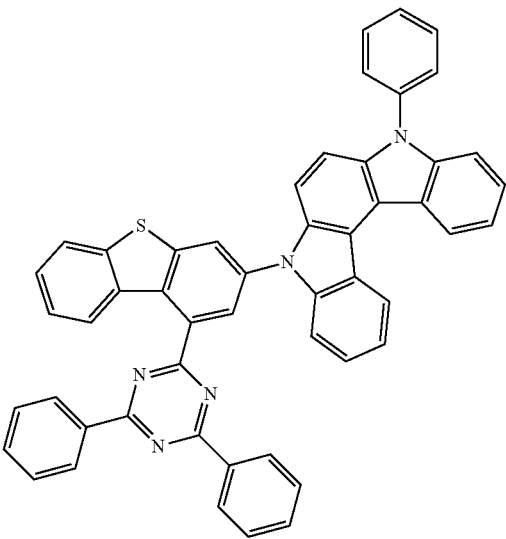
3-56
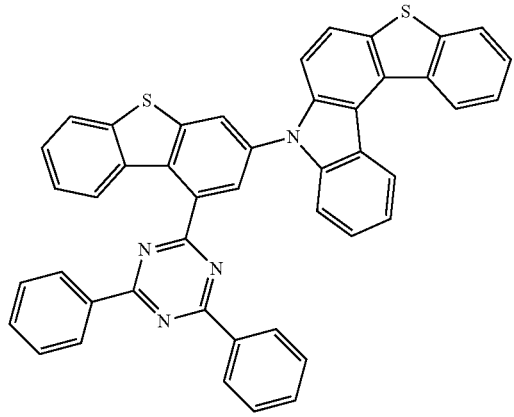
3-57
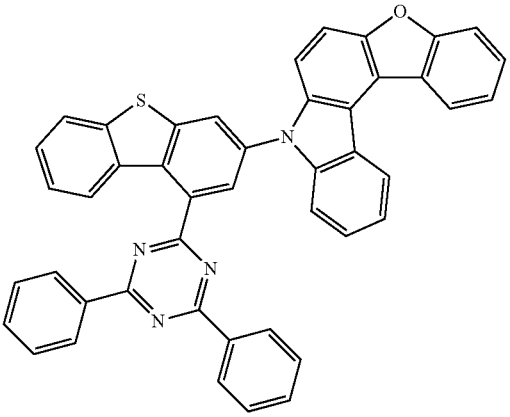

-continued
3-58
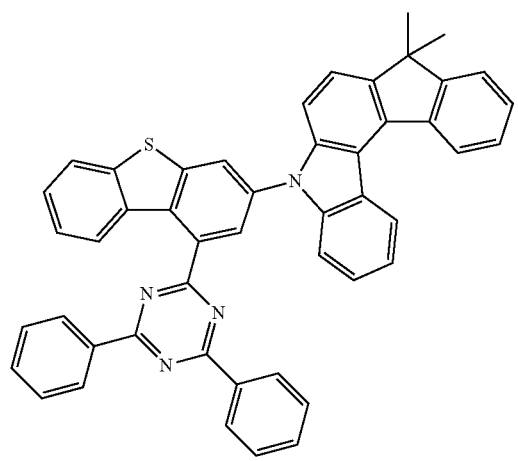
3-59
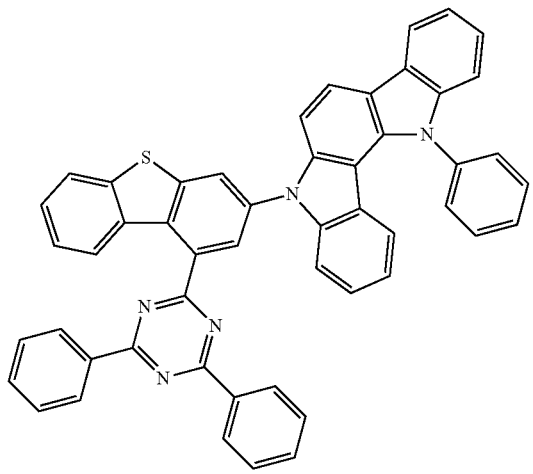
3-60
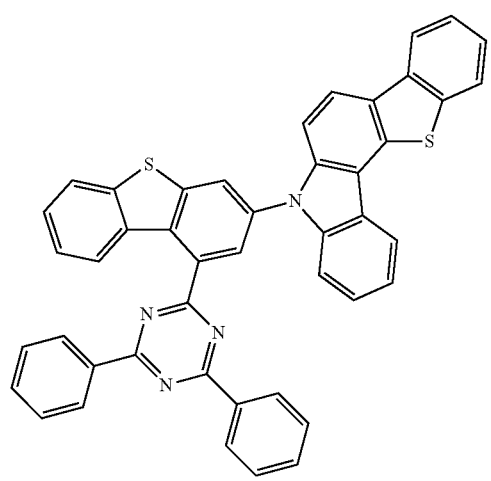
3-61
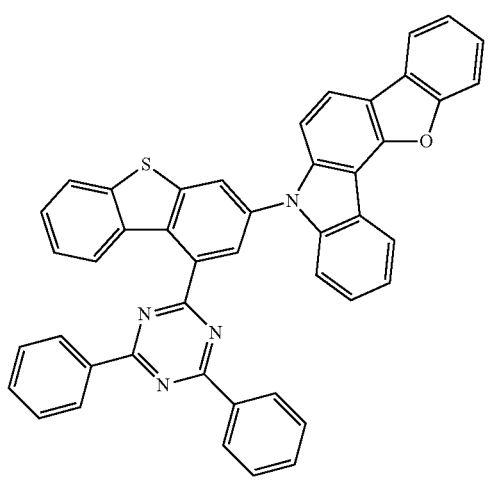
3-62
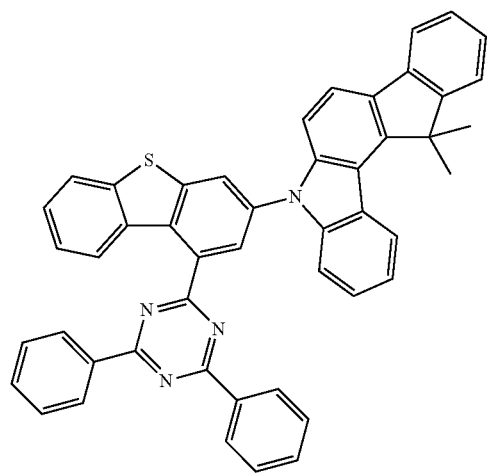
3-63
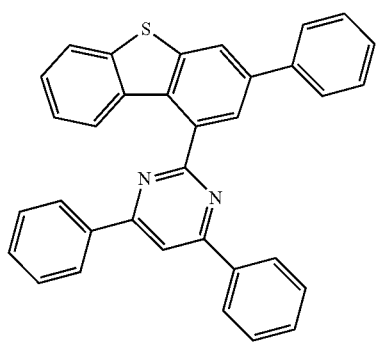

-continued
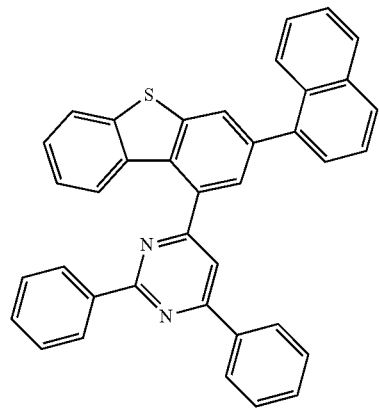
3-64
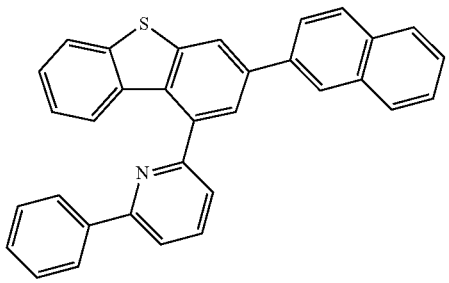
3-65
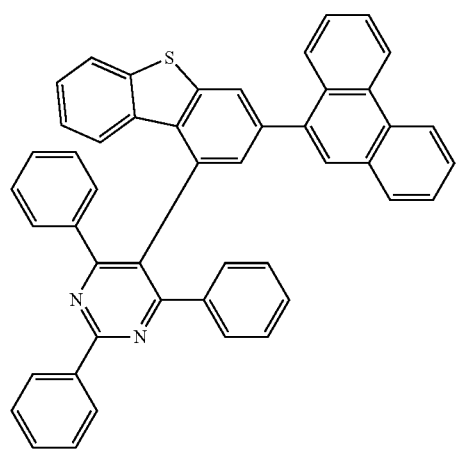
3-66
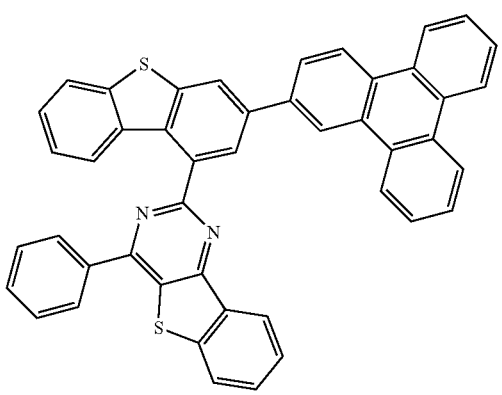
3-67
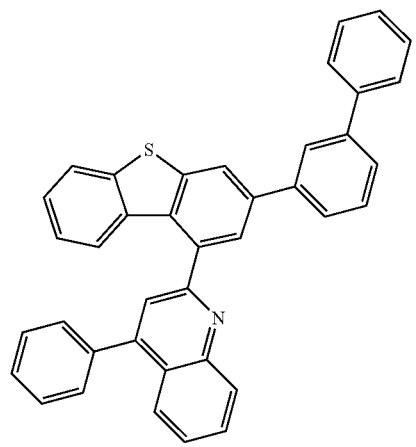
3-68
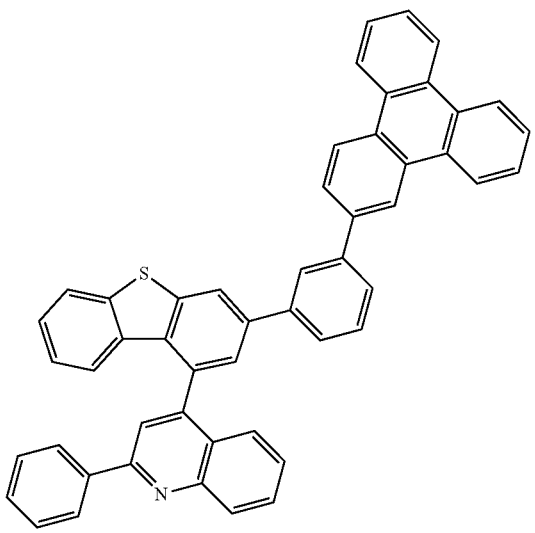
3-69

-continued
3-70
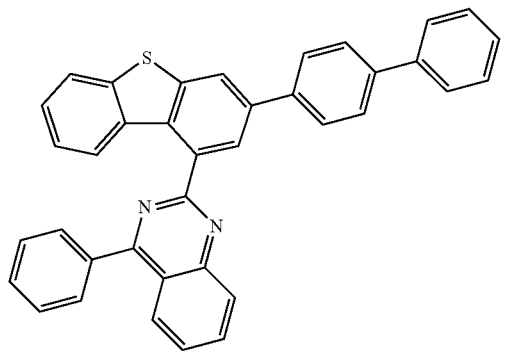
3-71
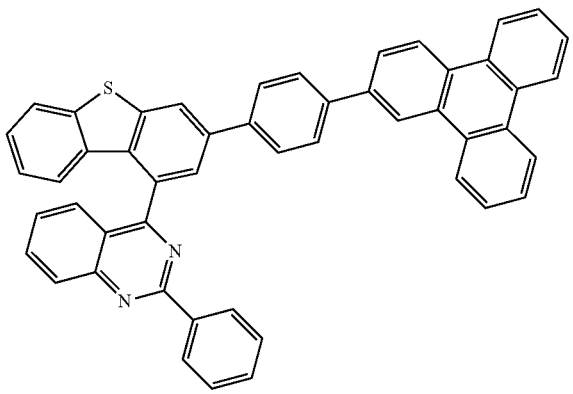
3-72
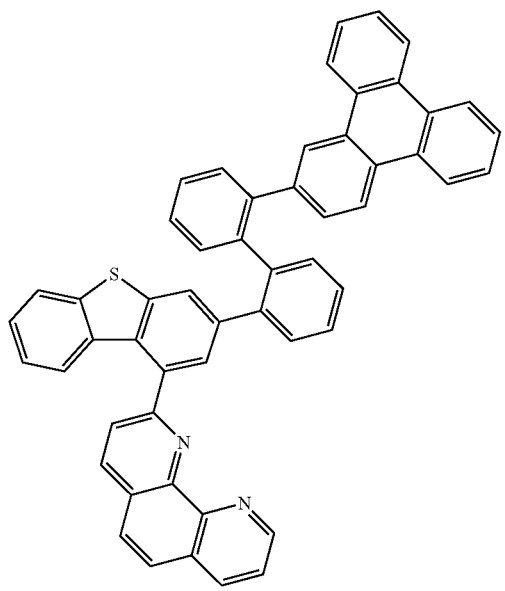
3-73
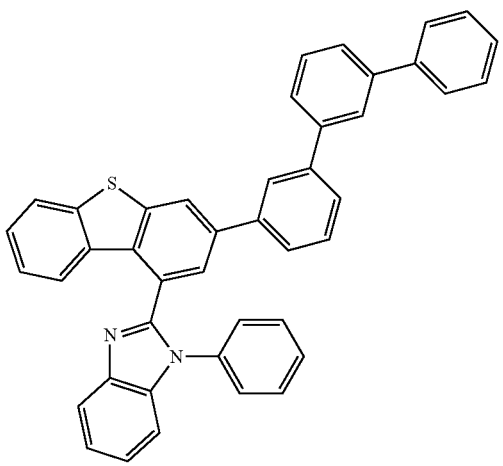
3-74
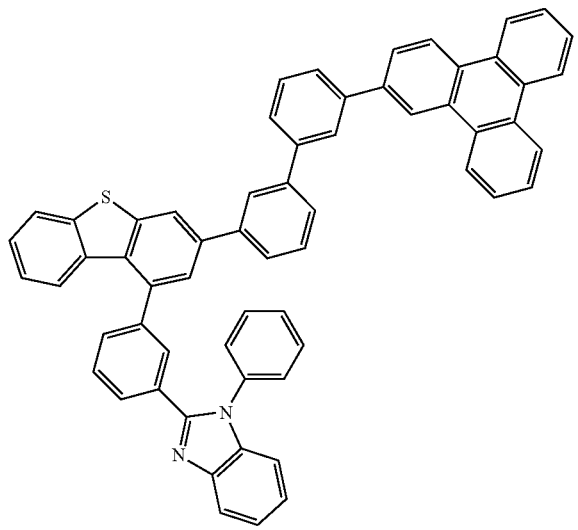
3-75
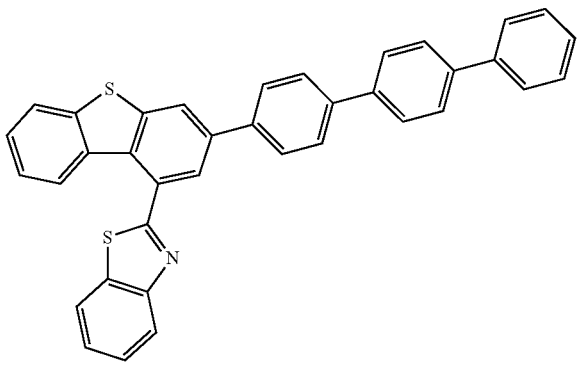

3-76
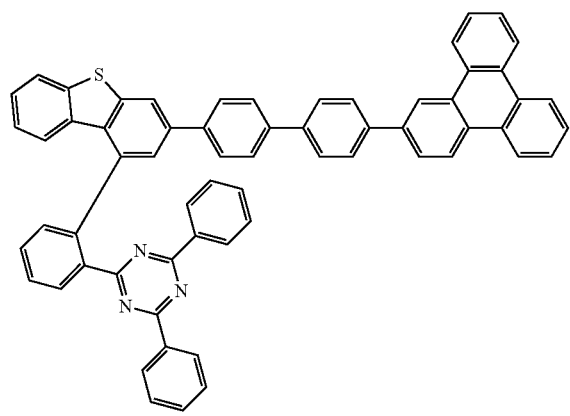
3-77
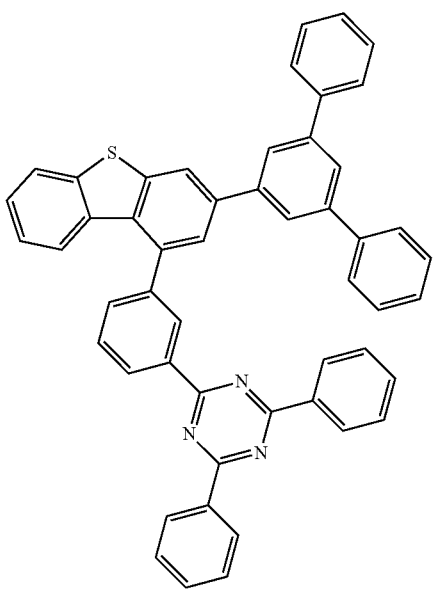
3-78
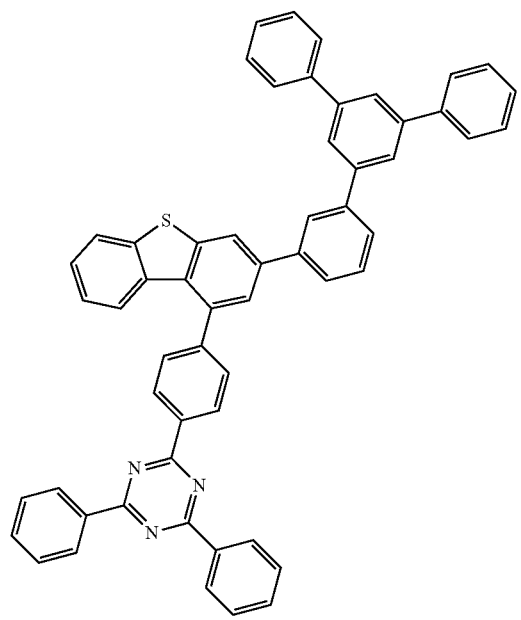
3-79
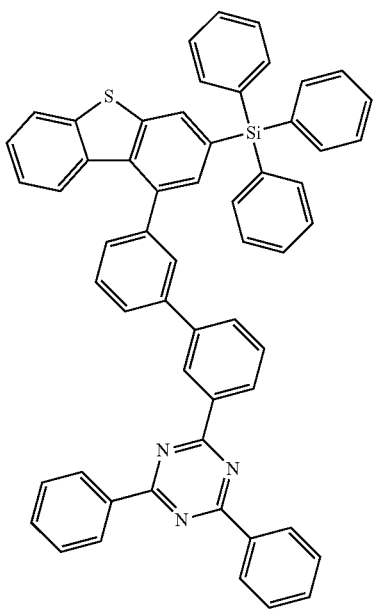

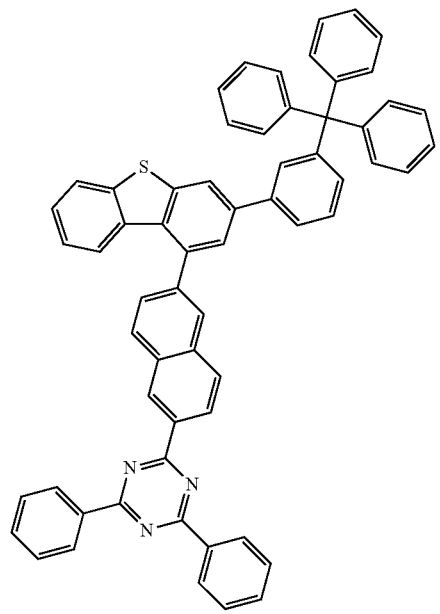
3-80
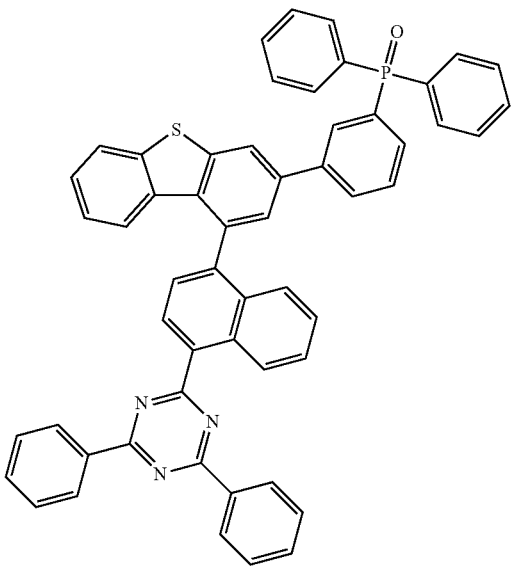
3-81
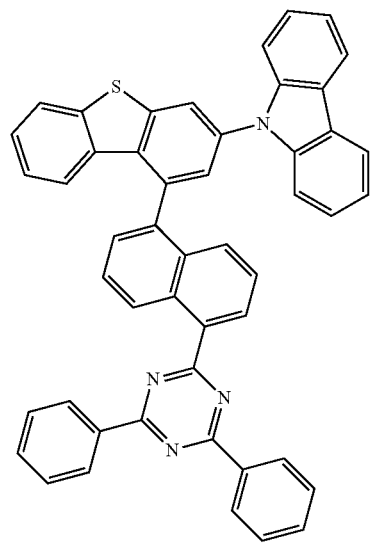
3-82
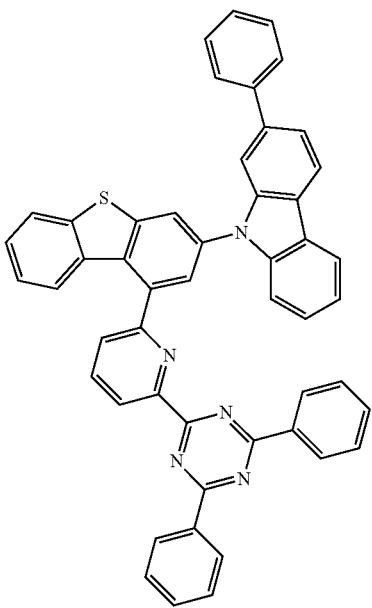
3-83

-continued
3-84
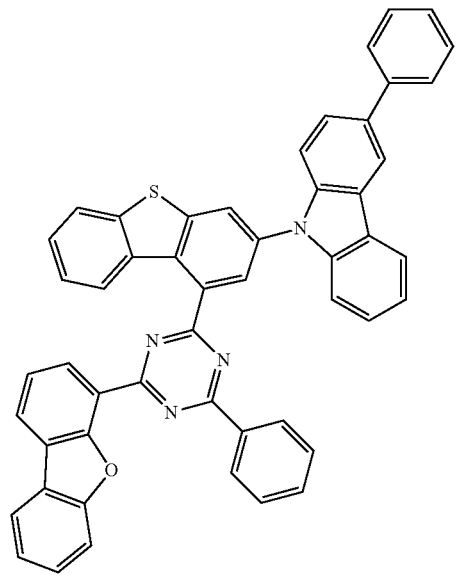
3-85
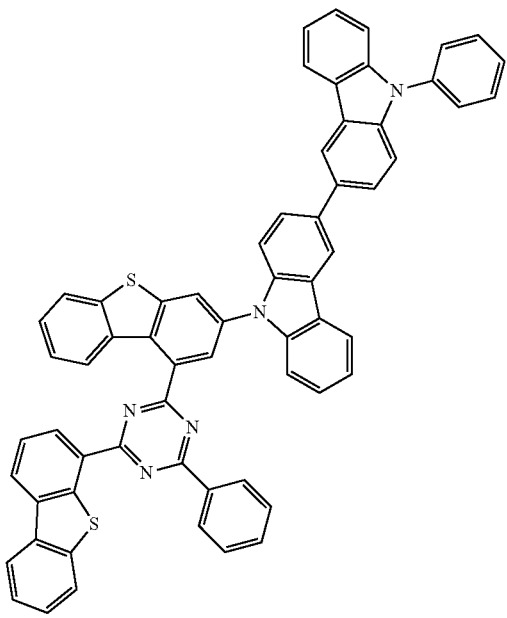
3-86
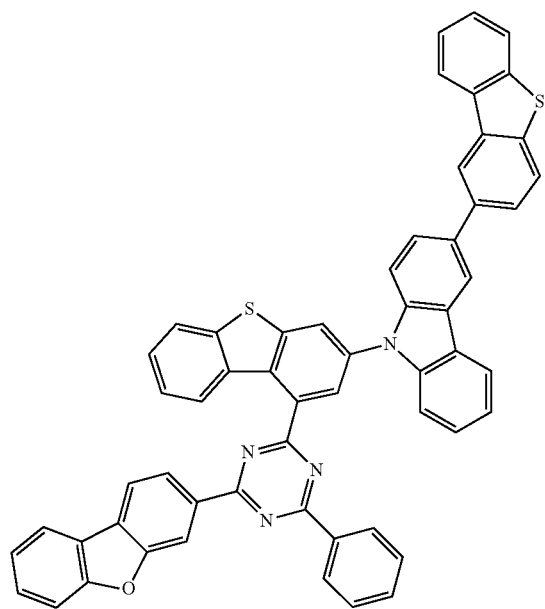
3-87
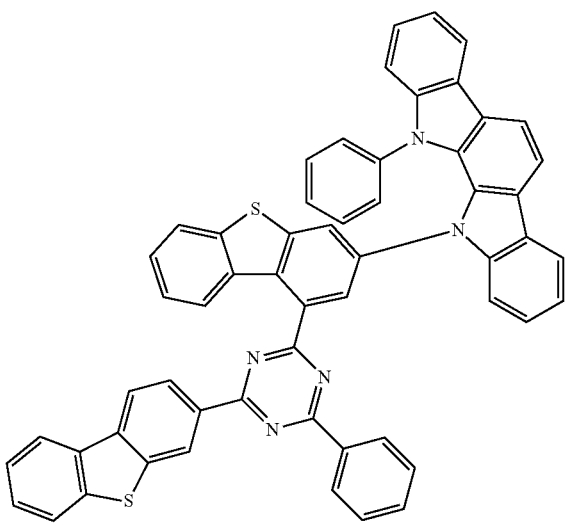

3-88
3-89
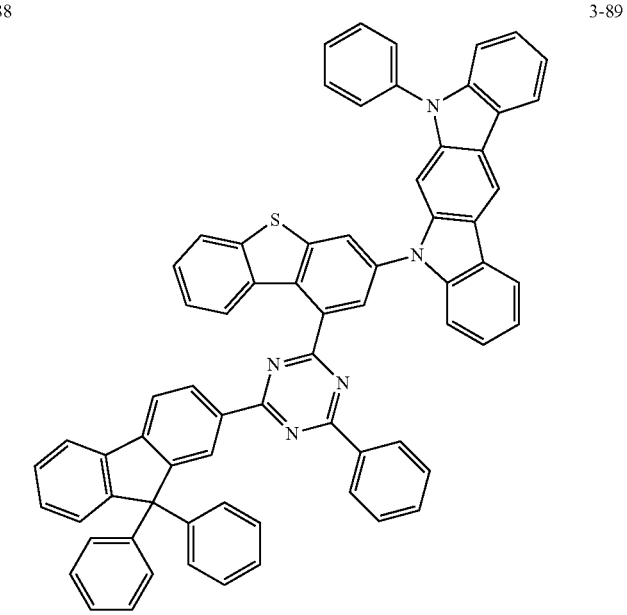
3-90
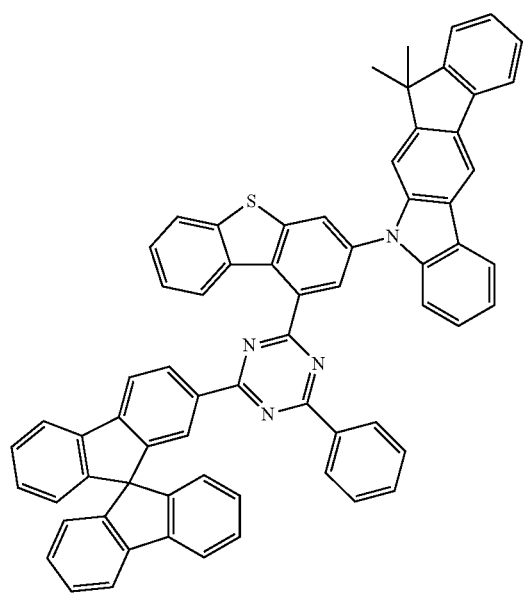
3-91
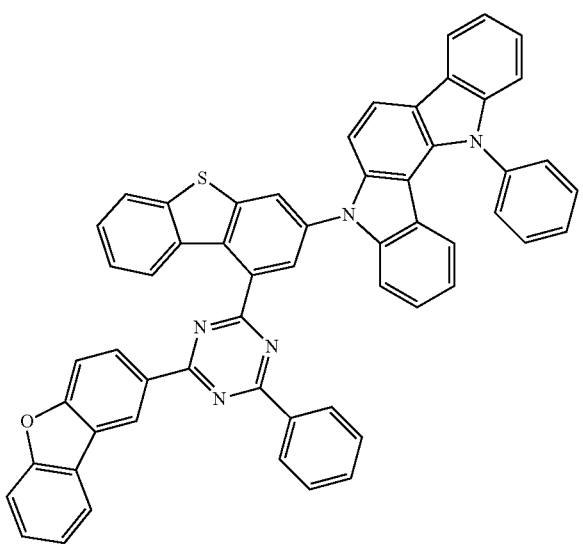

3-92
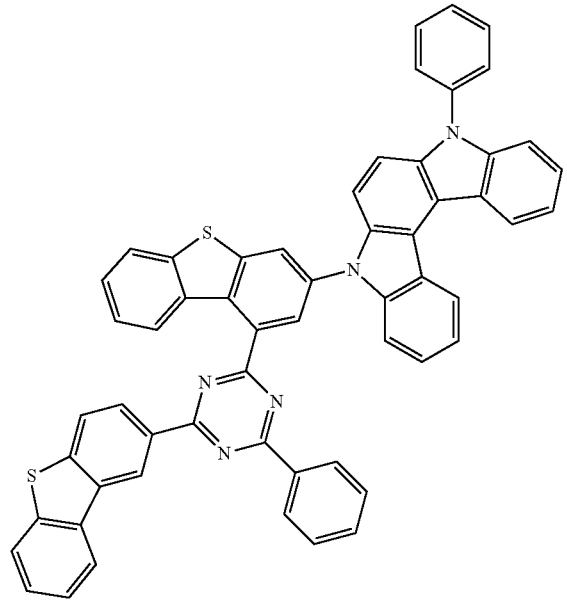
3-93
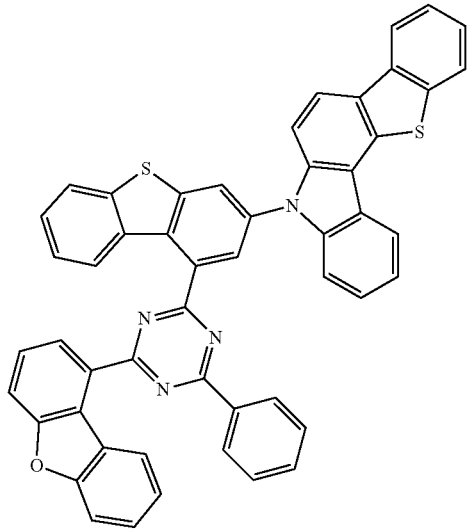
3-94
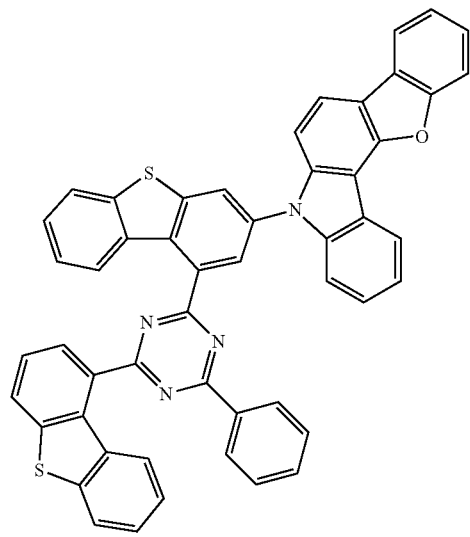
3-95
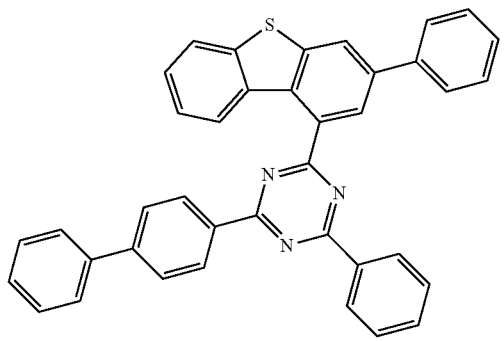
3-96
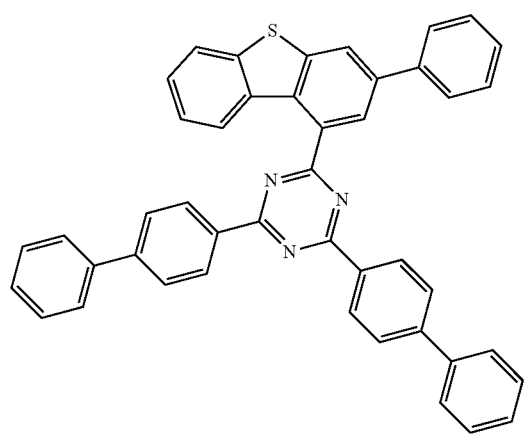
3-97
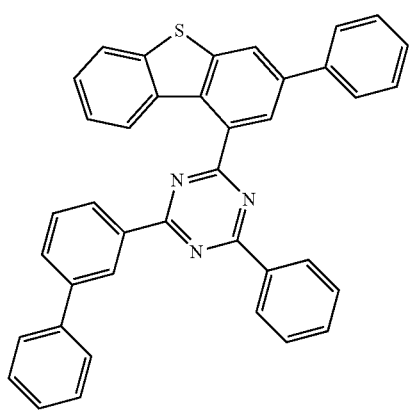

-continued
3-98
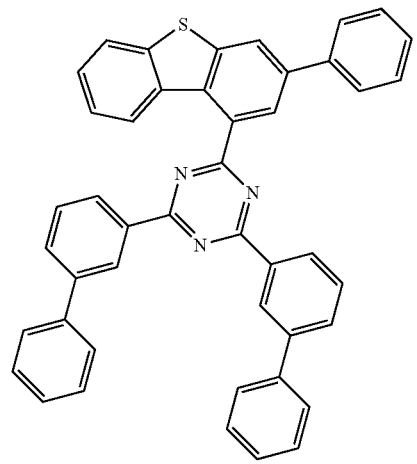
3-99
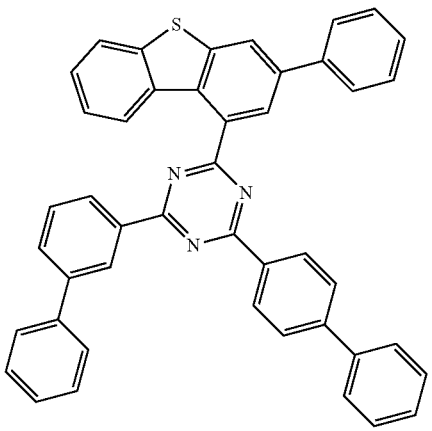
3-100
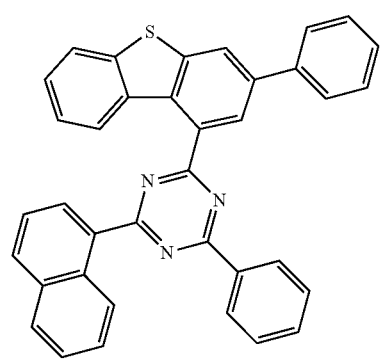
3-101
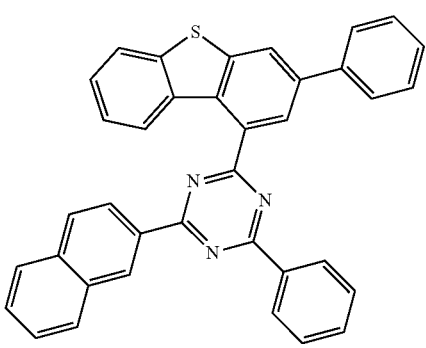
3-102
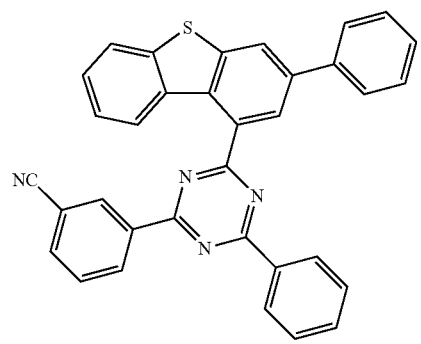
3-103
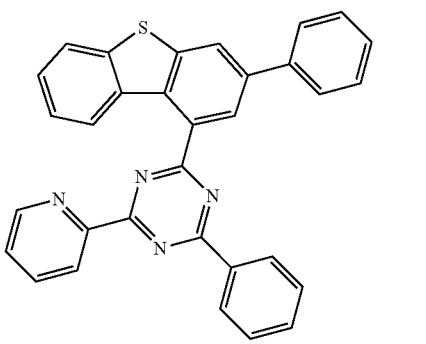
3-104
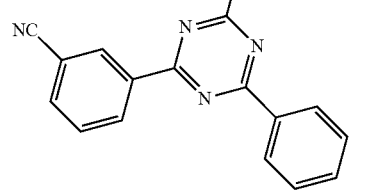
3-105
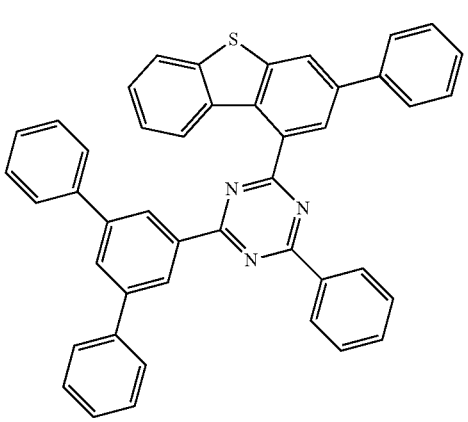

3-106
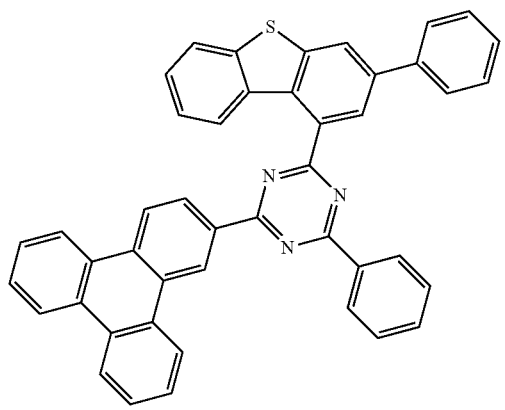
3-107
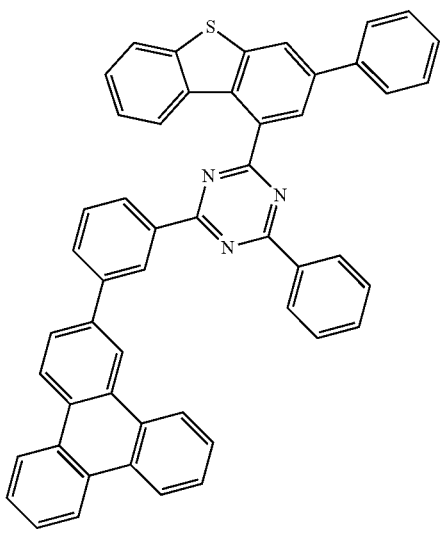
3-108
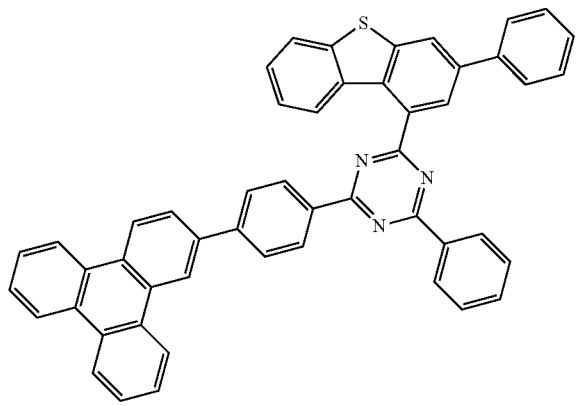
3-109
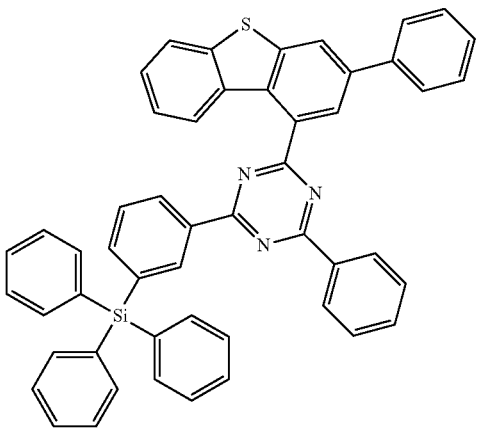
3-110
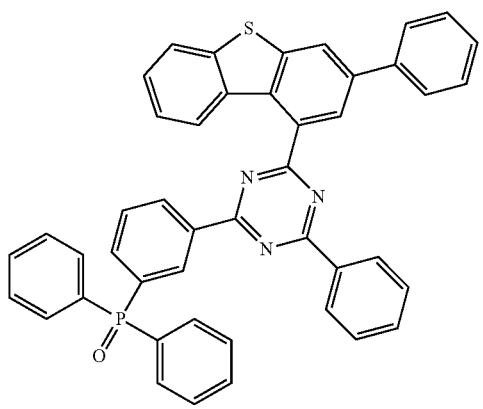
3-111
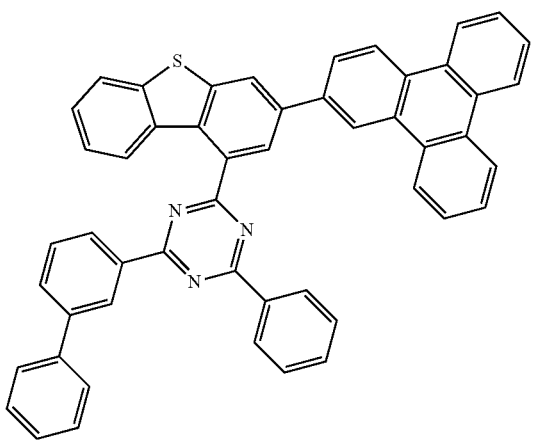

3-112
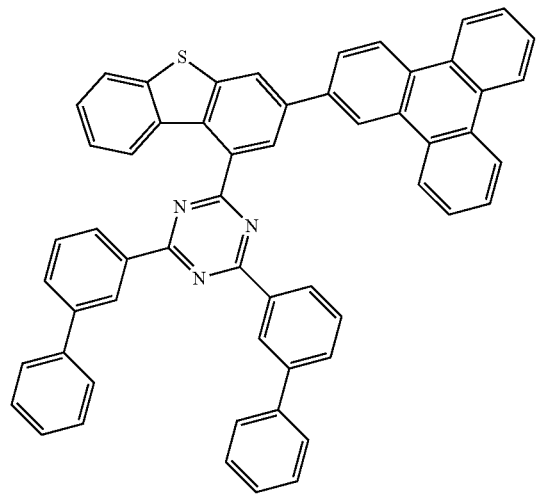
3-113
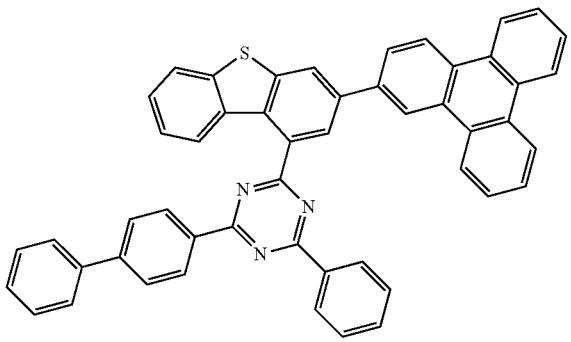
3-114
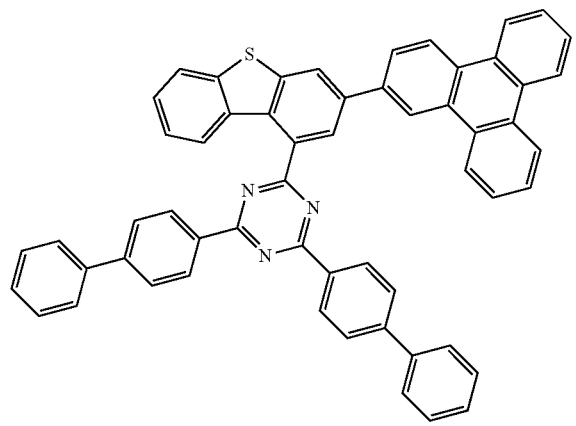
3-115
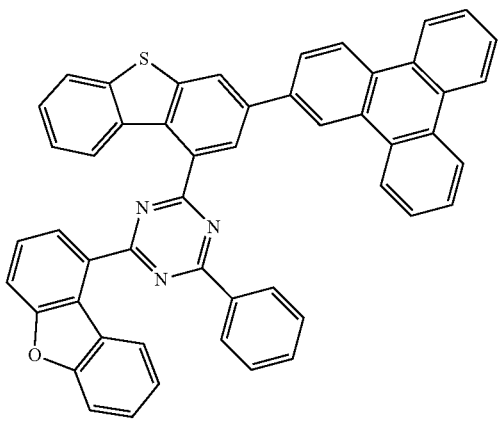
3-116
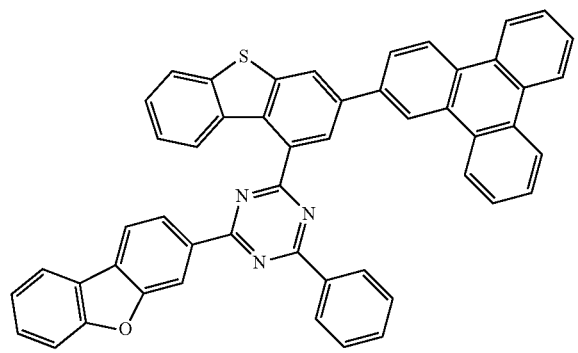
3-117
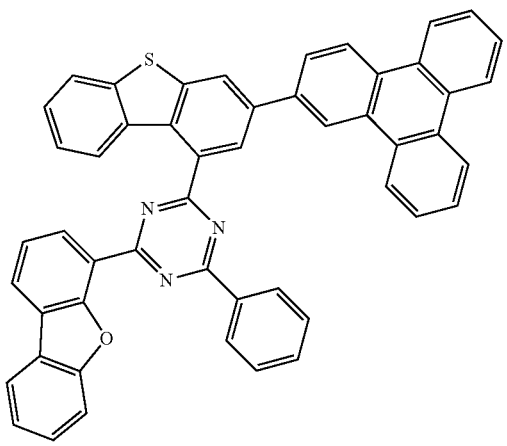

3-118
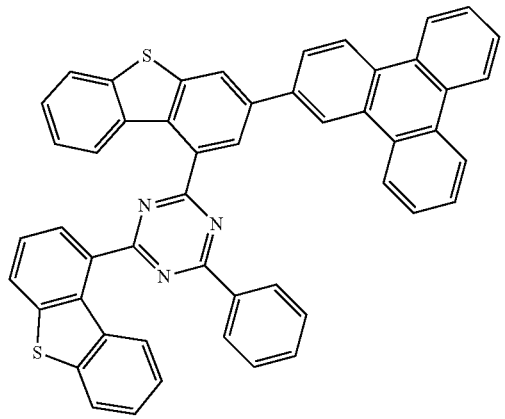
3-119
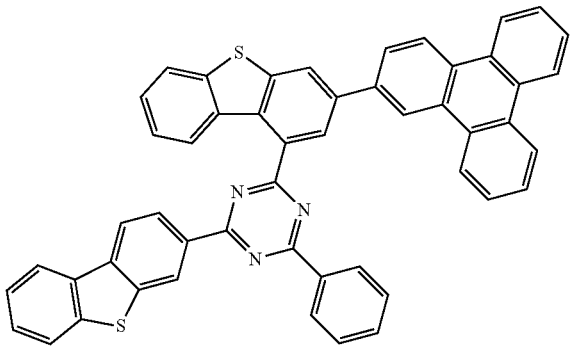
4-1
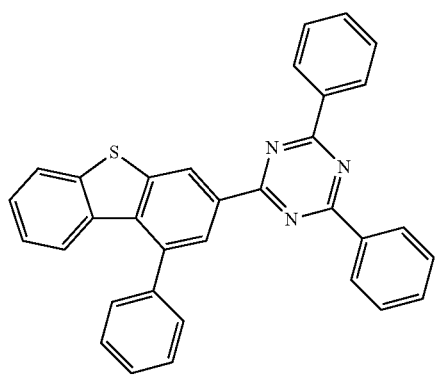
4-2
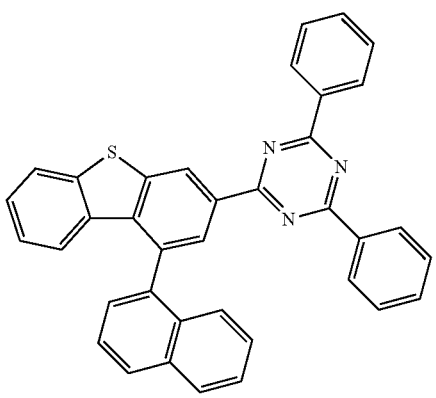
4-3
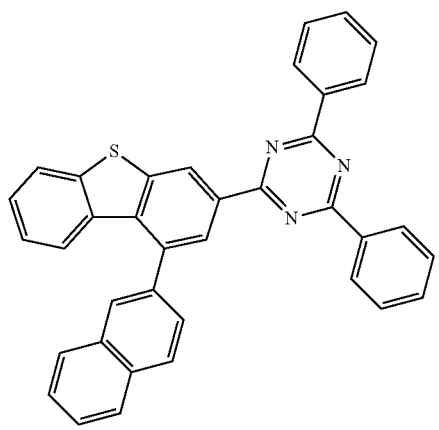
4-4
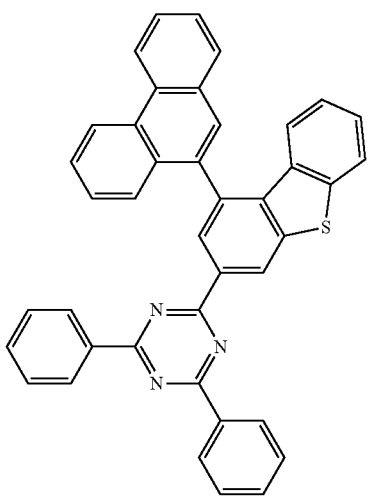

-continued
4-5
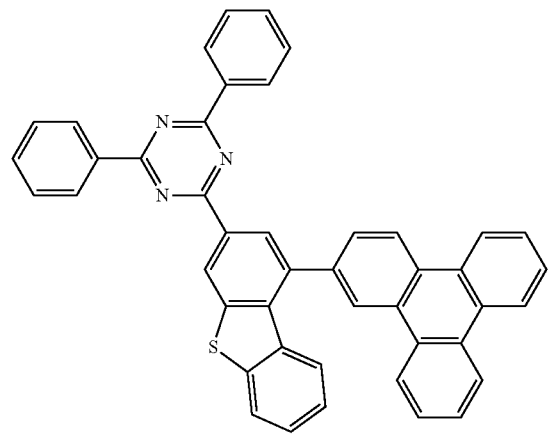
4-6
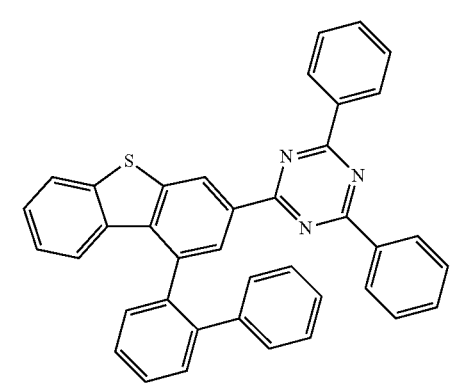
4-7
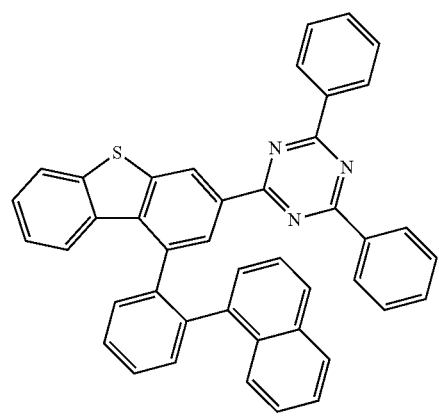
4-8
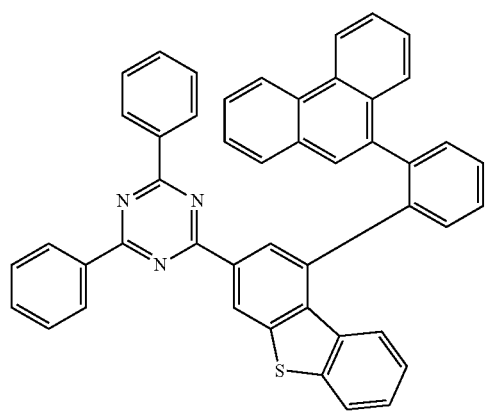
4-9
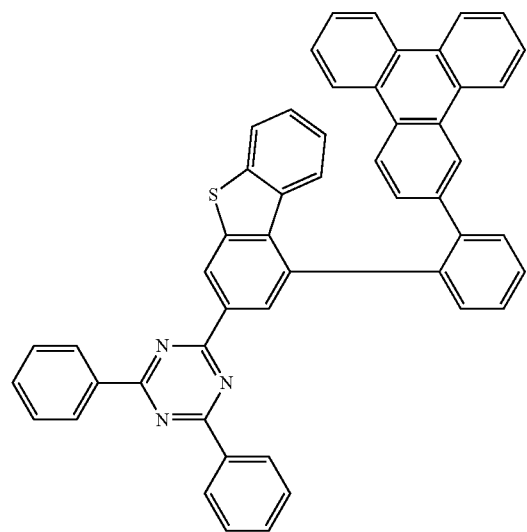
4-10
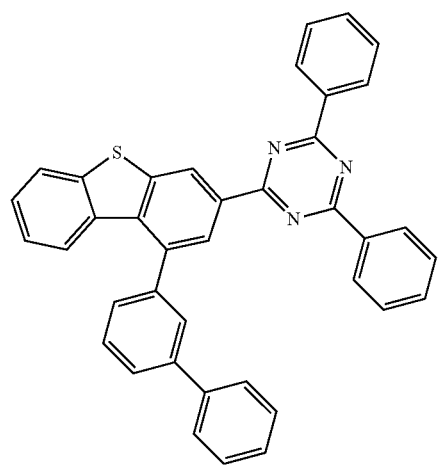

-continued
4-11
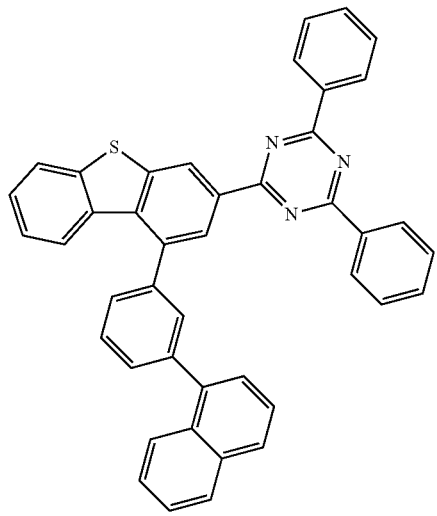
4-12
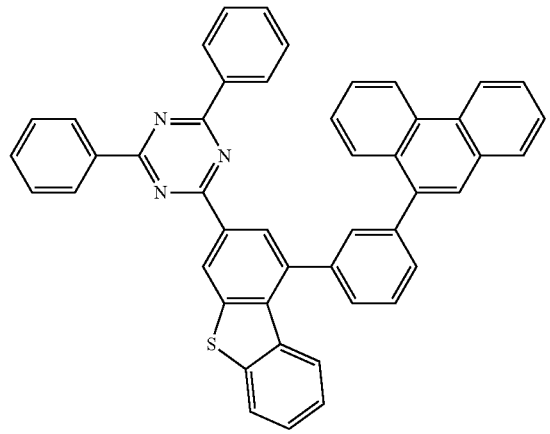
4-17
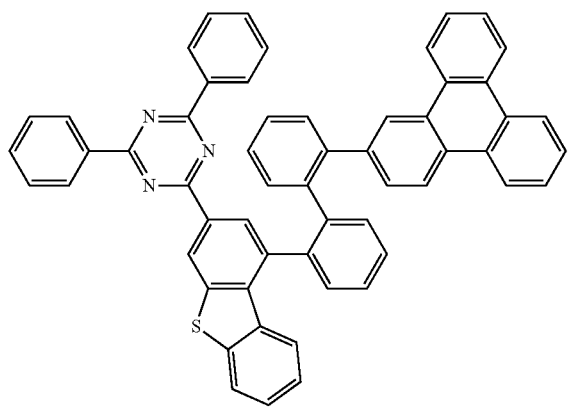
4-18
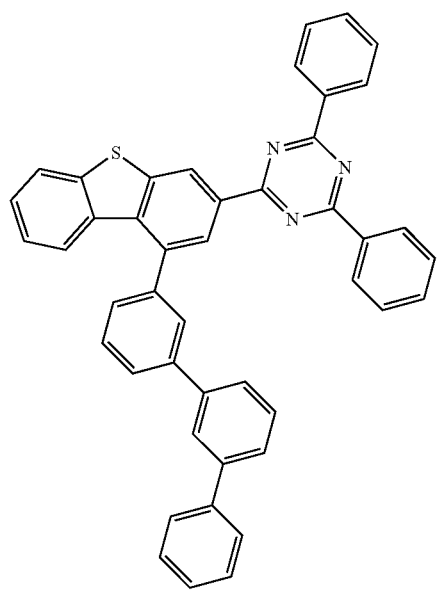
4-13
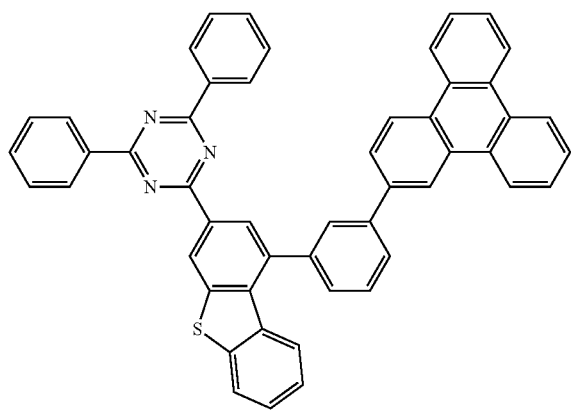
4-14
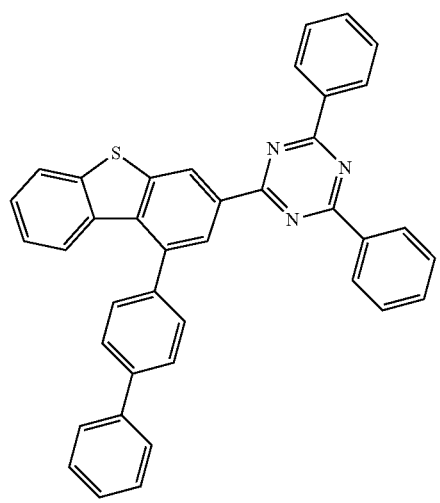

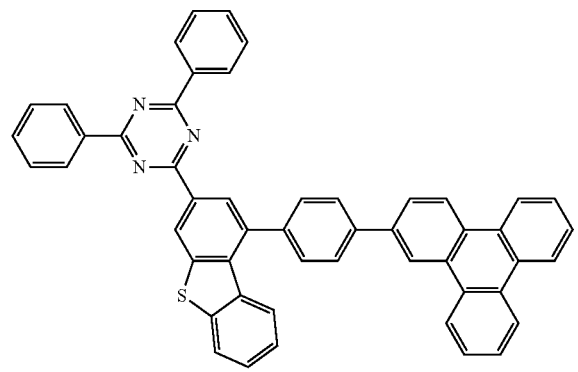
4-15
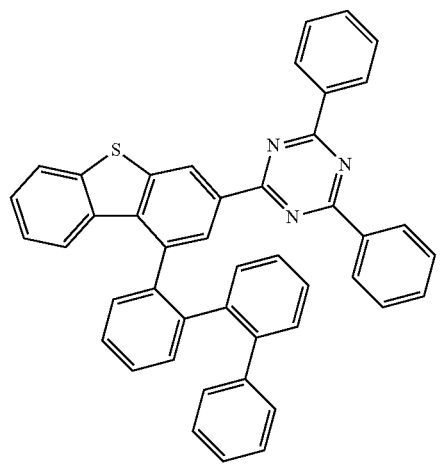
4-16
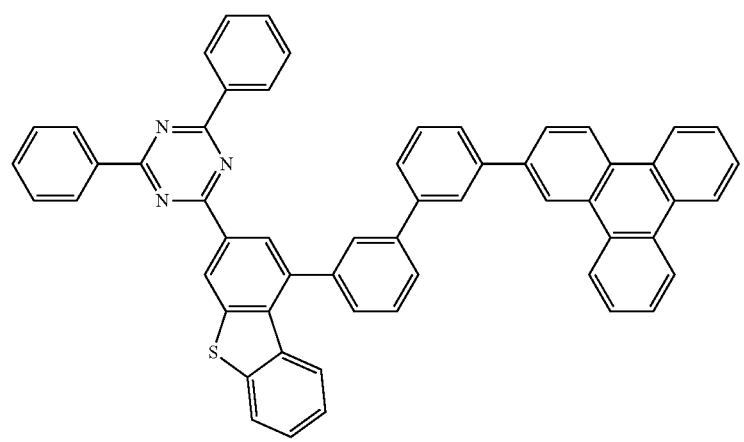
4-19
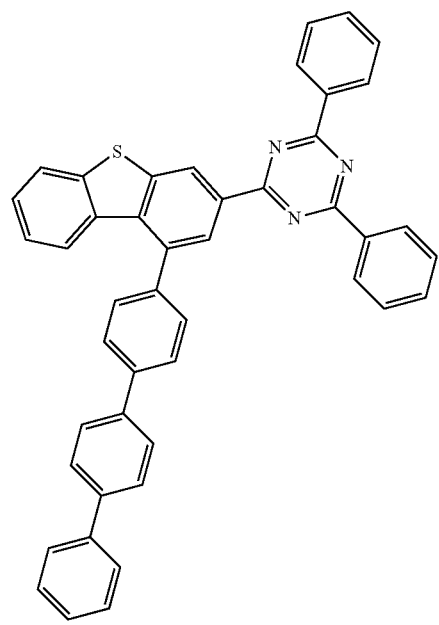
4-20

-continued
4-21
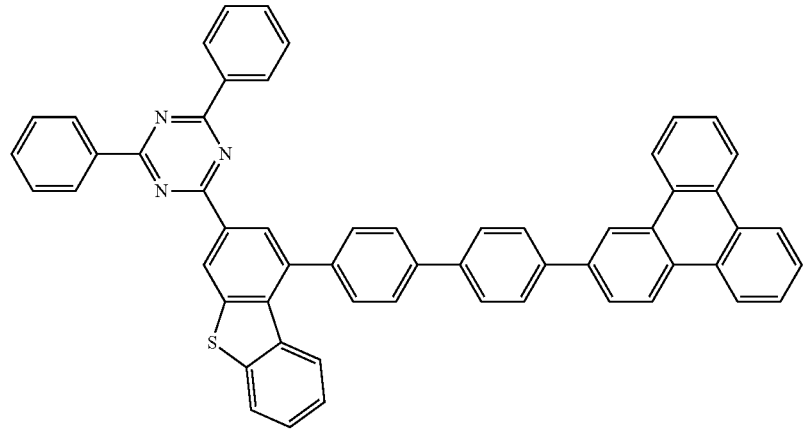
4-22
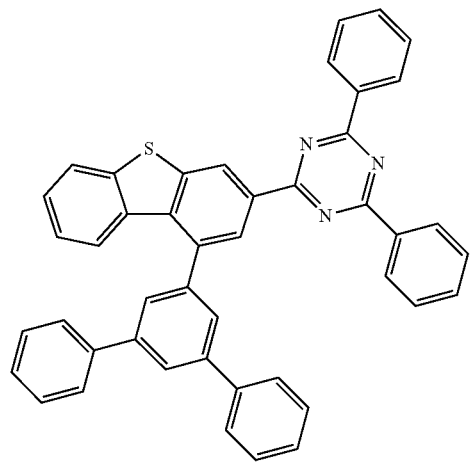
4-23
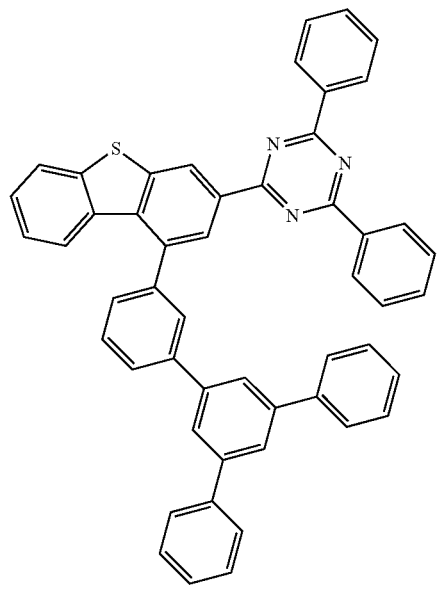
4-24
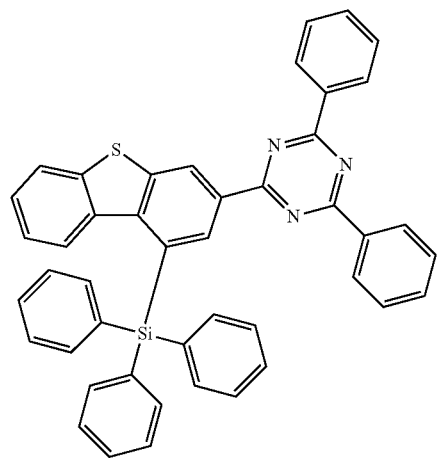
4-25
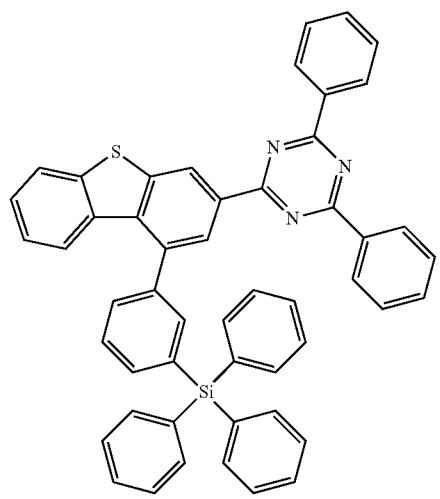

4-26
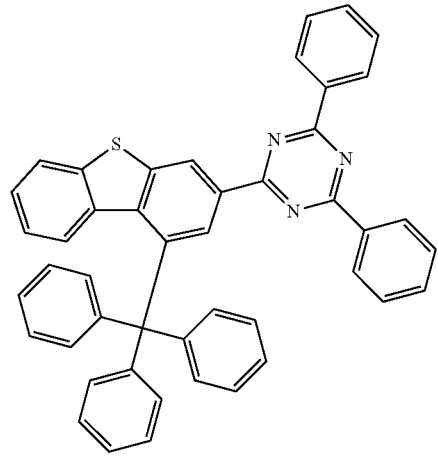
4-27
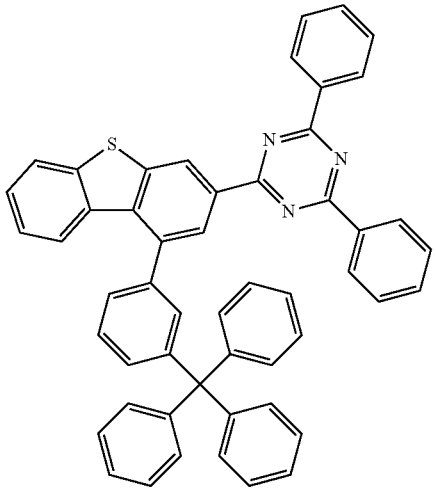
4-28
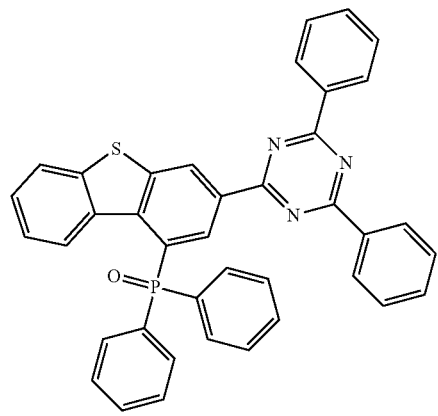
4-29
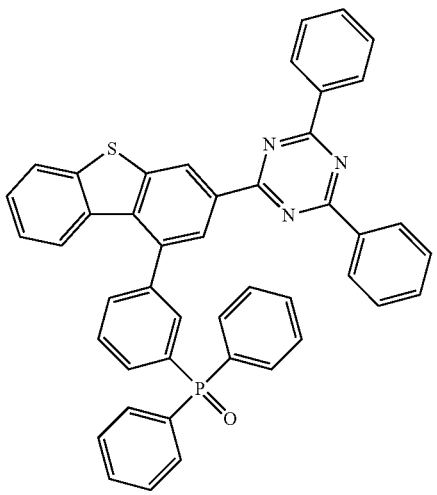
4-30
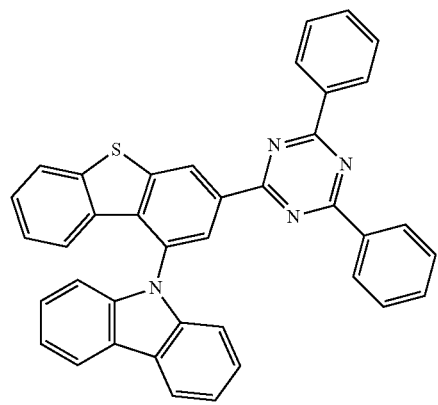
4-31
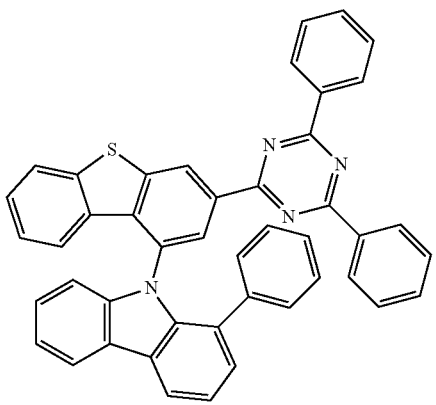

-continued
4-32
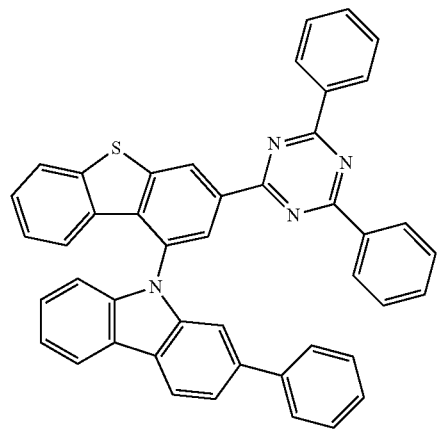
4-33
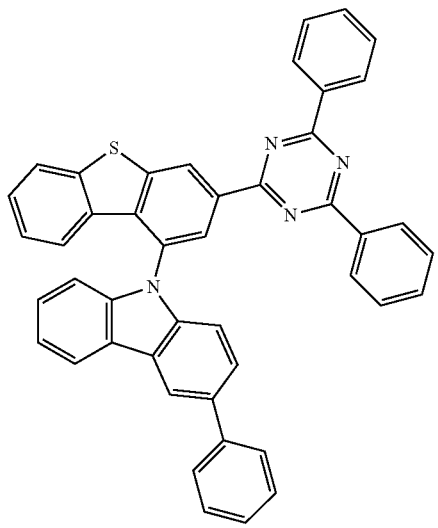
4-34
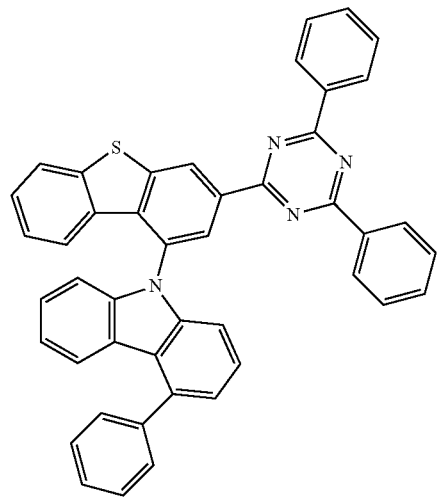
4-35
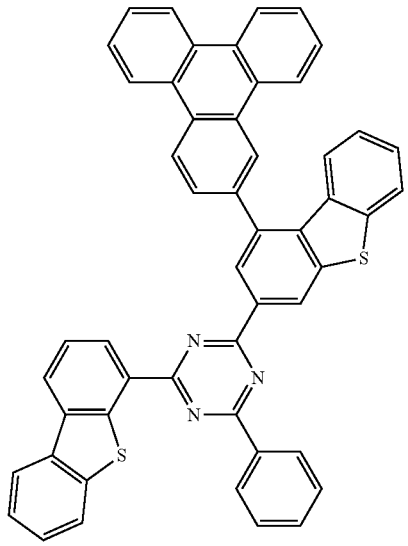
4-36
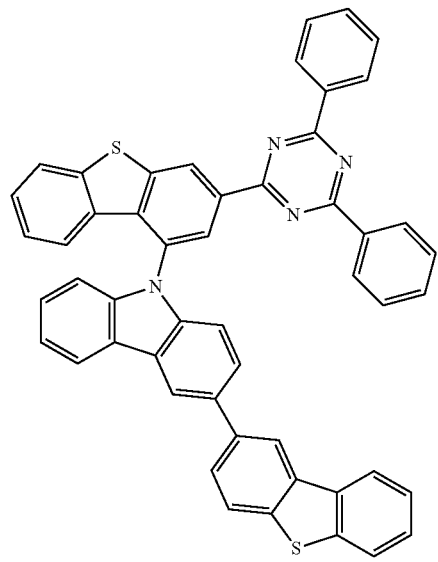
4-37
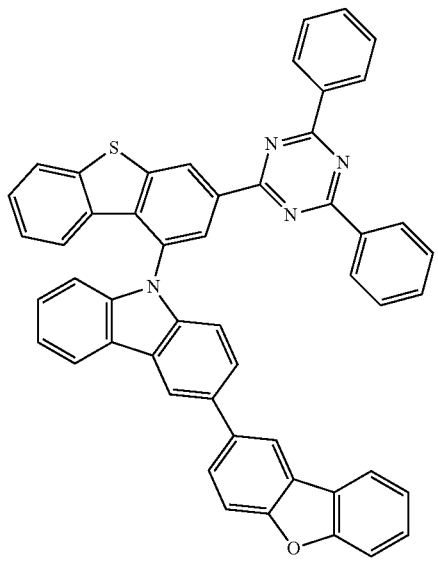

-continued
4-38
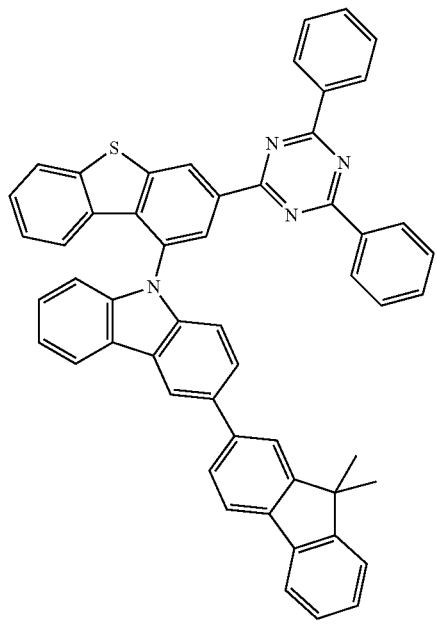
4-39
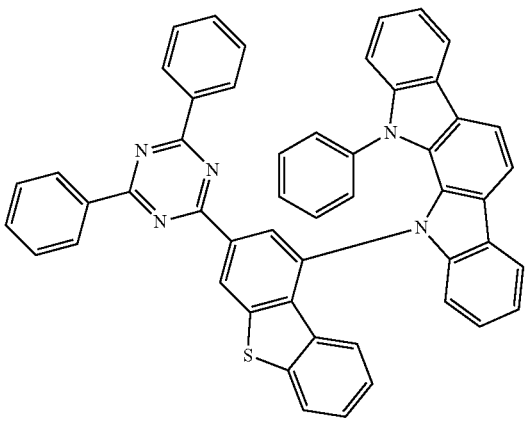
4-40
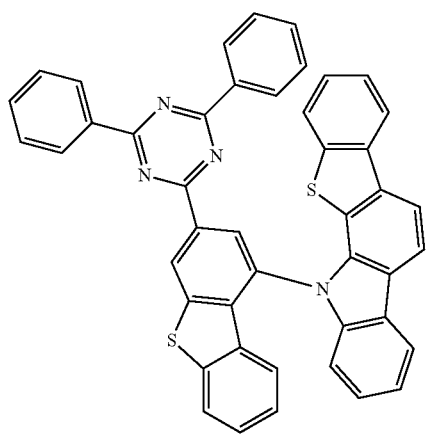
4-41
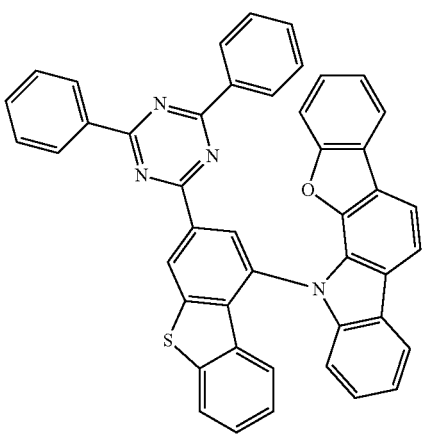
4-42
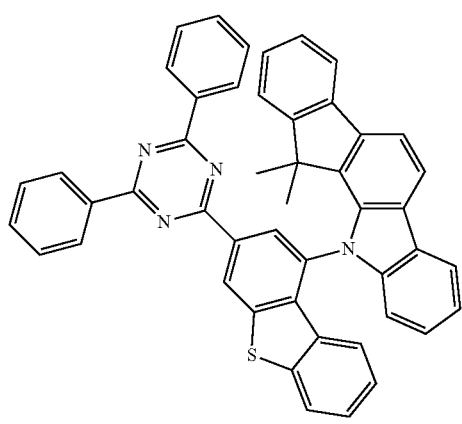
4-43
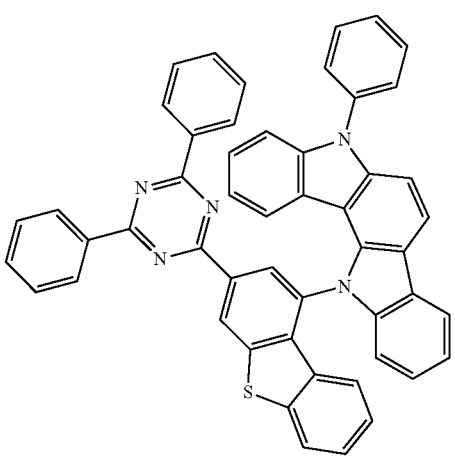

-continued
4-44
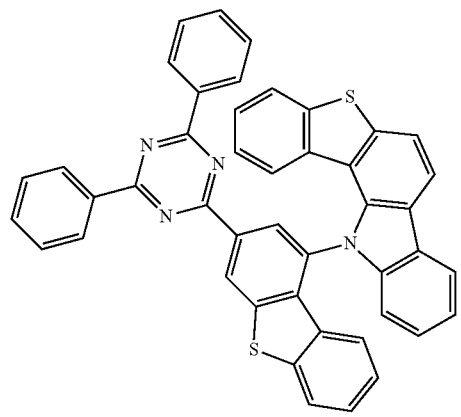
4-45
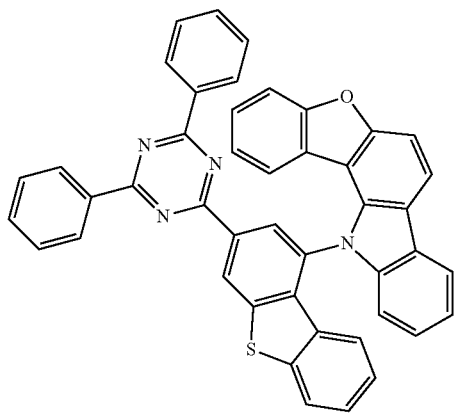
4-46
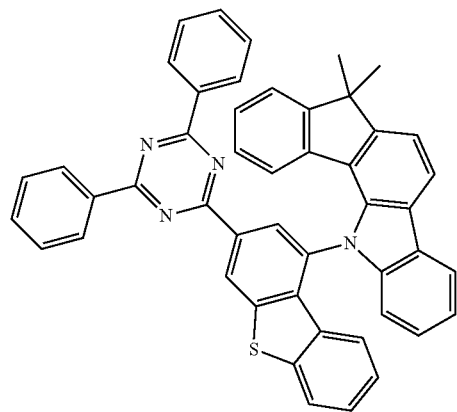
4-47
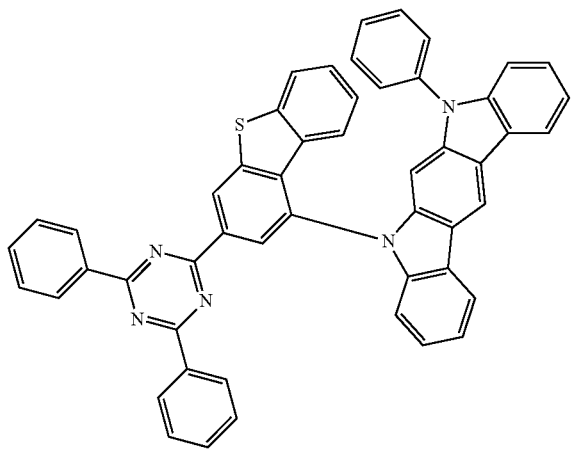
4-48
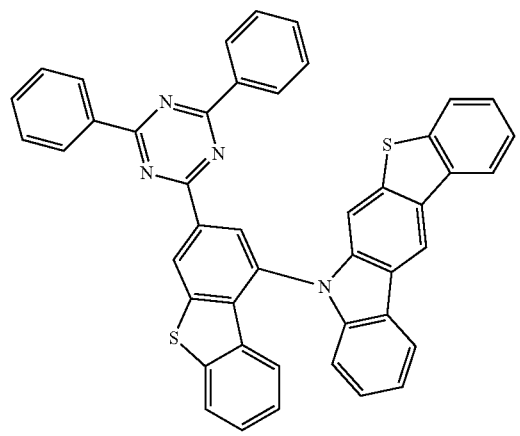
4-49
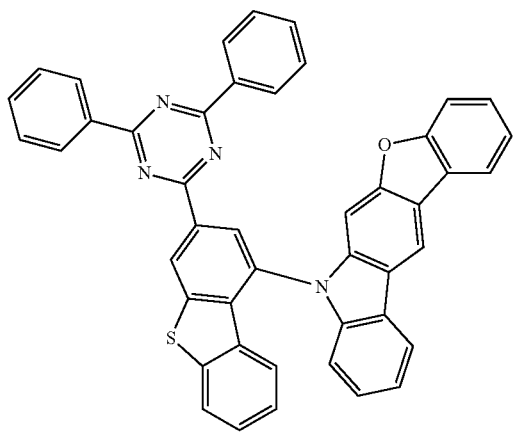

-continued
4-50
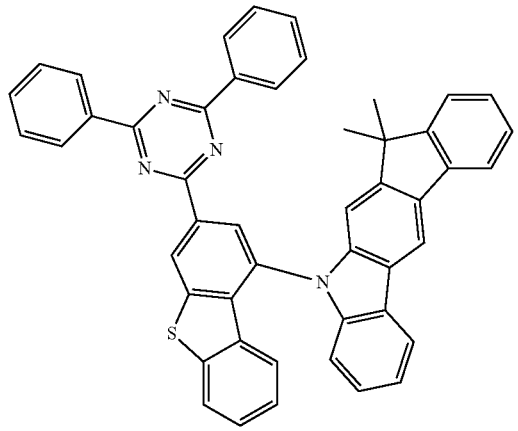
4-51
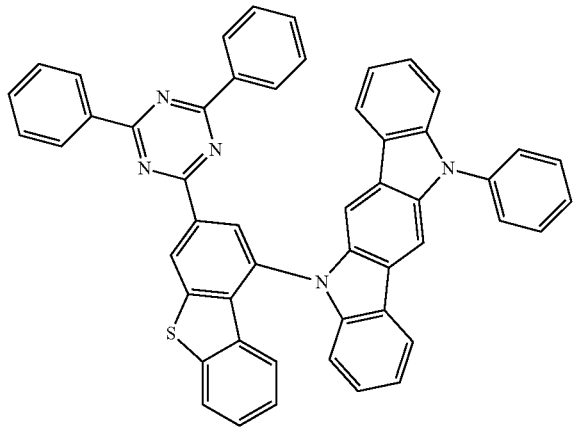
4-52
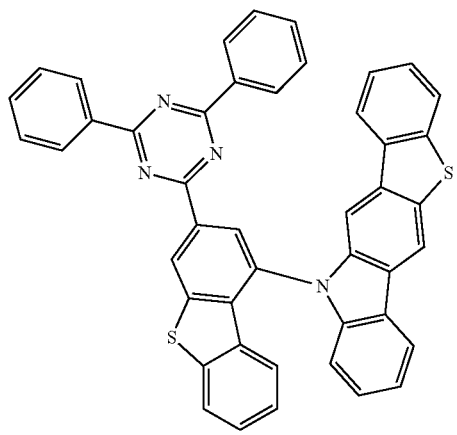
4-53
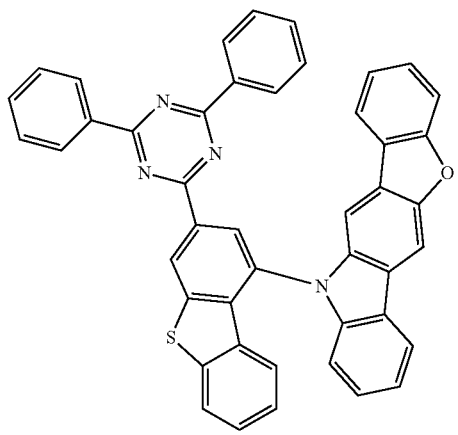
4-54
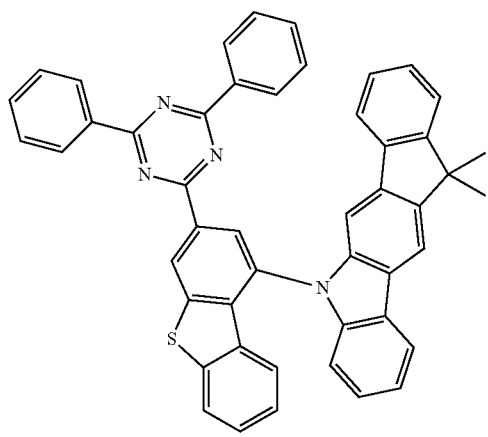
4-55
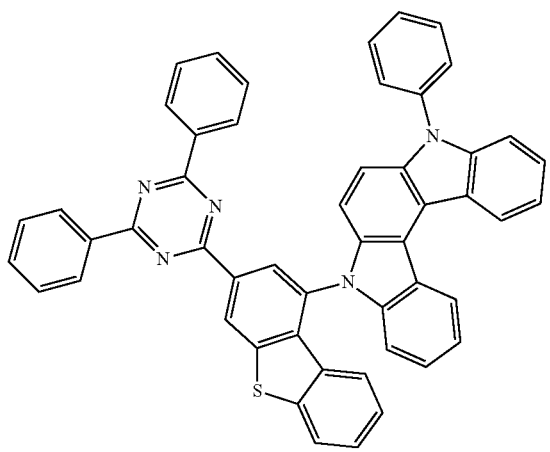

-continued
4-56
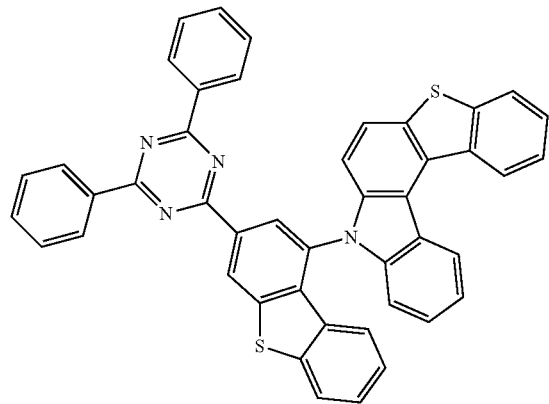
4-57
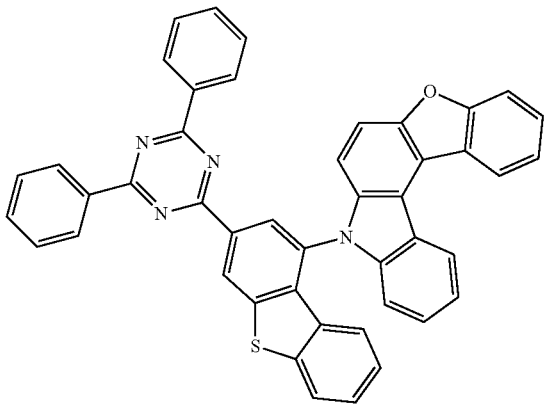
4-58
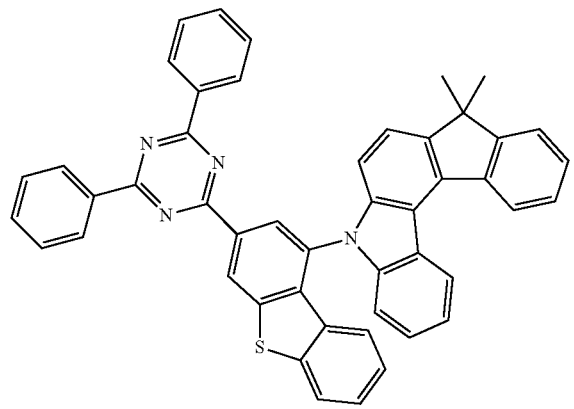
4-59
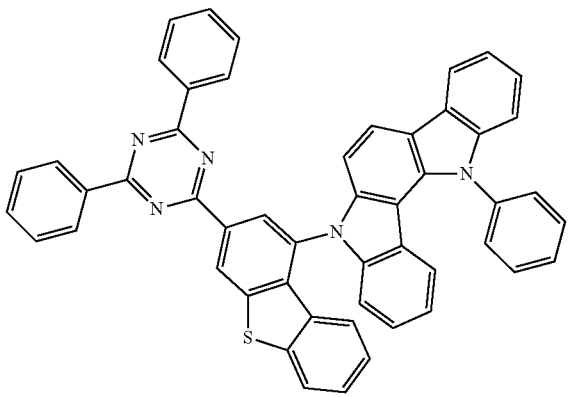
4-60
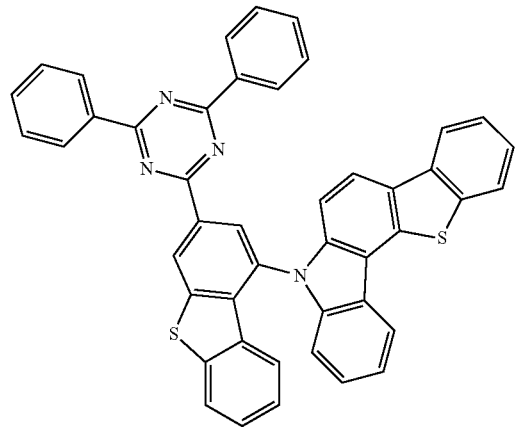
4-61
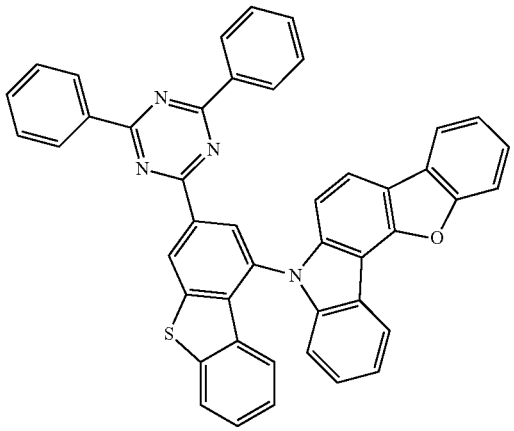

4-62
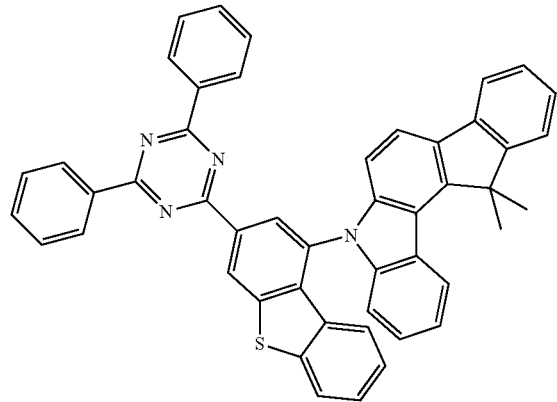
4-63
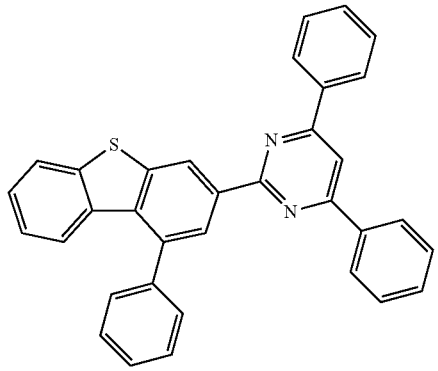
4-64
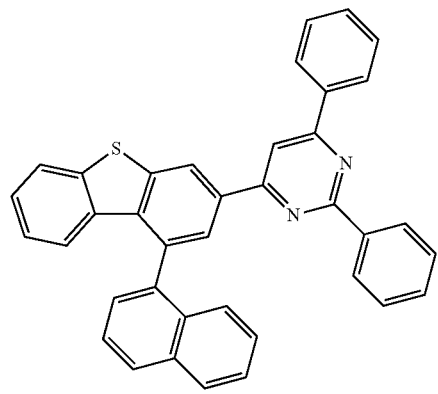
4-65
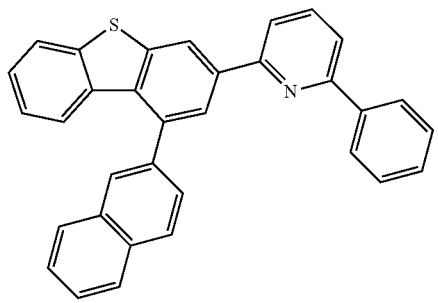
4-66
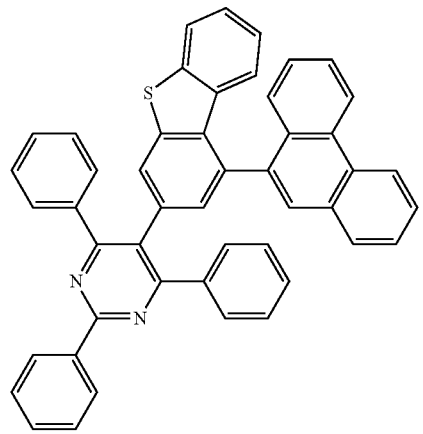
4-67
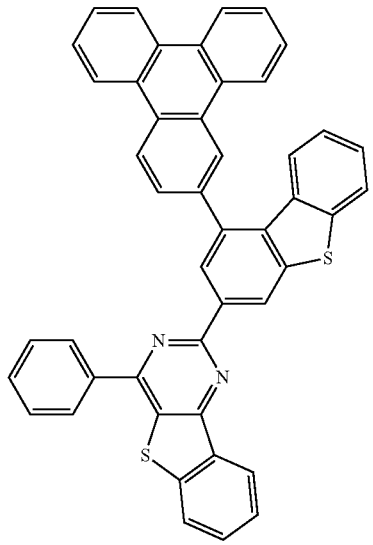

4-68
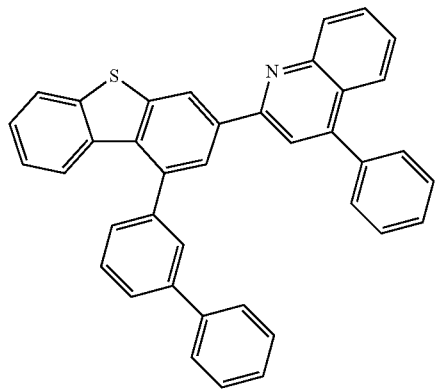
4-69
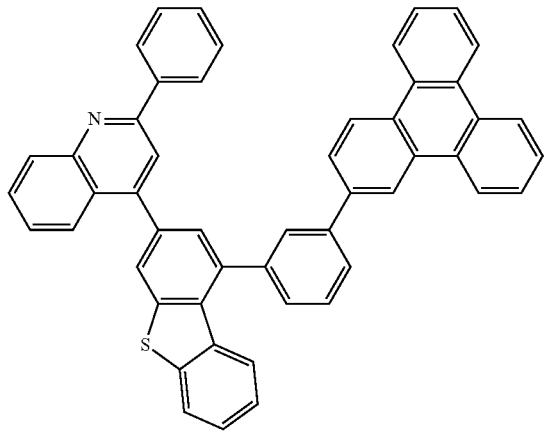
4-70
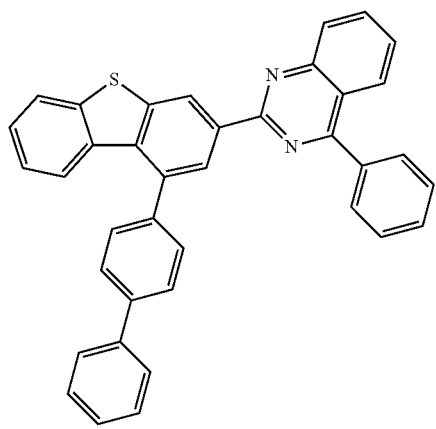
4-71
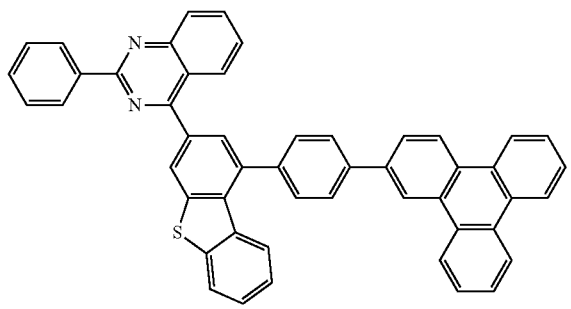
4-72
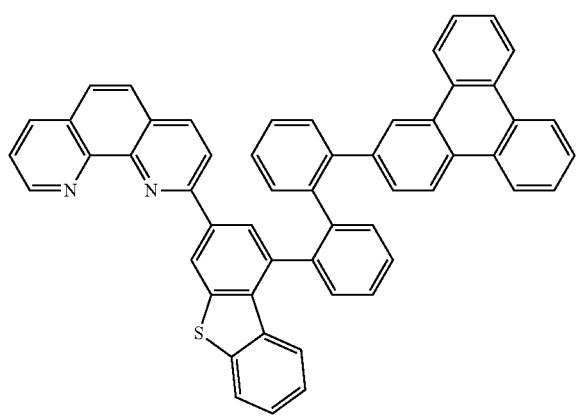
4-73
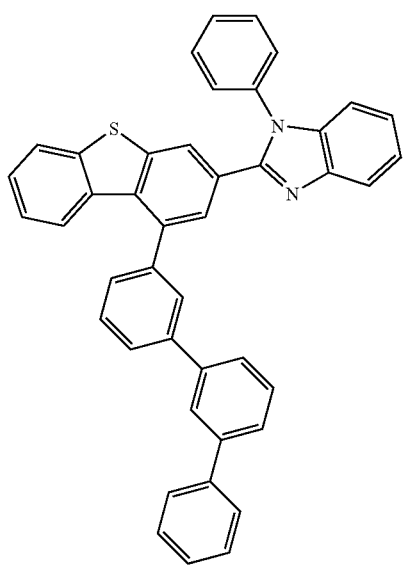

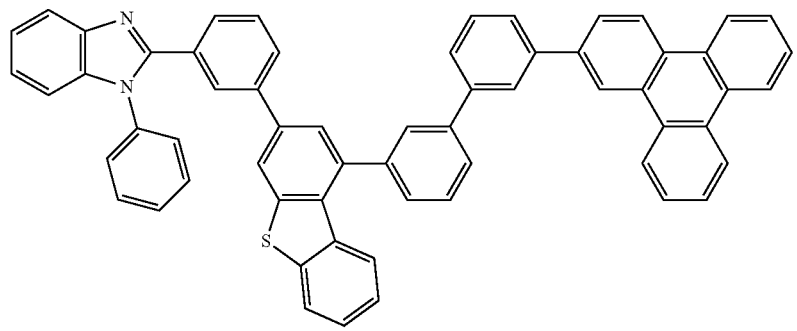
4-74
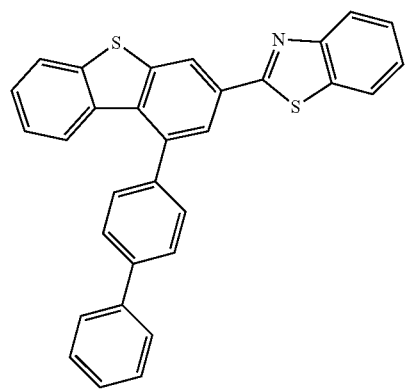
4-75
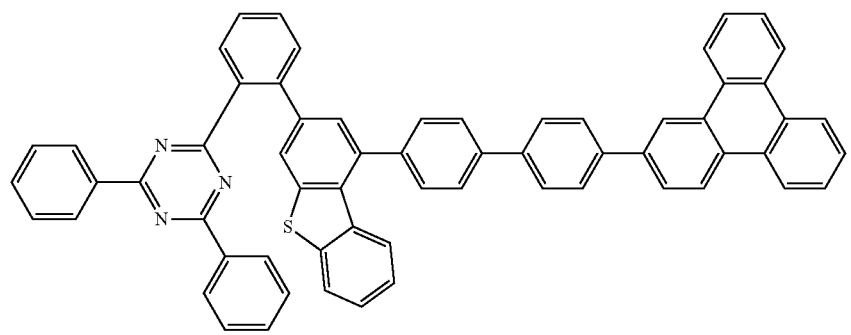
4-76

-continued
4-77
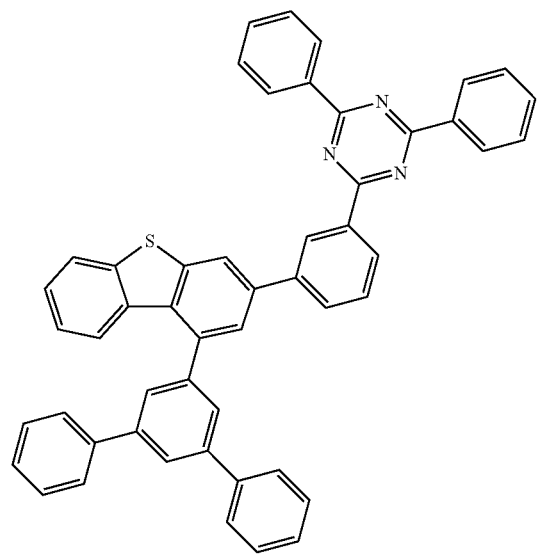
4-78
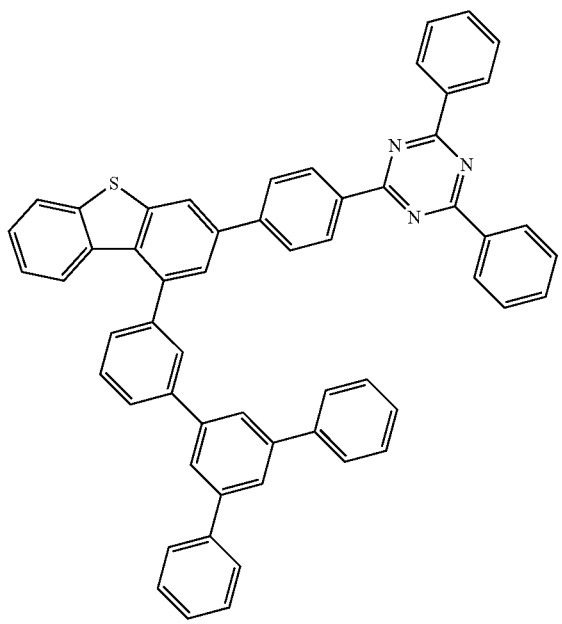
4-79
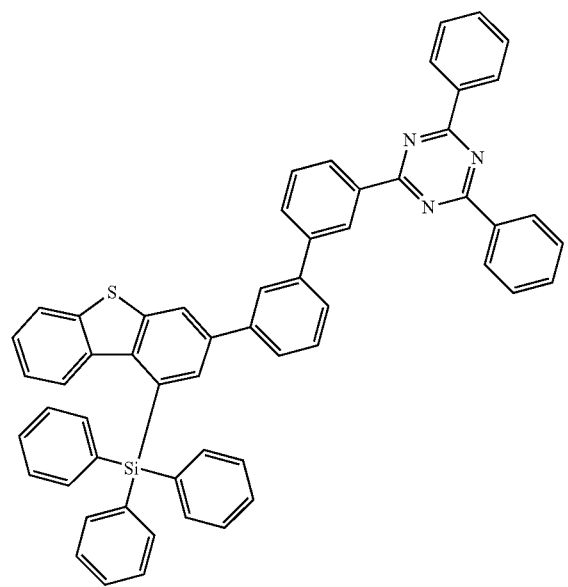
4-80
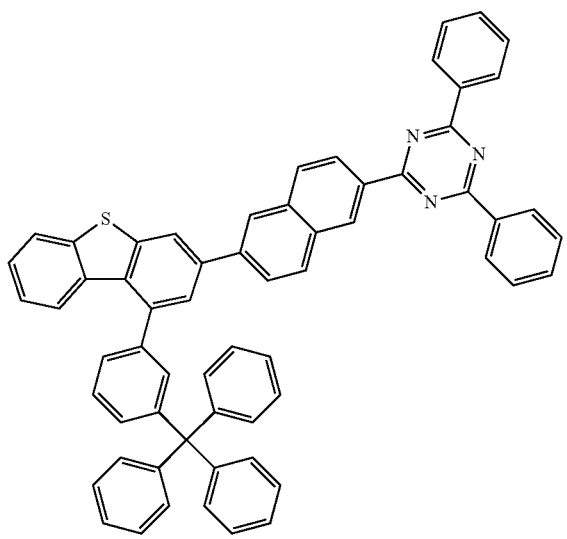

4-81
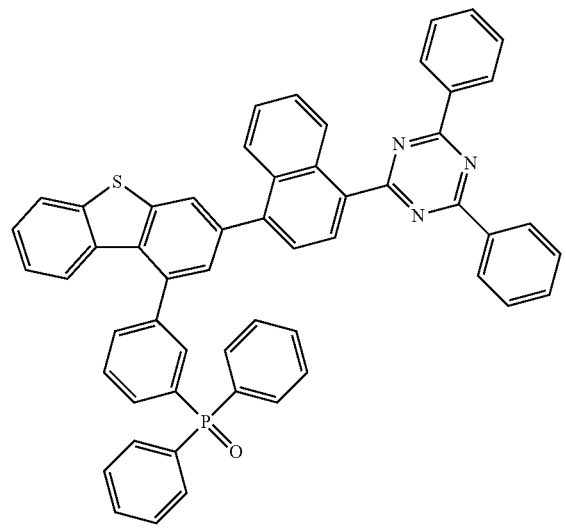
4-82
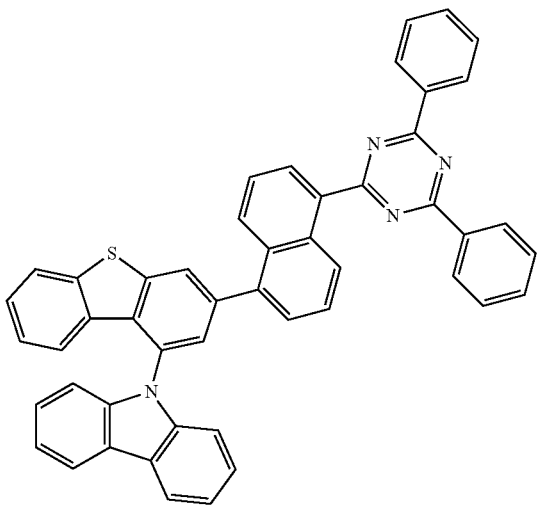
4-83
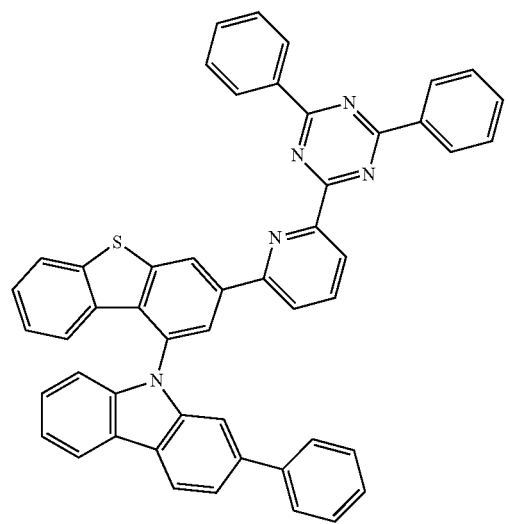
4-84
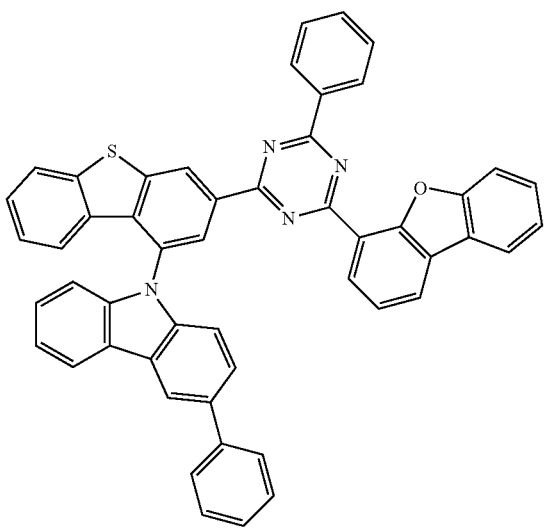

4-85
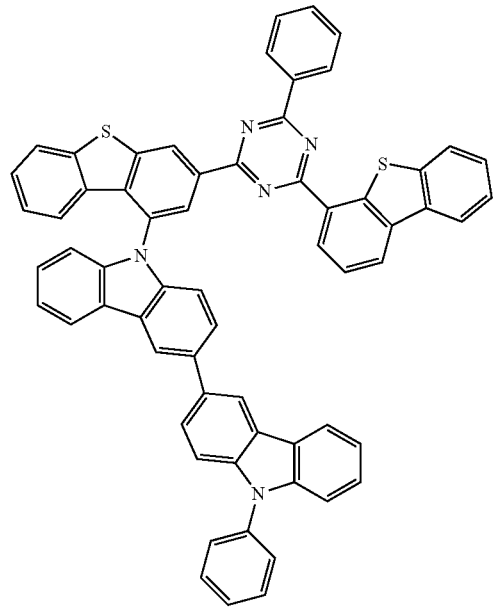
4-86
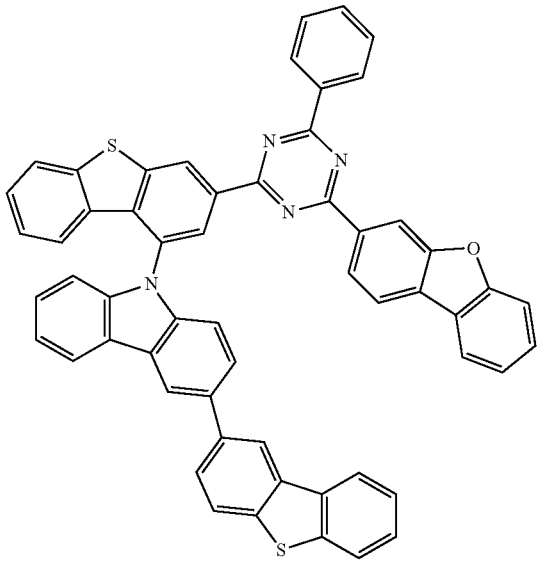
4-87
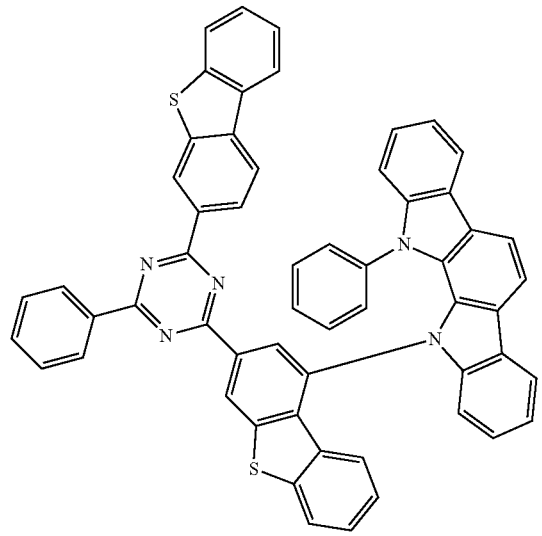
4-88
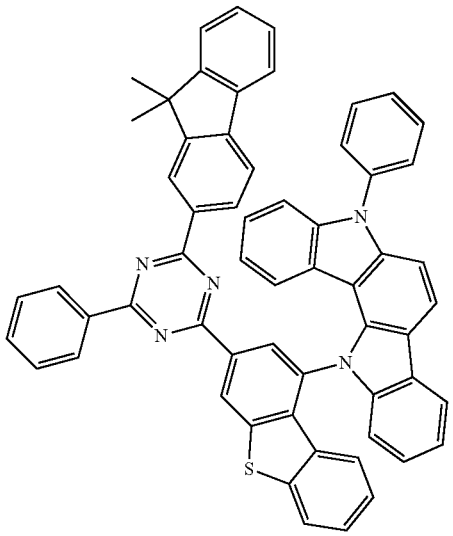

-continued
4-89
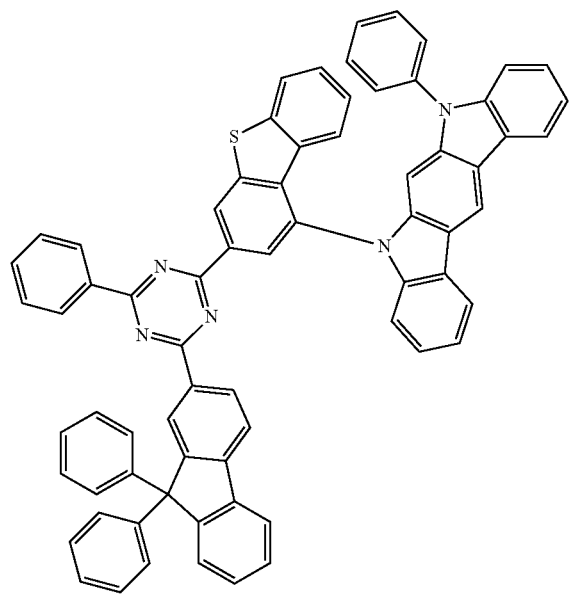
4-90
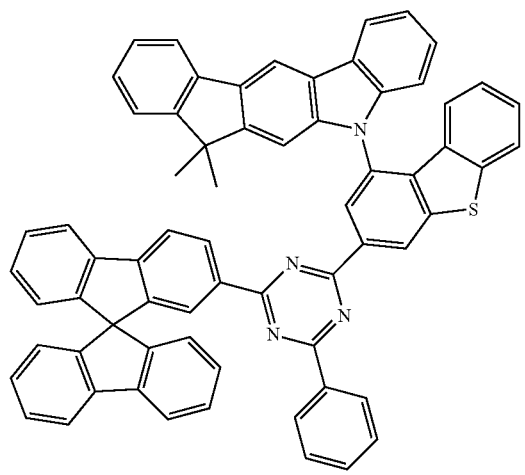
4-91
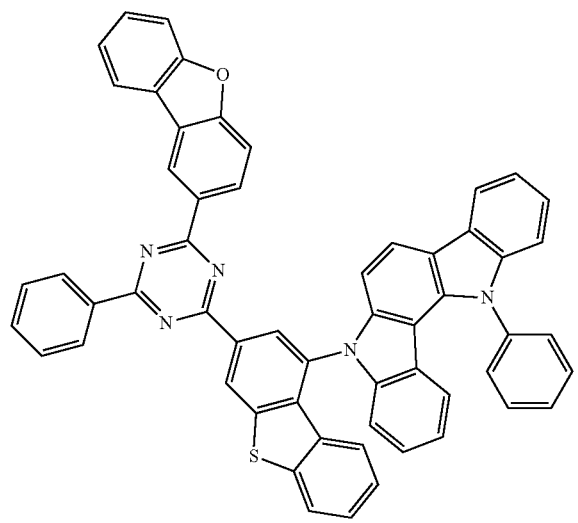
4-92
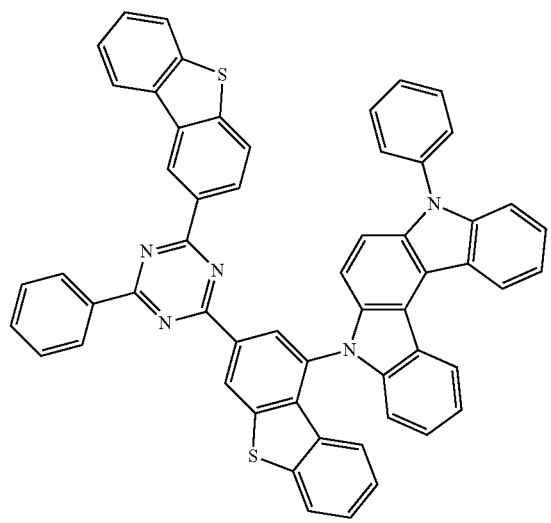
4-93
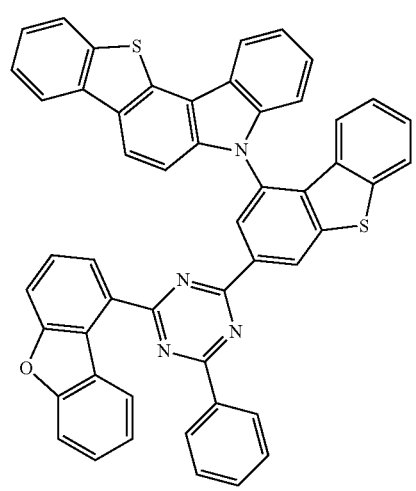
4-94
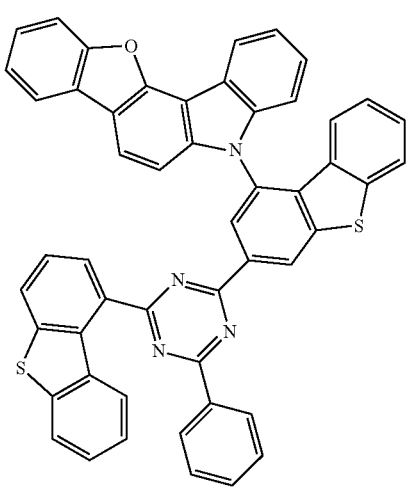

4-95
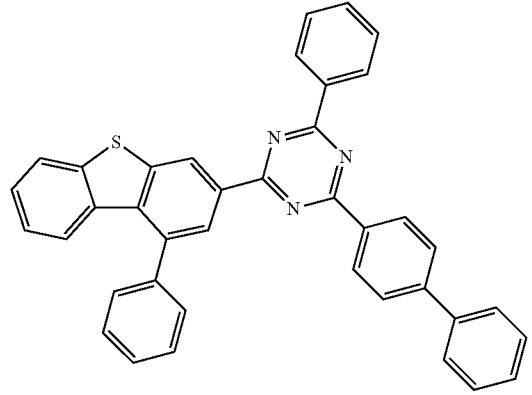
4-96
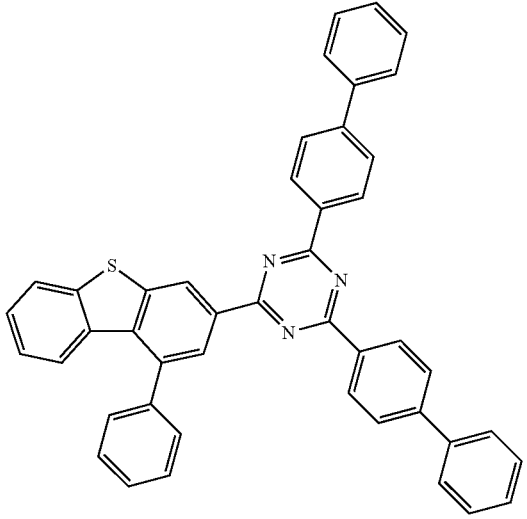
4-97
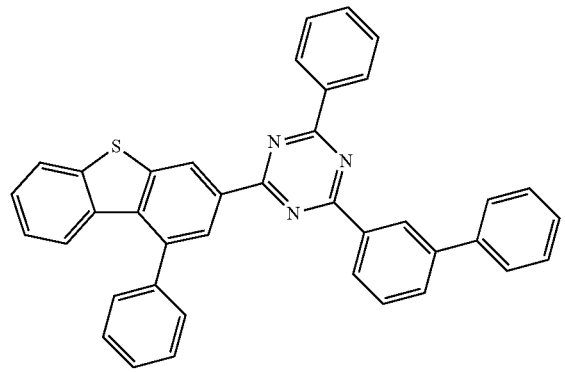
4-98
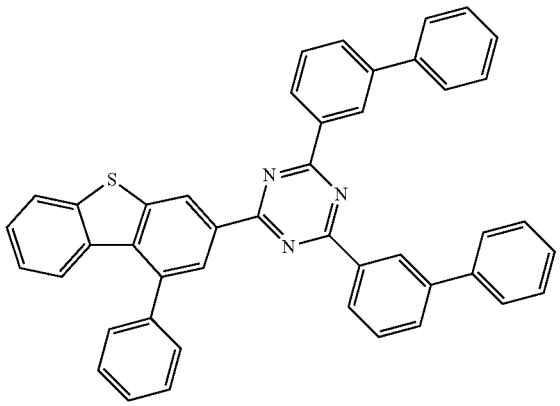
4-99
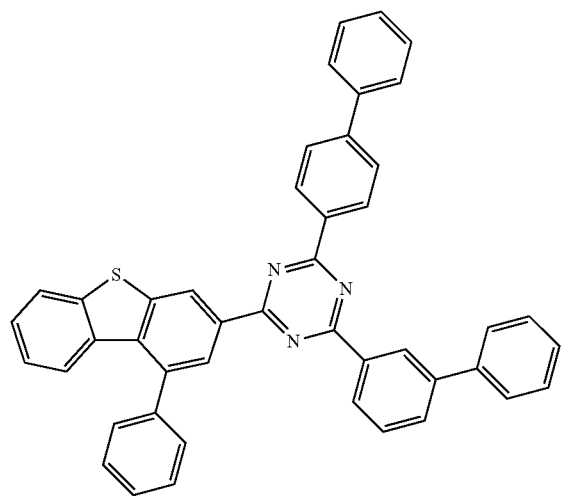
4-100
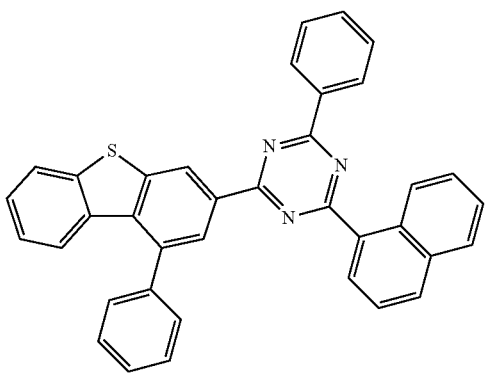

4-101
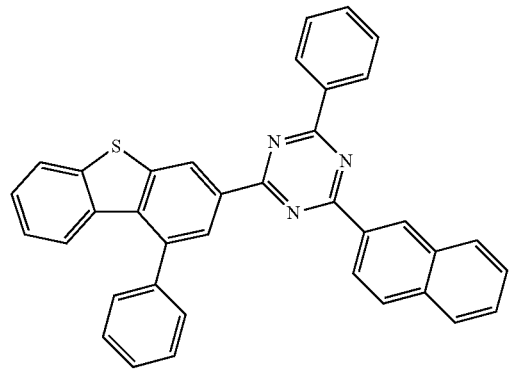
4-102
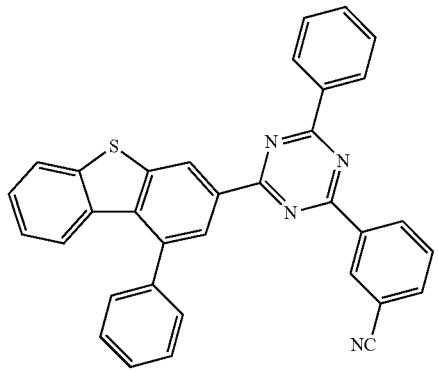
4-103
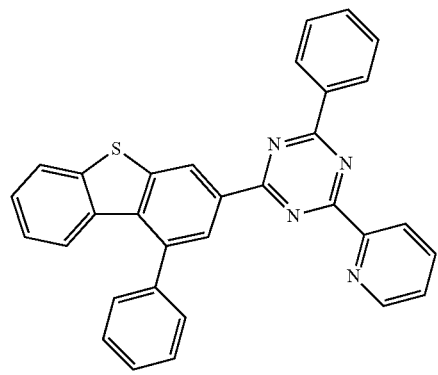
4-104
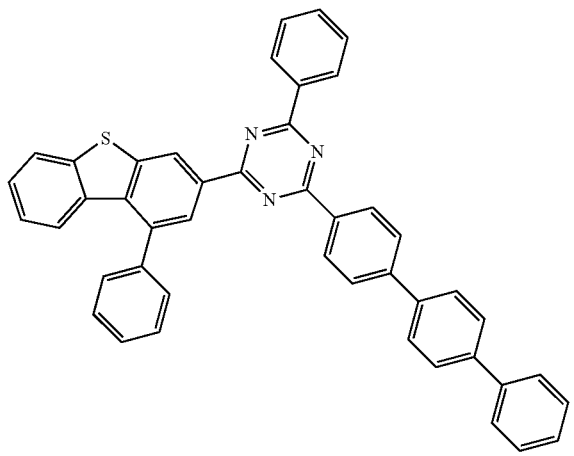
4-105
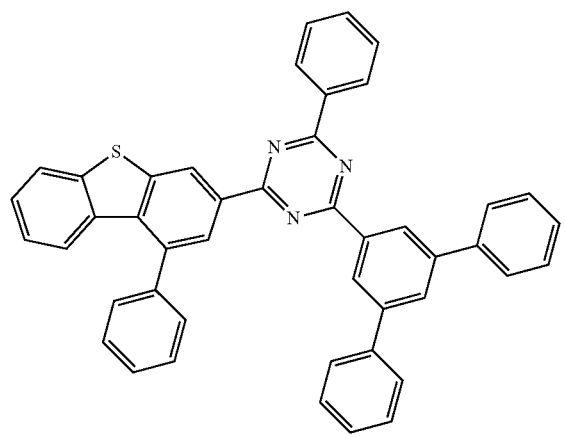
4-106
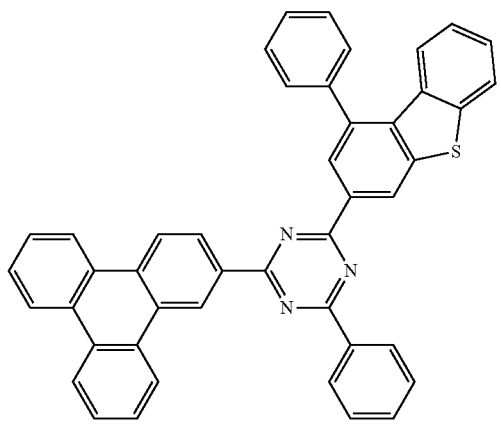

-continued
4-107
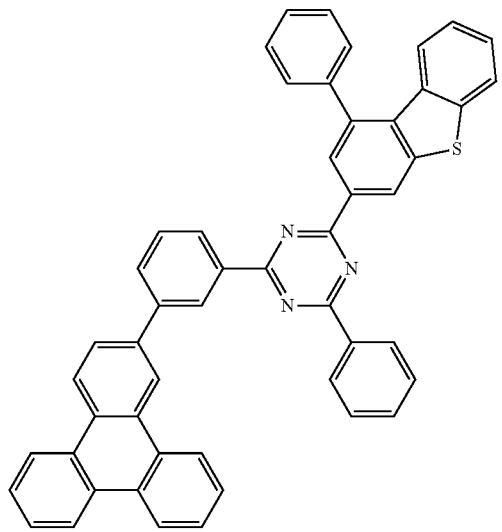
4-108
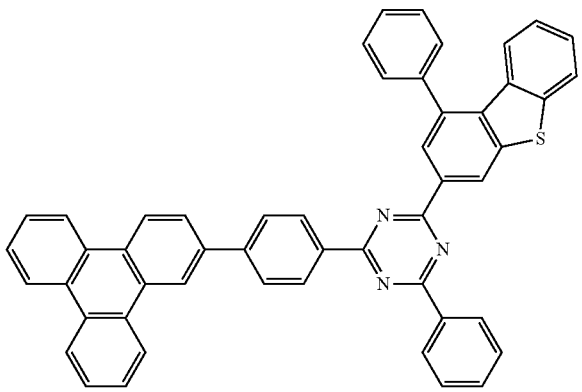
4-109
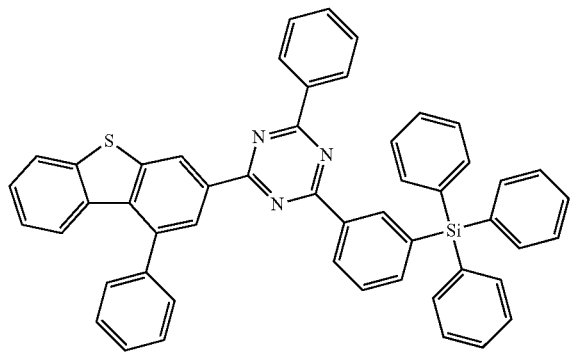
4-110
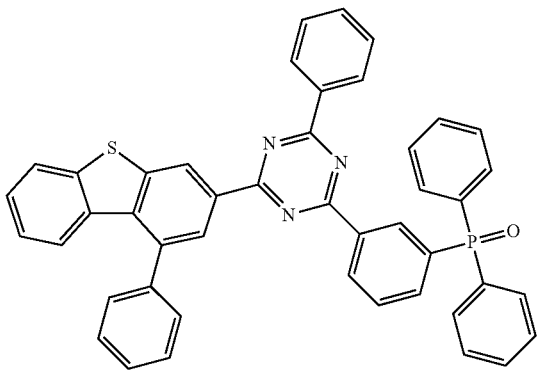
4-111
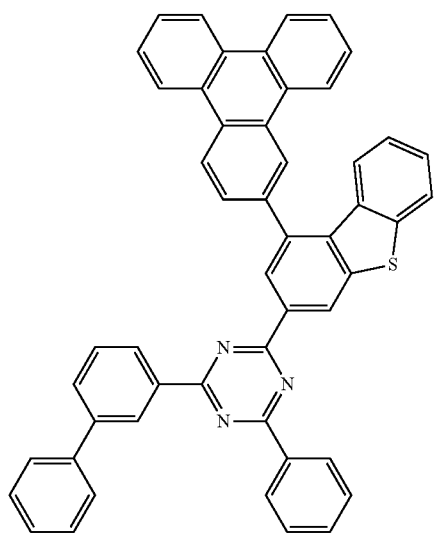
4-112
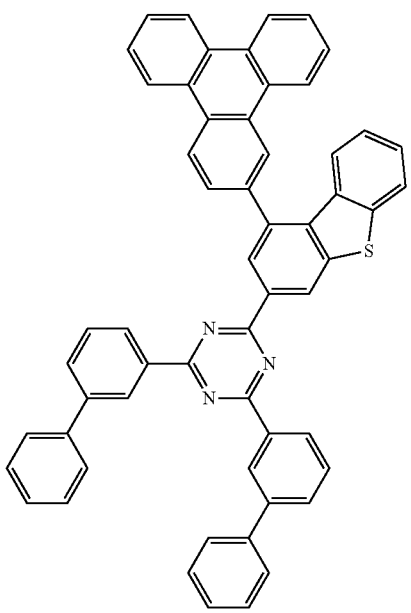 [SMILES: c1ccc(-c2cccc(-c3nc(-c4cccc(-c5ccccc5)c4)nc(-c4cc(-c5ccc6c7ccccc7c7ccccc7c6c5)c5c(c4)oc4ccccc45)n3)c2)cc1]

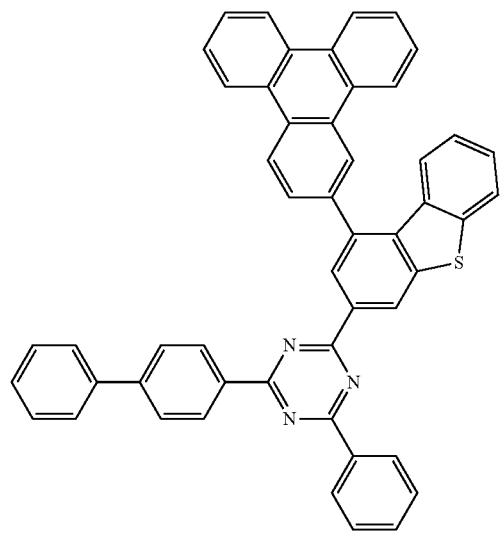
4-113
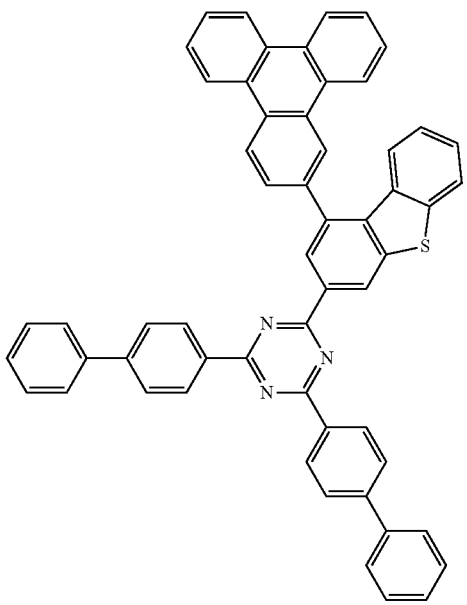
4-114
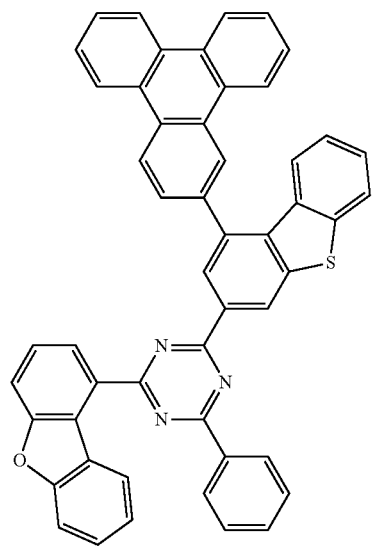
4-115
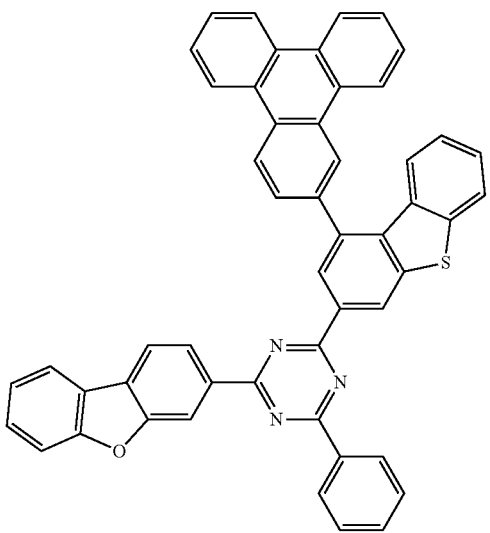
4-116

-continued
4-117
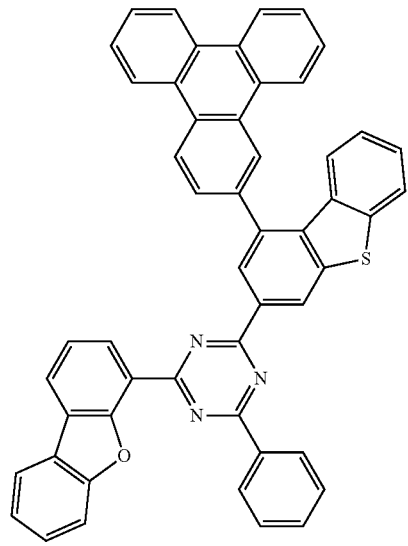
4-118
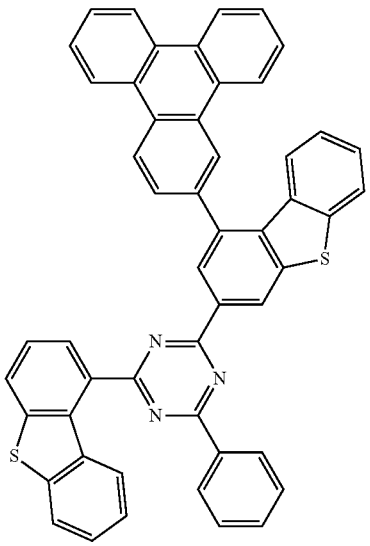
4-119
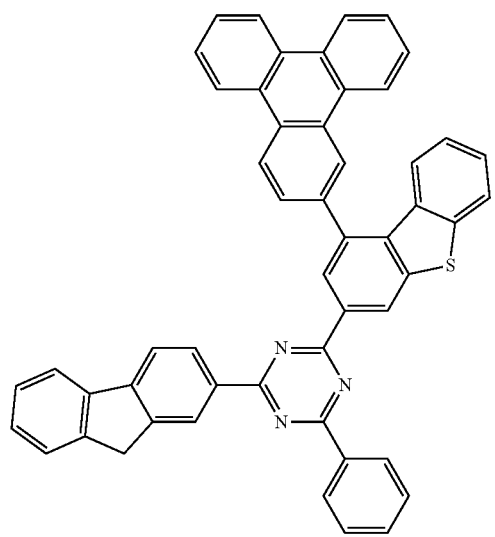
4-120
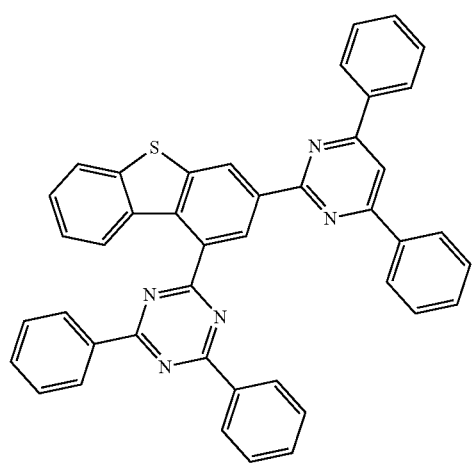
4-121
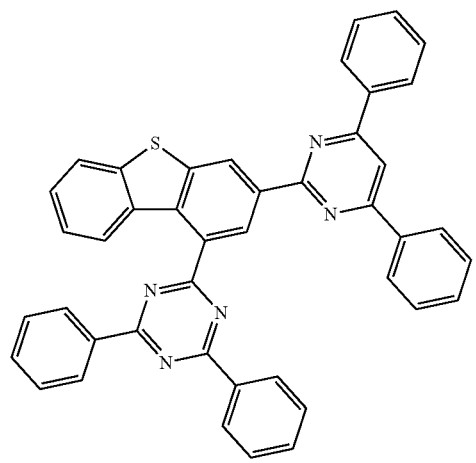
4-122
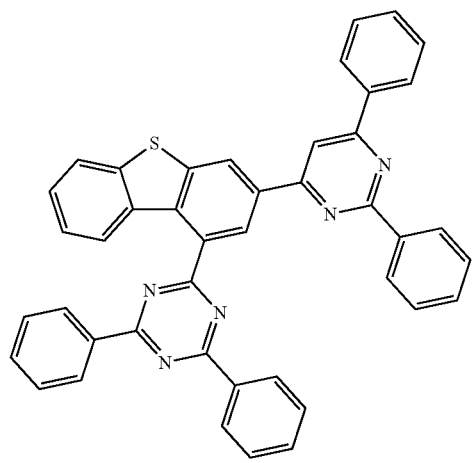

-continued
4-123
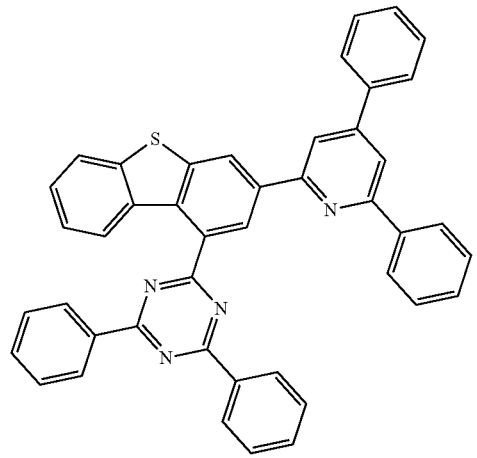
4-124
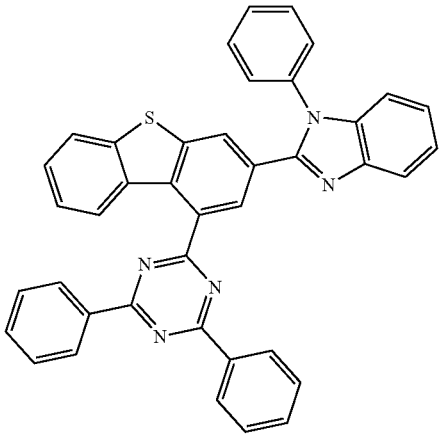
4-125
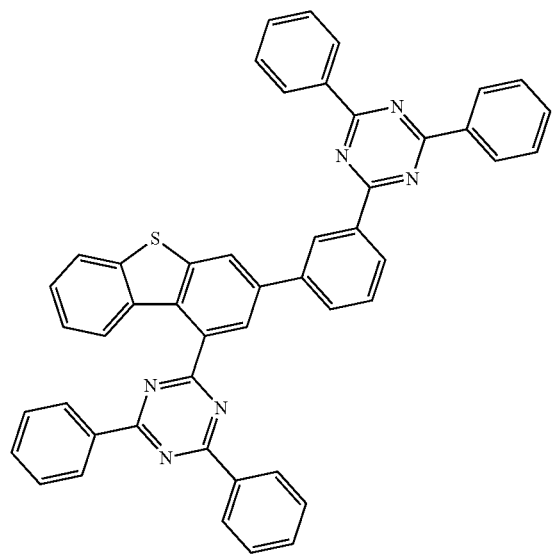
4-126
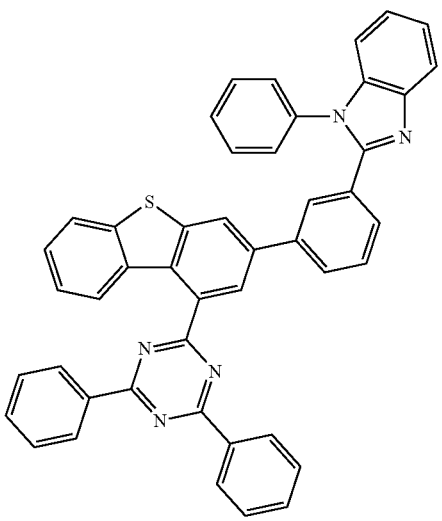
4-127
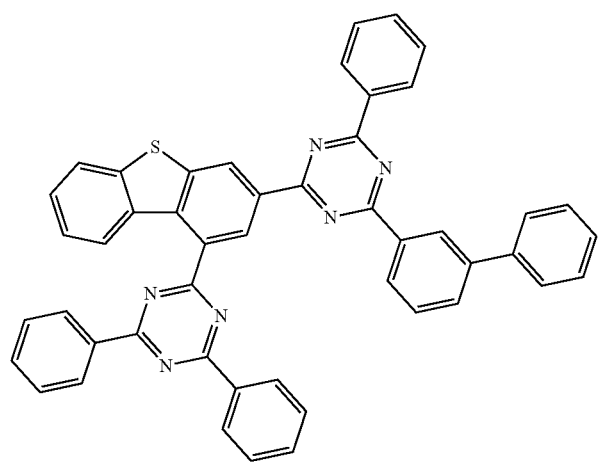
4-128
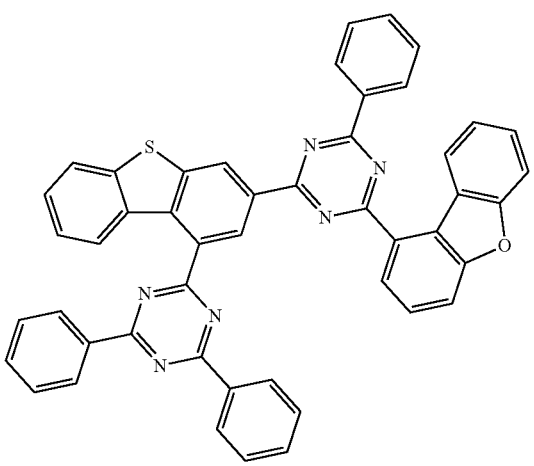

4-129
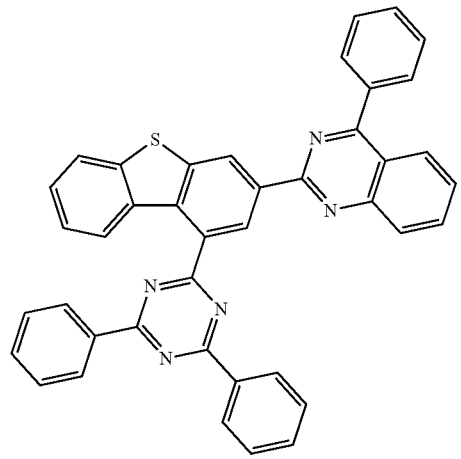
4-130
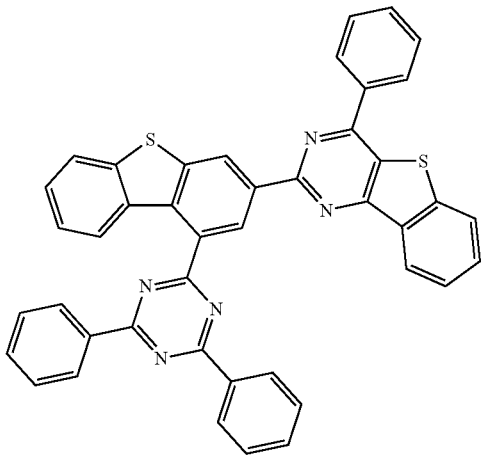
4-131
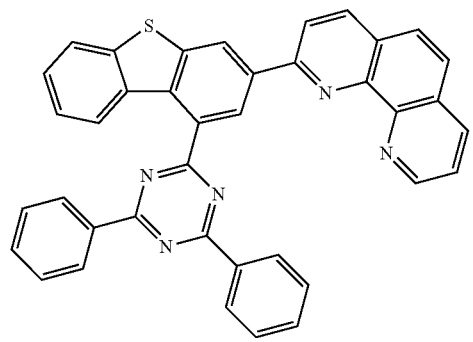
4-132
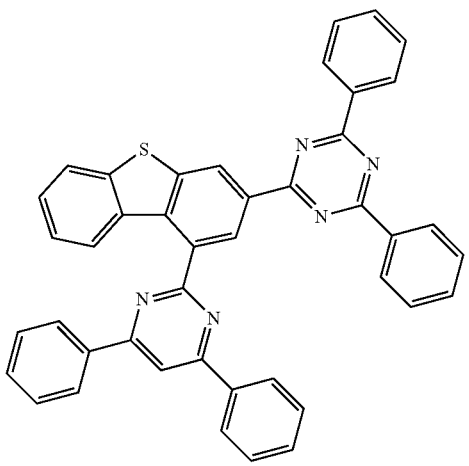
4-133
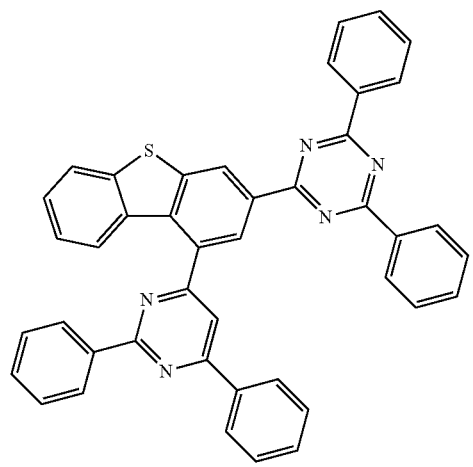
4-134
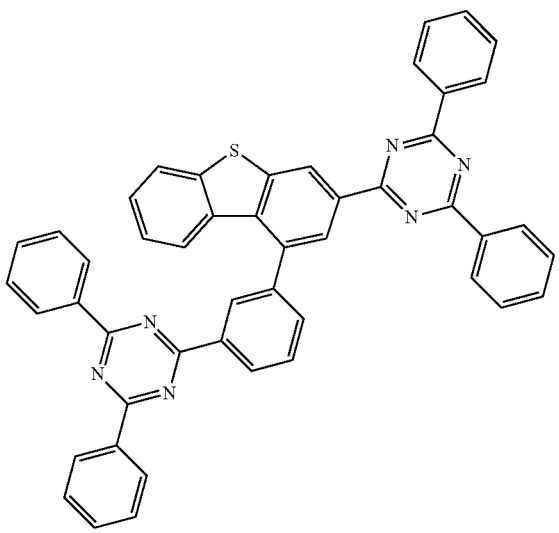

4-135

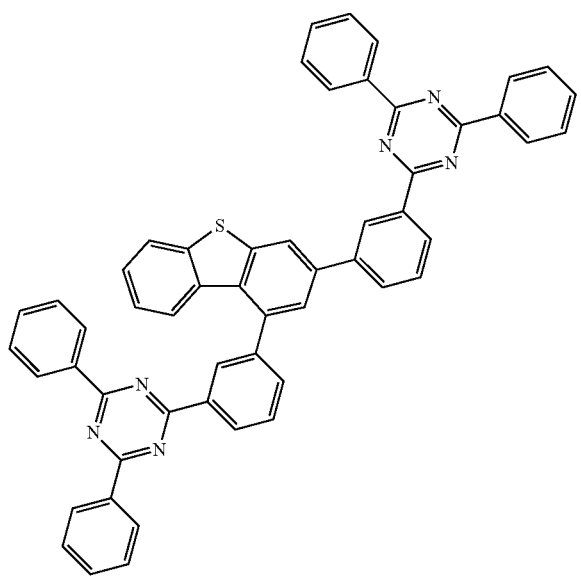

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound according to Chemical Formula 1.

Specific details on the heterocyclic compound represented by Chemical Formula 1 are the same as the descriptions provided above.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device. For example, the heterocyclic compound according to Chemical Formula 1 may be included in a host material of a blue light emitting layer of the blue organic light emitting device.

In one embodiment of the present application, the organic light emitting device may be a green organic light emitting device, and the heterocyclic compound according to Chemical Formula 1 may be used as a material of the green organic light emitting device. For example, the heterocyclic compound according to Chemical Formula 1 may be included in a host material of a green light emitting layer of the green organic light emitting device.

In one embodiment of the present application, the organic light emitting device may be a red organic light emitting device, and the heterocyclic compound according to Chemical Formula 1 may be used as a material of the red organic light emitting device. For example, the heterocyclic compound according to Chemical Formula 1 may be included in a host material of a red light emitting layer of the red organic light emitting device.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device of the present disclosure, the organic material layer comprises a light emitting layer, and the light emitting layer may comprise the heterocyclic compound.

In another organic light emitting device, the organic material layer comprises a light emitting layer, the light emitting layer comprises a host material, and the host material may comprise the heterocyclic compound.

As another embodiment, the organic material layer comprising the heterocyclic compound comprises the heterocyclic compound represented by Chemical Formula 1 as a host, and an iridium-based dopant may be used therewith.

In the organic light emitting device of the present disclosure, the organic material layer comprises an electron injection layer or an electron transfer layer, and the electron transfer layer or the electron injection layer may comprise the heterocyclic compound.

In another organic light emitting device, the organic material layer comprises an electron blocking layer or a hole blocking layer, and the electron blocking layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

One embodiment of the present application provides an organic light emitting device, wherein the organic material layer comprising the heterocyclic compound represented by Chemical Formula 1 further comprises a heterocyclic compound represented by the following Chemical Formula 3.

[Chemical Formula 3]

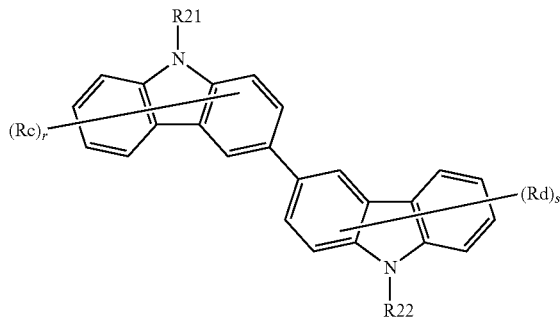

In Chemical Formula 3,

Rc and Rd are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —$SiR_{31}R_{32}R_{33}$; —$P(=O)R_{31}R_{32}$; and an amine group unsubstituted or substituted with a substituted or unsubstituted alkyl group, a substituted or unsubstituted aryl group or a substituted or unsubstituted heteroaryl group, or two or more groups adjacent to each other bond to each other to form a substituted or unsubstituted aliphatic or aromatic hydrocarbon ring, $R_{31}$, $R_{32}$, and $R_{33}$ are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group, $R_{21}$ and $R_{22}$ are the same as or different from each other, and each independently a substituted or unsubstituted aryl group; or a substituted or unsubstituted heteroaryl group, and r and s are an integer of 0 to 7, and when r and s are an integer of 2 or greater, substituents in the parentheses are the same as or different from each other.

In one embodiment of the present application, Rc and Rd may be hydrogen.

In one embodiment of the present application, R21 and R22 are the same as or different from each other, and may be each independently a substituted or unsubstituted aryl group having 6 to 60 carbon atoms.

In another embodiment, R21 and R22 are the same as or different from each other, and may be each independently a substituted or unsubstituted aryl group having 6 to 40 carbon atoms.

In another embodiment, R21 and R22 are the same as or different from each other, and may be each independently an aryl group having 6 to 40 carbon atoms unsubstituted or substituted with one or more substituents selected form the group consisting of an alkyl group having 1 to 40 carbon atoms, an aryl group having 6 to 40 carbon atoms, CN and SiRR'R".

In another embodiment, R21 and R22 are the same as or different from each other, and may be each independently a phenyl group unsubstituted or substituted with one or more substituents selected form the group consisting of CN, SiRR'R" and a phenyl group; a biphenyl group unsubstituted or substituted with a phenyl group; a naphthyl group; a triphenylene group; a dimethylfluorene group; a diphenylfluorene group; or a spirobifluorene group.

When including both the heterocyclic compound of Chemical Formula 1 and the heterocyclic compound of Chemical Formula 3 in an organic material layer of an organic light emitting device, more superior efficiency and lifetime effects are obtained. Such results may lead to a forecast that an exciplex phenomenon occurs when comprising the two compounds at the same time.

The exciplex phenomenon is a phenomenon of releasing energy having sizes of a donor (p-host) HOMO level and an acceptor (n-host) LUMO level due to electron exchanges between two molecules. When the exciplex phenomenon occurs between two molecules, reverse intersystem crossing (RISC) occurs, and as a result, internal quantum efficiency of fluorescence may increase up to 100%. When a donor (p-host) having favorable hole transfer capability and an acceptor (n-host) having favorable electron transfer capability are used as a host of a light emitting layer, holes are injected to the p-host and electrons are injected to the n-host, and therefore, a driving voltage may decrease, which resultantly helps with enhancement in the lifetime. In the present disclosure, it is identified that excellent device properties are obtained when using the heterocyclic compound of Chemical Formula 3 to have a donor role and the compound of Chemical Formula 1 to have an acceptor role as a light emitting layer host.

In the organic light emitting device according to one embodiment of the present application, Chemical Formula 3 may be represented by any one of the following heterocyclic compounds.
5-1
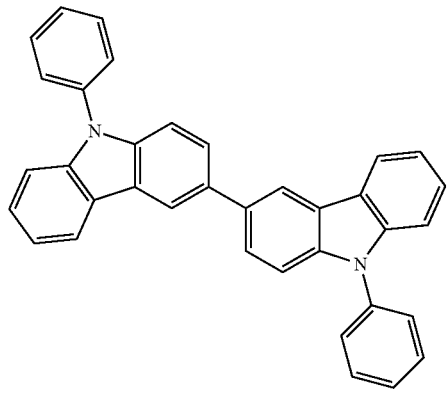
5-2
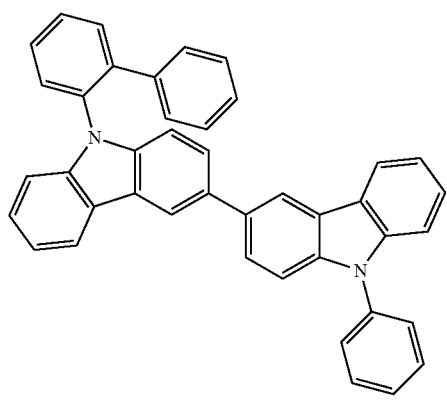
5-3
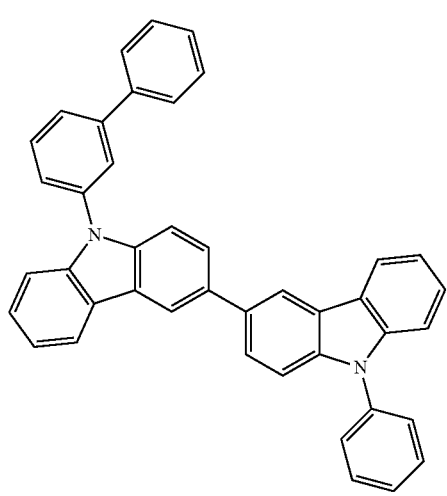
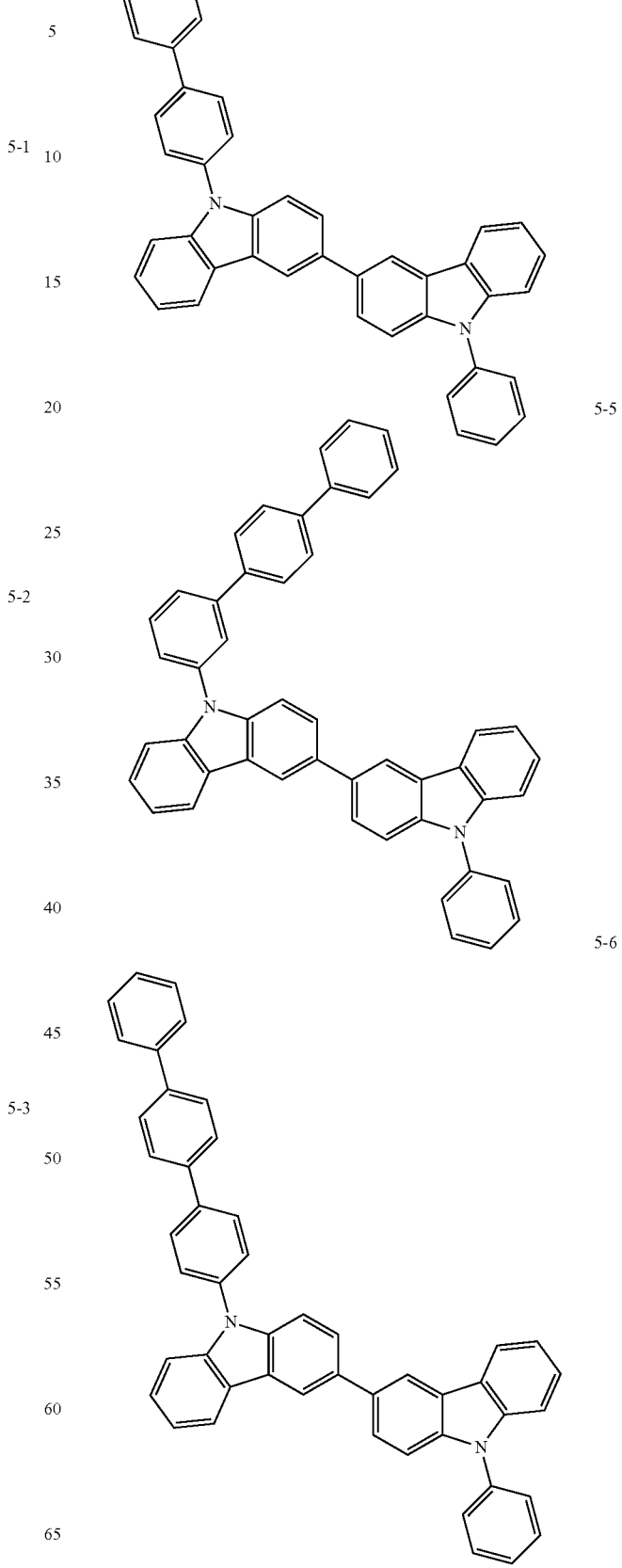

5-7
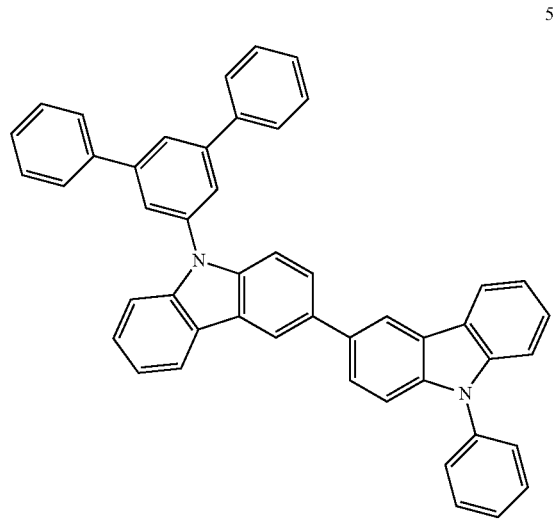
5-8
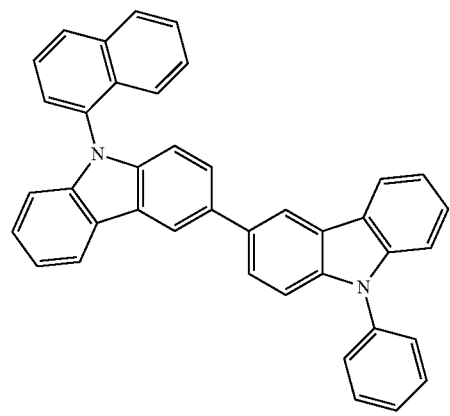
5-9
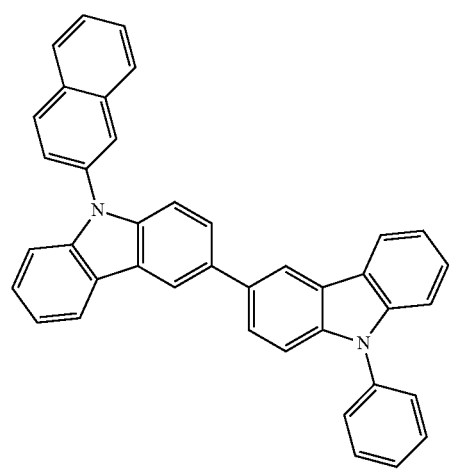
5-10
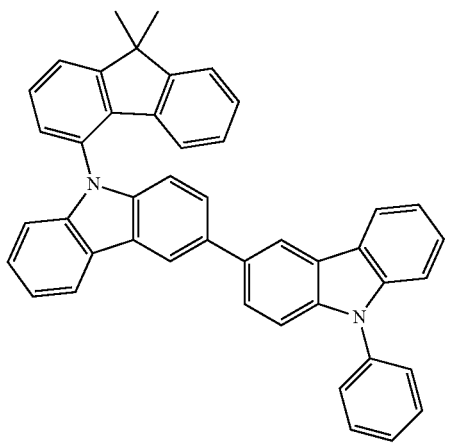
5-11
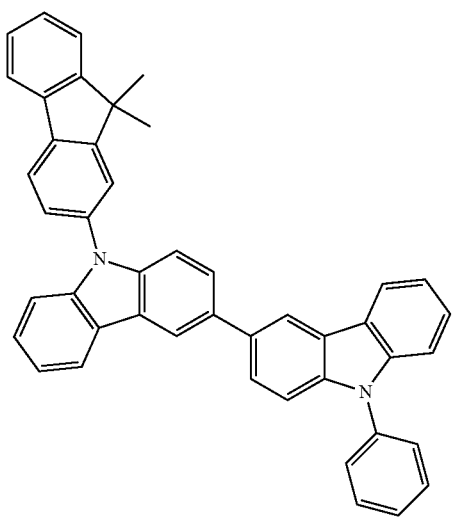
5-12
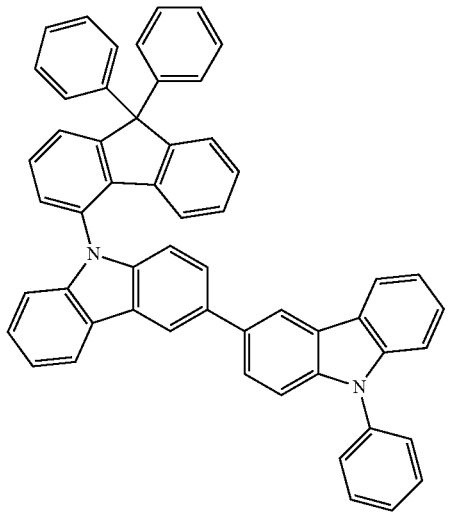

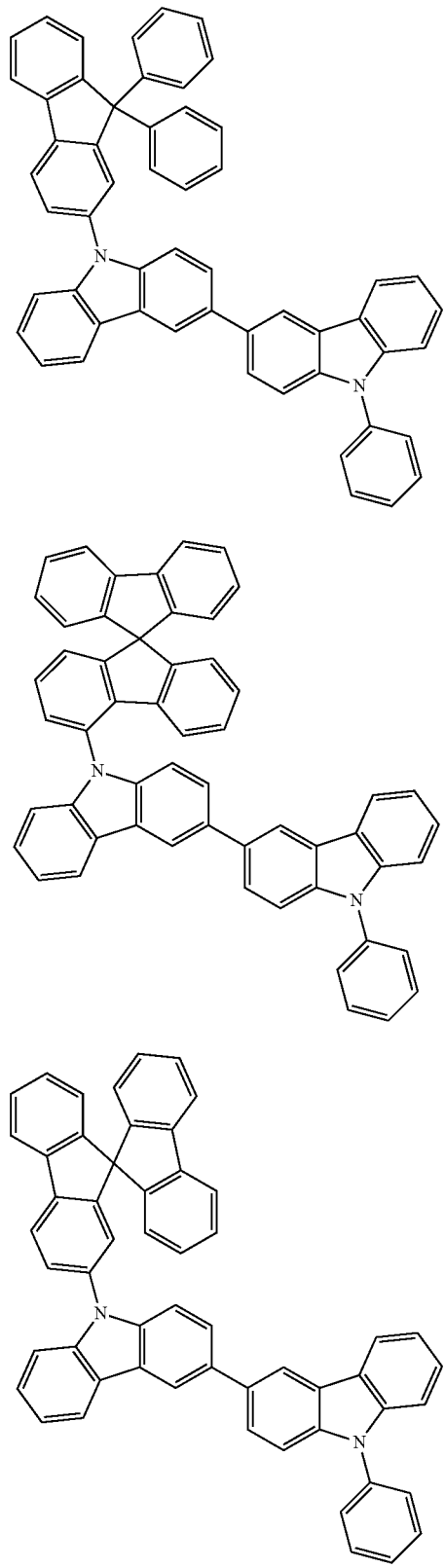
5-13
5-14
5-15
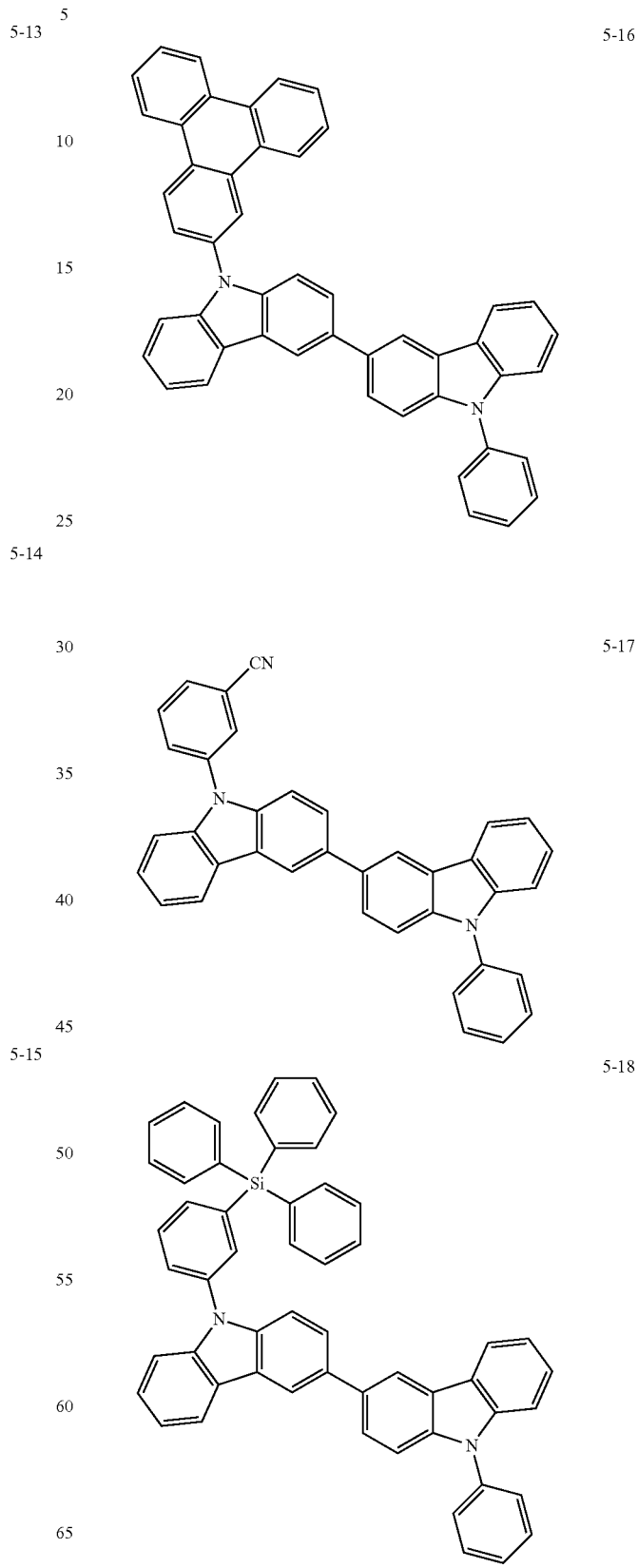
5-16
5-17
5-18

5-19
5-20
5-21
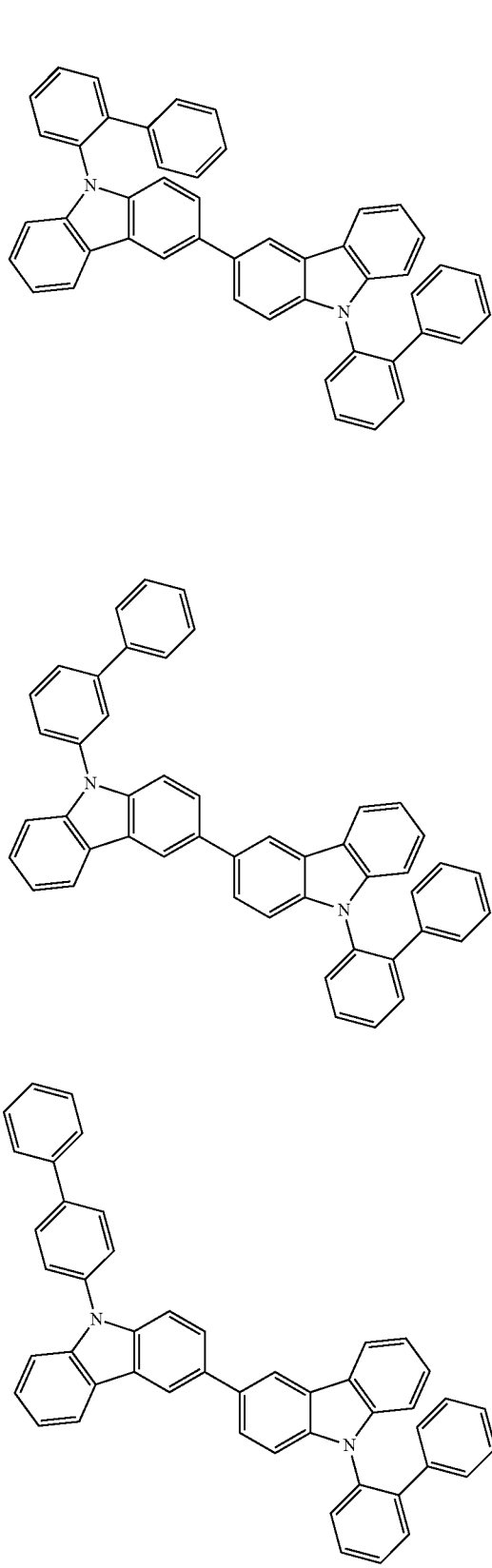
5-22
5-23
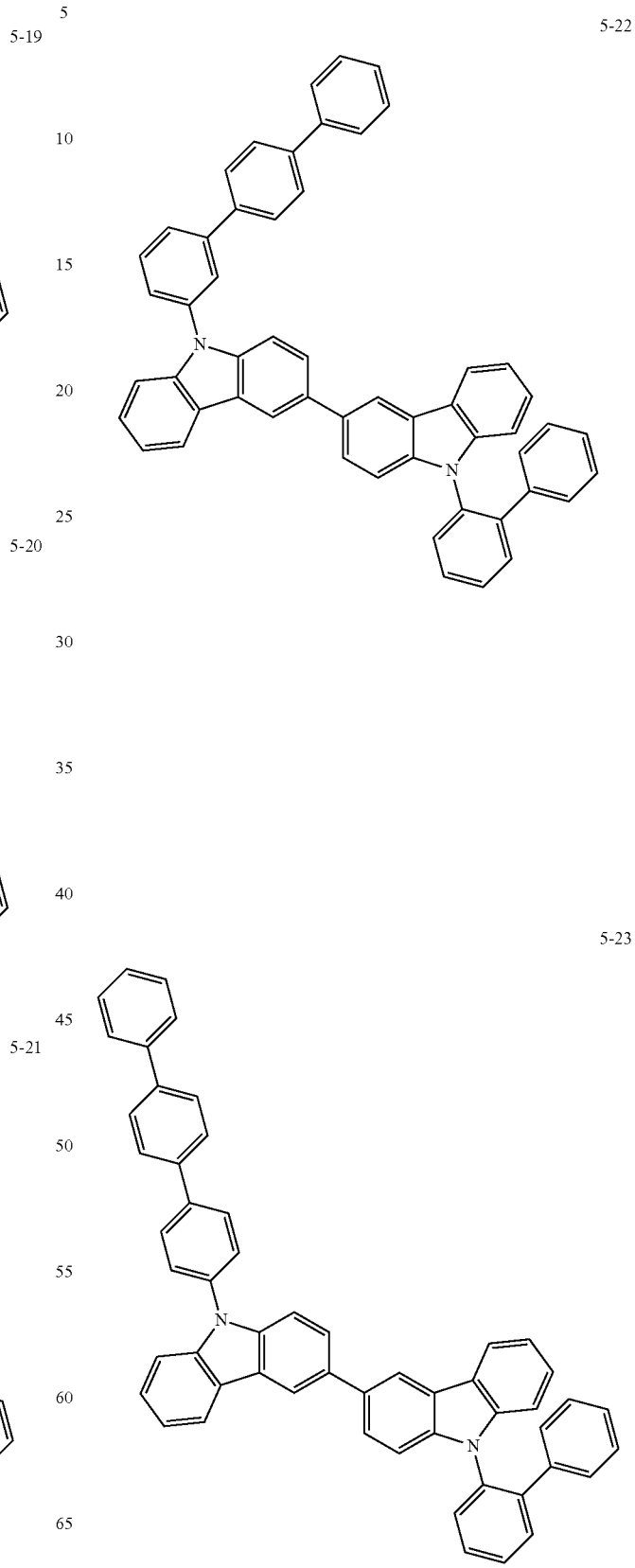

5-24
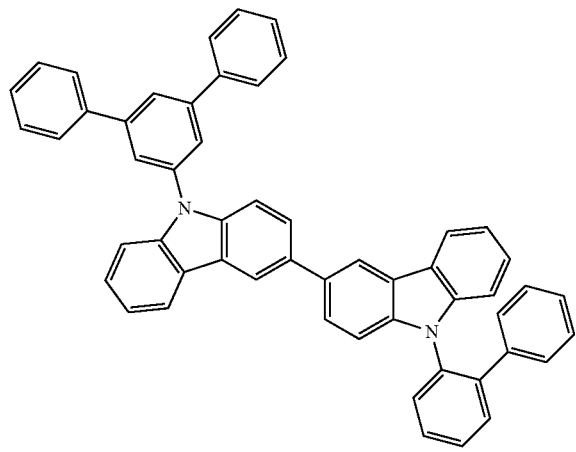
5-25
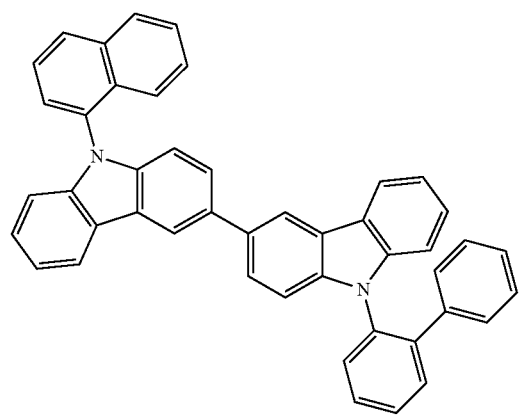
5-26
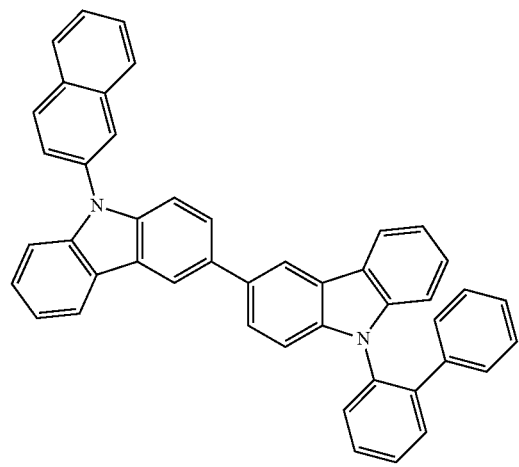
5-27
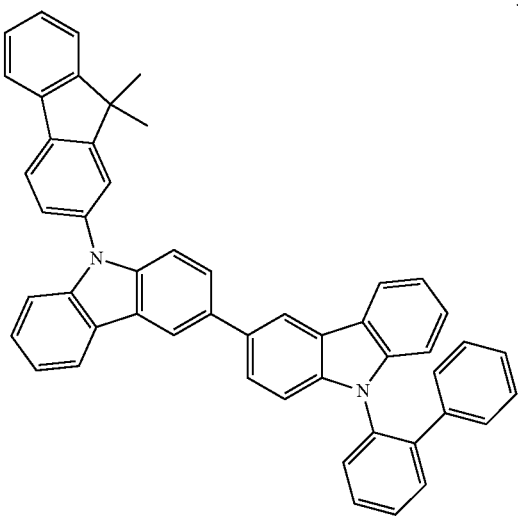
5-28
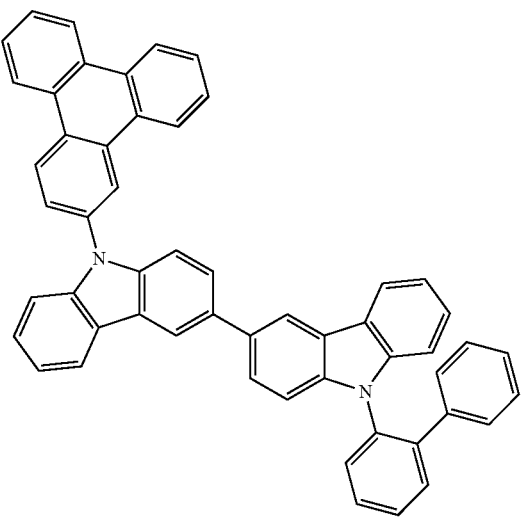
5-29
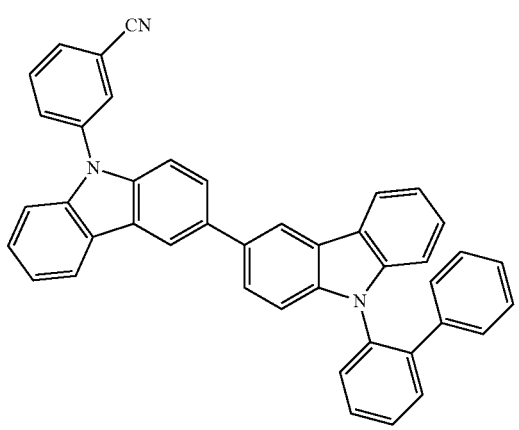

5-30
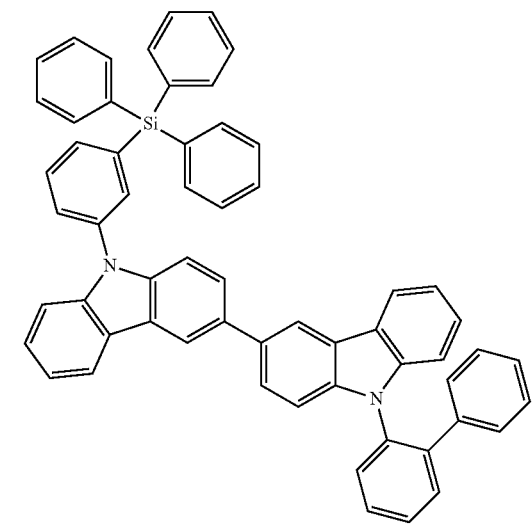
5-31
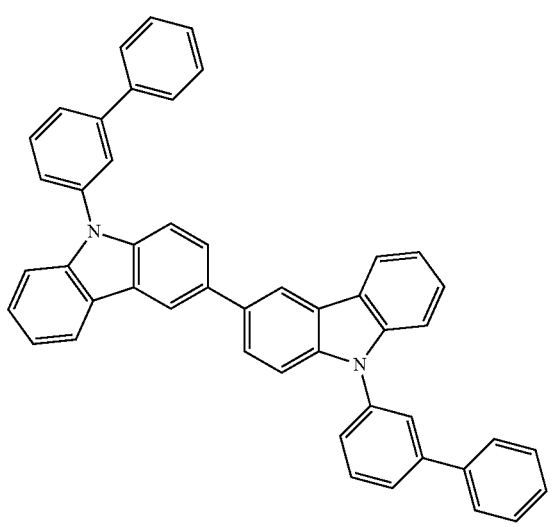
5-32
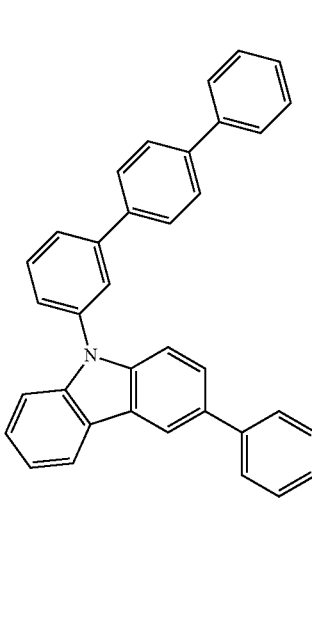
5-33
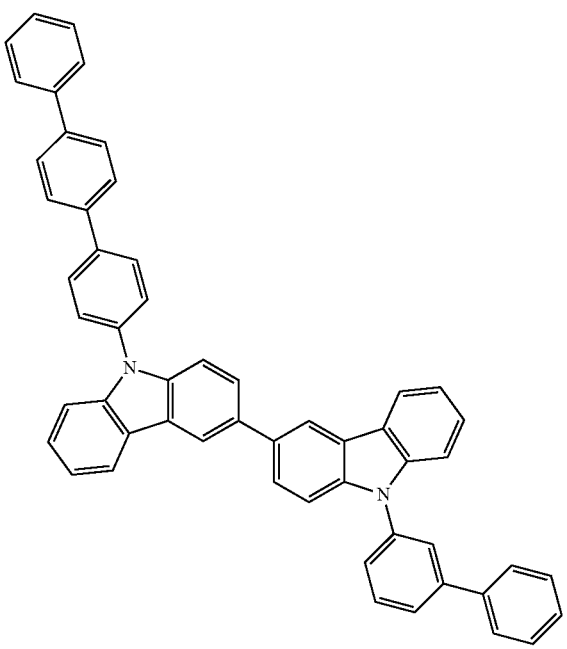
5-34

5-35
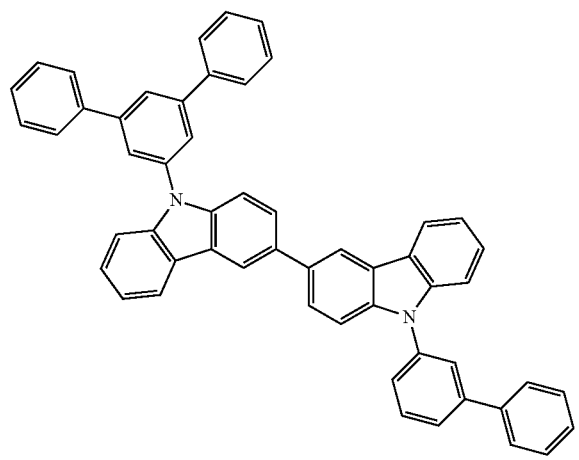
5-36
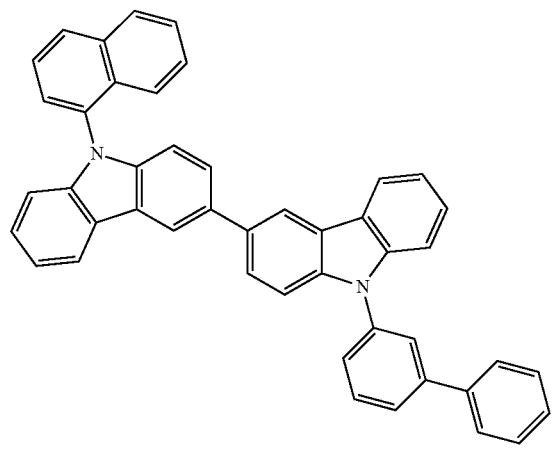
5-37
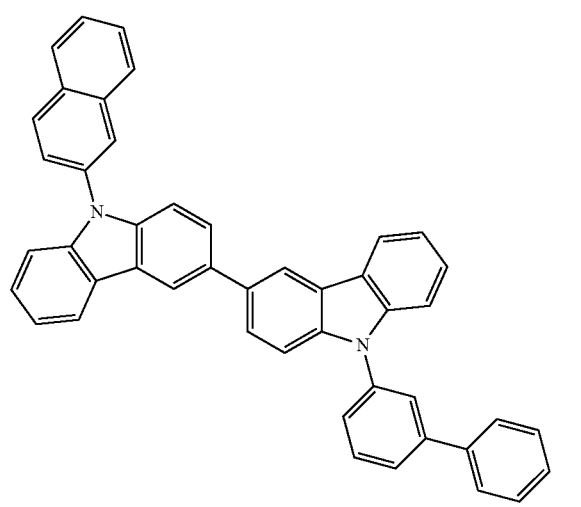
5-38
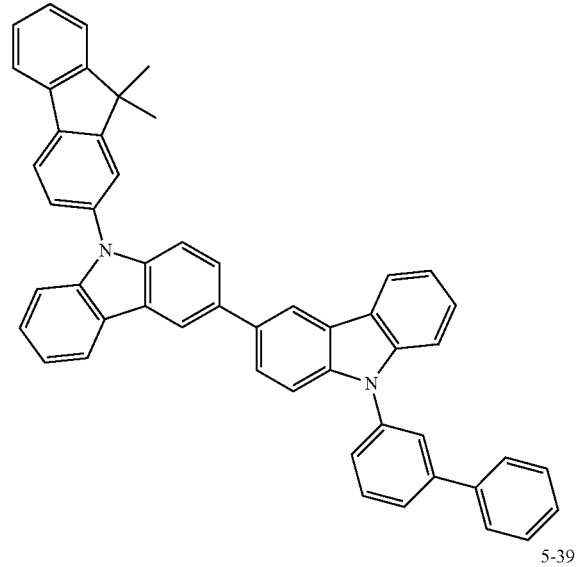
5-39
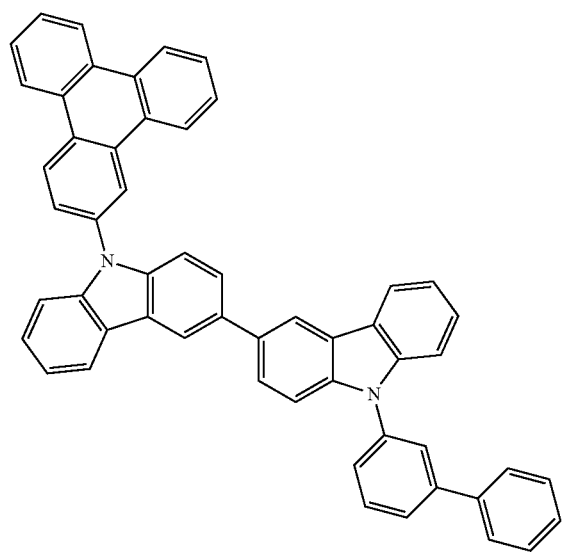
5-40
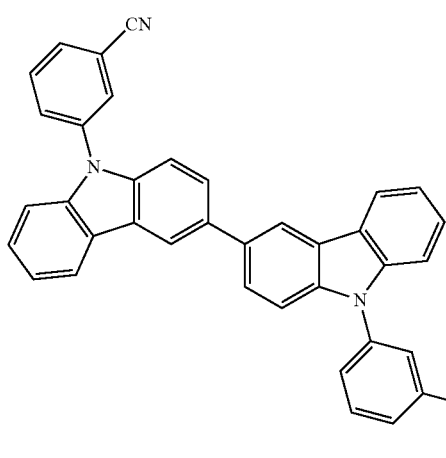

5-41
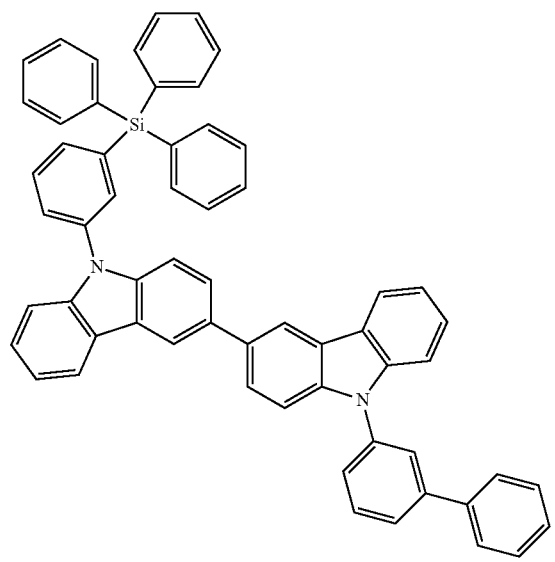
5-42
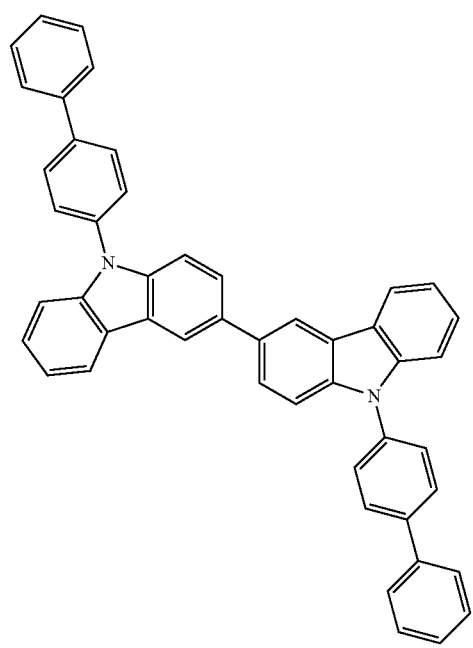
5-43
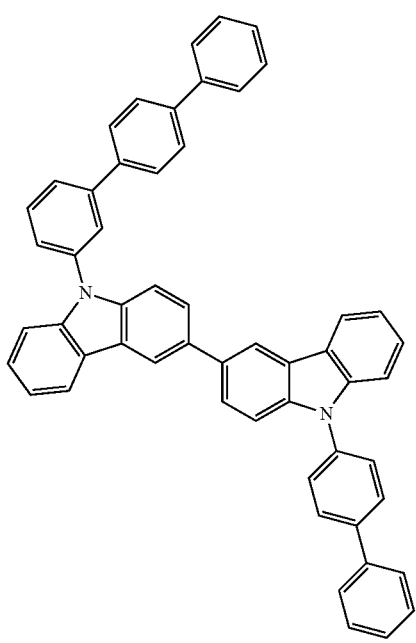
5-44
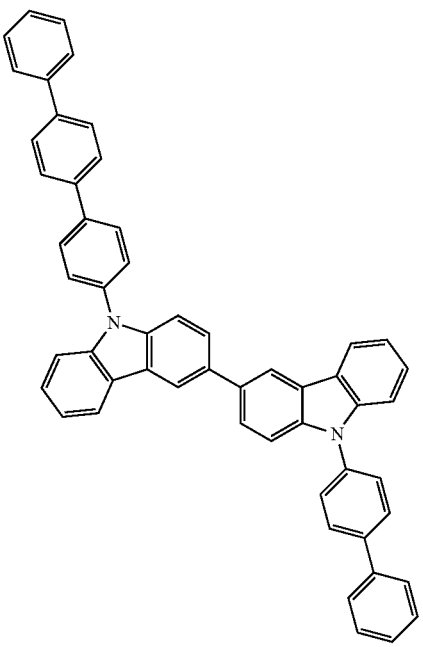

5-45
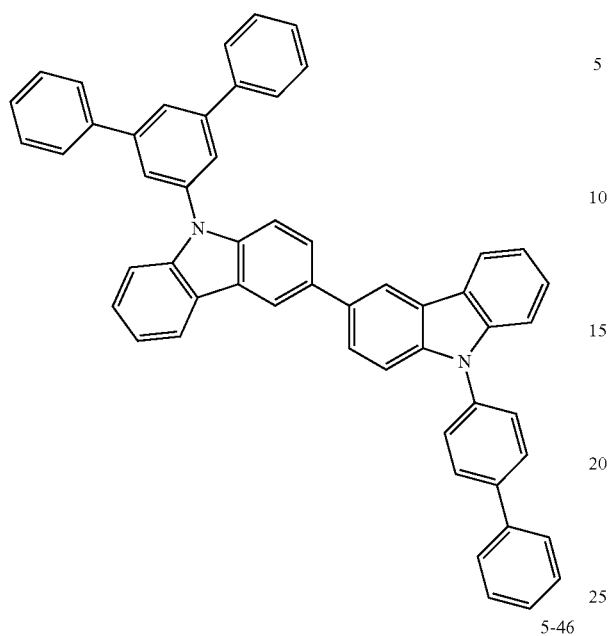
5-46
5-47
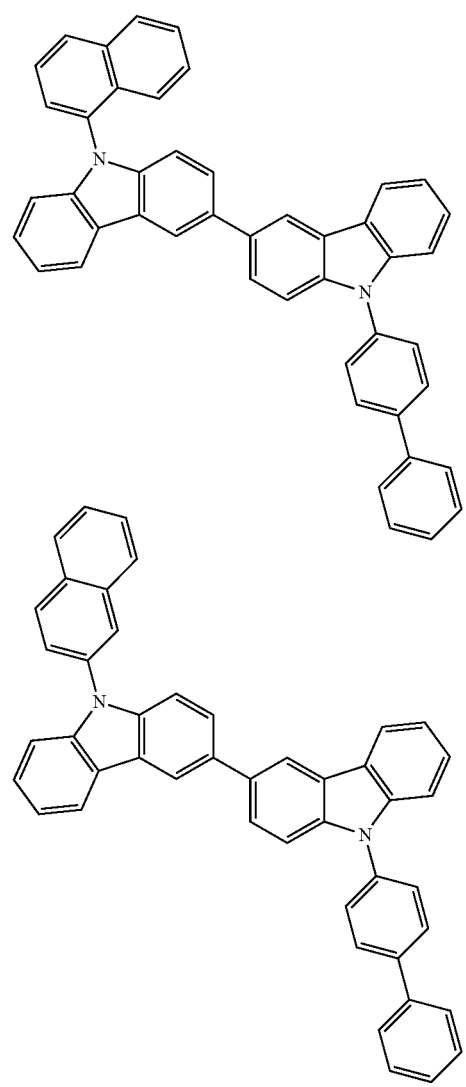
5-48
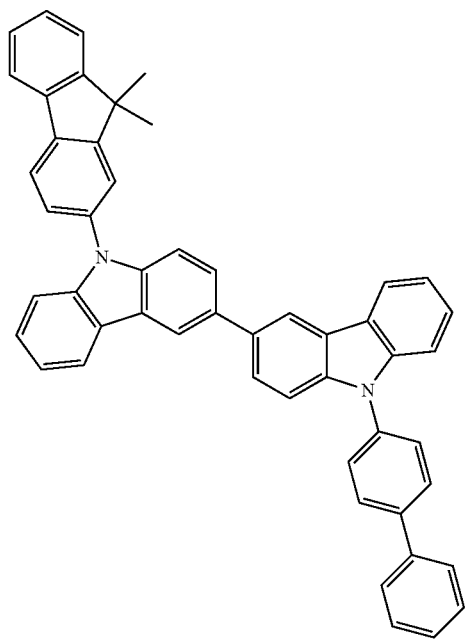
5-49
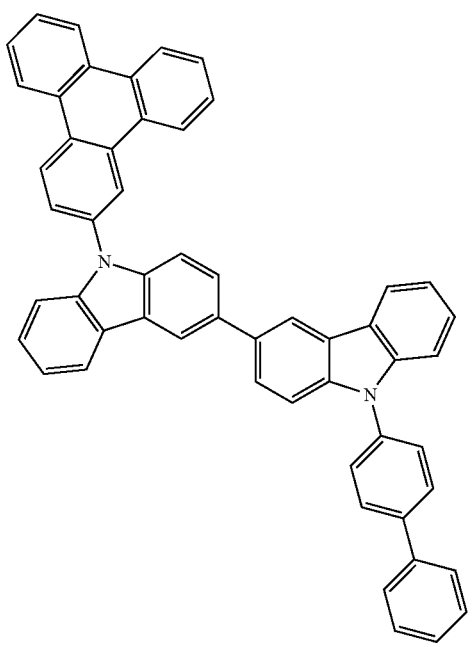

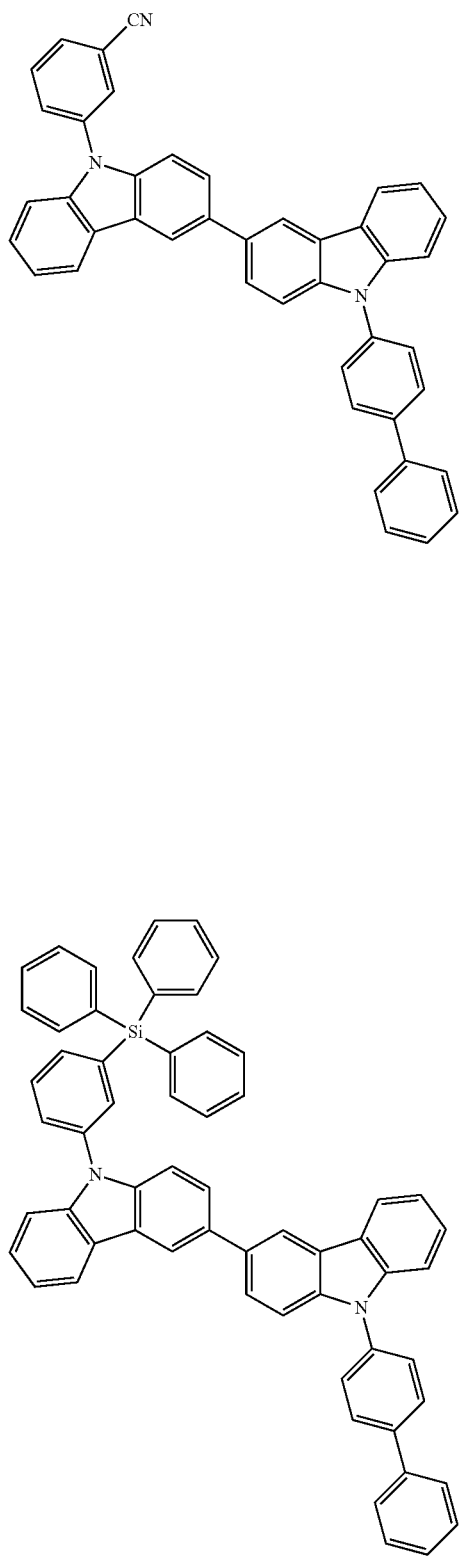
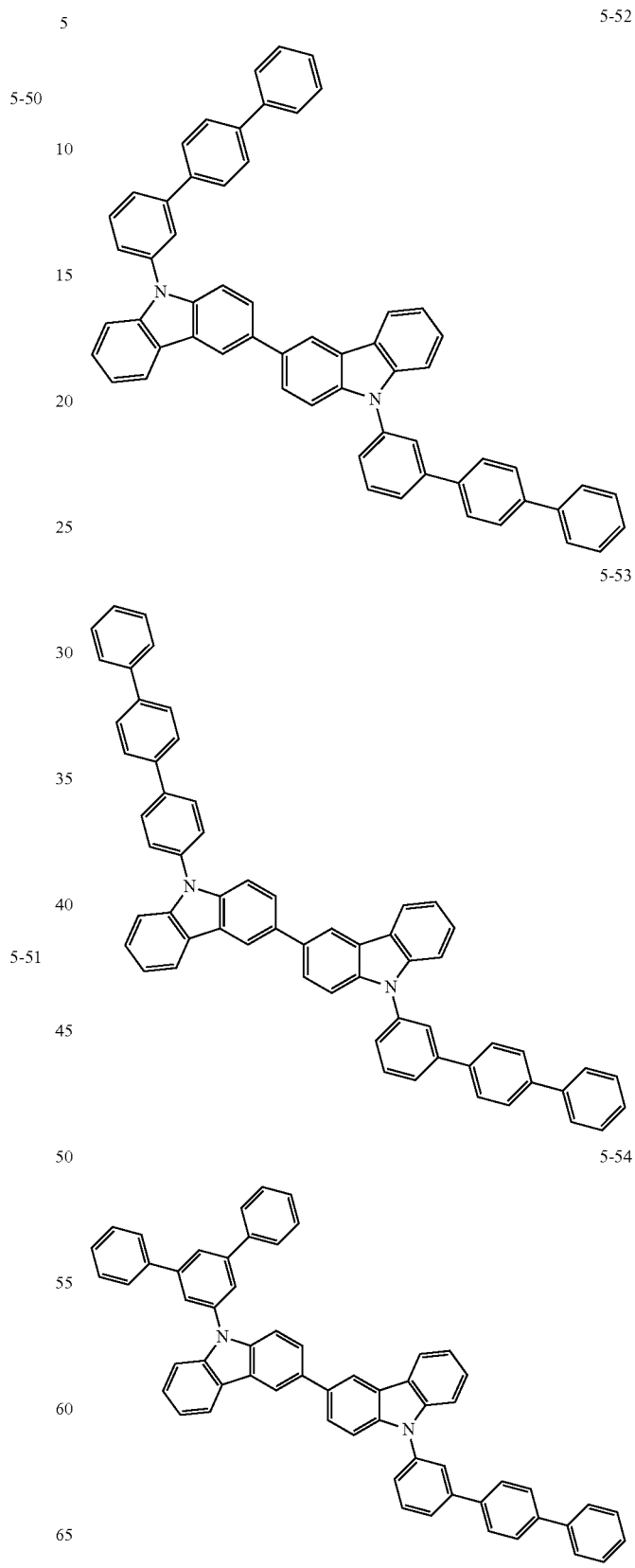

-continued
5-55
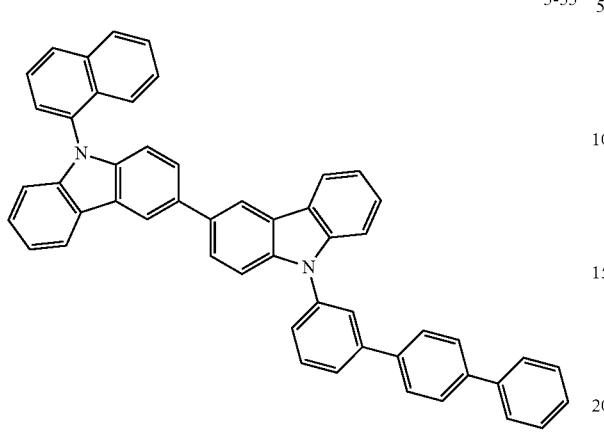
5-56
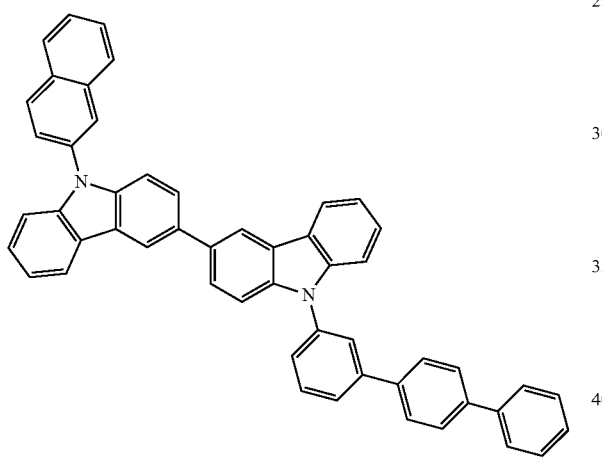
5-57
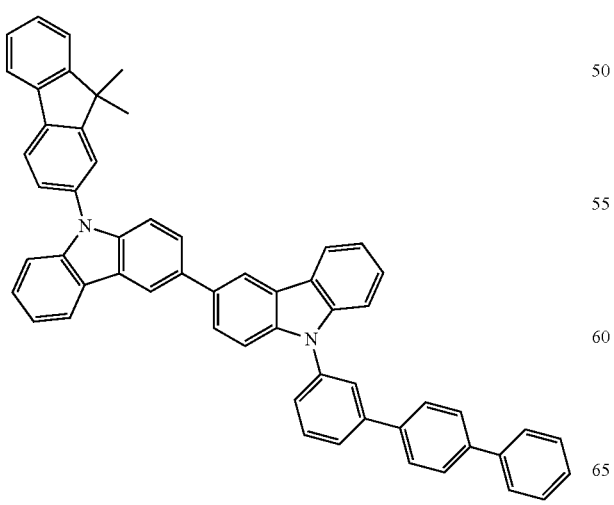
-continued
5-58
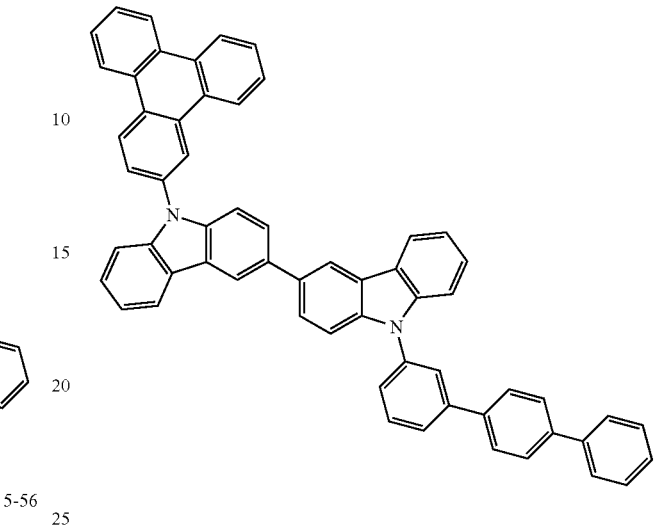
5-59
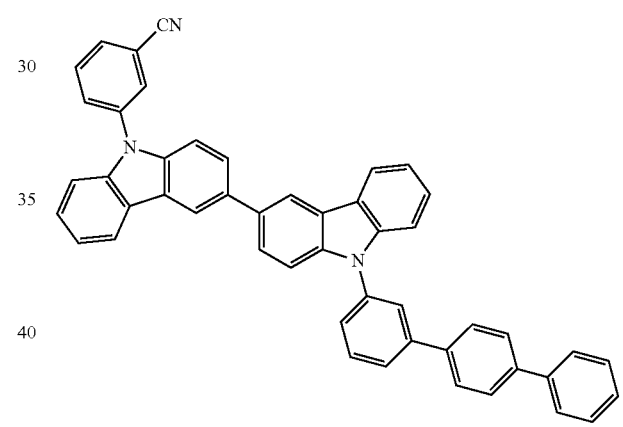
5-60
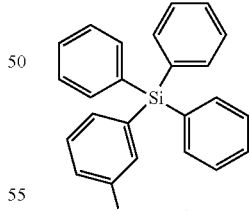

5-61
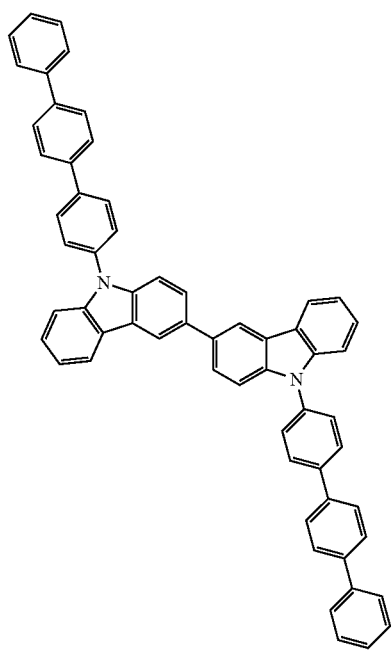
5-62
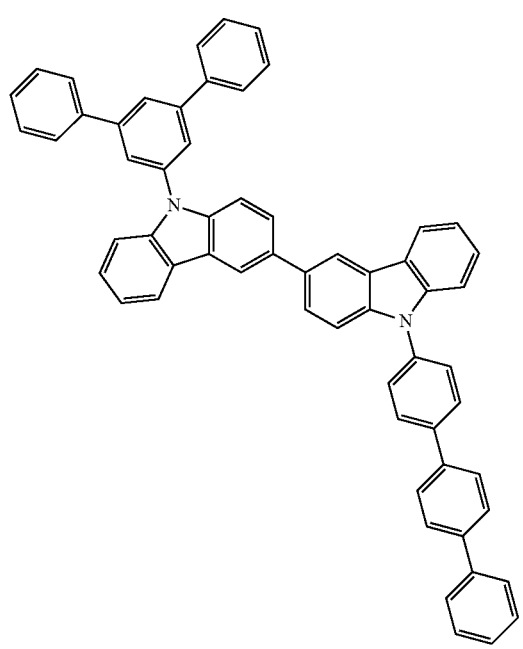
5-63
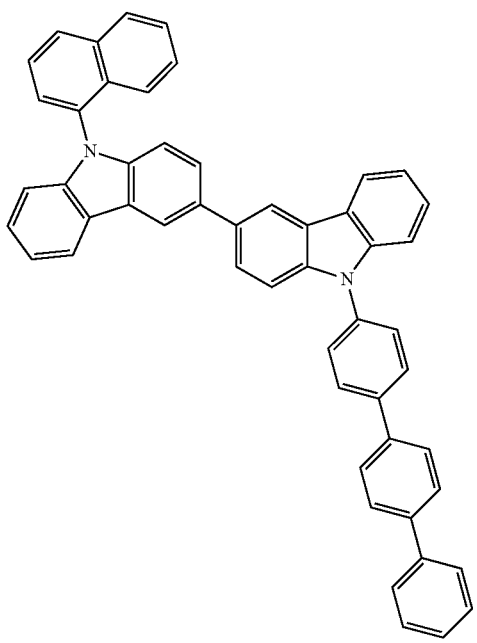
5-64

5-65
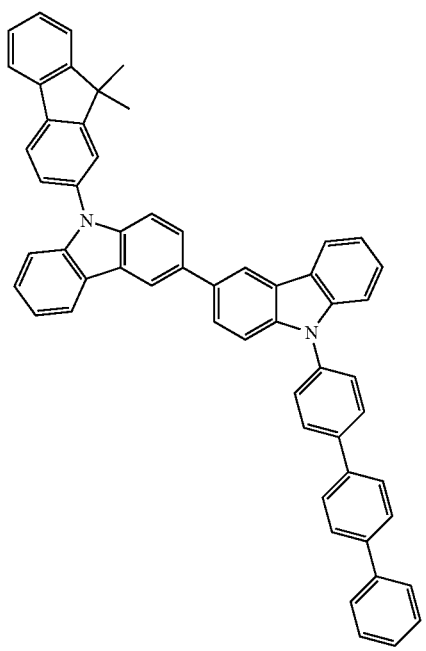
5-66
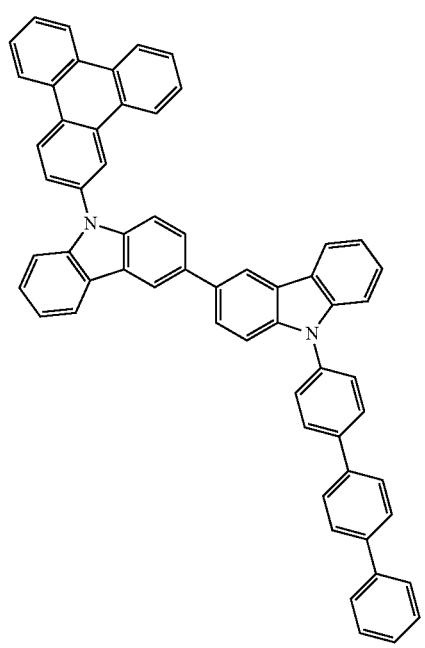
5-67
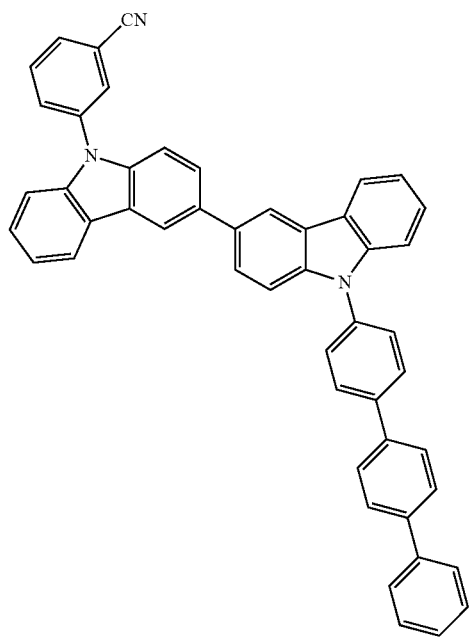
5-68
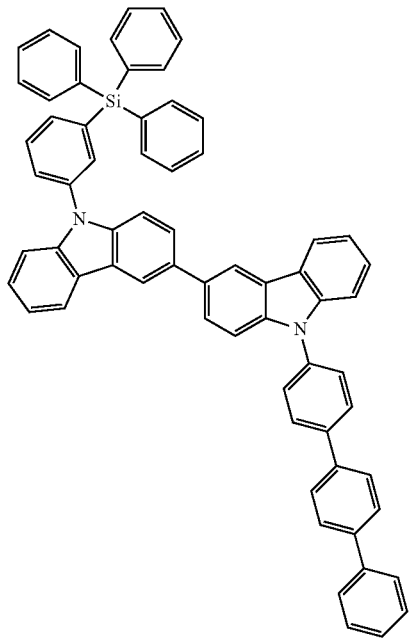

5-69
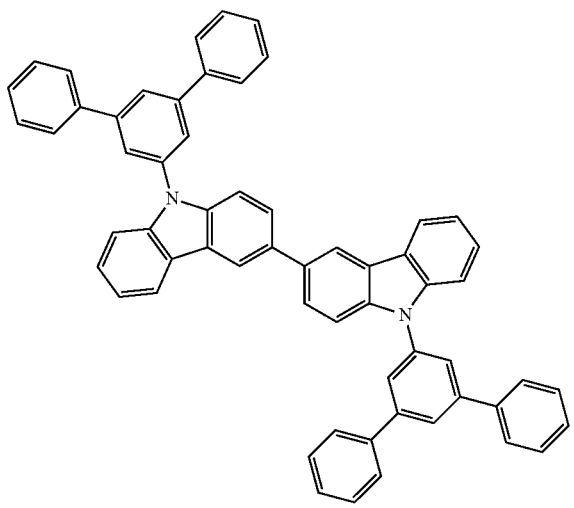
5-70
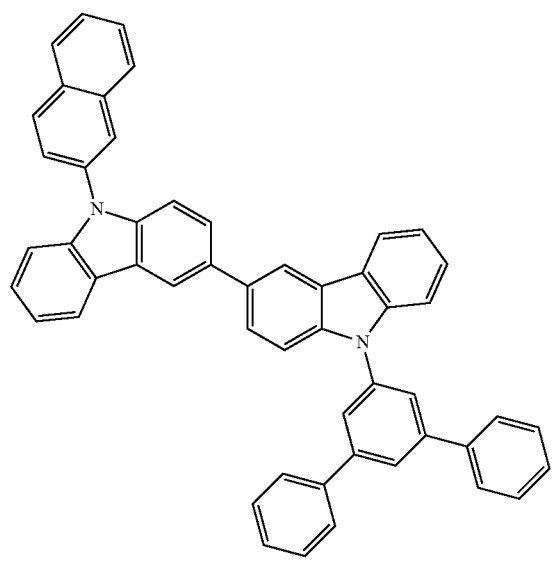
5-71
5-72
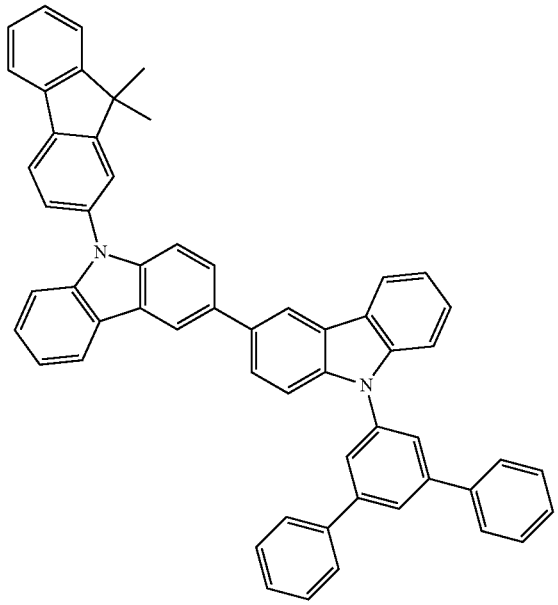
5-73
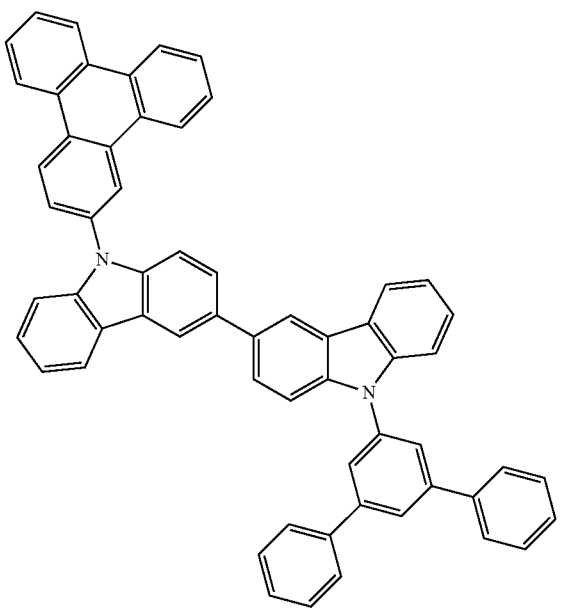

225
-continued
5-74
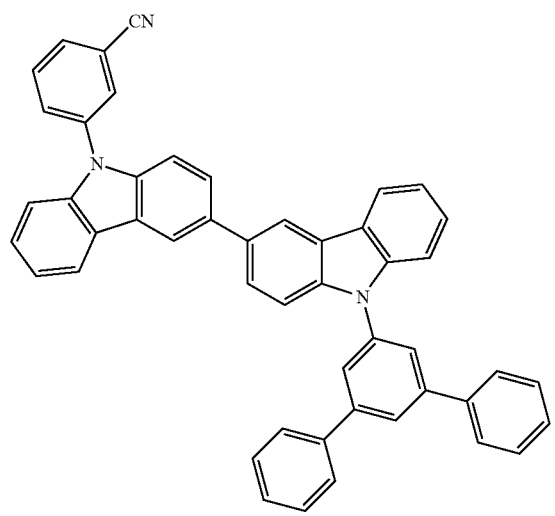
5-75
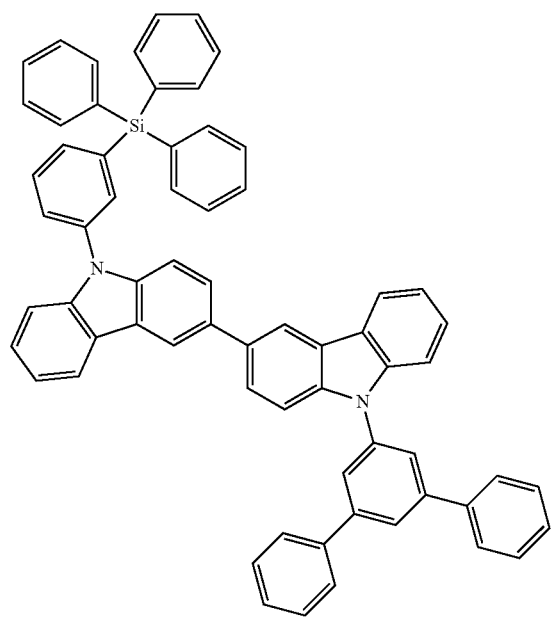
5-76
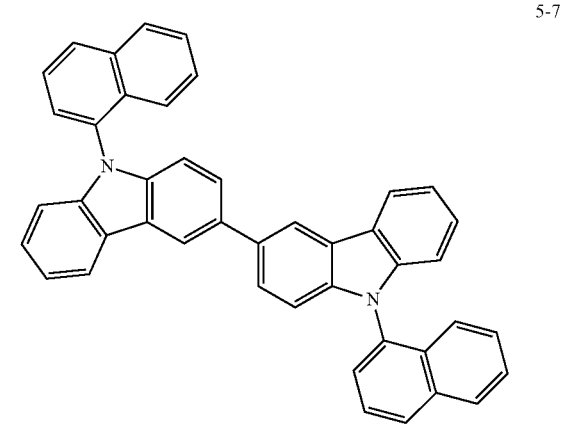
226
-continued
5-77
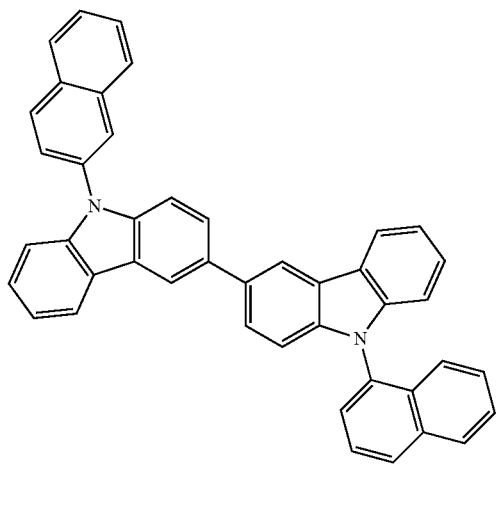
5-78
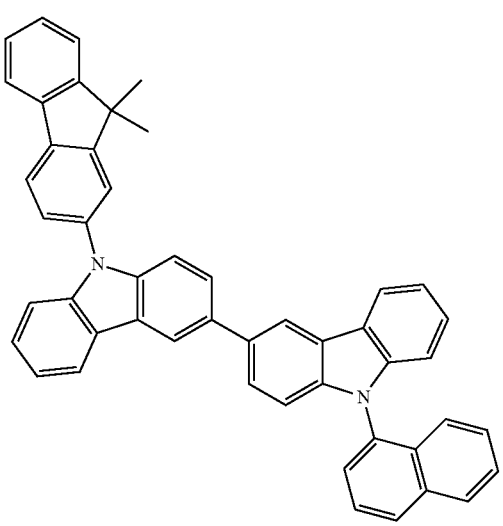
5-79
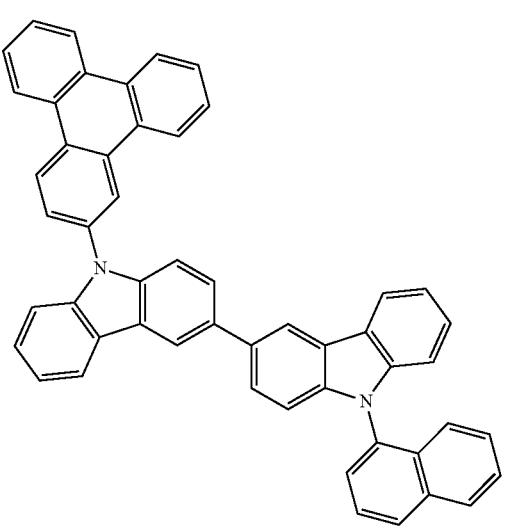

5-80
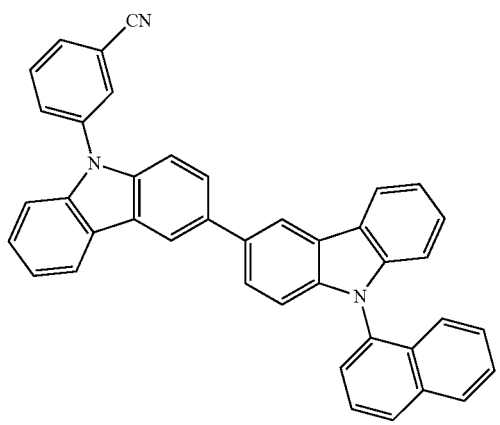
5-81
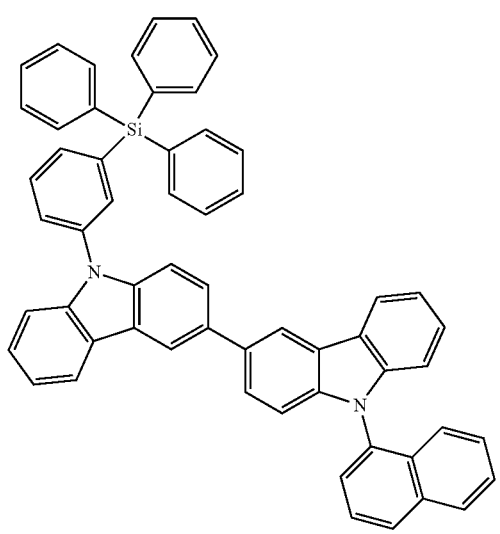
5-82
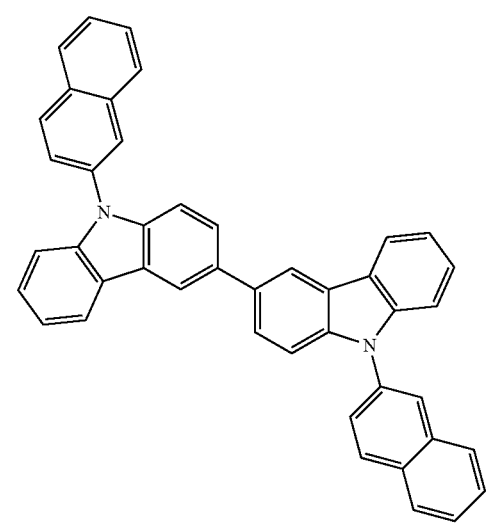
5-83
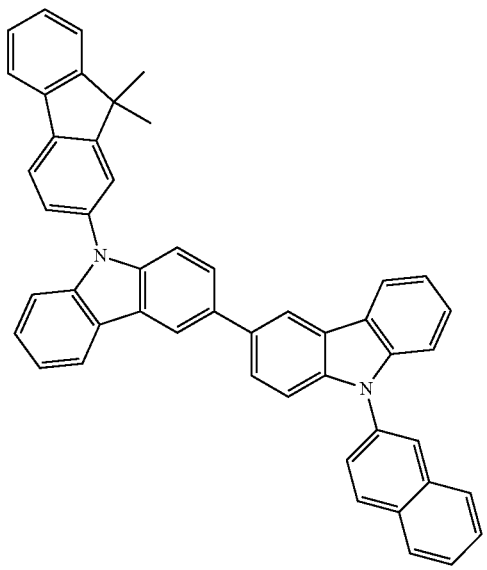
5-84
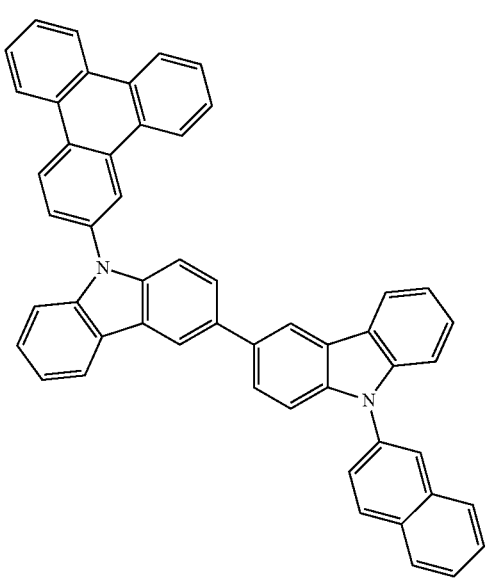
5-85
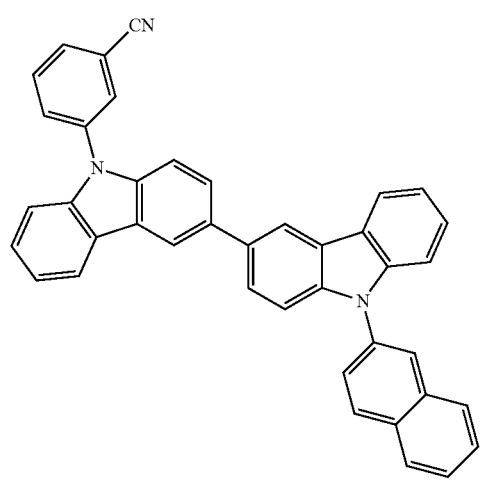

5-86
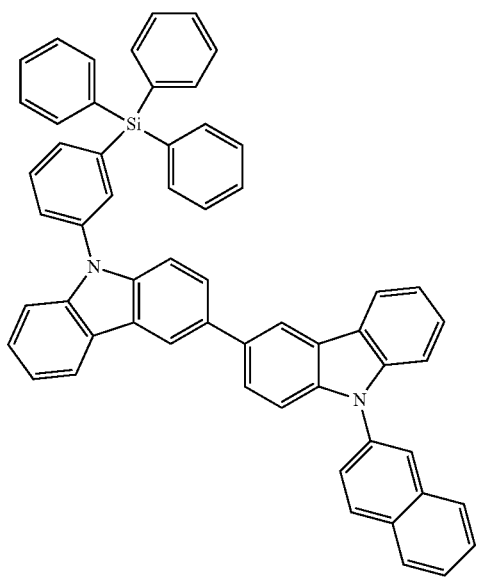
5-87
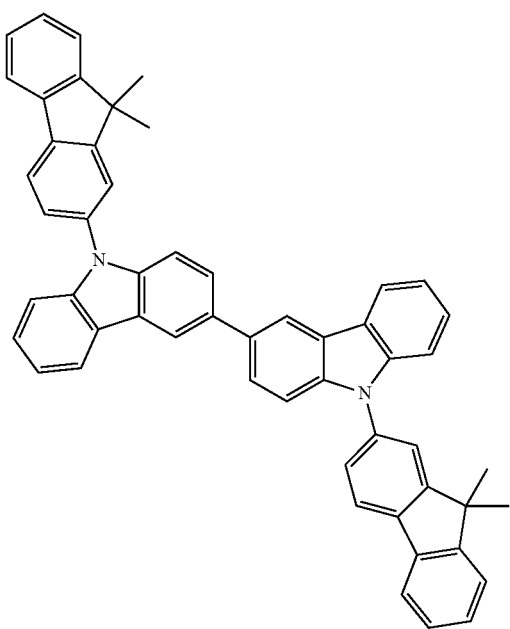
5-88
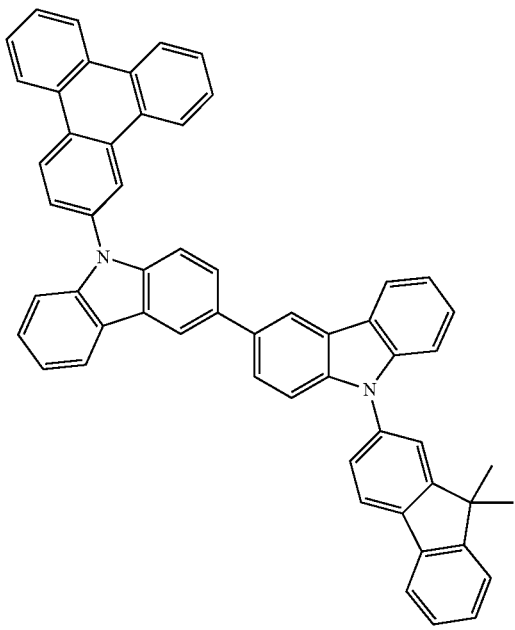
5-89

5-90
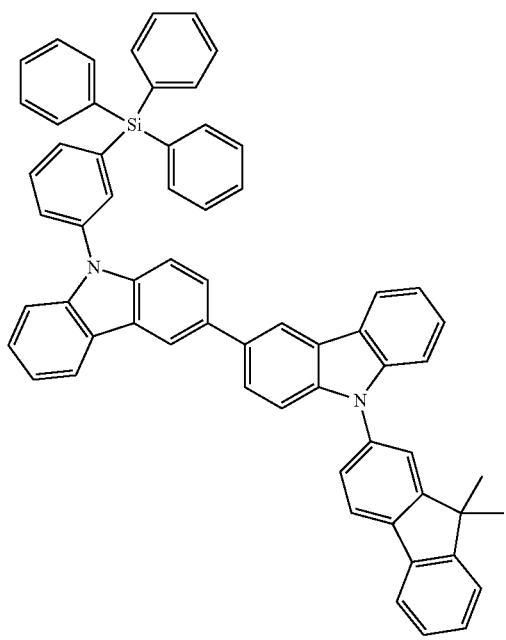
5-91
5-92
5-93
5-94
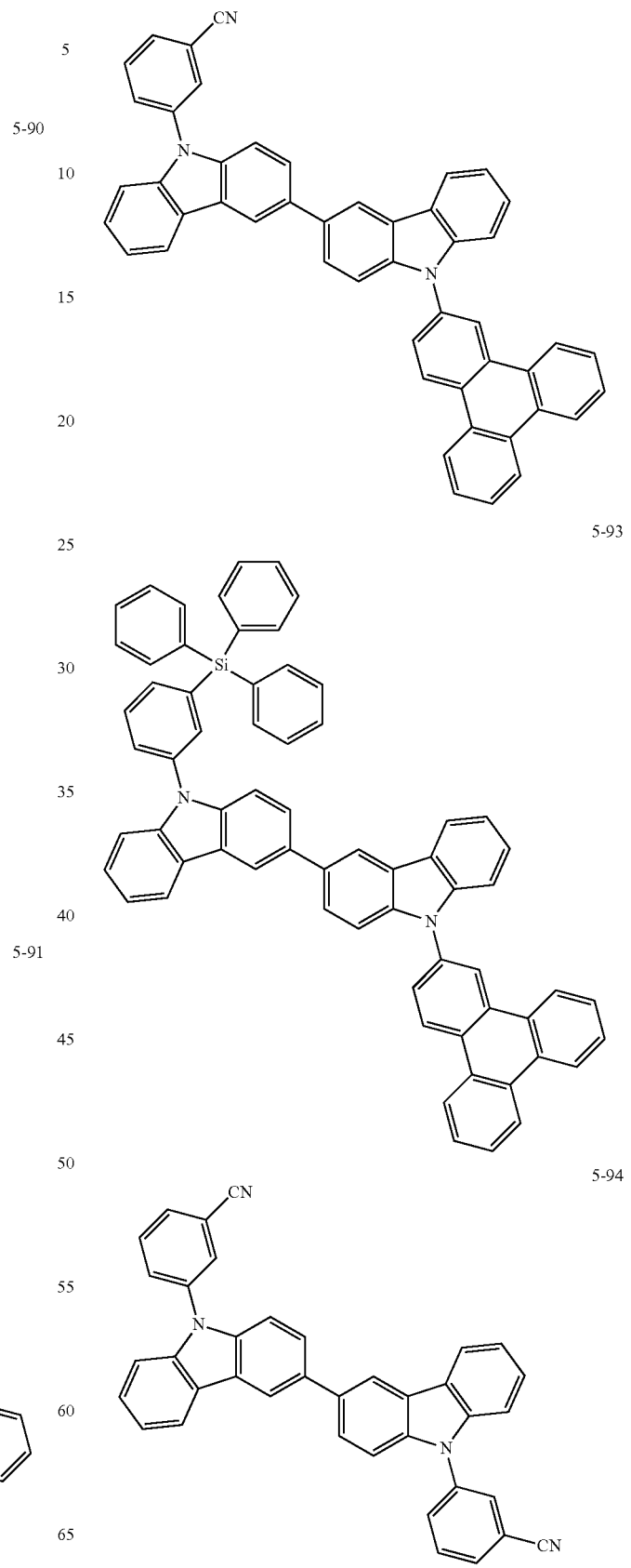

5-95

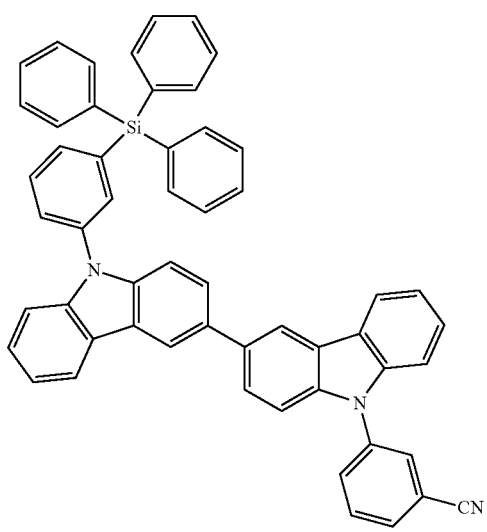

5-96

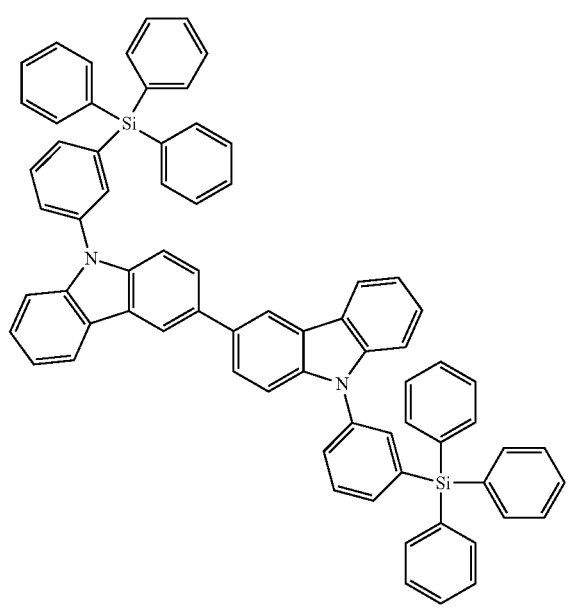

In the organic light emitting device of the present disclosure, the heterocyclic compound represented by Chemical Formula 1: the compound represented by Chemical Formula 3 may have a weight ratio of 1:10 to 10:1, 1:8 to 8:1, 1:5 to 5:1, or 1:2 to 2:1, however, the weight ratio is not limited thereto.

In the organic light emitting device of the present disclosure, the organic material layer may comprise a light emitting layer, and the light emitting layer may comprise the heterocyclic compound represented by Chemical Formula 1.

In another organic light emitting device, the organic material layer comprises a light emitting layer, the light emitting layer comprises a host material, and the host material may comprise the heterocyclic compound represented by Chemical Formula 1.

As another embodiment, the organic material layer comprising the heterocyclic compound comprises the heterocyclic compound represented by Chemical Formula 1 as a host, and a phosphorescent dopant may be used therewith.

As another embodiment, the organic material layer comprising the heterocyclic compound comprises the heterocyclic compound represented by Chemical Formula 1 as a host, and an iridium-based dopant may be used therewith.

In the organic light emitting device of the present disclosure, the organic material layer may comprise a light emitting layer, and the light emitting layer may comprise both the heterocyclic compound represented by Chemical Formula 1 and the heterocyclic compound represented by Chemical Formula 3.

In another organic light emitting device, the organic material layer comprises a light emitting layer, the light emitting layer comprises a host material, and the host material may comprise both the heterocyclic compound represented by Chemical Formula 1 and the heterocyclic compound represented by Chemical Formula 3.

As another embodiment, the organic material layer comprising the heterocyclic compound comprises both the heterocyclic compound represented by Chemical Formula 1 and the heterocyclic compound represented by Chemical Formula 3, and a phosphorescent dopant may be used therewith.

As another embodiment, the organic material layer comprising the heterocyclic compound comprises both the heterocyclic compound represented by Chemical Formula 1 and the heterocyclic compound represented by Chemical Formula 3, and an iridium-based dopant may be used therewith.

As a material of the phosphorescent dopant, those known in the art may be used.

For example, phosphorescent dopant materials represented by LL'MX', LL'L"M, LMX'X", L2MX' and L3M may be used, however, the scope of the present disclosure is not limited to these examples.

Herein, L, L', L", X' and X" are bidentate ligands different from each other, and M is a metal forming an octahedral complex.

M may include iridium, platinum, osmium and the like.

L is an anionic bidentate ligand coordinated to M as the iridium-based dopant by sp2 carbon and heteroatom, and X may function to trap electrons or holes. Nonlimiting examples of L may include 2-(1-naphthyl)benzoxazole, (2-phenylbenzoxazole), (2-phenylbenzothiazole), (2-phenylbenzothiazole), (7,8-benzoquinoline), (thiophene group pyrizine), phenylpyridine, benzothiophene group pyrizine, 3-methoxy-2-phenylpyridine, thiophene group pyrizine, tolylpyridine and the like. Nonlimiting examples of X' and X" may include acetylacetonate (acac), hexafluoroacetylacetonate, salicylidene, picolinate, 8-hydroxyquinolinate and the like.

More specific examples are described below, however, the phosphorescent dopant is not limited to these examples.

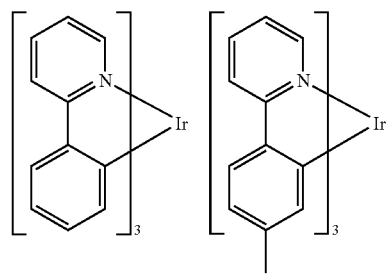

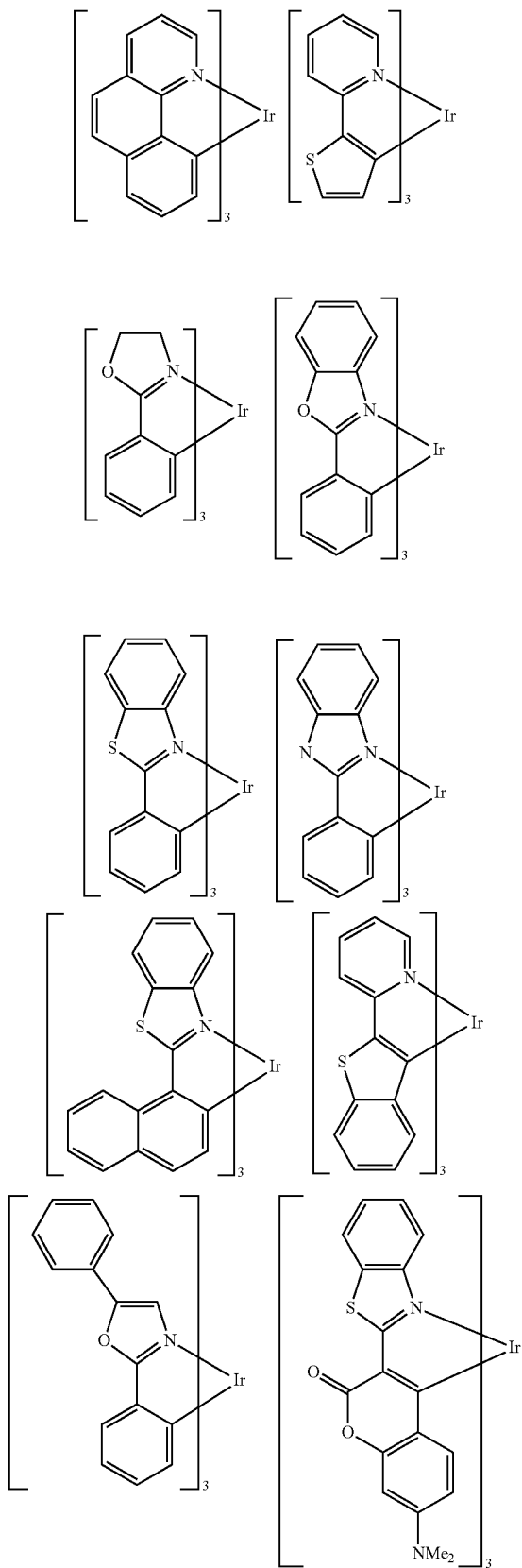

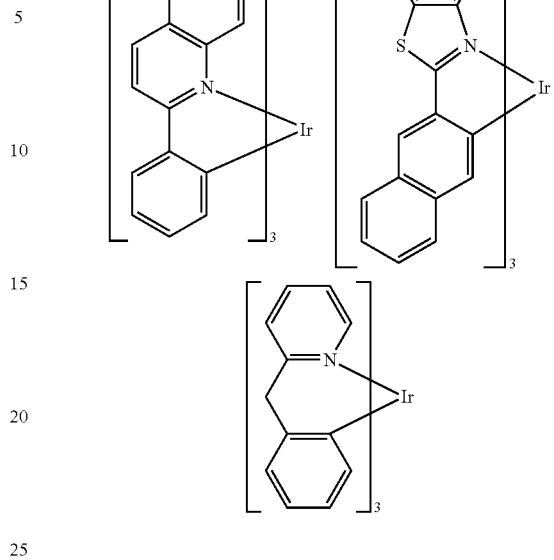

In one embodiment of the present application, as the iridium-based dopant, Ir(ppy)₃ may be used as a green phosphorescent dopant.

In one embodiment of the present application, the content of the dopant may be from 1% to 15%, preferably from 3% to 10% and more preferably from 5% to 10% based on the whole light emitting layer.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

One embodiment of the present application provides a composition for an organic material layer of an organic light emitting device comprising the heterocyclic compound represented by Chemical Formula 1 and the heterocyclic compound represented by Chemical Formula 3.

Specific details on the heterocyclic compound represented by Chemical Formula 1 and the heterocyclic compound represented by Chemical Formula 3 are the same as the descriptions provided above.

In the composition, the heterocyclic compound represented by Chemical Formula 1:the heterocyclic compound represented by Chemical Formula 3 may have a weight ratio of 1:10 to 10:1, 1:8 to 8:1, 1:5 to 5:1, or 1:2 to 2:1, however, the weight ratio is not limited thereto.

The composition may further comprise materials known in the art such as a solvent or an additive.

The composition may be used when forming an organic material of an organic light emitting device, and particularly, may be more preferably used when forming a host of a light emitting layer.

The composition has a form of simply mixing two or more compounds, and materials in a powder state may be mixed before forming an organic material layer of an organic light emitting device, or compounds in a liquid state may be mixed at a proper temperature or higher. The composition is in a solid state below the melting point of each material, and may maintain a liquid state when adjusting a temperature.

The composition may further comprise materials known in the art such as a solvent or an additive.

One embodiment of the present application provides a method for manufacturing an organic light emitting device, the method comprising preparing a substrate; forming a first electrode on the substrate; forming one or more organic material layers on the first electrode; and forming a second electrode on the organic material layer, wherein the forming of organic material layers comprises forming one or more organic material layers using the composition for an organic material layer according to one embodiment of the present application.

In the method for manufacturing an organic light emitting device according to one embodiment of the present application, the forming of organic material layers is forming using a method of thermal vacuum deposition after premixing the heterocyclic compound of Chemical Formula 1 and the heterocyclic compound of Chemical Formula 3.

The premixing means mixing materials of the heterocyclic compound of Chemical Formula 1 and the heterocyclic compound of Chemical Formula 3 in advance in one source of supply before depositing on an organic material layer.

The pre-mixed material may be referred to as the composition for an organic material layer according to one embodiment of the present application.

The organic material layer comprising Chemical Formula 1 may further comprise other materials as necessary.

The organic material layer comprising both Chemical Formula 1 and Chemical Formula 3 may further comprise other materials as necessary.

In the organic light emitting device according to one embodiment of the present application, materials other than the heterocyclic compound of Chemical Formula 1 or Chemical Formula 3 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri [phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

<Preparation Example 1> Preparation of Compound 1-5

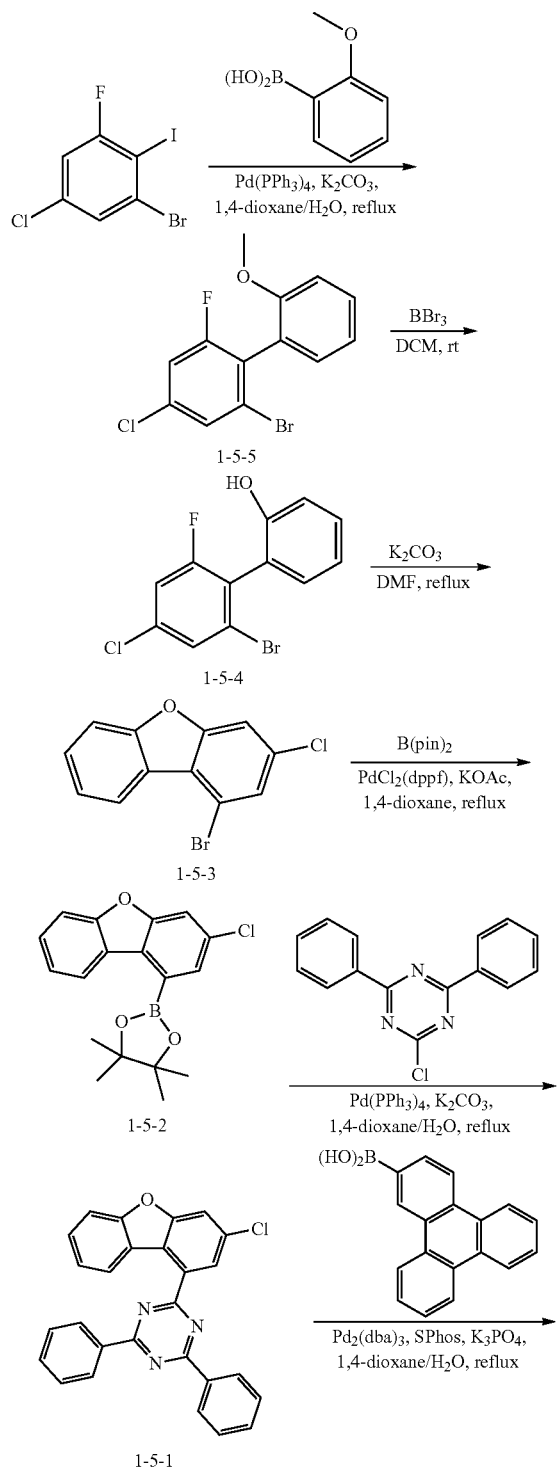

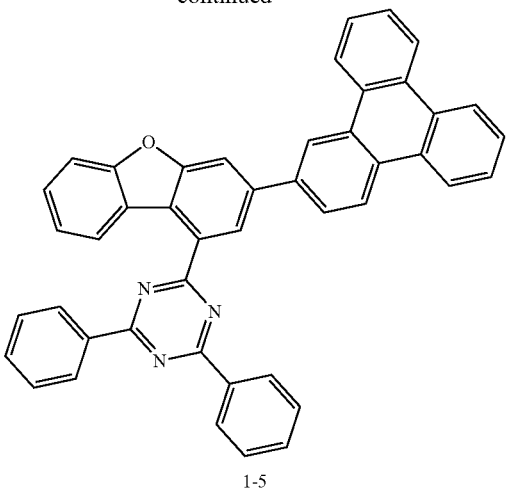

1) Preparation of Compound 1-5-5

After dissolving 1-bromo-5-chloro-3-fluoro-2-iodobenzene (200.0 g, 596.4 mM), (2-methoxyphenyl)boronic acid (82.4 g, 542.2 mM), Pd(PPh$_3$)$_4$ (31.3 g, 27.1 mM) and K$_2$CO$_3$ (150.0 g, 1084.4 mM) in 1,4-dioxane/H$_2$O (1 L/200 mL), the result was refluxed for 24 hours. After the reaction was completed, the result was extracted using distilled water and DCM at room temperature, the organic layer was dried with MgSO$_4$, and then the solvent was removed using a rotary evaporator. The reaction material was purified using column chromatography (DCM:Hex=1:10) to obtain target Compound 1-5-5 (137 g, 80%).

2) Preparation of Compound 1-5-4

After dissolving Compound 1-5-5 (82 g, 259.8 mM) and BBr$_3$ (49 mL, 519.7 mM) in DCM (800 mL), the result was refluxed for 1 hour. After the reaction was completed, the result was extracted using distilled water and DCM at room temperature, the organic layer was dried with MgSO$_4$, and then the solvent was removed using a rotary evaporator. The reaction material was purified using column chromatography (DCM:Hex=1:1) to obtain target Compound 1-5-4 (65.3 g, 83%).

3) Preparation of Compound 1-5-3

After dissolving Compound 1-5-4 (65.3 g, 216.5 mM) and K$_2$CO$_3$ (59.9 g, 433.1 mM) in DMF (300 mL), the result was refluxed for 4 hours. After the reaction was completed, the result was extracted using distilled water and DCM at room temperature, the organic layer was dried with MgSO$_4$, and then the solvent was removed using a rotary evaporator. The reaction material was purified using column chromatography (DCM:Hex=1:5) and recrystallized with methanol to obtain target Compound 1-5-3 (54.8 g, 90%).

4) Preparation of Compound 1-5-2

After dissolving Compound 1-5-3 (54 g, 191 mM), bis(pinacolato)diboron (73.0 g, 287.7 mM), PdCl$_2$(dppf) (7.0 g, 9.5 mM) and KOAc (56.2 g, 573.0 mM) in 1,4-dioxane (500 mL), the result was refluxed for 24 hours. After the reaction was completed, the result was extracted using distilled water and DCM at room temperature, the organic layer was dried with MgSO$_4$, and then the solvent was removed using a rotary evaporator. The reaction material was purified using column chromatography (DCM:Hex=1:3) and recrystallized with methanol to obtain target Compound 1-5-2 (53 g, 85%).

5) Preparation of Compound 1-5-1

After dissolving Compound 1-5-2 (53 g, 161.3 mM), 2-chloro-4,6-diphenyl-1,3,5-triazine (47.5 g, 177.4 mM), Pd(PPh)$_4$ (9.3 g, 8.1 mM) and K$_2$CO$_3$ (44.6 g, 322.6 mM) in 1,4-dioxane/H$_2$O (300/60 mL), the result was refluxed for 24 hours. After the reaction was completed, the result was extracted using distilled water and DCM at room temperature, the organic layer was dried with MgSO$_4$, and then the solvent was removed using a rotary evaporator. The reaction material was purified using column chromatography (DCM:Hex=1:3) and recrystallized with methanol to obtain target Compound 1-5-1 (57.3 g, 82%).

6) Preparation of Compound 1-5

After dissolving Compound 1-5-1 (57 g, 131.3 mM), triphenylen-2-ylboronic acid (42.9 g, 157.6 mM), Pd(PPh)$_4$ (7.6 g, 6.6 mM) and K$_2$CO$_3$ (36.3 g, 262.6 mM) in 1,4-dioxane/H$_2$O (300/60 mL), the result was refluxed for 24 hours. After the reaction was completed, the result was extracted using distilled water and DCM at room temperature, the organic layer was dried with MgSO$_4$, and then the solvent was removed using a rotary evaporator. The reaction material was purified using column chromatography (DCM:Hex=1:3) and recrystallized with methanol to obtain target Compound 1-5 (70.6 g, 86%).

Target Compound A was synthesized in the same manner as in the preparation of Preparation Example 1 except that Intermediate A of the following Table 1 was used instead of 2-chloro-4,6-diphenyl-1,3,5-triazine and Intermediate B of the following Table 1 was used instead of triphenylen-2-ylboronic acid.

TABLE 1
| Compound Number | Intermediate A | Intermediate B | Target Compound A | Yield |
|---|---|---|---|---|
| 1-1 | 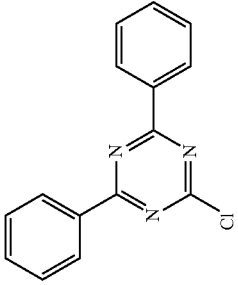 | 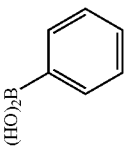 | 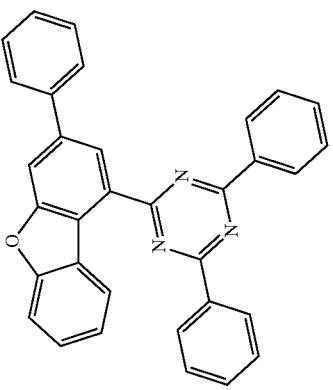 | 34% |
| 1-10 | | 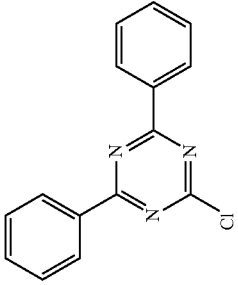 | 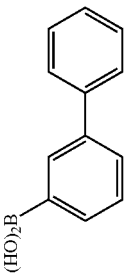 | 32% |

TABLE 1-continued

| Compound Number | Intermediate A | Intermediate B | Target Compound A | Yield |
|---|---|---|---|---|
| 1-13 | | | | 36% |
| 1-14 | | | | 33% |

TABLE 1-continued

| Compound Number | Intermediate A | Intermediate B | Target Compound A | Yield |
|---|---|---|---|---|
| 1-15 | | (structure) | (structure) | 35% |
| 1-18 | | (structure) | (structure) | 34% |

TABLE 1-continued

| Compound Number | Intermediate A | Intermediate B | Target Compound A | Yield |
|---|---|---|---|---|
| 1-19 | | (HO)₂B-[phenyl-phenyl-triphenylene] | [dibenzofuran-triazine-phenyl-phenyl-triphenylene structure] | 32% |
| 1-20 | | (HO)₂B-[biphenyl-phenyl] | [dibenzofuran-triazine-biphenyl-phenyl structure] | 36% |

TABLE 1-continued

| Compound Number | Intermediate A | Intermediate B | Target Compound A | Yield |
|---|---|---|---|---|
| 1-21 | | | | 33% |
| 1-22 | | | | 35% |

TABLE 1-continued

| Compound Number | Intermediate A | Intermediate B | Target Compound A | Yield |
|---|---|---|---|---|
| 1-23 | | (structure shown) | (structure shown) | 34% |

TABLE 1-continued
| Compound Number | Intermediate A | Intermediate B | Target Compound A | Yield |
|---|---|---|---|---|
| 1-25 | 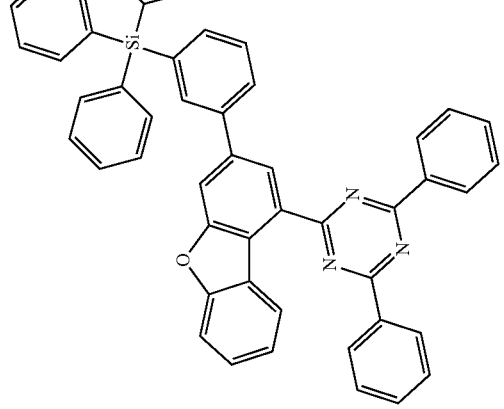 | 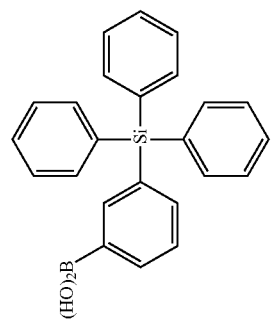 | 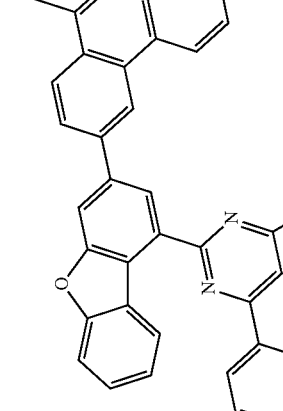 | 34% |
| 1-67 | 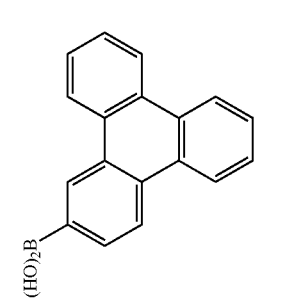 | 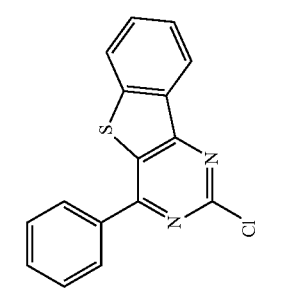 |  | 32% |

TABLE 1-continued
| Compound Number | Intermediate A | Intermediate B | Target Compound A | Yield |
|---|---|---|---|---|
| 1-70 | 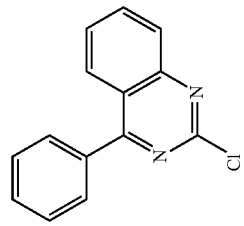 | 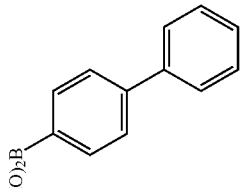 | 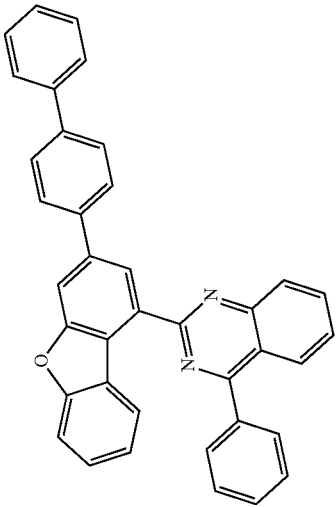 | 36% |
| 1-74 | 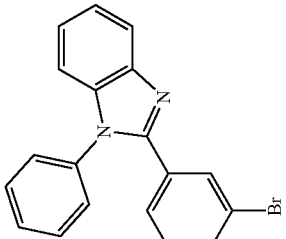 | 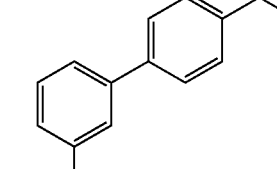 | 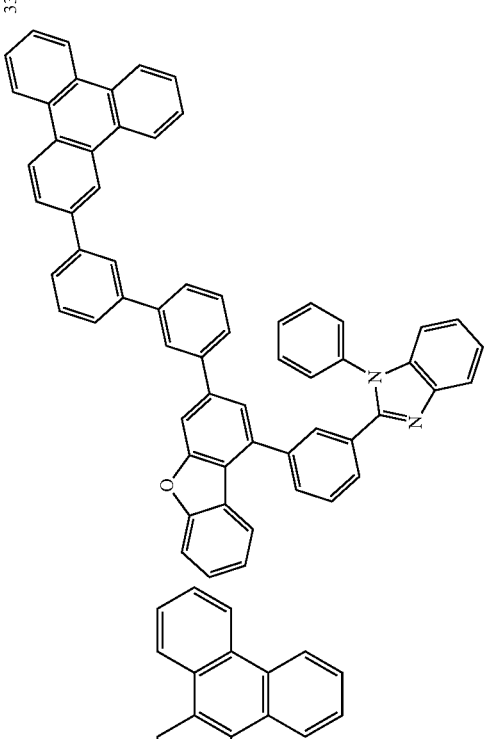 | 33% |

TABLE 1-continued
| Compound Number | Intermediate A | Intermediate B | Target Compound A | Yield |
|---|---|---|---|---|
| 1-77 | 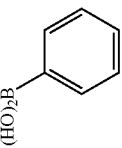 | 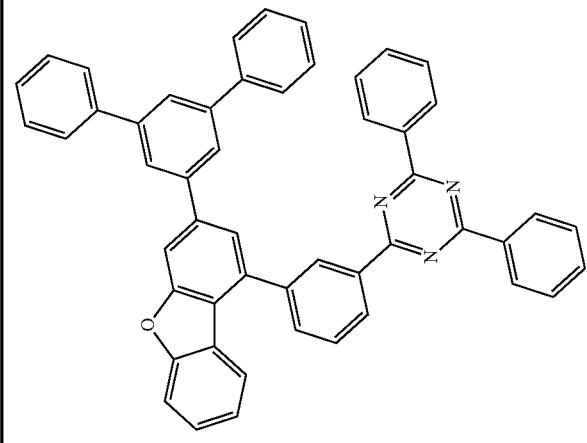 | 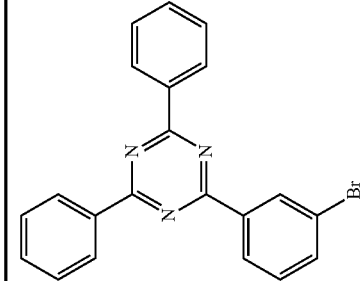 | 35% |
| 1-106 | 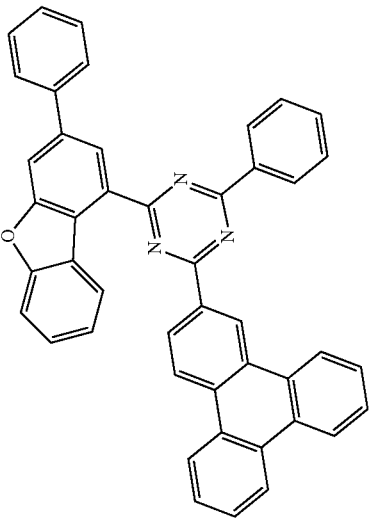 | 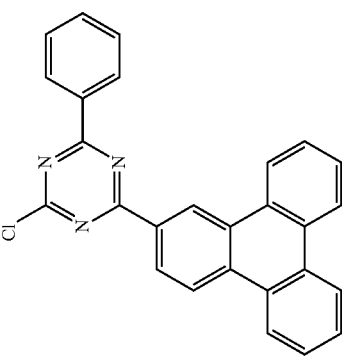 | 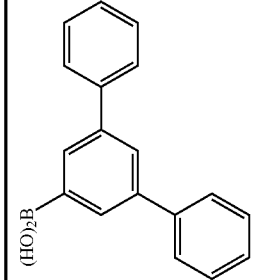 | 34% |

TABLE 1-continued
| Compound Number | Intermediate A | Intermediate B | Target Compound A | Yield |
|---|---|---|---|---|
| 1-107 | 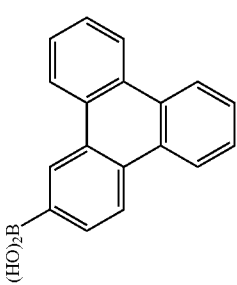 | | 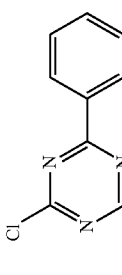 | 32% |
| 1-112 | 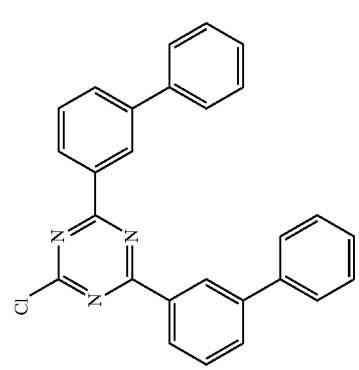 | 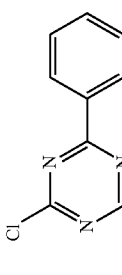 | 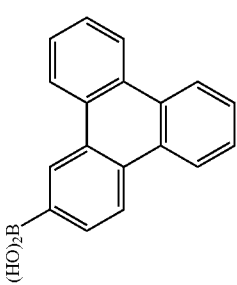 | 36% |

TABLE 1-continued

| Compound Number | Intermediate A | Intermediate B | Target Compound A | Yield |
|---|---|---|---|---|
| 1-114 | | | | 33% |
| 1-115 | | | | 35% |

<Preparation Example 2> Preparation of Compound 1-30

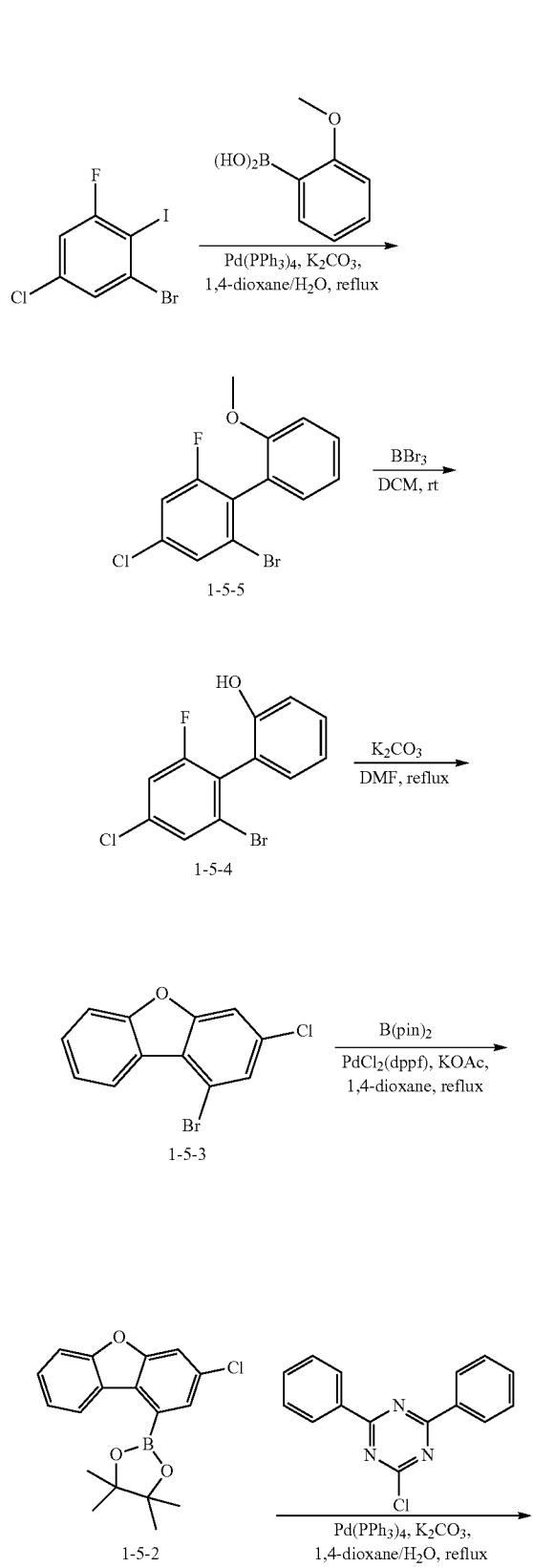

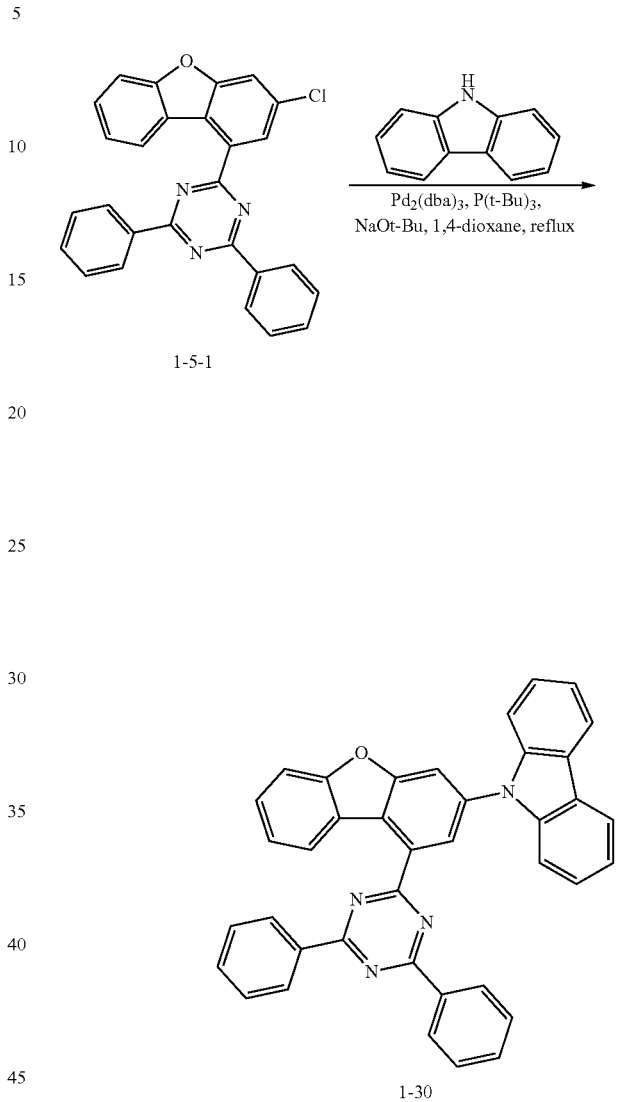

1) Preparation of Compound 1-30

After dissolving Compound 1-5-1 (10 g, 23.0 mM), 9H-carbazole (42.9 g, 4.2 mM), Pd$_2$(dba)$_3$ (1.1 g, 1.2 mM), P(t-Bu)$_3$ (1.5 mL, 2.3 mM) and NaOt-Bu (4.4 g, 46 mM) in 1,4-dioxane (200 mL), the result was refluxed for 24 hours. After the reaction was completed, the result was extracted using distilled water and DCM at room temperature, the organic layer was dried with MgSO$_4$, and then the solvent was removed using a rotary evaporator. The reaction material was purified using column chromatography (DCM:Hex=1:3) and recrystallized with methanol to obtain target Compound 1-30 (11.2 g, 86%).

Target Compound A was synthesized in the same manner as in the preparation of Preparation Example 2 except that Intermediate A of the following Table 2 was used instead of 2-chloro-4,6-diphenyl-1,3,5-triazine and Intermediate B of the following Table 2 was used instead of 9H-carbazole.

TABLE 2

| Compound Number | Intermediate A | Intermediate B | Target Compound A | Yield |
|---|---|---|---|---|
| 1-32 | | | | 36% |
| 1-33 | | | | 32% |
| 1-39 | | | | 32% |

TABLE 2-continued

| Compound Number | Intermediate A | Intermediate B | Target Compound A | Yield |
|---|---|---|---|---|
| 1-47 | | [structure] | [structure] | 34% |
| 1-50 | | [structure] | [structure] | 33% |
| 1-83 | [structure] | [structure] | [structure] | 32% |

TABLE 2-continued
| Compound Number | Intermediate A | Intermediate B | Target Compound A | Yield |
|---|---|---|---|---|
| 1-84 | | | | 33% |
<Preparation Example 3> Preparation of Compound 2-5
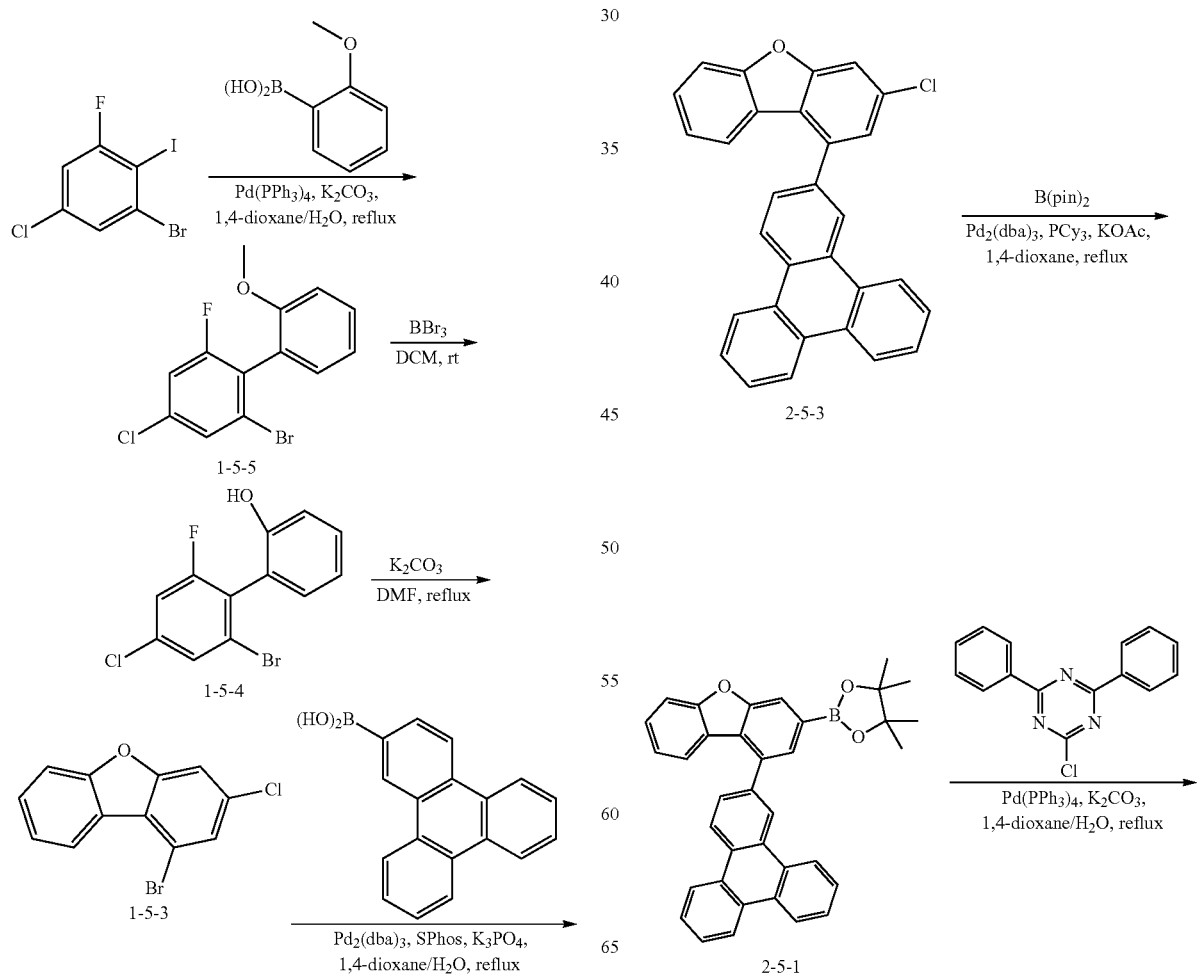

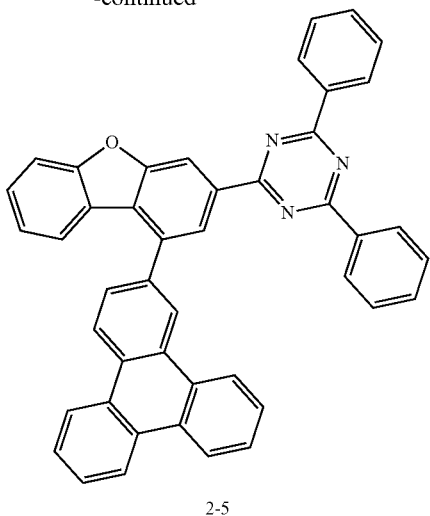

2-5

1) Preparation of Compound 2-5-2

After dissolving Compound 1-5-3 (10 g, 35.5 mM), triphenylen-2-ylboronic acid (10.6 g, 39.1 mM), Pd$_2$(dba)$_3$ (1.6 g, 1.8 mM), SPhos (1.5 g, 3.55 mM) and K$_3$PO$_4$ (15.1 g, 71.0 mM) in 1,4-dioxane/H$_2$O (200/40 mL), the result was refluxed for 24 hours. After the reaction was completed, the result was extracted using distilled water and DCM at room temperature, the organic layer was dried with MgSO$_4$, and then the solvent was removed using a rotary evaporator. The reaction material was purified using column chromatography (DCM:Hex=1:3) and recrystallized with methanol to obtain target Compound 2-5-2 (13.1 g, 86%).

2) Preparation of Compound 2-5-1

After dissolving Compound 2-5-2 (13 g, 30.3 mM), bis(pinacolato)diboron (73.0 g, 11.5 mM), Pd$_2$(dba)$_3$ (2.8 g, 3.0 mM), PCy$_3$ (1.7 g, 6.1 mM) and KOAc (8.9 g, 90.9 mM) in 1,4-dioxane (100 mL), the result was refluxed for 24 hours. After the reaction was completed, the result was extracted using distilled water and DCM at room temperature, the organic layer was dried with MgSO$_4$, and then the solvent was removed using a rotary evaporator. The reaction material was purified using column chromatography (DCM:Hex=1:3) and recrystallized with methanol to obtain target Compound 2-5-1 (14 g, 89%).

3) Preparation of Compound 2-5

After dissolving Compound 2-5-1 (14 g, 26.9 mM), 2-chloro-4,6-diphenyl-1,3,5-triazine (7.9 g, 29.6 mM), Pd(PPh)$_4$ (1.5 g, 1.3 mM) and K$_2$CO$_3$ (7.4 g, 53.8 mM) in 1,4-dioxane/H$_2$O (200/40 mL), the result was refluxed for 24 hours. After the reaction was completed, the result was extracted using distilled water and DCM at room temperature, the organic layer was dried with MgSO$_4$, and then the solvent was removed using a rotary evaporator. The reaction material was purified using column chromatography (DCM:Hex=1:3) and recrystallized with methanol to obtain target Compound 2-5 (13.8 g, 82%).

Target Compound A was synthesized in the same manner as in the preparation of Preparation Example 3 except that Intermediate A of the following Table 3 was used instead of triphenylen-2-ylboronic acid and Intermediate B of the following Table 3 was used instead of 2-chloro-4,6-diphenyl-1,3,5-triazine.

TABLE 3

| Compound Number | Intermediate A | Intermediate B | Target Compound A | Yield |
|---|---|---|---|---|
| 2-13 | (HO)₂B-phenyl-triphenylene | 2-chloro-4,6-diphenyl-1,3,5-triazine | (triazine-dibenzofuran-phenyl-triphenylene target compound) | 32% |
| 2-20 | (HO)₂B-[1,1':4',1''-terphenyl] | 2-chloro-4,6-diphenyl-1,3,5-triazine | (triazine-dibenzofuran-terphenyl target compound) | 36% |

TABLE 3-continued
| Compound Number | Intermediate A | Intermediate B | Target Compound A | Yield |
|---|---|---|---|---|
| 2-23 | 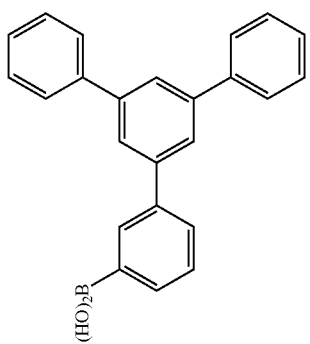 | | 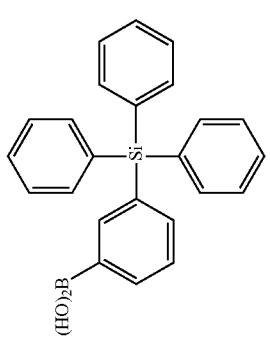 | 33% |
| 2-25 | 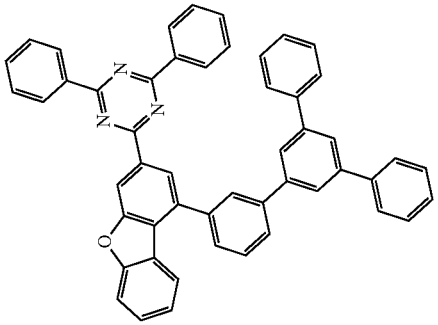 | | 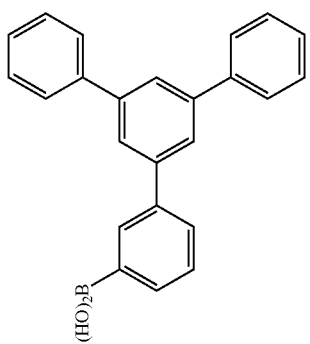 | 35% |

TABLE 3-continued
| Compound Number | Intermediate A | Intermediate B | Target Compound A | Yield |
|---|---|---|---|---|
| 2-107 | 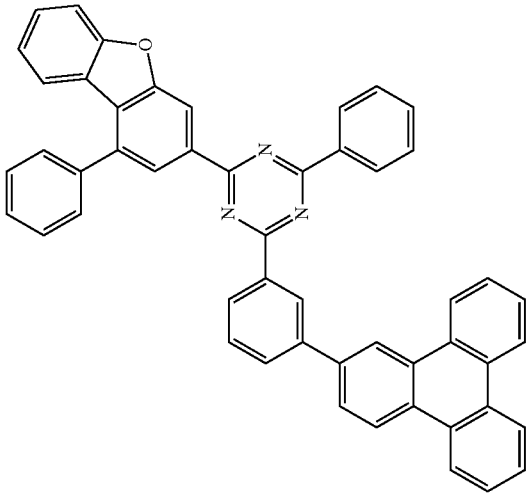 | 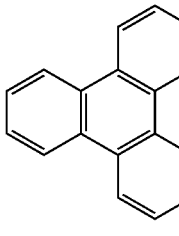 |  | 33% |

TABLE 3-continued
| Compound Number | Intermediate A | Intermediate B | Target Compound A | Yield |
|---|---|---|---|---|
| 2-112 | 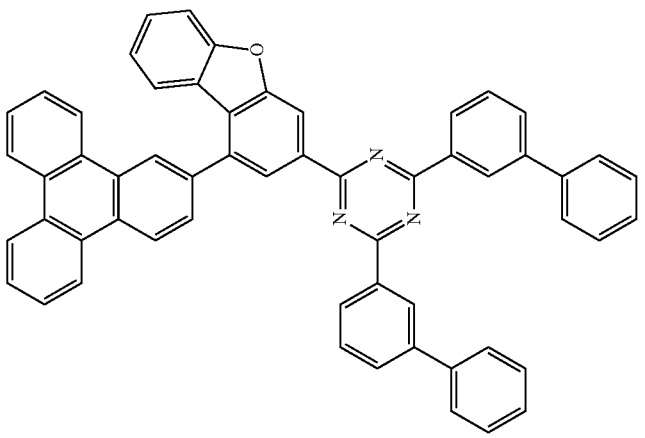 | 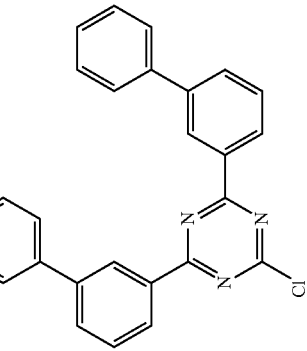 | 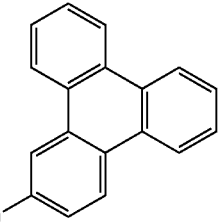 | 35% |

\<Preparation Example 4\> Preparation of Compound 2-33

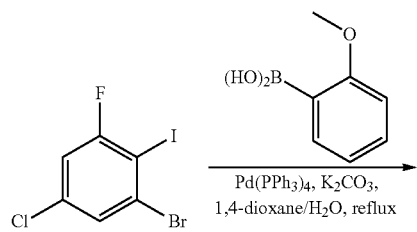

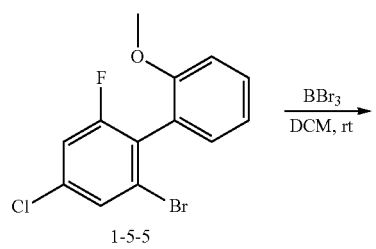

1-5-5

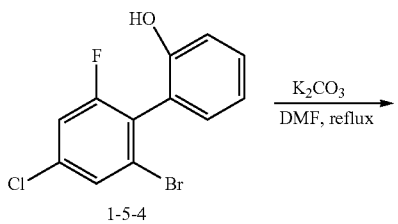

1-5-4

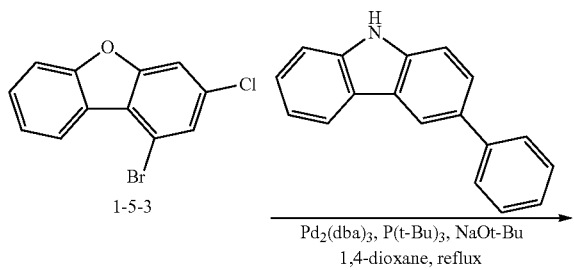

1-5-3

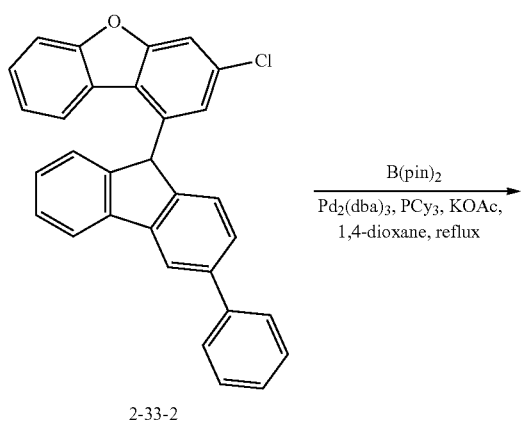

2-33-2

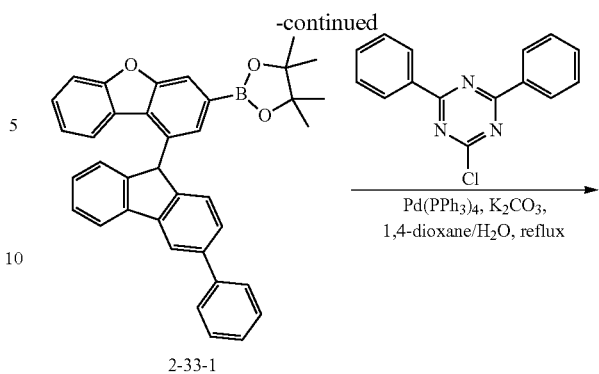

2-33-1

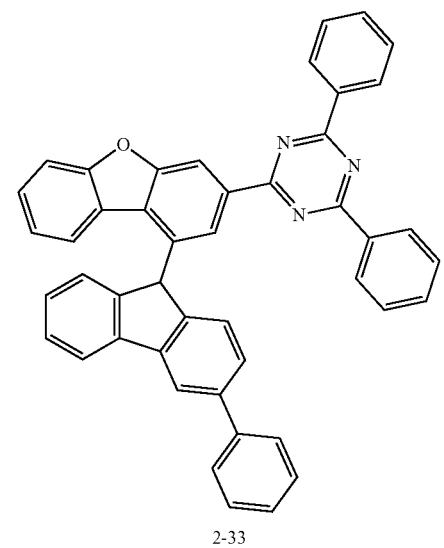 [SMILES: c1ccc(-c2ccc3c(c2)-c2ccccc2C3c2cc(-c3nc(-c4ccccc4)nc(-c4ccccc4)n3)cc3oc4ccccc4c23)cc1]

2-33

1) Preparation of Compound 2-33-2

After dissolving Compound 1-5-3 (10 g, 35.5 mM), 3-phenyl-9H-carbazole (7.2 g, 29.6 mM), Pd$_2$(dba)$_3$ (1.4 g, 1.5 mM), P(t-Bu)$_3$ (2.0 mL, 3.0 mM) and NaOt-Bu (5.7 g, 59.2 mM) in 1,4-dioxane (200 mL), the result was refluxed for 24 hours. After the reaction was completed, the result was extracted using distilled water and DCM at room temperature, the organic layer was dried with MgSO$_4$, and then the solvent was removed using a rotary evaporator. The reaction material was purified using column chromatography (DCM:Hex=1:3) and recrystallized with methanol to obtain target Compound 2-33-2 (11.3 g, 86%).

2) Preparation of Compound 2-33-1

After dissolving Compound 2-33-2 (10 g, 22.5 mM), bis(pinacolato)diboron (8.6 g, 33.7 mM), Pd$_2$(dba)$_3$ (2.1 g, 2.3 mM), PCy$_3$ (1.3 g, 4.5 mM) and KOAc (6.6 g, 67.5 mM) in 1,4-dioxane (200 mL), the result was refluxed for 24 hours. After the reaction was completed, the result was extracted using distilled water and DCM at room temperature, the organic layer was dried with MgSO$_4$, and then the solvent was removed using a rotary evaporator. The reaction material was purified using column chromatography (DCM: Hex=1:3) and recrystallized with methanol to obtain target Compound 2-33-1 (10.7 g, 89%).

2) Preparation of Compound 2-33

After dissolving Compound 2-33-1 (10 g, 18.7 mM), 2-chloro-4,6-diphenyl-1,3,5-triazine (5.5 g, 20.5 mM), Pd(PPh)$_4$ (1.1 g, 0.9 mM) and K$_2$CO$_3$ (5.2 g, 37.4 mM) in 1,4-dioxane/H$_2$O (200/40 mL), the result was refluxed for 24 hours. After the reaction was completed, the result was extracted using distilled water and DCM at room temperature, the organic layer was dried with MgSO$_4$, and then the solvent was removed using a rotary evaporator. The reaction material was purified using column chromatography (DCM:Hex=1:3) and recrystallized with methanol to obtain target Compound 2-33 (9.8 g, 82%).

Target Compound A was synthesized in the same manner as in the preparation of Preparation Example 4 except that Intermediate A of the following Table 4 was used instead of 3-phenyl-9H-carbazole and Intermediate B of the following Table 4 was used instead of 2-chloro-4,6-diphenyl-1,3,5-triazine.

TABLE 4

| Compound Number | Intermediate A | Intermediate B | Target Compound A | Yield |
|---|---|---|---|---|
| 2-47 | | | | 36% |

<Preparation Example 5> Preparation of Compound 3-5-3

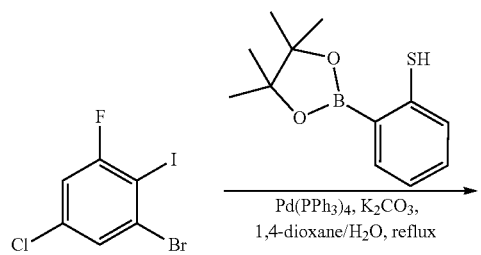

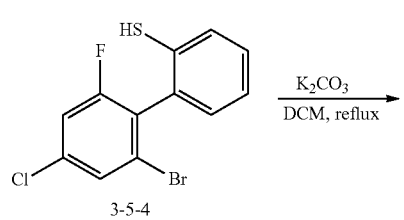

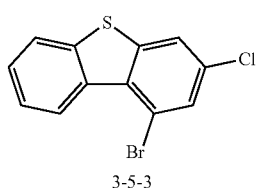

1) Preparation of Compound 3-5-4

After dissolving 1-bromo-5-chloro-3-fluoro-2-iodobenzene (20.0 g, 59.6 mM), 2-(4,4,5,5-tetramethyl-1,3,2-dioxaborolan-2-yl)benzenethiol (12.8 g, 54.2 mM), Pd(PPh$_3$)$_4$ (3.1 g, 2.7 mM) and K$_2$CO$_3$ (15.0 g, 108.4 mM) in 1,4-dioxane/H$_2$O (200/40 mL), the result was refluxed for 24 hours. After the reaction was completed, the result was extracted using distilled water and DCM at room temperature, the organic layer was dried with MgSO$_4$, and then the solvent was removed using a rotary evaporator. The reaction material was purified using column chromatography (DCM:Hex=1:10) to obtain target Compound 3-5-4 (13.8 g, 80%).

2) Preparation of Compound 3-5-3

After dissolving Compound 3-5-4 (6.9 g, 21.6 mM) and K$_2$CO$_3$ (59.9 g, 43.3 mM) in DMF (60 mL), the result was refluxed for 4 hours. After the reaction was completed, the result was extracted using distilled water and DCM at room temperature, the organic layer was dried with MgSO$_4$, and then the solvent was removed using a rotary evaporator. The reaction material was purified using column chromatography (DCM:Hex=1:5) and recrystallized with methanol to obtain target Compound 3-5-3 (5.8 g, 90%).

Target Compound A was synthesized in the same manner as in the preparation of Compounds 1-5-2 to 1-5 of Preparation Example 1 except that Intermediate A of the following Table 5 was used instead of 2-chloro-4,6-diphenyl-1,3,5-triazine and Intermediate B of the following Table 5 was used instead of triphenylen-2-ylboronic acid.

TABLE 5

| Compound Number | Intermediate A | Intermediate B | Target Compound A | Yield |
|---|---|---|---|---|
| 3-5 | | | | 34% |
| 3-13 | | | | 36% |
| 3-107 | | | | 32% |

Target Compound A was synthesized in the same manner as in the preparation of Preparation Example 2 except that Intermediate A of the following Table 6 was used instead of 2-chloro-4,6-diphenyl-1,3,5-triazine and Intermediate B of the following Table 6 was used instead of 9H-carbazole.

TABLE 6

| Compound Number | Intermediate A | Intermediate B | Target Compound A | Yield |
|---|---|---|---|---|
| 3-33 | | | | 35% |

Target Compound A was synthesized in the same manner as in the preparation of Preparation Example 3 except that Intermediate A of the following Table 7 was used instead of triphenylen-2-ylboronic acid and Intermediate B of the following Table 7 was used instead of 2-chloro-4,6-diphenyl-1,3,5-triazine.

Target Compound A was synthesized in the same manner as in the preparation of Preparation Example 4 except that Intermediate A of the following Table 8 was used instead of 3-phenyl-9H-carbazole and Intermediate B of the following Table 8 was used instead of 2-chloro-4,6-diphenyl-1,3,5-triazine.

TABLE 7

| Compound Number | Intermediate A | Intermediate B | Target Compound A | Yield |
|---|---|---|---|---|
| 4-5 | | | | 32% |
| 4-13 | | | | 32% |

TABLE 8

| Compound Number | Intermediate A | Intermediate B | Target Compound A | Yield |
|---|---|---|---|---|
| 4-33 | (3-phenylcarbazole) | 2-chloro-4,6-diphenyl-1,3,5-triazine | (structure shown) | 32% |

<Preparation Example 6> Synthesis of Compound 5-3

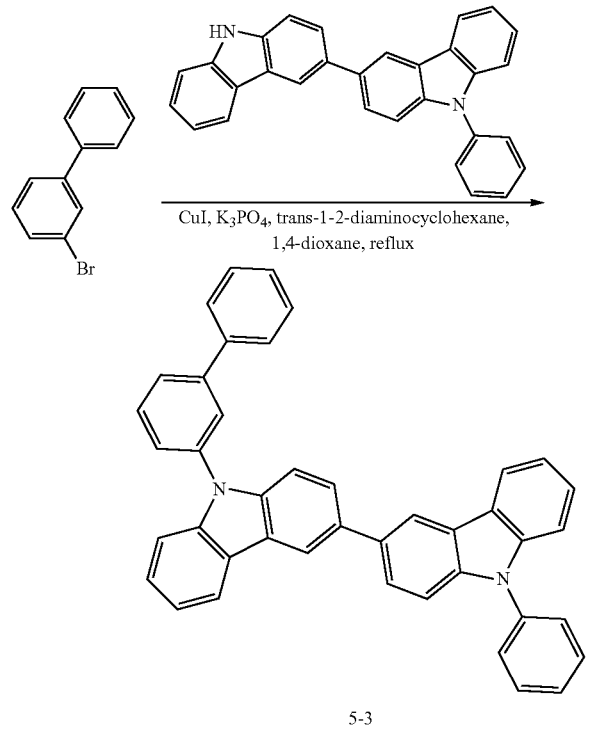

5-3

1) Preparation of Compound 5-3

After dissolving 3-bromo-1,1'-biphenyl (3.7 g, 15.8 mM), 9-phenyl-9H,9'H-3,3'-bicarbazole (6.5 g, 15.8 mM), CuI (3.0 g, 15.8 mM), trans-1,2-diaminocyclohexane (1.9 mL, 15.8 mM) and $K_3PO_4$ (3.3 g, 31.6 mM) in 1,4-oxane (100 mL), the result was refluxed for 24 hours. After the reaction was completed, the result was extracted using distilled water and DCM at room temperature, the organic layer was dried with $MgSO_4$, and then the solvent was removed using a rotary evaporator. The reaction material was purified using column chromatography (DCM:Hex=1:3) and recrystallized with methanol to obtain target Compound 5-3 (7.5 g, 85%).

Target Compound A was synthesized in the same manner as in the preparation of Preparation Example 6 except that Intermediate A of the following Table 9 was used instead of 3-bromo-1,1'-biphenyl and Intermediate B of the following Table 9 was used instead of 9-phenyl-9H,9'H-3,3'-bicarbazole.

TABLE 9
| Compound Number | Intermediate A | Intermediate B | Target Compound A | Yield |
|---|---|---|---|---|
| 5-4 | 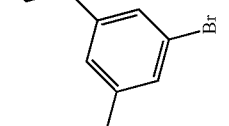 | 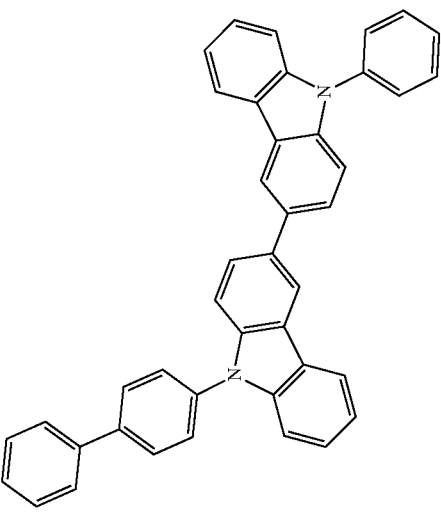 | 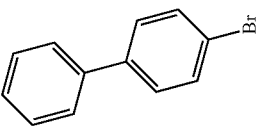 | 83% |
| 5-7 | 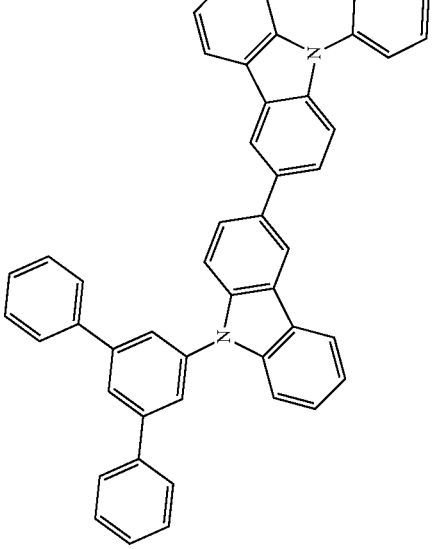 | | 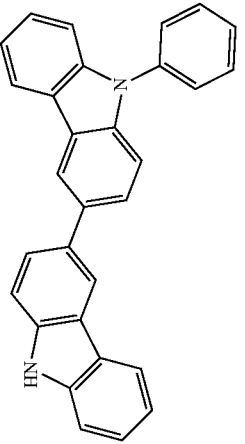 | 84% |

TABLE 9-continued

| Compound Number | Intermediate A | Intermediate B | Target Compound A | Yield |
|---|---|---|---|---|
| 5-31 | | | | 81% |
| 5-32 | | | | 80% |

TABLE 9-continued
| Compound Number | Intermediate A | Intermediate B | Target Compound A | Yield |
|---|---|---|---|---|
| 5-42 | 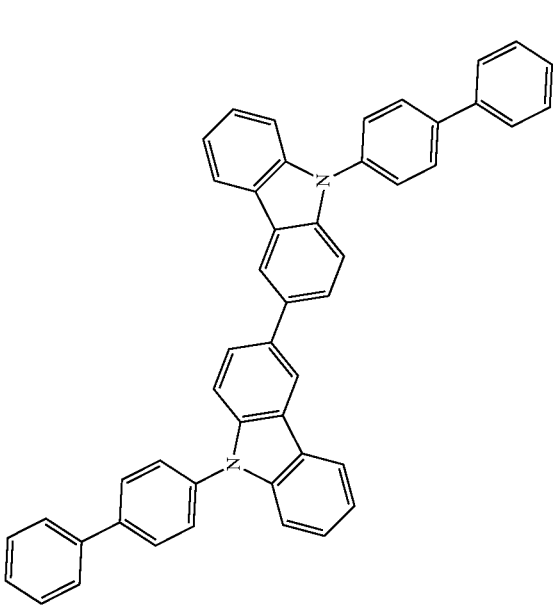 | 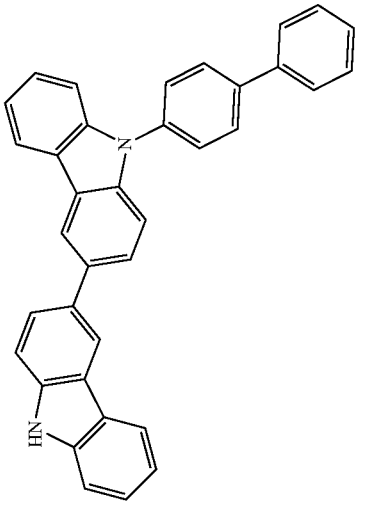 | 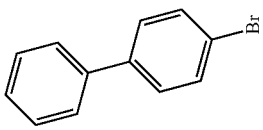 | 82% |

Compounds other than the compounds described in Tables 1 to 9 were also prepared in the same manner as in the methods described in the preparation examples provided above.

The following Table 10 and Table 11 present 1H NMR data and FD-MS data of the synthesized compounds, and through the following data, syntheses of target compounds may be identified.

TABLE 10

| Compound Number | $^1$H NMR (CDCl$_3$, 200 Mz) |
|---|---|
| 1-1 | δ = 8.28 (4H, d), 7.89 (1H, d), 7.41~7.66 (16H, m) |
| 1-5 | δ = 9.15 (1H, s), 8.93 (2H, d), 8.28 (4H, d), 8.04~8.18 (4H, m), 7.82~7.89 (5H, m), 7.32-7.66 (11H, m) |
| 1-10 | δ = 8.28 (4H, d), 7.89 (1H, d), 7.32~7.70 (20H, m) |
| 1-13 | δ = 9.15 (1H, s), 8.93 (2H, d), 8.28 (4H, d), 8.04~8.18 (4H, m), 7.82~7.89 (5H, m), 7.32~7.70 (15H, m) |
| 1-14 | δ = 8.28 (4H, d), 7.89 (1H, d), 7.25~7.66 (20H, m) |
| 1-15 | δ = 9.15 (1H, s), 8.93 (2H, d), 8.04~8.18 (4H, m), 8.82~8.89 (5H, m), 7.25~7.66 (15H, m) |
| 1-18 | δ = 8.28 (4H, d), 7.89 (1H, d), 7.32~7.70 (24H, m) |
| 1-19 | δ = 9.15 (1H, s), 8.93 (2H, d), 8.28 (4H, d), 8.12~8.18 (3H, m), 7.82~7.89 (5H, m), 7.32~7.70 (19H, m) |
| 1-20 | δ = 8.28 (4H, d), 7.89 (1H, d), 7.25~7.60 (23H, m) |
| 1-21 | δ = 9.15 (1H, s), 8.93 (2H, d), 8.28 (4H, d), 8.04 (1H, d), 7.82~7.89 (5H, m), 7.25~7.66 (19H, m) |
| 1-22 | δ = 8.28 (4H, d), 7.89 (1H, d), 7.32~7.66 (24H, m) |
| 1-23 | δ = 8.28 (4H, d), 7.89 (1H, d), 7.32~7.70 (28H, m) |
| 1-25 | δ = 8.28 (4H, d), 7.89 (1H, d), 7.76 (1H, s), 7.32~7.66 (29H, m) |
| 1-30 | δ = 8.55 (1H, d), 8.28 (4H, d), 8.12 (1H, d), 7.89~7.94 (2H, m), 7.63~7.69 (4H, m), 7.25~7.51 (12H, m) |
| 1-32 | δ = 8.55 (1H, d), 8.28 (4H, d), 7.89~7.94 (2H, m), 7.79 (1H, d), 7.62~7.69 (4H, m), 7.25~7.52 (15H, m) |
| 1-33 | δ = 8.55 (1H, d), 8.28 (4H, d), 7.87~7.94 (3H, m), 7.77(1H, s), 7.66~7.69 (4H, m), 7.25~7.52 (15H, m) |
| 1-39 | δ = 8.55 (2H, d), 8.28 (4H, d), 8.12 (1H, d), 7.89~7.94 (3H, m), 7.25~7.69 (21H, m) |
| 1-47 | δ = 8.55 (1H, d), 8.28 (4H, d), 8.12 (1H, d), 7.89~7.94 (2H, m), 7.25~7.69 (23H, m) |
| 1-50 | δ = 8.55 (1H, d), 8.28 (4H, d), 8.09 (1H, d), 7.61~7.69 (5H, m), 7.24~7.51 (13H, m), 1.72 (6H, s) |
| 1-67 | δ = 9.15 (1H, s), 8.93 (2H, d), 7.79~8.18 (13H, m), 7.82~7.89 (5H, m), 7.38~7.66 (10H, m) |
| 1-70 | δ = 8.16 (1H, d), 7.79~7.89 (5H, m), 7.25~7.66 (18H, m) |
| 1-74 | δ = 9.15 (1H, s), 8.93 (2H, d), 8.56 (1H, d), 8.12~8.24 (4H, m), 8.04 (1H, d), 7.82~7.89 (5H, m), 7.32~7.70 (22H, m), 7.22 (2H, d) |
| 1-77 | δ = 8.24~8.28 (5H, m), 7.89 (1H, d), 7.32~7.70 (27H, m) |
| 1-79 | δ = 8.24~8.28 (5H, m), 7.89 (1H, d), 7.32~7.66 (33H, m) |
| 1-83 | δ = 8.55 (1H, d), 8.28 (4H, d), 8.17~8.18 (2H, m), 7.89~7.94 (3H, m), 7.75~7.79 (3H, m), 7.22~7.52 (16H, m) |
| 1-84 | δ = 8.55 (1H, d), 8.28 (2H, d), 7.77~7.94 (7H, m), 7.66~7.69 (5H, m), 7.25~7.52 (15H, m) |
| 1-106 | δ = 9.15 (1H, s), 8.93 (2H, d), 8.28 (2H, d), 8.12~8.18 (3H,m), 8.04 (1H, d), 7.82~7.89 (5H, m), 7.32~7.66 (13H, m) |
| 1-107 | δ = 9.15 (1H, s), 8.93 (2H, d), 8.12~8.28 (6H, m), 8.04 (1H, d), 7.82~7.89 (5H, m), 7.32~7.70 (16H, m) |
| 1-112 | δ = 9.15 (1H, s), 8.93 (2H, d), 8.12~8.24 (5H, m), 8.04 (1H, d), 7.82~7.89( 5H, m), 7.32~7.70 (21H, m) |
| 1-114 | δ = 9.15 (1H, s), 8.93 (2H, d), 8.12~8.18 (3H, m), 8.04 (1H, d), 7.82~7.89 (9H, m), 7.25~7.66 (19H, m) |
| 1-115 | δ = 9.15 (1H, s), 8.93 (2H, d), 8.28 (2H, d), 8.04~8.18 (4H, m), 7.75~7.89 (7H, m), 7.32~7.66 (13H, m) |

TABLE 10-continued

| Compound Number | $^1$H NMR (CDCl$_3$, 200 Mz) |
|---|---|
| 2-5 | δ = 9.15 (1H, s), 8.93 (2H, d), 8.28 (4H, d), 8.04~8.18 (4H, m), 7.82~7.89 (5H, m), 7.32~7.66 (11H, m) |
| 2-13 | δ = 9.15 (1H, s), 8.93 (2H, d), 8.28 (4H, d), 8.04~8.18 (4H, m), 7.82~7.89 (5H, m), 7.32~7.89 (15H, m) |
| 2-20 | δ = 8.28 (4H, d), 8.89 (1H, d), 7.66 (1H, d), 8.04~8.18 (4H, m), 7.82~7.89 (5H, m), 7.25~7.60 (23H, m) |
| 2-23 | δ = 8.28 (4H, d), 8.89 (1H, d), 7.32~7.70 (28H, m) |
| 2-25 | δ = 8.28 (4H, d), 8.89 (1H, d), 7.76 (1H, s), 7.32~7.66 (29H, m) |
| 2-33 | δ = 8.55 (1H, d), 8.28 (4H, d), 7.87~7.95 (4H, m), 7.77 (1H, s), 7.66~7.69 (3H, m), 7.25~7.52 (15H, m) |
| 2-47 | δ = 8.55 (1H, d), 8.28 (4H, d), 8.12 (1H, d), 7.94~7.89 (3H, m), 7.87~8.00 (5H, m), 7.77 (2H, s), 7.25~7.66 (22H, m) |
| 2-107 | δ = 9.15 (1H, s), 8.93 (2H, d), 8.04~8.28 (7H, m), 7.79~7.89 (7H, m), 7.32~7.70 (14H, m) |
| 2-112 | δ = 9.15 (1H, s), 8.93 (2H, d), 8.12~8.24 (5H, m), 8.04 (1H, d), 7.82~7.89 (5H, m), 7.32~7.70 (21H, m) |
| 3-5 | δ = 9.15 (1H, s), 8.93 (2H, d), 8.45 (1H, d), 8.28 (4H, d), 7.98~8.18 (6H, m), 7.77~7.88 (5H, m), 7.41~7.52 (8H, m) |
| 3-13 | δ = 9.15 (1H, s), 8.93 (2H, d), 8.45 (1H, d), 8.28 (4H, d), 8.12~8.18 (3H, m), 7.98~8.04 (3H, m), 7.77~7.88 (3H, m), 7.70 (1H, s), 7.41~7.57 (11H, m) |
| 3-33 | δ = 8.55 (1H, d), 8.45 (1H, d), 8.28 (4H, d), 7.87~7.98 (4H, m), 7.77 (1H, s), 7.69~7.71 (2H, m), 7.25~7.52 (15H, m) |
| 3-107 | δ = 9.15 (1H, s), 8.93 (2H, d), 8.45 (1H, d), 8.28 (4H, d), 8.12~8.28 (6H, m), 7.98~8.04 (3H, m), 7.77~7.88 (5H, m), 7.70 (1H, s), 7.41~7.57 (12H, m) |
| 4-5 | δ = 9.15 (1H, s), 8.93 (2H, d), 8.45 (1H, d), 8.28 (4H, d), 7.98~8.18 (6H, m), 7.77~7.88 (5H, m), 7.70 (1H, s), 7.41~7.52 (8H, m) |
| 4-13 | δ = 9.15 (1H, s), 8.93 (2H, d), 8.45 (1H, d), 8.28 (4H, d), 8.12~8.18 (3H, m), 7.98~8.04 (3H, m), 7.77~7.88 (5H, m), 7.70 (1H, s), 7.41~7.57 (11H, m) |
| 4-33 | δ = 8.55 (1H, d), 8.45 (1H, d), 8.28 (4H, d), 7.87~7.98 (2H, m), 7.77 (1H, s), 7.69~7.71 (2H, m), 7.77 (2H, s), 7.25~7.52 (15H, m) |
| 5-3 | δ = 8.55 (1H, d), 8.30 (1H, d), 8.21~8.13 (3H, m), 7.99~7.89 (3H, m), 7.77~7.35 (17H, m), 7.20~7.16 (2H, m) |
| 5-4 | δ = 8.55 (1H, d), 8.30 (1H, d), 8.19~8.13 (2H, m), 7.99~7.89 (8H, m), 7.77~7.75 (3H, m), 7.62~7.35 (11H, m), 7.20~7.16 (2H, m) |
| 5-7 | δ = 8.55 (1H, d), 8.31~8.30 (3H, d), 8.19~8.13 (2H, m), 7.99~7.89 (5H, m), 7.77~7.75 (5H, m), 7.62~7.35 (14H, m), 7.20~7.16 (2H, m) |
| 5-31 | δ = 8.55 (1H, d), 8.30 (1H, d), 8.21~8.13 (4H, m), 7.99~7.89 (4H, m), 7.77~7.35 (20H, m), 7.20~7.16 (2H, m) |
| 5-32 | δ = 8.55 (1H, d), 8.30 (1H, d), 8.21~8.13 (3H, m), 7.99~7.89 (8H, m), 7.77~7.35 (17H, m), 7.20~7.16 (2H, m) |

TABLE 11

| Compound | FD-MS | Compound | FD-MS |
|---|---|---|---|
| 1-1 | m/z = 475.17 ($C_{33}H_{21}N_3O$ = 475.54) | 1-5 | m/z = 625.22 ($C_{45}H_{27}N_3O$ = 625.72) |
| 1-10 | m/z = 551.20 ($C_{39}H_{25}N_3O$ = 551.64) | 1-13 | m/z = 701.25 ($C_{51}H_{31}N_3O$ = 701.81) |
| 1-14 | m/z = 551.20 ($C_{39}H_{25}N_3O$ = 551.64) | 1-15 | m/z = 701.25 ($C_{51}H_{31}N_3O$ = 701.81) |
| 1-18 | m/z = 627.23 ($C_{45}H_{29}N_3O$ = 627.73) | 1-19 | m/z = 777.28 ($C_{57}H_{35}N_3O$ = 777.91) |
| 1-20 | m/z = 627.23 ($C_{45}H_{29}N_3O$ = 627.73) | 1-21 | m/z = 777.28 ($C_{57}H_{35}N_3O$ = 777.91) |
| 1-22 | m/z = 627.23 ($C_{45}H_{29}N_3O$ = 627.73) | 1-23 | m/z = 703.26 ($C_{51}H_{33}N_3O$ = 703.83) |
| 1-25 | m/z = 733.25 ($C_{51}H_{35}N_3OSi$ = 733.93) | 1-30 | m/z = 564.20 ($C_{39}H_{24}N_4O$ = 564.63) |
| 1-32 | m/z = 640.23 ($C_{45}H_{28}N_4O$ = 640.73) | 1-33 | m/z = 640.23 ($C_{45}H_{28}N_4O$ = 640.73) |
| 1-39 | m/z = 729.25 ($C_{51}H_{31}N_5O$ = 729.82) | 1-47 | m/z = 729.25 ($C_{51}H_{31}N_5O$ = 729.82) |
| 1-50 | m/z = 680.26 ($C_{48}H_{32}N_4O$ = 680.79) | 1-67 | m/z = 654.18 ($C_{46}H_{26}N_2OS$ = 654.78) |
| 1-70 | m/z = 524.19 ($C_{38}H_{24}N_2O$ = 524.61) | 1-74 | m/z = 814.30 ($C_{61}H_{38}N_2O$ = 814.97) |
| 1-77 | m/z = 703.26 ($C_{51}H_{33}N_3O$ = 803.83) | 1-79 | m/z = 809.29 ($C_{57}H_{39}N_3OSi$ = 810.02) |
| 1-83 | m/z = 717.25 ($C_{50}H_{31}N_5O$ = 717.81) | 1-84 | m/z = 730.24 ($C_{51}H_{30}N_4O_2$ = 730.81) |
| 1-106 | m/z = 625.22 ($C_{45}H_{27}N_3O$ = 625.72) | 1-107 | m/z = 701.25 ($C_{51}H_{31}N_3O$ = 701.81) |
| 1-112 | m/z = 777.28 ($C_{57}H_{35}N_3O$ = 777.91) | 1-114 | m/z = 777.28 ($C_{57}H_{35}N_3O$ = 777.91) |
| 1-115 | m/z = 715.23 ($C_{51}H_{29}N_3O_2$ = 777.79) | 2-5 | m/z = 625.22 ($C_{45}H_{27}N_3O$ = 625.72) |
| 2-13 | m/z = 701.25 ($C_{51}H_{31}N_3O$ = 801.81) | 2-20 | m/z = 627.23 ($C_{45}H_{29}N_3O$ = 627.73) |
| 2-23 | m/z = 703.26 ($C_{51}H_{33}N_3O$ = 703.83) | 2-25 | m/z = 733.25 ($C_{51}H_{35}N_3OSi$ = 733.93) |
| 2-33 | m/z = 640.23 ($C_{45}H_{28}N_4O$ = 640.73) | 2-47 | m/z = 729.25 ($C_{51}H_{31}N_5O$ = 729.82) |
| 2-107 | m/z = 701.25 ($C_{51}H_{31}N_3O$ = 701.81) | 2-112 | m/z = 777.28 ($C_{57}H_{35}N_3O$ = 777.91) |
| 3-5 | m/z = 641.19 ($C_{45}H_{27}N_3S$ = 641.78) | 3-13 | m/z = 717.22 ($C_{51}H_{31}N_3S$ = 717.88) |
| 3-33 | m/z = 656.20 ($C_{45}H_{28}N_4S$ = 656.80) | 3-107 | m/z = 717.22 ($C_{51}H_{31}N_3S$ = 717.88) |
| 4-5 | m/z = 641.19 ($C_{45}H_{27}N_3S$ = 641.78) | 4-13 | m/z = 717.22 ($C_{51}H_{31}N_3S$ = 717.88) |
| 4-33 | m/z = 656.20 ($C_{45}H_{28}N_4S$ = 656.80) | 4-35 | m/z = 821.26 ($C_{57}H_{35}N_5S$ = 821.99) |
| 5-3 | m/z = 560.23 ($C_{42}H_{28}N_2$ = 560.70) | 5-4 | m/z = 560.23 ($C_{42}H_{28}N_2$ = 560.70) |
| 5-7 | m/z = 636.26 ($C_{48}H_{32}N_2$ = 636.80) | 5-31 | m/z = 636.26 ($C_{48}H_{32}N_2$ = 636.80) |
| 5-32 | m/z = 636.26 ($C_{48}H_{32}N_2$ = 636.80) | | |

<Experimental Example 1>—Manufacture of Organic Light Emitting Device

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. The light emitting layer was deposited to 400 Å using the compound described in Chemical Formula 1 as a host, and Ir(ppy)$_3$ was deposited as a green phosphorescent dopant by 7% doping with respect to the deposited thickness of the light emitting layer. After that, BCP was deposited to 60 Å as a hole blocking layer, and Alq$_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-6}$ torr to $10^{-8}$ torr for each material to be used in the OLED manufacture.

For the organic electroluminescent devices manufactured as above, electroluminescent light emission (EL) properties were measured using M7000 manufactured by McScience Inc., and with the measurement results, $T_{90}$ was measured when standard luminance was 6,000 cd/m$^2$ using a lifetime measurement system (M6000) manufactured by McScience Inc.

Results of measuring driving voltage, light emission efficiency, color coordinate (CIE) and lifetime of the organic light emitting devices manufactured according to the present disclosure are as shown in the following Table 12.

TABLE 12

| | Light Emitting layer Compound | Driving Voltage (V) | Efficiency (cd/A) | Color Coordinate (x, y) | Lifetime ($T_{90}$) |
|---|---|---|---|---|---|
| Example 1 | 1-1 | 4.45 | 72.8 | (0.251, 0.714) | 189 |
| Example 2 | 1-5 | 4.41 | 75.8 | (0.231, 0.711) | 293 |
| Example 3 | 1-10 | 4.69 | 69.2 | (0.231, 0.712) | 179 |
| Example 4 | 1-13 | 4.67 | 71.2 | (0.251, 0.723) | 320 |
| Example 5 | 1-14 | 4.32 | 71.5 | (0.251, 0.713) | 199 |
| Example 6 | 1-15 | 4.33 | 74.2 | (0.241, 0.714) | 221 |
| Example 7 | 1-18 | 4.66 | 71.2 | (0.251, 0.714) | 187 |
| Example 8 | 1-19 | 4.31 | 79.2 | (0.246, 0.717) | 297 |
| Example 9 | 1-20 | 4.66 | 71.1 | (0.248, 0.711) | 196 |
| Example 10 | 1-21 | 4.33 | 75.2 | (0.247, 0.727) | 227 |
| Example 11 | 1-22 | 4.36 | 78.9 | (0.242, 0.713) | 239 |
| Example 12 | 1-23 | 4.41 | 75.8 | (0.231, 0.711) | 249 |
| Example 13 | 1-25 | 4.45 | 72.8 | (0.251, 0.714) | 176 |
| Example 14 | 1-30 | 4.71 | 57.2 | (0.243, 0.714) | 152 |
| Example 15 | 1-32 | 5.62 | 53.2 | (0.243, 0.714) | 158 |
| Example 16 | 1-33 | 4.38 | 76.4 | (0.241, 0.711) | 171 |
| Example 17 | 1-39 | 4.81 | 55.9 | (0.243, 0.693) | 112 |
| Example 18 | 1-47 | 4.21 | 67.0 | (0.247, 0.727) | 122 |
| Example 19 | 1-50 | 4.33 | 69.1 | (0.233, 0.701) | 140 |
| Example 20 | 1-67 | 5.69 | 57.2 | (0.243, 0.716) | 143 |
| Example 21 | 1-70 | 4.73 | 52.2 | (0.234, 0.714) | 111 |
| Example 22 | 1-74 | 4.69 | 67.2 | (0.243, 0.714) | 142 |
| Example 23 | 1-77 | 5.23 | 55.0 | (0.247, 0.727) | 152 |
| Example 24 | 1-79 | 5.73 | 54.2 | (0.233, 0.713) | 147 |
| Example 25 | 1-83 | 5.74 | 55.2 | (0.251, 0.724) | 103 |
| Example 26 | 1-84 | 4.66 | 71.1 | (0.241, 0.715) | 175 |
| Example 27 | 1-106 | 4.38 | 76.4 | (0.241, 0.711) | 200 |

TABLE 12-continued

| | Light Emitting layer Compound | Driving Voltage (V) | Efficiency (cd/A) | Color Coordinate (x, y) | Lifetime (T₉₀) |
|---|---|---|---|---|---|
| Example 28 | 1-107 | 4.11 | 72.2 | (0.231, 0.711) | 211 |
| Example 29 | 1-112 | 4.13 | 79.2 | (0.247, 0.727) | 355 |
| Example 30 | 1-114 | 4.41 | 75.8 | (0.231, 0.711) | 332 |
| Example 31 | 1-115 | 4.42 | 75.7 | (0.251, 0.714) | 221 |
| Example 32 | 2-5 | 4.67 | 71.2 | (0.251, 0.714) | 288 |
| Example 33 | 2-13 | 4.45 | 72.8 | (0.251, 0.718) | 315 |
| Example 34 | 2-20 | 4.69 | 77.2 | (0.243, 0.714) | 192 |
| Example 35 | 2-23 | 4.31 | 79.2 | (0.246, 0.717) | 243 |
| Example 36 | 2-25 | 4.41 | 68.4 | (0.246, 0.717) | 176 |
| Example 37 | 2-33 | 4.69 | 69.2 | (0.231, 0.712) | 166 |
| Example 38 | 2-47 | 4.75 | 51.2 | (0.254, 0.724) | 119 |
| Example 39 | 2-107 | 4.48 | 70.2 | (0.241, 0.714) | 206 |
| Example 40 | 2-112 | 4.66 | 71.2 | (0.251, 0.724) | 340 |
| Example 41 | 2-120 | 4.45 | 72.2 | (0.251, 0.704) | 216 |
| Example 42 | 3-5 | 4.66 | 71.1 | (0.248, 0.711) | 271 |
| Example 43 | 3-13 | 4.32 | 78.3 | (0.241, 0.711) | 310 |
| Example 44 | 3-33 | 4.66 | 71.1 | (0.248, 0.711) | 164 |
| Example 45 | 3-107 | 4.67 | 71.2 | (0.251, 0.714) | 201 |
| Example 46 | 4-5 | 4.35 | 79.2 | (0.241, 0.714) | 261 |
| Example 47 | 4-13 | 4.66 | 71.2 | (0.251, 0.714) | 302 |
| Example 48 | 4-33 | 4.63 | 71.1 | (0.241, 0.711) | 161 |
| Comparative Example 1 | Ref. 1 | 5.14 | 48.9 | (0.246, 0.717) | 47 |
| Comparative Example 2 | Ref. 2 | 5.26 | 47.6 | (0.255, 0.698) | 35 |
| Comparative Example 3 | Ref. 3 | 5.64 | 43.9 | (0.236, 0.696) | 41 |
| Comparative Example 4 | Ref. 4 | 5.54 | 45.9 | (0.246, 0.686) | 30 |
| Comparative Example 5 | Ref. 5 | 5.67 | 46.4 | (0.231, 0.711) | 19 |
| Comparative Example 6 | Ref. 6 | 5.32 | 42.2 | (0.231, 0.712) | 85 |
| Comparative Example 7 | Ref. 7 | 5.33 | 49.2 | (0.247, 0.727) | 93 |
| Comparative Example 8 | Ref. 8 | 5.66 | 45.8 | (0.233, 0.701) | 68 |
| Comparative Example 9 | Ref. 9 | 5.31 | 45.7 | (0.243, 0.693) | 77 |
| Comparative Example 10 | 5-3 | 4.83 | 50.9 | (0.233, 0.703) | 91 |
| Comparative Example 11 | 5-4 | 4.69 | 69.2 | (0.231, 0.712) | 96 |
| Comparative Example 12 | 5-7 | 5.21 | 57.0 | (0.247, 0.727) | 85 |
| Comparative Example 13 | 5-31 | 4.75 | 51.2 | (0.254, 0.724) | 79 |
| Comparative Example 14 | 5-32 | 4.48 | 70.2 | (0.241, 0.714) | 86 |

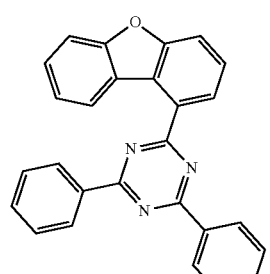

Ref. 1

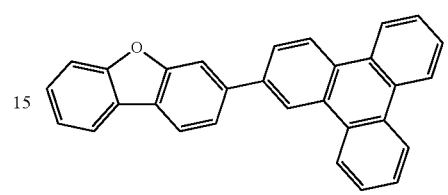

Ref. 2

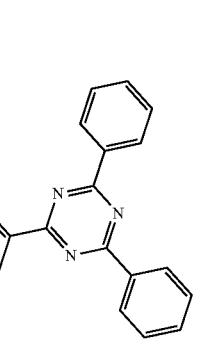

Ref. 3

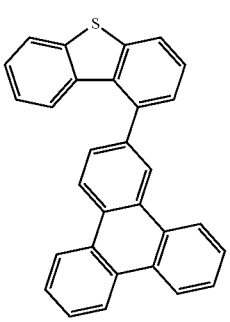

Ref. 4

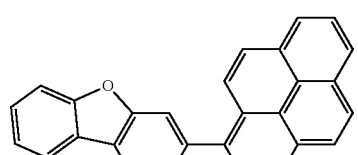

Ref. 5

TABLE 12-continued

| Light Emitting layer Compound | Driving Voltage (V) | Efficiency (cd/A) | Color Coordinate (x, y) | Lifetime ($T_{90}$) |
|---|---|---|---|---|

Ref. 6

Ref. 7

Ref. 8

Ref. 9

<Experimental Example 2>—Manufacture of Organic Light Emitting Device

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. The light emitting layer was deposited to 400 Å in one source of supply after pre-mixing one type of the compound described in Chemical Formula 1 and one type of the compound described in Chemical Formula 3 as a host, and Ir(ppy)$_3$ was deposited as a green phosphorescent dopant by 7% doping with respect to the deposited thickness of the light emitting layer. After that, BCP was deposited to 60 Å as a hole blocking layer, and Alq$_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-6}$ torr to $10^{-8}$ torr for each material to be used in the OLED manufacture.

For the organic electroluminescent devices manufactured as above, electroluminescent light emission (EL) properties were measured using M7000 manufactured by McScience Inc., and with the measurement results, $T_{90}$ was measured when standard luminance was 6,000 cd/m$^2$ using a lifetime measurement system (M6000) manufactured by McScience Inc.

Results of measuring driving voltage, light emission efficiency, color coordinate (CIE) and lifetime of the organic light emitting devices manufactured according to the present disclosure are as shown in the following Table 13.

TABLE 13

| | Light Emitting Layer Compound | Ratio | Driving Voltage (V) | Efficiency (cd/A) | Color Coordinate (x, y) | Lifetime ($T_{90}$) |
|---|---|---|---|---|---|---|
| Example 53 | 1-13: 5-3 | 1:8 | 4.73 | 54.2 | (0.233, 0.714) | 378 |
| Example 54 | | 1:5 | 4.71 | 57.2 | (0.243, 0.714) | 384 |
| Example 55 | | 1:2 | 4.35 | 79.2 | (0.241, 0.714) | 499 |
| Example 56 | | 1:1 | 4.41 | 75.8 | (0.231, 0.711) | 491 |
| Example 57 | | 2:1 | 4.67 | 71.2 | (0.251, 0.714) | 440 |
| Example 58 | | 5:1 | 4.32 | 68.3 | (0.241, 0.711) | 491 |
| Example 59 | | 8:1 | 4.21 | 67.0 | (0.247, 0.727) | 365 |
| Example 60 | 1-5: 5-4 | 1:2 | 4.33 | 74.2 | (0.241, 0.714) | 462 |
| Example 61 | | 1:1 | 4.42 | 72.2 | (0.231, 0.711) | 453 |
| Example 62 | | 2:1 | 4.66 | 71.2 | (0.251, 0.714) | 428 |
| Example 63 | 1-23: 5-7 | 1:2 | 4.38 | 76.4 | (0.241, 0.711) | 439 |
| Example 64 | | 1:1 | 4.45 | 72.8 | (0.251, 0.714) | 422 |
| Example 65 | | 2:1 | 4.66 | 71.1 | (0.241, 0.711) | 400 |
| Example 66 | | 1:2 | 4.33 | 75.2 | (0.247, 0.727) | 469 |
| Example 67 | 1-19: 5-31 | 1:1 | 4.48 | 70.2 | (0.241, 0.714) | 443 |
| Example 68 | | 2:1 | 4.69 | 69.2 | (0.231, 0.711) | 418 |
| Example 69 | 1-112: 5-32 | 1:2 | 4.33 | 75.2 | (0.247, 0.729) | 579 |
| Example 70 | | 1:1 | 4.48 | 70.2 | (0.241, 0.718) | 446 |
| Example 71 | | 2:1 | 4.69 | 69.2 | (0.231, 0.717) | 425 |
| Example 72 | 1-114: | 1:2 | 4.33 | 75.2 | (0.247, 0.723) | 520 |

TABLE 13-continued

| | Light Emitting Layer Compound | Ratio | Driving Voltage (V) | Efficiency (cd/A) | Color Coordinate (x, y) | Lifetime ($T_{90}$) |
|---|---|---|---|---|---|---|
| Example 73 | 5-32 | 1:1 | 4.48 | 70.2 | (0.241, 0.712) | 482 |
| Example 74 | | 2:1 | 4.69 | 69.2 | (0.231, 0.716) | 443 |
| Example 75 | 2-112: | 1:2 | 4.31 | 79.2 | (0.246, 0.717) | 486 |
| Example 76 | 5-32 | 1:1 | 4.42 | 75.7 | (0.251, 0.714) | 458 |
| Example 77 | | 2:1 | 4.66 | 71.1 | (0.241, 0.711) | 436 |

As can be seen from the results of Table 12, the organic electroluminescent device using the light emitting layer material of the organic electroluminescent device of the present disclosure had lower driving voltage, and significantly improved lifetime as well as having enhanced light emission efficiency compared to Comparative Examples 1 to 6.

Based on the results of Tables 12 and 13, more superior efficiency and lifetime effects were obtained when including both the compound of Chemical Formula 1 and the compound of Chemical Formula 3. Such results may lead to a forecast that an exciplex phenomenon occurs when including the two compounds at the same time.

The exciplex phenomenon is a phenomenon of releasing energy having sizes of a donor (p-host) HOMO level and an acceptor (n-host) LUMO level due to electron exchanges between two molecules. When the exciplex phenomenon occurs between two molecules, reverse intersystem crossing (RISC) occurs, and as a result, internal quantum efficiency of fluorescence may increase up to 100%. When a donor (p-host) having favorable hole transfer capability and an acceptor (n-host) having favorable electron transfer capability are used as a host of a light emitting layer, holes are injected to the p-host and electrons are injected to the n-host, and therefore, a driving voltage may decrease, which resultantly helps with enhancement in the lifetime. In the present disclosure, it was identified that excellent device properties were obtained when using the heterocyclic compound of Chemical Formula 3 to have a donor role and the compound of Chemical Formula 1 to have an acceptor role as a light emitting layer host.

Particularly, Comparative Examples 10 to 14 of Table 12 are cases where the compound corresponding to Chemical Formula 3 of the present application was used alone in the organic light emitting device, and it was identified that efficiency was not favorable, and particularly, a lifetime was not favorable compared to when using both the compounds corresponding to Chemical Formula 1 of the present application and Chemical Formula 3 of the present application in the organic light emitting device.

It was identified that, when there was no -(L2)m-(Z)n substituent of Chemical Formula 1 of the present application as in the compounds of Comparative Examples 1 and 3, the HOMO was localized to dibenzofuran and dibenzothiophene, which was not able to effectively stabilize holes resulting in a decrease in the lifetime. In addition, it was identified that the LUMO was delocalized to -(L1)p-N-Het and dibenzofuran of Chemical Formula 1 of the subject application, and when there was no dibenzofuran, the LUMO was localized to triazine, which was not able to effectively stabilize electrons resulting in a decrease in the lifetime.

It was identified that, when there was no -(L1)p-N-Het substituent of Chemical Formula 1 of the subject application as in the compounds of Comparative Examples 2 and 4, electron mobility decreased breaking a balance between holes and electrons in the light emitting layer, and as a result, the lifetime was reduced.

It was identified that, when having pyrene as in the compound of Comparative Example 5, a $T_1$ energy level was low of approximately 2.0 eV, and energy was not readily transferred from the host to the dopant, which reduced light emission efficiency.

The compound of Comparative Example 6 has the same position of substitution as the compound of the present disclosure, however, the bonding is at No. 3 position of carbazole instead of N of carbazole. In addition, the compounds of Comparative Examples 8 and 9 have a different position of substitution from the compound of the present disclosure. It was identified that, in the compounds of Comparative Examples 6, 8 and 9, the HOMO was delocalized from dibenzofuran to carbazole, and this increased hole mobility compared to when the HOMO was delocalized from dibenzofuran to triphenylene as in Compounds 1 to 5 of the present application breaking a balance between holes and electrons in the light emitting layer, and as a result, the lifetime was reduced.

The compound of Comparative Example 7 has the same position of substitution as the compound of the present disclosure, but includes a fluorene group as a substituent. It was identified that a methyl group of the fluorene group was thermally unstable causing deformation in the host, and as a result, the lifetime of the device was reduced.

The invention claimed is:
1. A heterocyclic compound represented by the following Chemical Formula 4 or 5:

[Chemical Formula 4]

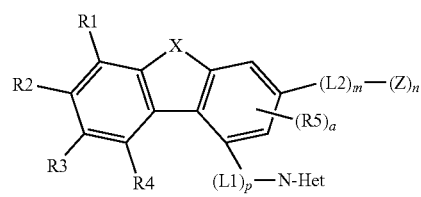

[Chemical Formula 5]

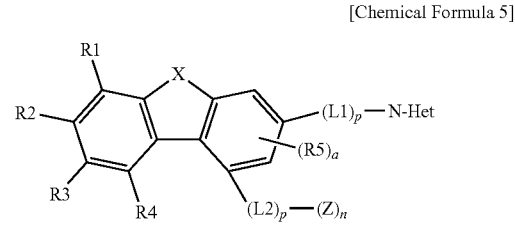

wherein, in Chemical Formulae 4 and 5,
N-Het is represented by any one of the following Chemical Formulae 7 to 12:

[Chemical Formula 7]

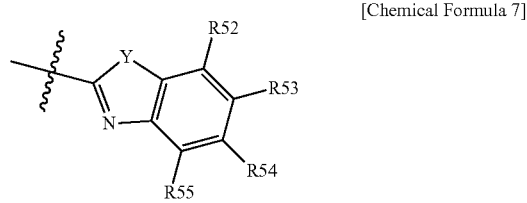

-continued

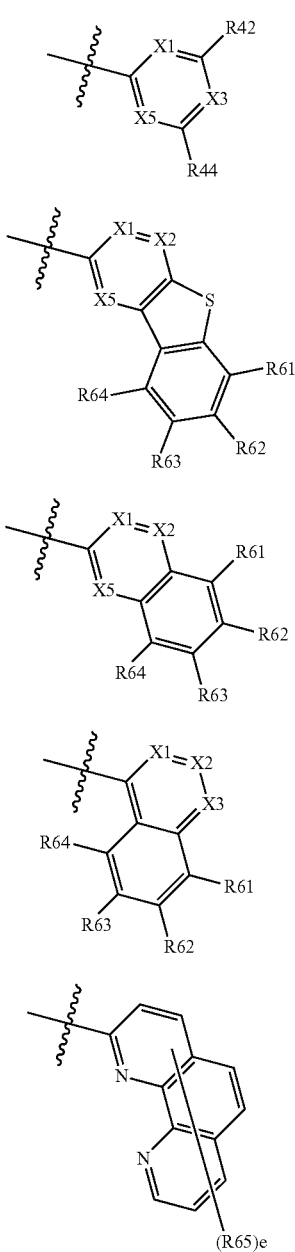

[Chemical Formula 8]

[Chemical Formula 9]

[Chemical Formula 10]

[Chemical Formula 11]

[Chemical Formula 12]

in Chemical Formulae 7 to 12,
X1 is CR41 or N, X2 is CR42 or N, X3 is CR43 or N, and X5 is CR45 or N;
in Chemical Formula 8, one or more of X1, X3 and X5 are N;
in Chemical Formulae 9 and 10, one or more of X1, X2 and X5 are N;
in Chemical Formula 11, one or more of X1 to X3 are N;
Y is NR51 or S;
R41 to R45 and R51 to R55 are the same as or different from each other, and each independently selected from the group consisting of hydrogen; deuterium; a halogen group; —CN; a substituted or unsubstituted alkyl group; a substituted or unsubstituted aryl group; a substituted or unsubstituted heteroaryl group; P(=O)RR'; SiRR'R"; and an amine group unsubstituted or substituted with a substituted or unsubstituted alkyl group, a substituted or unsubstituted aryl group or a substituted or unsubstituted heteroaryl group, or two or more groups adjacent to each other bond to each other to form a substituted or unsubstituted aromatic hydrocarbon ring or a substituted or unsubstituted heteroring;

R61 to R65 are the same as or different from each other, and each independently selected from the group consisting of hydrogen; deuterium; a halogen group; —CN; a substituted or unsubstituted alkyl group; a substituted or unsubstituted aryl group; a substituted or unsubstituted heteroaryl group; P(=O)RR'; SiRR'R"; and an amine group unsubstituted or substituted with a substituted or unsubstituted alkyl group, a substituted or unsubstituted aryl group or a substituted or unsubstituted heteroaryl group, or two or more groups adjacent to each other bond to each other to form a substituted or unsubstituted aliphatic or aromatic hydrocarbon ring; and e is an integer of 0 to 7, and when e is 2 or greater, substituents in the parentheses are the same as or different from each other, X is O; or S;

L1 and L2 are the same as or different from each other, and each independently a direct bond; a substituted or unsubstituted arylene group formed with one to three 6-membered rings;

or a substituted or unsubstituted heteroarylene group, p and m are an integer of 1 to 3, and when p is 2 or greater, L1s are the same as or different from each other, and when m is 2 or greater, L2s are the same as or different from each other; and Z is a phenyl group; a biphenyl group; a naphthyl group; a phenanthrene group; a triphenylene group; a methyl group unsubstituted or substituted with a phenyl group; a triazine group unsubstituted or substituted with one or more substituents selected form the group consisting of a phenyl group and a dibenzofuran group; a pyrimidine group unsubstituted or substituted with a phenyl group; an imidazole group unsubstituted or substituted with a phenyl group; a quinoline group unsubstituted or substituted with a phenyl group; P(=O)RR'; or SiRR'R" or represented by the following Chemical Formula 2, n is an integer of 1 to 5, and when n is 2 or greater, Zs are the same as or different from each other,

[Chemical Formula 2]

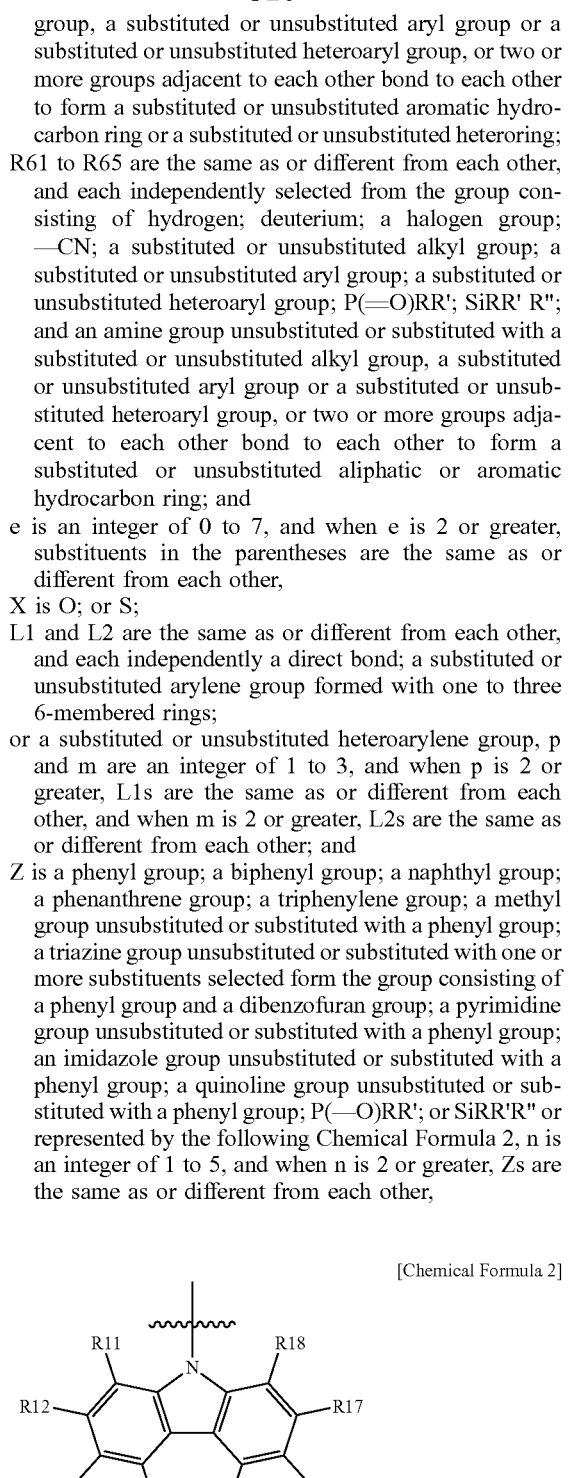

in Chemical Formula 2,
R11 to R18 are the same as or different from each other, and each independently hydrogen; or a substituted or unsubstituted heteroaryl group; or two or more groups adjacent to each other bond to each other to form a substituted or unsubstituted aromatic hydrocarbon ring or a substituted or unsubstituted heteroring;
at least one of R11 to R18 is a substituted or unsubstituted heteroaryl group; or two or more groups adjacent to each other bond to each other to form a substituted or unsubstituted aromatic hydrocarbon ring or a substituted or unsubstituted heterorings, Z and N-Het are different from each other, R1 to R5 are hydrogen; and R, R' and R" are the same as or different from each other, and each independently selected from the group consisting of hydrogen; deuterium; halogen; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; and a substituted or unsubstituted amine group, or two or more groups adjacent to each other bond to each other to form a substituted or unsubstituted aromatic hydrocarbon ring or a substituted or unsubstituted heterorings, a is an integer of 0 to 2, and when a is 2 or greater, R5s are the same as or different from each other.

2. The heterocyclic compound of claim 1, wherein Chemical Formula 4 or 5 is represented by any one of the following compounds:

1-1
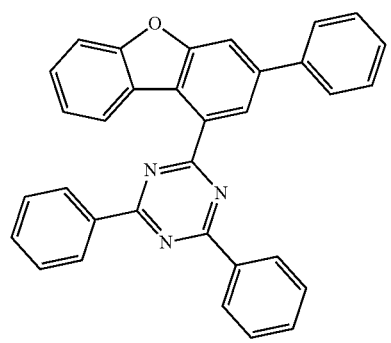

1-2
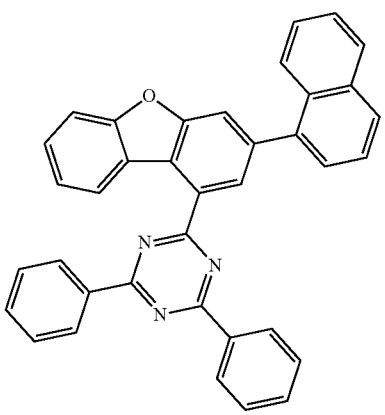

1-3
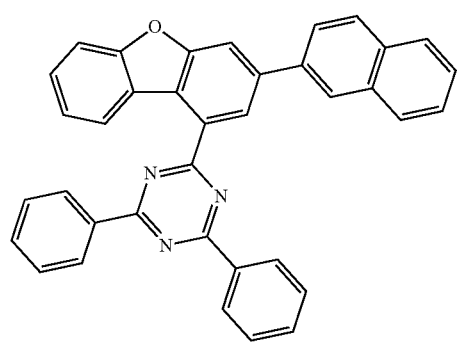

1-4
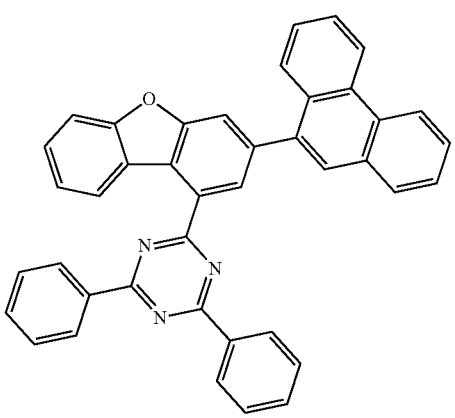

1-5
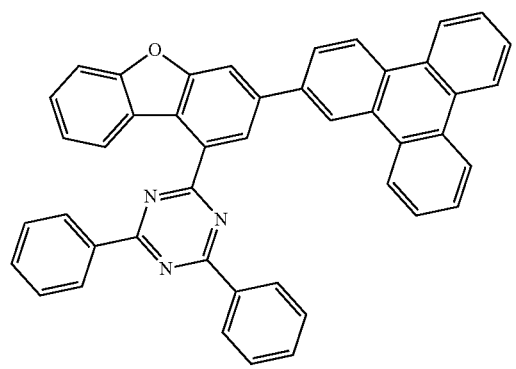

1-6
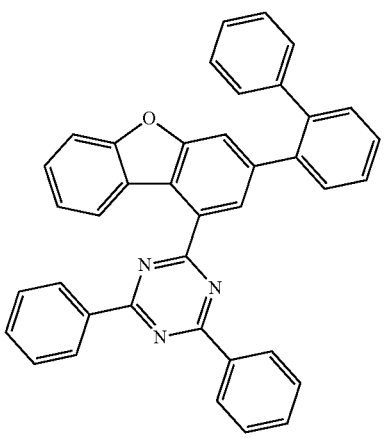

-continued
1-7
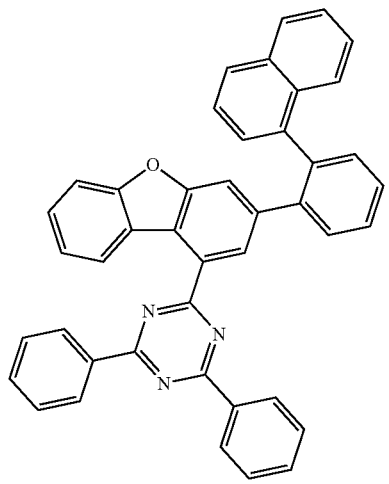
1-8
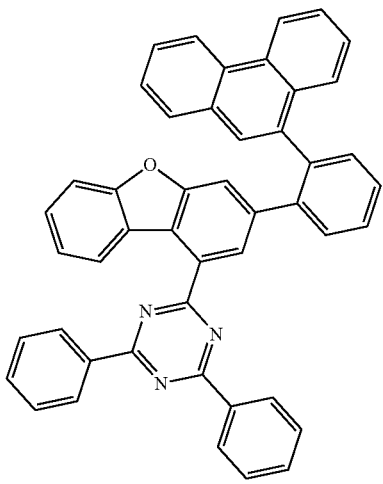
1-9
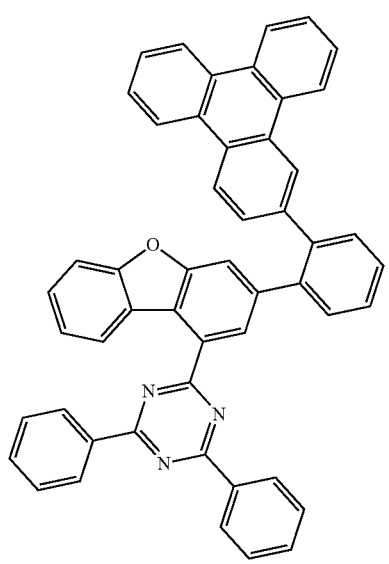
1-10
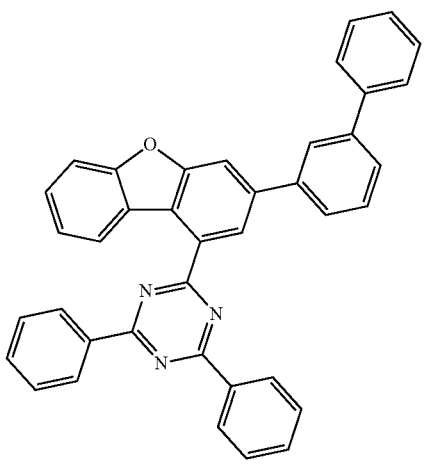
1-11
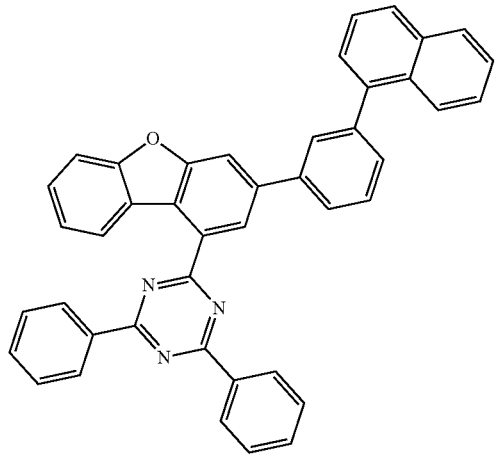
1-12
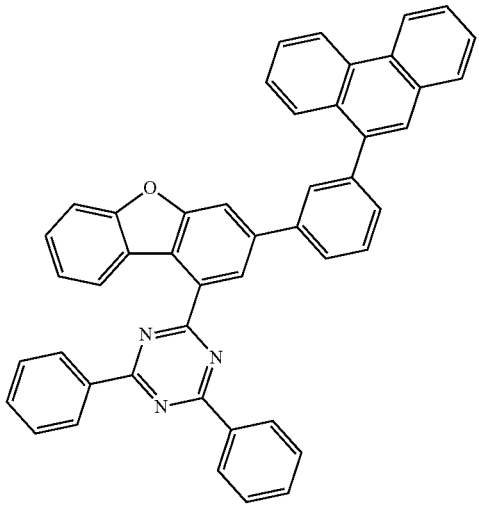

1-13
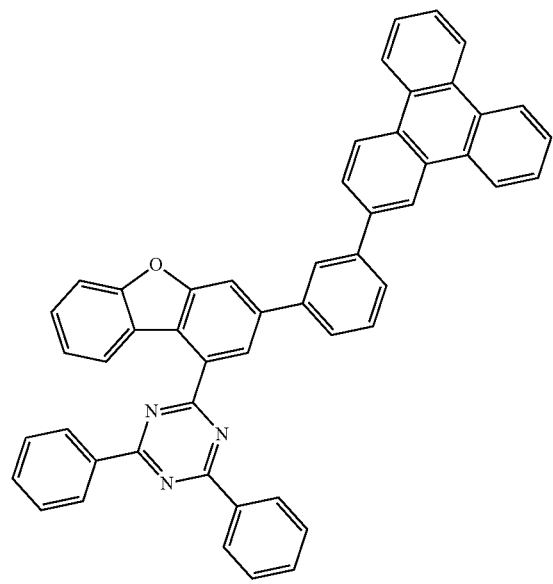
1-14
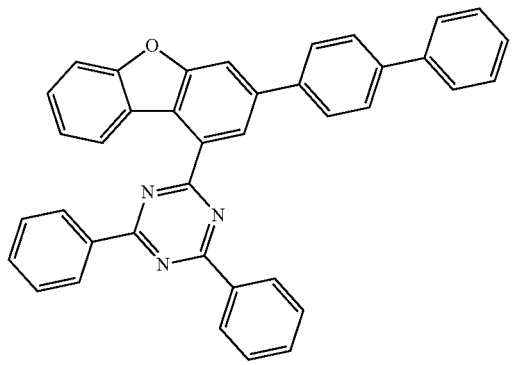
1-15
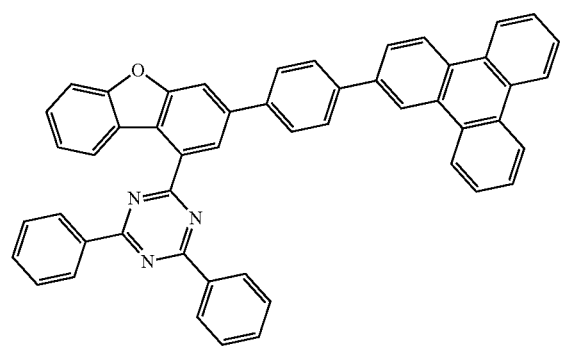
1-16
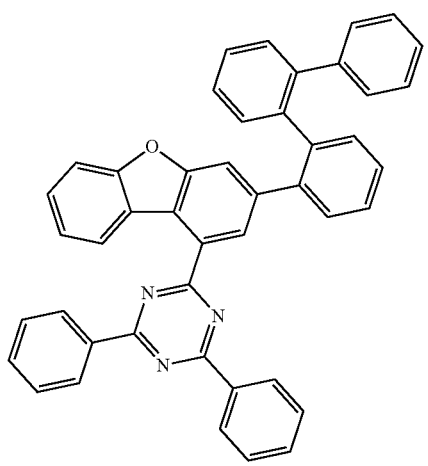

-continued
1-17
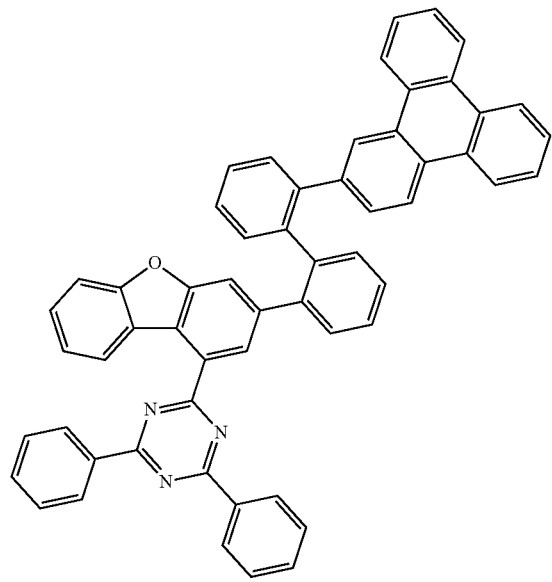
1-18
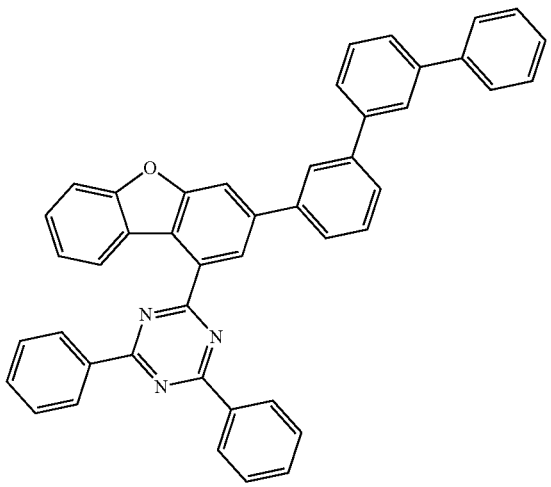
1-19
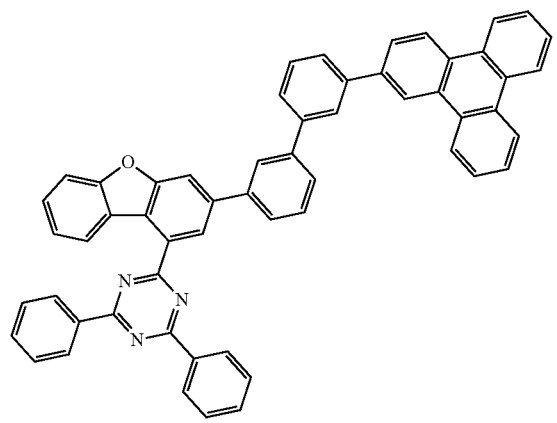
1-20
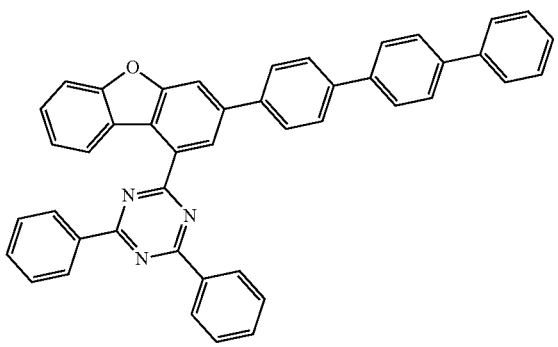
1-21
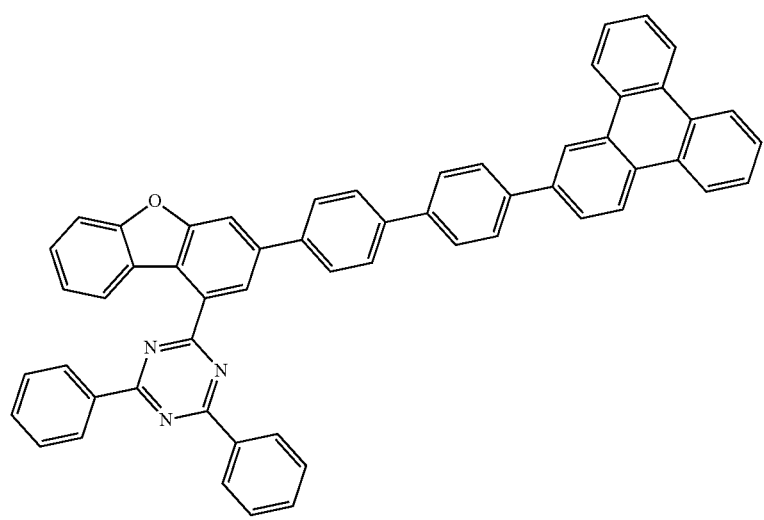

-continued
1-22
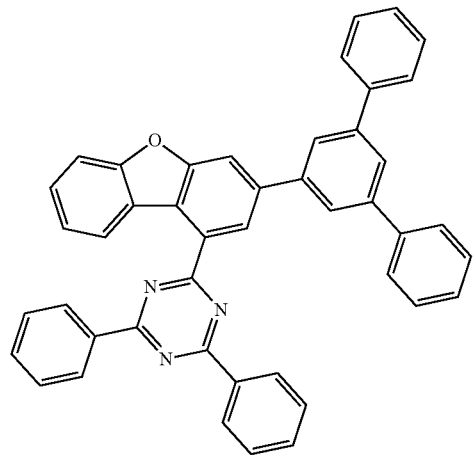
1-23
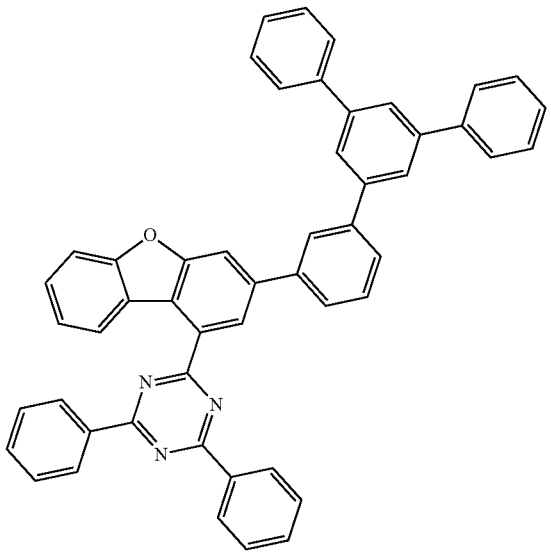
1-24
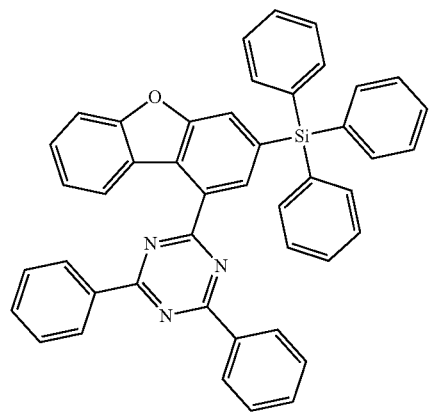
1-25
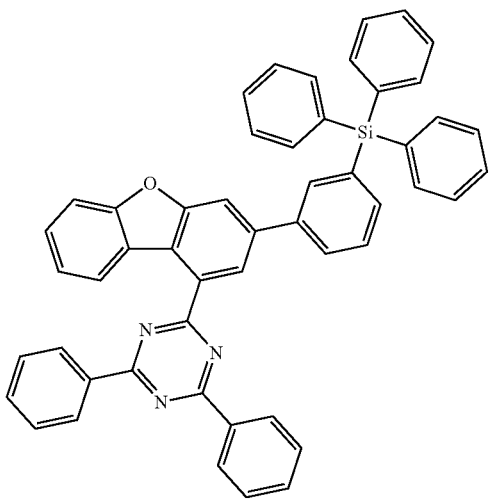
1-26
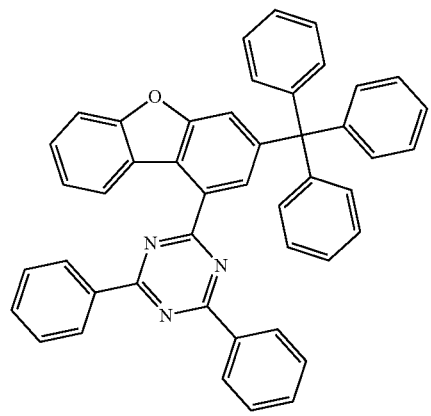
1-27
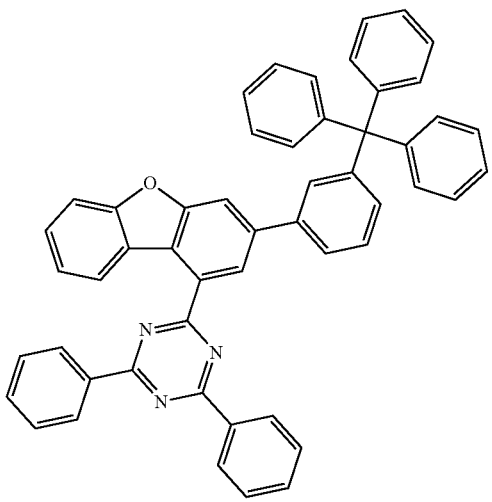

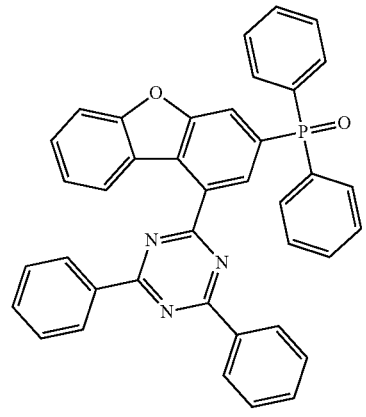 1-28
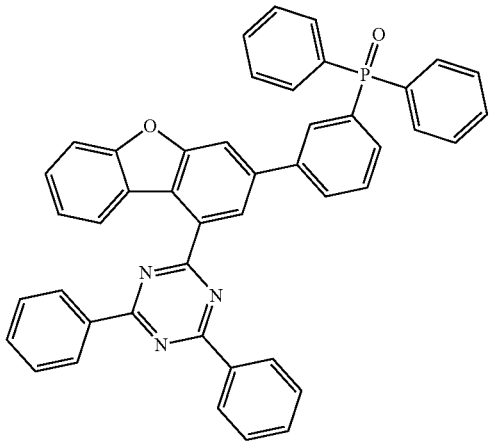 1-29
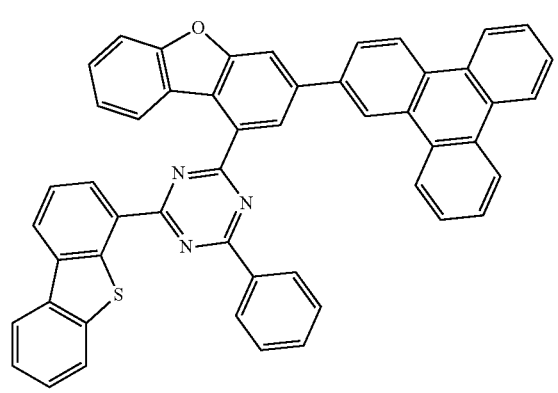 1-35
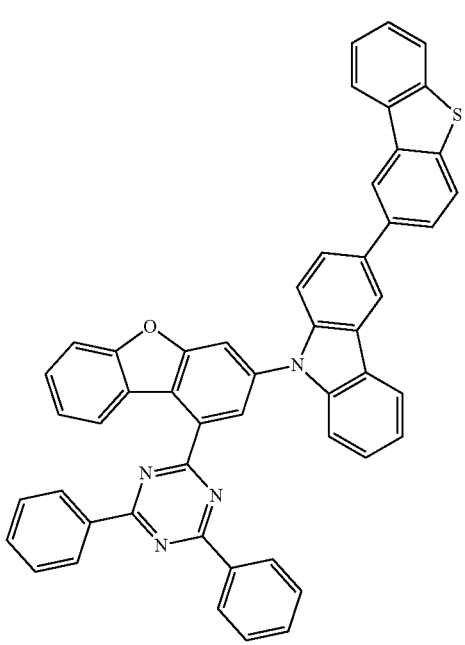 1-36

-continued
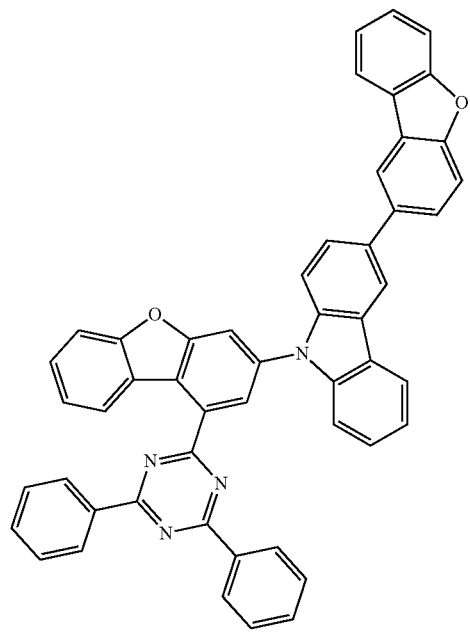
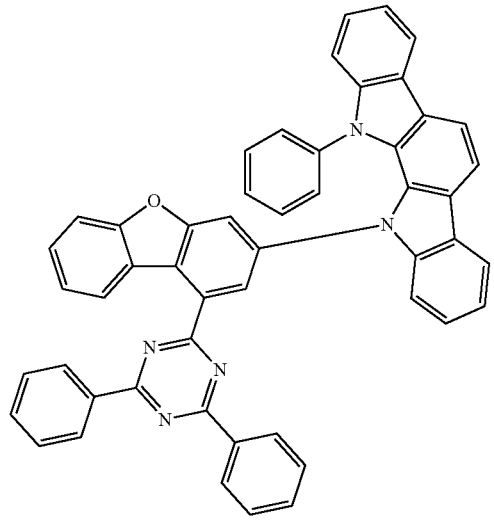
1-39
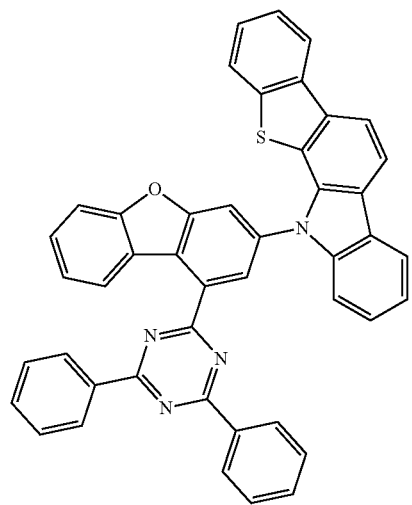
1-40
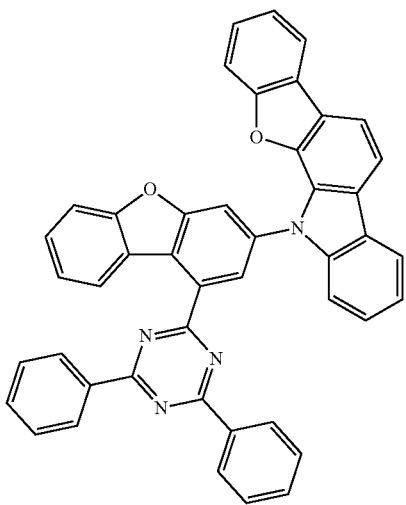
1-41

-continued
1-42
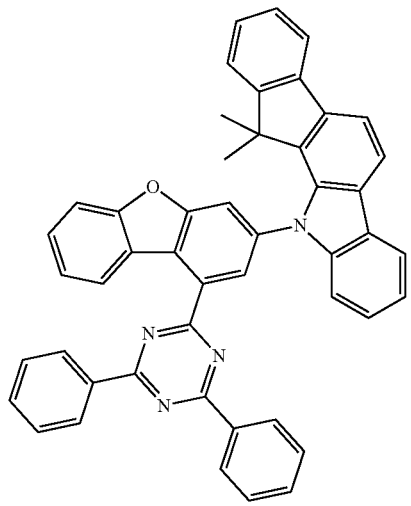
1-43
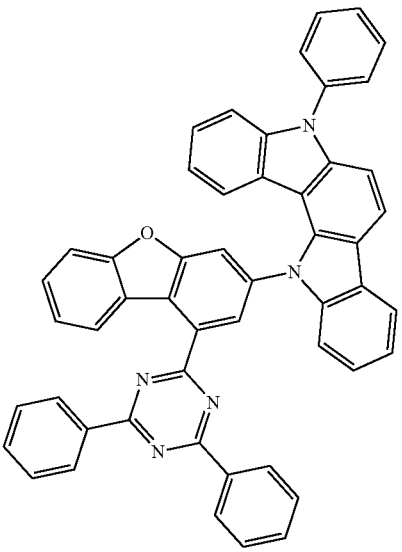
1-44
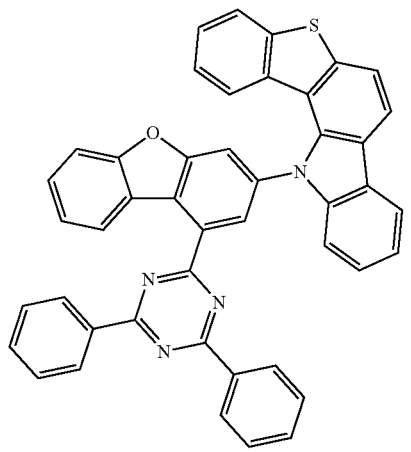
1-45
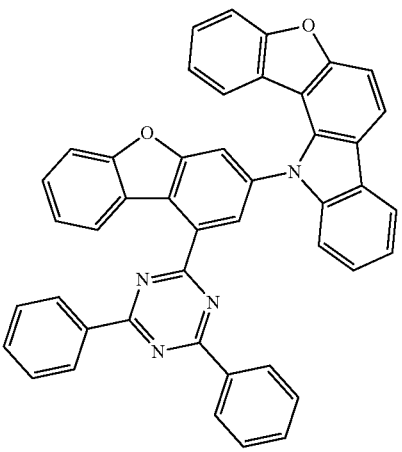
1-46
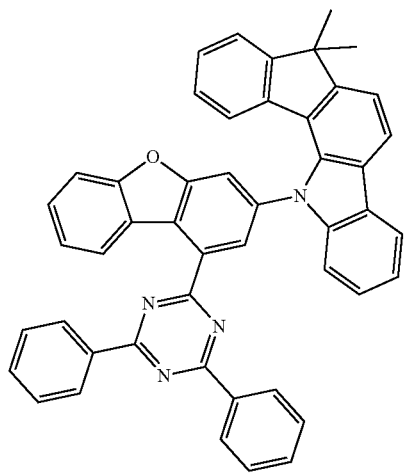
1-47
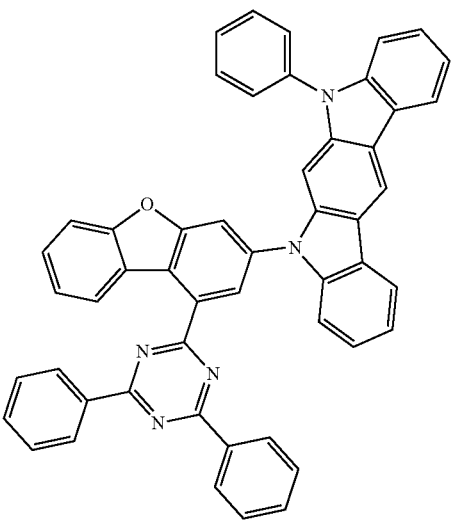

-continued
1-48
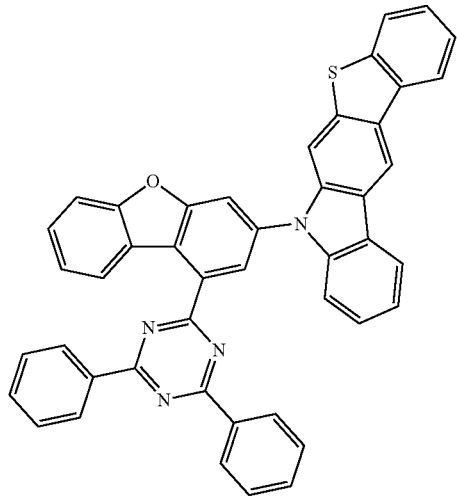
1-49
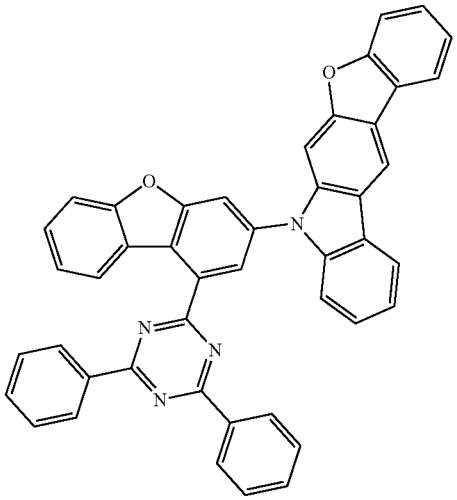
1-50
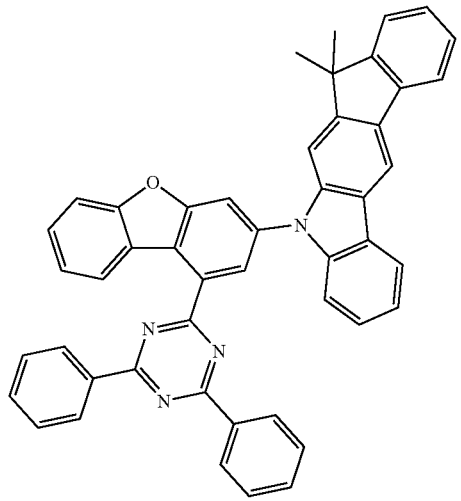
1-51
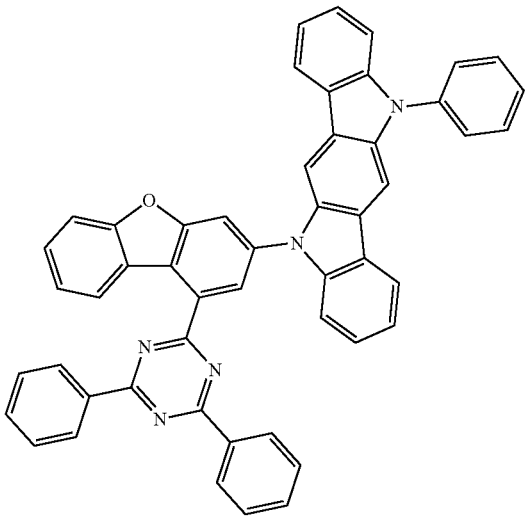
1-52
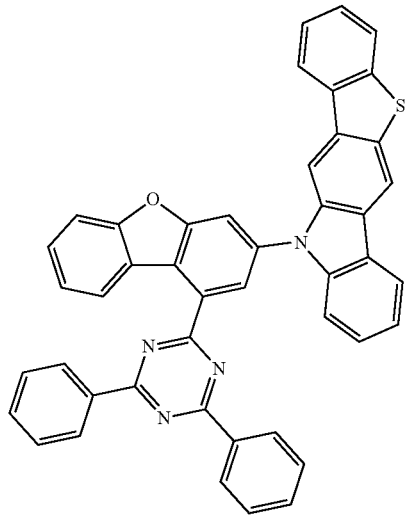
1-53
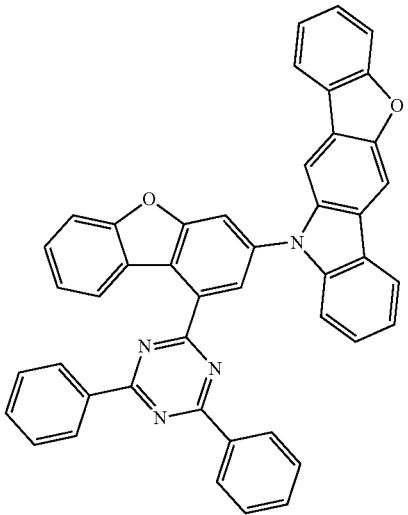

-continued
1-54
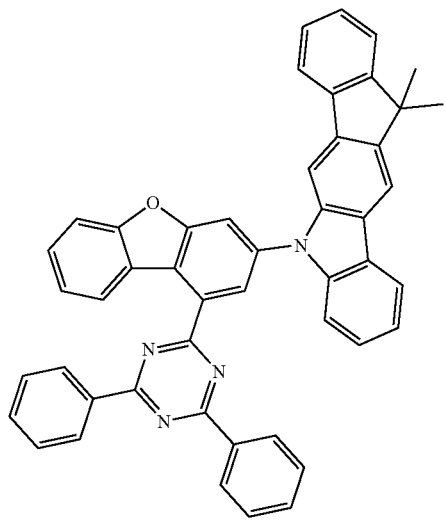
1-55
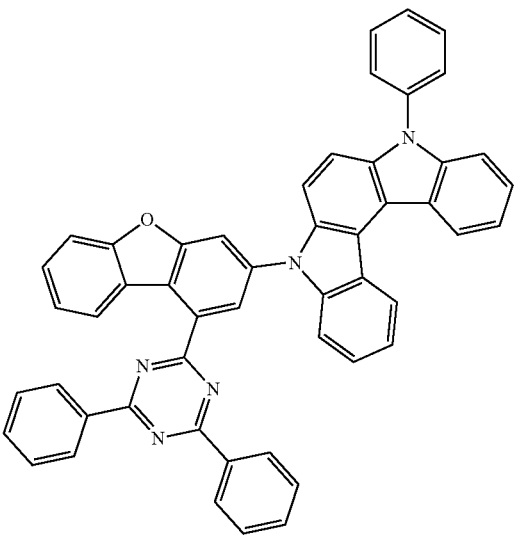
1-56
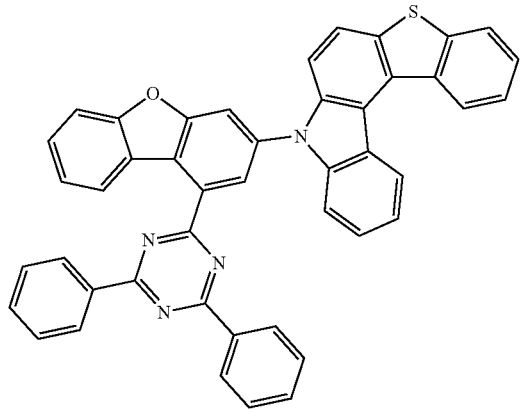
1-57
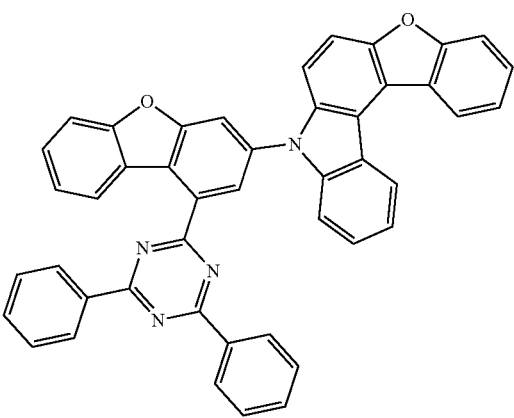
1-58
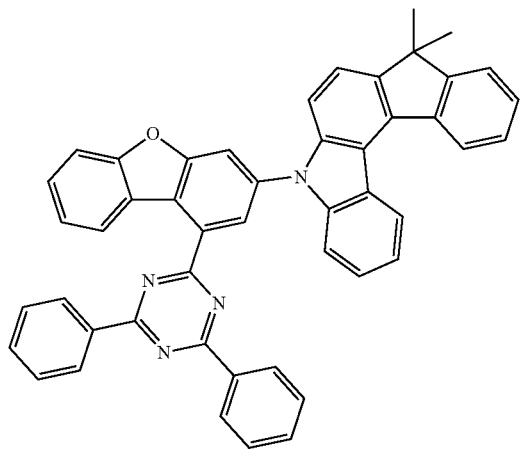
1-59
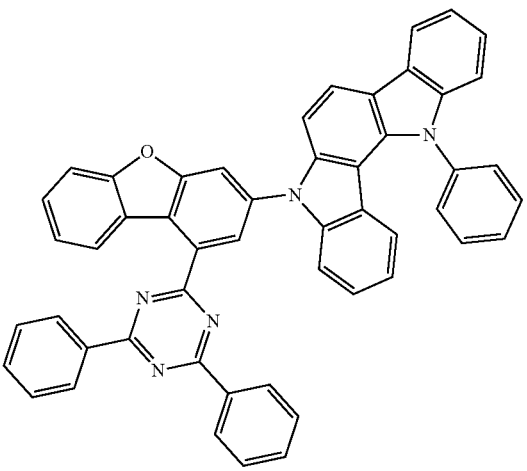

1-60
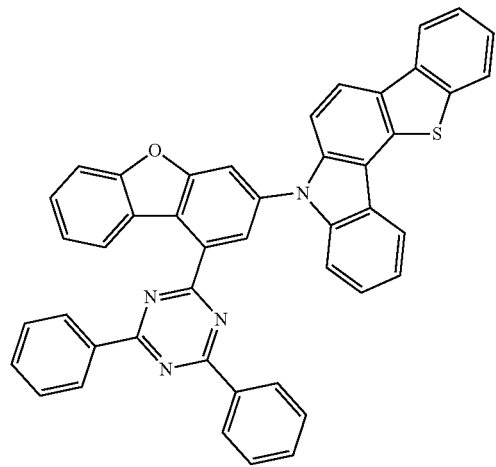
1-61
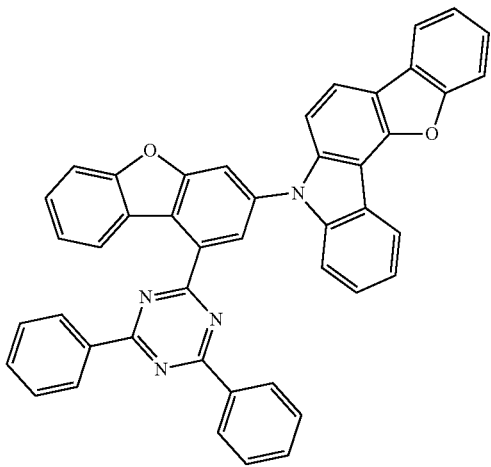
1-62
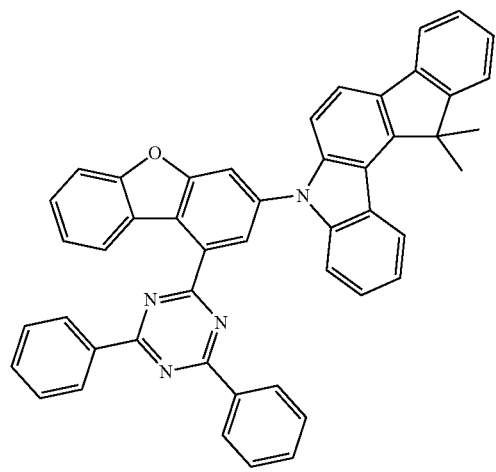
1-63
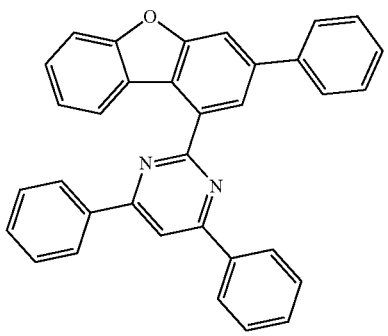
1-64
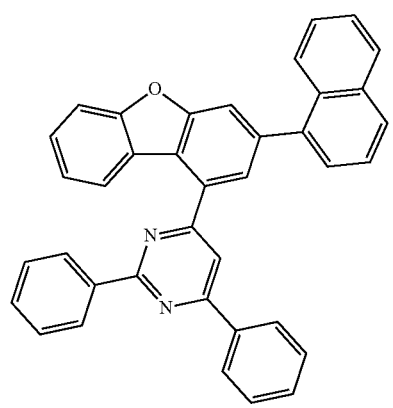
1-65
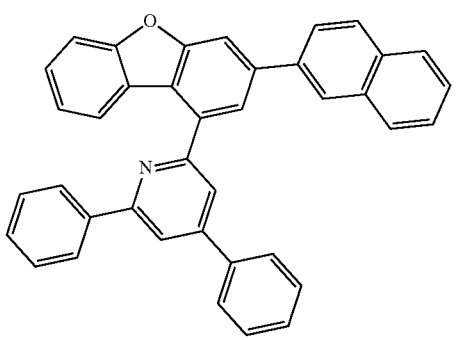

-continued
1-66
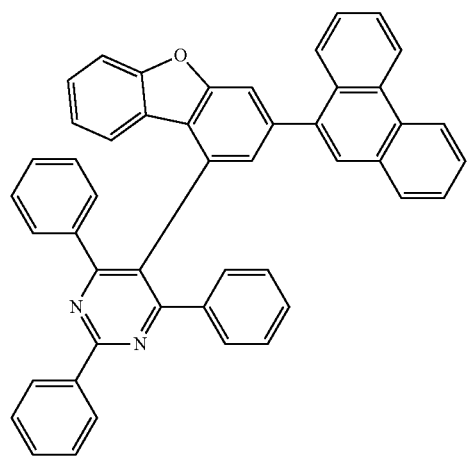
1-67
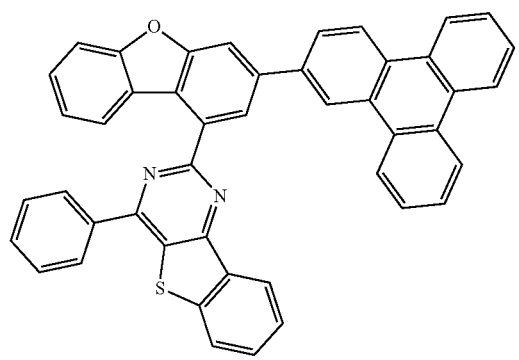
1-68
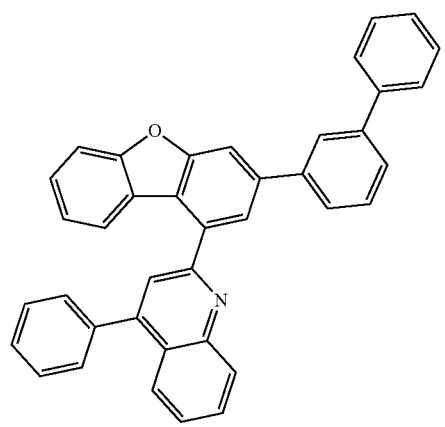
1-69
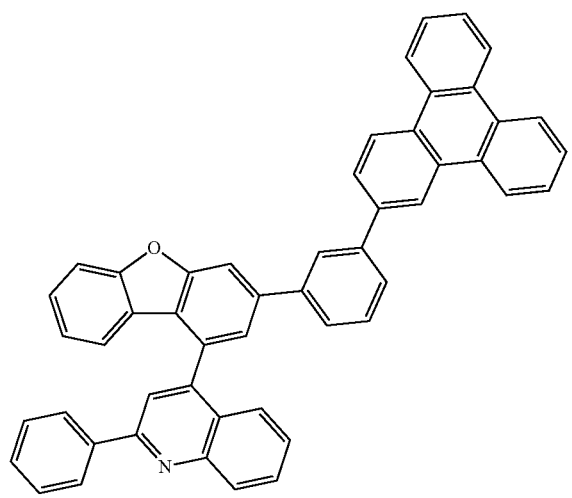
1-70
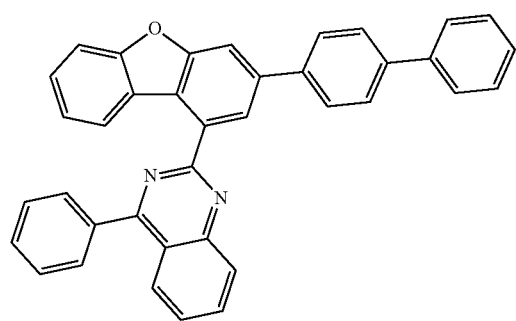
1-71
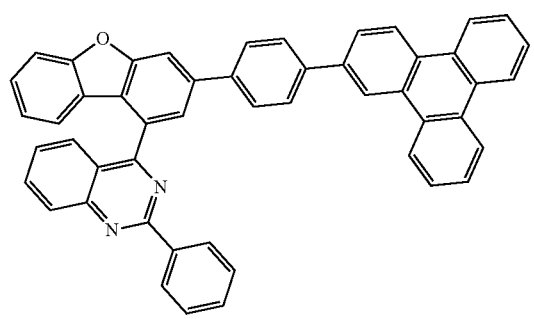

-continued
1-72
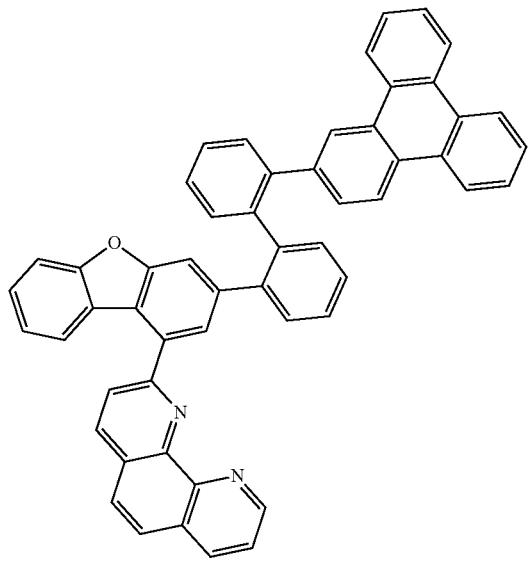
1-73
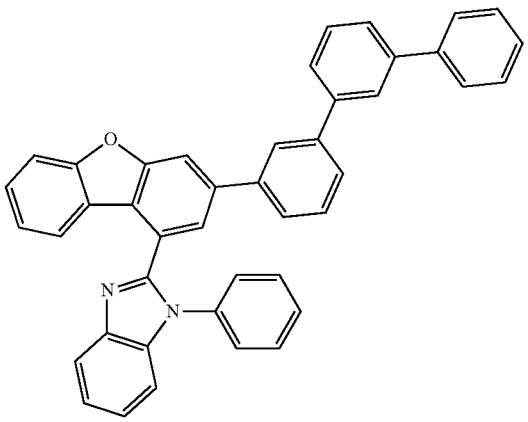
1-74
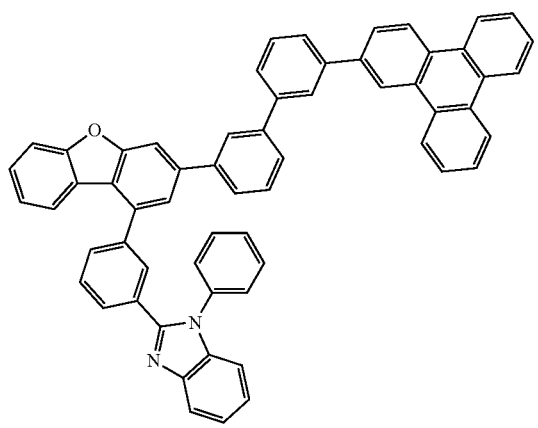
1-75
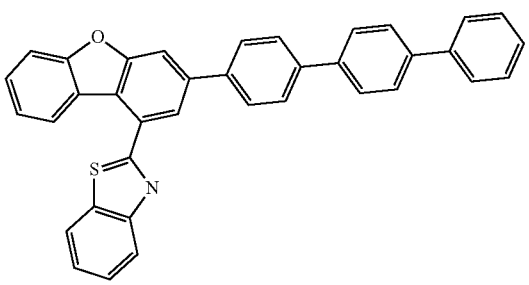
1-76
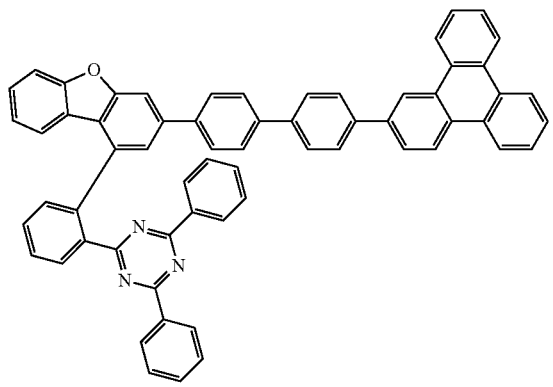
1-77
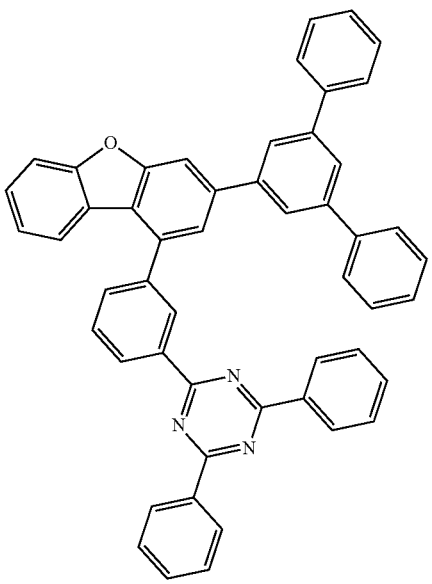

1-78
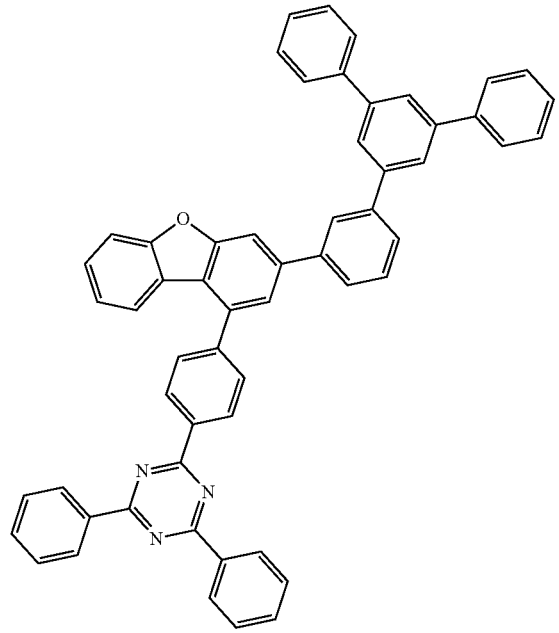
1-79
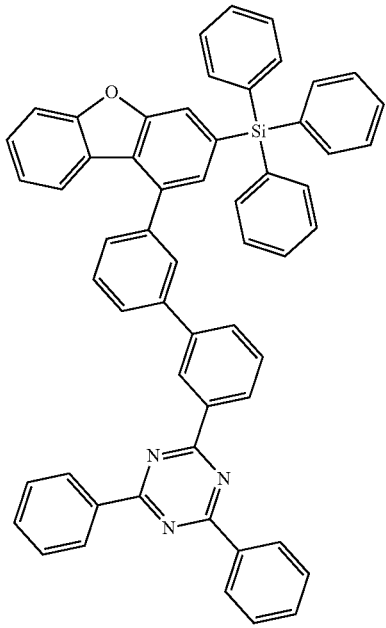
1-80
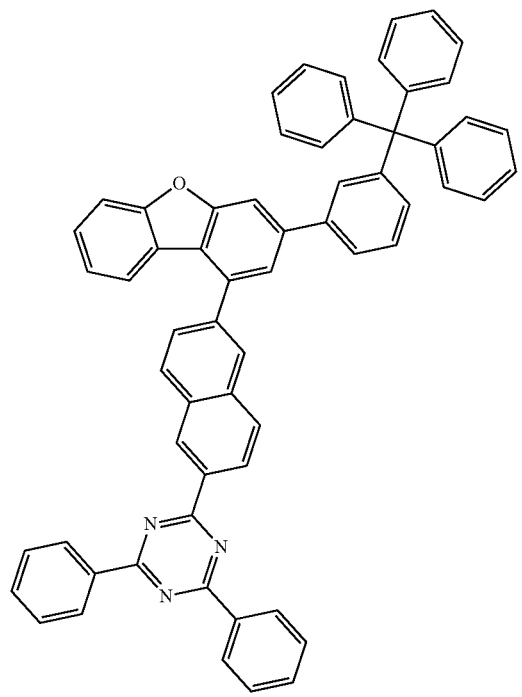
1-81
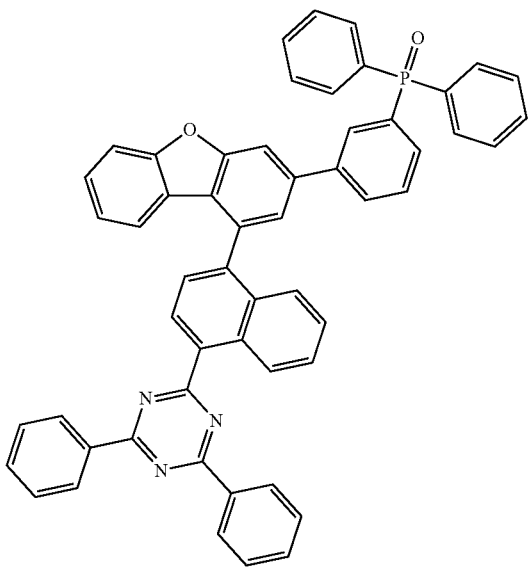

1-85
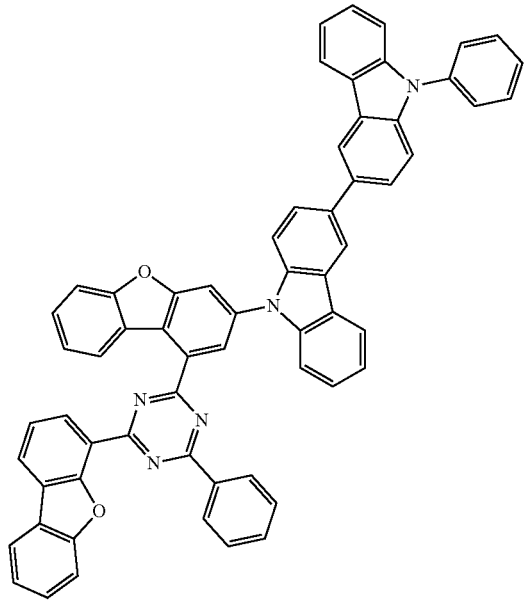
1-86
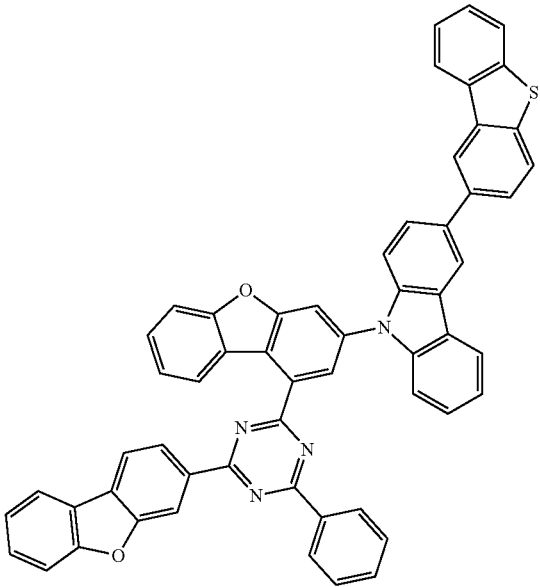
1-87
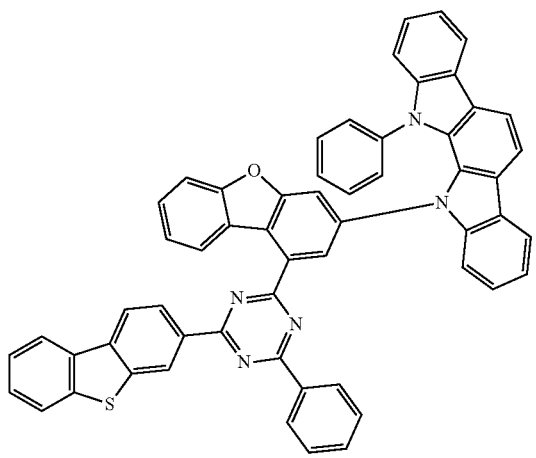
1-88
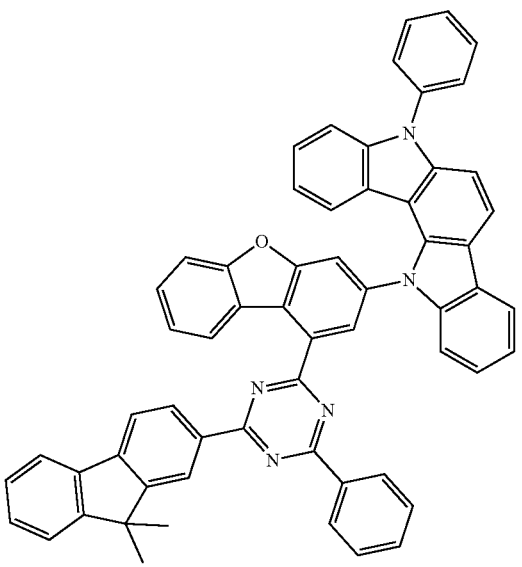

1-89
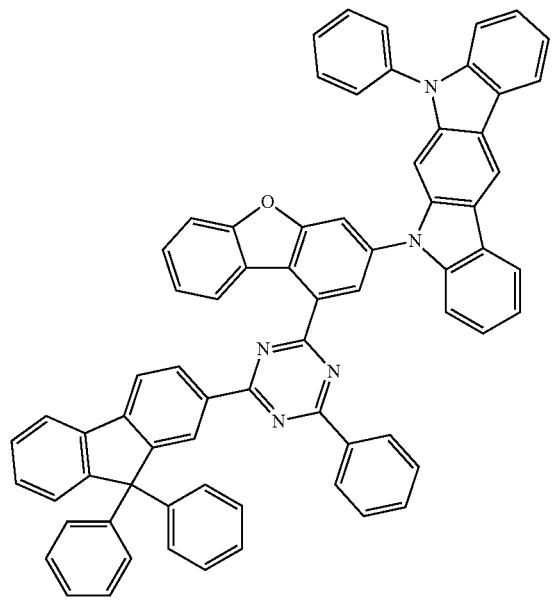
1-90
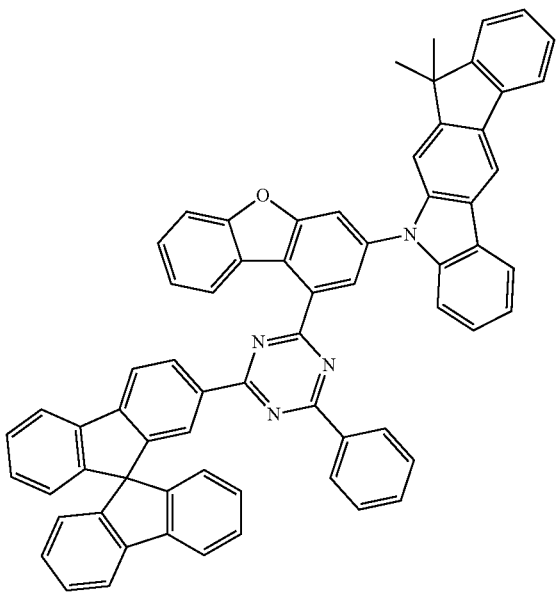
1-91
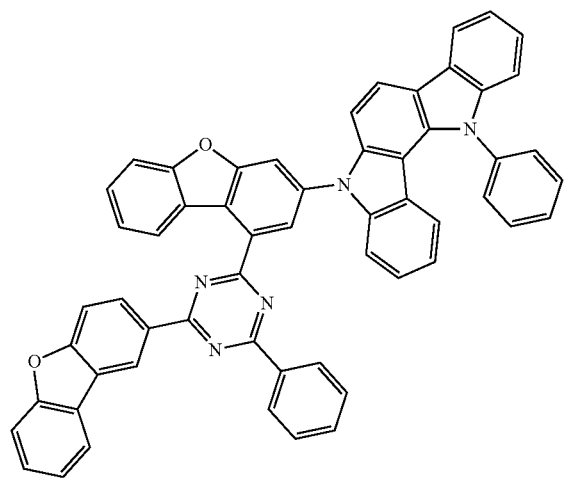
1-92
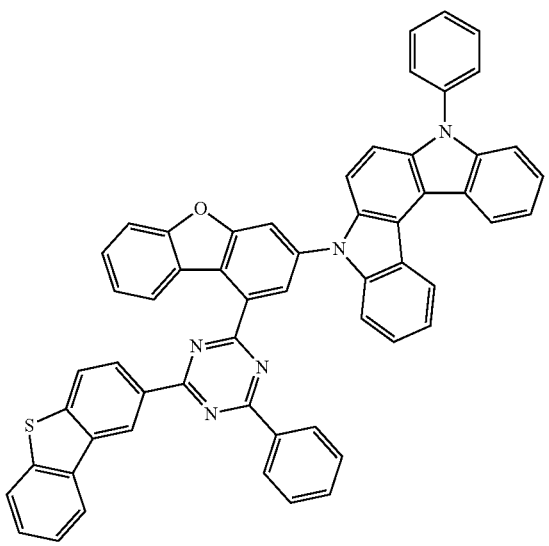

-continued
1-93
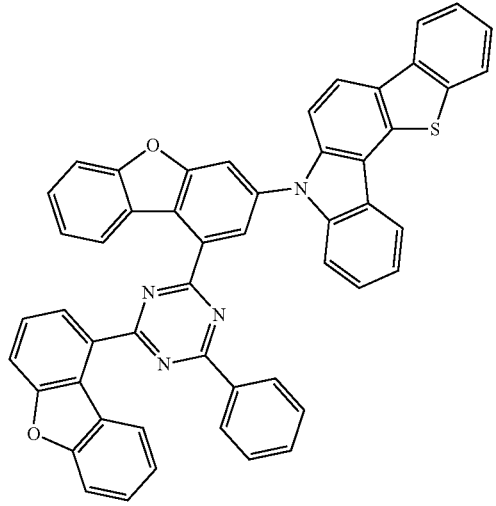
1-94
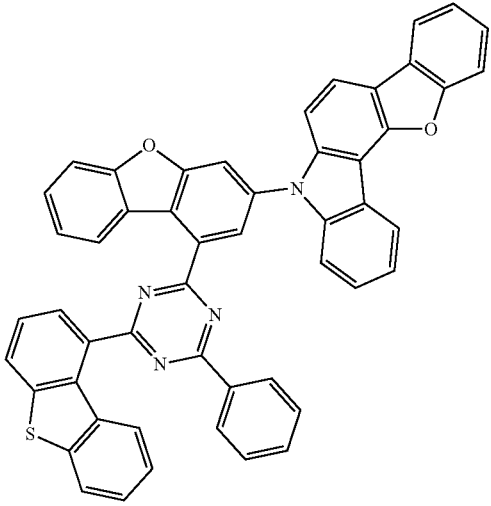
1-95
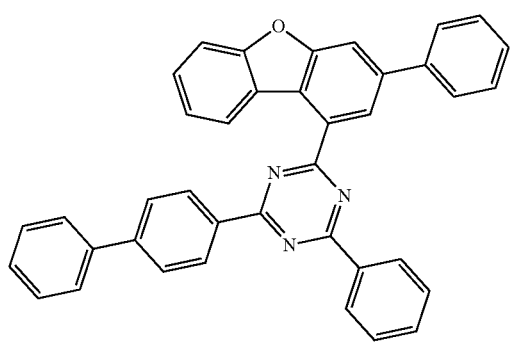
1-96
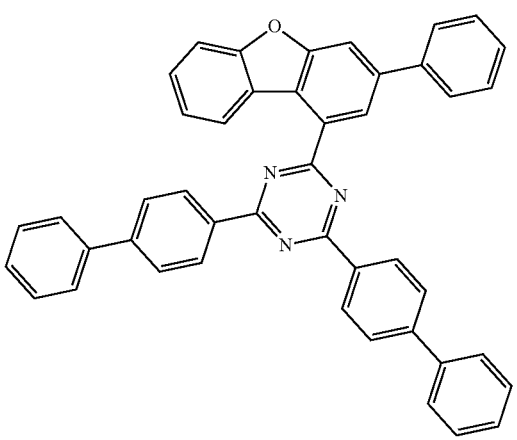
1-97
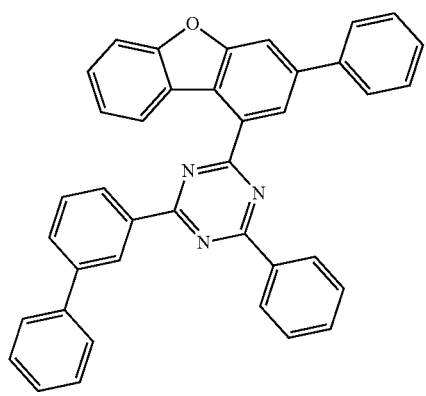
1-98
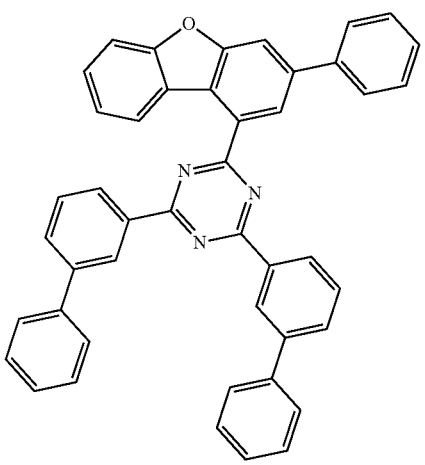

1-99
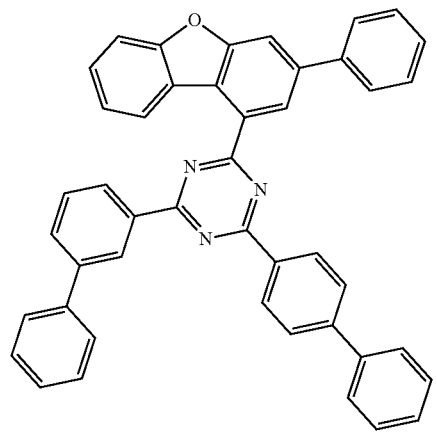
1-100
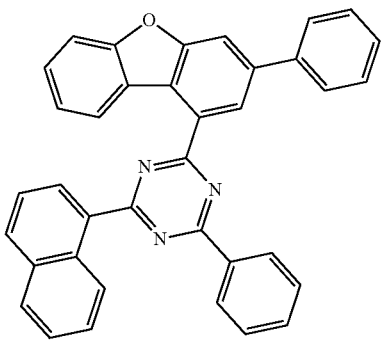
1-101
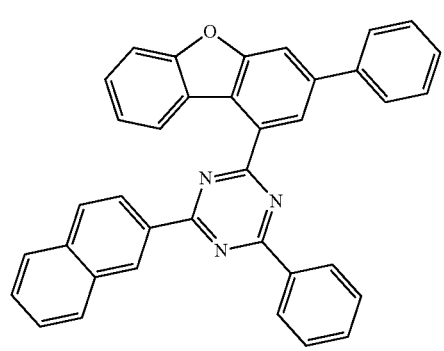
1-102
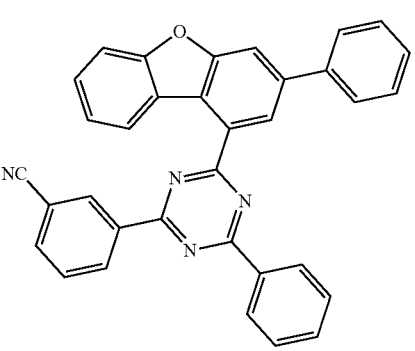
1-103
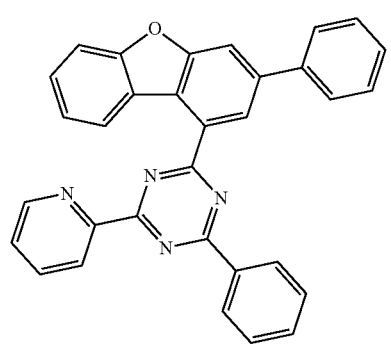
1-104
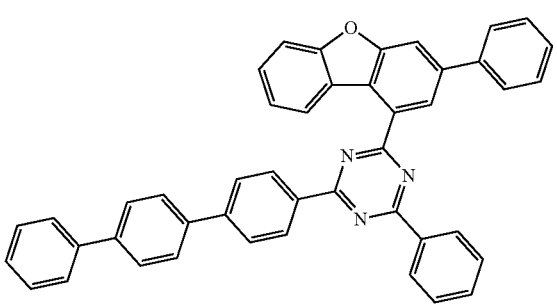
1-105
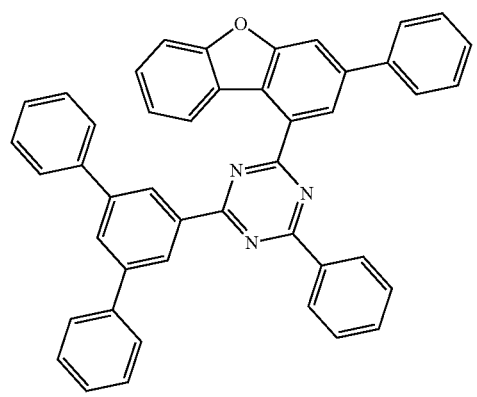
1-106
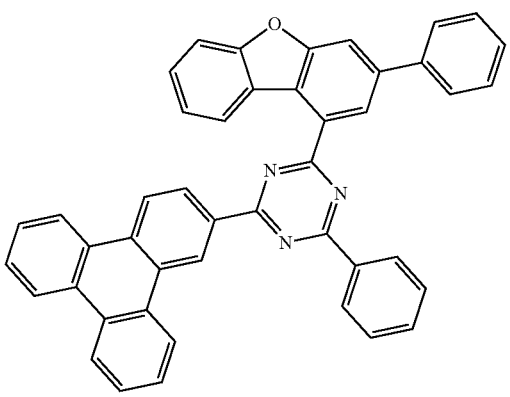

-continued
1-107
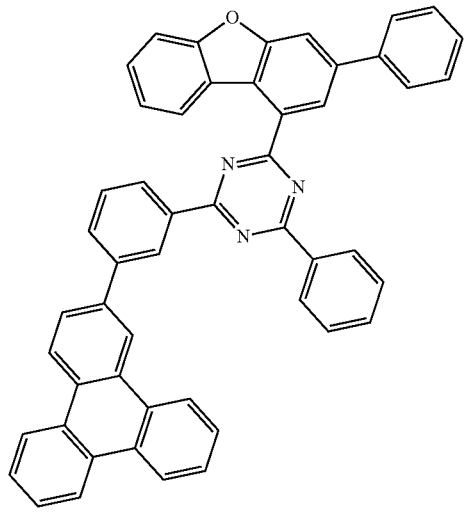
1-108
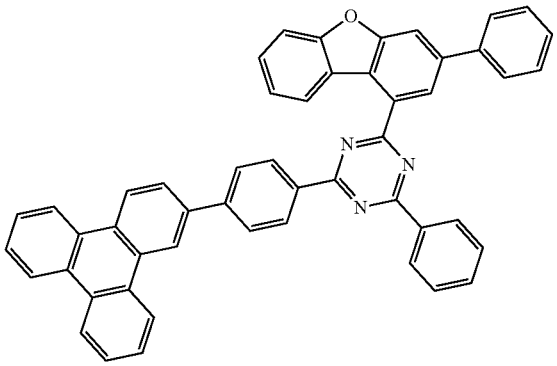
1-109
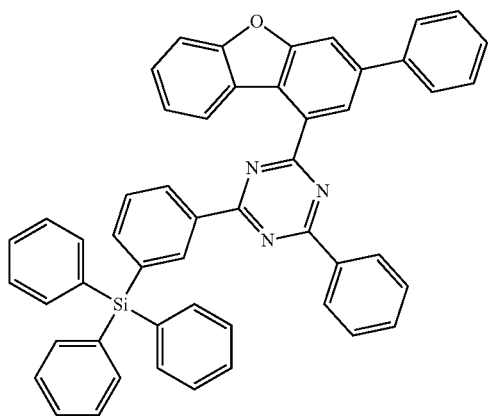
1-110
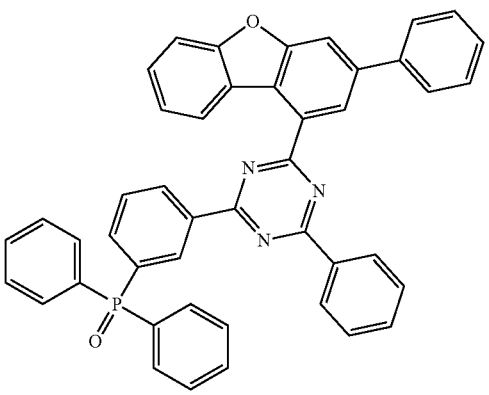
1-111
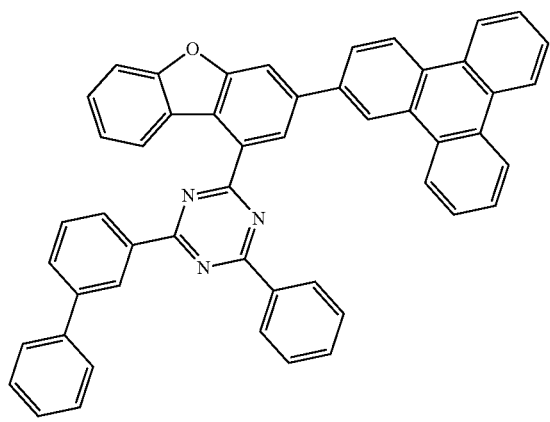
1-112
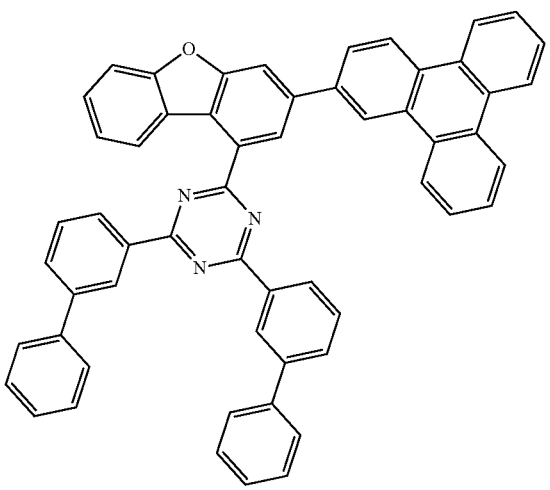

-continued
1-113
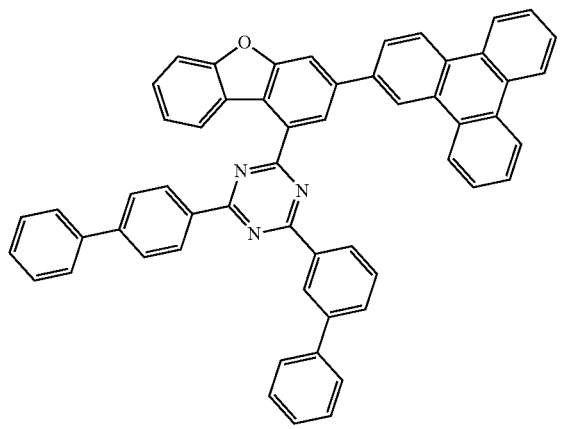
1-114
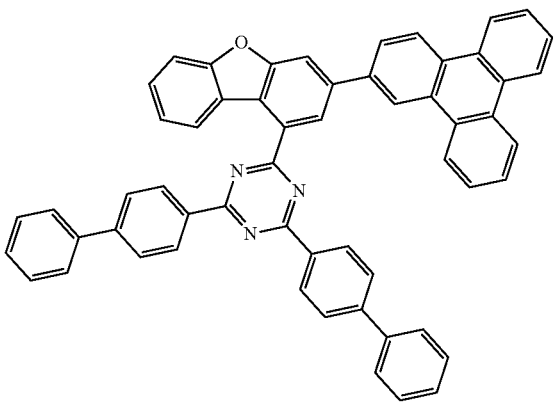
1-116
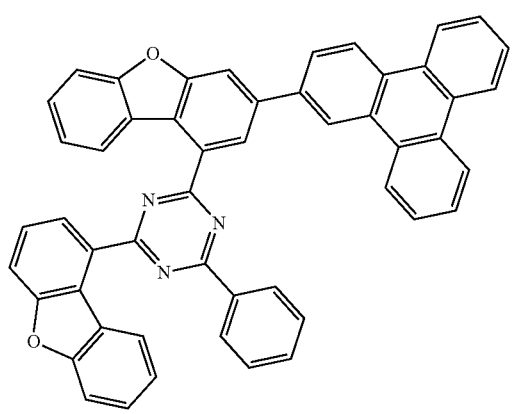
1-115
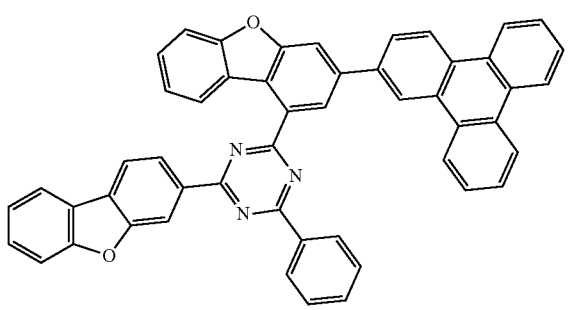
1-117
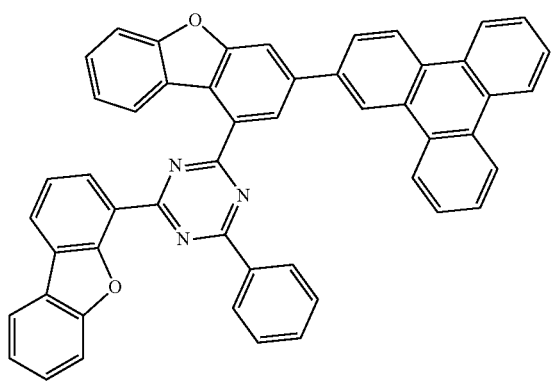
1-118
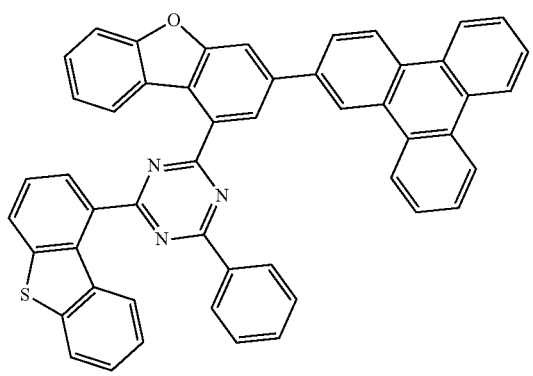
1-119
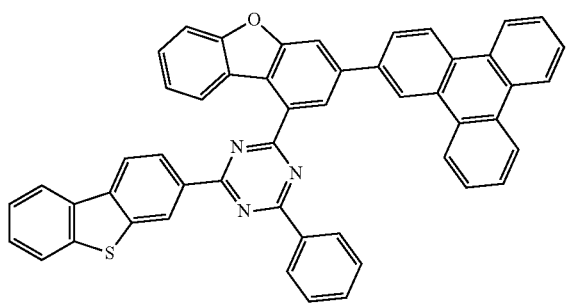
2-1
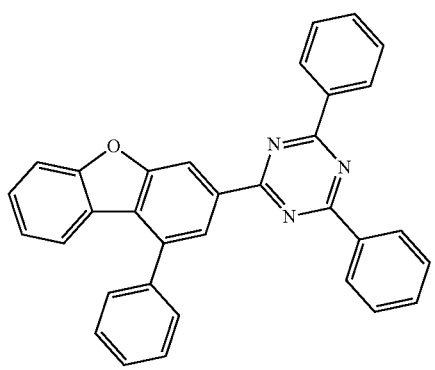

-continued
2-2
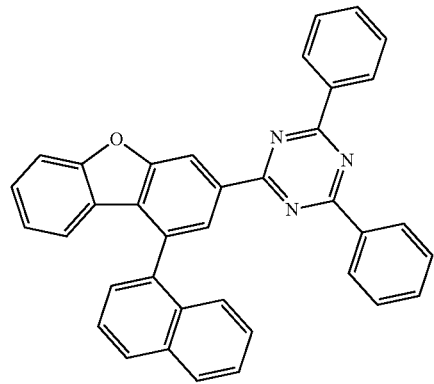
2-3
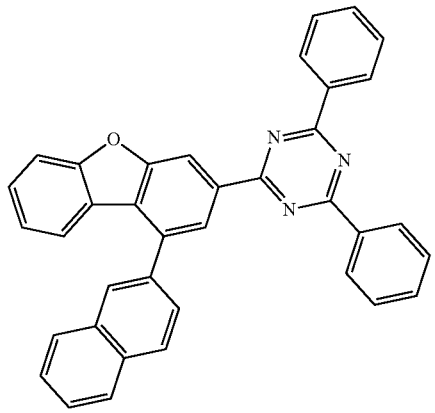
2-4
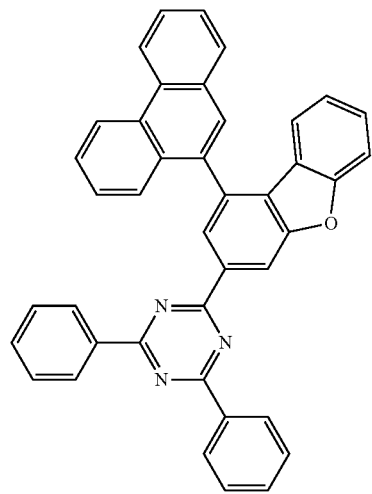
2-5
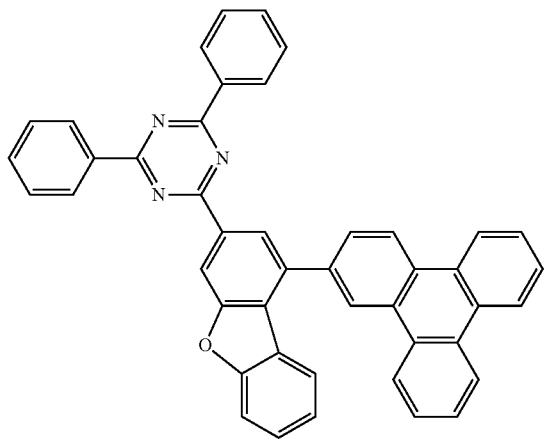
2-6
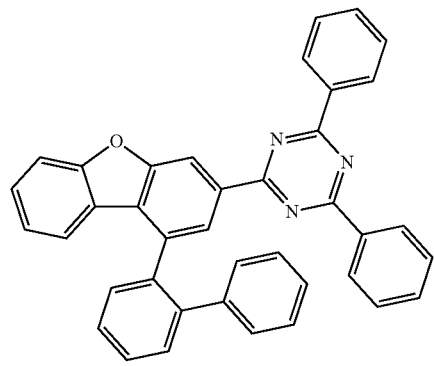
2-7
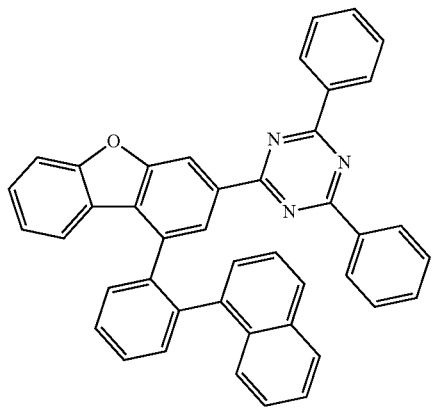

-continued
2-8
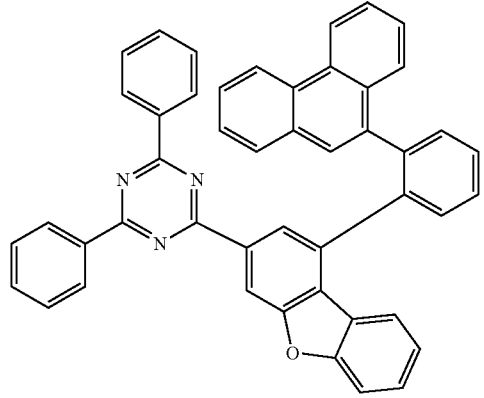
2-9
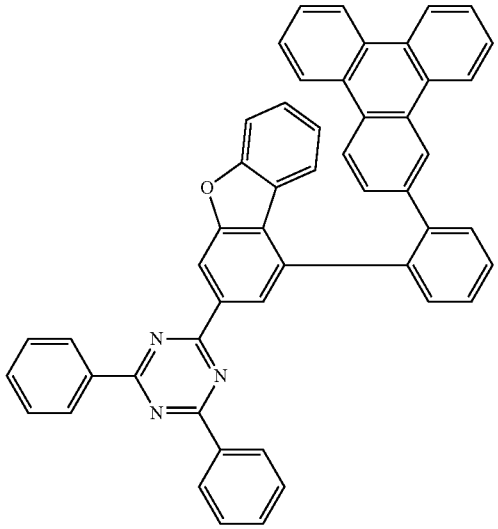
2-10
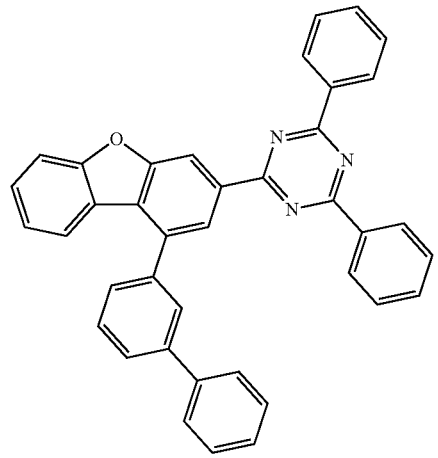
2-11
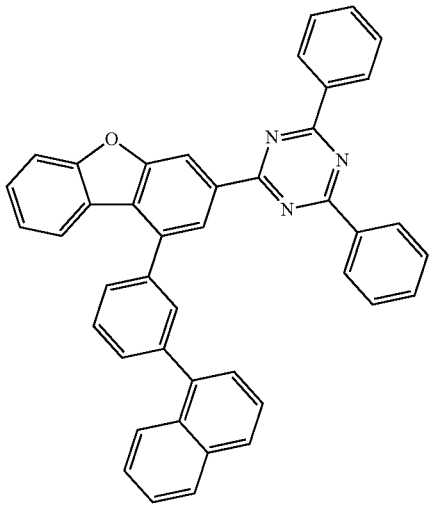
2-12
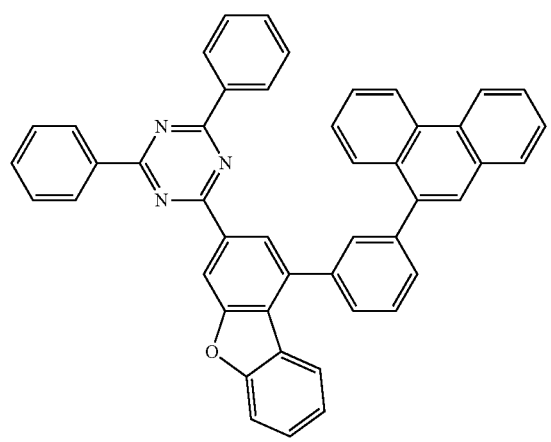
2-13
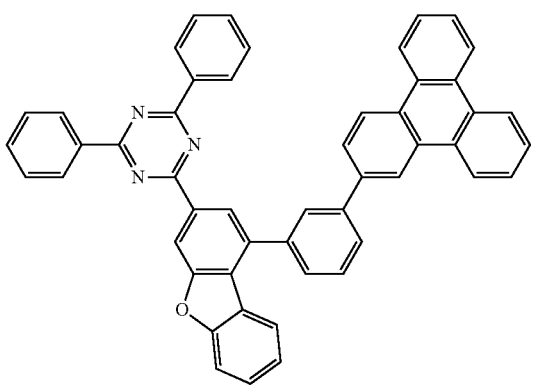

-continued
2-14
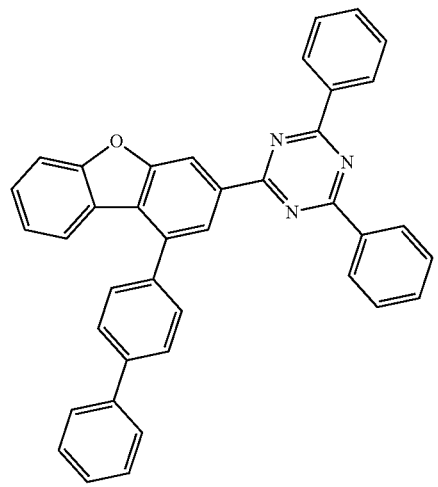
2-15
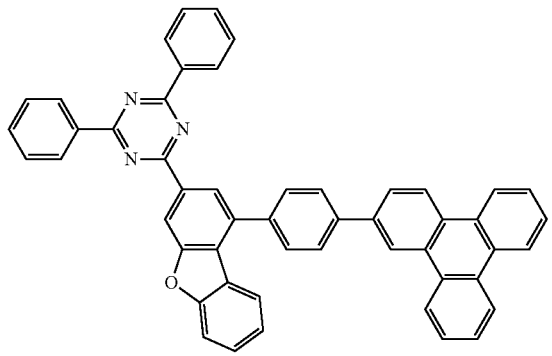
2-16
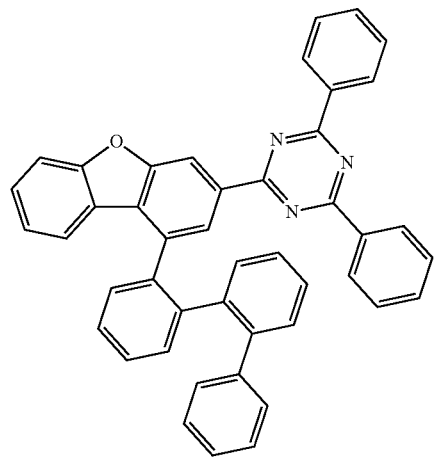
2-17
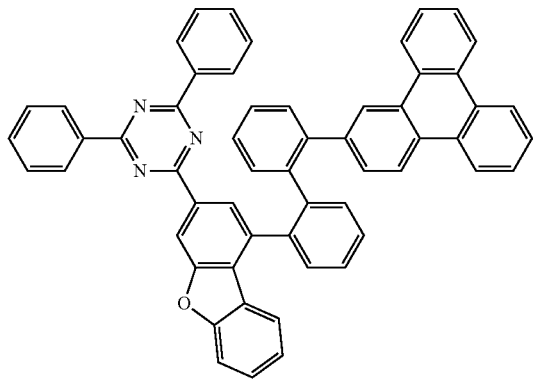
2-18
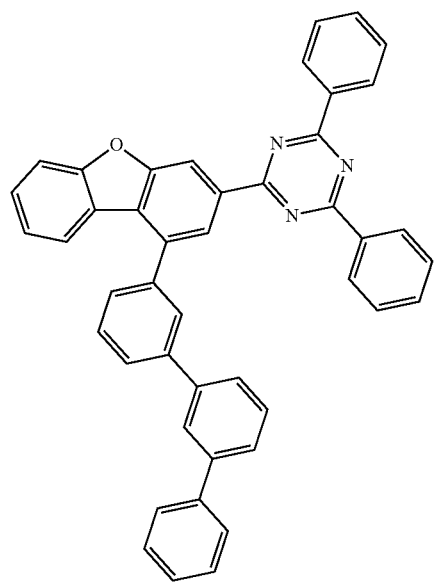
2-19
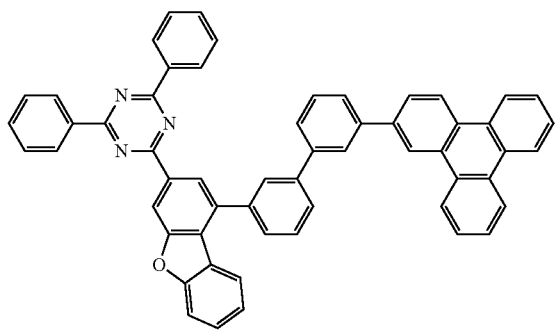

2-20
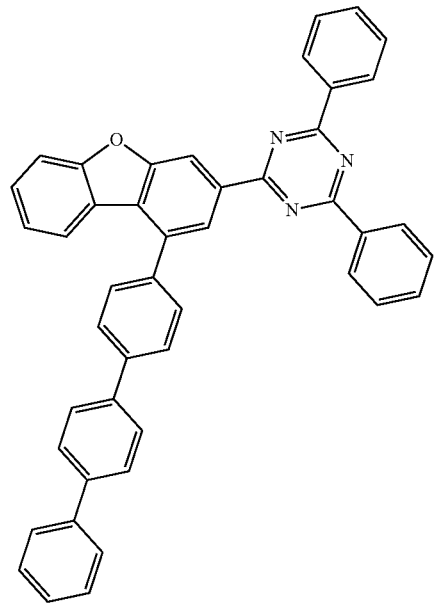
2-21
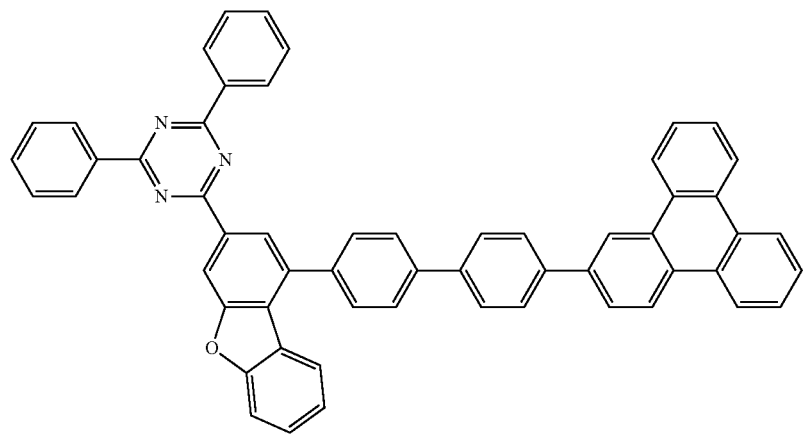
2-22
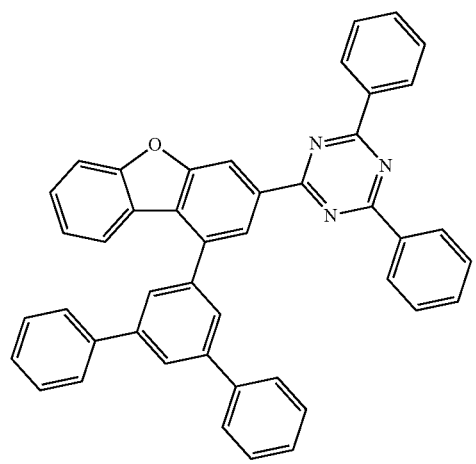
2-23
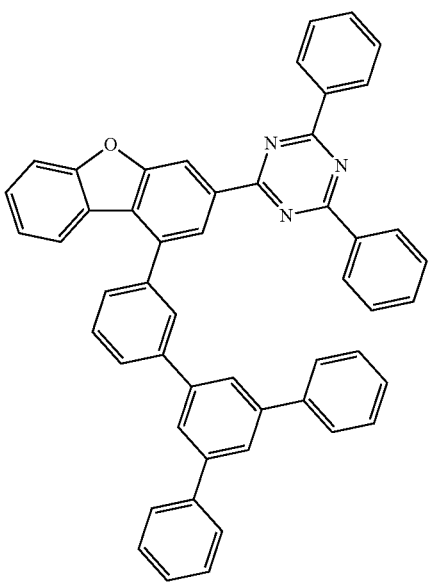

2-24
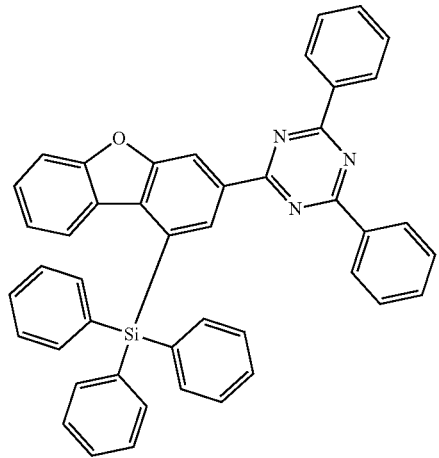
2-25
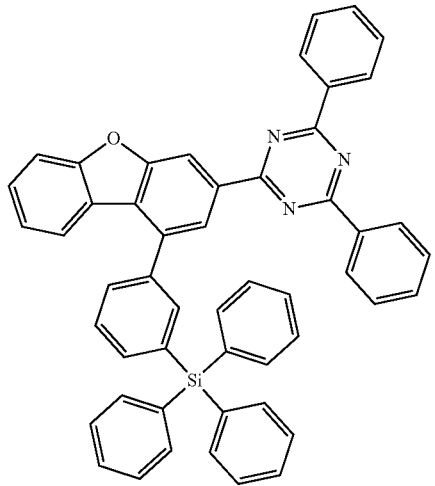
2-26
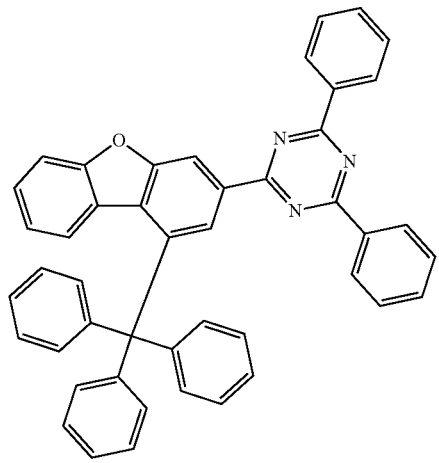
2-27
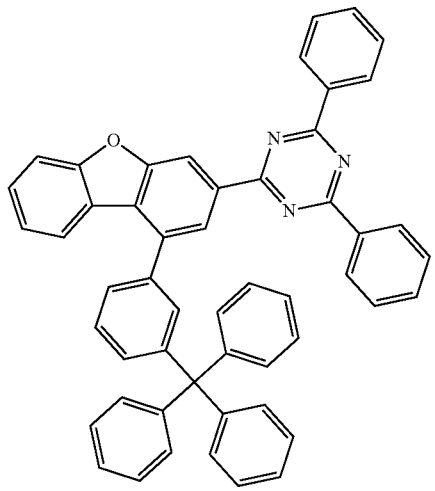
2-28
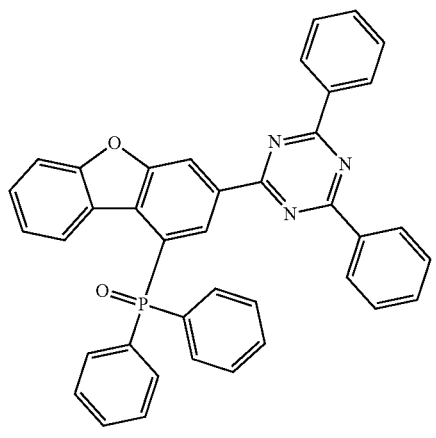
2-29
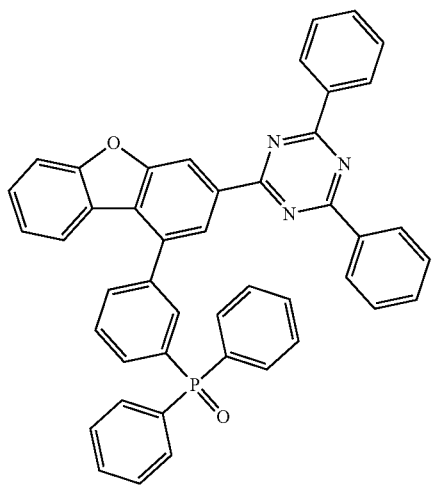

-continued
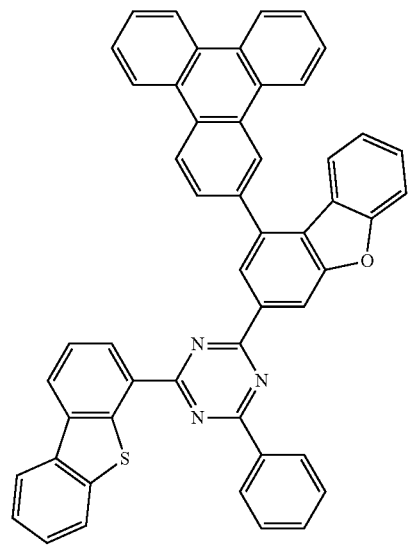
2-35
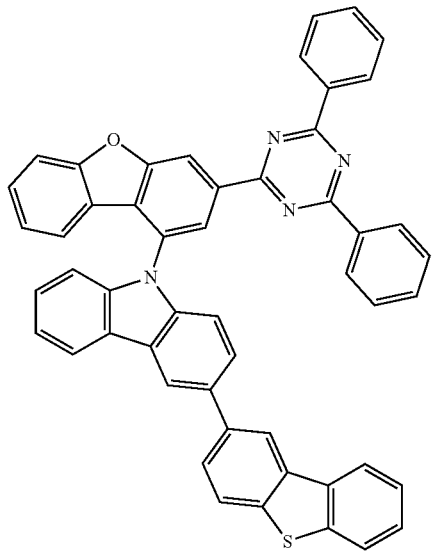
2-36
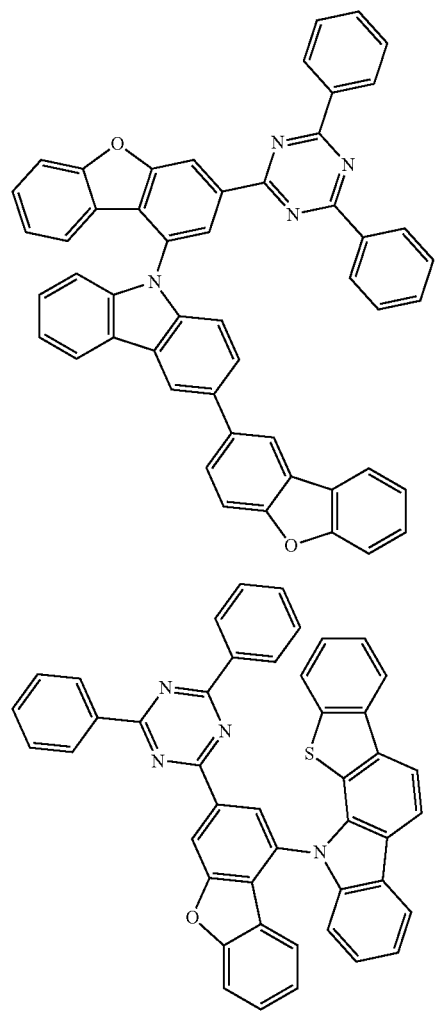
2-37
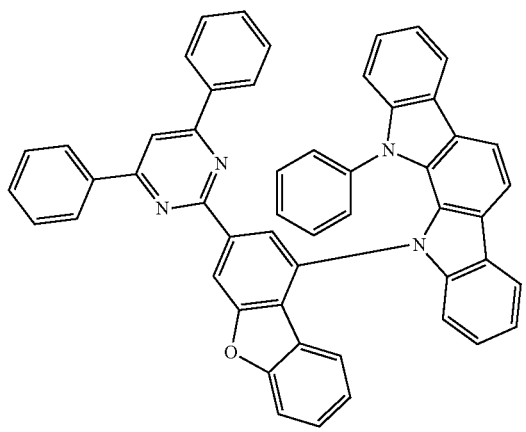
2-39
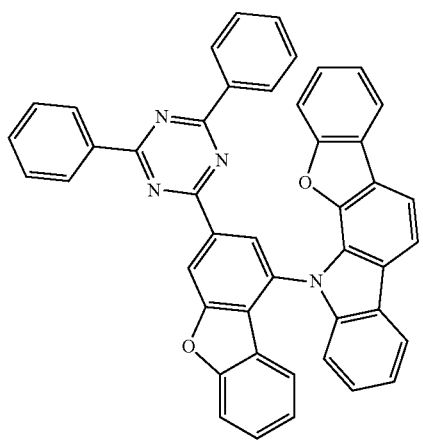
2-40
2-41

-continued
2-42
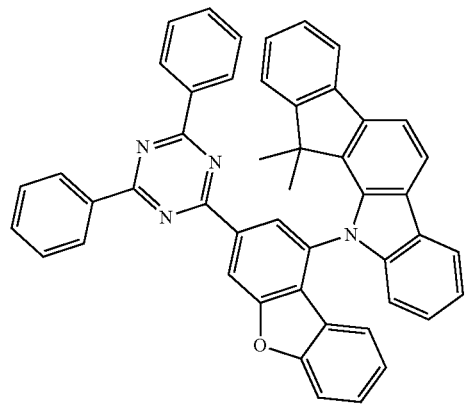
2-43
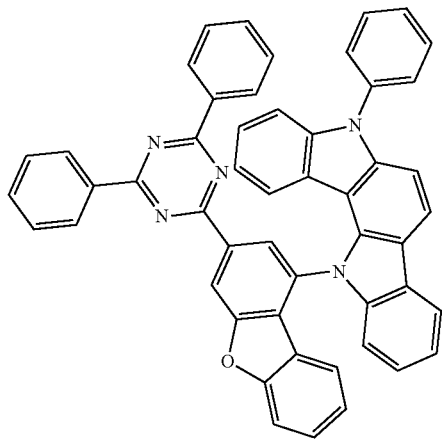
2-44
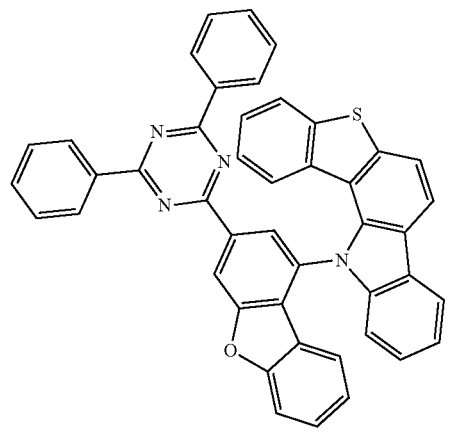
2-45
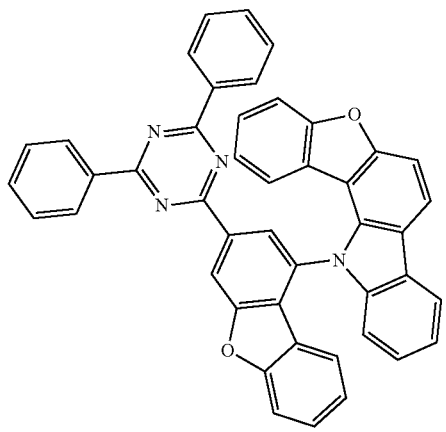
2-46
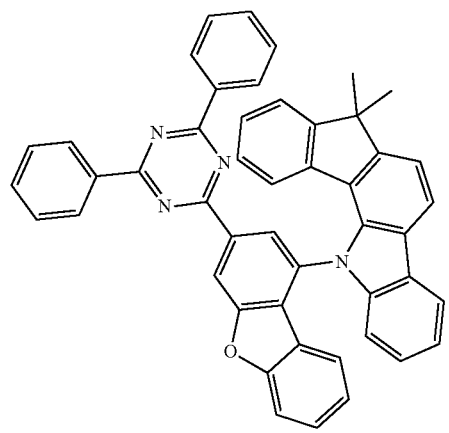
2-47
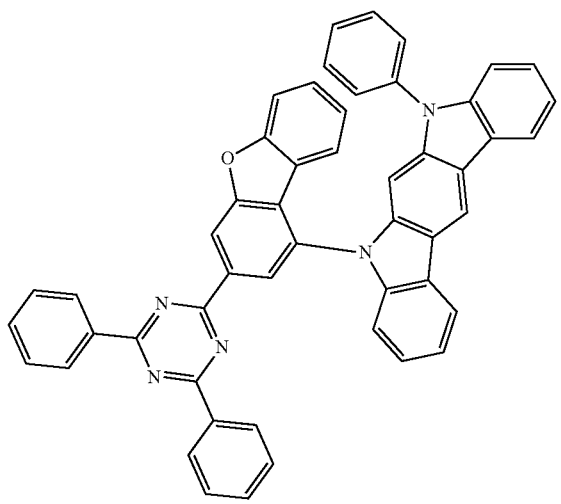 [SMILES: c1ccc(-c2nc(-c3ccccc3)nc(-c3cc(-n4c5ccccc5c5cc6c7ccccc7n(-c7ccccc7)c6cc54)c4c(c3)oc3ccccc34)n2)cc1]

-continued
2-48
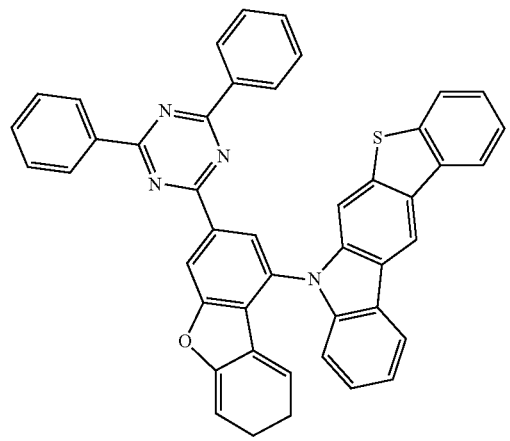
2-49
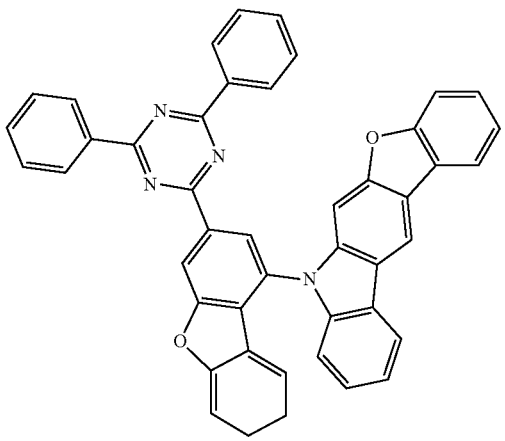
2-50
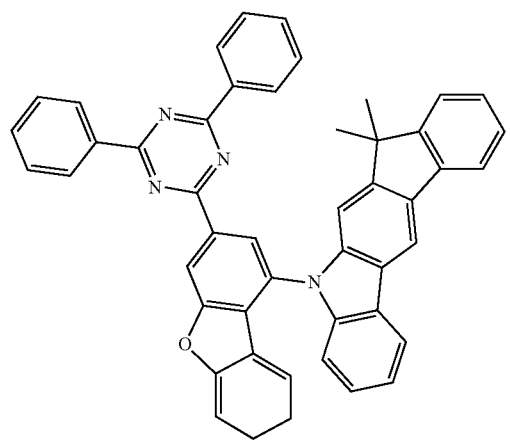
2-51
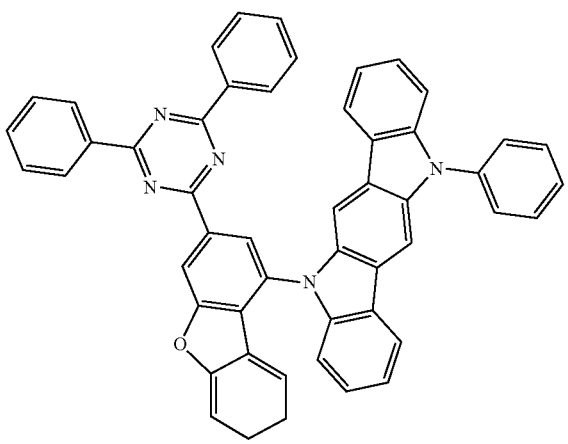
2-52
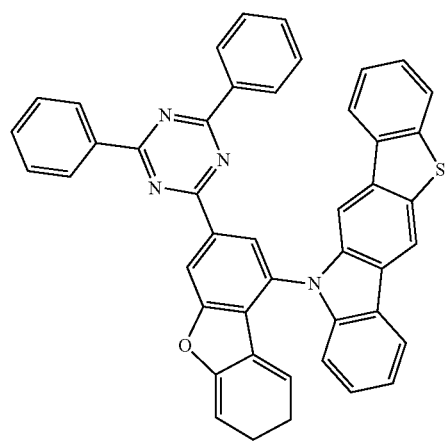
2-53
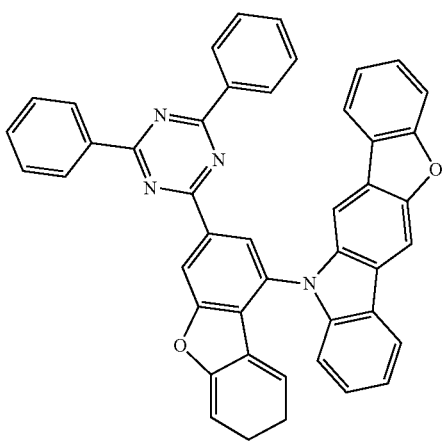

-continued
2-54
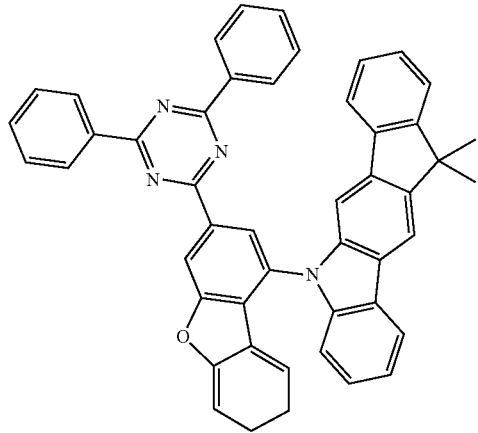
2-55
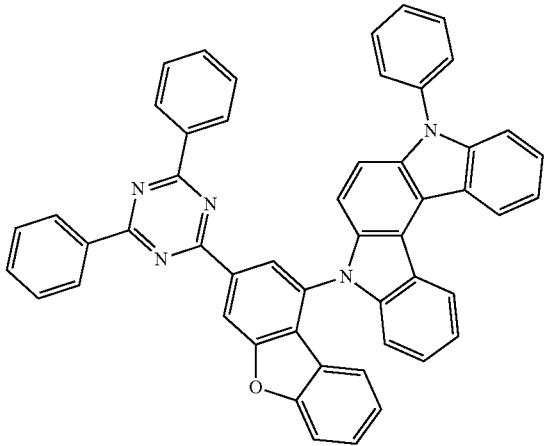
2-56
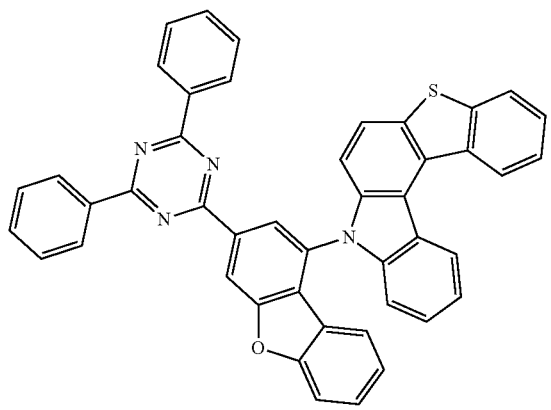
2-57
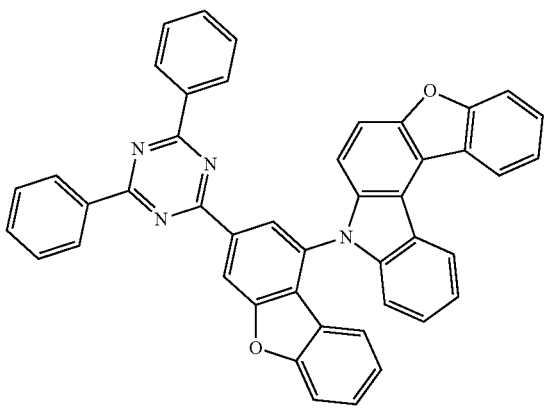
2-58
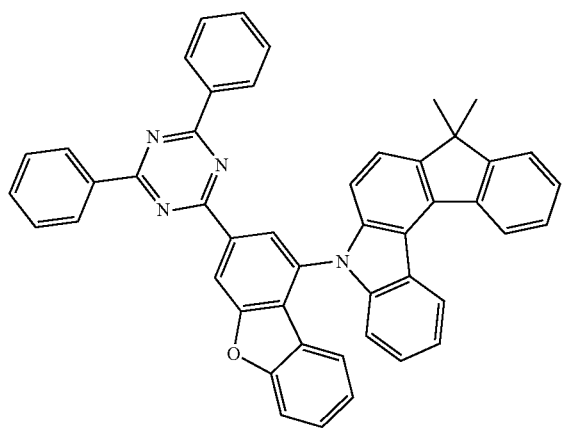
2-59
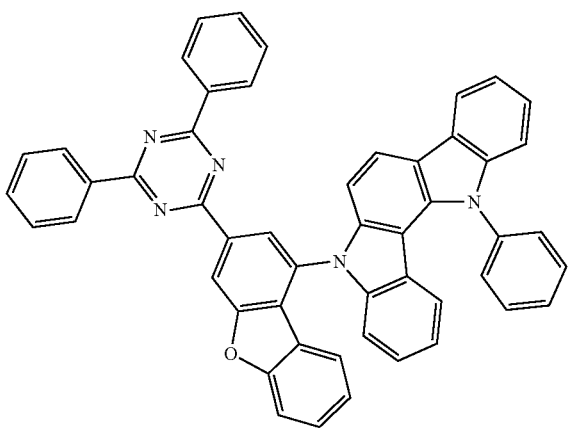

-continued
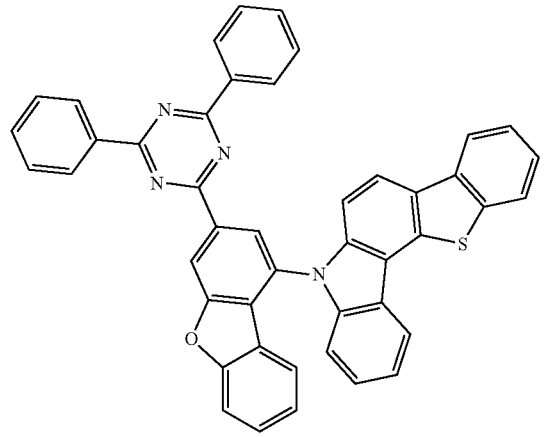
2-60
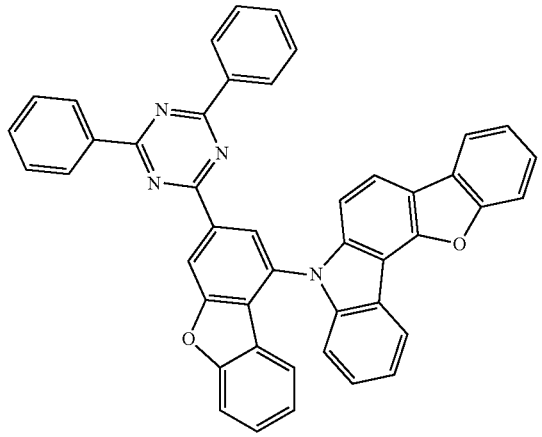
2-61
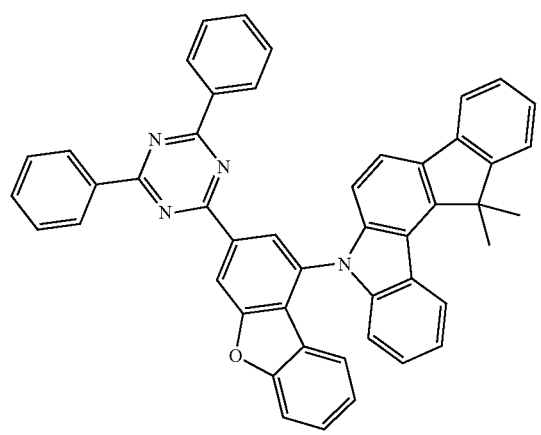
2-62
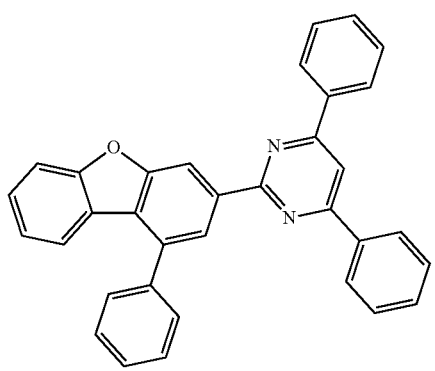
2-63
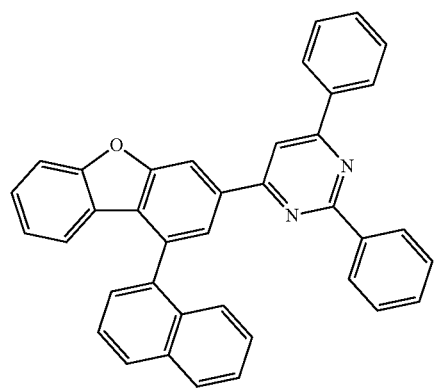
2-64
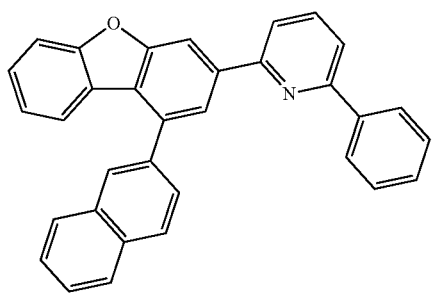
2-65

-continued
2-66
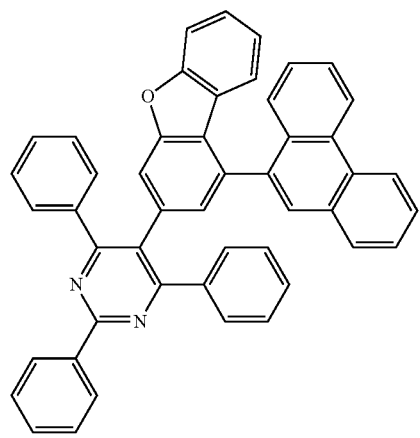
2-67
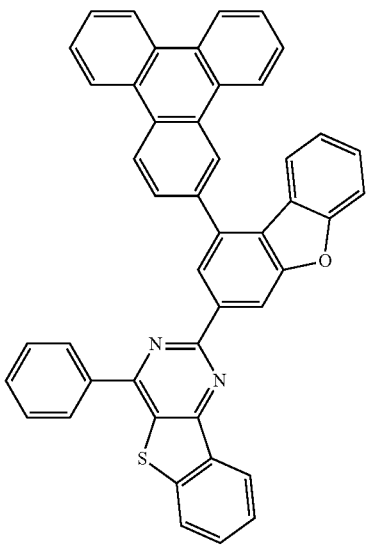
2-68
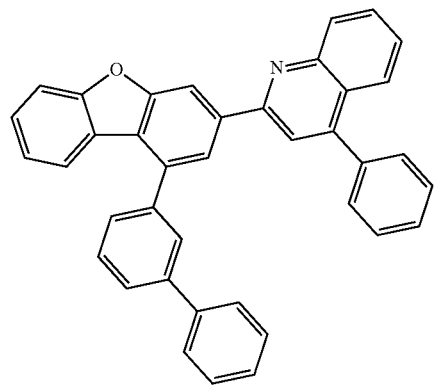
2-69
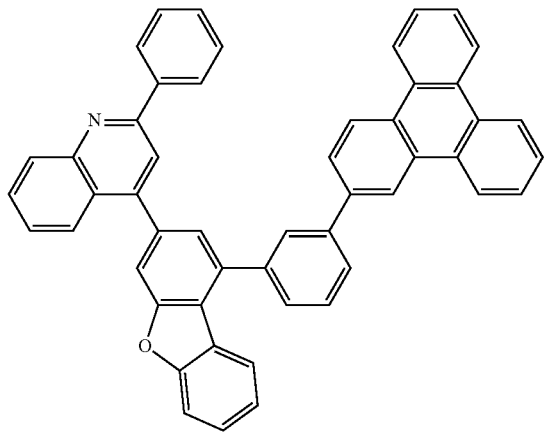
2-70
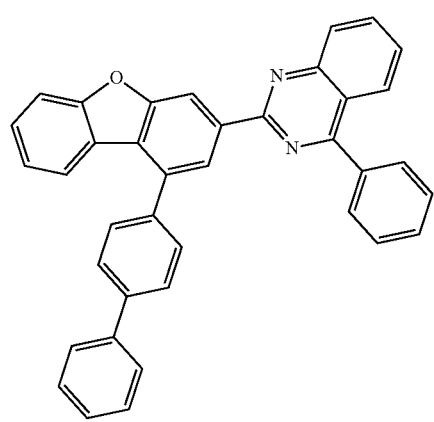
2-71
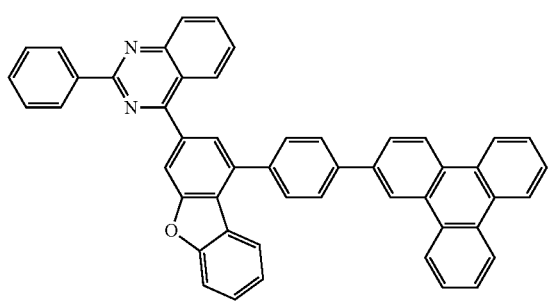

-continued
2-72
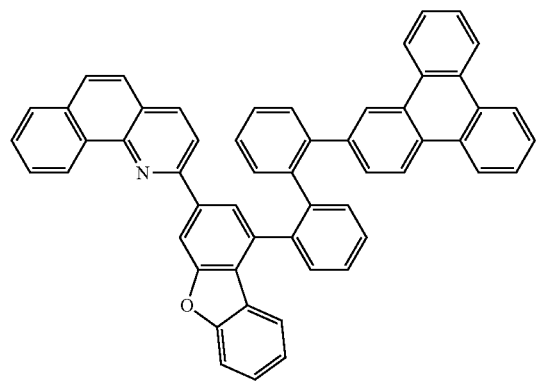
2-73
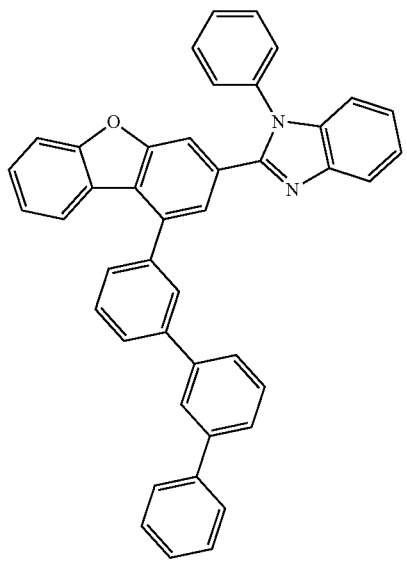
2-74
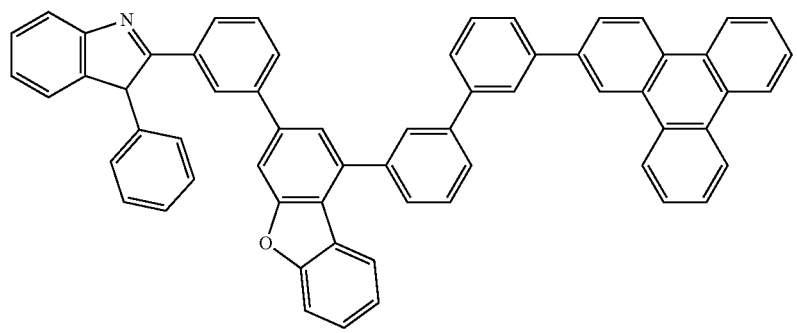
2-75
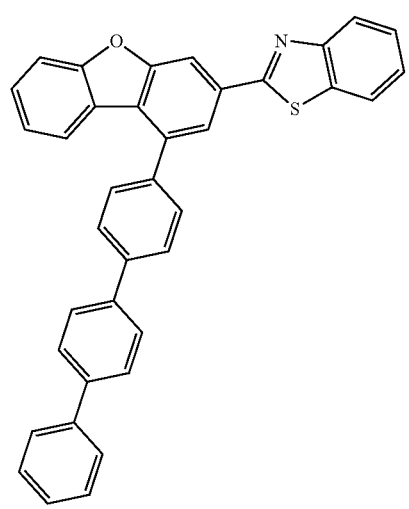

2-76
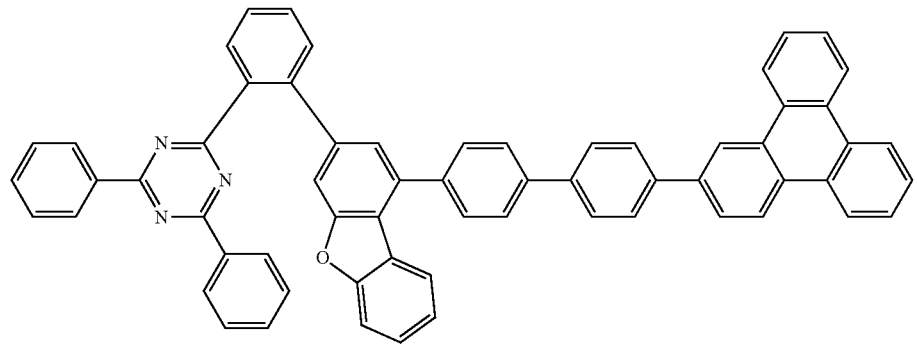
2-77 2-78
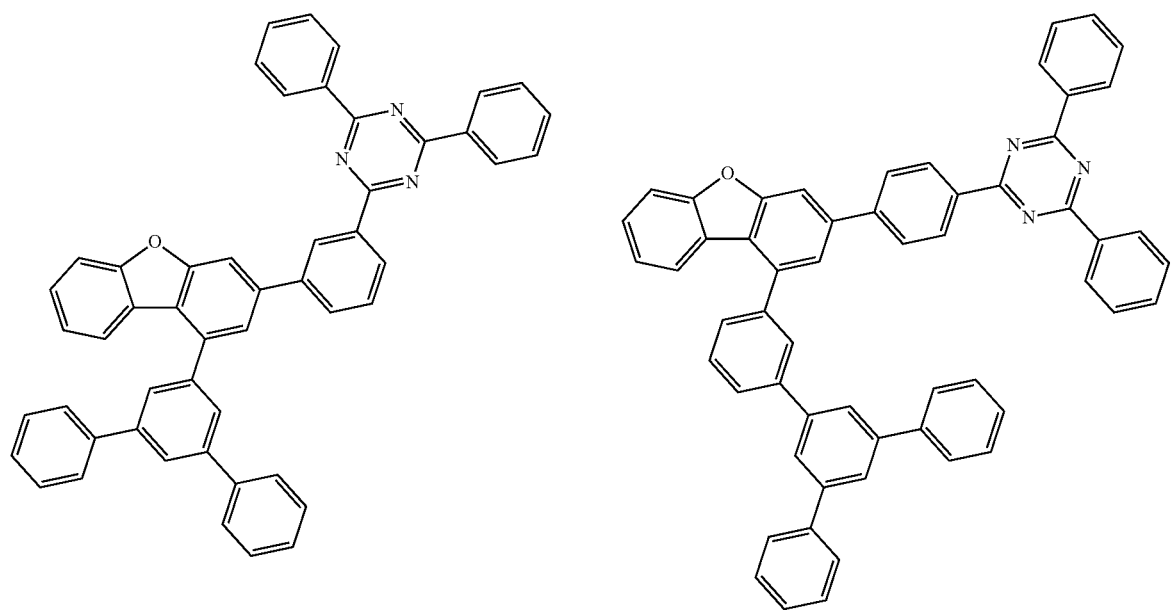
2-79 2-80
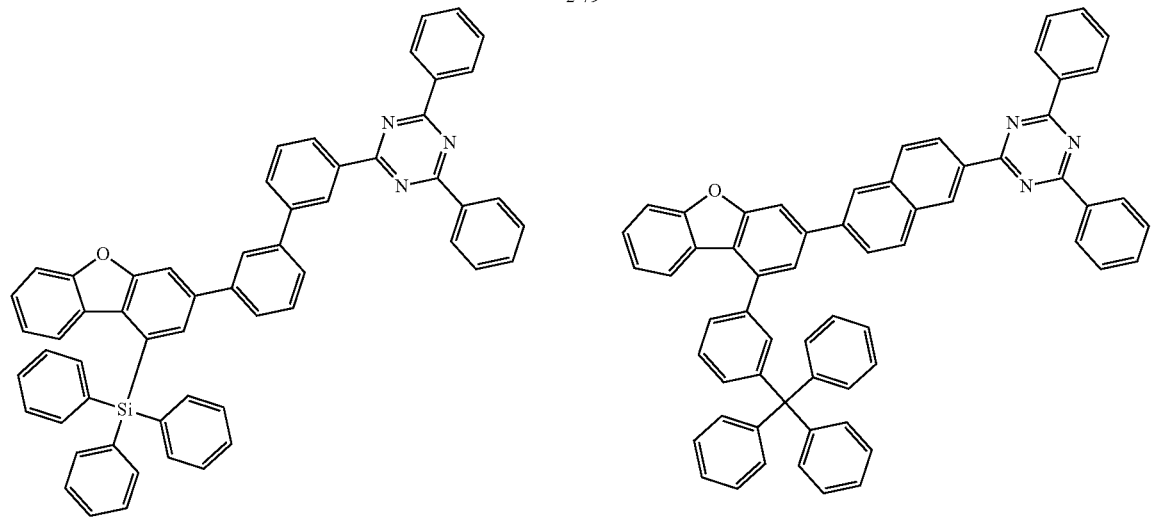

-continued
2-81
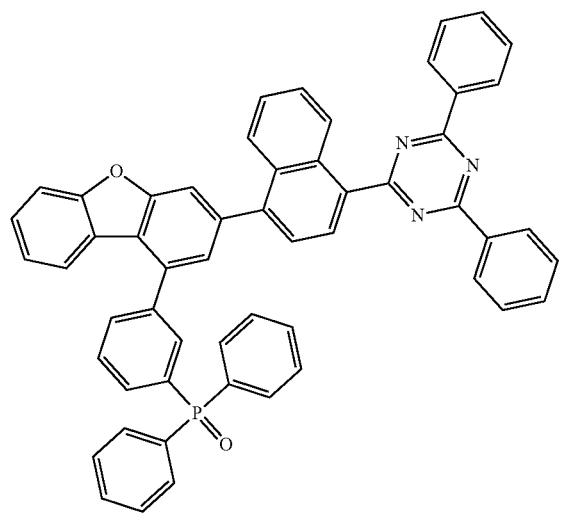
2-85
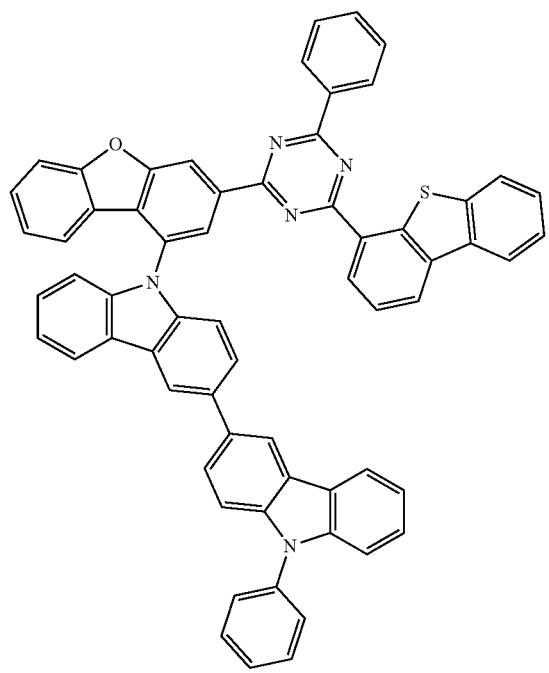
2-86
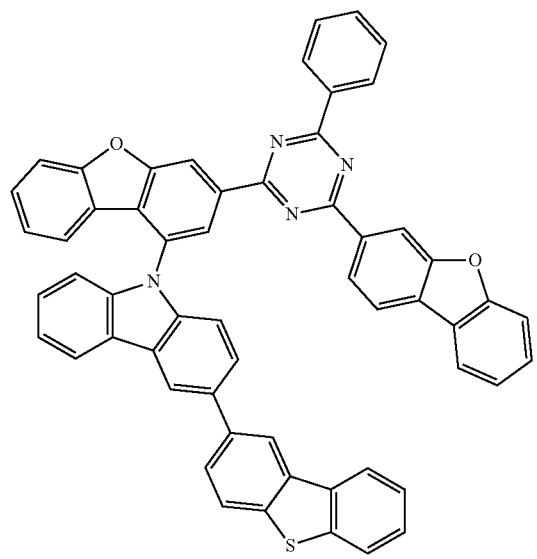
2-87
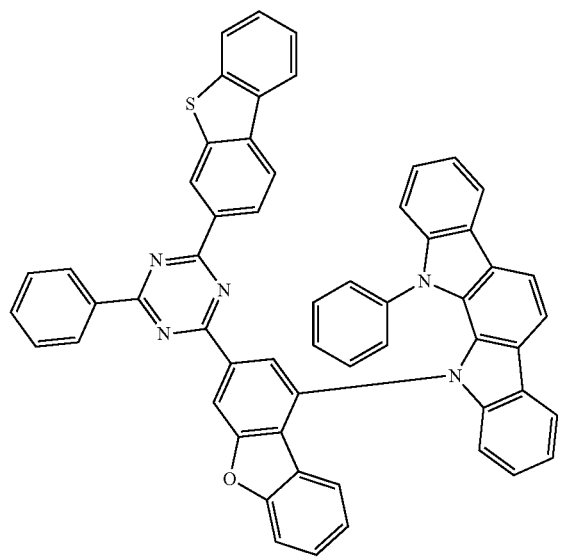

2-88
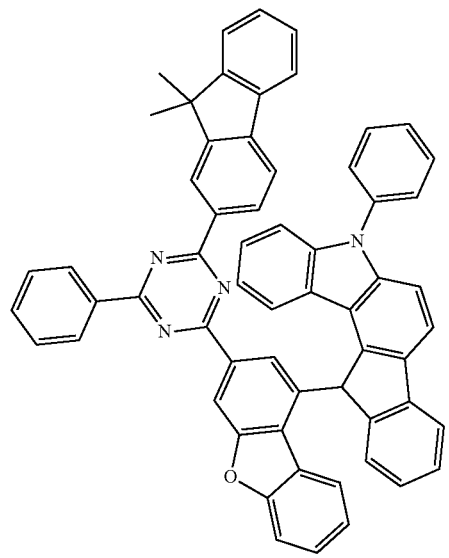
2-89
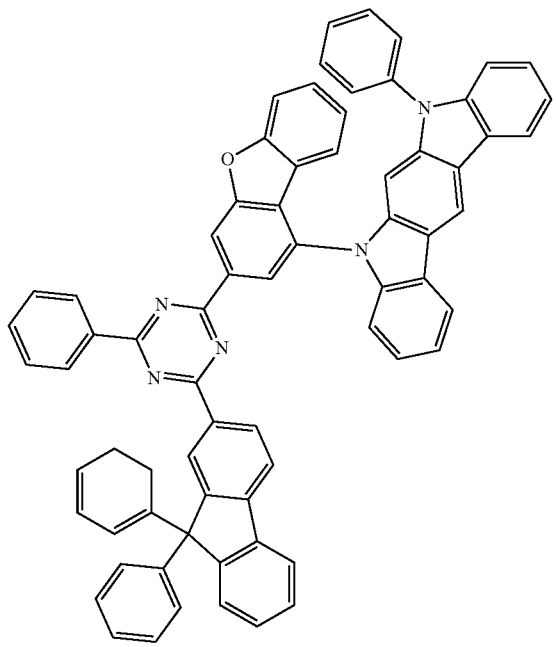
2-90
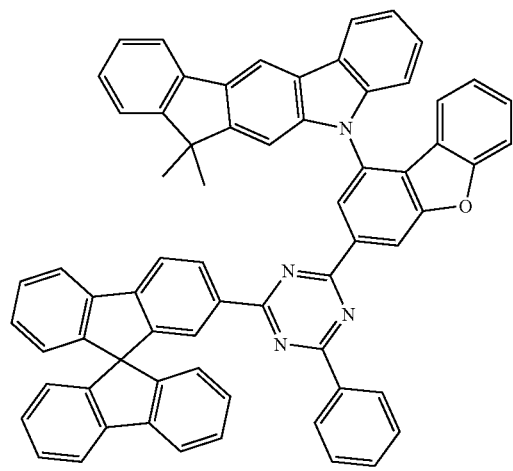
2-91
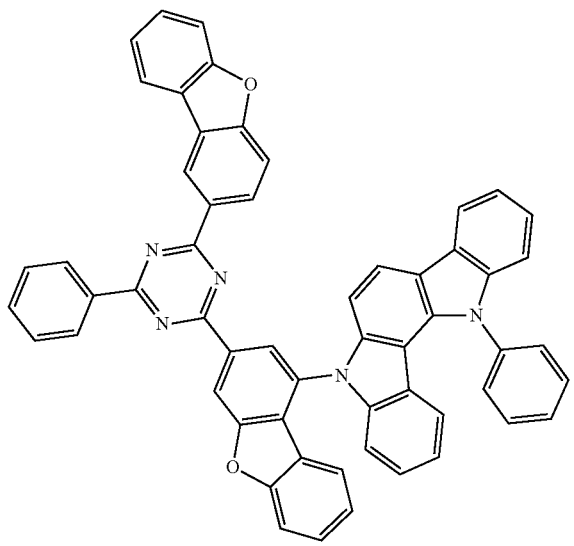

-continued
2-92
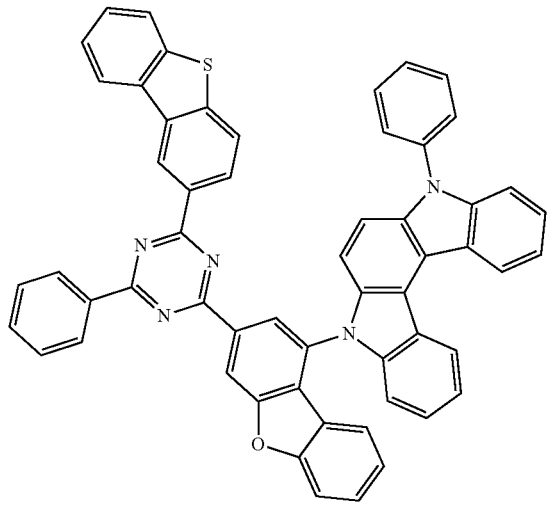
2-93
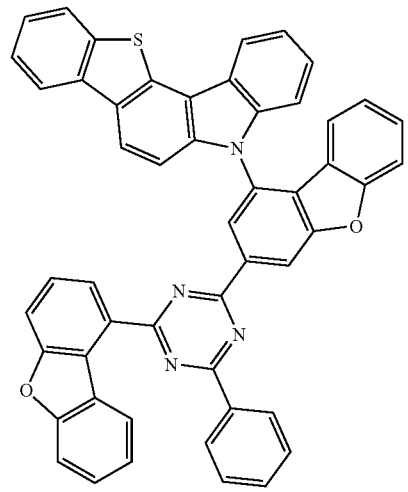
2-94
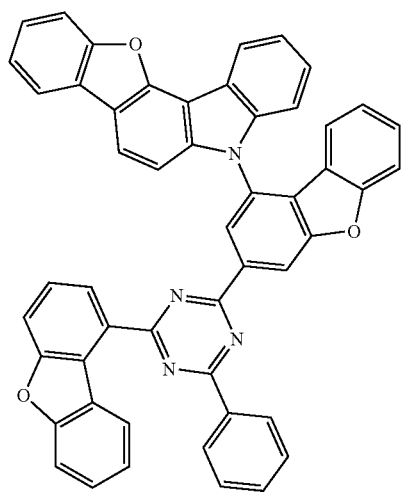
2-95
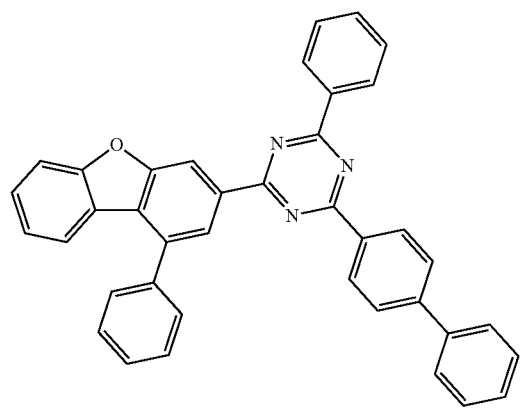
2-96
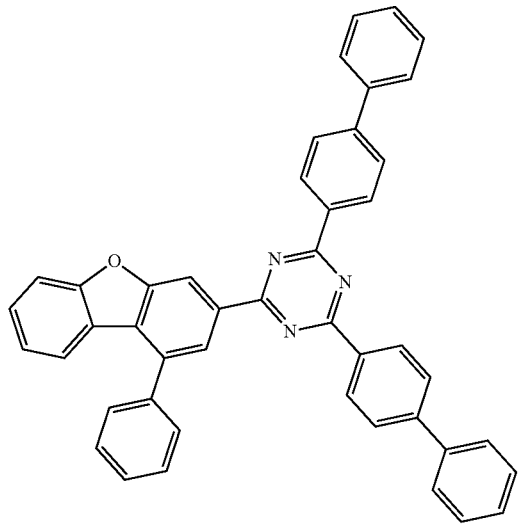
2-97
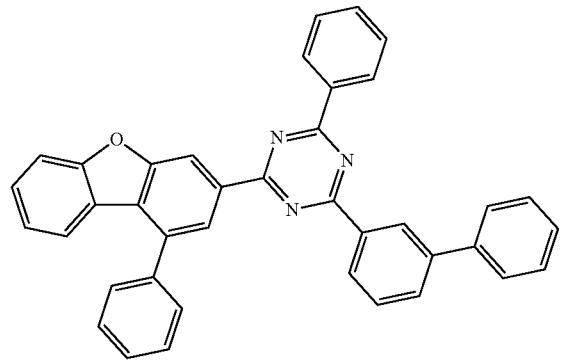

2-98
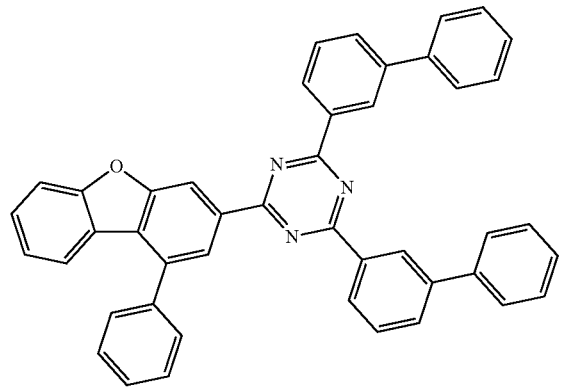
2-99
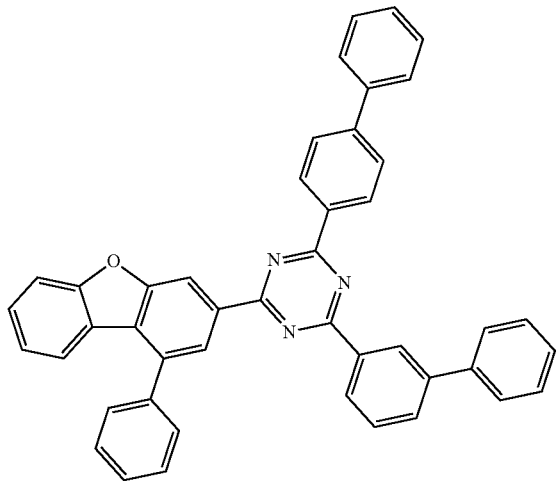
2-100
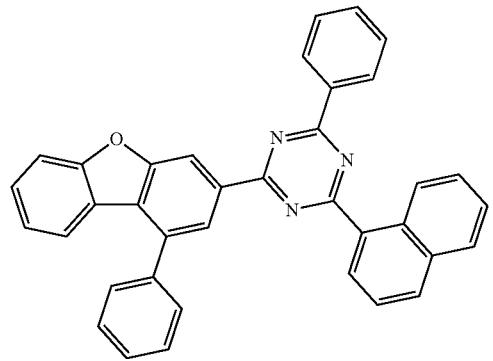
2-101
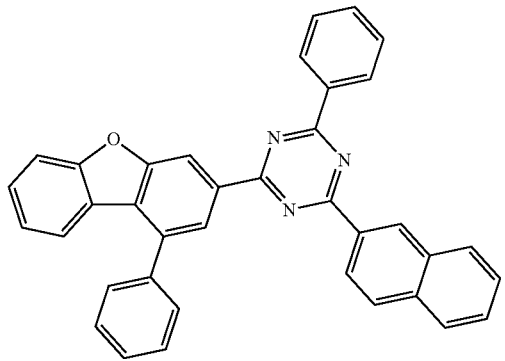
2-102
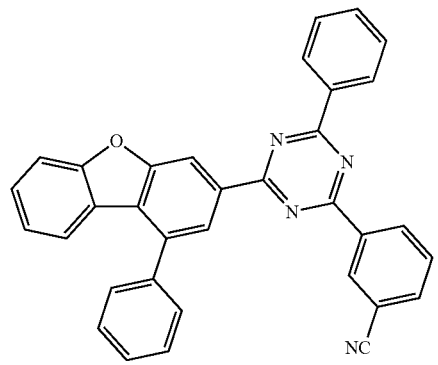
2-103
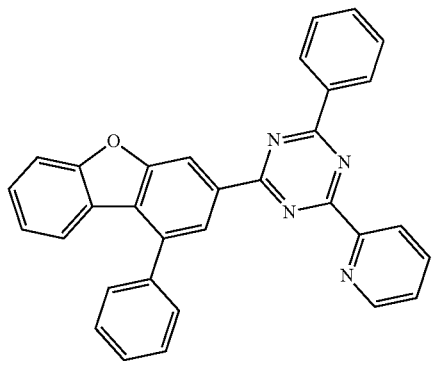

-continued
2-104
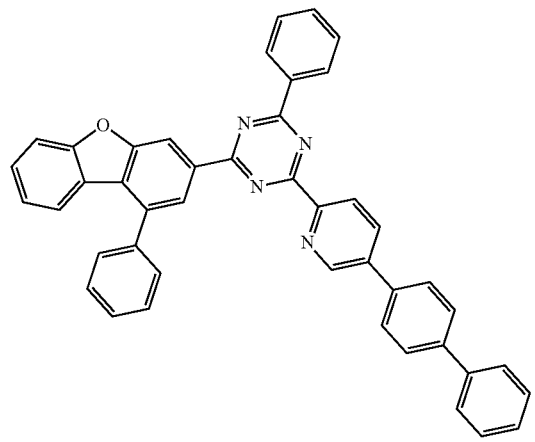
2-105
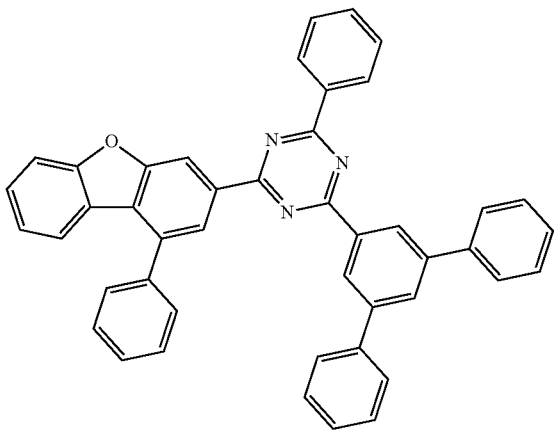
2-106
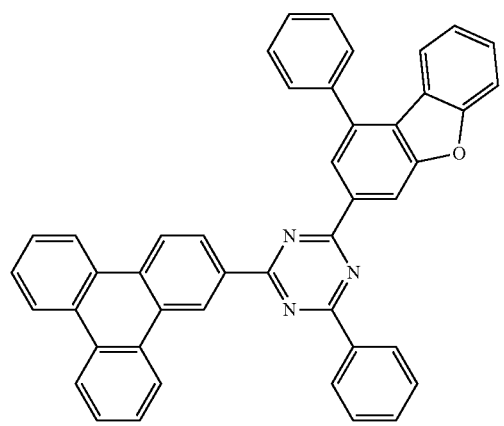
2-107
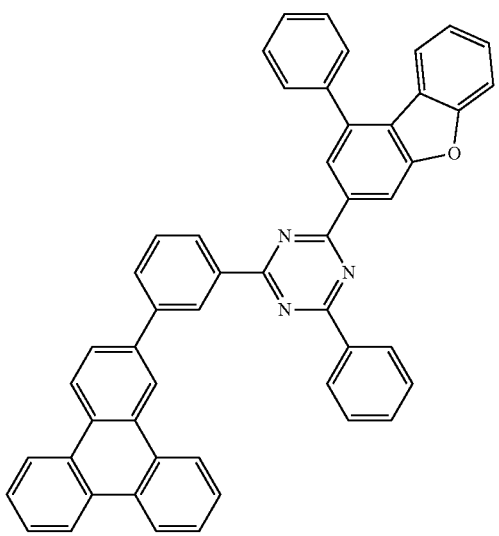
2-108
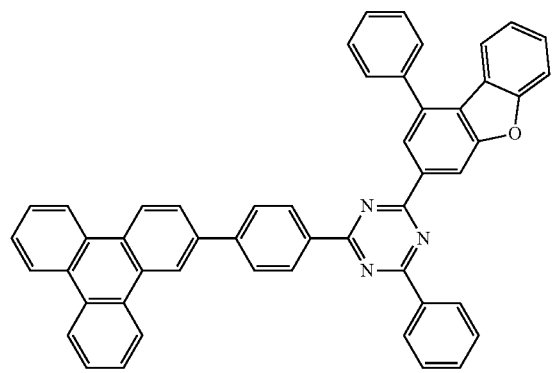
2-109
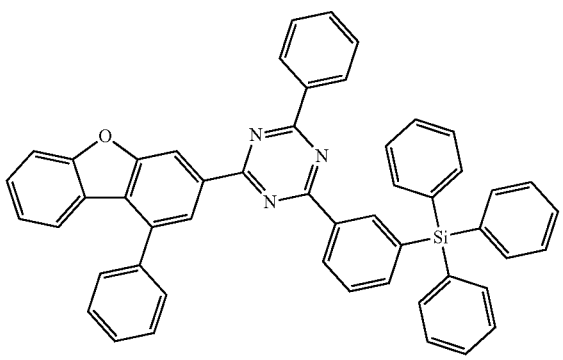

2-110
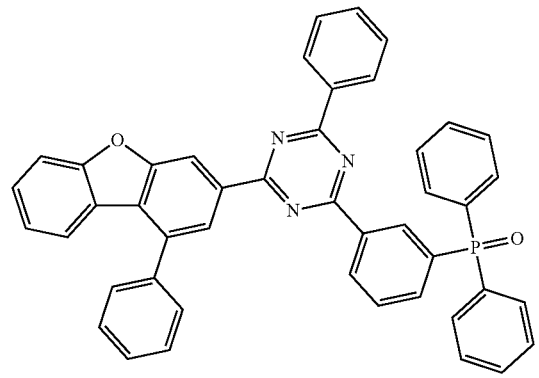
2-111
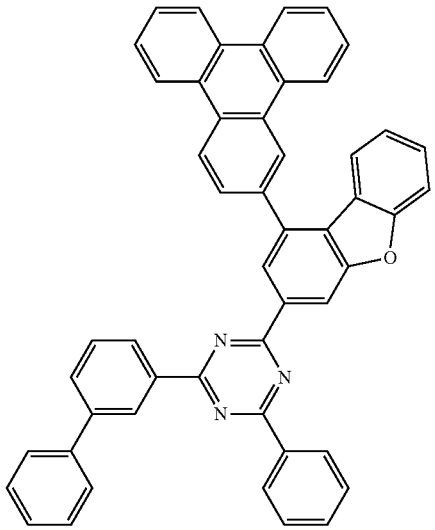
2-112
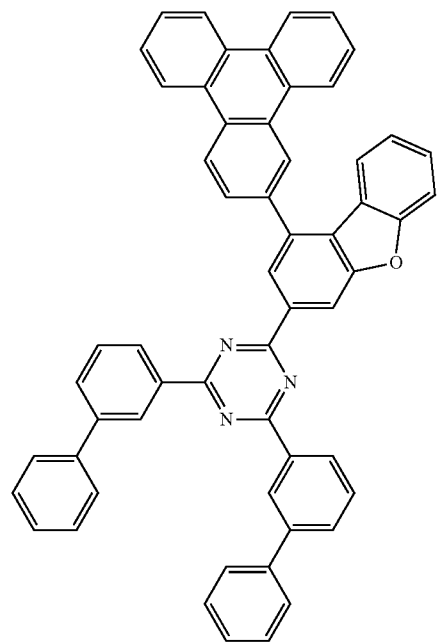
2-113
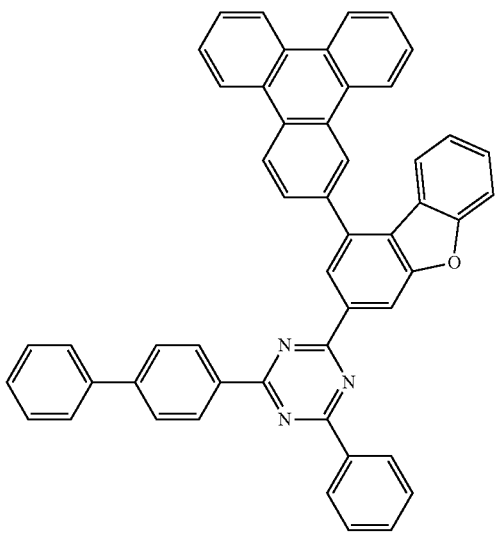

-continued
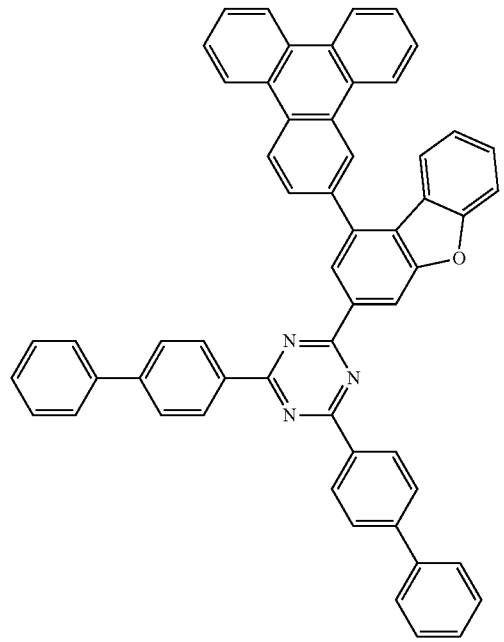
2-114
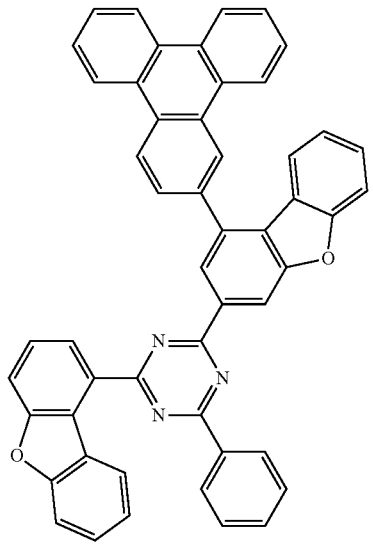
2-115
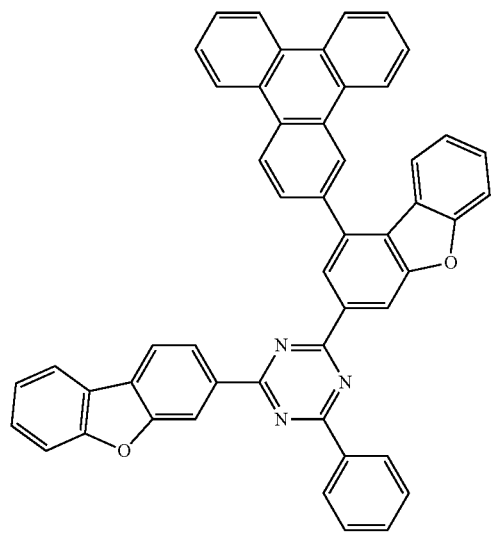
2-116
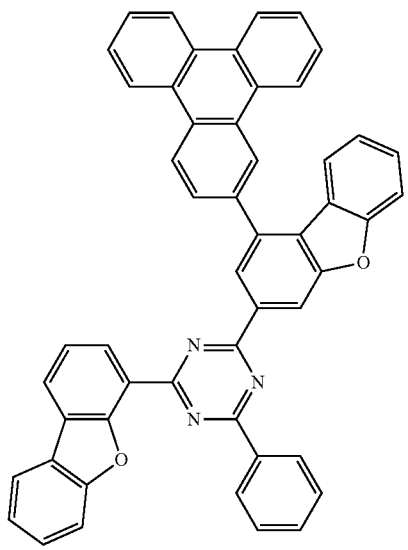
2-117

-continued
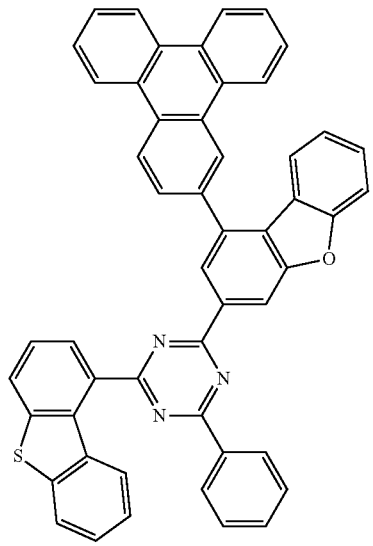
2-118
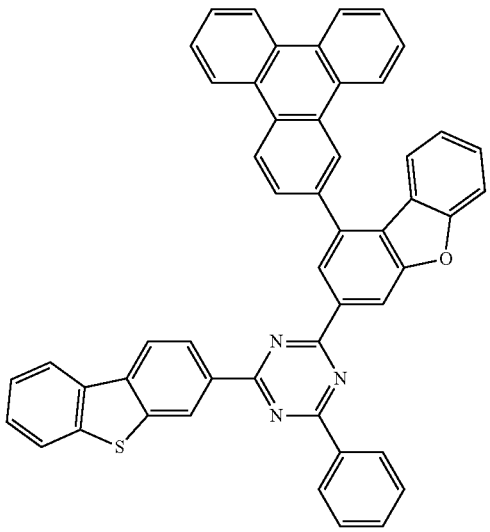
2-119
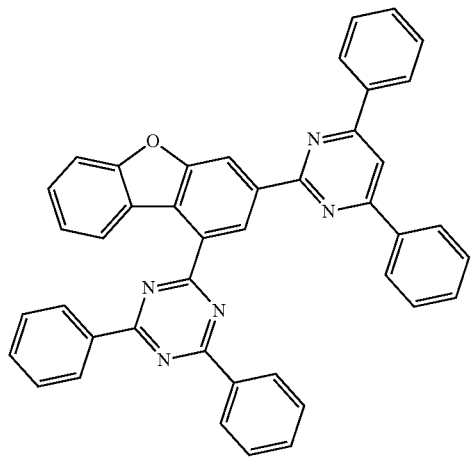
2-121
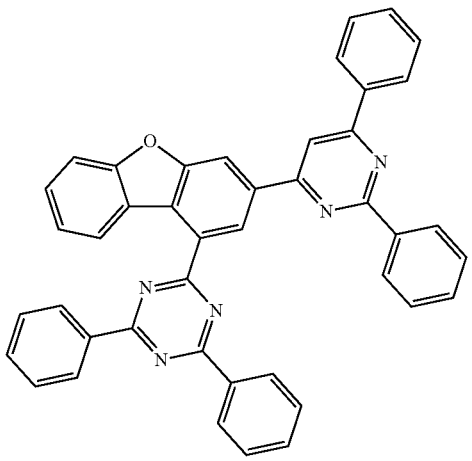
2-122
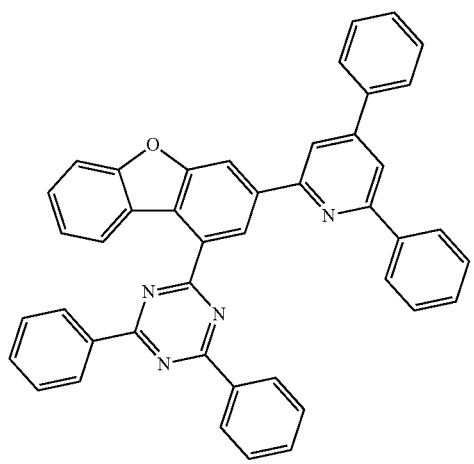
2-123
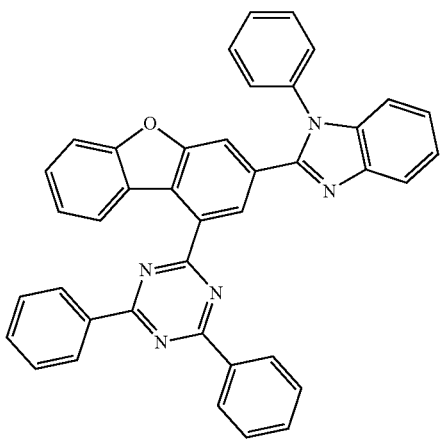
2-124

2-126 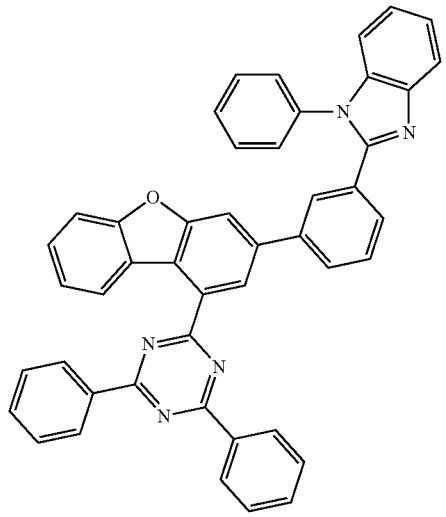
2-127 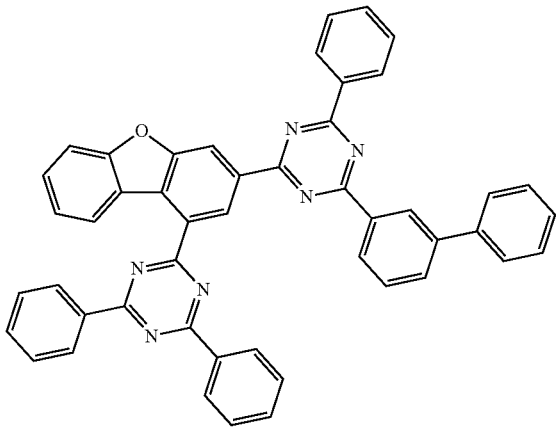
2-128 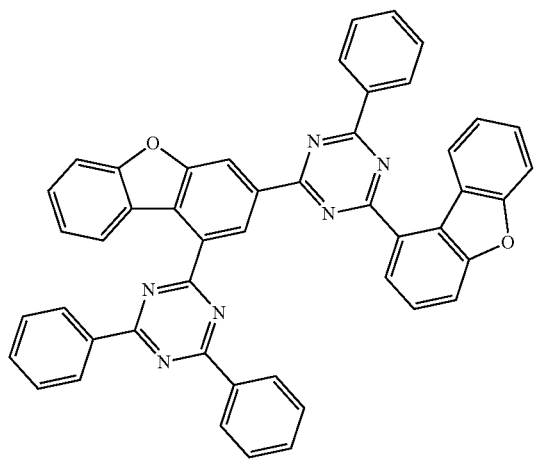
2-129 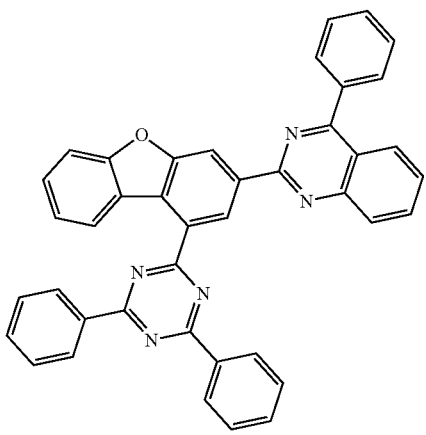
2-130 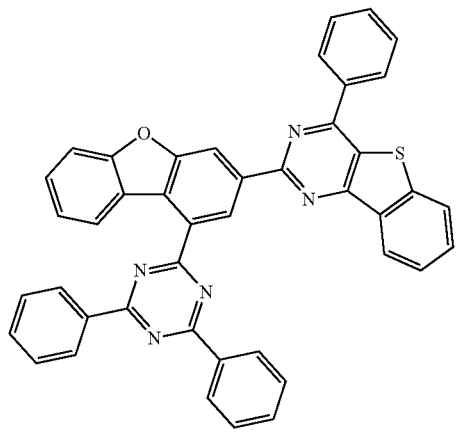
2-131 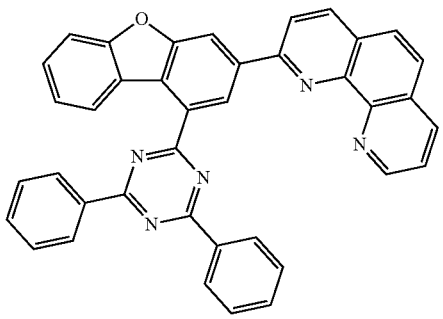

-continued
2-132
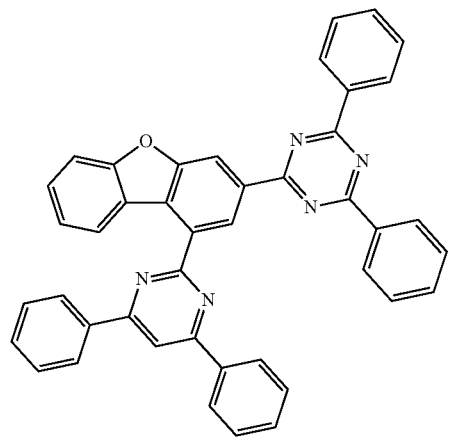
2-133
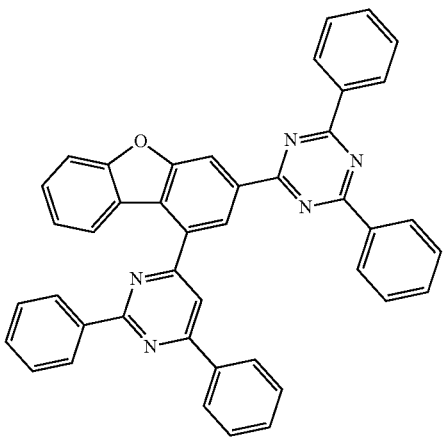
3-1
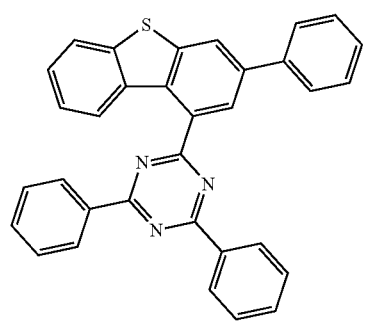
3-2
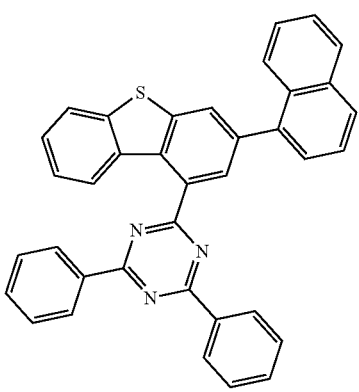
3-3
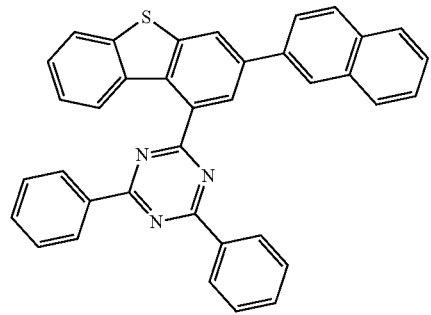
3-4
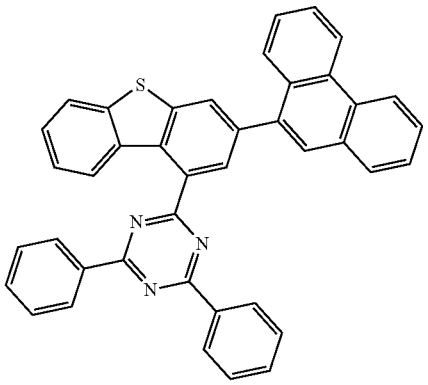
3-5
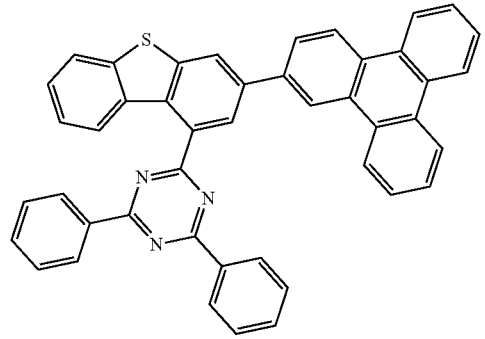 [SMILES: c1ccc(-c2nc(-c3ccccc3)nc(-c3cc(-c4ccc5c6ccccc6c6ccccc6c5c4)cc4sc5ccccc5c34)n2)cc1]
3-6
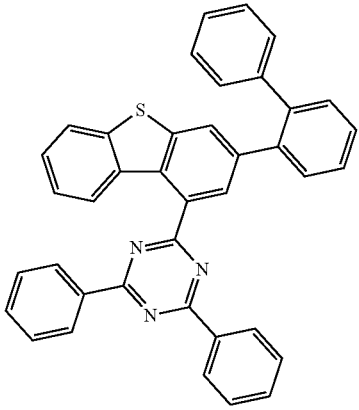

-continued
3-7
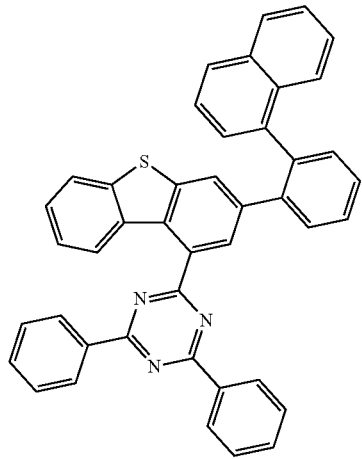
3-8
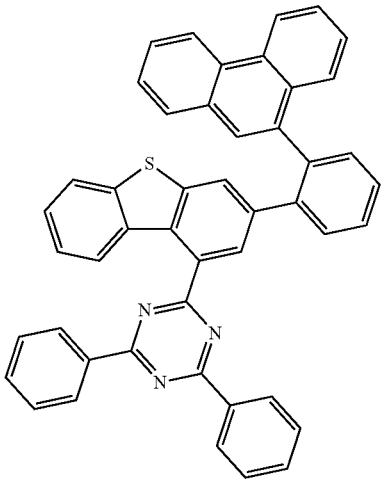
3-9
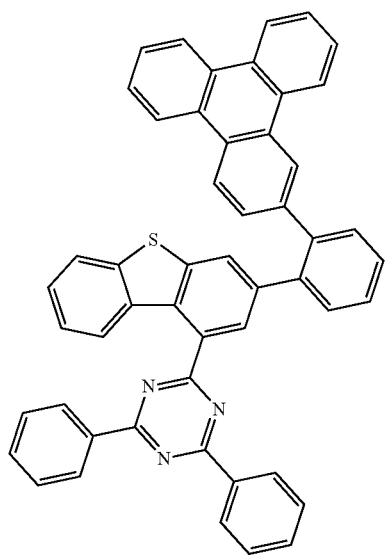
3-10
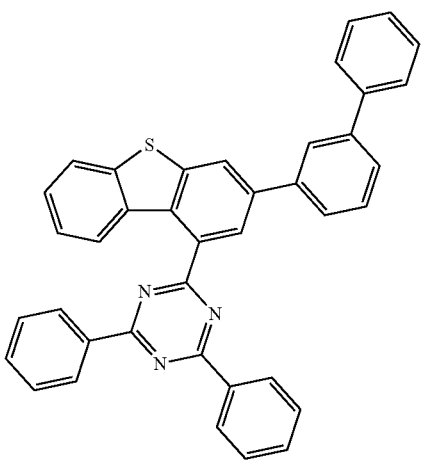
3-11
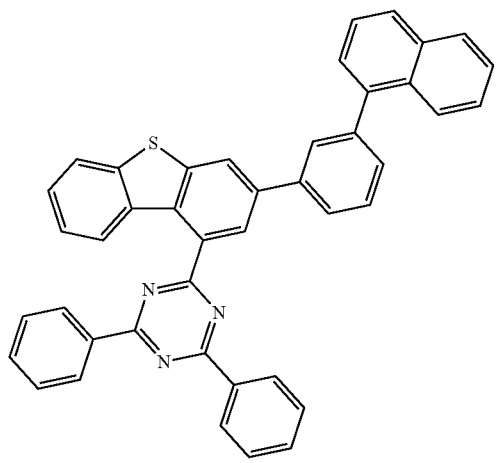
3-12
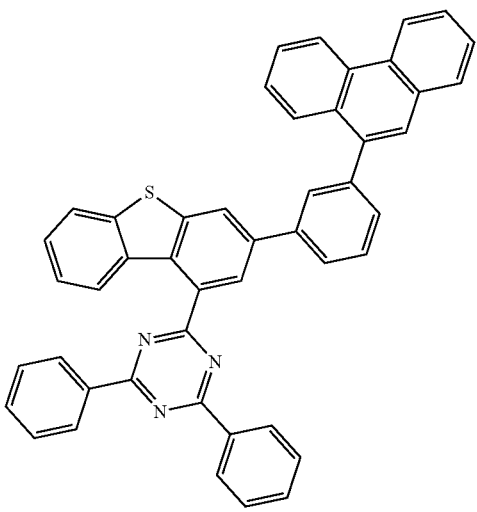

3-13
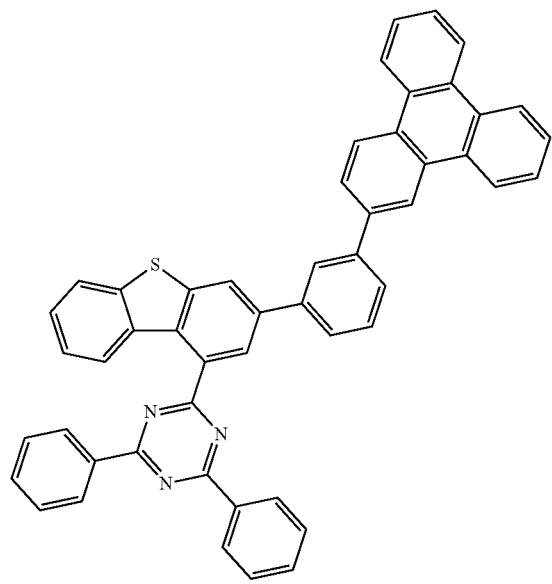
3-14
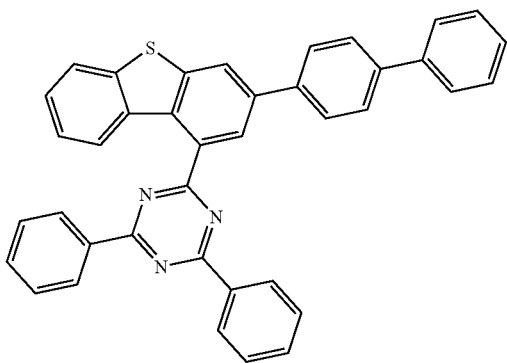
3-15
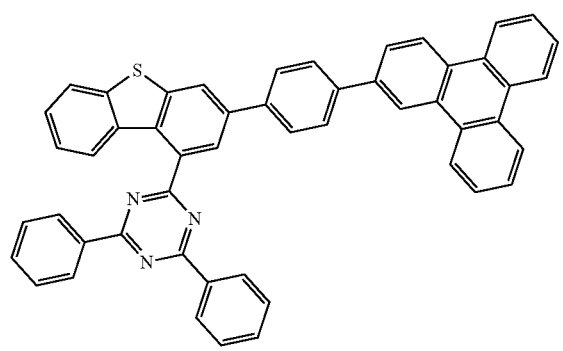
3-16
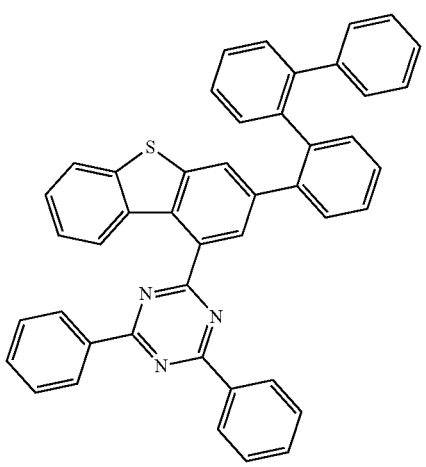

-continued
3-17
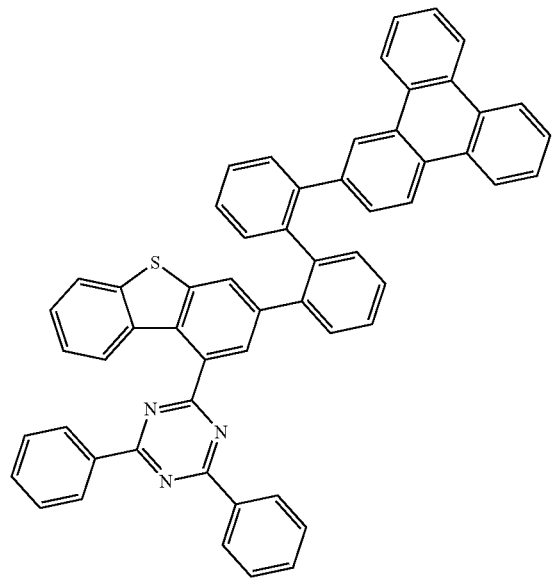
3-18
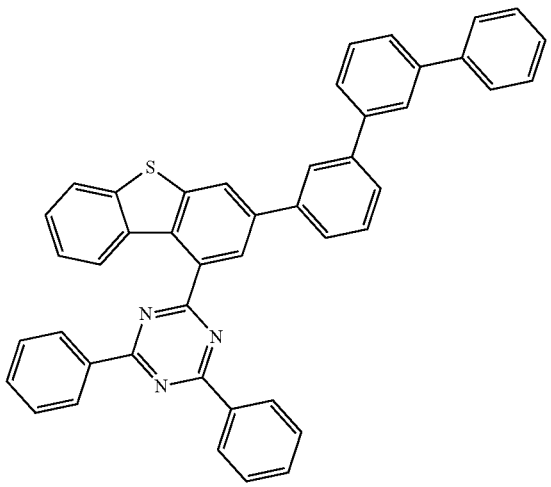
3-19
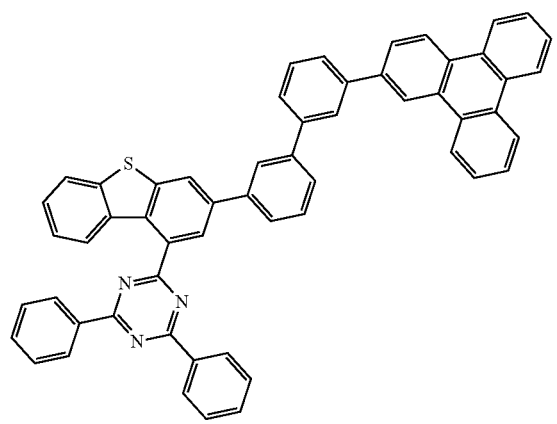
3-20
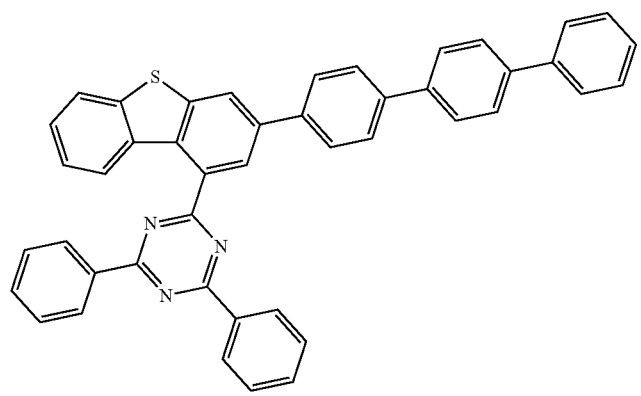

3-21
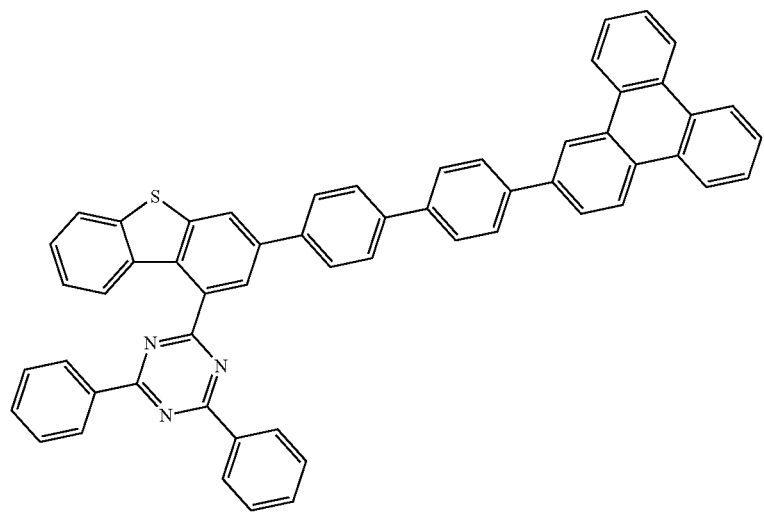
3-22
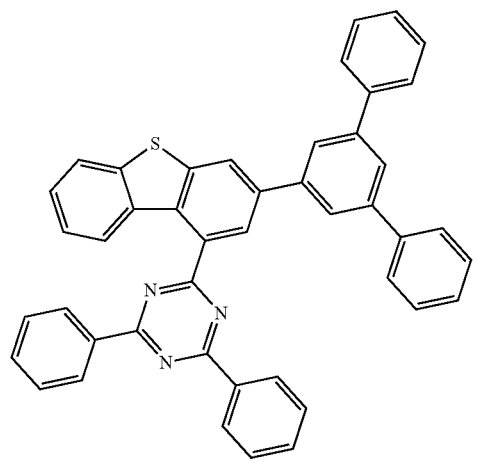
3-23
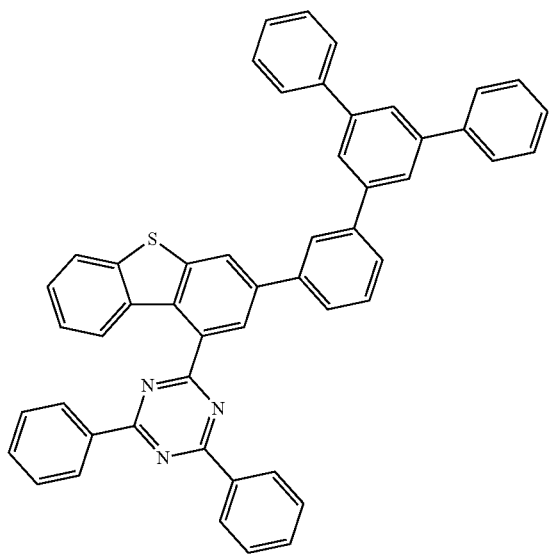
3-24
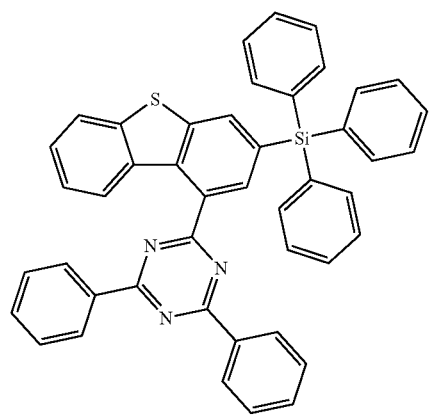
3-25
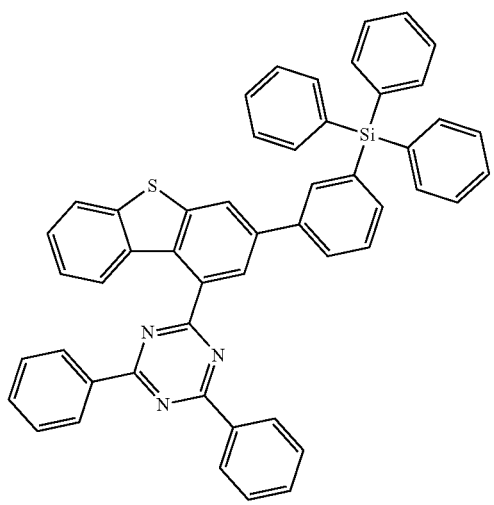

-continued
3-26
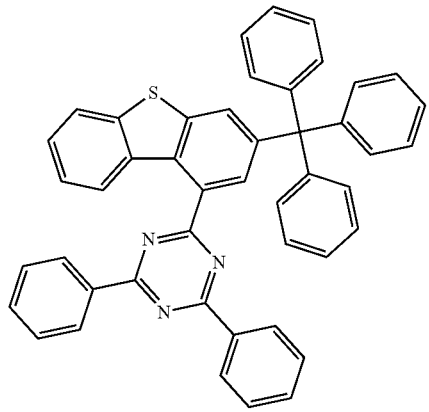
3-27
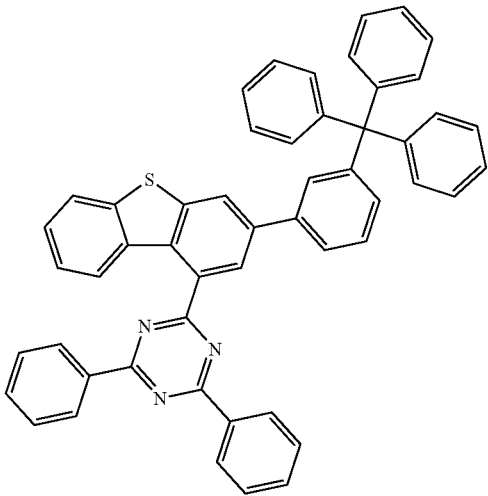
3-28
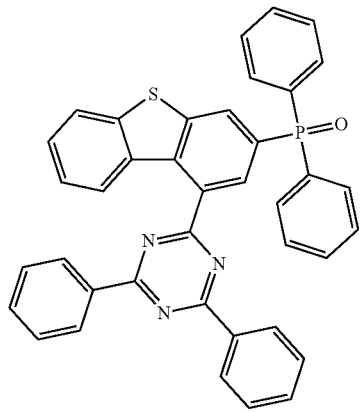
3-29
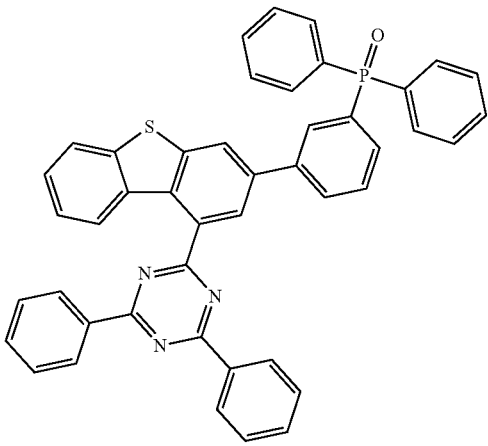
3-35
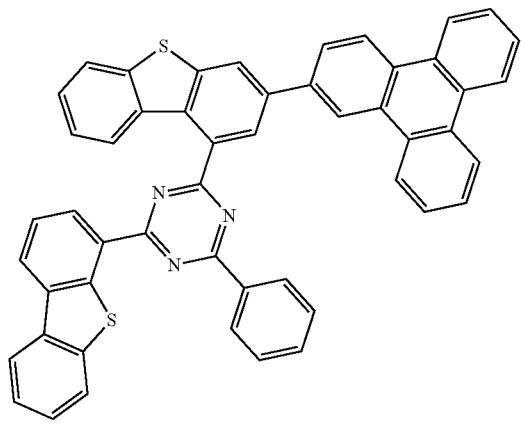
3-36
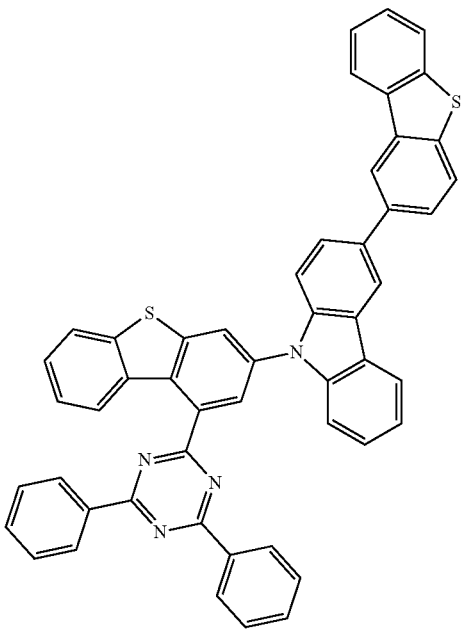

-continued
3-37
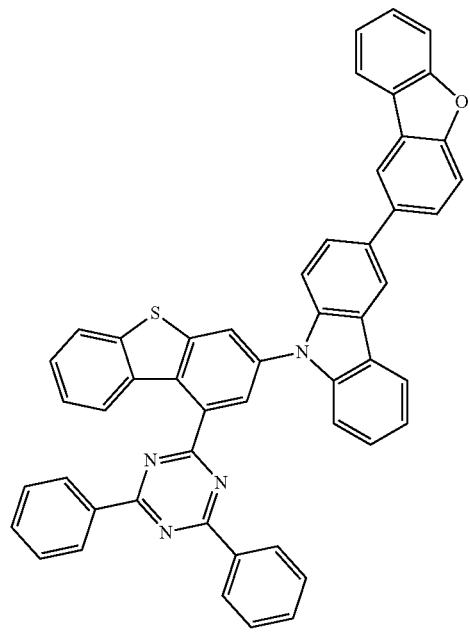
3-39
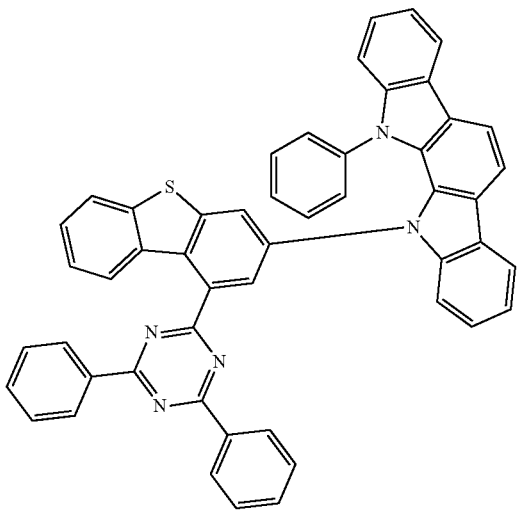
3-40
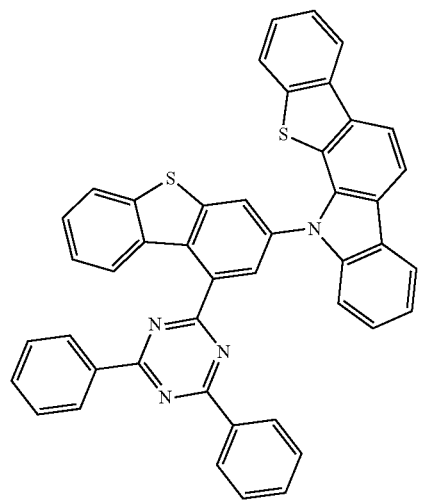

409  410
3-41
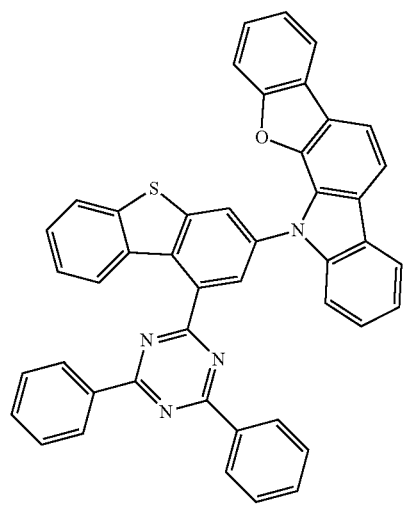
3-42
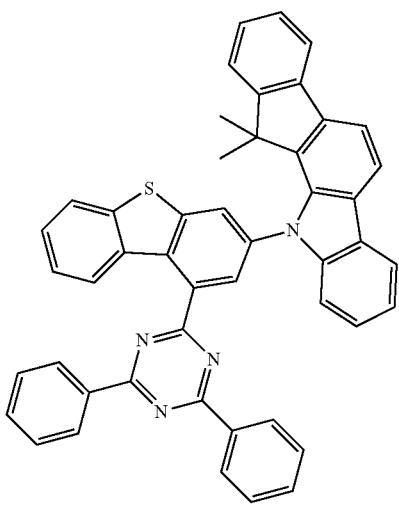
3-43
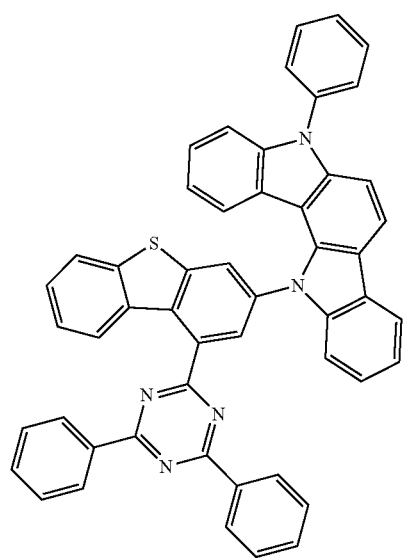
3-44
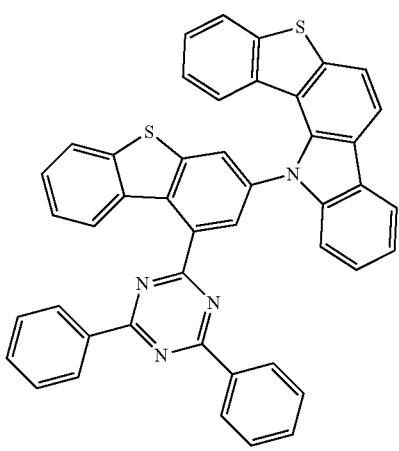
3-45
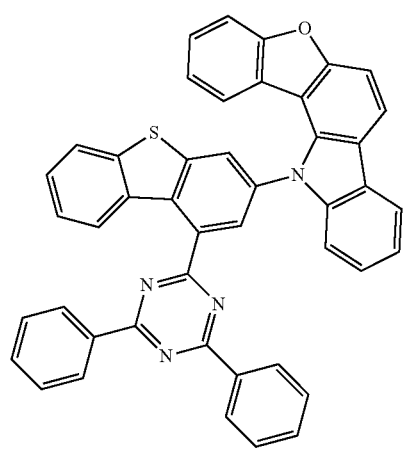
3-46
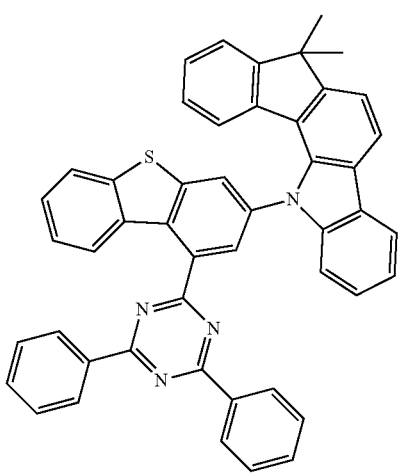

-continued
3-47
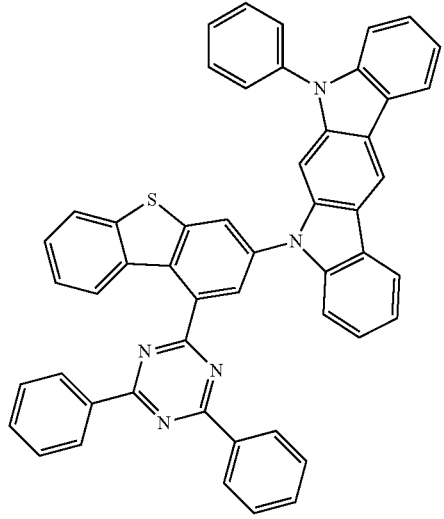
3-48
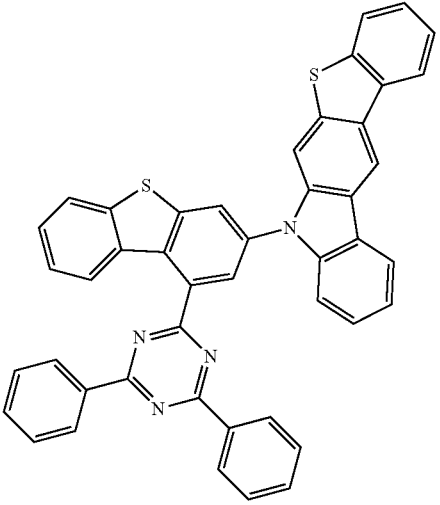
3-49
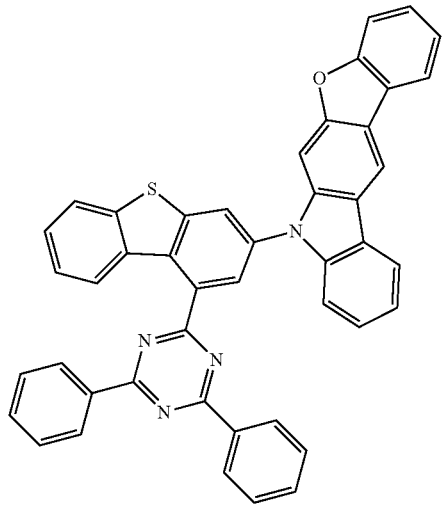
3-50
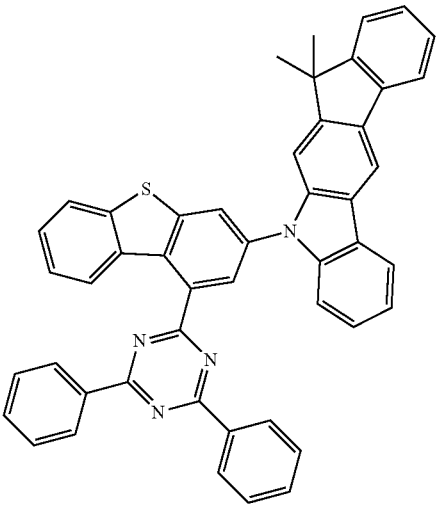
3-51
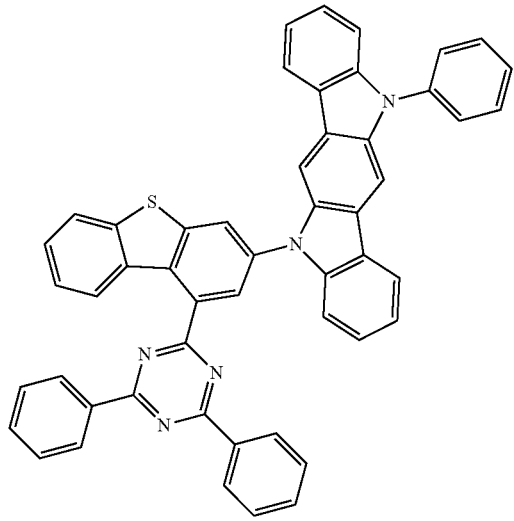
3-52
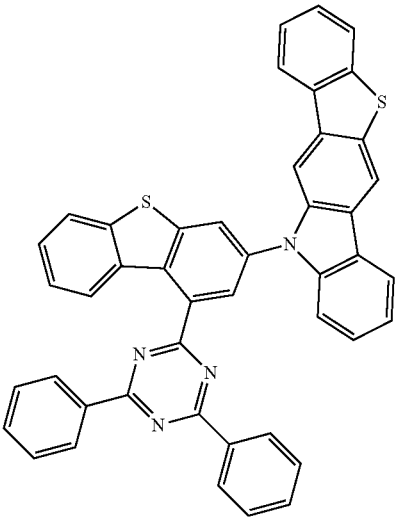

3-53
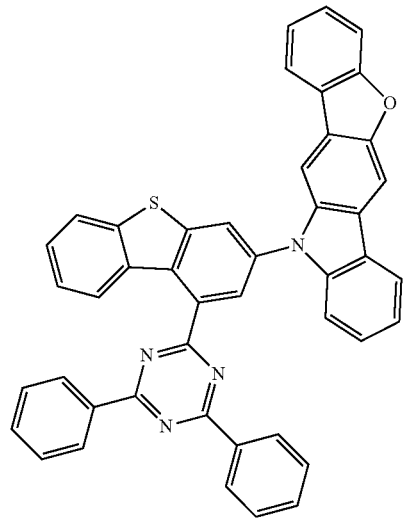
3-54
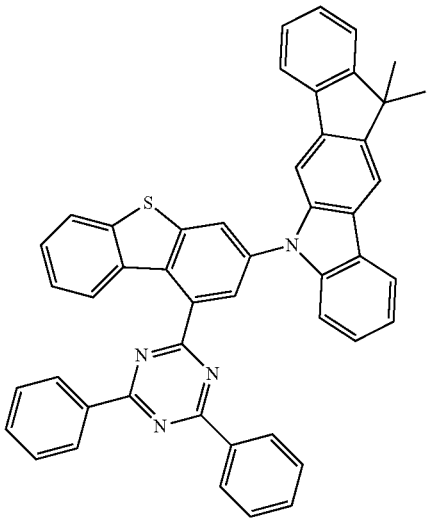
3-55
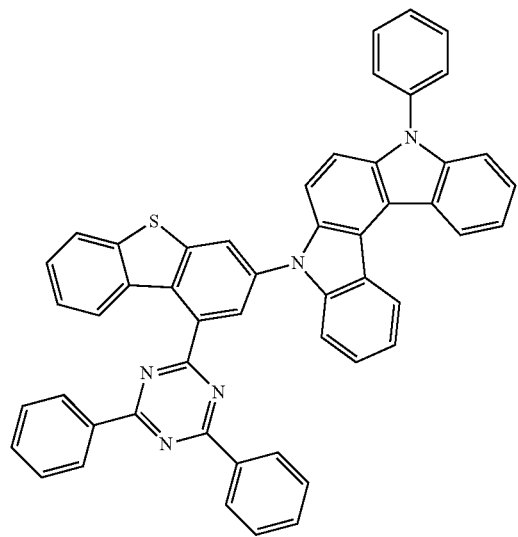
3-56
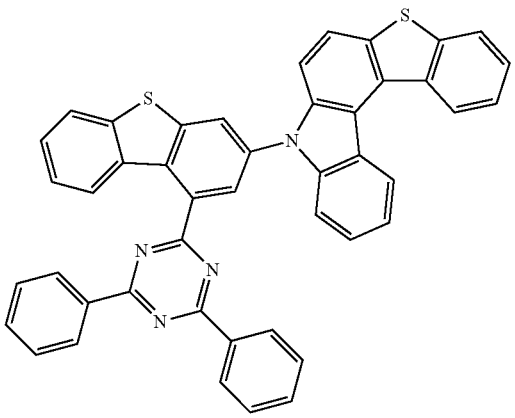
3-57
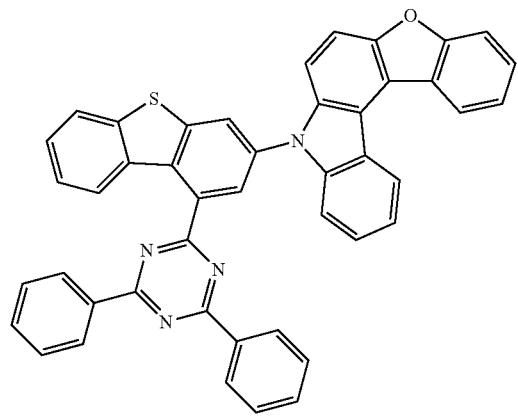
3-58
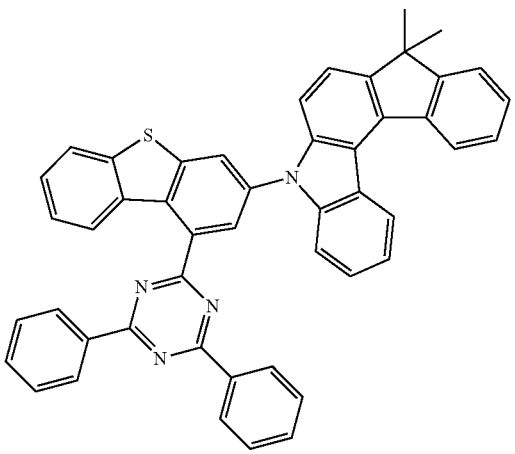

-continued
3-59
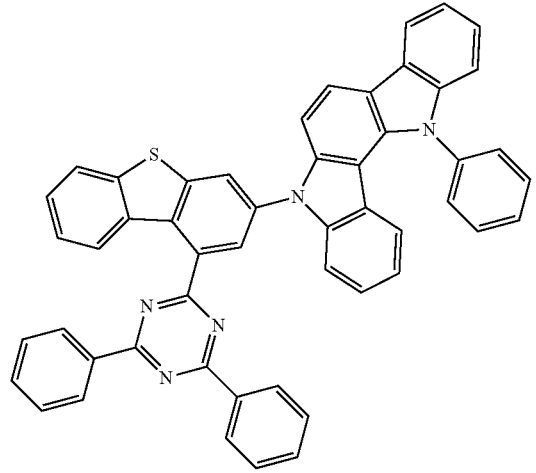
3-60
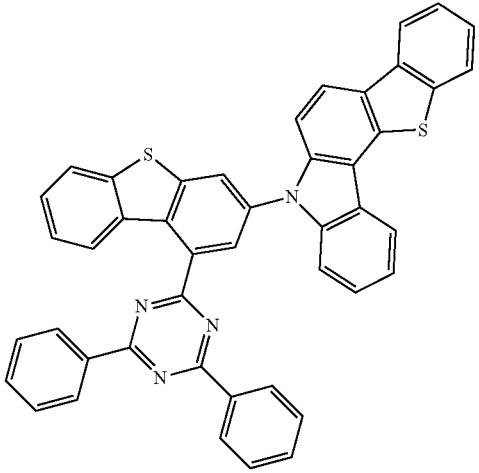
3-61
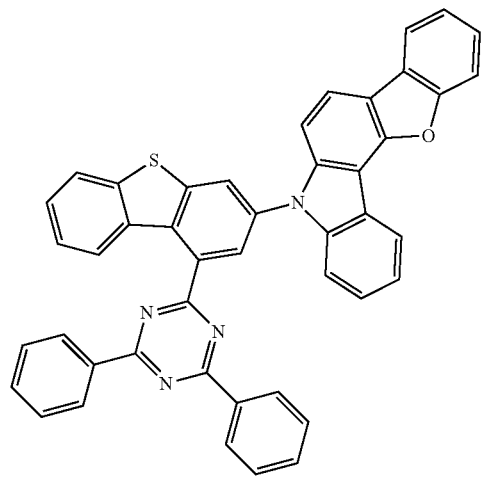
3-62
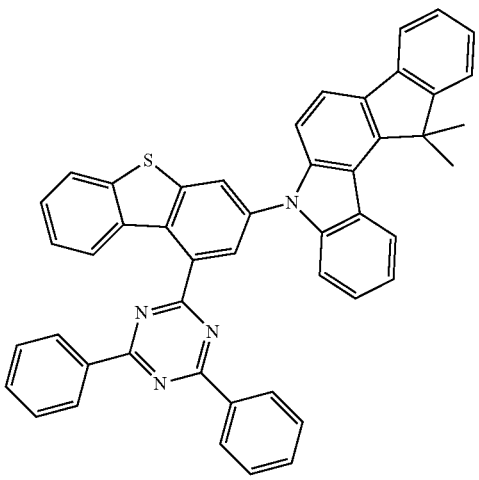
3-63
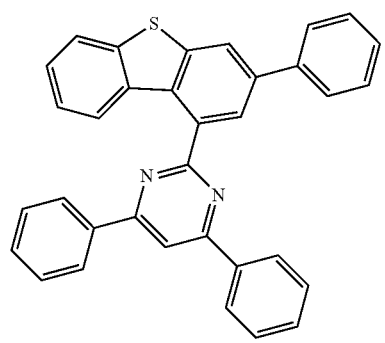
3-64
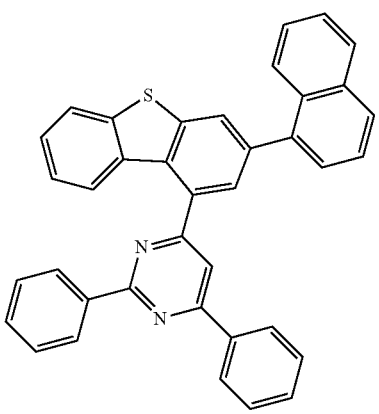

-continued
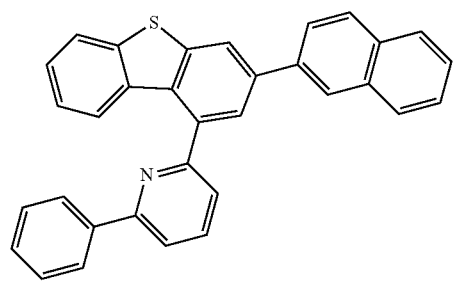
3-65
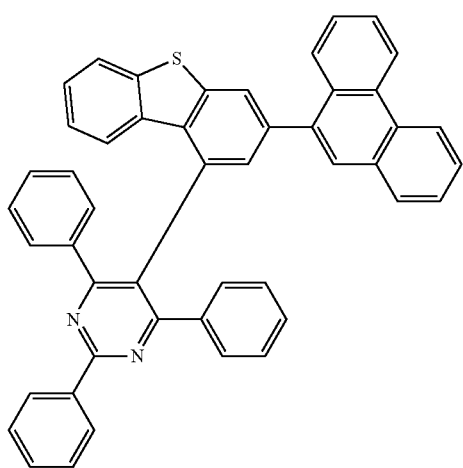
3-66
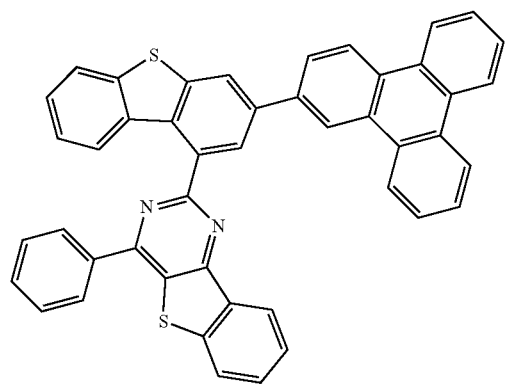
3-67
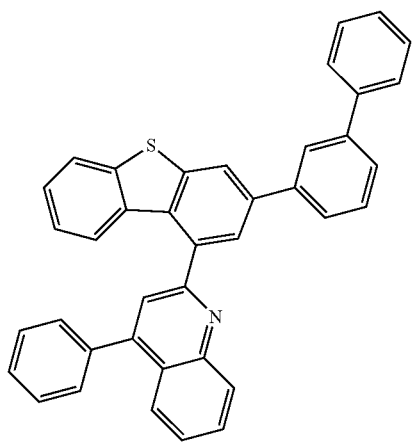
3-68
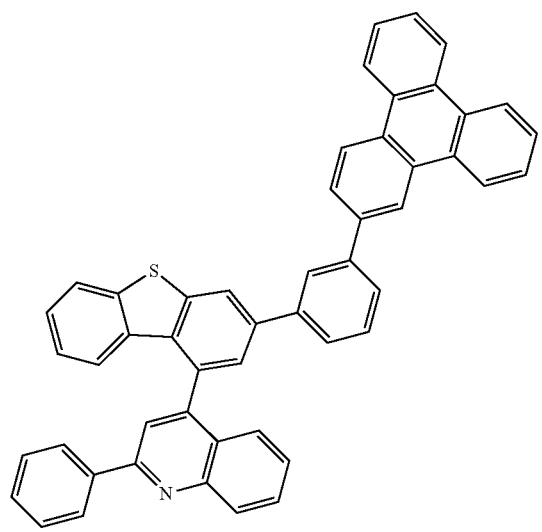
3-69
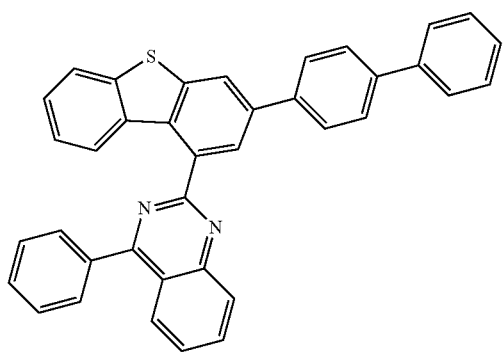
3-70

-continued
3-71
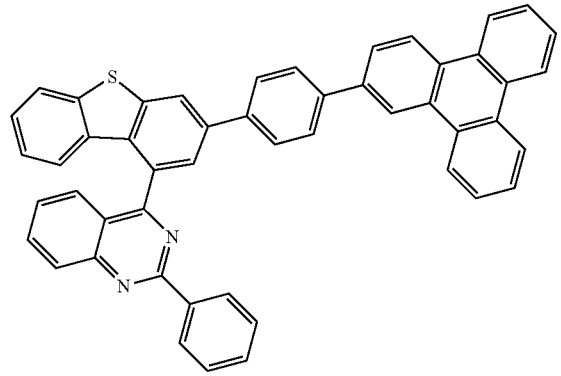
3-72
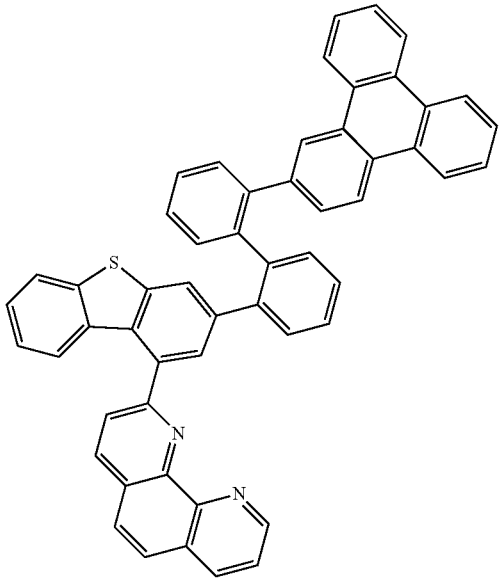
3-73
3-74
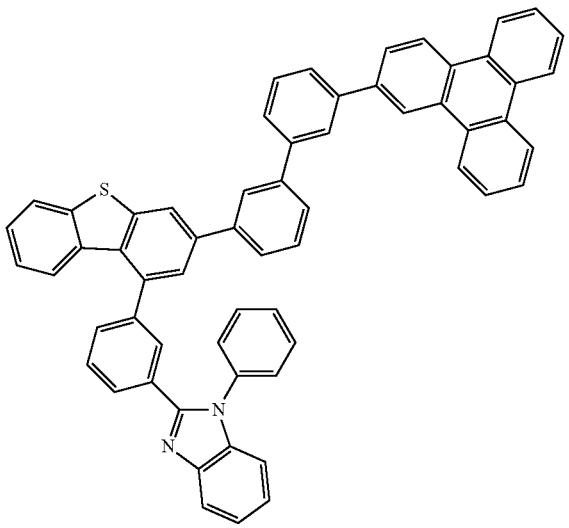
3-75
3-76

3-77
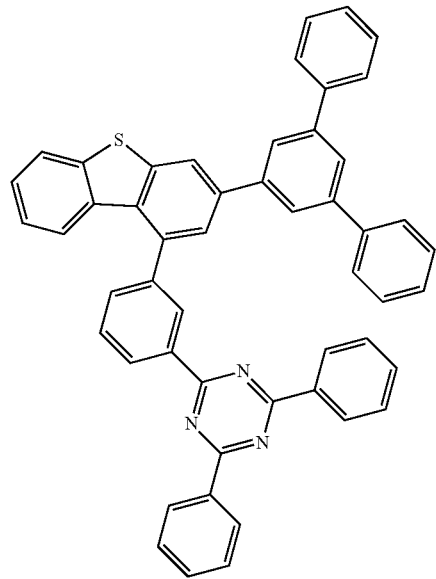
3-78
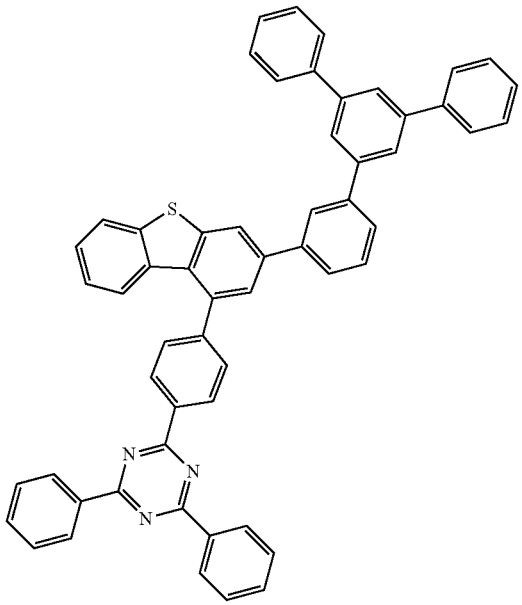
3-79
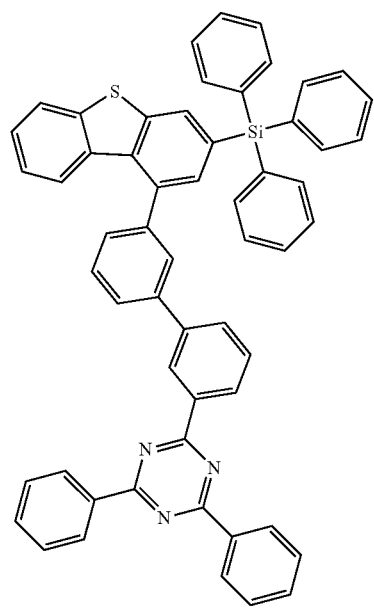
3-80
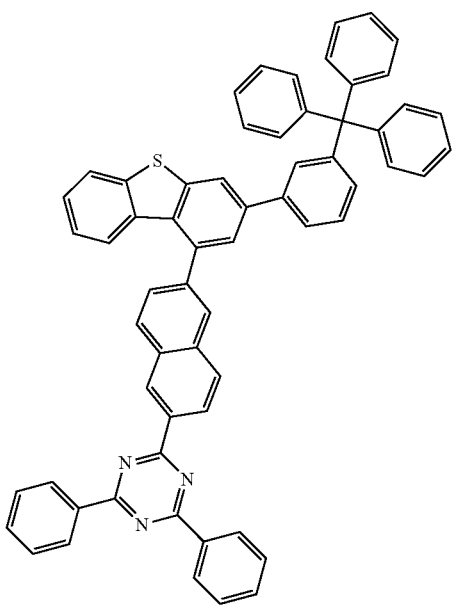

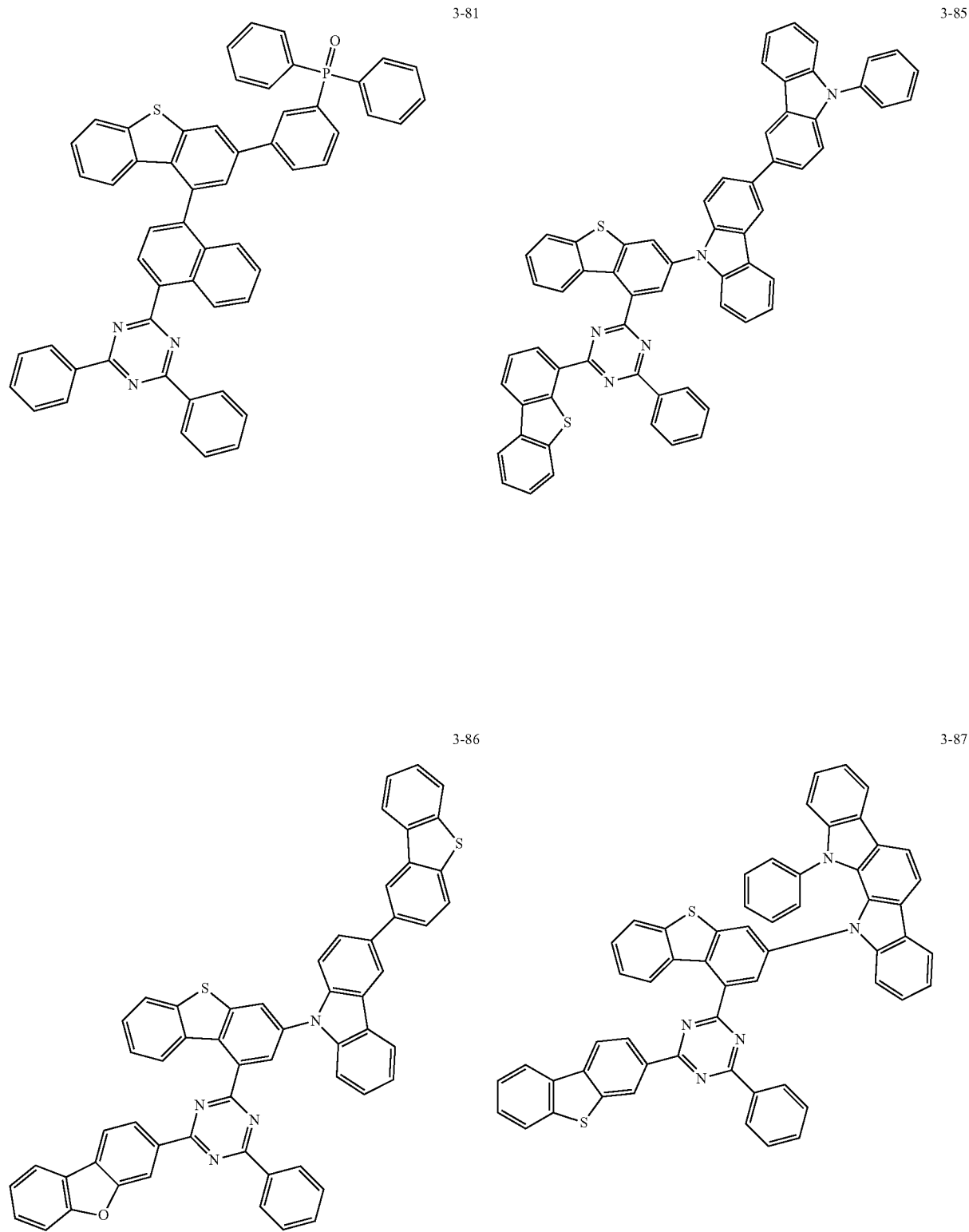

-continued
3-88
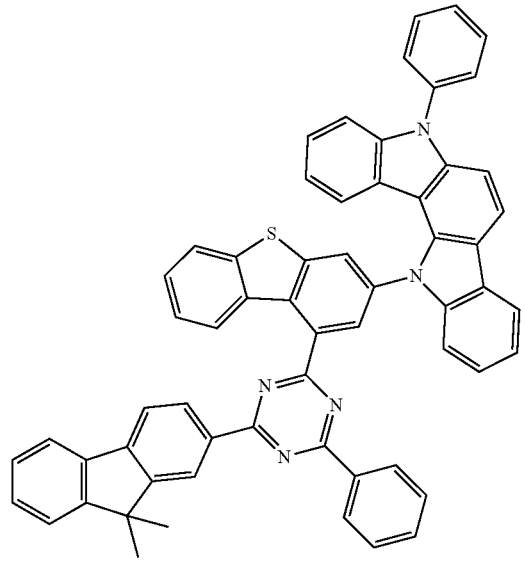
3-89
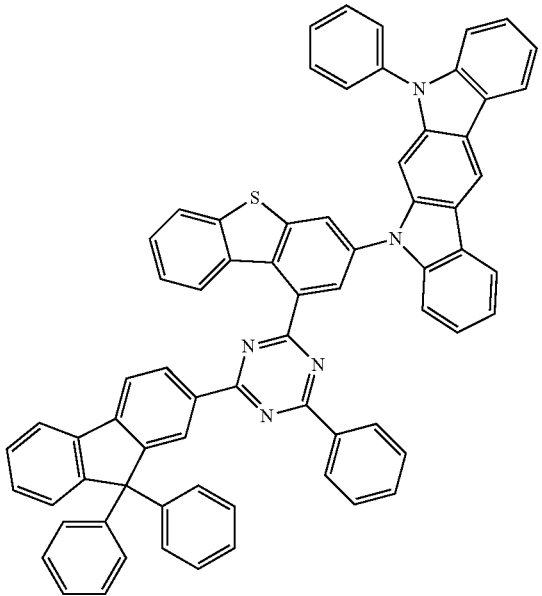
3-90
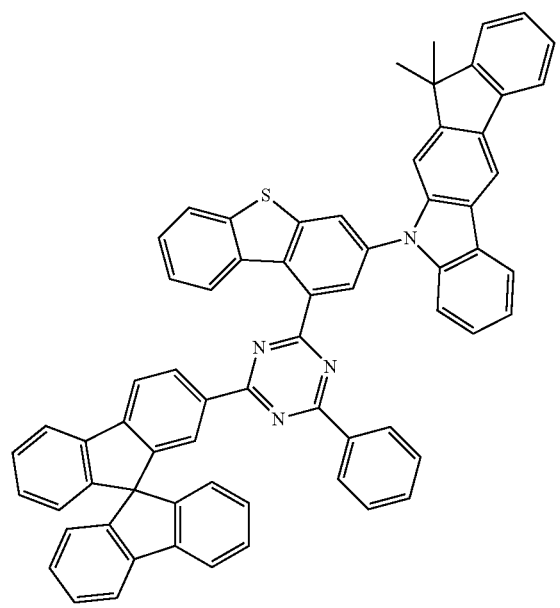
3-91
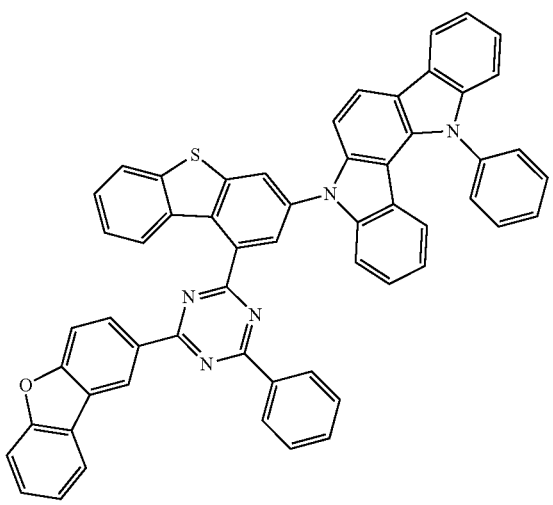

3-92
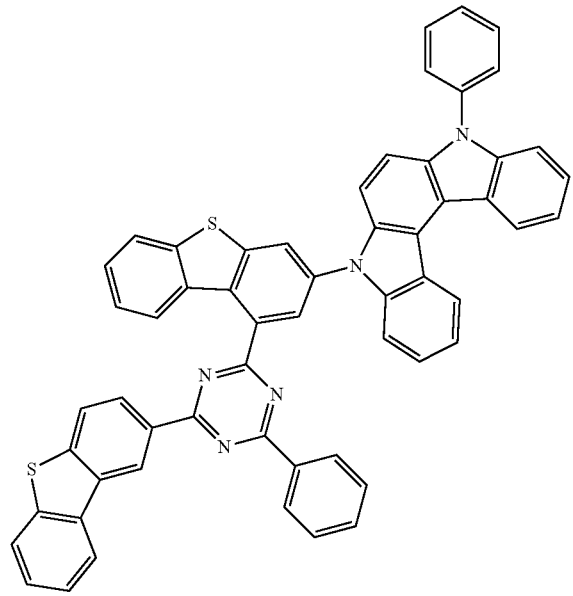
3-93
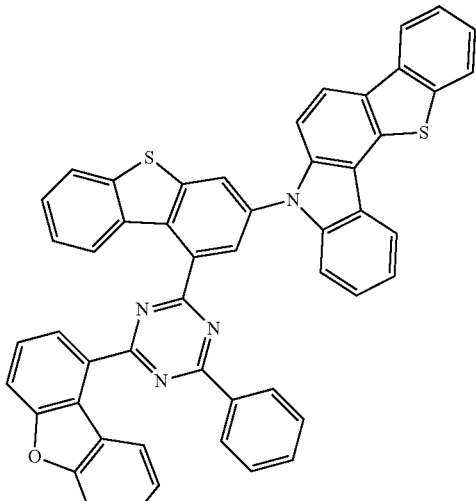
3-94
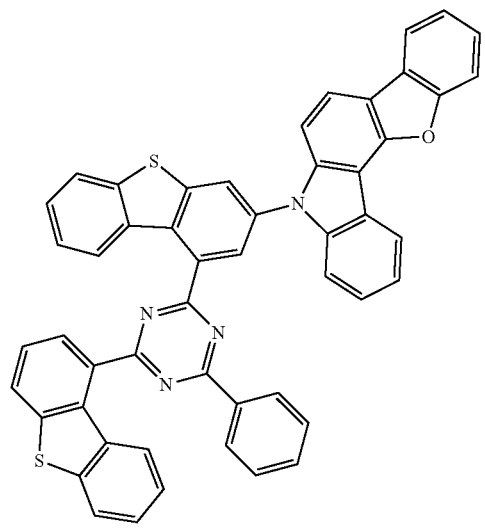
3-95
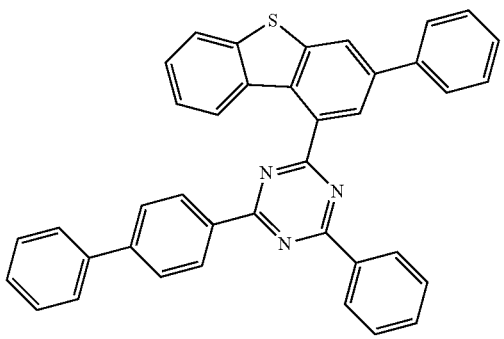
3-96
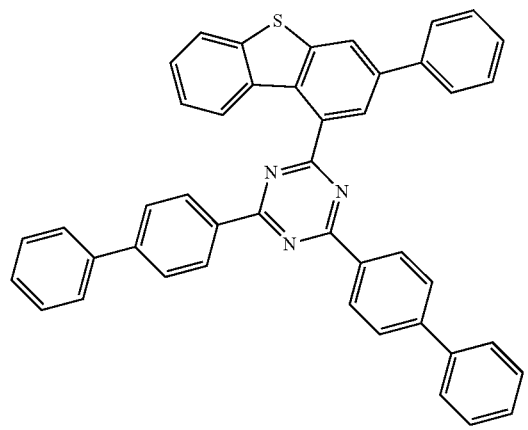
3-97
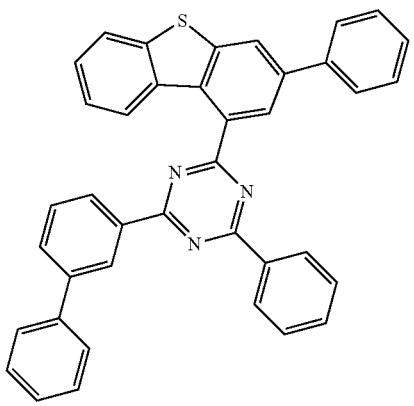

-continued
3-98
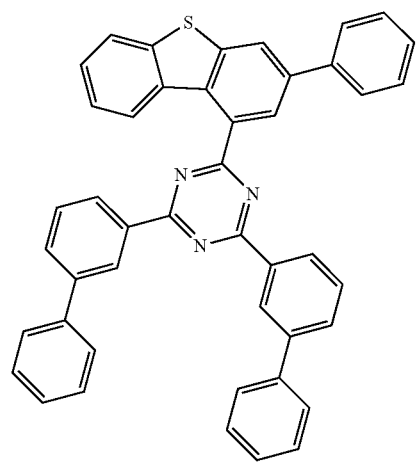
3-99
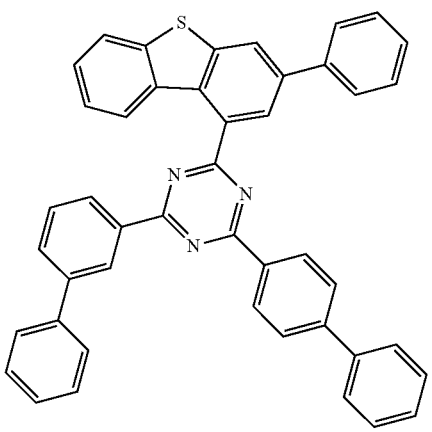
3-100
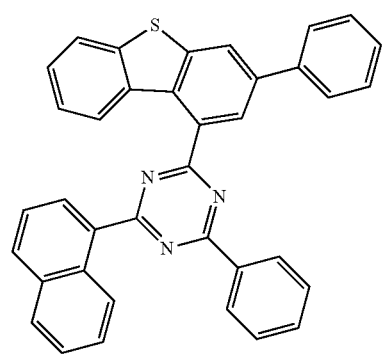
3-101
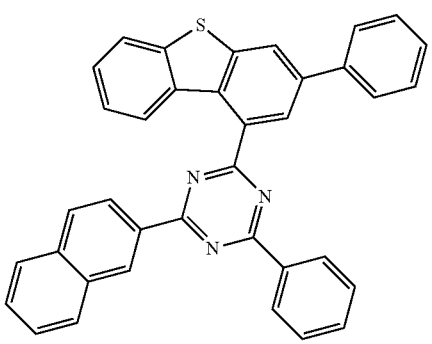
3-102
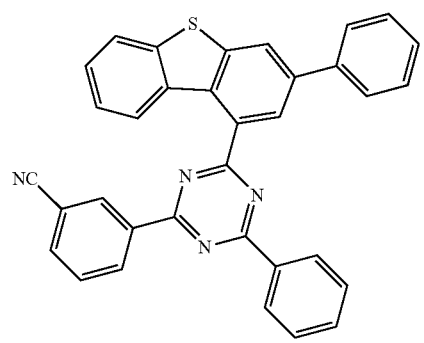
3-103
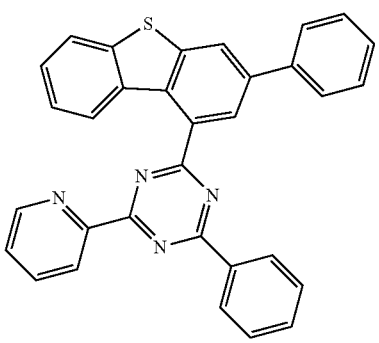
3-104
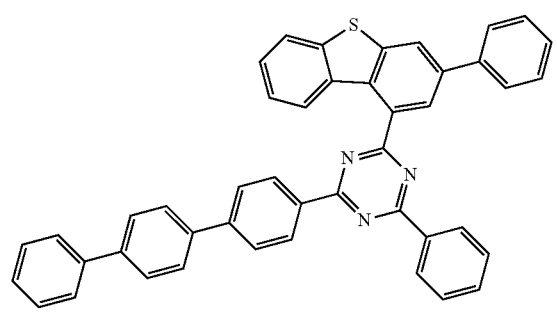
3-105
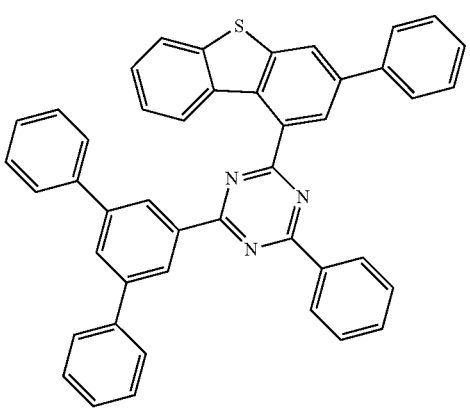

-continued
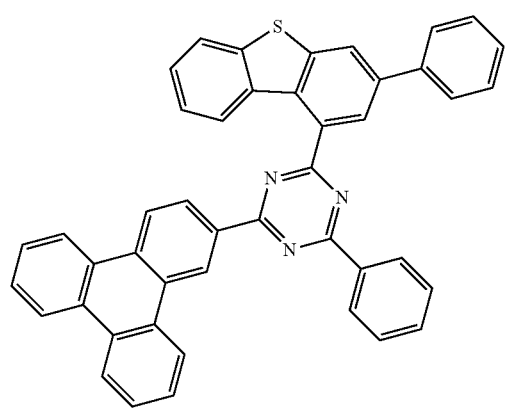
3-106
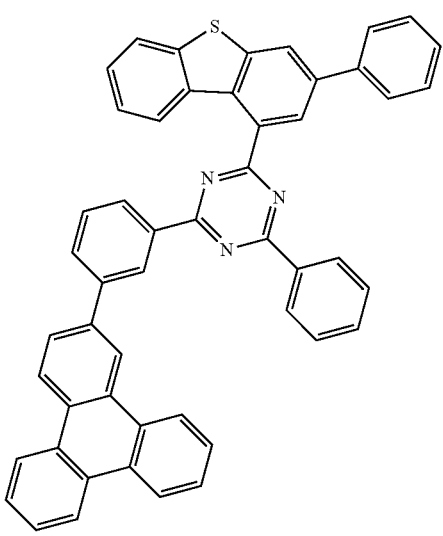
3-107
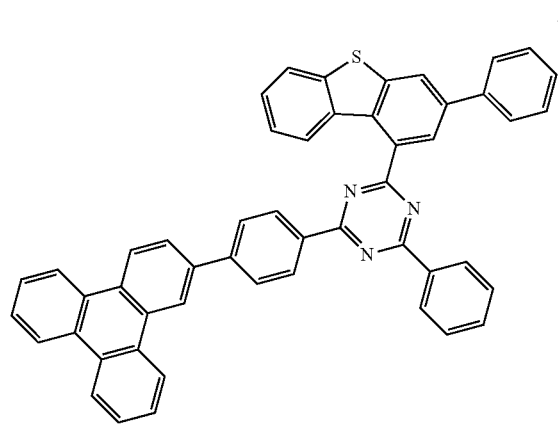
3-108
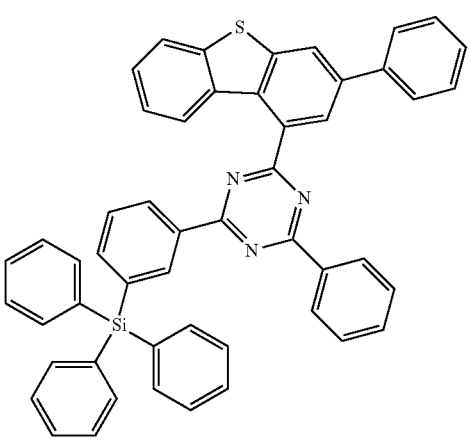
3-109
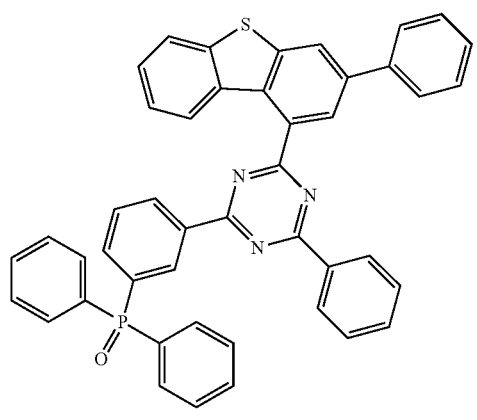
3-110
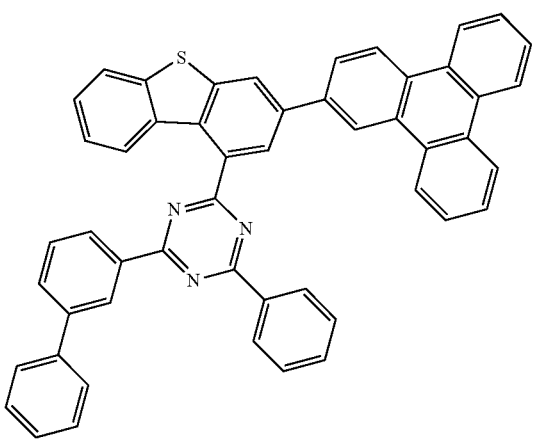
3-111

3-112
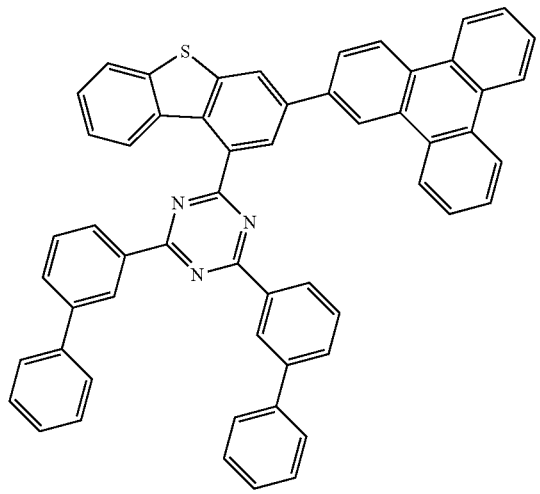
3-113
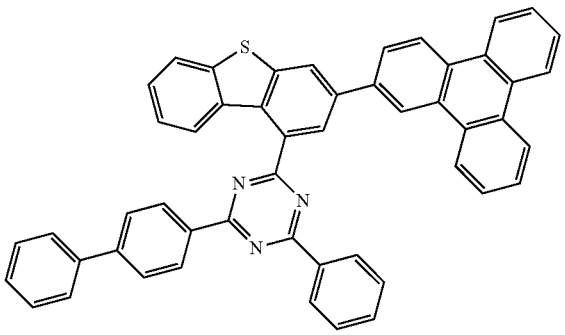
3-114
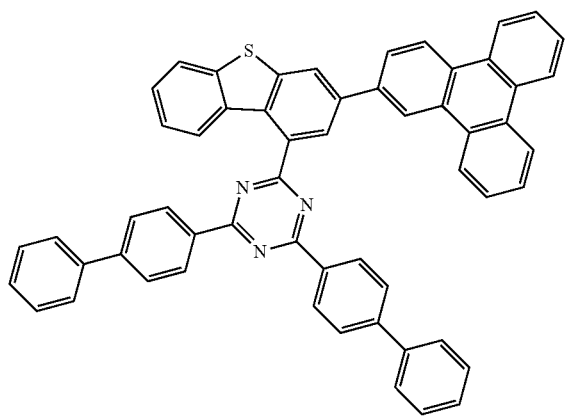
3-115
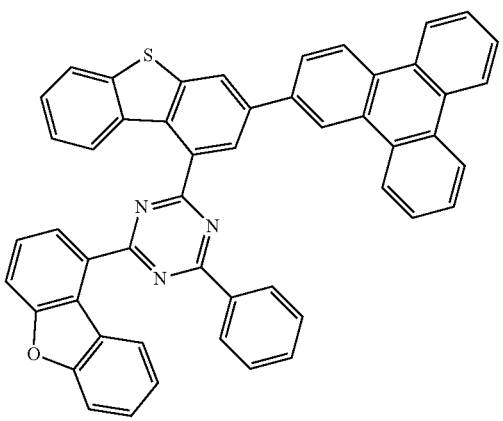
3-116
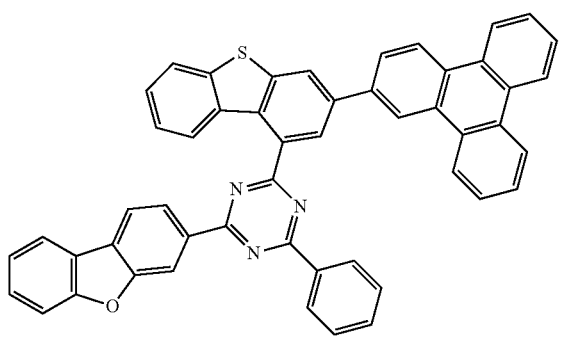
3-117
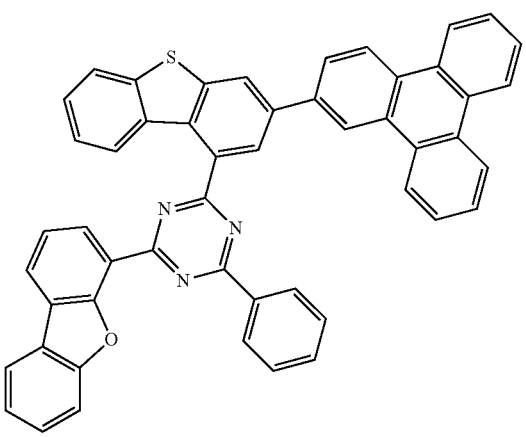

3-118
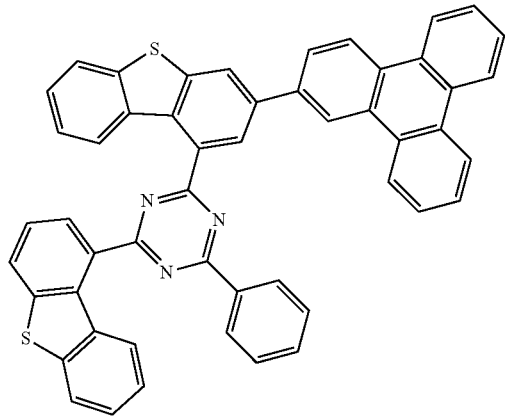
3-119
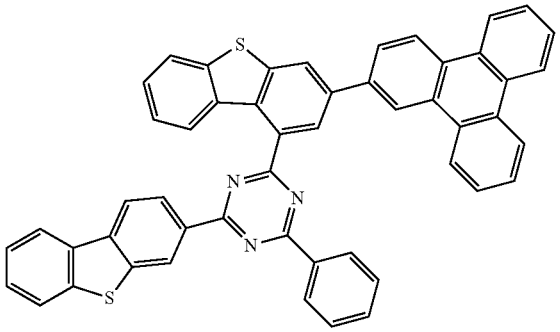
4-1
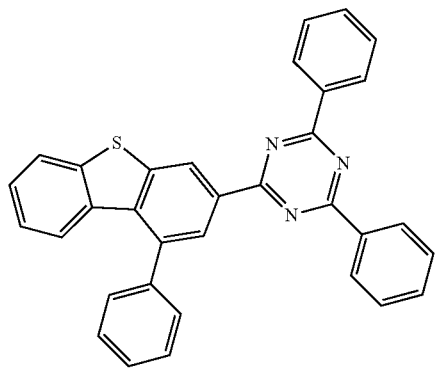
4-2
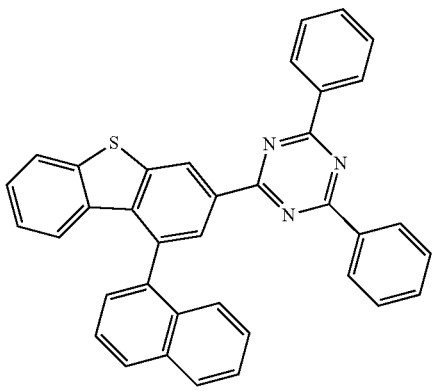
4-3
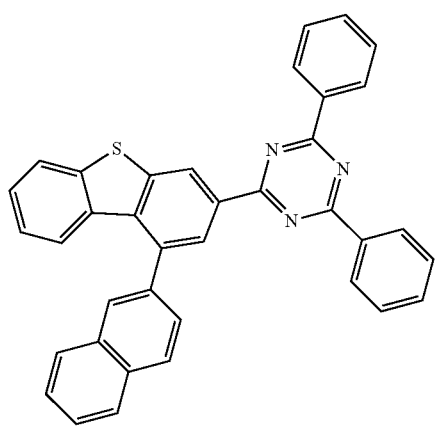
4-4
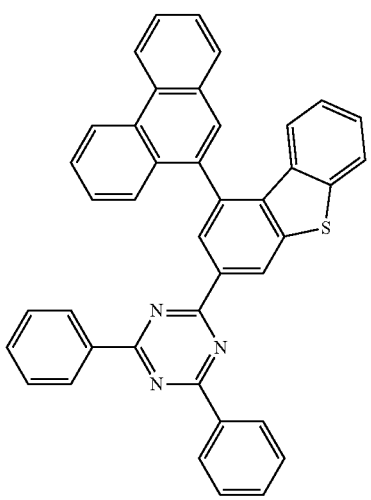

4-5
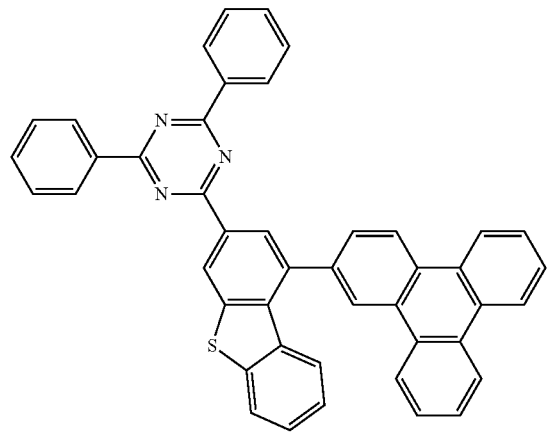
4-6
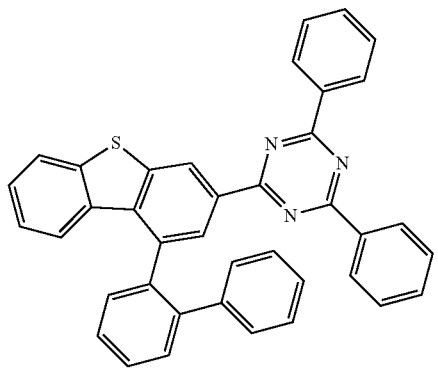
4-7
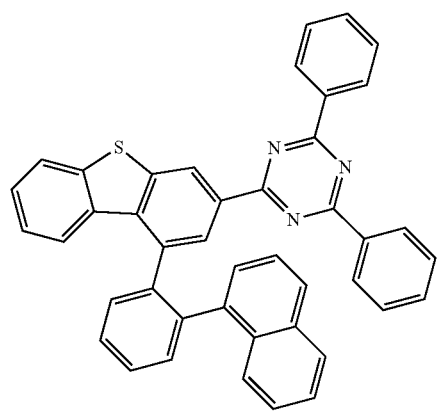
4-8
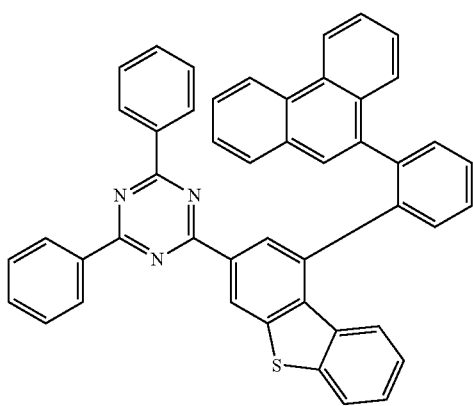
4-9
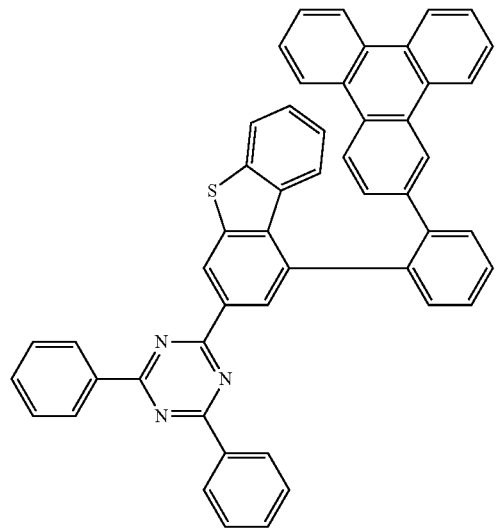
4-10
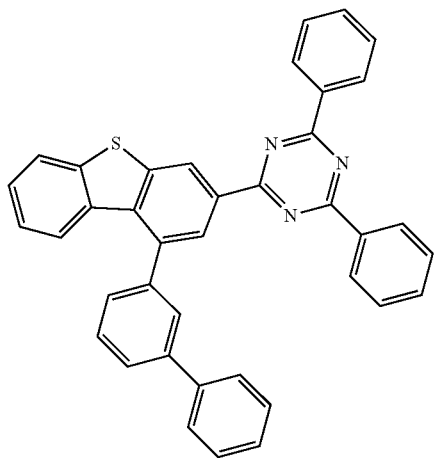

-continued
4-11
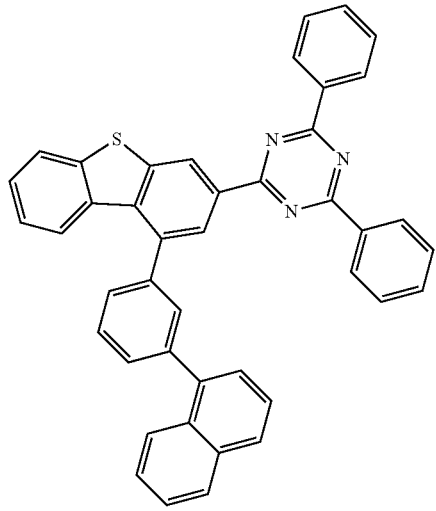
4-12
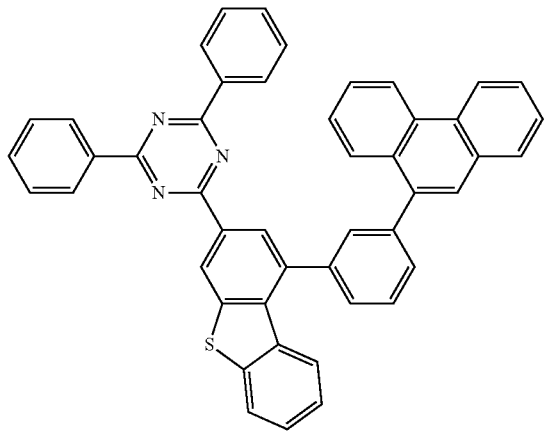
4-13
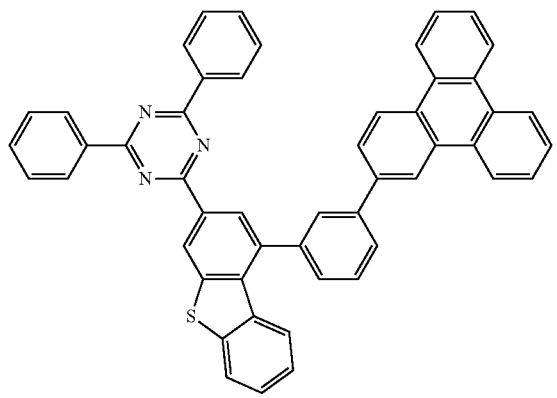
4-14
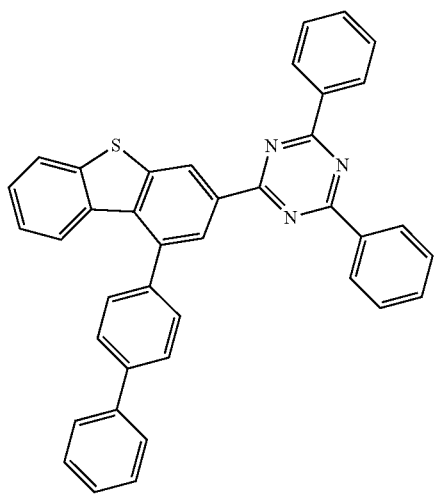
4-15
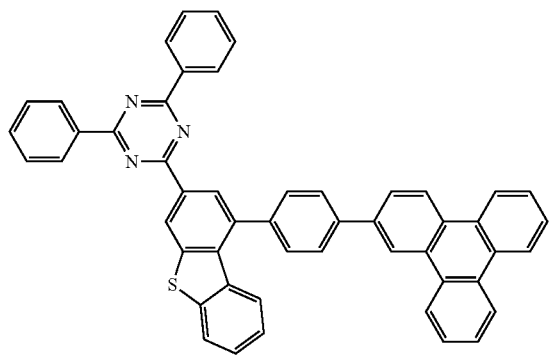
4-16
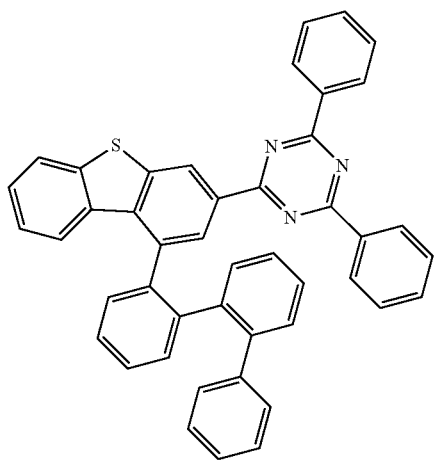

-continued
4-17
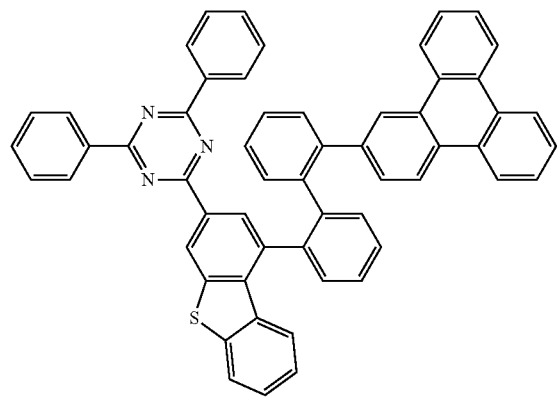
4-18
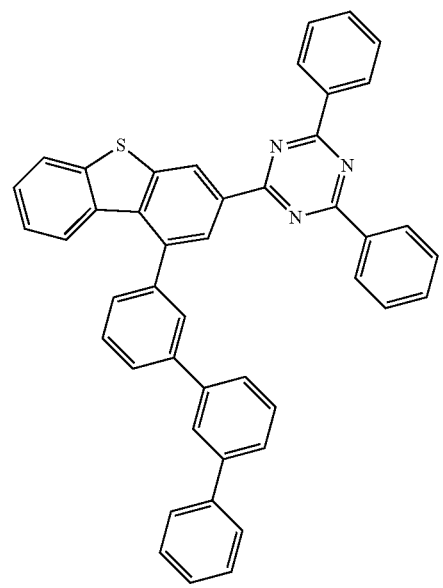
4-19
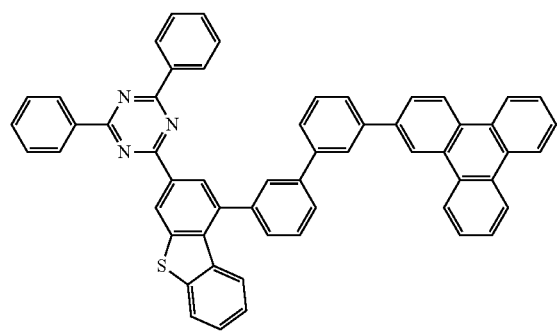
4-20
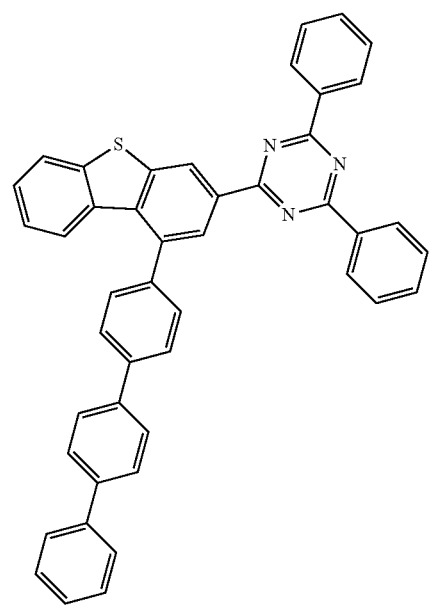
4-21
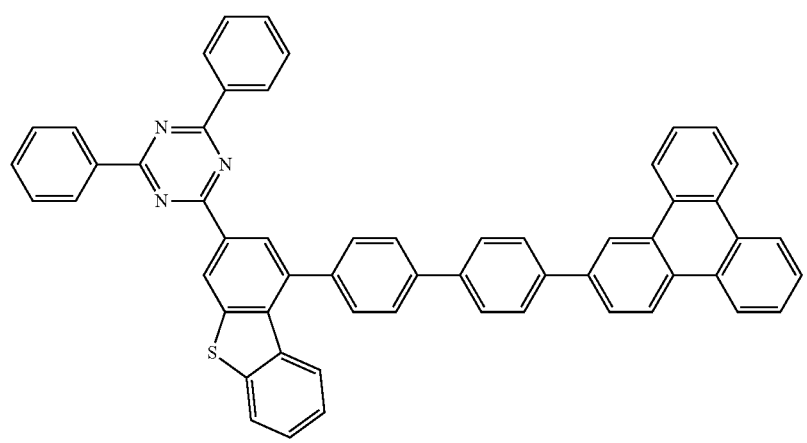

-continued
4-22
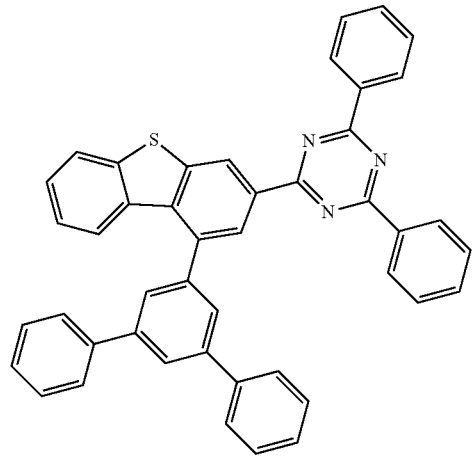
4-23
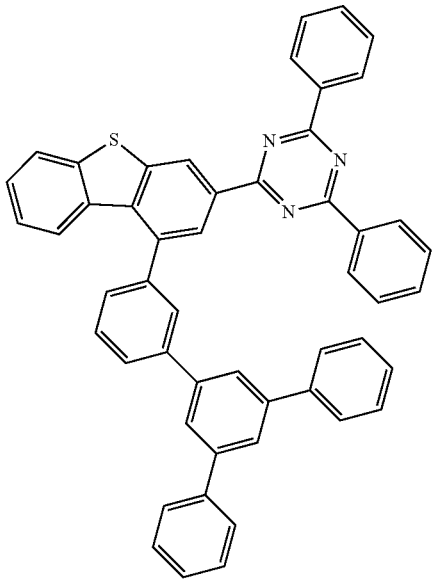
4-24
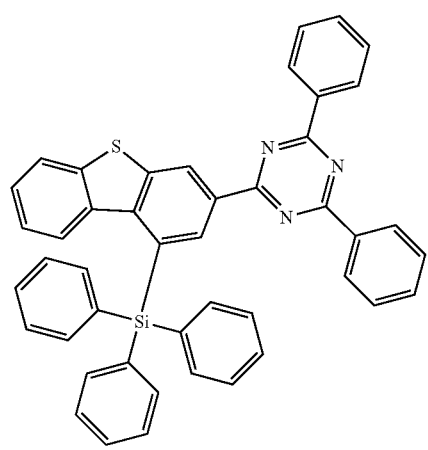
4-25
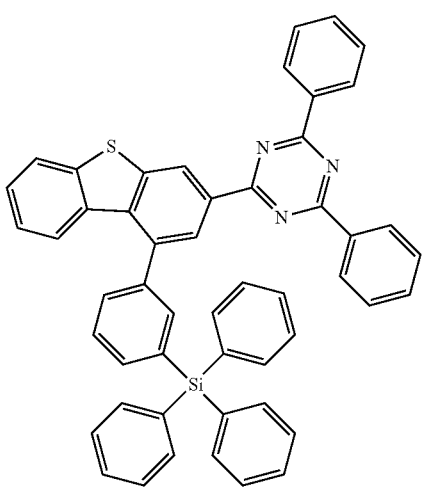
4-26
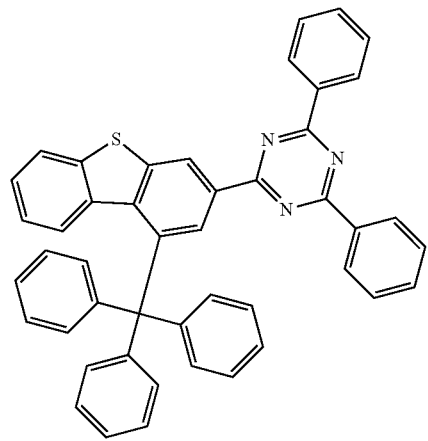
4-27
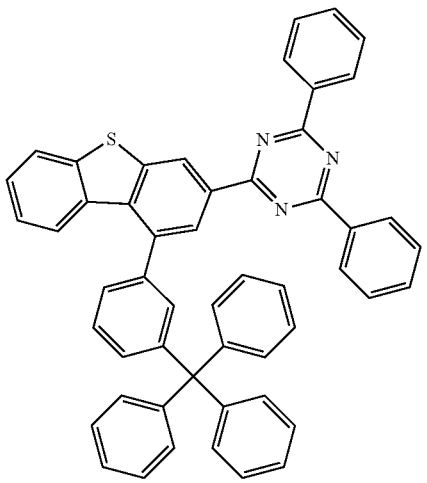

-continued
4-28
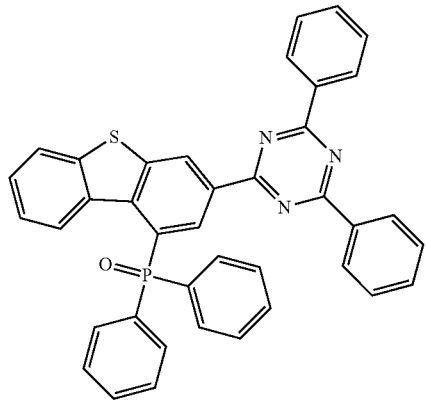
4-29
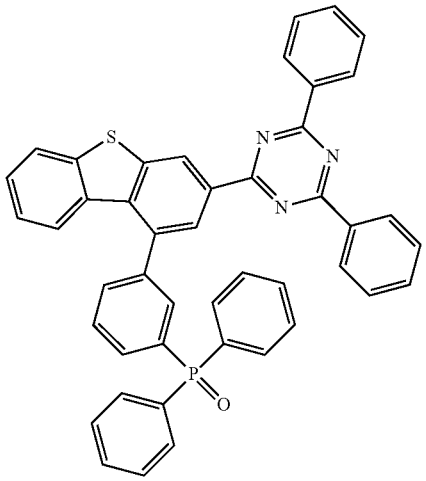
4-35
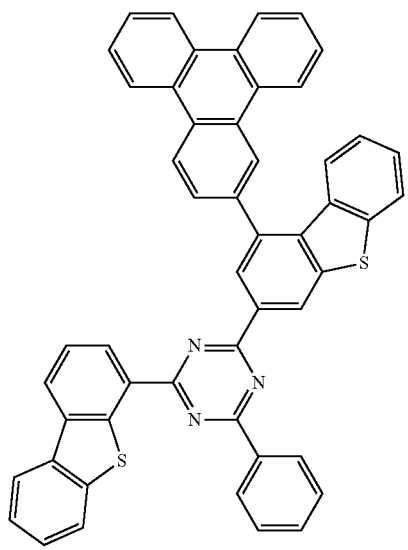
4-36
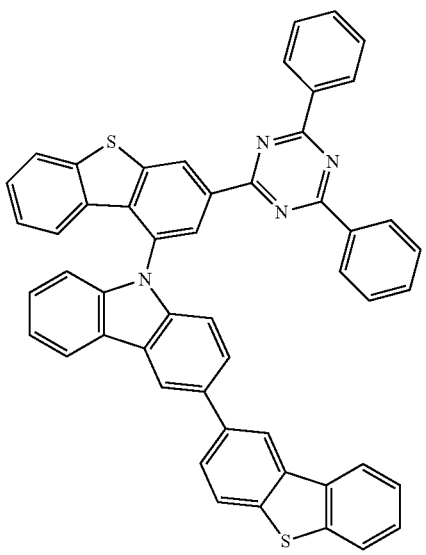
4-37
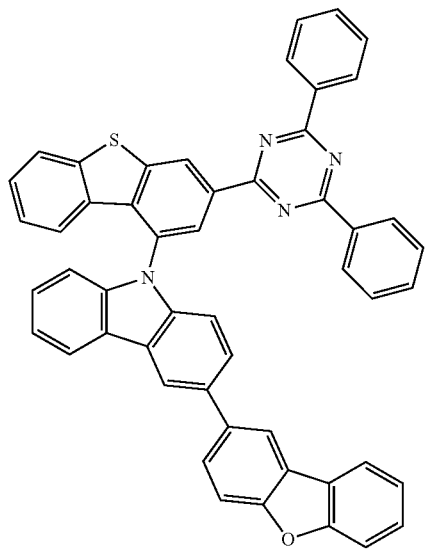
4-39
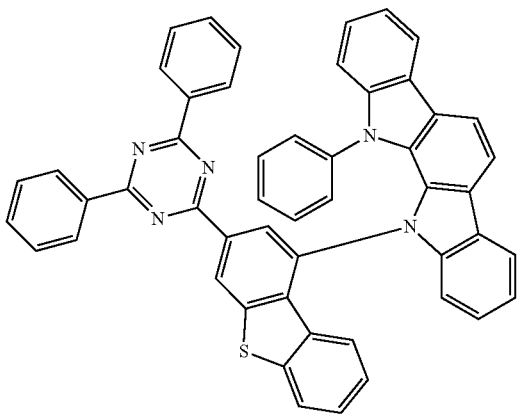

-continued
4-40
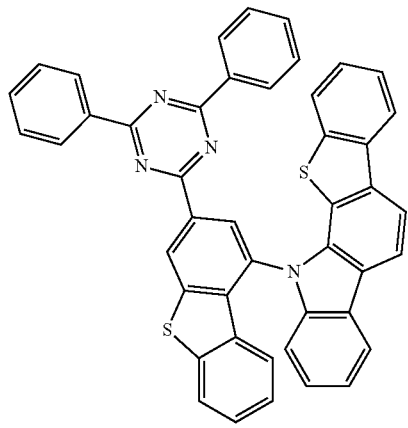
4-41
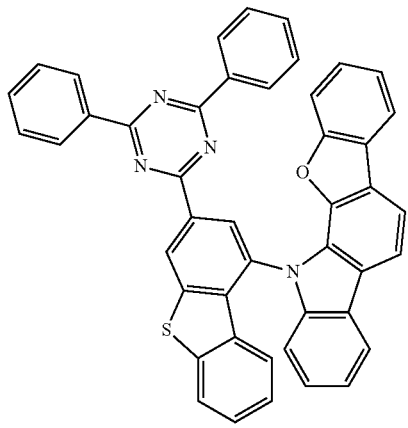
4-42
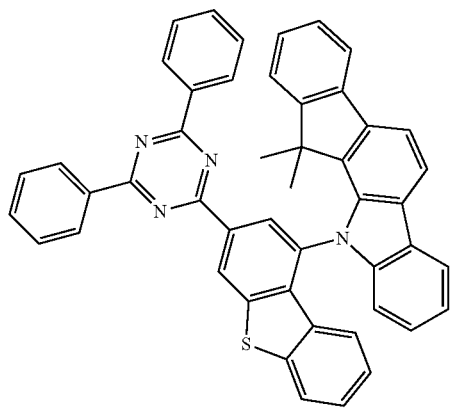
4-43
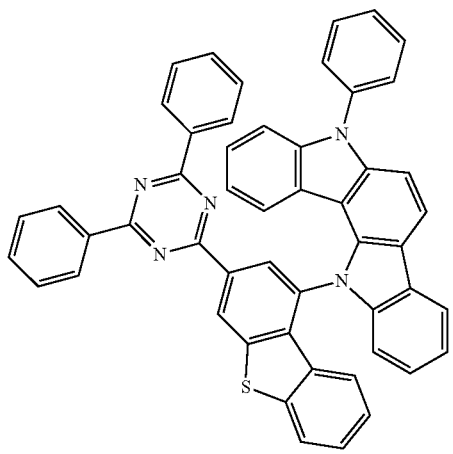
4-44
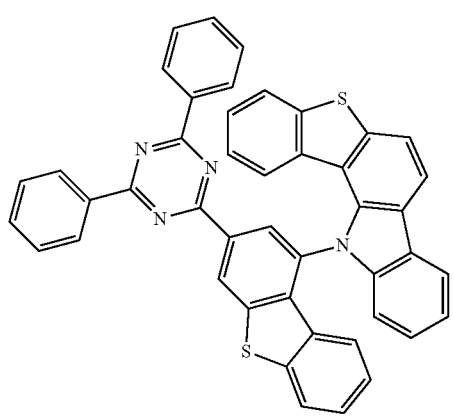
4-45
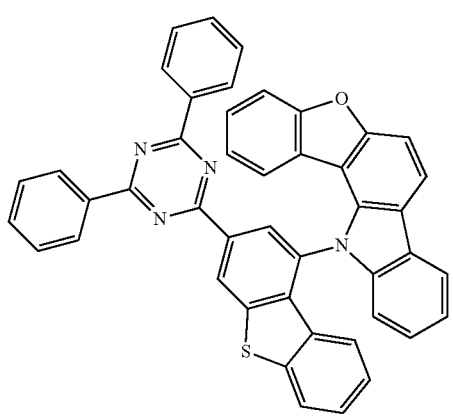

-continued
4-46
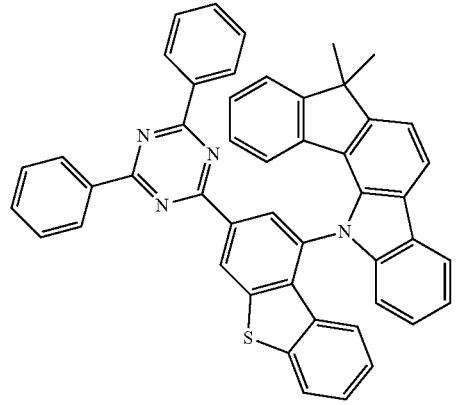
4-47
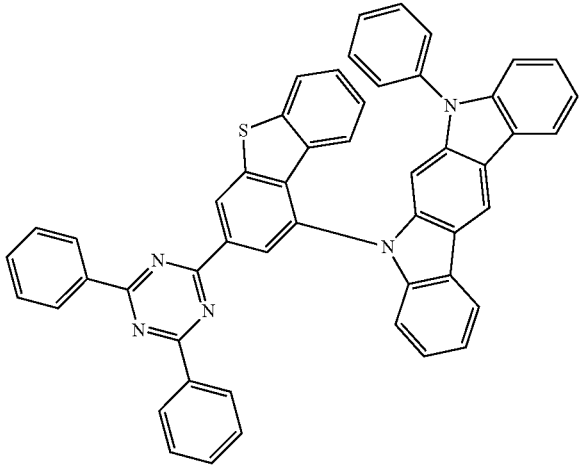
4-48
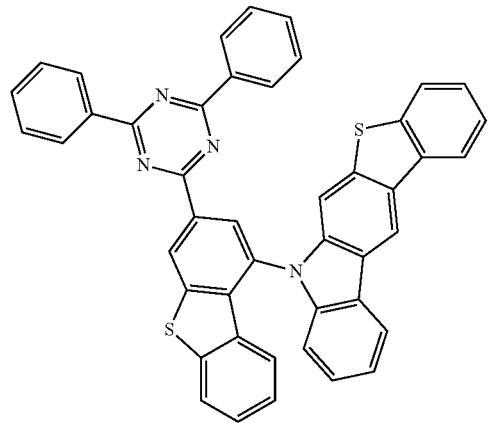
4-49
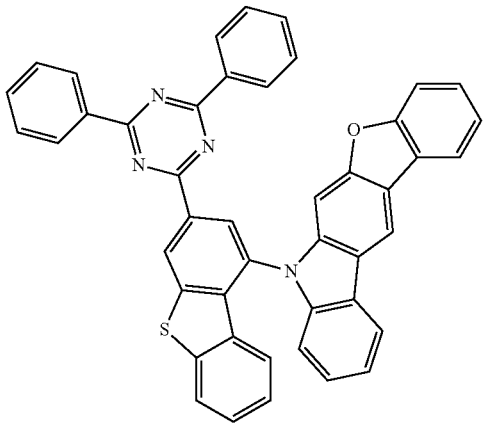
4-50
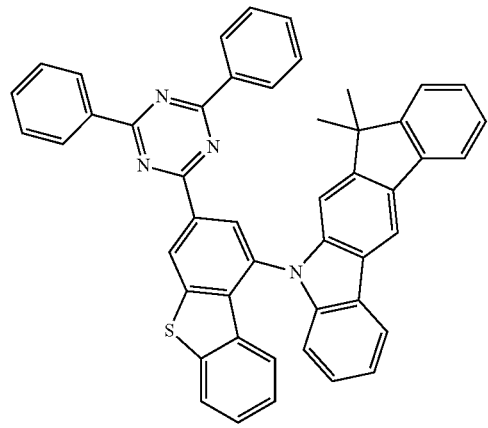
4-51
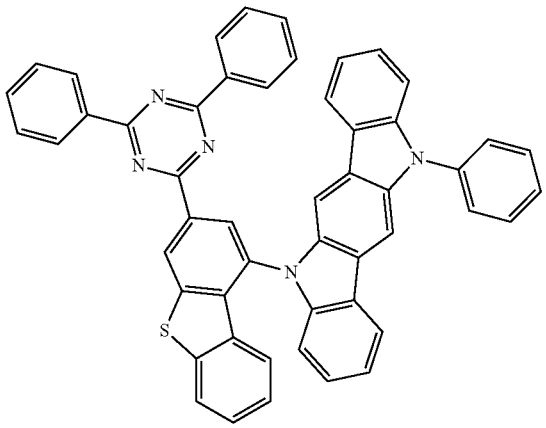

-continued
4-52
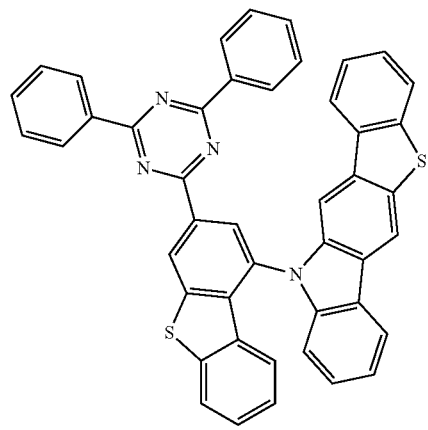
4-53
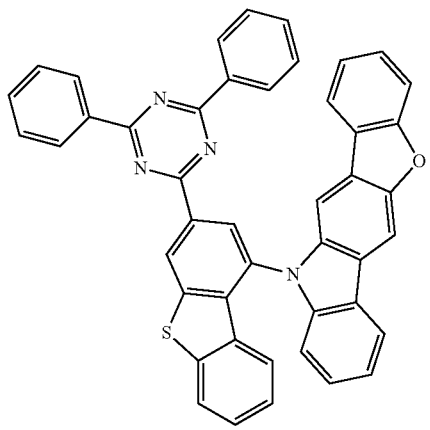
4-54
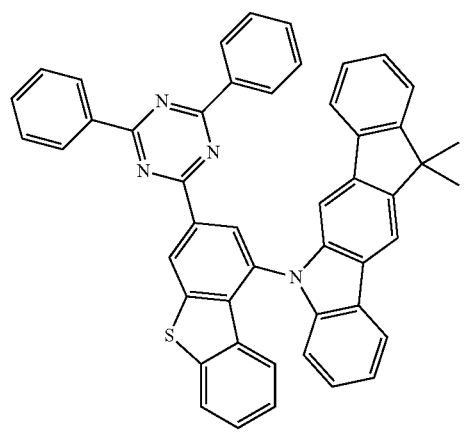
4-55
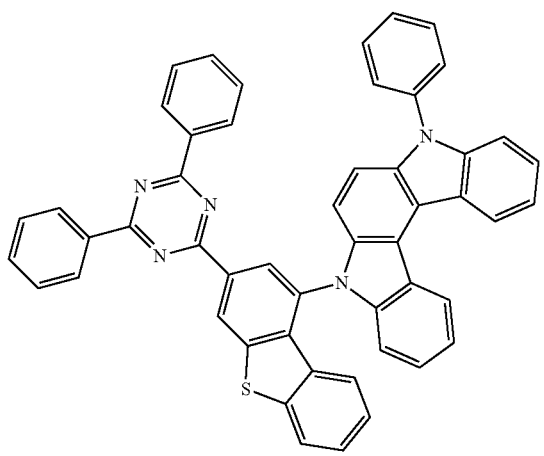
4-56
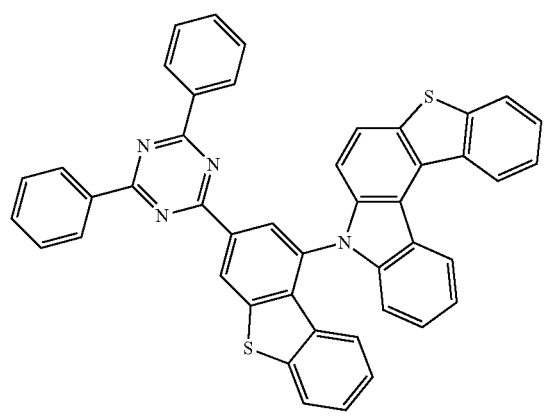
4-57
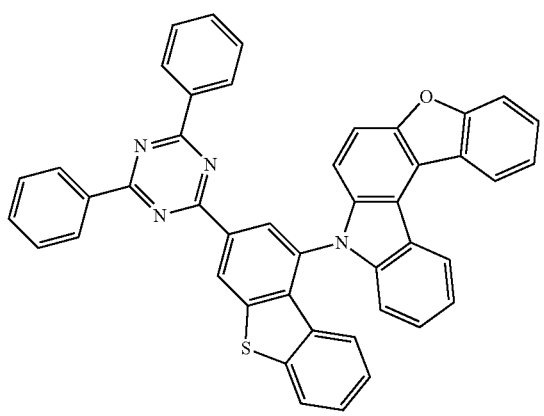

-continued
4-58
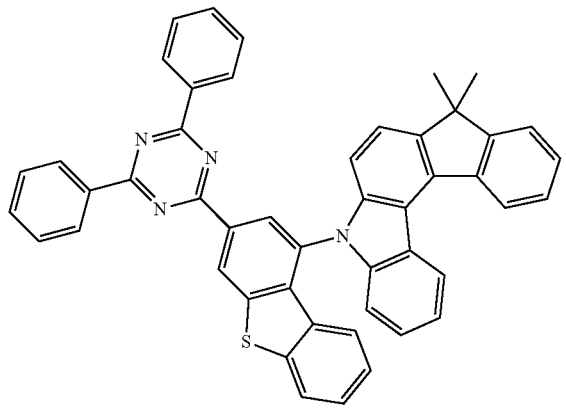
4-59
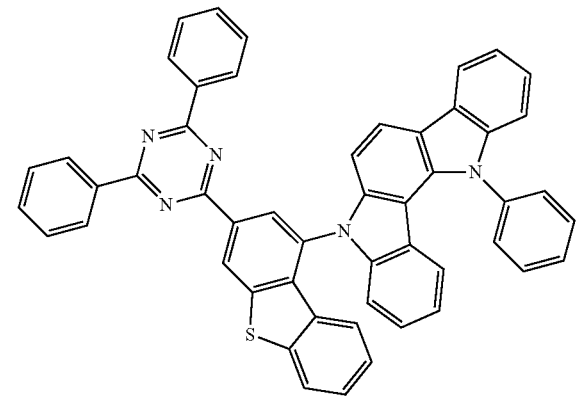
4-60
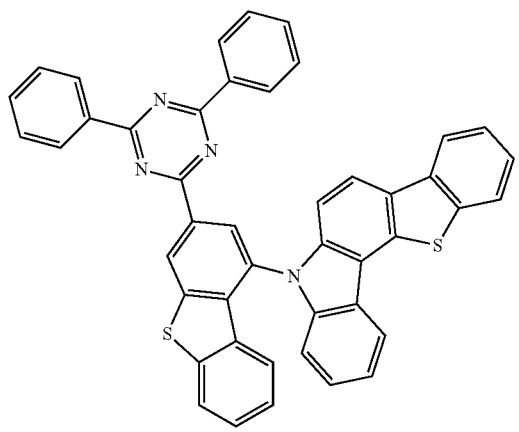
4-61
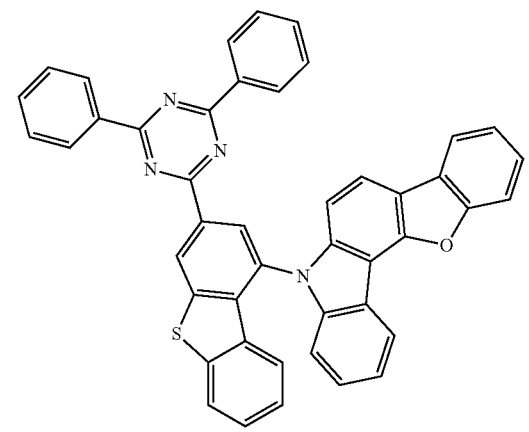
4-62
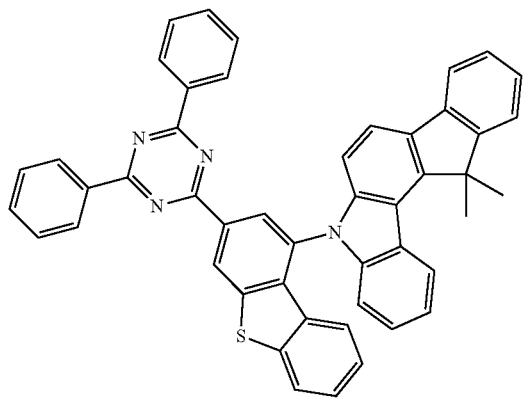
4-63
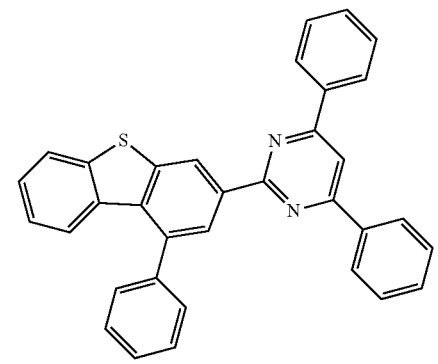
4-64
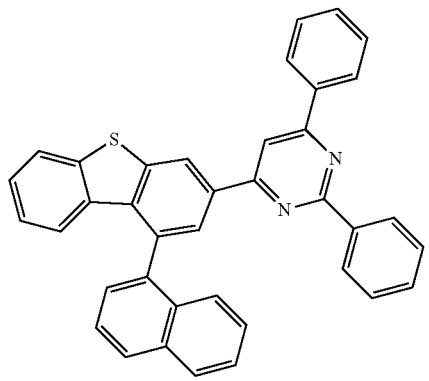
4-65
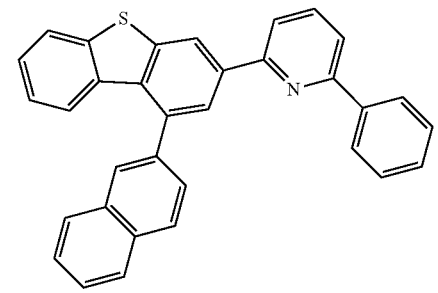

-continued
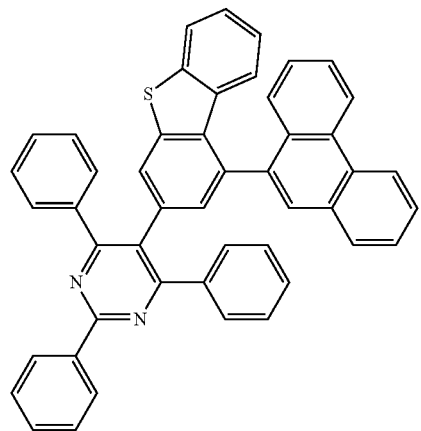
4-66
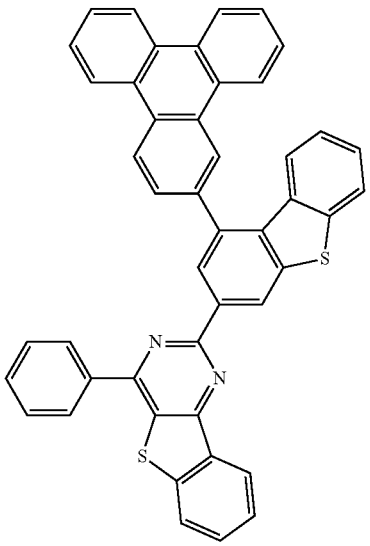
4-67
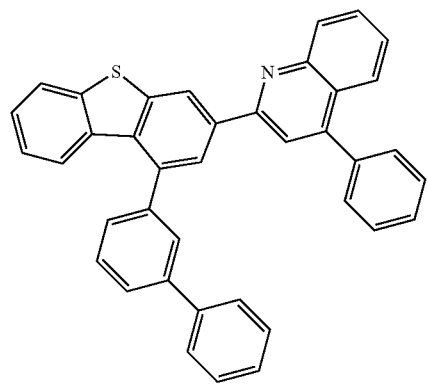
4-68
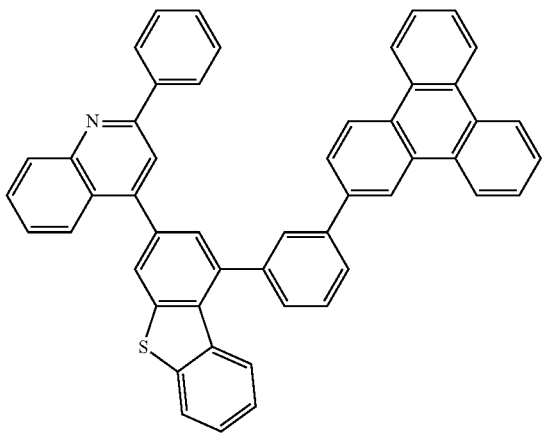
4-69
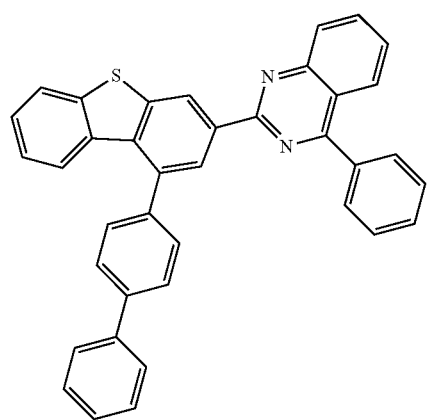
4-70
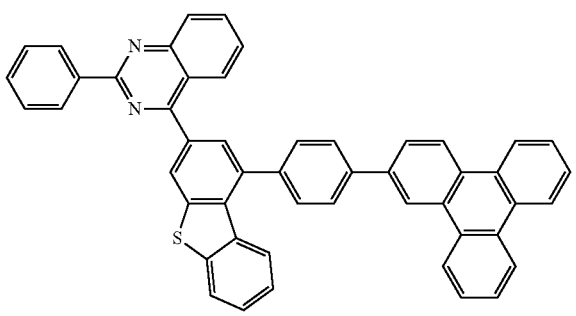
4-71

4-72
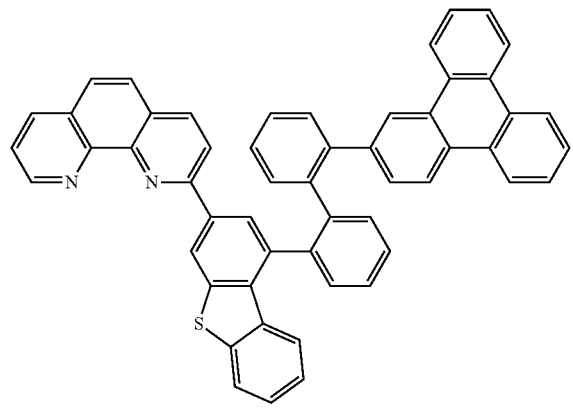
4-73
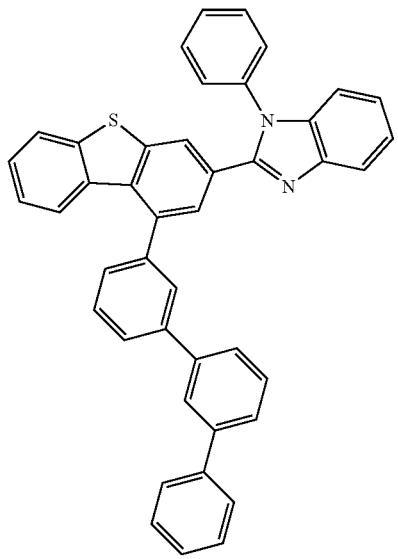
4-74
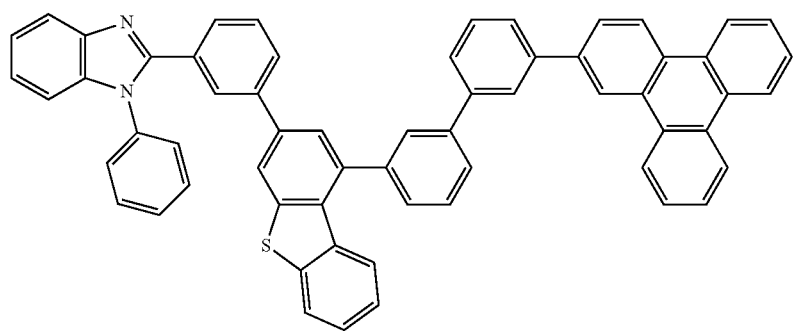
4-75
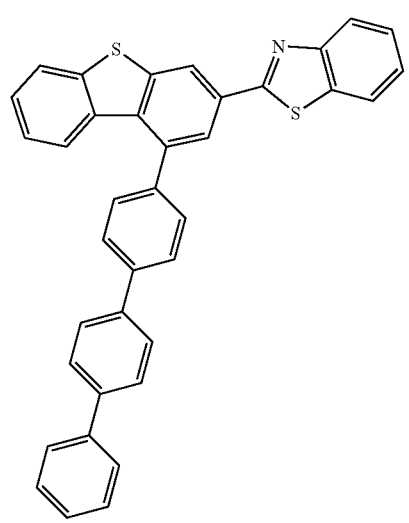

-continued
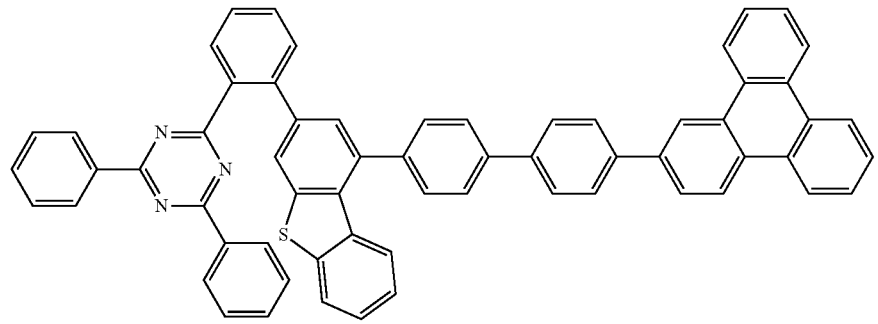
4-76
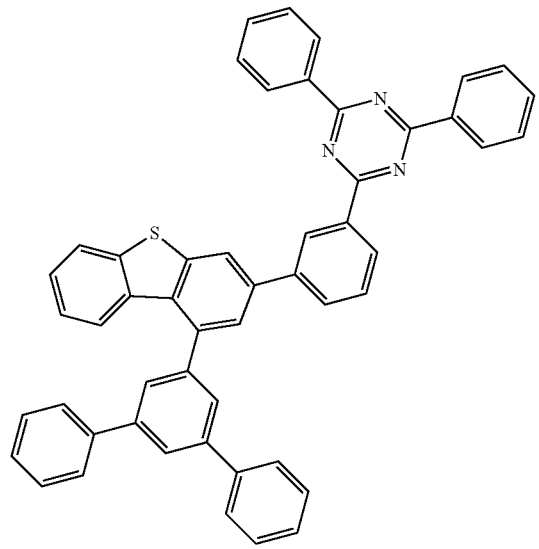
4-77
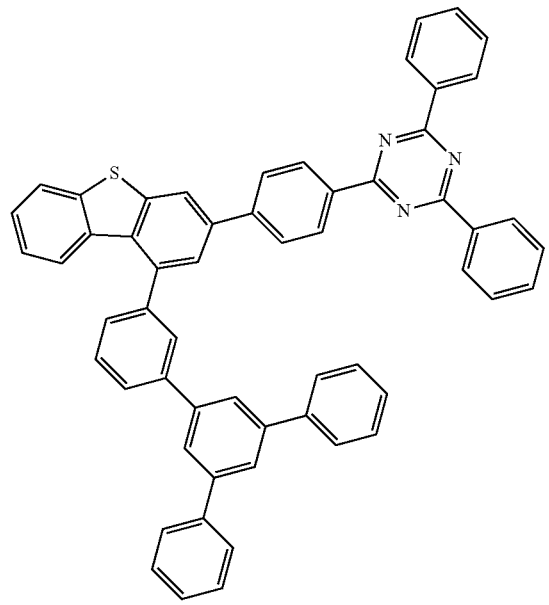
4-78
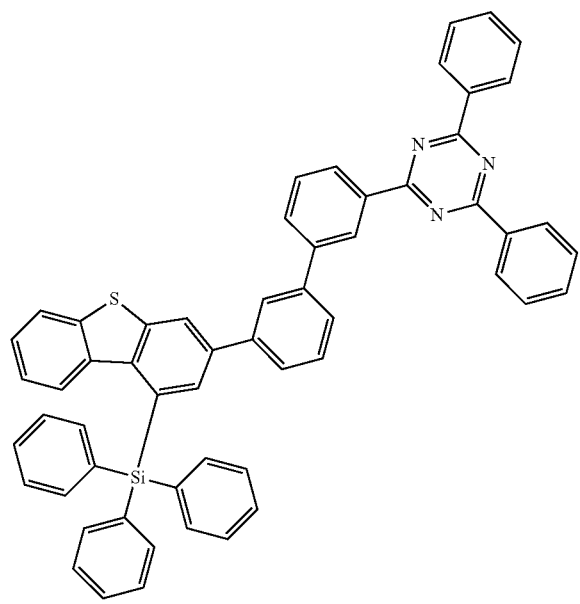
4-79
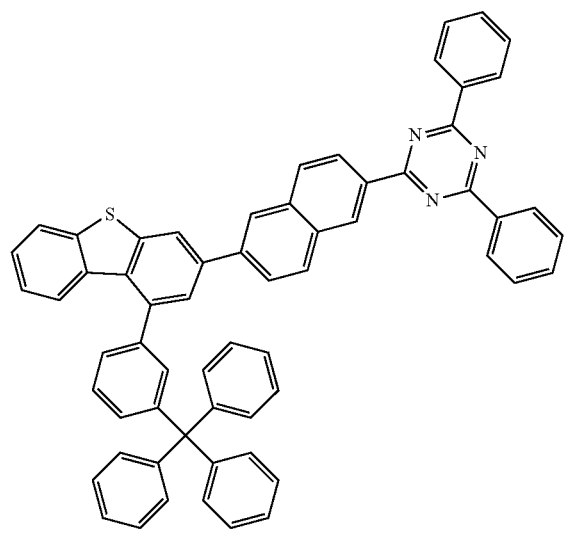
4-80

4-81
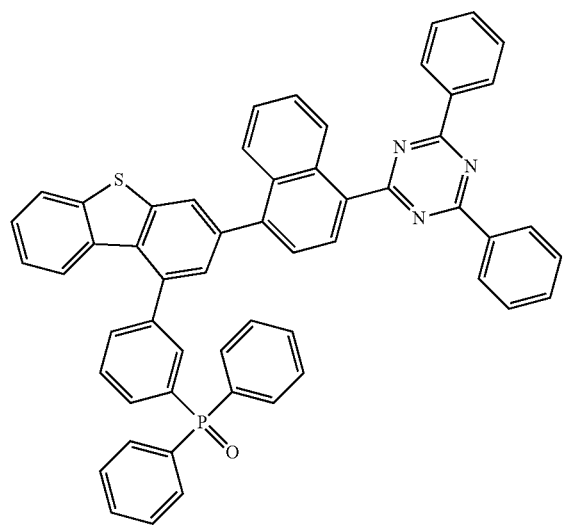
4-85
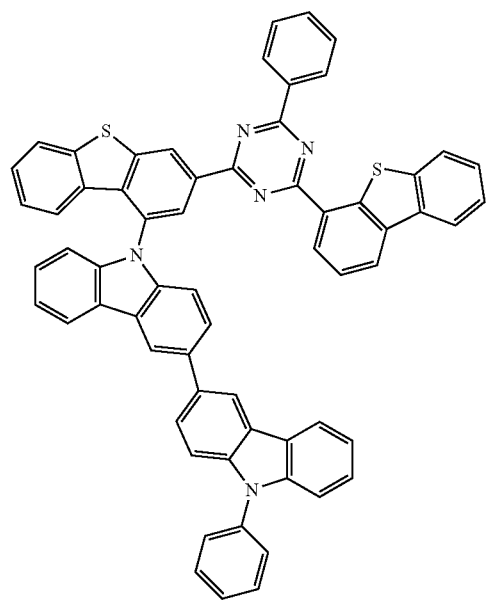
4-86
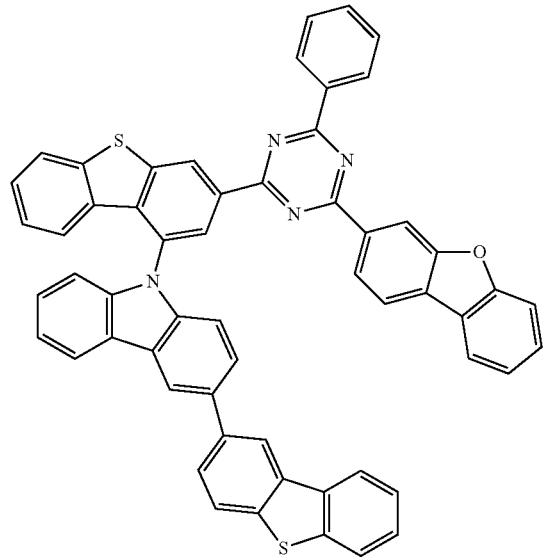
4-87
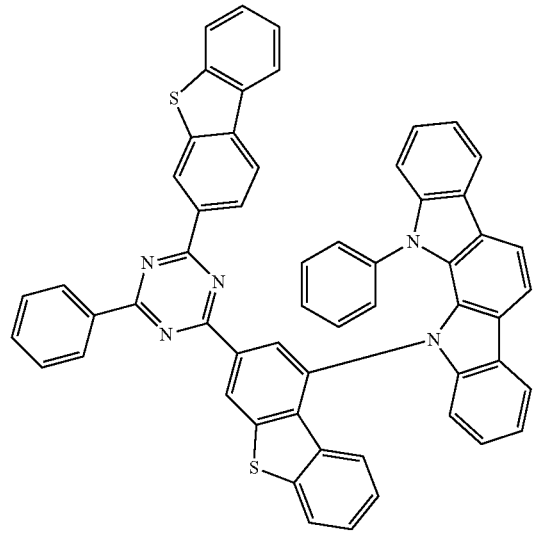

4-88
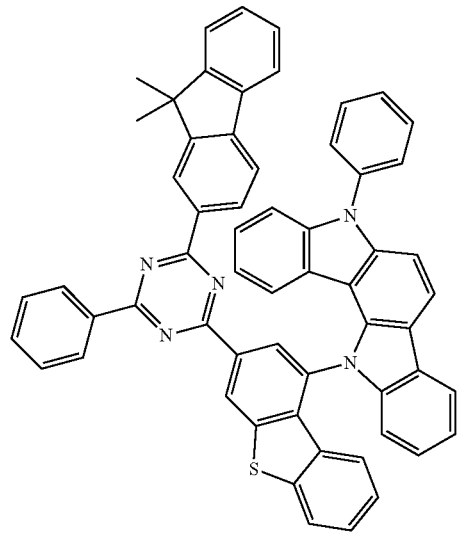
4-89
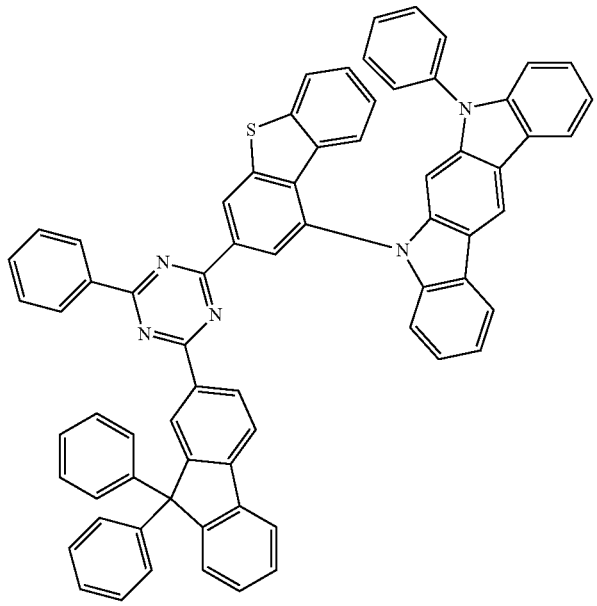
4-90
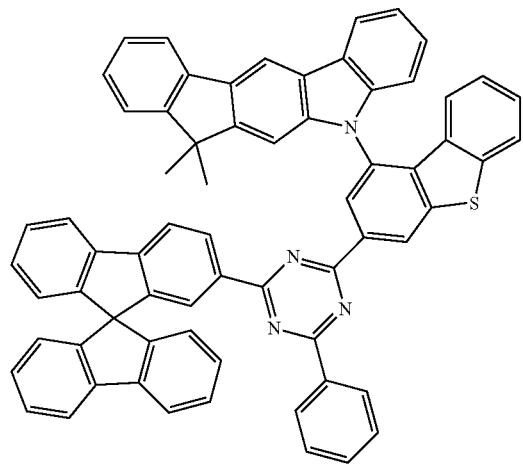
4-91
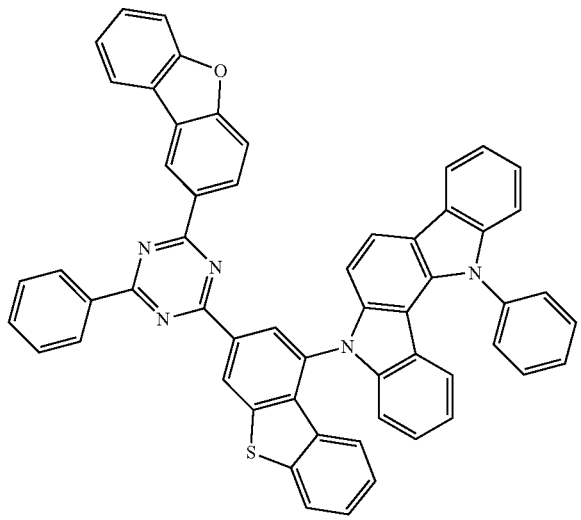

-continued
4-92
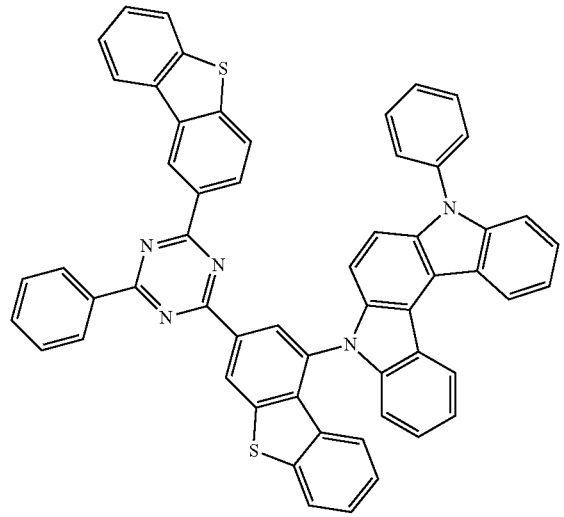
4-93
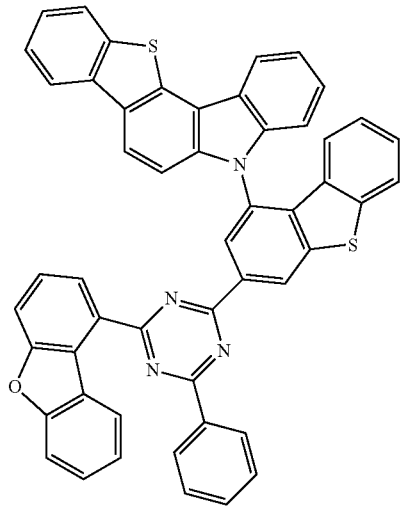
4-94
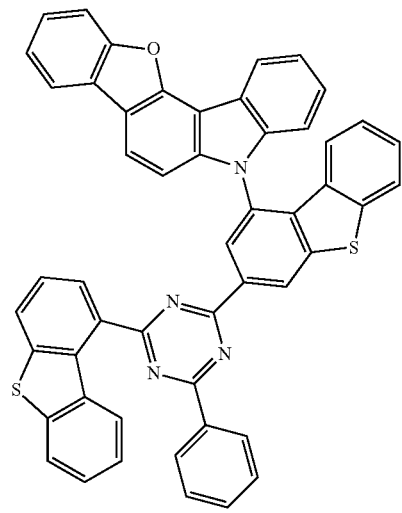
4-95
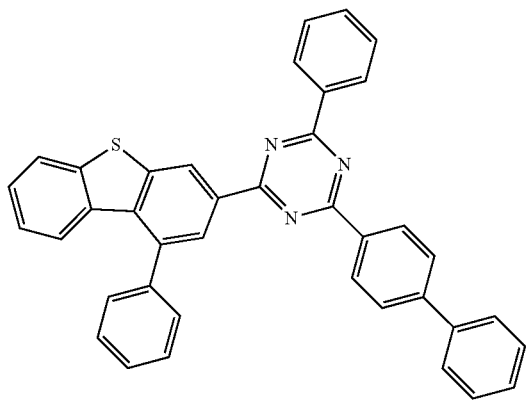
4-96
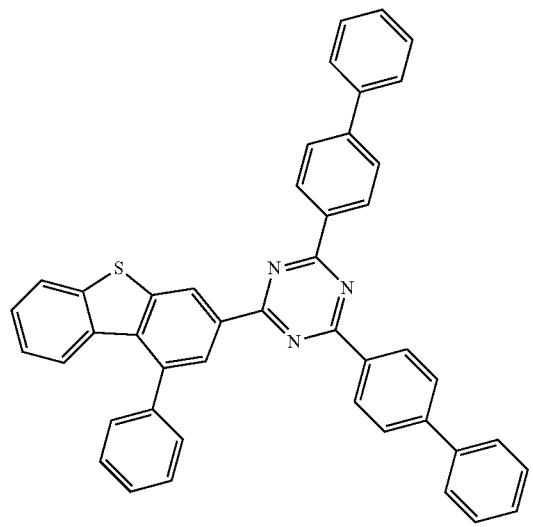
4-97
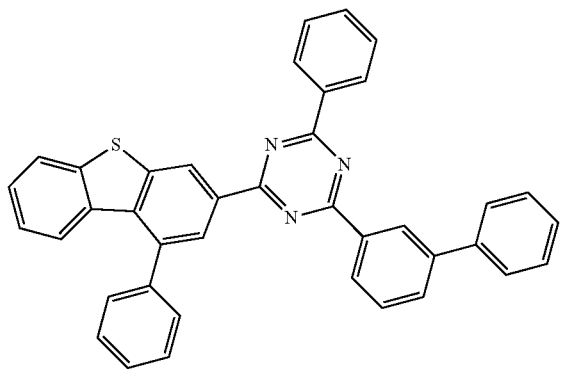

4-98
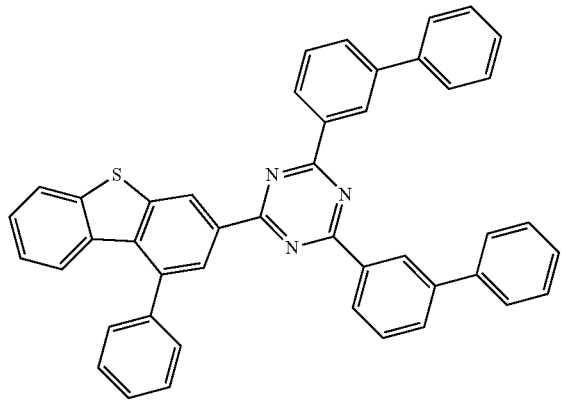
4-99
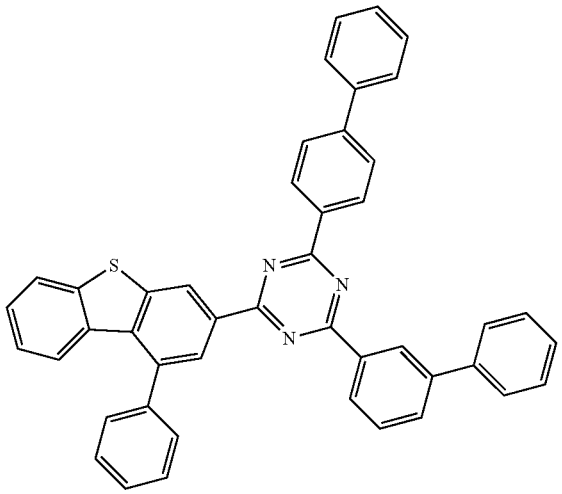
4-100
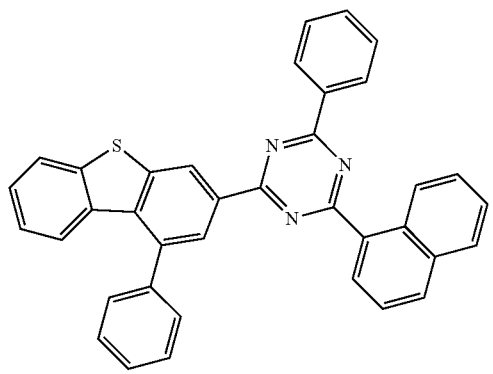
4-101
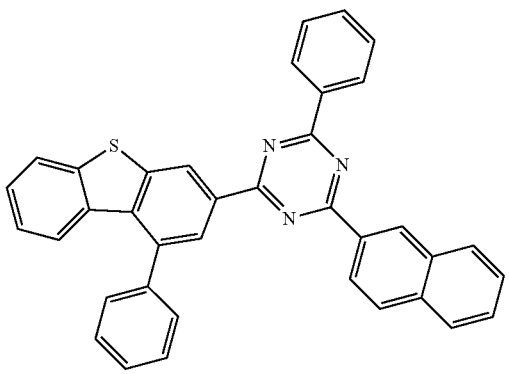
4-102
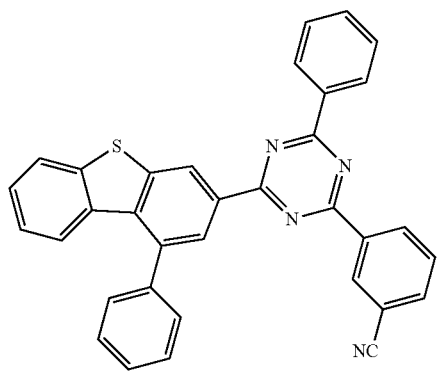
4-103
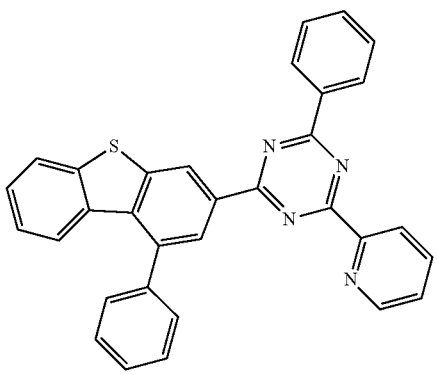

4-104
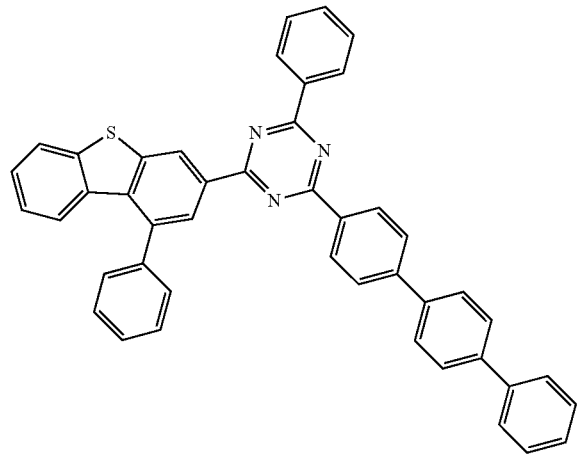
4-105
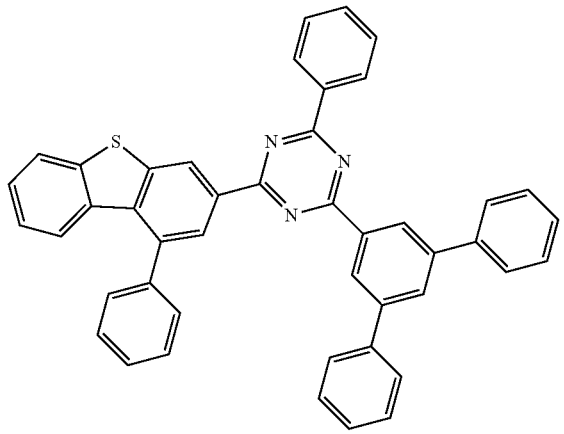
4-106
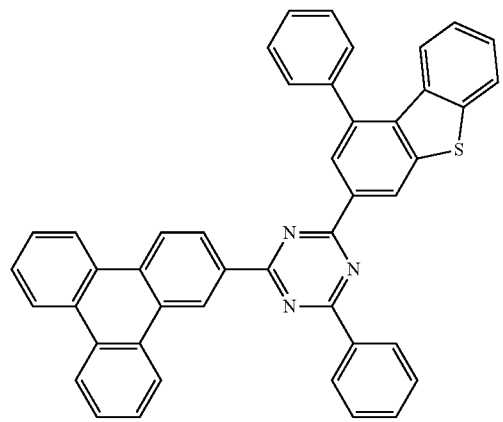
4-107
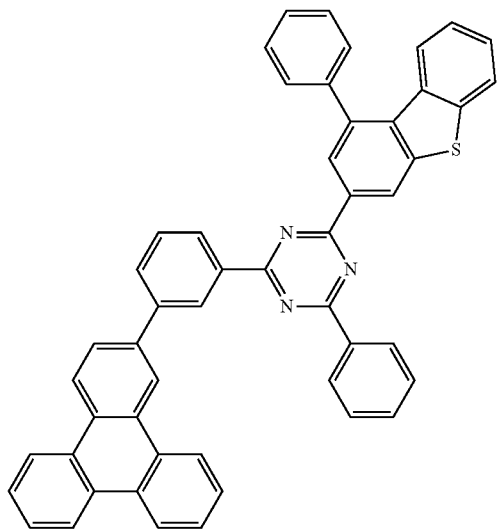
4-108
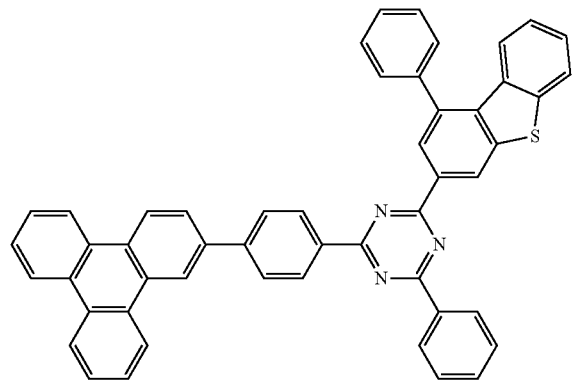
4-109
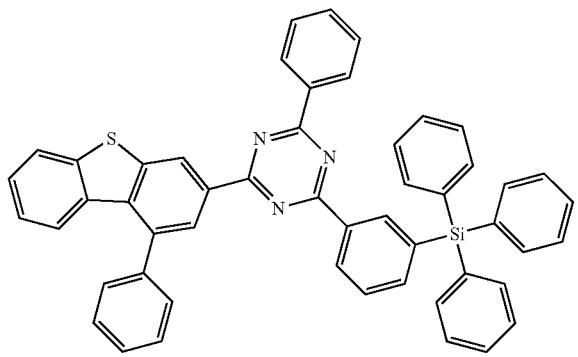

4-110
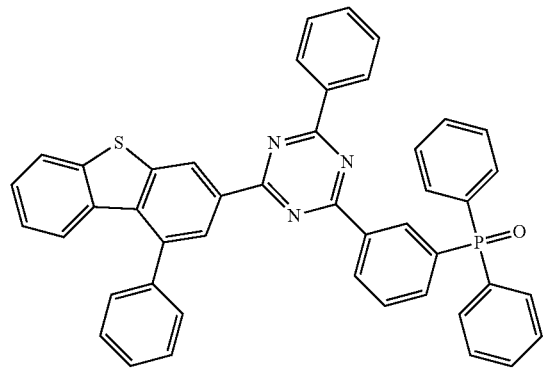
4-111
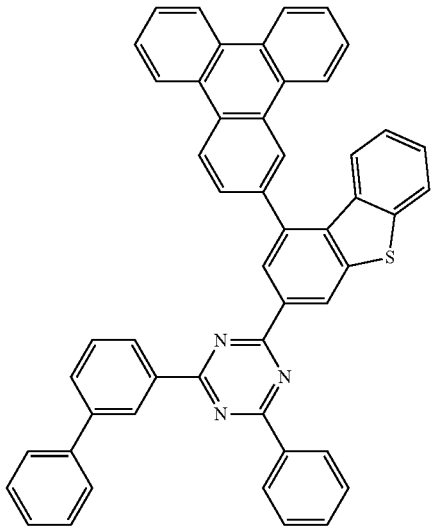
4-112
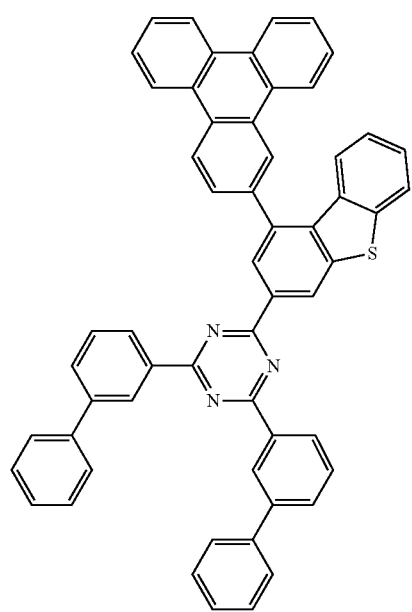
4-113
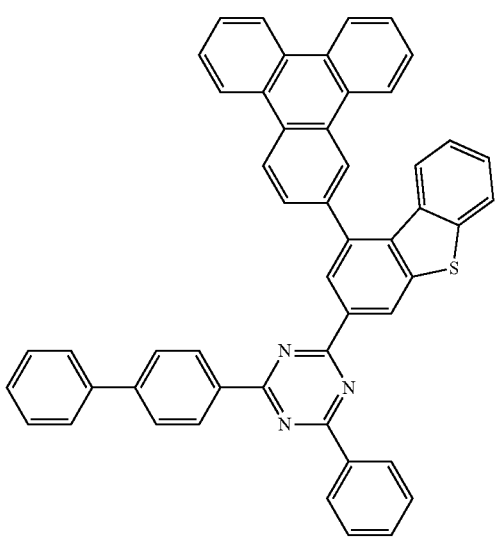

4-114
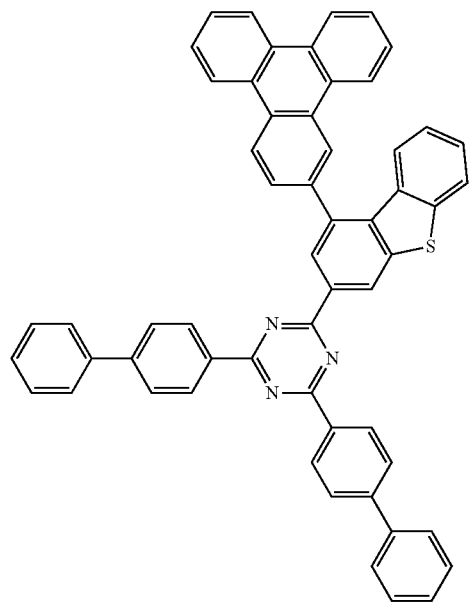
4-115
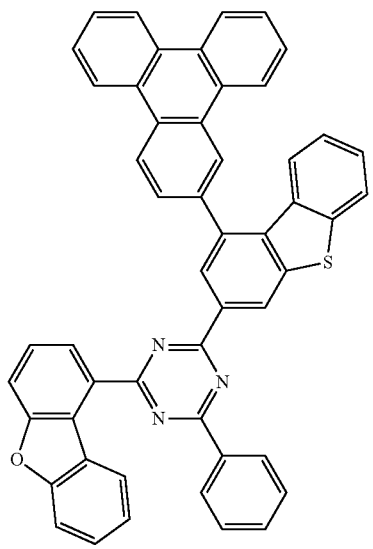
4-116
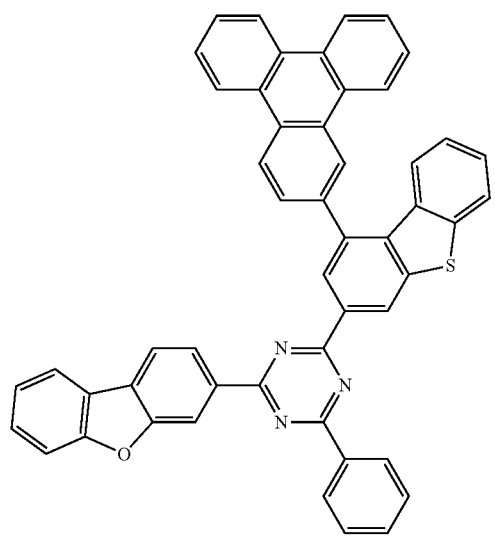
4-117
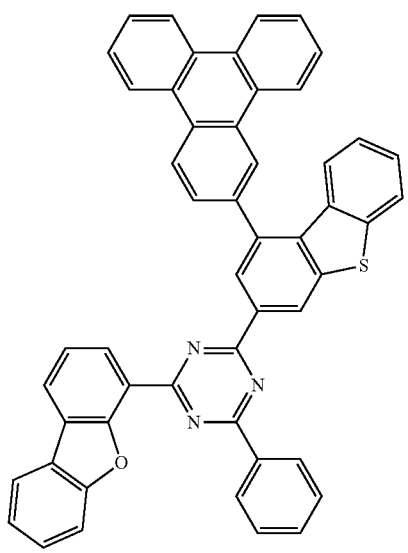

-continued
4-118
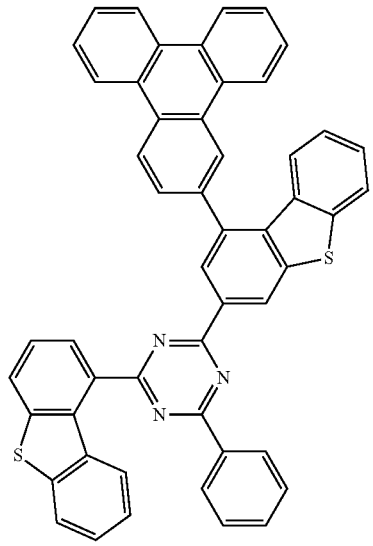
4-119
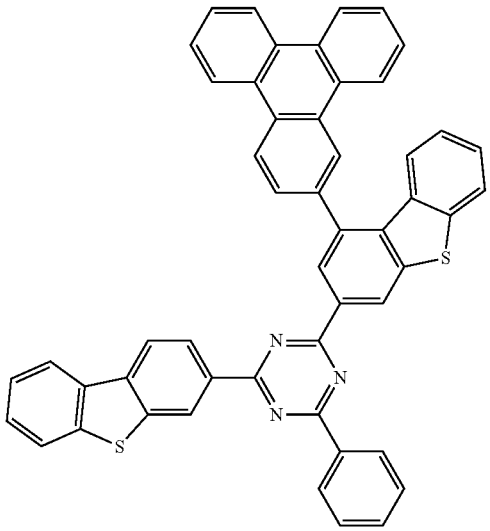
4-120
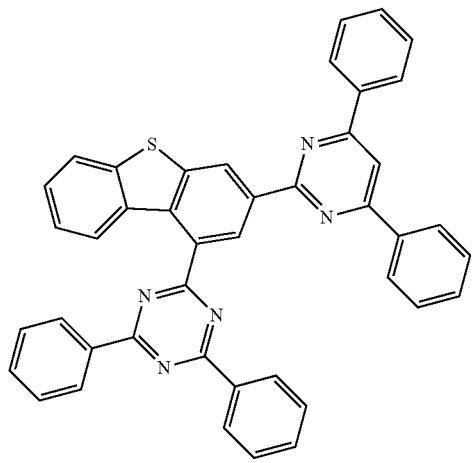
4-121
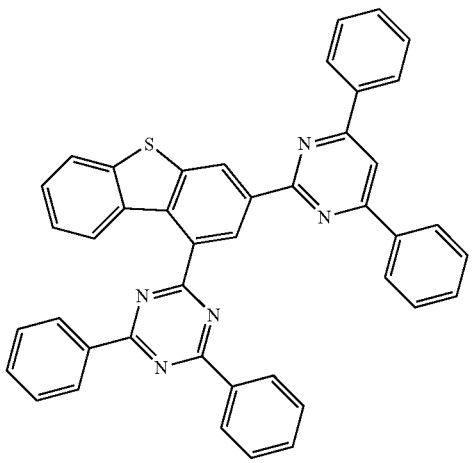
4-122
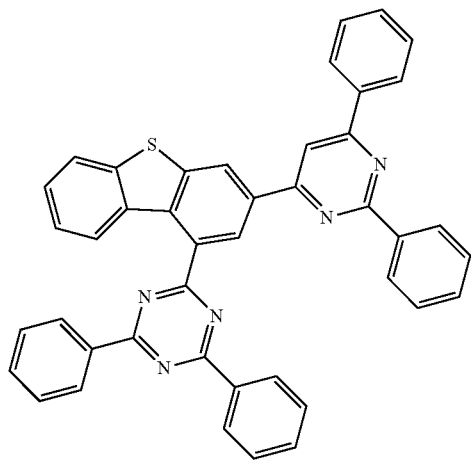
4-123
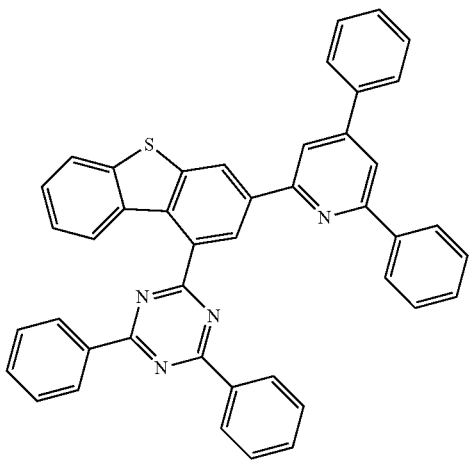

-continued
| 4-124 | 4-126 |
|---|---|
| 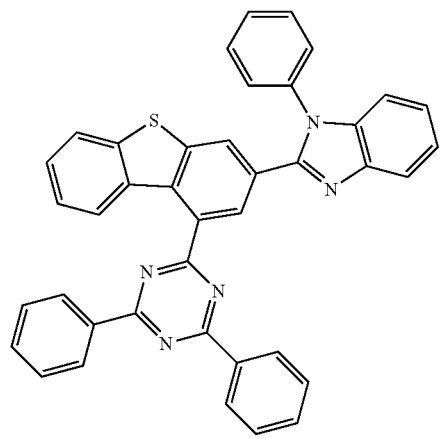 | 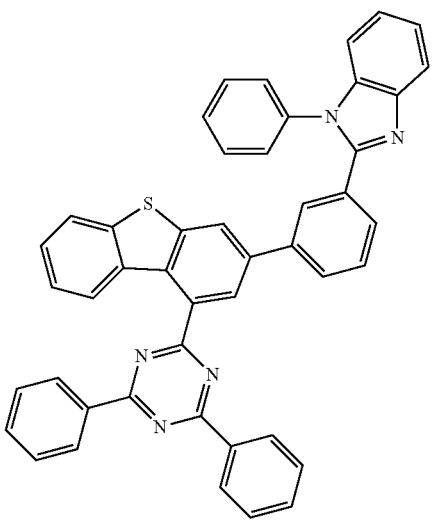 |
| 4-127 | 4-128 |
|---|---|
| 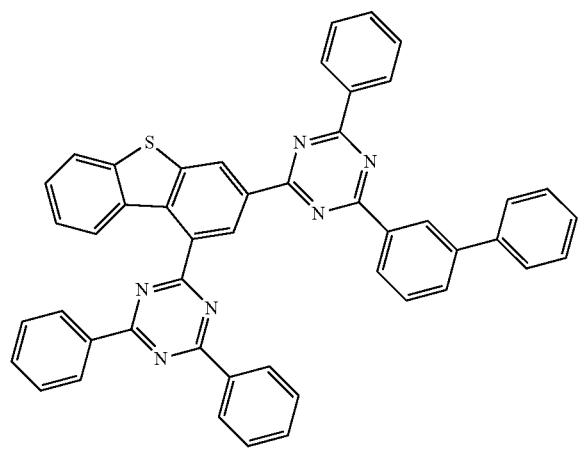 | 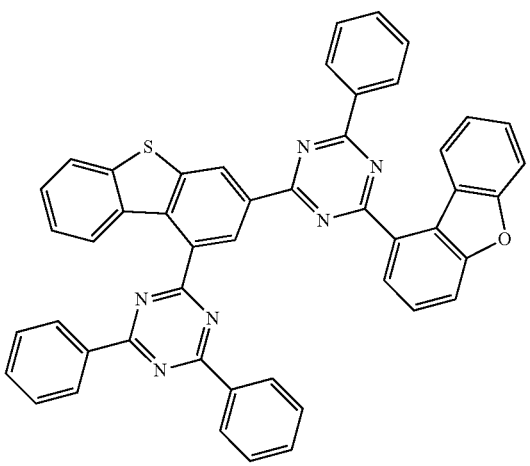 |
| 4-129 | 4-130 |
|---|---|
| 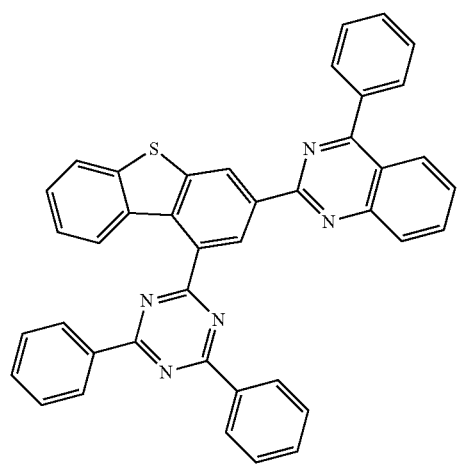 | 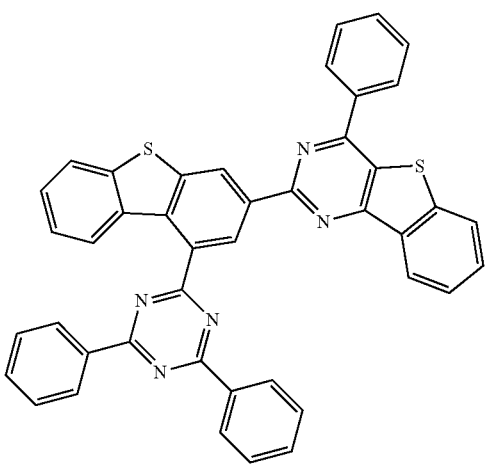 |

4-131

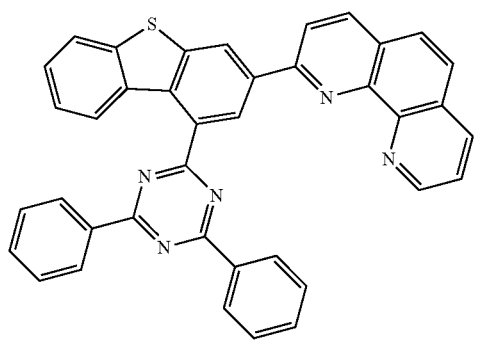

4-132

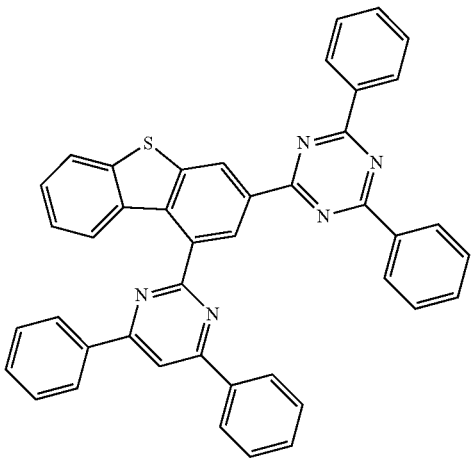

4-133

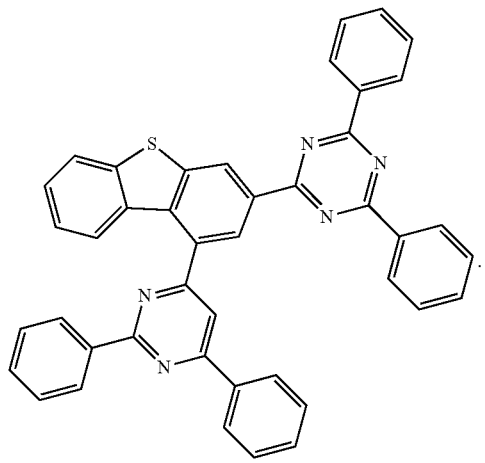

3. An organic light emitting device comprising:
a first electrode;
a second electrode provided opposite to the first electrode; and
one or more organic material layers provided between the first electrode and the second electrode,
wherein one or more layers of the organic material layers comprise the heterocyclic compound of claim 1.

4. The organic light emitting device of claim 3, wherein the organic material layer comprising the heterocyclic compound represented by Chemical Formula 4 or 5 further comprises a heterocyclic compound represented by the following Chemical Formula 3:

[Chemical Formula 3]

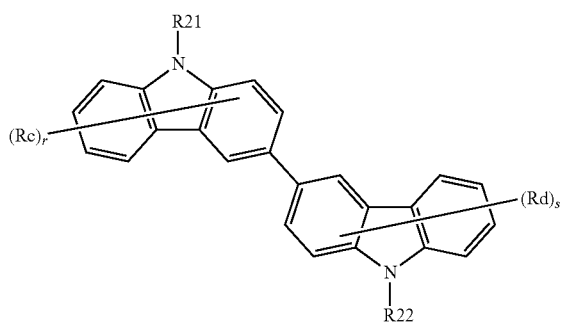

in Chemical Formula 3,
Rc and Rd are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiR$_{31}$R$_{32}$R$_{33}$; —P(=O)R$_{31}$R$_{32}$; and an amine group unsubstituted or substituted with a substituted or unsubstituted alkyl group, a substituted or unsubstituted aryl group or a substituted or unsubstituted heteroaryl group, or two or more groups adjacent to each other bond to each other to form a substituted or unsubstituted aliphatic or aromatic hydrocarbon ring, R$_{31}$, R$_{32}$, and R$_{33}$ are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group, R21 and R22 are the same as or different from each other, and each independently a substituted or unsubstituted aryl group; or a substituted or unsubstituted heteroaryl group, and r and s are an integer of 0 to 7, and when r and s are an integer of 2 or greater, substituents in the parentheses are the same as or different from each other.

5. The organic light emitting device of claim 4, wherein Chemical Formula 3 is represented by any one of the following heterocyclic compounds:
5-1
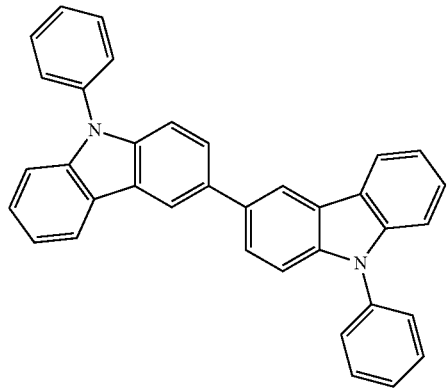
5-2
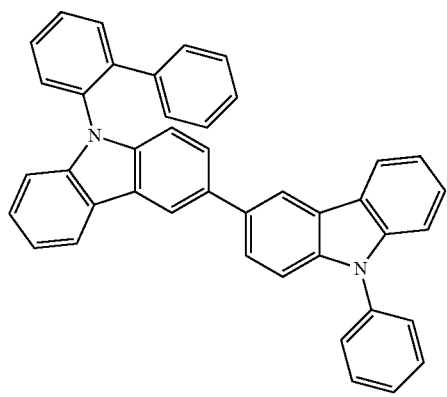
5-3
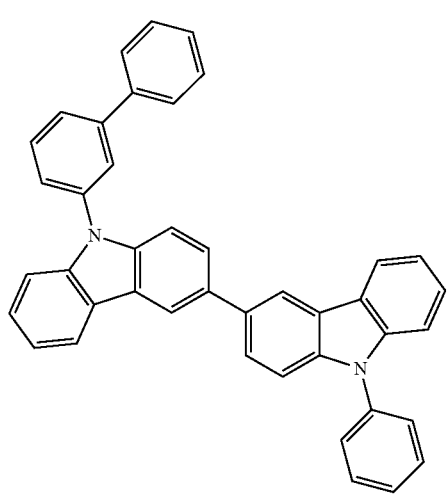
-continued
5-4
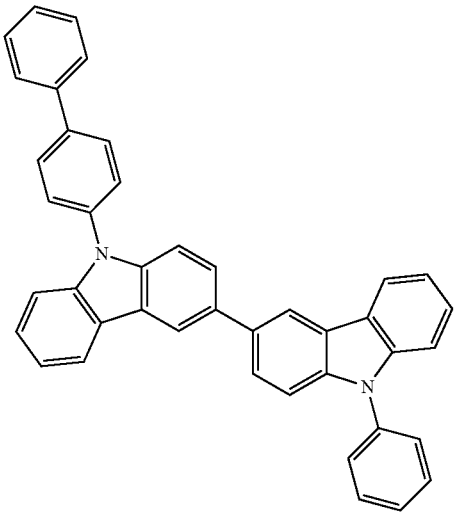
5-5
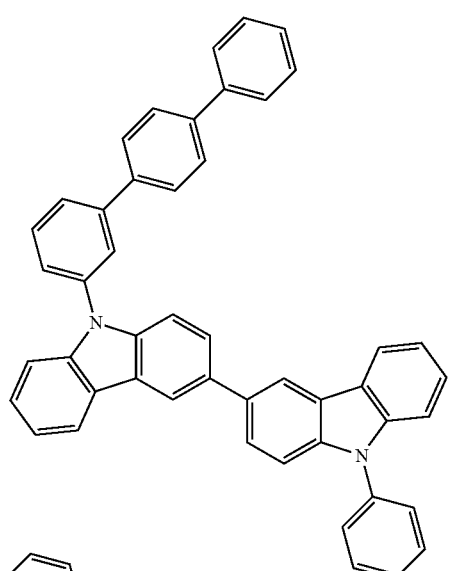
5-6
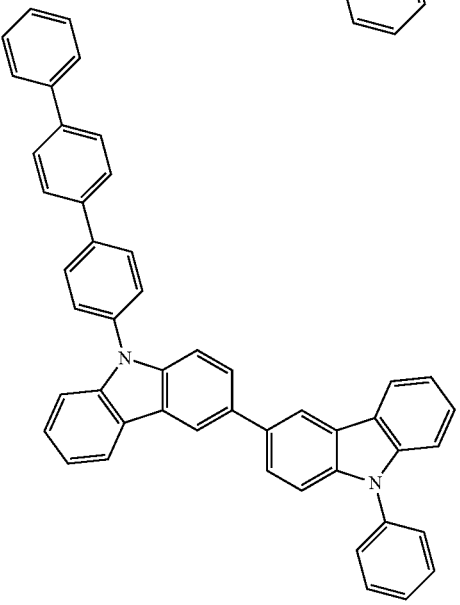

5-7
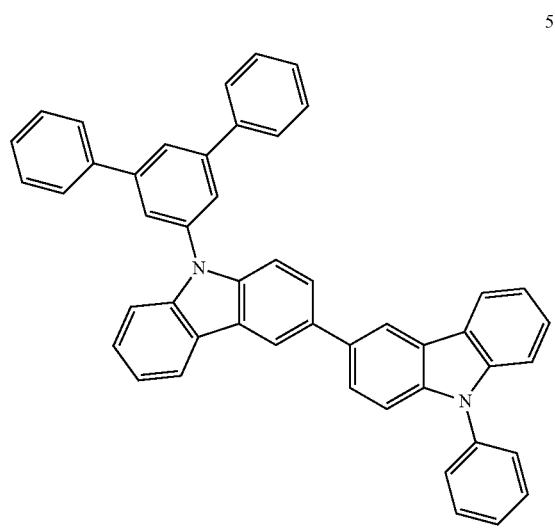
5-8
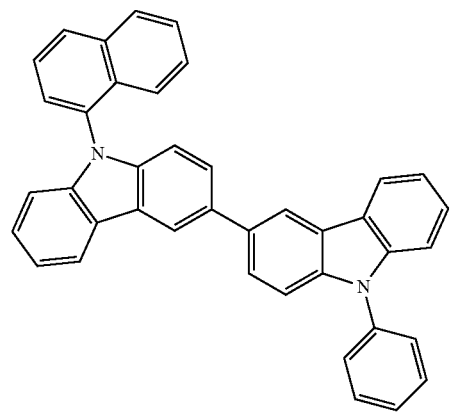
5-9
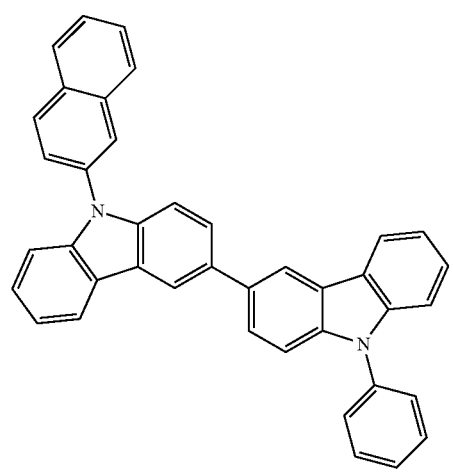
5-10
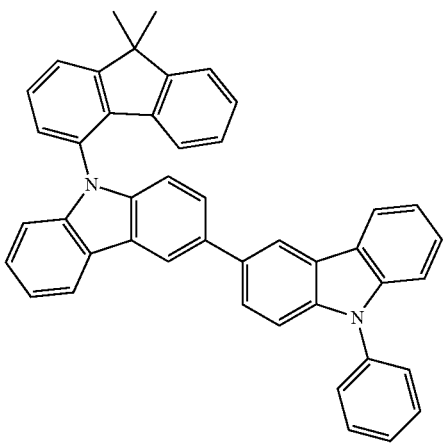
5-11
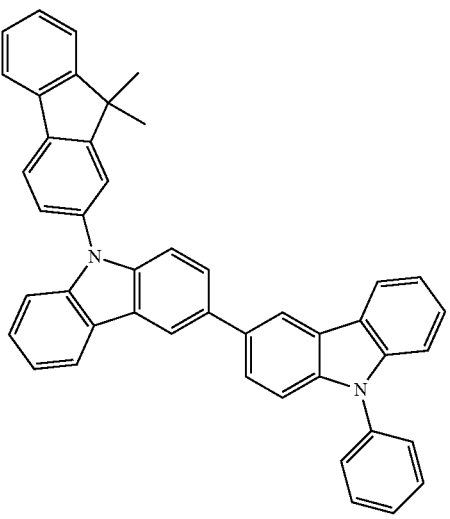
5-12
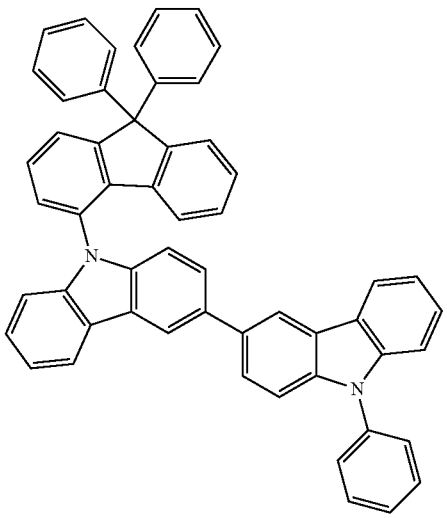

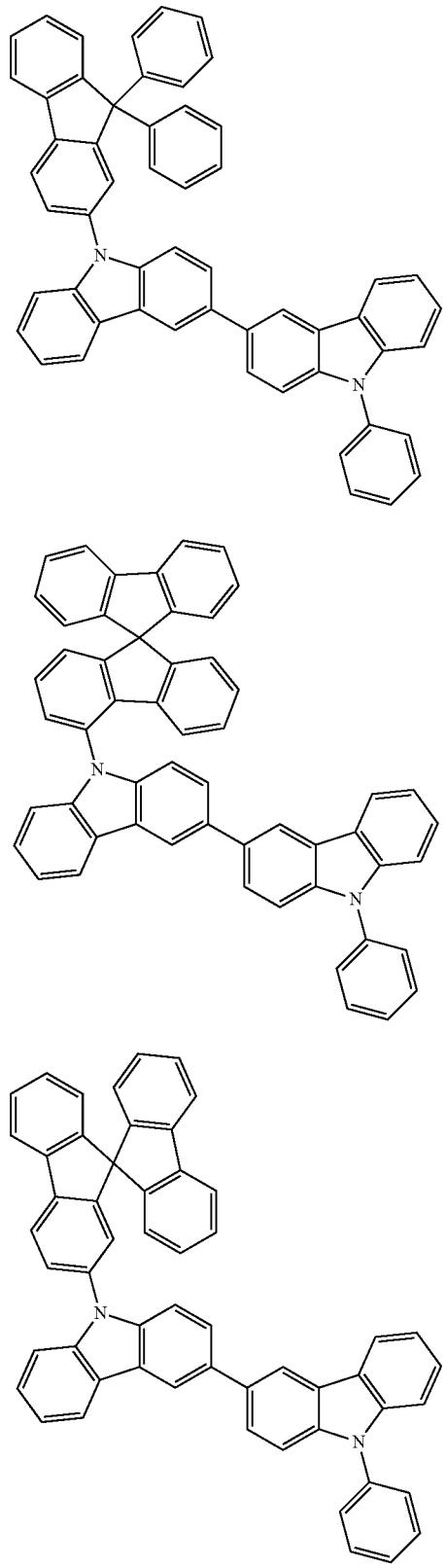
5-13
5-14
5-15
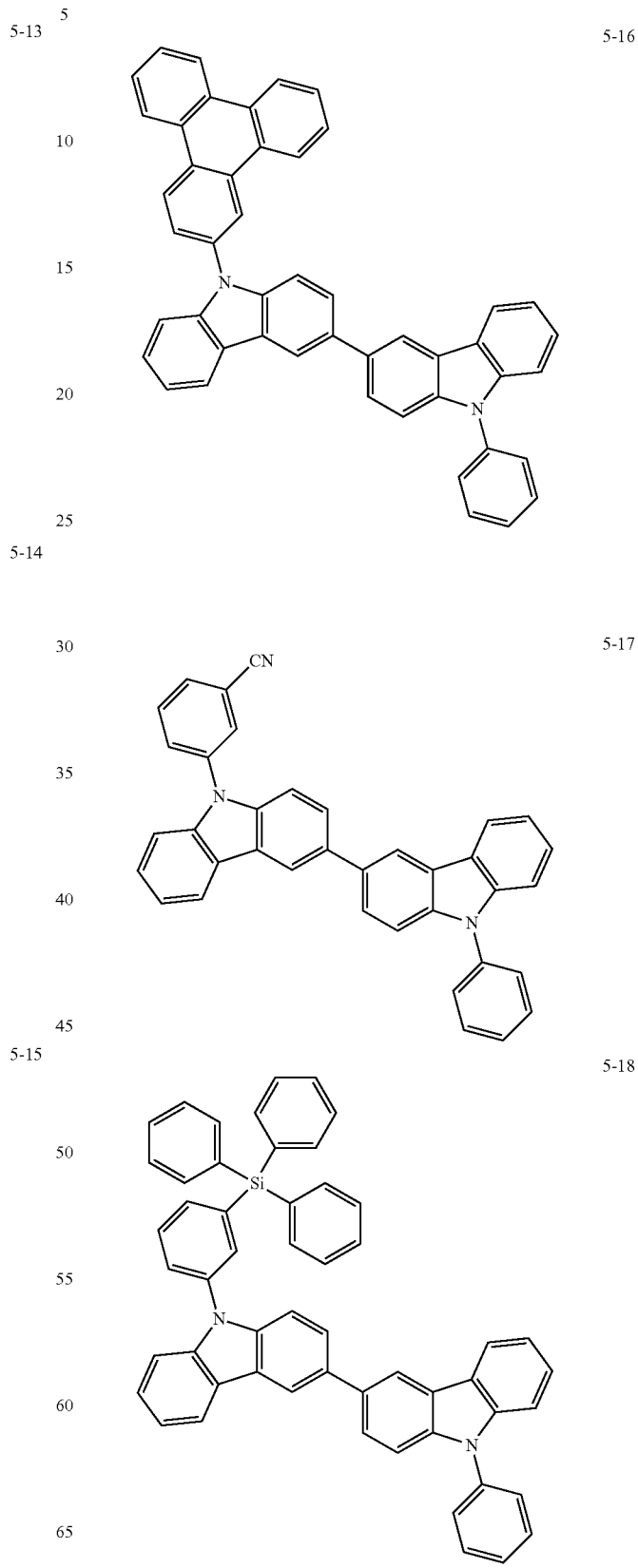
5-16
5-17
5-18

487
-continued
488
-continued
5-19
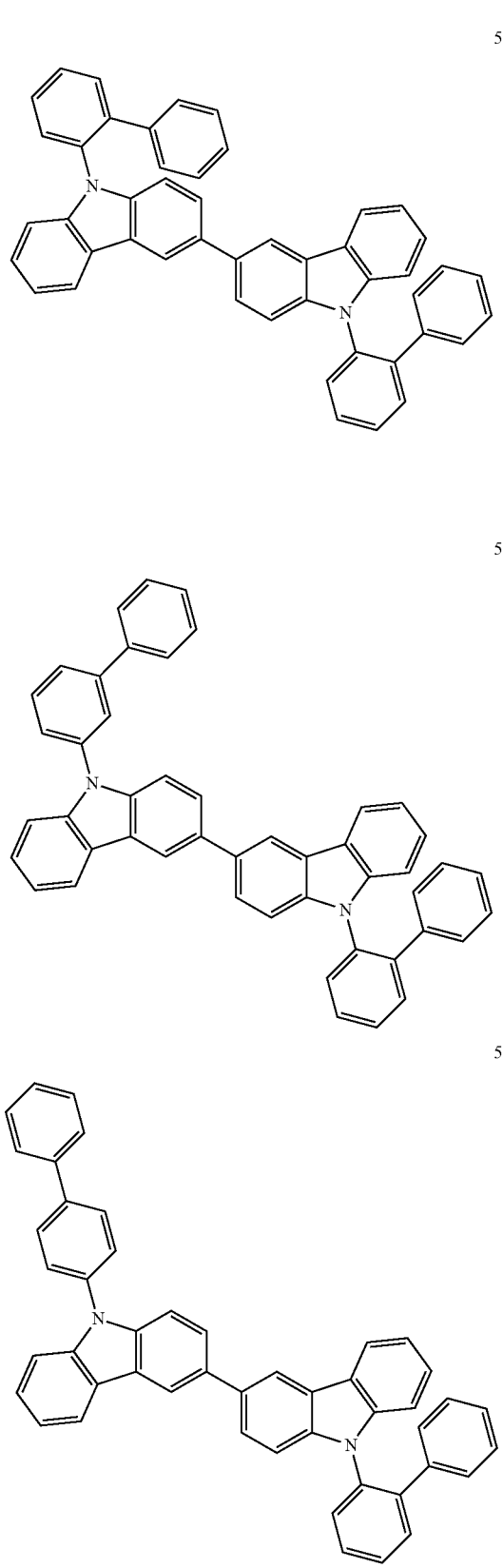
5-20
5-21
5-22
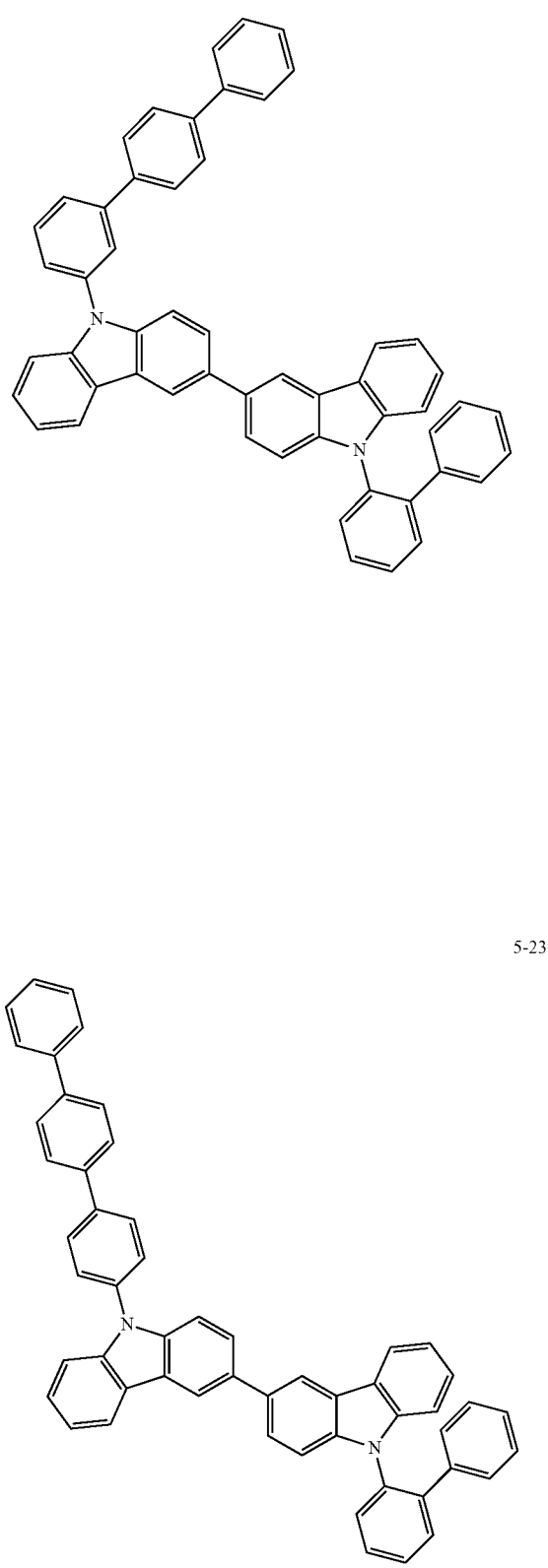
5-23

489
-continued
5-24
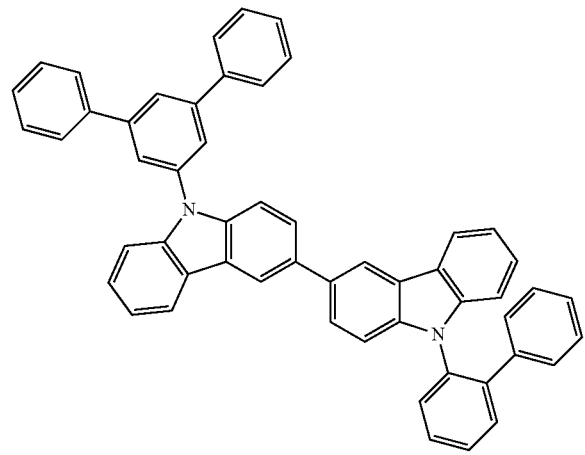
5-25
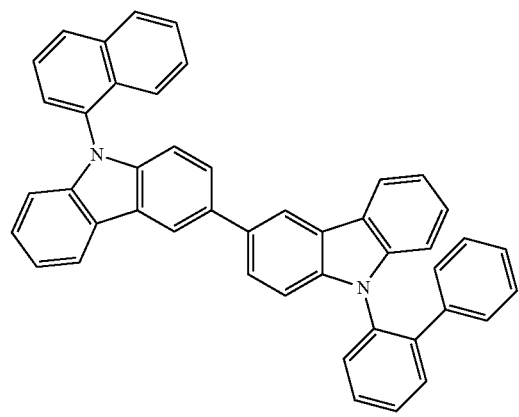
5-26
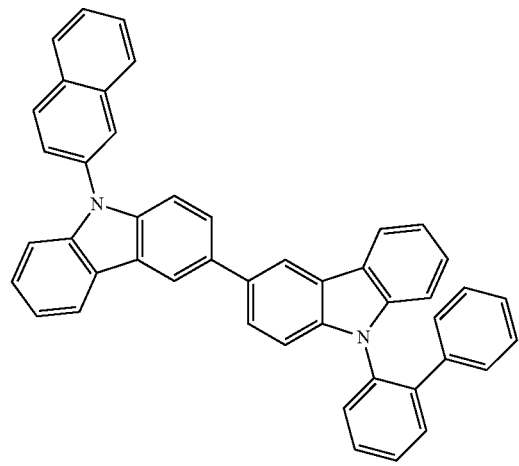
490
-continued
5-27
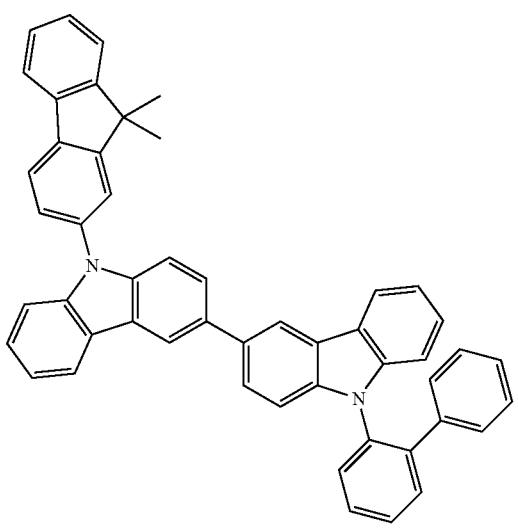
5-28
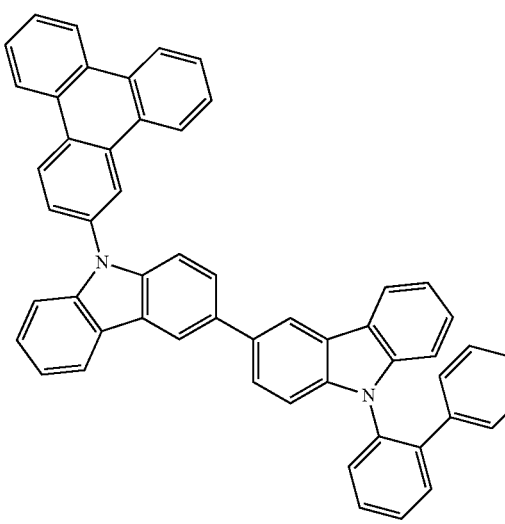
5-29
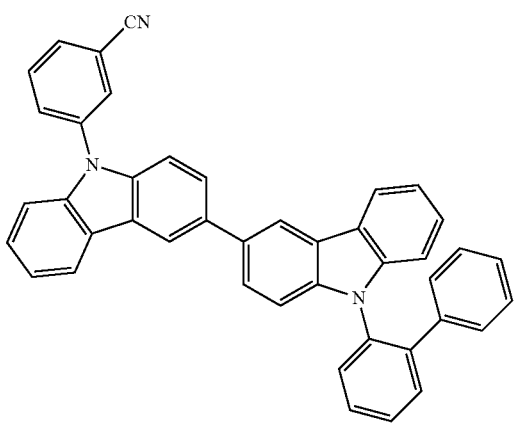

5-30
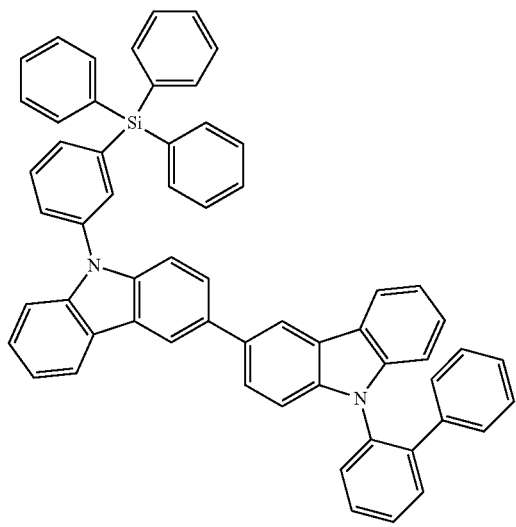
5-31
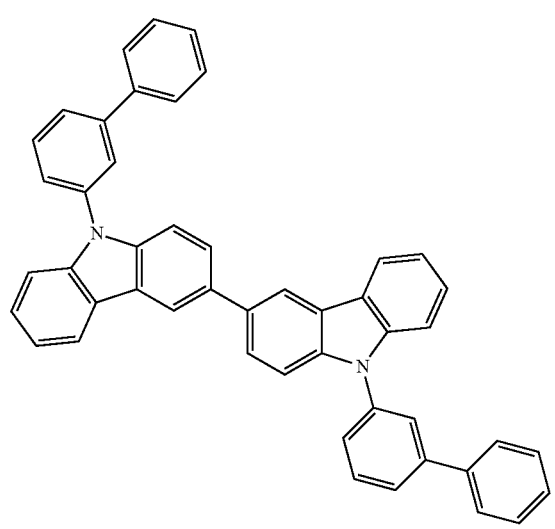
5-32
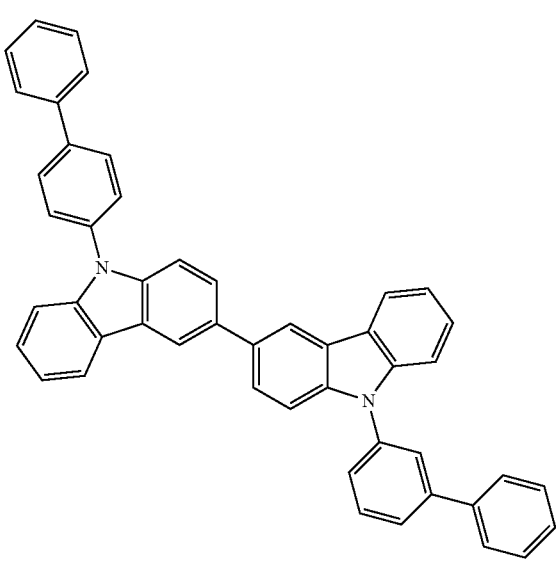
5-33
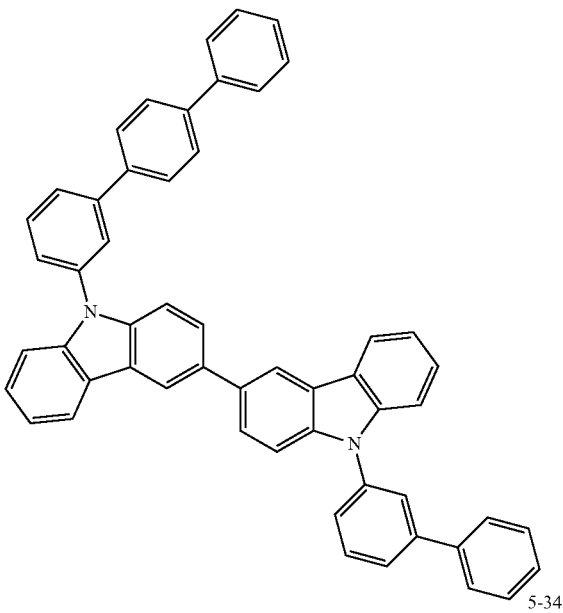
5-34
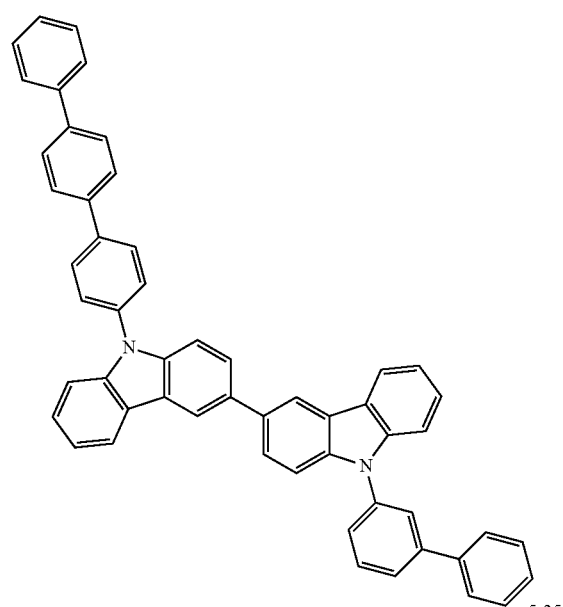
5-35
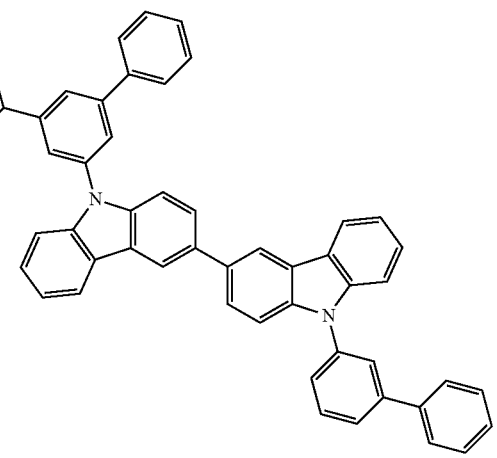

493
-continued
5-36
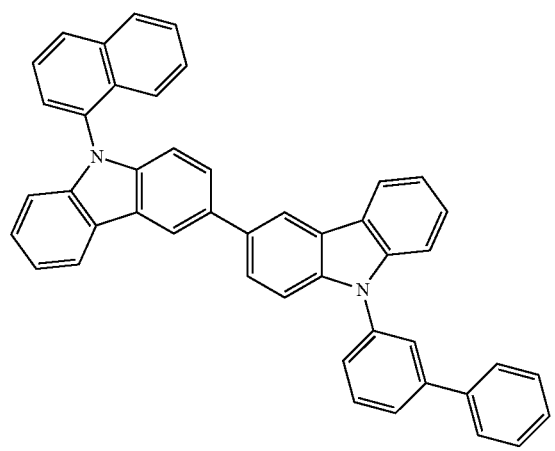
5-37
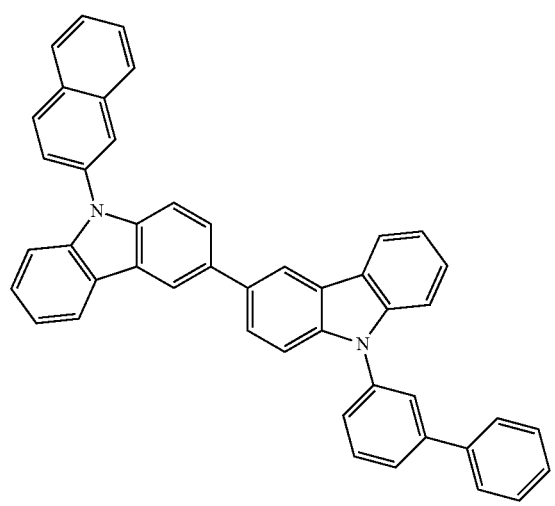
5-38
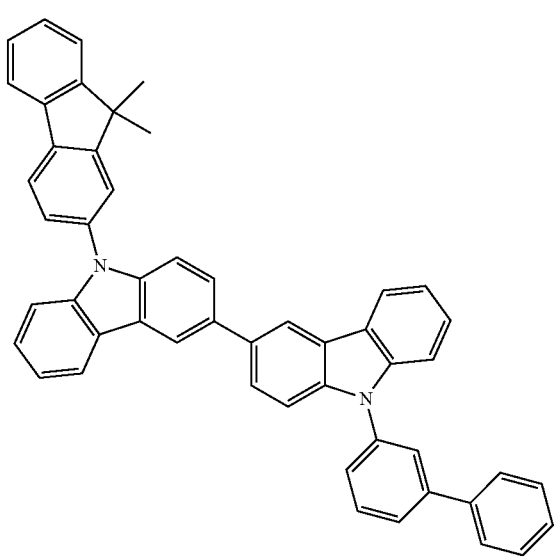
494
-continued
5-39
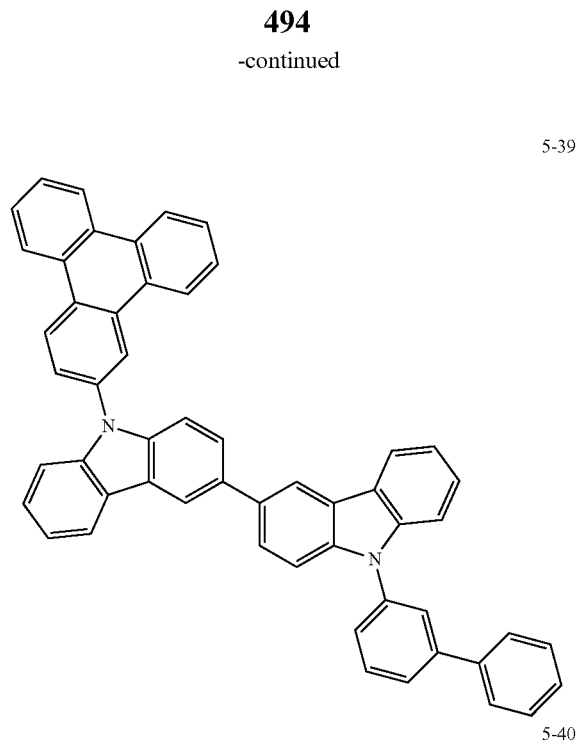
5-40
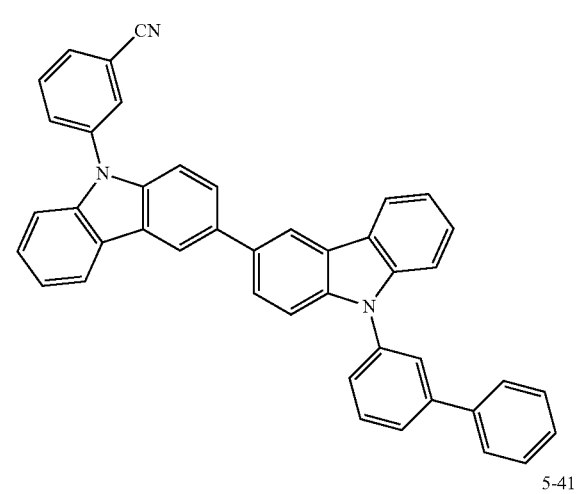
5-41
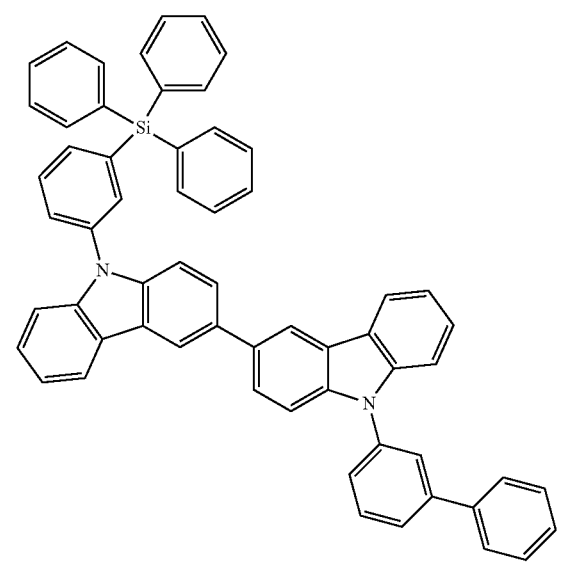

-continued
5-42
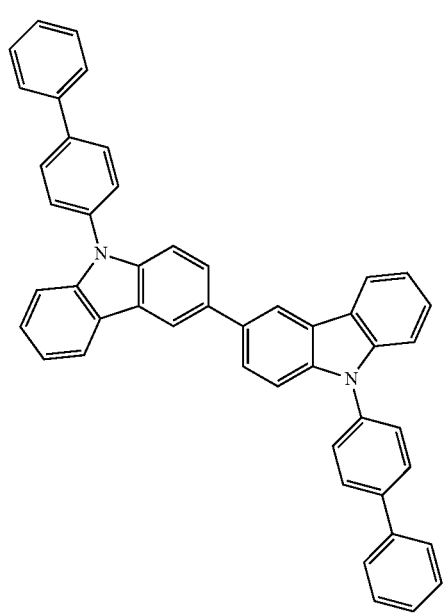
5-44
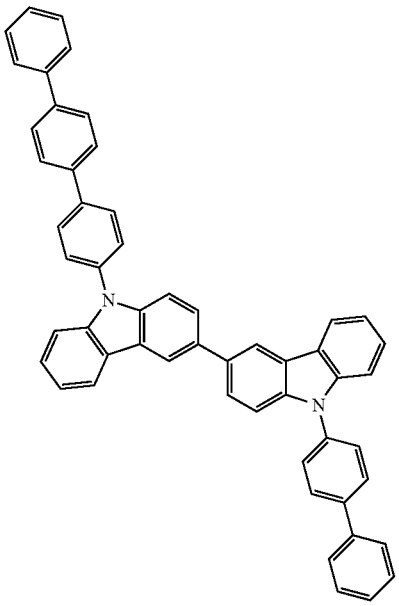
5-43
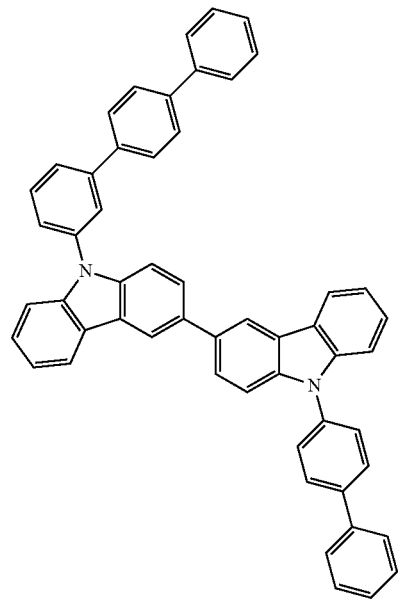
5-45
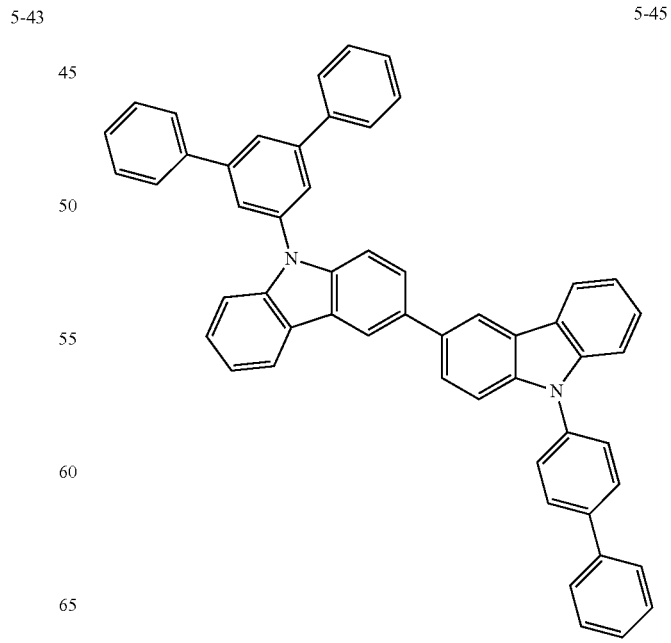

5-46
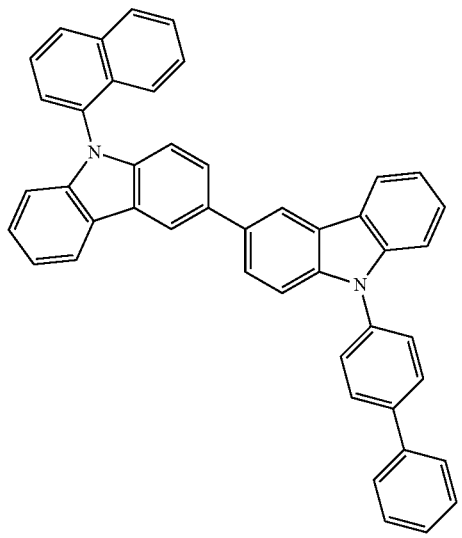
5-47
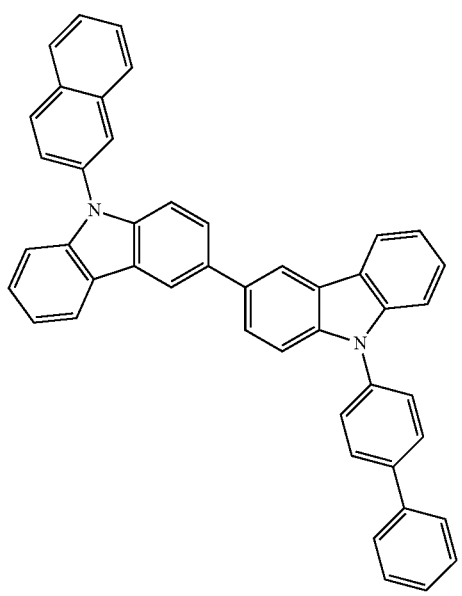
5-48
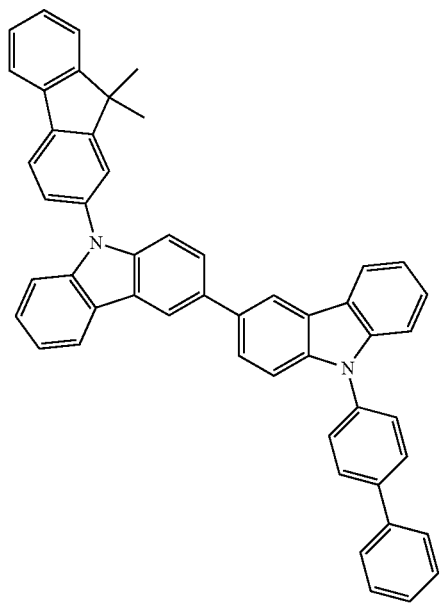
5-49
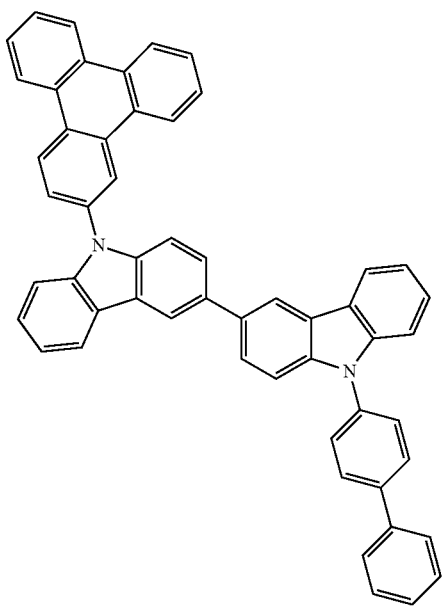

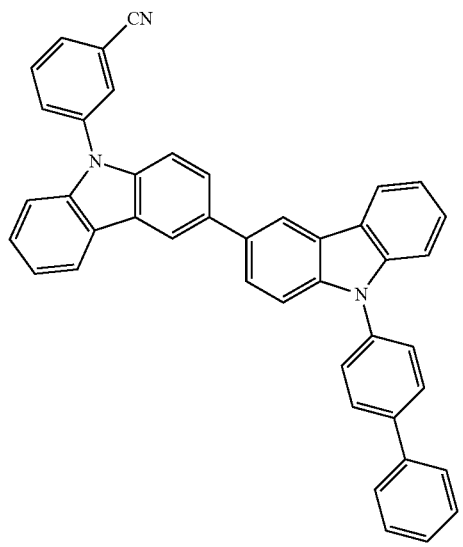
5-50
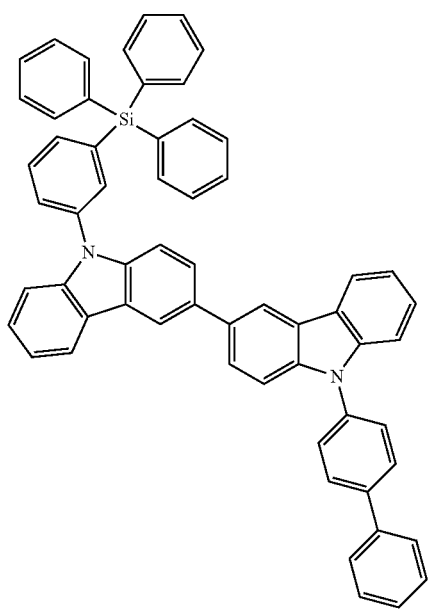
5-51
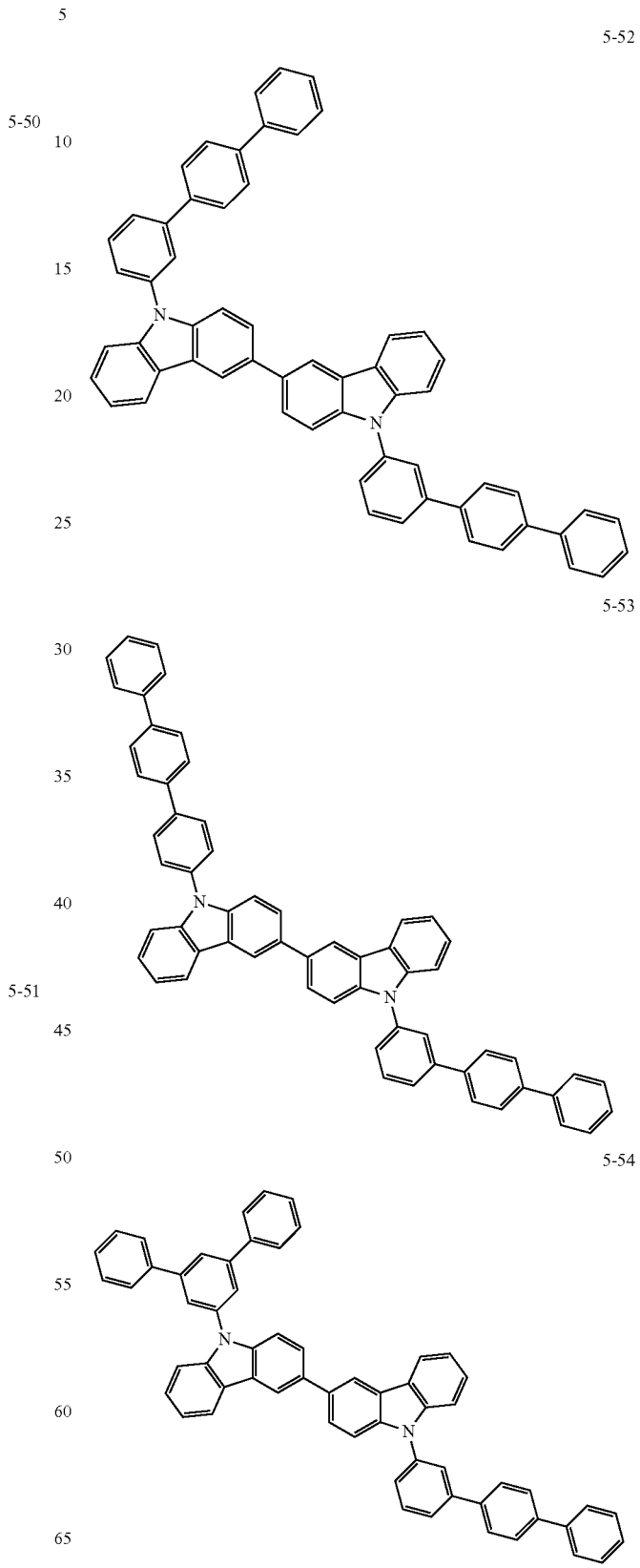
5-52
5-53
5-54

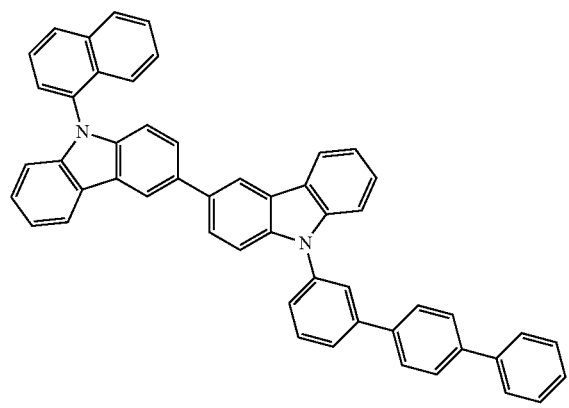
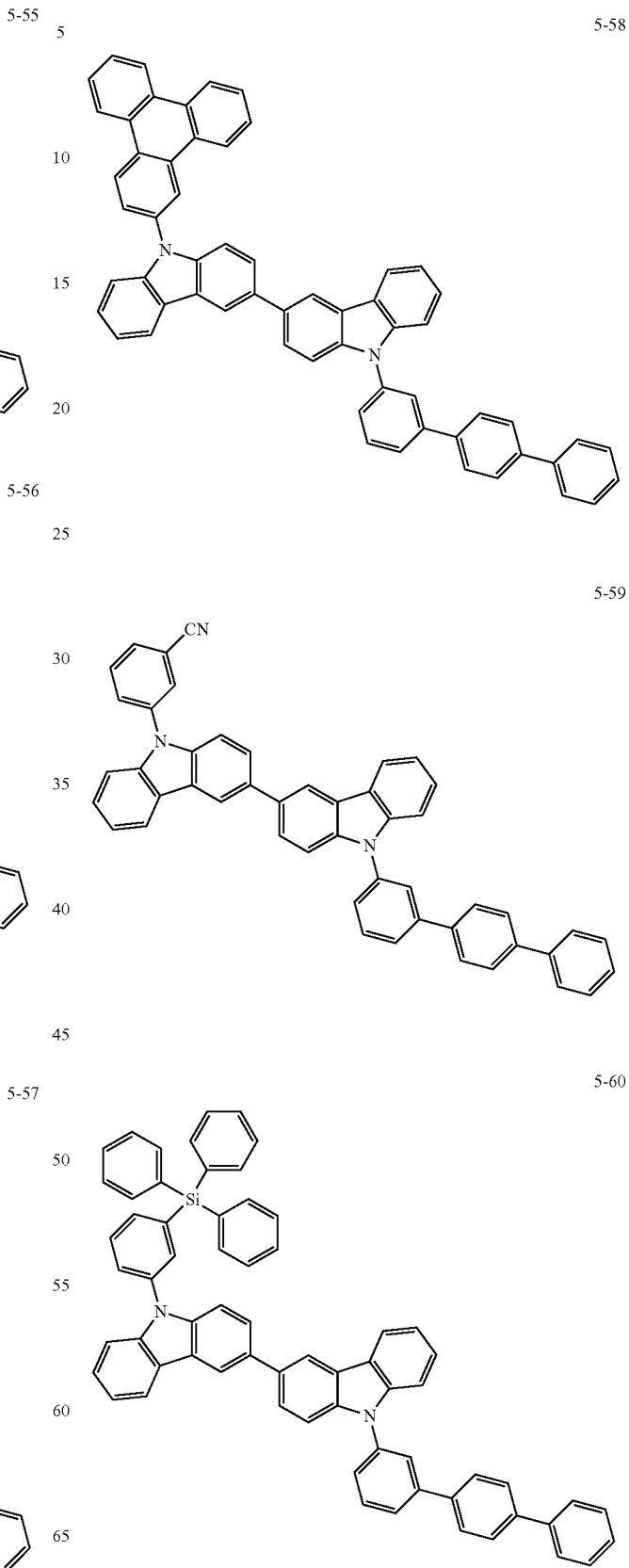

5-61
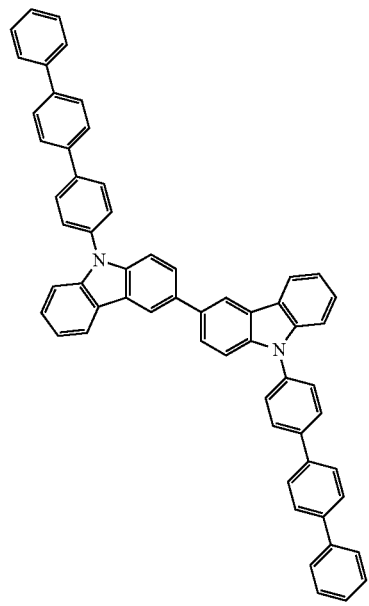
5-63
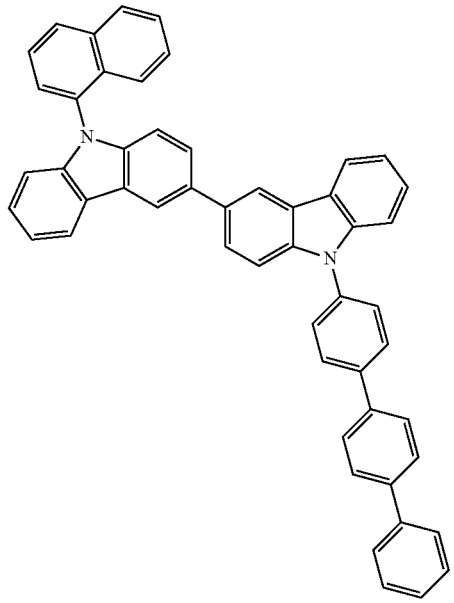
5-62
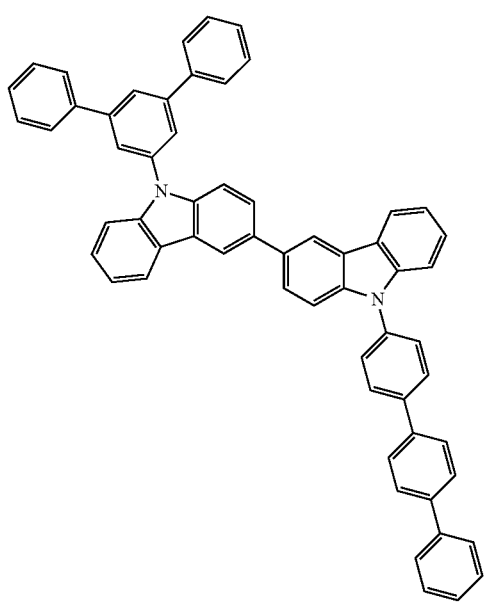
5-64
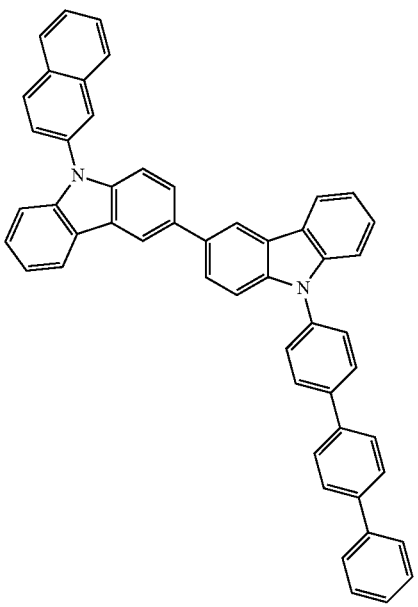

5-65
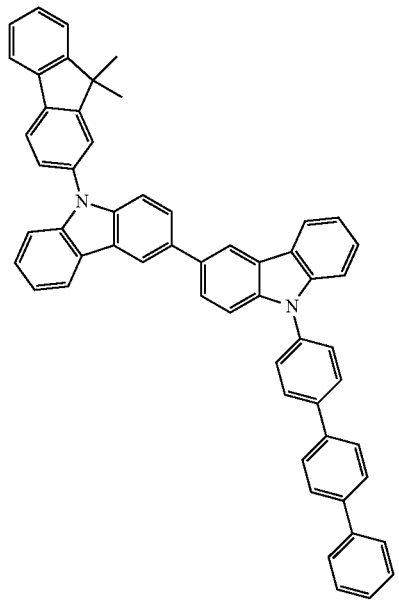
5-66
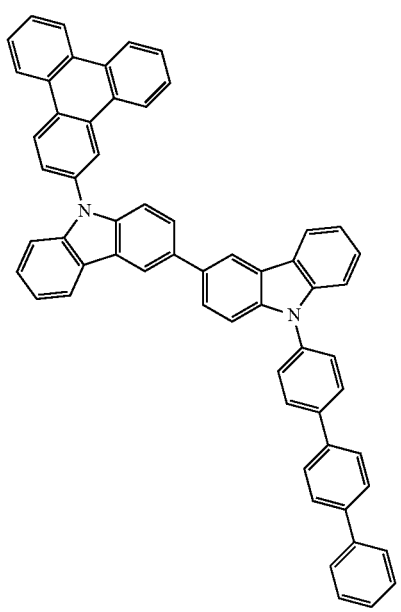
5-67
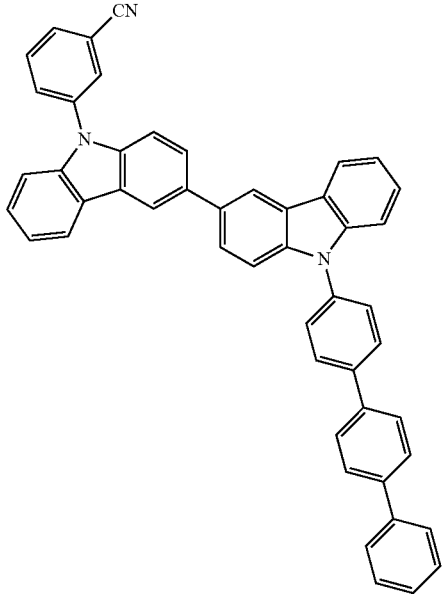
5-68
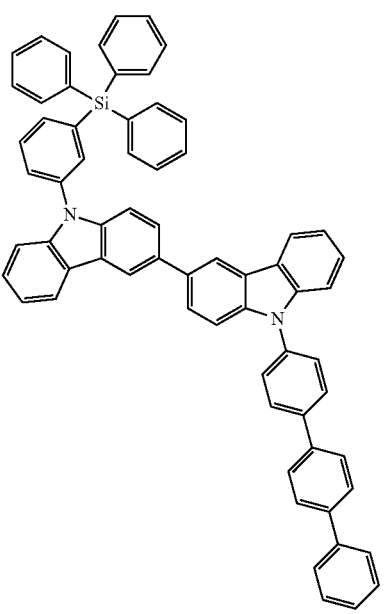

507
-continued
5-69
5-70
5-71
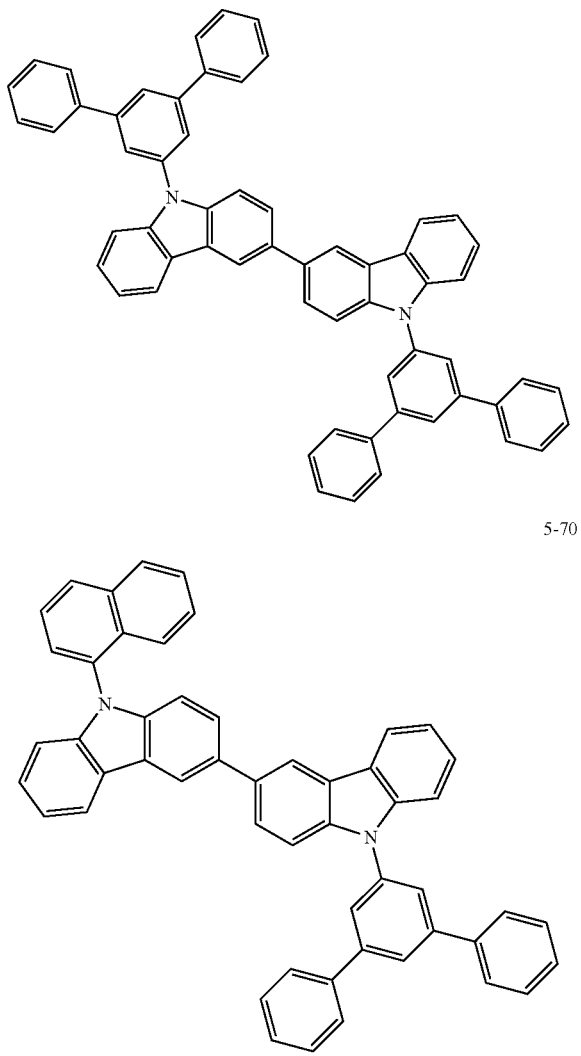
508
-continued
5-72
5-73
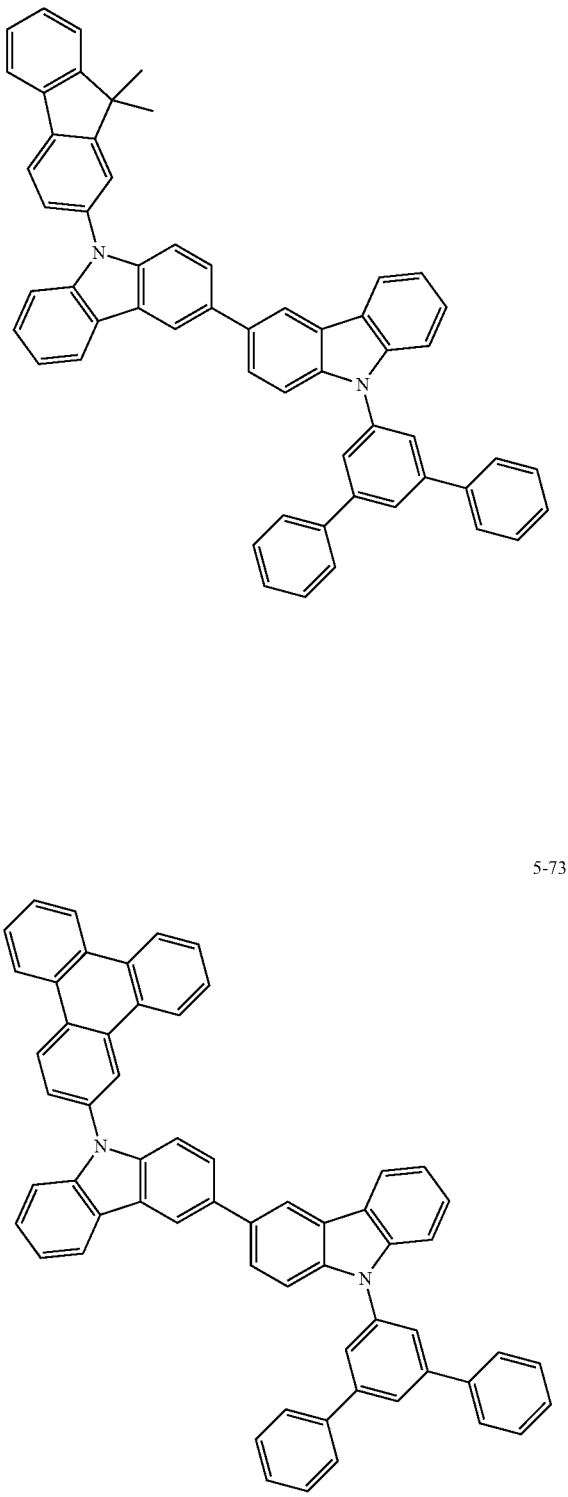

5-74
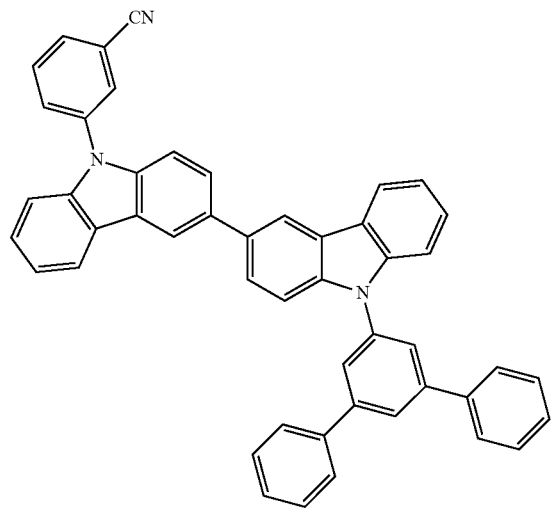
5-75
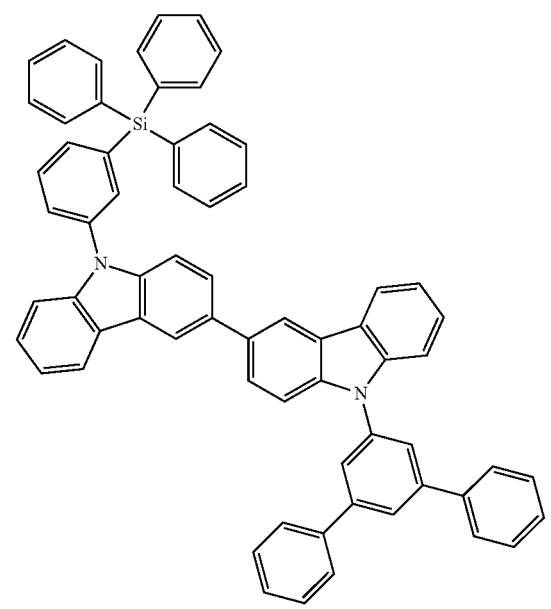
5-76
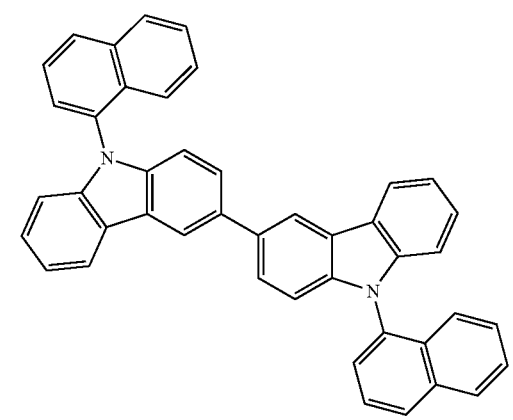
5-77
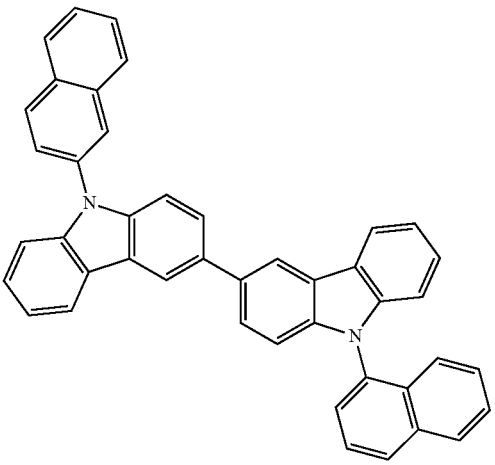
5-78
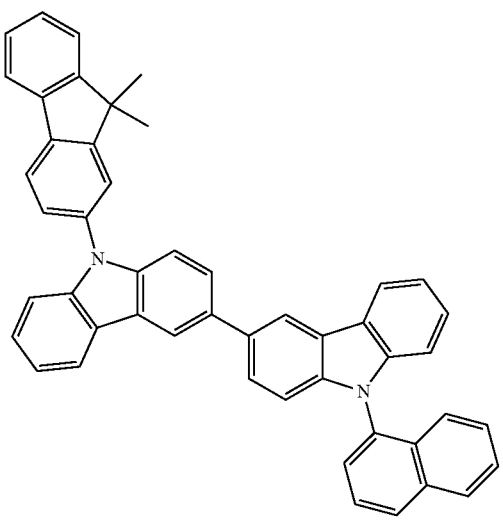
5-79
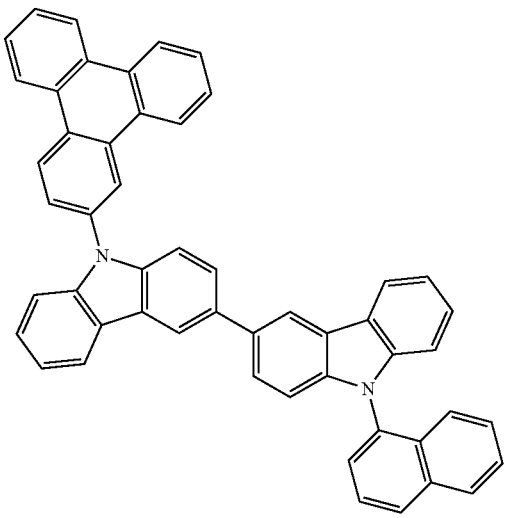

511
-continued
5-80
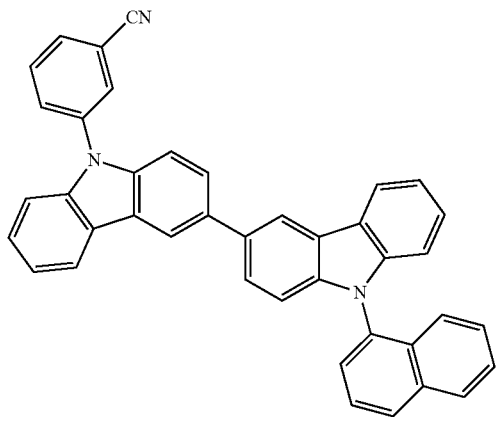
5-81
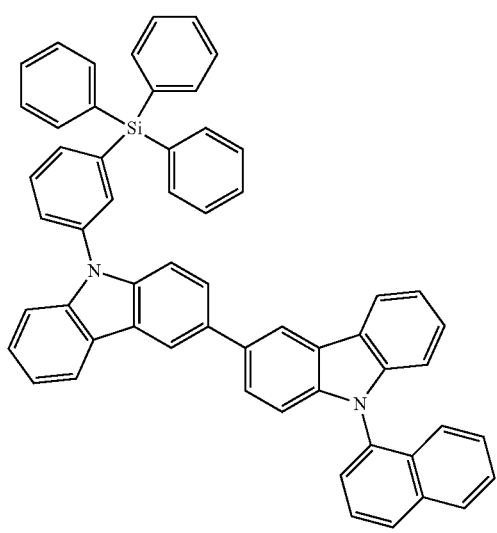
5-82
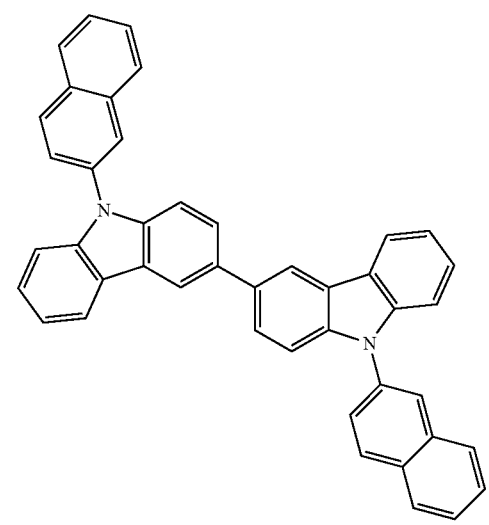
512
-continued
5-83
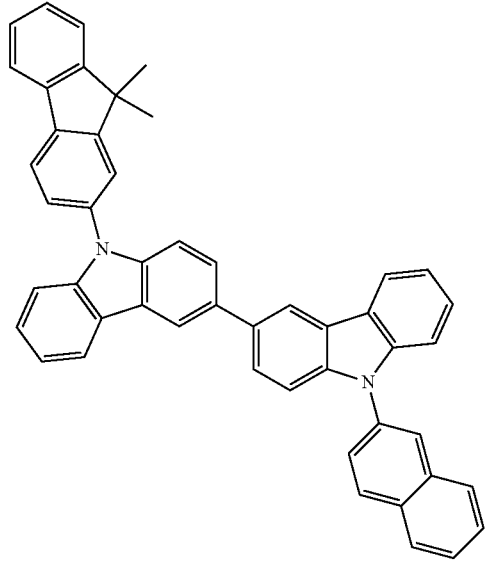
5-84
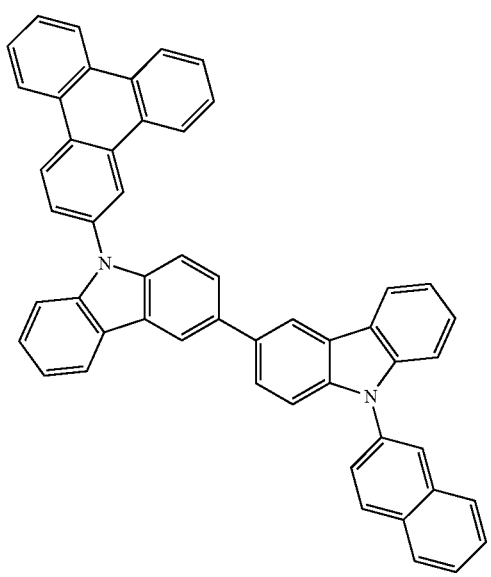
5-85
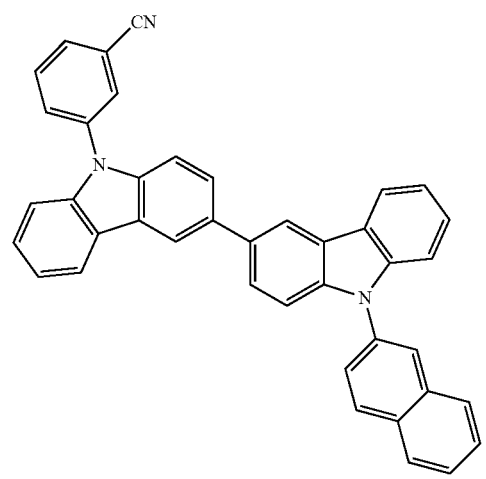

513
-continued
5-86
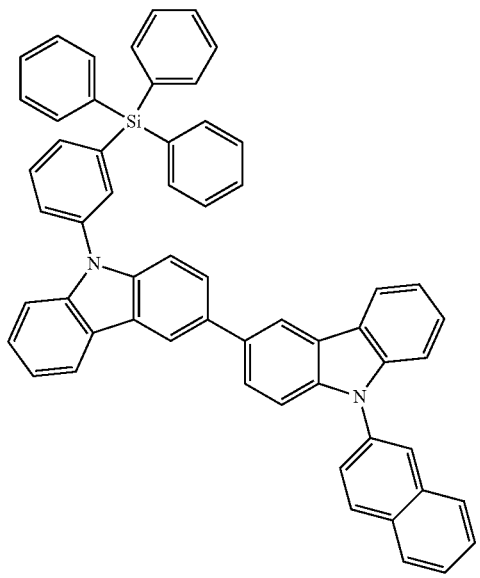
5-87
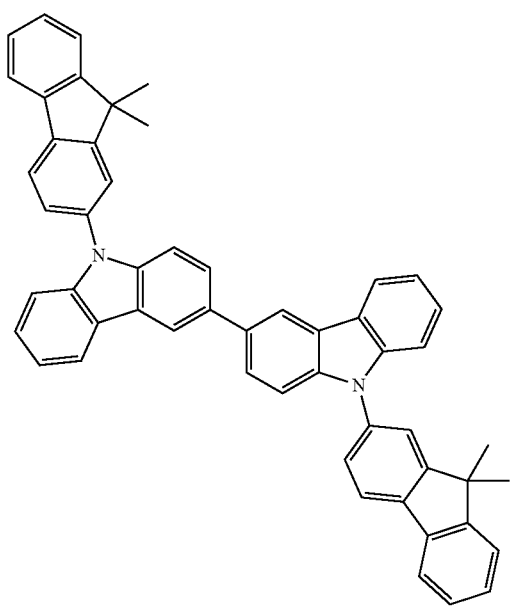
514
-continued
5-88
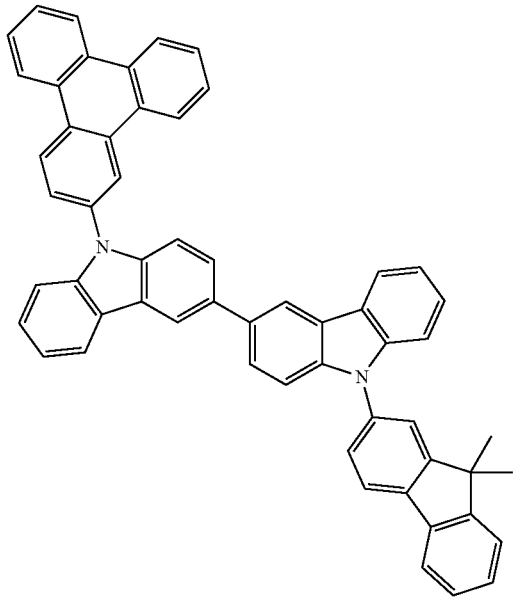
5-89

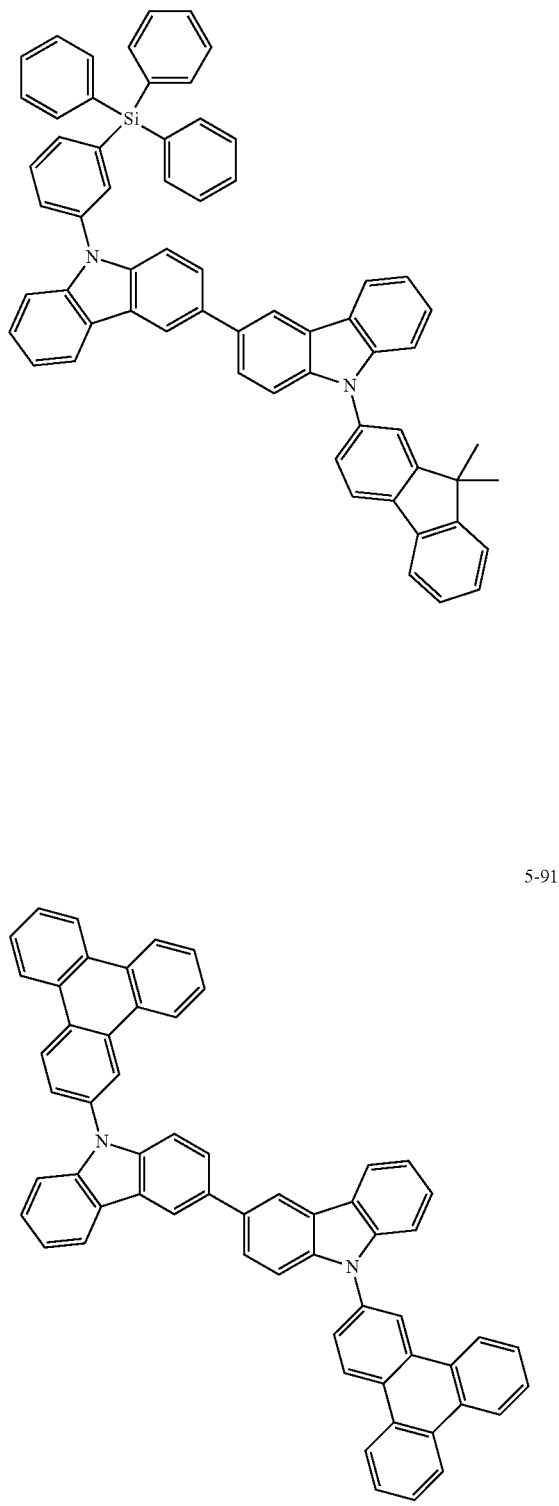
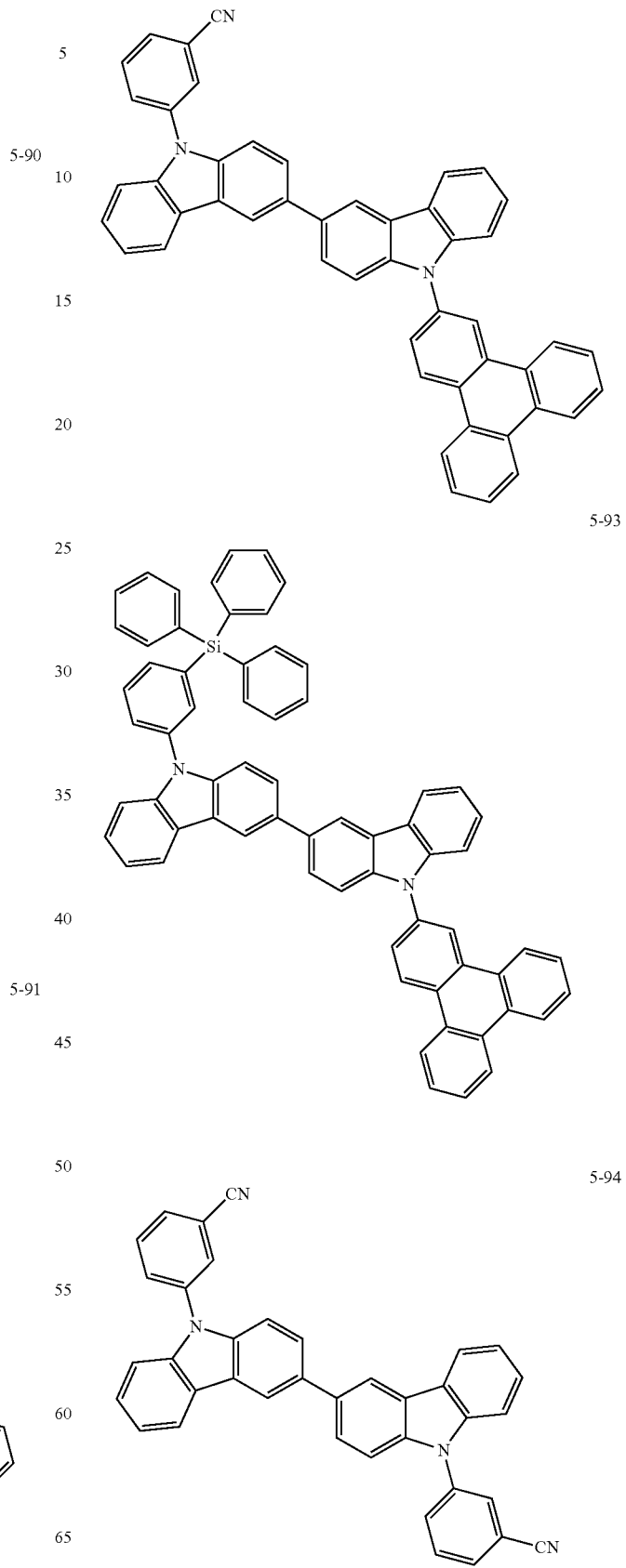

-continued 5-95

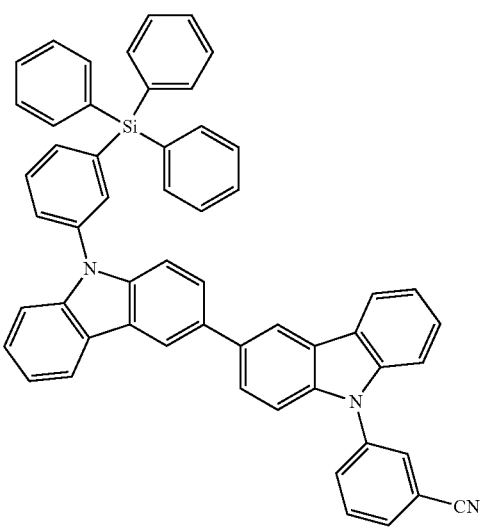

5-96

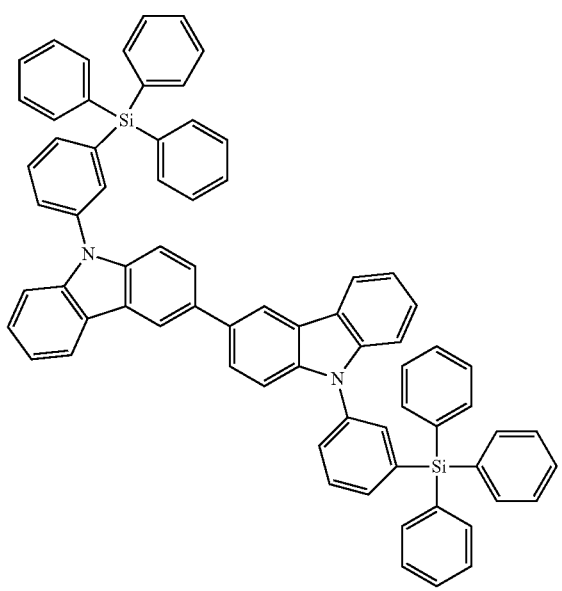

6. The organic light emitting device of claim 4, wherein R21 and R22 are the same as or different from each other, and each independently a substituted or unsubstituted C6 to C40 aryl group.

7. The organic light emitting device of claim 3, wherein the organic material layer comprises a light emitting layer, and the light emitting layer comprises the heterocyclic compound.

8. The organic light emitting device of claim 3, wherein the organic material layer comprises a light emitting layer, the light emitting layer comprises a host material, and the host material comprises the heterocyclic compound.

9. The organic light emitting device of claim 3, wherein the organic material layer comprises an electron injection layer or an electron transfer layer, and the electron injection layer or the electron transfer layer comprises the heterocyclic compound.

10. The organic light emitting device of claim 3, wherein the organic material layer comprises an electron blocking layer or a hole blocking layer, and the electron blocking layer or the hole blocking layer comprises the heterocyclic compound.

11. The organic light emitting device of claim 3, further comprising one, two or more layers selected from the group consisting of a light emitting layer, a hole injection layer, a hole transfer layer, an electron injection layer, an electron transfer layer, an electron blocking layer and a hole blocking layer.

12. A composition for an organic material layer of an organic light emitting device comprising:
the heterocyclic compound of claim 1; and
a heterocyclic compound represented by the following Chemical Formula 3:

[Chemical Formula 3]

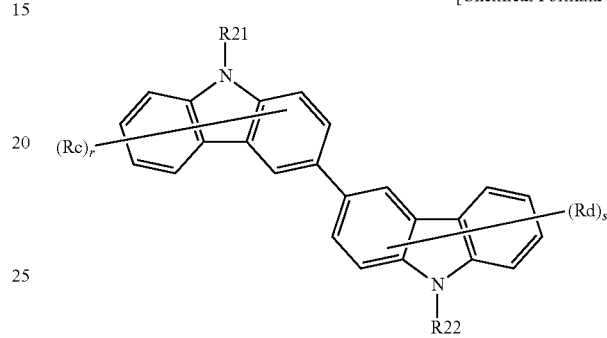

wherein, in Chemical Formula 3,
Rc and Rd are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiR$_{31}$R$_{32}$R$_{33}$; —P(=O)R$_{31}$R$_{32}$; and an amine group unsubstituted or substituted with a substituted or unsubstituted alkyl group, a substituted or unsubstituted aryl group or a substituted or unsubstituted heteroaryl group, or two or more groups adjacent to each other bond to each other to form a substituted or unsubstituted aliphatic or aromatic hydrocarbon ring;
R$_{31}$, R$_{32}$, and R$_{33}$ are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group;
R21 and R22 are the same as or different from each other, and each independently a substituted or unsubstituted aryl group; or a substituted or unsubstituted heteroaryl group; and
r and s are an integer of 0 to 7, and when r and s are an integer of 2 or greater, substituents in the parentheses are the same as or different from each other.

13. A method for manufacturing an organic light emitting device, the method comprising:
preparing a substrate;
forming a first electrode on the substrate;
forming one or more organic material layers on the first electrode; and
forming a second electrode on the organic material layer, wherein the forming of organic material layers comprises forming one or more organic material layers using the composition for an organic material layer of claim 12.

14. The method for manufacturing an organic light emitting device of claim 13, wherein the forming of organic material layers is forming using a thermal vacuum deposition method after pre-mixing the heterocyclic compound of Chemical Formula 4 and 5 and the heterocyclic compound of Chemical Formula 3.

* * * * *